United States Patent
Li et al.

(10) Patent No.: US 11,504,375 B2
(45) Date of Patent: *Nov. 22, 2022

(54) ERBB/BTK INHIBITORS

(71) Applicant: Dizal (Jiangsu) Pharmaceutical Co., Ltd., Shanghai (CN)

(72) Inventors: Zhengtao Li, Shanghai (CN); Hao Zou, Shanghai (CN); Wei Zhu, Shanghai (CN); Changmao Shen, Shanghai (CN); Rumin Wang, Shanghai (CN); Wengeng Liu, Shanghai (CN); Xiang Chen, Shanghai (CN); Honchung Tsui, Shanghai (CN); Zhenfan Yang, Shanghai (CN); Xiaolin Zhang, Shanghai (CN)

(73) Assignee: DIZAL (JIANGSU) PHARMACEUTICAL CO., LTD., Jiangsu (CN)

(*) Notice: Subject to any disclaimer, the term of this patent is extended or adjusted under 35 U.S.C. 154(b) by 0 days.

This patent is subject to a terminal disclaimer.

(21) Appl. No.: 17/224,121

(22) Filed: Apr. 7, 2021

(65) Prior Publication Data

US 2021/0252005 A1 Aug. 19, 2021

Related U.S. Application Data

(63) Continuation of application No. 16/910,208, filed on Jun. 24, 2020, now Pat. No. 11,007,198, and a continuation of application No. PCT/CN2019/073355, filed on Jan. 28, 2019.

(30) Foreign Application Priority Data

Jan. 31, 2018 (WO) ............... PCT/CN2018/074791
Nov. 30, 2018 (WO) ............... PCT/CN2018/118569

(51) Int. Cl.
| | | |
|---|---|---|
| *C07D 401/12* | (2006.01) | |
| *A61K 31/53* | (2006.01) | |
| *C07D 251/48* | (2006.01) | |
| *C07D 405/12* | (2006.01) | |
| *C07D 487/04* | (2006.01) | |
| *A61K 31/505* | (2006.01) | |
| *A61K 31/506* | (2006.01) | |
| *C07D 403/12* | (2006.01) | |
| *C07D 239/48* | (2006.01) | |

(52) U.S. Cl.
CPC ............ *A61K 31/53* (2013.01); *A61K 31/505* (2013.01); *A61K 31/506* (2013.01); *C07D 239/48* (2013.01); *C07D 251/48* (2013.01); *C07D 401/12* (2013.01); *C07D 403/12* (2013.01); *C07D 405/12* (2013.01); *C07D 487/04* (2013.01)

(58) Field of Classification Search
CPC .. C07D 239/48; C07D 251/48; C07D 403/12; A61K 31/505; A61K 31/506; A61K 31/53
See application file for complete search history.

(56) References Cited

U.S. PATENT DOCUMENTS

| 8,338,439 B2 | 12/2012 | Singh et al. |
| 11,007,198 B2 * | 5/2021 | Li .............................. A61P 9/02 |

FOREIGN PATENT DOCUMENTS

| CN | 105384694 A | 3/2016 |
|---|---|---|
| CN | 106083736 A | 11/2016 |
| CN | 106883213 A | 6/2017 |
| CN | 106905245 A | 6/2017 |
| CN | 106928150 A | 7/2017 |
| EP | 3392245 A1 | 10/2018 |
| EP | 3398939 A1 | 11/2018 |
| RU | 2330021 C2 | 7/2008 |
| WO | 2009158571 A1 | 12/2009 |
| WO | 2013/138502 A1 | 9/2013 |
| WO | 2014071832 A1 | 5/2014 |
| WO | 2015/003658 A1 | 1/2015 |
| WO | 2015023703 A1 | 2/2015 |
| WO | 2017101803 A1 | 6/2017 |
| WO | 2017/114500 A1 | 7/2017 |
| WO | 2017219500 A1 | 12/2017 |
| WO | 2019/177375 A1 | 9/2019 |

OTHER PUBLICATIONS

Ulrich, Crystallization, Kirk-Othmer Encyclopedia of Chemical Technology, pp. 1-7, 2002.*
Vippagunta et al., Crystalline Solids, Advanced Drug Delivery Reviews 48 (2001), pp. 3-26.*
Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-1101 O, 1995.*
Johnson et al., Relationships between drug activity in NCI preclinical in vitro and in vivo models and early clinical trials, British Journal of Cancer, 84(10):1424-1431, 2001.*
Gura et al., Systems for identifying new drugs are often faulty, Science, 278:1041-1042, 1997.*
Ten Hacken et al., Microenvironment dependency in Chronic Lymphocytic Leukemia: The basis for new targeted therapies, 11 pages, Pharmacology & Therapeutics 144, (2014) pp. 338-348.*

(Continued)

*Primary Examiner* — Deepak R Rao
(74) *Attorney, Agent, or Firm* — Jun He Law Offices P.C.; Zhaohui Wang

(57) ABSTRACT

Disclosed are compounds inhibiting ErbBs (e.g., EGFR or Her 2), especially mutant forms of ErbBs, and BTK, pharmaceutically acceptable salts, hydrates, solvates or stereoisomers thereof and pharmaceutical compositions comprising the compounds. The compound and the pharmaceutical composition can effectively treat ErbBs (especially mutant forms of ErbBs) or BTK associated diseases, including cancer.

23 Claims, No Drawings

(56) References Cited

OTHER PUBLICATIONS

Zhou et al., Interaction-site prediction for protein complexes: a critical assessment, Bioinformatics, vol. 23, No. 17, pp. 2203-2209, 2007.*
Acute Leukemia, Merck Manual (Online Edition) 6 pages, pp. 1-6 (2013).*
International Search Report of PCT Application No. PCT/CN2019/073355, dated Apr. 28, 2019.
Written Opinion of the International Searching Authority of PCT Application No. PCT/CN2019/073355, dated Apr. 28, 2019.
The First Office Action for Chinese Patent Application No. 202010659802.9, dated Mar. 3, 2021.
Dyson G. et al., "Chemistry synthetic medicinal substances", trans, from English yaz., M.: 1964, pp. 16-19.
M.D. Mashkovsky, "Medicinal means", Moscow, NewWave, publishers. B. Divov, 2001, vol. 1, p. 11, 12.
Belikov V.G., Pharmaceutical chemistry, textbook, 2007, Moscow, "MEDpress-inform", pp. 27-29.
Official Action for Russian Patent Application No. 2020127393/04 (048239), dated Feb. 19, 2021.
The First Examination Report (FER) for the corresponding Indian Patent Application No. 202017036944, dated Mar. 24, 2022.
Yongfei Chen et al., "Discvoery of N-(5-((5-chloro-4-((2-(isopropylsulfonyl)phenyl)amino)pyrimidin-2-yl)amino)-4-methoxy-2-(4-methyl-1,4-diazepan-1-yl)phenyl)acrylamide (CHMFL-ALK/EGFR-050) as a potent ALK/EGFR dual kinase inhibitor capable of overcoming a variety of ALK/EGFR associated drug resistant mutants in NSCLC", European Journal of Medicinal Chemistry, vol. 139, Oct. 1, 2017 (Oct. 1, 2017), pp. 674-697, XP055600563, Amsterdam, NL, ISSN: 0223-5234, DOI: 10.1016/j.ejmech.2017.08.035, p. 680; table 2; compund 42.
The extended European search report for EP19748259.9, dated Jul. 28, 2021.
The second office action for the corresponding CN application No. 202010659802.9, dated Aug. 18, 2021.

* cited by examiner

ERBB/BTK INHIBITORS

CROSS-REFERENCE TO RELATED APPLICATIONS

This application is a continuation of U.S. Ser. No. 16/910, 208, filed on Jun. 24, 2020, which is a continuation of PCT Patent Application No. PCT/CN2019/073355, filed on Jan. 28, 2019, which claims foreign priority of PCT Patent Application No. PCT/2018/118569, filed on Nov. 30, 2018, now abandoned and PCT Patent Application No. PCT/2018/074791, filed on Jan. 31, 2018, now abandoned. Each of these applications is hereby incorporated by reference herein in its entirety.

FIELD OF THE DISCLOSURE

The present disclosure relates to compounds that inhibit ErbBs (e.g., EGFR or Her2) especially mutant forms of ErbBs, and/or inhibit Bruton's tyrosine kinase (BTK). The present disclosure also relates to a pharmaceutical composition comprising one or more of the compounds as an active ingredient, and use of the compounds in the manufacture of medicaments for treating disorders associated with mutant forms of ErbBs (e.g., EGFR or Her2) and/or with BTK.

BACKGROUND

ErbB family receptor tyrosine kinases act to transmit signals from the outside of a cell to the inside by activating secondary messaging effectors via a phosphorylation event at their tyrosine phosphorylation residues. A variety of cellular processes are modulated by these signals, including proliferation, carbohydrate utilization, protein synthesis, angiogenesis, cell growth, and cell survival. Deregulation of ErbB family signalling modulates proliferation, invasion, metastasis, angiogenesis, and tumour cell survival and may be associated with many human cancers, including those of the lung, head and neck and breast cancers. Detailed reviews of ErbB receptor signalling and its involvement in turnourigenesis are provided in New England Journal of Medicine, 2008, Vol. 358:1160-74 and Biochemical and Biophysical Research Communications, 2004, Vol. 319: 1-11.

EGFR has been found to be overexpressed and/or mutated in many cancers such as gliomas and non-small-cell lung carcinoma. Anticancer drugs targeting EGFR are now clinically available, including, for example, gefitinib (IRESSAT®), erlotinib (TARCEVA®), lapatinib (TYKERB®, TYVERB®), panitumumab (VECTIBIX), cetuximab (ERBITUX), osimertinib (TAGRISSO, AZD9291) and afatinib (GIOTRIF). In the majority of patients that relapse, acquired drug resistance, mutation of EGFR at the residue T790M has been detected in at least half of such clinically resistant patients. Moreover, T790M mutation may also be pre-existing, for example, there are patients with the L858R/T790M mutation who never received gefitinib treatment, and germline EGFR T790M mutations are linked with certain familial lung cancers, suggesting there may be an independent, oncogenic role for the T790M mutation. Current drugs in development, including second generation covalent inhibitors, such as BIBW2992, HKI-272 and PF-0299804, are effective against the T790M mutation resistant to existing drugs but exhibit dose-limiting toxicities due to concurrent inhibition of wild type (WT) EGFR. Adverse effects, such as skin rash and diarrhea, which are considered to be related to inhibition of WT EGFR signalling pathways in normal skin and gut cells, were also reported in >60% NSCLC patients treated with gefitinib or erlotinib (Zhou C C et al. Journal of Clinical Oncology, 2011, Vol. 12: 735-42; Mok T S et al. New England Journal of Medicine, 2009, Vol. 361: 947-57).

EGFR exon 20 insertions were found in about 4-9.2% of EGFR mutant lung cancers (Mitsudomin and Yatabe FEBS J., 2010; 277 (2):301-8), most of which occur in the region encoding amino acids 767 through 774 of exon 20, within the loop that follows the C-helix of the kinase domain of EGFR (Yasuda et al. Lancet Oncol., 2012; 13(1): e2331). Patients with lung cancer harboring typical EGFR exon 20 insertion mutations were reported as not responding to gefitinib or erlotinib or afatinib (Yasuda et al. Lancet Oncol., 2012, 13(1): e23-31; Yasuda et al. Sci Transl Med., 2013, 5(216):216ra177).

Her2 overexpression can occur in breast, ovarian, bladder, non-small-cell lung carcinoma, as well as several other tumor types. Clinically available anticancer drugs targeting Her2 include Trastuzumab (also known as Herceptin). Although two thirds of breast cancer patients respond well to herceptin, some Her2-positive breast cancer patients do not respond to the drug. It is possible that the non-responding group of patients may have a drug resistant mutation in Her2. A four amino acid YVMA insertion mutation occurs at codon 775 in exon 20 of Her2 was also found in around 2-4% non-smoking non-small cell lung cancer patients, and the patients having such Her2 YVMA mutation were found largely resistant to known EGFR inhibitors (Arcila et al. Clin Cancer Res., 2012, 18:4910-4918).

Bruton's tyrosine kinase (BTK) is a member of the src-related Tec family of cytoplasmic tyrosine kinases, which are predominantly expressed in B cells, and distributed in the lymphatic system, hematopoietic and hematological systems. BTK plays a key role in the B-cell receptor signaling pathway of B-cells, which is required for the development, activation and survival of B-cells. BTK inhibitors have therefore been developed with the aim of treating B-cell malignancies that are dependent on BCR signaling, such as chronic lymphocytic leukemia (CLL) and non-Hodgkin's lymphoma (NHL), mantle cell lymphoma (MCL), and diffuse large B-cell lymphoma (DLBCL). BTK has also been implicated in promotion of Toll-like receptor signaling, which regulates macrophage activation and production of proinflammatory cytokines. Several studies have demonstrated crosstalk between BTK and TLR signaling pathways to mediate transactivation of downstream cascades. Furthermore, BTK is found to play a critical role in regulation of immunity. BTK has become an attractive target for the treatment of not only B-cell malignancies but also for the treatment of autoimmune diseases. (See Ping et al., Oncotarget, 2017, 8(24):39218-39229). Anticancer drugs targeting BTK are now clinically available, including Ibrutinib, which is an irreversible, small-molecule BTK inhibitor that has been approved for the treatment of CLL mantle cell lymphoma (MCL) and Waldenstrom's macroglobulinemia (WM).

Accordingly, there remains a need to develop novel ErbB (especially, EGFR or Her2) inhibitors, which have better selectivity to mutant EGFR over WT EGFR, or has better selectivity to mutant Her2 over WT Her2. There also remains a need to develop novel BTK inhibitors.

SUMMARY

In one aspect, the present disclosure provides a compound represented by Formula (I):

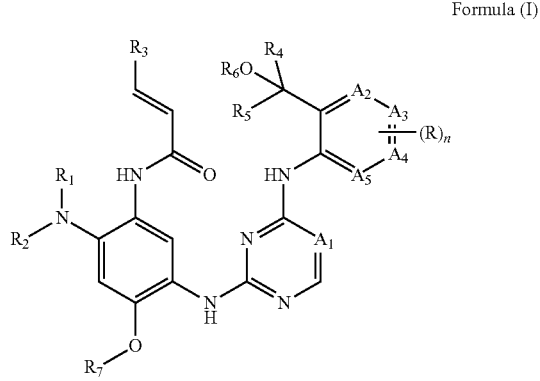

Formula (I)

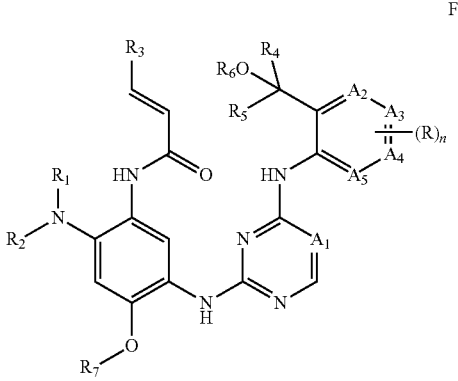

Formula (I)

or a pharmaceutically acceptable salt, ester, hydrate, solvate or stereoisomer thereof.

In another aspect, the present disclosure provides a pharmaceutical composition comprising one or more compounds of Formula (I), pharmaceutically acceptable salts, ester, hydrates, solvates or stereoisomers thereof.

In another aspect, the present disclosure further provides a compound of Formula (I), or a pharmaceutically acceptable salt, ester, hydrate, solvate or stereoisomer thereof, or a pharmaceutical composition of one or more of the foregoing, for use as a medicament for inhibiting ErbB, preferably EGFR or HER2, more preferably inhibiting one or more mutant forms of EGFR or HER2.

In yet another aspect, the present disclosure provides use of the compounds of Formula (I), pharmaceutically acceptable salts, esters, hydrates, solvates or stereoisomers thereof, or a pharmaceutical composition of one or more of the foregoing in the manufacture of a medicament for inhibiting ErbB, preferably EGFR or HER2, more preferably one or more mutant forms of EGFR or HER2 in a subject.

In another aspect, the present disclosure provides a method for inhibiting ErbB, preferably EGFR or HER2, more preferably one or more mutant forms of EGFR or HER2, by using one or more compounds of Formula (I), pharmaceutically acceptable salts, esters, hydrates, solvates or stereoisomers thereof or the pharmaceutical composition of one or more of the foregoing.

In another aspect, the present disclosure provides a method for treating an ErbB-related disorder (e.g., cancer), by using the compounds of Formula (I), pharmaceutically acceptable salts, esters, hydrates, solvates or stereoisomers thereof or the pharmaceutical composition of one or more of the foregoing.

In a further aspect, the present disclosure provides a compound of Formula (I), a pharmaceutically acceptable salt, ester, hydrate, solvate or stereoisomer thereof, in combination with a second therapeutic agent, preferably an anti-tumour agent.

In another aspect, the present disclosure provides a combined use of a compound of Formula (I), a pharmaceutically acceptable salt, ester, hydrate, solvate or stereoisomer thereof, and a second therapeutic agent, preferably an anti-tumour agent.

DETAILED DESCRIPTION

Compounds

In one aspect, the present disclosure provides compounds of Formula (I):

or a pharmaceutically acceptable salt, ester, hydrate, solvate or stereoisomer thereof, wherein, $A_1$ is N or $CR_8$;

$A_2$, $A_3$, $A_4$ and $A_5$ are each independently N or $CR_9$, wherein no more than one of $A_2$, $A_3$, $A_4$ and $A_5$ is N;

$R_1$ and $R_2$ are each independently hydrogen or $C_{1-12}$ alkyl optionally mono- or independently multi-substituted by one or more of halogen, hydroxyl, —$NR^aR^b$, $C_{1-12}$ alkyl, $C_{1-12}$ alkoxy, 3-10 membered saturated or unsaturated carbocyclyl, 3-10 membered saturated or unsaturated heterocyclyl, wherein each of $C_{1-12}$ alkyl, $C_{1-12}$ alkoxy, 3-10 membered saturated or unsaturated carbocyclyl, 3-10 membered saturated or unsaturated heterocyclyl can be unsubstituted or mono- or multi-substituted by $C_{1-12}$ alkyl, wherein, $R^a$ and $R^b$ are each independently selected from hydrogen or $C_{1-12}$ alkyl, which can be optionally mono- or independently multi-substituted by deuterium, tritium, halogen, hydroxyl, or $C_{1-12}$ alkoxy, or $R^a$ and $R^b$ taken together with the nitrogen atom to which they are bound form a 3-10 membered saturated or unsaturated heterocyclyl optionally mono- or multi-substituted by halogen, hydroxyl, or $C_{1-12}$ alkyl;

or, $R_1$ and $R_2$ taken together with the nitrogen atom to which they are bound form a 3-12 membered monocyclic or polycyclic ring optionally comprising one or more additional heteroatoms selected from N, O, and S, which can be optionally mono- or independently multi-substituted by halogen, hydroxyl, $C_{1-12}$ alkyl, $C_{1-12}$ alkoxy, —$NR^aR^b$, or —$C_{1-12}$ alkyl-$NR^aR^b$;

$R_3$ is H, $C_{1-12}$ alkyl, or —$C_{1-12}$ alkyl-$NR^aR^b$;

$R_4$ and $R_5$ are each independently $C_{1-6}$ alkyl optionally mono- or independently multi-substituted by one or more of deuterium, tritium, halogen, hydroxyl, $C_{1-12}$ alkyl, or $C_{1-12}$ alkoxy, or, $R_4$ and $R_5$ taken together with the carbon atom to which they are bound form a 3-10 membered monocyclic or polycyclic ring optionally comprising one or more heteroatoms selected from N, O, and S, which can be optionally mono- or independently multi-substituted by one or more of deuterium, tritium, halogen, hydroxyl, $C_{1-12}$ alkyl, or $C_{1-12}$ alkoxy, $R_6$ is hydrogen, or $C_{1-12}$ alkyl, which can be optionally mono- or independently multi-substituted by deuterium, tritium, halogen, hydroxyl, $C_{1-12}$ alkyl or $C_{1-12}$ alkoxy, $R_7$ is hydrogen, or $C_{1-12}$ alkyl, which can be optionally mono- or multi-substituted by deuterium, tritium, halogen, or hydroxyl, $R_8$ is hydrogen, deuterium, tritium, halogen, cyano, hydroxyl, $C_{1-12}$ alkyl, $C_{1-12}$ alkoxyl, which can be optionally mono- or independently multi-substituted by one or more of deuterium, tritium, halogen, or $C_{1-12}$ alkyl;

$R_9$ is null, hydrogen, deuterium, tritium, halogen, cyano, hydroxyl, $C_{1-12}$ alkyl, $C_{1-12}$ alkoxyl, which can be optionally mono- or independently multi-substituted by one or more of deuterium, tritium, halogen, or $C_{1-12}$ alkyl;

n is 0, 1, 2, 3, or 4;

each R is independently hydrogen, deuterium, tritium, halogen, cyano, hydroxyl, $C_{1-12}$ alkyl, $C_{1-12}$ alkoxy, 3-10 membered saturated or unsaturated carbocyclyl, or 3-10 membered saturated or unsaturated heterocyclyl which is fused with the ring to which it is bound, which can be optionally mono- or independently multi-substituted by one or more of deuterium, tritium, halogen, or $C_{1-12}$ alkyl.

In some embodiments, $A_1$ in Formula (I) is N. In some embodiments, $A_1$ in Formula (I) is $CR_8$, wherein Rx is hydrogen, deuterium, tritium, halogen, cyano, hydroxyl, $C_{1-12}$ alkyl, $C_{1-12}$ alkoxyl, which can be optionally mono- or independently multi-substituted by one or more of deuterium, tritium, halogen, or $C_{1-12}$ alkyl. In some embodiments, $A_1$ in Formula (I) is CH.

In some embodiments, the compounds of the present disclosure are represented by Formula (Ia):

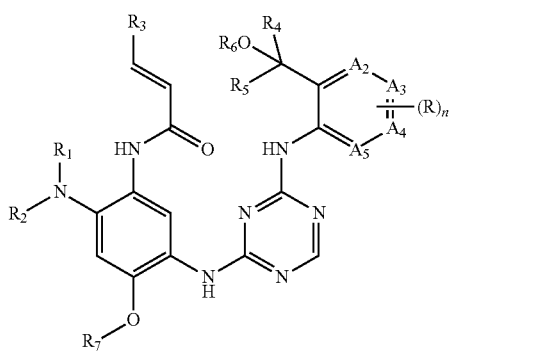

Formula (Ia)

or a pharmaceutically acceptable salt, ester, hydrate, solvate or stereoisomer thereof, wherein, $A_2$, $A_3$, $A_4$ and $A_5$ are each independently N or $CR_9$, wherein no more than one of $A_2$, $A_3$, $A_4$ and $A_5$ is N;

$R_1$ and $R_2$ are each independently hydrogen or $C_{1-12}$ alkyl optionally mono- or independently multi-substituted by one or more of halogen, hydroxyl, —$NR^aR^b$, $C_{1-12}$ alkyl, $C_{1-12}$ alkoxy, 3-10 membered saturated or unsaturated carbocyclyl, 3-10 membered saturated or unsaturated heterocyclyl, wherein each of $C_{1-12}$ alkyl, $C_{1-12}$ alkoxy, 3-10 membered saturated or unsaturated carbocyclyl, 3-10 membered saturated or unsaturated heterocyclyl can be unsubstituted or mono- or multi-substituted by $C_{1-12}$ alkyl, wherein, $R^a$ and $R^b$ are each independently selected from hydrogen or $C_{1-12}$ alkyl, which can be optionally mono- or independently multi-substituted by deuterium, tritium, halogen, hydroxyl, or $C_{1-12}$ alkoxy, or $R^a$ and $R^b$ taken together with the nitrogen atom to which they are bound form a 3-10 membered saturated or unsaturated heterocyclyl optionally mono- or multi-substituted by halogen, hydroxyl, or $C_{1-12}$ alkyl;

or, $R_1$ and $R_2$ taken together with the nitrogen atom to which they are bound form a 3-12 membered monocyclic or polycyclic ring optionally comprising one or more additional heteroatoms selected from N, O, and S, which can be optionally mono- or independently multi-substituted by halogen, hydroxyl, $C_{1-12}$ alkyl, $C_{1-12}$ alkoxy, —$NR^aR^b$, or —$C_{1-12}$ alkyl-$NR^aR^b$;

$R_3$ is H, $C_{1-12}$ alkyl, or —$C_{1-12}$ alkyl-$NR^aR^b$;

$R_4$ and $R_5$ are each independently $C_{1-6}$ alkyl optionally mono- or independently multi-substituted by one or more of deuterium, tritium, halogen, hydroxyl, $C_{1-12}$ alkyl, or $C_{1-12}$ alkoxy, or, $R_4$ and $R_5$ taken together with the carbon atom to which they are bound form a 3-10 membered monocyclic or polycyclic ring optionally comprising one or more heteroatoms selected from N, O, and S, which can be optionally mono- or independently multi-substituted by one or more of deuterium, tritium, halogen, hydroxyl, $C_{1-12}$ alkyl, or $C_{1-12}$ alkoxy, $R_6$ is hydrogen, or $C_{1-12}$ alkyl, which can be optionally mono- or independently multi-substituted by deuterium, tritium, halogen, hydroxyl, $C_{1-12}$ alkyl or $C_{1-12}$ alkoxy, $R_7$ is hydrogen, or $C_{1-12}$ alkyl, which can be optionally mono- or multi-substituted by deuterium, tritium, halogen, or hydroxyl, $R_9$ is null, hydrogen, deuterium, tritium, halogen, cyano, hydroxyl, $C_{1-12}$ alkyl, $C_{1-12}$ alkoxyl, which can be optionally mono- or independently multi-substituted by one or more of deuterium, tritium, halogen, or $C_{1-12}$ alkyl;

n is 0, 1, 2, 3, or 4;

each R is independently hydrogen, deuterium, tritium, halogen, cyano, hydroxyl, $C_{1-12}$ alkyl, $C_{1-12}$ alkoxy, 3-10 membered saturated or unsaturated carbocyclyl, or 3-10 membered saturated or unsaturated heterocyclyl which is fused with the ring to which it is bound, which can be optionally mono- or independently multi-substituted by one or more of deuterium, tritium, halogen, or $C_{1-12}$ alkyl.

In some embodiments, the compounds of the present disclosure are represented by Formula (Ib):

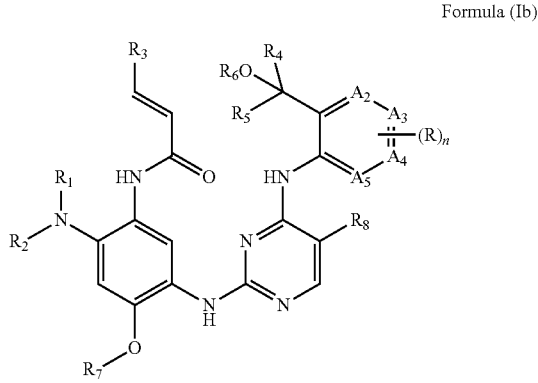

Formula (Ib)

or a pharmaceutically acceptable salt, ester, hydrate, solvate or stereoisomer thereof, wherein, $A_2$, $A_3$, $A_4$ and $A_5$ are each independently N or $CR_9$, wherein no more than one of $A_2$, $A_3$, $A_4$ and $A_5$ is N;

$R_1$ and $R_2$ are each independently hydrogen or $C_{1-12}$ alkyl optionally mono- or independently multi-substituted by one or more of halogen, hydroxyl, —$NR^aR^b$, $C_{1-12}$ alkyl, $C_{1-12}$ alkoxy, 3-10 membered saturated or unsaturated carbocyclyl, 3-10 membered saturated or unsaturated heterocyclyl, wherein each of $C_{1-12}$ alkyl, $C_{1-12}$ alkoxy, 3-10 membered saturated or unsaturated carbocyclyl, 3-10 membered saturated or unsaturated heterocyclyl can be unsubstituted or mono- or multi-substituted by $C_{1-12}$ alkyl, wherein, $R^a$ and $R^b$ are each independently selected from hydrogen or $C_{1-12}$ alkyl, which can be optionally monoor independently multi-substituted by deuterium, tritium, halogen, hydroxyl, or $C_{1-12}$ alkoxy, or $R^a$ and $R^b$ taken together with the nitrogen atom to which they are bound form a 3-10 membered saturated or unsaturated heterocyclyl optionally mono- or multi-substituted by halogen, hydroxyl, or $C_{1-12}$ alkyl;

or, $R_1$ and $R_2$ taken together with the nitrogen atom to which they are bound form a 3-12 membered monocyclic or polycyclic ring optionally comprising one or more additional heteroatoms selected from N, O, and S, which can be optionally mono- or independently multi-substituted by halogen, hydroxyl, $C_{1-12}$ alkyl, $C_{1-12}$ alkoxy, $-NR^aR^b$, or $-C_{1-12}$ alkyl-$NR^aR^b$;

$R_3$ is H, $C_{1-12}$ alkyl, or $-C_{1-12}$ alkyl-$NR^aR^b$;

$R_4$ and $R_5$ are each independently $C_{1-6}$ alkyl optionally mono- or independently multi-substituted by one or more of deuterium, tritium, halogen, hydroxyl, $C_{1-12}$ alkyl, or $C_{1-12}$ alkoxy, or, $R_4$ and $R_5$ taken together with the carbon atom to which they are bound form a 3-10 membered monocyclic or polycyclic ring optionally comprising one or more heteroatoms selected from N, O, and S, which can be optionally mono- or independently multi-substituted by one or more of deuterium, tritium, halogen, hydroxyl, $C_{1-12}$ alkyl, or $C_{1-12}$ alkoxy, $R_6$ is hydrogen, or $C_{1-12}$ alkyl, which can be optionally mono- or independently multi-substituted by deuterium, tritium, halogen, hydroxyl, $C_{1-12}$ alkyl or $C_{1-12}$ alkoxy, $R_7$ is hydrogen, or $C_{1-12}$ alkyl, which can be optionally mono- or multi-substituted by deuterium, tritium, halogen, or hydroxyl, $R_8$ is hydrogen, deuterium, tritium, halogen, cyano, hydroxyl, $C_{1-12}$ alkyl, $C_{1-12}$ alkoxyl, which can be optionally mono- or independently multi-substituted by one or more of deuterium, tritium, halogen, or $C_{1-12}$ alkyl;

$R_9$ is null, hydrogen, deuterium, tritium, halogen, cyano, hydroxyl, $C_{1-12}$ alkyl, $C_{1-12}$ alkoxyl, which can be optionally mono- or independently multi-substituted by one or more of deuterium, tritium, halogen, or $C_{1-12}$ alkyl;

n is 0, 1, 2, 3, or 4;

each R is independently hydrogen, deuterium, tritium, halogen, cyano, hydroxyl, $C_{1-12}$ alkyl, $C_{1-12}$ alkoxy, 3-10 membered saturated or unsaturated carbocyclyl, or 3-10 membered saturated or unsaturated heterocyclyl which is fused with the ring to which it is bound, which can be optionally mono- or independently multi-substituted by one or more of deuterium, tritium, halogen, or $C_{1-12}$ alkyl.

In some embodiments, one of $A_2$, $A_3$, $A_4$ and $A_5$ in Formula (I), Formula (Ia) or Formula (Ib) is N and the rest are each independently $CR_9$. In some embodiments, $A_2$, $A_3$, $A_4$ and $A_5$ in Formula (I), Formula (Ia) or Formula (Ib) are each independently $CR_9$. In some embodiment, when $A_2$, $A_3$, $A_4$ or $A_5$ in Formula (I), Formula (Ia) or Formula (Ib) is $CR_9$ which is further substituted by R, $R_9$ is null.

In some embodiments, n is 2, $A_2$ and $A_5$ are CH, $A_3$ and $A_4$ are each independently CH which is further substituted by R, R is independently halogen.

In some embodiments, $R_1$ and $R_2$ in Formula (I), Formula (Ia) or Formula (Ib) are each independently substituted or unsubstituted $C_{1-12}$ alkyl which can be optionally mono- or independently multi-substituted by one or more of halogen, hydroxyl, $-NR^aR^b$, $C_{1-12}$ alkyl, $C_{1-12}$ alkoxy, 3-10 membered saturated or unsaturated carbocyclyl, 3-10 membered saturated or unsaturated heterocyclyl, wherein each of $C_{1-12}$ alkyl, $C_{1-12}$ alkoxy, 3-10 membered saturated or unsaturated carbocyclyl, 3-10 membered saturated or unsaturated heterocyclyl can be unsubstituted or mono- or multi-substituted by $C_{1-12}$ alkyl, wherein, $R^a$ and $R^b$ are each independently selected from hydrogen or $C_{1-12}$ alkyl, which can be optionally mono- or independently multi-substituted by deuterium, tritium, halogen, hydroxyl, or $C_{1-12}$ alkoxy, or $R^a$ and $R^b$ taken together with the nitrogen atom to which they are bound form a 3-10 membered saturated or unsaturated heterocyclyl optionally mono- or multi-substituted by halogen, hydroxyl, or $C_{1-12}$ alkyl.

In some embodiments, $R_1$ and $R_2$ in Formula (I), Formula (Ia) or Formula (Ib) taken together with the nitrogen atom to which they are bound form a 3-12 membered monocyclic or polycyclic ring optionally comprising one or more additional heteroatoms selected from N, O, and S, which can be optionally mono- or independently multi-substituted by halogen, hydroxyl, $C_{1-12}$ alkyl, $C_{1-12}$ alkoxy, $-NR^aR^b$, or $-C_{1-12}$ alkyl-$NR^aR^b$, wherein, $R^a$ and $R^b$ are each independently selected from hydrogen or $C_{1-12}$ alkyl, which can be optionally mono- or independently multi-substituted by deuterium, tritium, halogen, hydroxyl, or $C_{1-12}$ alkoxy, or $R^a$ and $R^b$ taken together with the nitrogen atom to which they are bound form a 3-10 membered saturated or unsaturated heterocyclyl optionally mono- or multi-substituted by halogen, hydroxyl, or $C_{1-12}$ alkyl.

In some embodiments, $R_1$ and $R_2$ in Formula (I), Formula (Ia) of Formula (Ib) are each independently selected from:

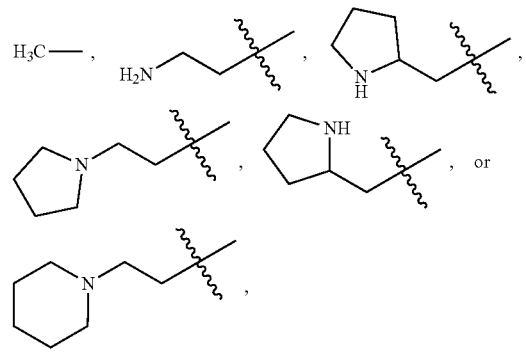

which can be optionally mono- or independently multi-substituted by deuterium, tritium, halogen, hydroxyl, $C_{1-12}$ alkoxy, or $C_{1-12}$ alkyl, wherein $C_{1-12}$ alkyl can be optionally mono- or independently multi-substituted by deuterium, tritium, halogen, or hydroxyl.

In some embodiments, $R_1$ and $R_2$ in Formula (I), Formula (Ia) of Formula (Ib) are each independently selected from:

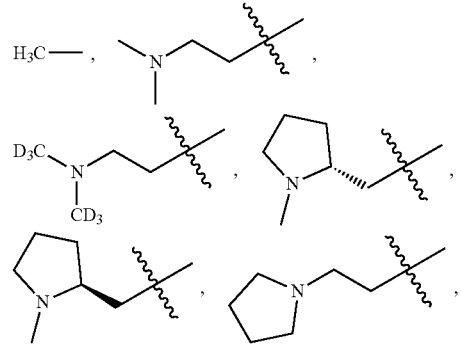

-continued

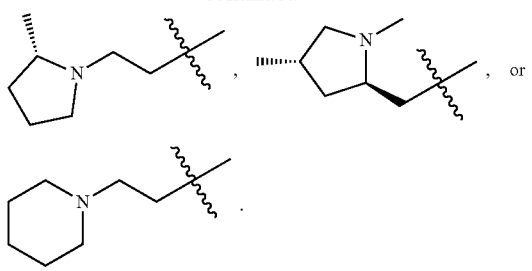

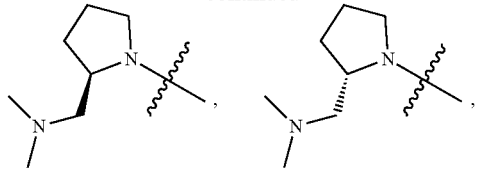

In some embodiments, $R_1$ and $R_2$ in Formula (I), Formula (Ia) of Formula (Ib) taken together with the nitrogen atom to which they are bound to form a 3-12 membered monocyclic or polycyclic ring selected from:

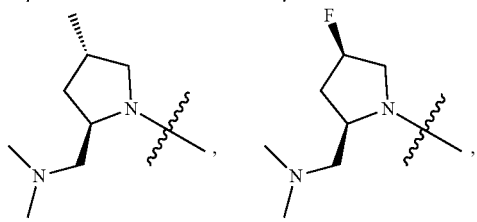

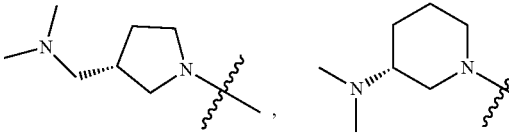

which can be optionally mono- or independently multi-substituted by halogen, hydroxyl, $C_{1-12}$ alkyl, $C_{1-12}$ alkoxy, —$NR^aR^b$, or —$C_{1-12}$ alkyl-$NR^aR^b$.

In some embodiments, $R_1$ and $R_2$ in Formula (I), Formula (Ia) of Formula (Ib) taken together with the nitrogen atom to which they are bound to form:

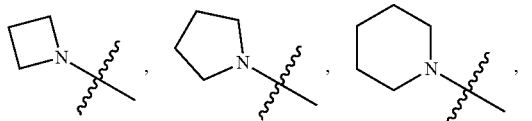

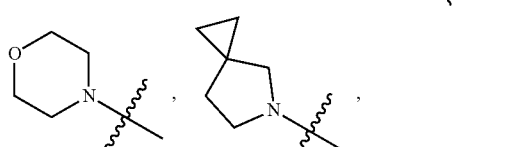

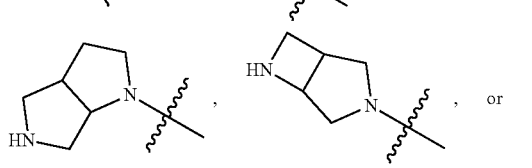

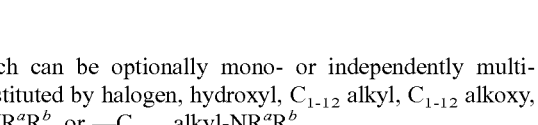

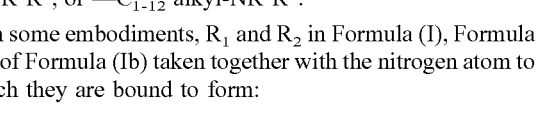

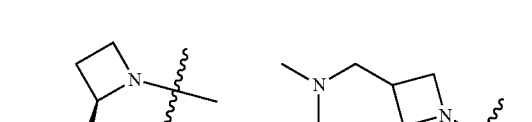

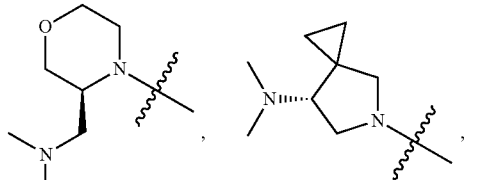

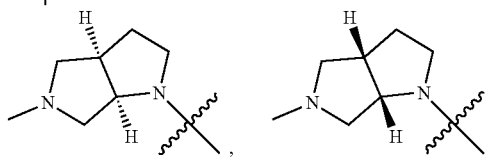

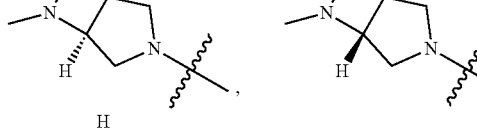

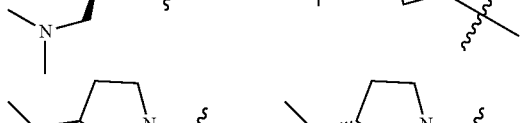

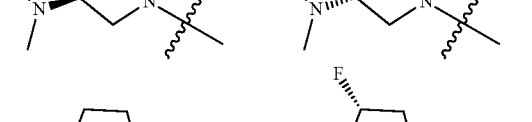

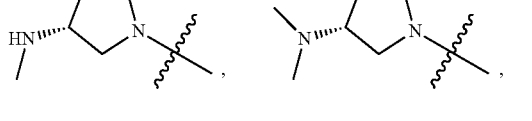

In some embodiments, $R_4$ and $R_5$ in Formula (I), Formula (Ia) or Formula (Ib) are each independently substituted or unsubstituted $C_{1-6}$ alkyl which can be optionally mono- or independently multi-substituted by one or more of deuterium, tritium, halogen, hydroxyl, $C_{1-12}$ alkyl, or $C_{1-12}$ alkoxy. In some embodiments, $R_4$ and $R_5$ in Formula (I), Formula (Ia) or Formula (Ib) are each independently unsubstituted $C_{1-6}$ alkyl.

In some embodiments, $R_4$ and $R_5$ in Formula (I), Formula (Ia) or Formula (Ib) taken together with the carbon atom to which they are bound form a 3-10 membered monocyclic or polycyclic ring optionally comprising one or more heteroatoms selected from N, O, and S, which can be optionally mono- or independently multi-substituted by one or more of deuterium, tritium, halogen, hydroxyl, $C_{1-12}$ alkyl, or $C_{1-12}$ alkoxy.

In some embodiments, $R_6$ in Formula (I), Formula (Ia) or Formula (Ib) is hydrogen, deuterium, or tritium.

In some embodiments, $R_7$ in Formula (I), Formula (Ia) or Formula (Ib) is methyl, difluoromethyl or trifluoromethyl.

Exemplary compounds 1-98 of Formula (I) are set forth in Table 1 below.

TABLE 1

Exemplary Compounds 1-98

| Compound No. | Compound Structure and Nomenclature |
|---|---|
| 1 | 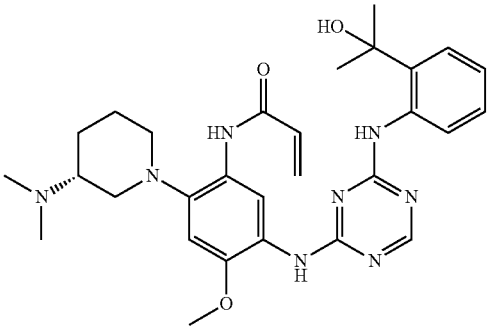 [SMILES: C=CC(=O)Nc1cc(Nc2ncnc(Nc3ccccc3C(C)(C)O)n2)c(OC)cc1N1CCC[C@@H](N(C)C)C1] (R)-N-(2-(3-(dimethylamino)piperidin-1-yl)-5-(4-(2-(2-hydroxypropan-2-yl)phenylamino)-1,3,5-triazin-2-ylamino)-4-methoxyphenyl)acrylamide |
| 2 | 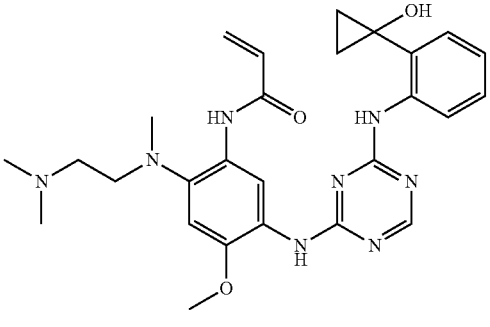 [SMILES: C=CC(=O)Nc1cc(Nc2ncnc(Nc3ccccc3C3(O)CC3)n2)c(OC)cc1N(C)CCN(C)C] N-(2-((2-(dimethylamino)ethyl)(methyl)amino)-5-(4-(2-(1-hydroxycyclopropyl)phenylamino)-1,3,5-triazin-2-ylamino)-4-methoxyphenyl)acrylamide |
| 3 | 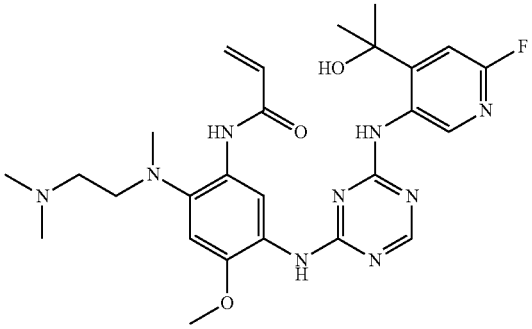 [SMILES: C=CC(=O)Nc1cc(Nc2ncnc(Nc3cnc(F)cc3C(C)(C)O)n2)c(OC)cc1N(C)CCN(C)C] N-(2-((2-(dimethylamino)ethyl)(methyl)amino)-5-(4-(6-fluoro-4-(2-hydroxypropan-2-yl)pyridin-3-ylamino)-1,3,5-triazin-2-ylamino)-4-methoxyphenyl)acrylamide |

TABLE 1-continued

Exemplary Compounds 1-98

| Compound No. | Compound Structure and Nomenclature |
|---|---|
| 4 | 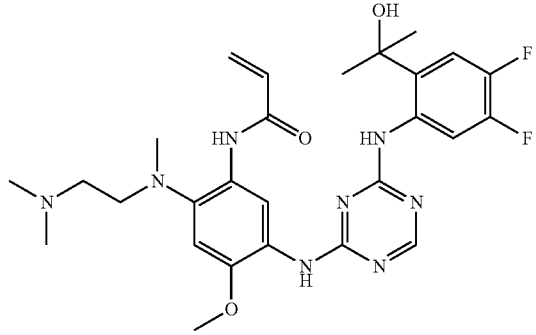 [SMILES: C=CC(=O)Nc1cc(Nc2ncnc(Nc3cc(F)c(F)cc3C(C)(C)O)n2)c(OC)cc1N(C)CCN(C)C]<br>N-(5-(4-(4,5-difluoro-2-(2-hydroxypropan-2-yl)phenylamino)-1,3,5-triazin-2-ylamino)-2-((2-(dimethylamino)ethyl)(methyl)amino)-4-methoxyphenyl)acrylamide |
| 5 | 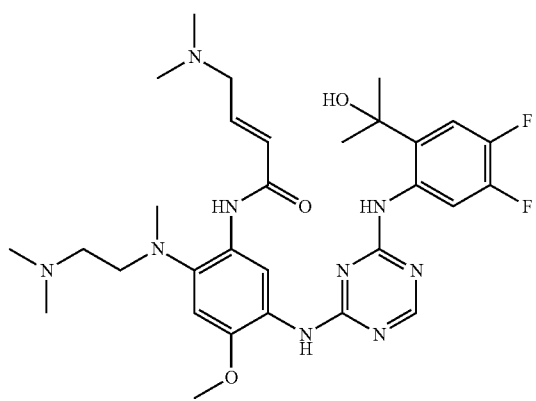 [SMILES: COc1cc(N(C)CCN(C)C)c(NC(=O)/C=C/CN(C)C)cc1Nc1ncnc(Nc2cc(F)c(F)cc2C(C)(C)O)n1]<br>(E)-N-(5-(4-(4,5-difluoro-2-(2-hydroxypropan-2-yl)phenylamino)-1,3,5-triazin-2-ylamino)-2-((2-(dimethylamino)ethyl)(methyl)amino)-4-methoxyphenyl)-4-(dimethylamino)but-2-enamide |
| 6 | 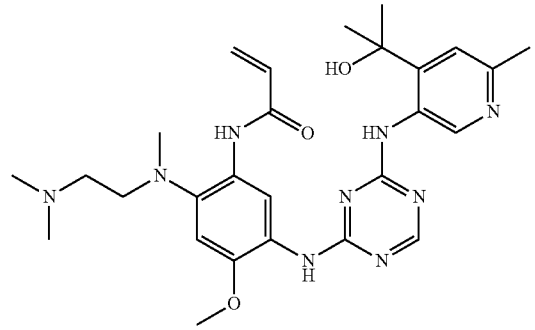<br>N-(2-((2-(dimethylamino)ethyl)(methyl)amino)-5-(4-(4-(2-hydroxypropan-2-yl)-6-methylpyridin-3-ylamino)-1,3,5-triazin-2-ylamino)-4-methoxyphenyl)acrylamide |

TABLE 1-continued

Exemplary Compounds 1-98

| Compound No. | Compound Structure and Nomenclature |
|---|---|
| 7 | 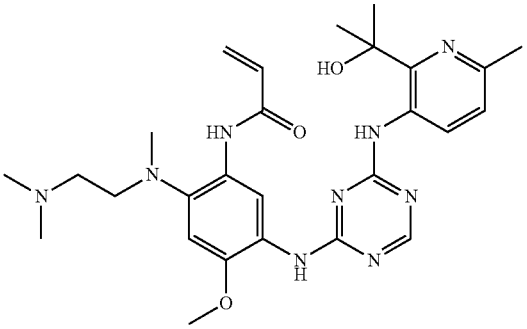<br>N-(2-((2-(dimethylamino)ethyl)(methyl)amino)-5-(4-(2-(2-hydroxypropan-2-yl)-6-methylpyridin-3-ylamino)-1,3,5-triazin-2-ylamino)-4-methoxyphenyl)acrylamide |
| 8 | 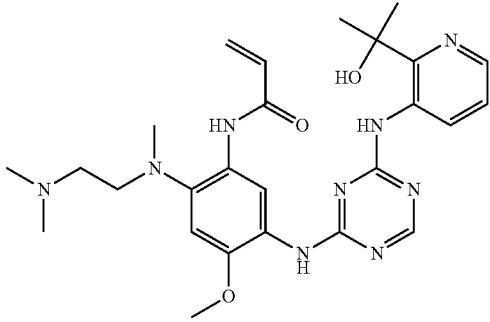 [SMILES: C=CC(=O)Nc1cc(Nc2ncnc(Nc3cccnc3C(C)(C)O)n2)c(OC)cc1N(C)CCN(C)C]<br>N-(2-((2-(dimethylamino)ethyl)(methyl)amino)-5-(4-(2-(2-hydroxypropan-2-yl)pyridin-3-ylamino)-1,3,5-triazin-2-ylamino)-4-methoxyphenyl)acrylamide |
| 9 | 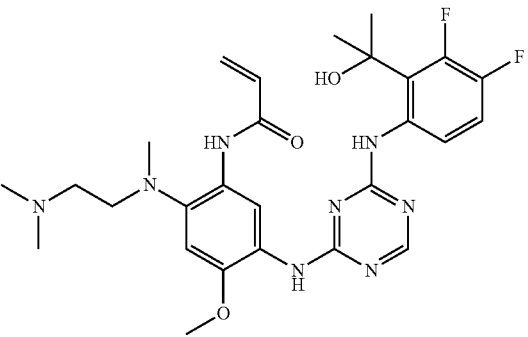 [SMILES: C=CC(=O)Nc1cc(Nc2ncnc(Nc3ccc(F)c(F)c3C(C)(C)O)n2)c(OC)cc1N(C)CCN(C)C]<br>N-(5-(4-(3,4-difluoro-2-(2-hydroxypropan-2-yl)phenylamino)-1,3,5-triazin-2-ylamino)-2-((2-(dimethylamino)ethyl)(methyl)amino)-4-methoxyphenyl)acrylamide |

TABLE 1-continued

Exemplary Compounds 1-98

| Compound No. | Compound Structure and Nomenclature |
|---|---|
| 10 | 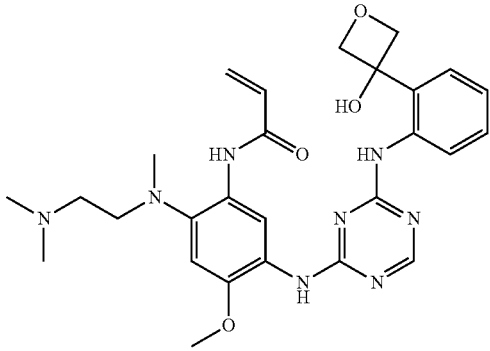 [SMILES: C=CC(=O)Nc1cc(Nc2ncnc(Nc3ccccc3C3(O)COC3)n2)c(OC)cc1N(C)CCN(C)C]<br>N-(2-((2-(dimethylamino)ethyl)(methyl)amino)-5-(4-(2-(3-hydroxyoxetan-3-yl)phenylamino)-1,3,5-triazin-2-ylamino)-4-methoxyphenyl)acrylamide |
| 11 | 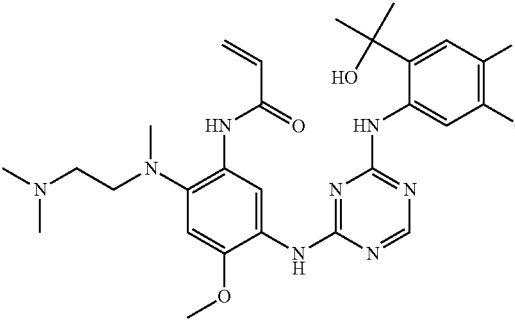<br>N-(5-(4-(5-chloro-4-fluoro-2-(2-hydroxypropan-2-yl)phenylamino)-1,3,5-triazin-2-ylamino)-2-((2-(dimethylamino)ethyl)(methyl)amino)-4-methoxyphenyl)acrylamide |
| 12 | 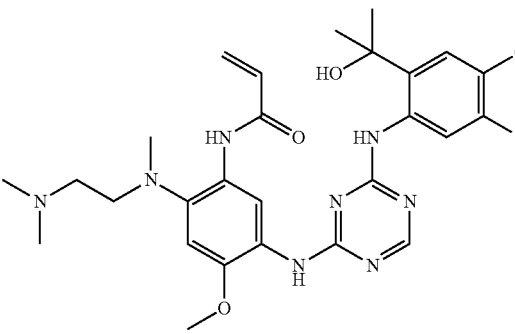<br>N-(5-(4-(4-chloro-5-fluoro-2-(2-hydroxypropan-2-yl)phenylamino)-1,3,5-triazin-2-ylamino)-2-((2-(dimethylamino)ethyl)(methyl)amino)-4-methoxyphenyl)acrylamide |

TABLE 1-continued

Exemplary Compounds 1-98

| Compound No. | Compound Structure and Nomenclature |
|---|---|
| 13 | 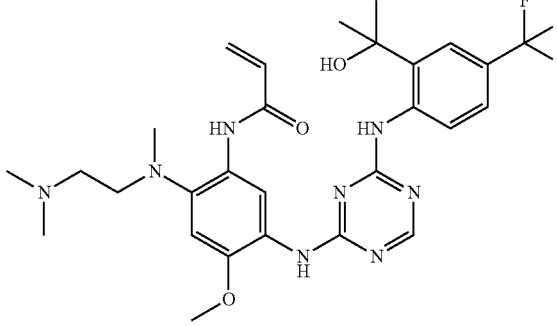<br>N-(2-((2-(dimethylamino)ethyl)(methyl)amino)-5-(4-(2-(2-hydroxypropan-2-yl)-4-(trifluoromethyl)phenylamino)-1,3,5-triazin-2-ylamino)-4-methoxyphenyl)acrylamide |
| 14 | 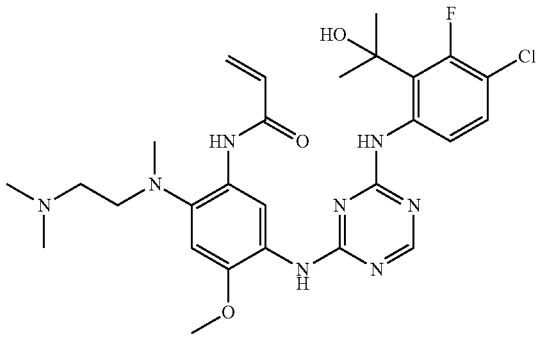 [SMILES: C=CC(=O)Nc1cc(Nc2ncnc(Nc3ccc(Cl)c(F)c3C(C)(C)O)n2)c(OC)cc1N(C)CCN(C)C]<br>N-(5-(4-(4-chloro-3-fluoro-2-(2-hydroxypropan-2-yl)phenylamino)-1,3,5-triazin-2-ylamino)-2-((2-(dimethylamino)ethyl)(methyl)amino)-4-methoxyphenyl)acrylamide |
| 15 | 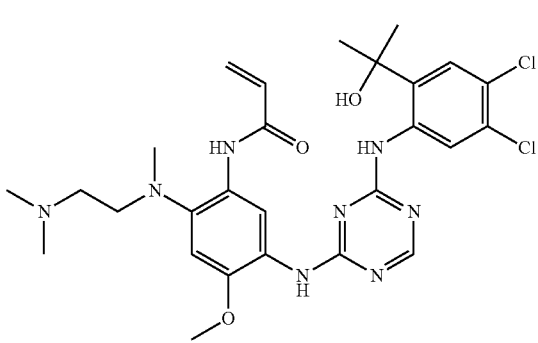 [SMILES: C=CC(=O)Nc1cc(Nc2ncnc(Nc3cc(Cl)c(Cl)cc3C(C)(C)O)n2)c(OC)cc1N(C)CCN(C)C]<br>N-(5-(4-(4,5-dichloro-2-(2-hydroxypropan-2-yl)phenylamino)-1,3,5-triazin-2-ylamino)-2-((2-(dimethylamino)ethyl)(methyl)amino)-4-methoxyphenyl)acrylamide |

TABLE 1-continued

Exemplary Compounds 1-98

| Compound No. | Compound Structure and Nomenclature |
|---|---|
| 16 | 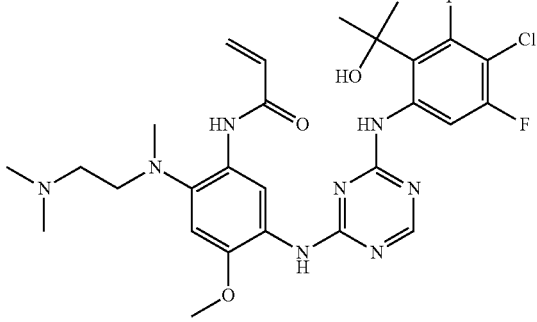
N-(5-(4-(4-chloro-3,5-difluoro-2-(2-hydroxypropan-2-yl)phenylamino)-1,3,5-triazin-2-ylamino)-2-((2-(dimethylamino)ethyl)(methyl)amino)-4-methoxyphenyl)acrylamide |
| 17 | 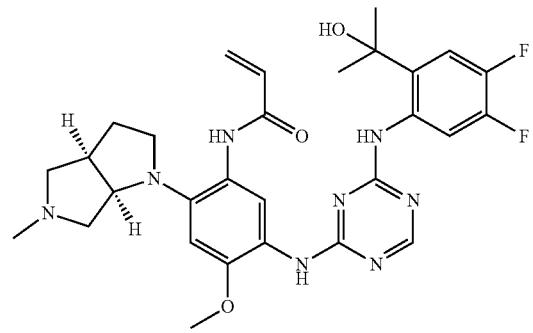 [SMILES: C=CC(=O)Nc1cc(Nc2ncnc(Nc3cc(F)c(F)cc3C(C)(C)O)n2)c(OC)cc1N1CC[C@@H]2CN(C)C[C@@H]21]
N-(5-(4-(4,5-difluoro-2-(2-hydroxypropan-2-yl)phenylamino)-1,3,5-triazin-2-ylamino)-4-methoxy-2-((3aR,6aR)-5-methylhexahydropyrrolo[3,4-b]pyrrol-1(2H)-yl)phenyl)acrylamide |
| 18 | 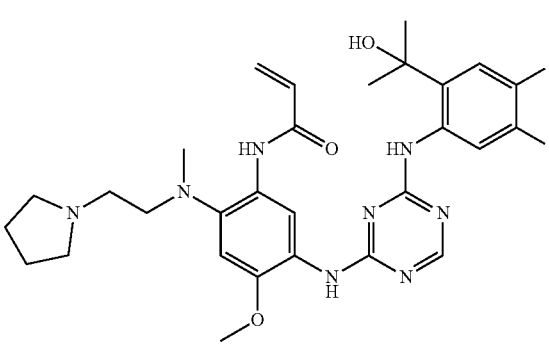
N-(5-(4-(4,5-difluoro-2-(2-hydroxypropan-2-yl)phenylamino)-1,3,5-triazin-2-ylamino)-4-methoxy-2-(methyl(2-(pyrrolidin-1-yl)ethyl)amino)phenyl)acrylamide |

TABLE 1-continued

Exemplary Compounds 1-98

| Compound No. | Compound Structure and Nomenclature |
|---|---|
| 19 | 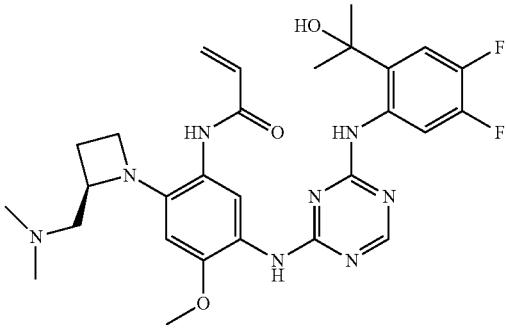 [SMILES: C=CC(=O)Nc1cc(Nc2ncnc(Nc3cc(F)c(F)cc3C(C)(C)O)n2)c(OC)cc1N1CC[C@@H]1CN(C)C]<br>(R)-N-(5-(4-(4,5-difluoro-2-(2-hydroxypropan-2-yl)phenylamino)-1,3,5-triazin-2-ylamino)-2-(2-((dimethylamino)methyl)azetidin-1-yl)-4-methoxyphenyl)acrylamide |
| 20 | 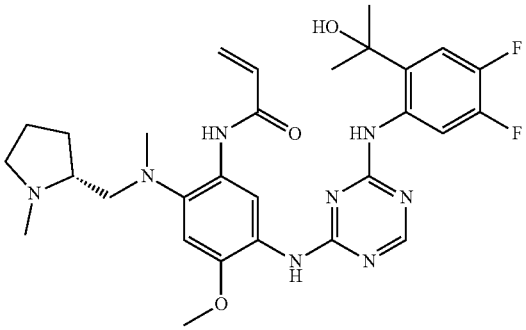 [SMILES: C=CC(=O)Nc1cc(Nc2ncnc(Nc3cc(F)c(F)cc3C(C)(C)O)n2)c(OC)cc1N(C)C[C@H]1CCCN1C]<br>(R)-N-(5-(4-(4,5-difluoro-2-(2-hydroxypropan-2-yl)phenylamino)-1,3,5-triazin-2-ylamino)-4-methoxy-2-(methyl((1-methylpyrrolidin-2-yl)methyl)amino)phenyl)acrylamide |
| 21 | 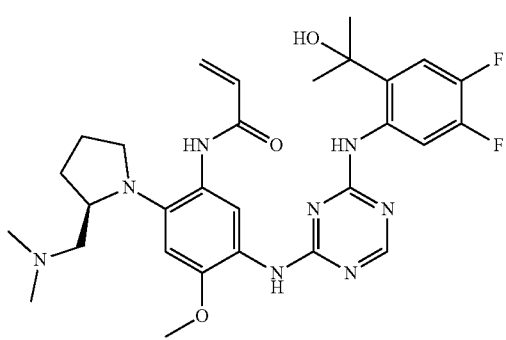 [SMILES: C=CC(=O)Nc1cc(Nc2ncnc(Nc3cc(F)c(F)cc3C(C)(C)O)n2)c(OC)cc1N1CCC[C@@H]1CN(C)C]<br>(R)-N-(5-(4-(4,5-difluoro-2-(2-hydroxypropan-2-yl)phenylamino)-1,3,5-triazin-2-ylamino)-2-(2-((dimethylamino)methyl)pyrrolidin-1-yl)-4-methoxyphenyl)acrylamide |

TABLE 1-continued

Exemplary Compounds 1-98

| Compound No. | Compound Structure and Nomenclature |
|---|---|
| 22 | 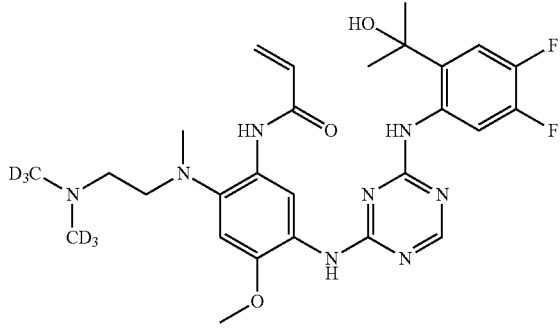 [SMILES: [2H]C([2H])([2H])N(CCN(C)c1cc(OC)c(Nc2ncnc(Nc3cc(F)c(F)cc3C(C)(C)O)n2)cc1NC(=O)C=C)C([2H])([2H])[2H]]<br>N-(2-((2-(bis(methyl-d₃)amino)ethyl)(methyl)amino)-5-((4-((4,5-difluoro-2-(2-hydroxypropan-2-yl)phenyl)amino)-1,3,5-triazin-2-yl)amino)-4-methoxyphenyl)acrylamide |
| 23 | 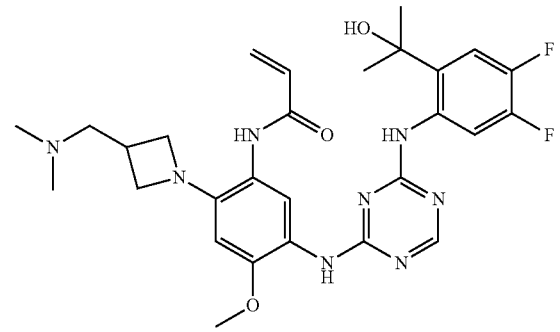 [SMILES: C=CC(=O)Nc1cc(Nc2ncnc(Nc3cc(F)c(F)cc3C(C)(C)O)n2)c(OC)cc1N1CC(CN(C)C)C1]<br>N-(5-(4-(4,5-difluoro-2-(2-hydroxypropan-2-yl)phenylamino)-1,3,5-triazin-2-ylamino)-2-(3-((dimethylamino)methyl)azetidin-1-yl)-4-methoxyphenyl)acrylamide |
| 24 | 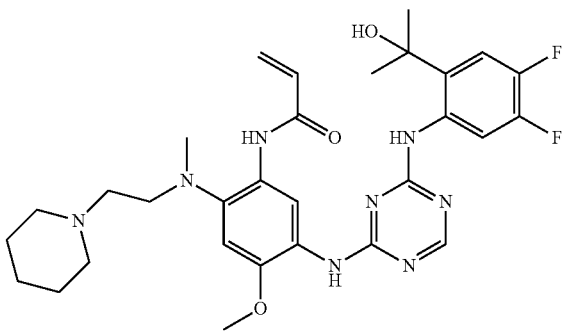 [SMILES: C=CC(=O)Nc1cc(Nc2ncnc(Nc3cc(F)c(F)cc3C(C)(C)O)n2)c(OC)cc1N(C)CCN1CCCCC1]<br>N-(5-(4-(4,5-difluoro-2-(2-hydroxypropan-2-yl)phenylamino)-1,3,5-triazin-2-ylamino)-4-methoxy-2-(methyl(2-(piperidin-1-yl)ethyl)amino)phenyl)acrylamide |

TABLE 1-continued

Exemplary Compounds 1-98

| Compound No. | Compound Structure and Nomenclature |
|---|---|
| 25 | 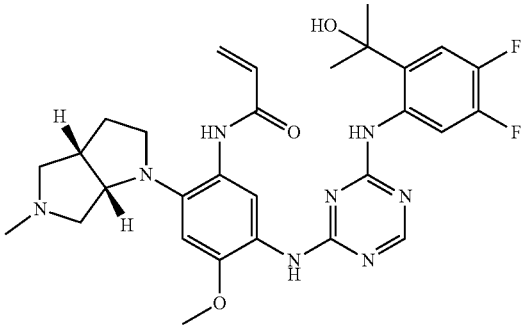 [SMILES: C=CC(=O)Nc1cc(Nc2ncnc(Nc3cc(F)c(F)cc3C(C)(C)O)n2)c(OC)cc1N1CC[C@H]2CN(C)C[C@H]21]

N-(5-(4-(4,5-difluoro-2-(2-hydroxypropan-2-yl)phenylamino)-1,3,5-triazin-2-ylamino)-4-methoxy-2-((3aS,6aS)-5-methylhexahydropyrrolo[3,4-b]pyrrol-1(2H)-yl)phenyl)acrylamide |
| 26 | 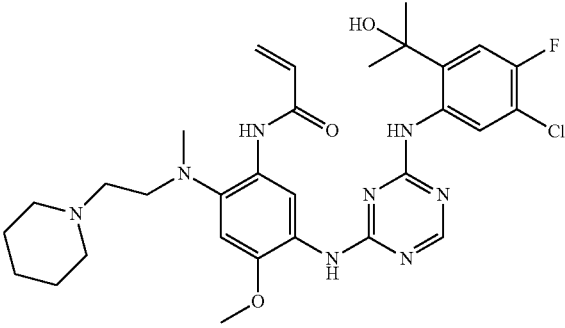 [SMILES: C=CC(=O)Nc1cc(Nc2ncnc(Nc3cc(Cl)c(F)cc3C(C)(C)O)n2)c(OC)cc1N(C)CCN1CCCCC1]

N-(5-(4-(5-chloro-4-fluoro-2-(2-hydroxypropan-2-yl)phenylamino)-1,3,5-triazin-2-ylamino)-4-methoxy-2-(methyl(2-(piperidin-1-yl)ethyl)amino)phenyl)acrylamide |
| 27 | 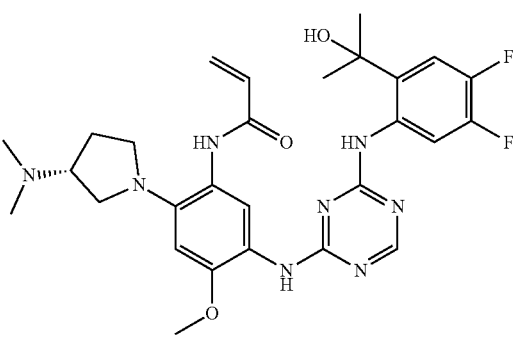 [SMILES: C=CC(=O)Nc1cc(Nc2ncnc(Nc3cc(F)c(F)cc3C(C)(C)O)n2)c(OC)cc1N1CC[C@@H](N(C)C)C1]

(R)-N-(5-(4-(4,5-difluoro-2-(2-hydroxypropan-2-yl)phenylamino)-1,3,5-triazin-2-ylamino)-2-(3-(dimethylamino)pyrrolidin-1-yl)-4-methoxyphenyl)acrylamide |

TABLE 1-continued

Exemplary Compounds 1-98

| Compound No. | Compound Structure and Nomenclature |
|---|---|
| 28 | 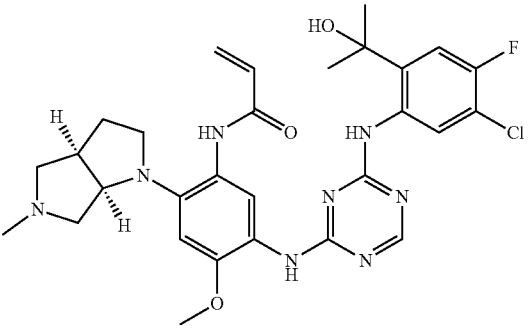 [SMILES: C=CC(=O)Nc1cc(Nc2ncnc(Nc3cc(Cl)c(F)cc3C(C)(C)O)n2)c(OC)cc1N1CC[C@@H]2CN(C)C[C@@H]21]<br>N-(5-(4-(5-chloro-4-fluoro-2-(2-hydroxypropan-2-yl)phenylamino)-1,3,5-triazin-2-ylamino)-4-methoxy-2-((3aR,6aR)-5-methylhexahydropyrrolo[3,4-b]pyrrol-1(2H)-yl)phenyl)acrylamide |
| 29 | 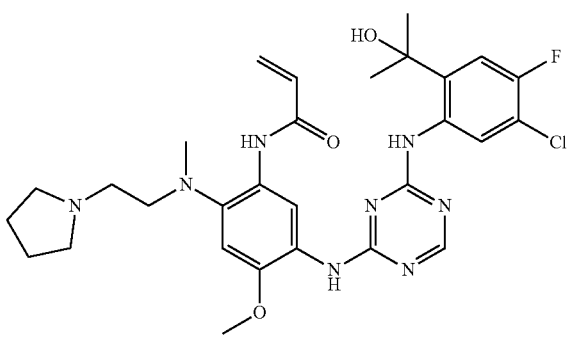 [SMILES: C=CC(=O)Nc1cc(Nc2ncnc(Nc3cc(Cl)c(F)cc3C(C)(C)O)n2)c(OC)cc1N(C)CCN1CCCC1]<br>N-(5-(4-(5-chloro-4-fluoro-2-(2-hydroxypropan-2-yl)phenylamino)-1,3,5-triazin-2-ylamino)-4-methoxy-2-(methyl(2-(pyrrolidin-1-yl)ethyl)amino)phenyl)acrylamide |
| 30 | 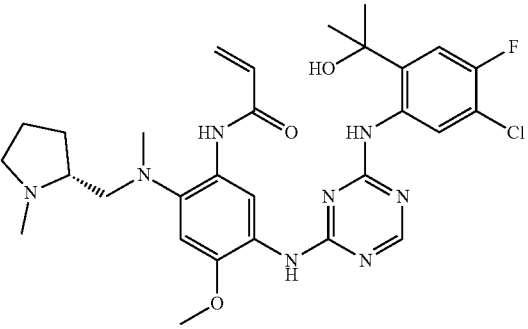 [SMILES: C=CC(=O)Nc1cc(Nc2ncnc(Nc3cc(Cl)c(F)cc3C(C)(C)O)n2)c(OC)cc1N(C)C[C@H]1CCCN1C]<br>(R)-N-(5-(4-(5-chloro-4-fluoro-2-(2-hydroxypropan-2-yl)phenylamino)-1,3,5-triazin-2-ylamino)-4-methoxy-2-(methyl((1-methylpyrrolidin-2-yl)methyl)amino)phenyl)acrylamide |

TABLE 1-continued

Exemplary Compounds 1-98

| Compound No. | Compound Structure and Nomenclature |
|---|---|
| 31 | 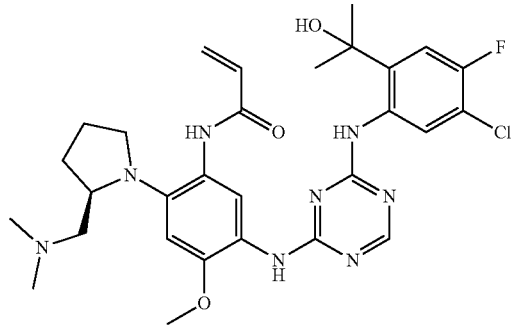 [SMILES: C=CC(=O)Nc1cc(Nc2ncnc(Nc3cc(Cl)c(F)cc3C(C)(C)O)n2)c(OC)cc1N1CCC[C@@H]1CN(C)C]
(R)-N-(5-(4-(5-chloro-4-fluoro-2-(2-hydroxypropan-2-yl)phenylamino)-1,3,5-triazin-2-ylamino)-2-(2-(((dimethylamino)methyl)pyrrolidin-1-yl)-4-methoxyphenyl)acrylamide |
| 32 | 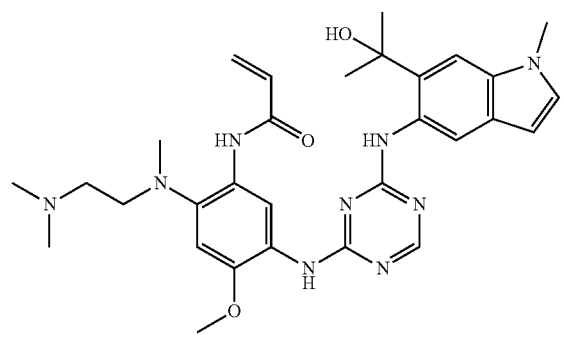 [SMILES: C=CC(=O)Nc1cc(Nc2ncnc(Nc3cc4ccn(C)c4cc3C(C)(C)O)n2)c(OC)cc1N(C)CCN(C)C]
N-(2-((2-(dimethylamino)ethyl)(methyl)amino)-5-(4-(6-(2-hydroxypropan-2-yl)-1-methyl-1H-indol-5-ylamino)-1,3,5-triazin-2-ylamino)-4-methoxyphenyl)acrylamide |
| 33 | 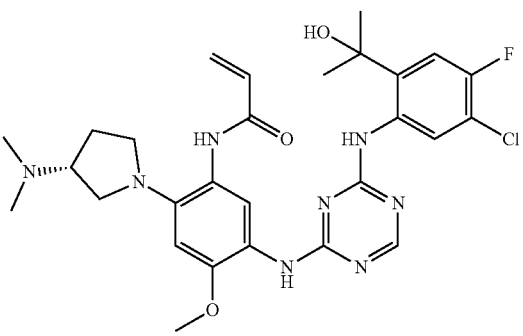 [SMILES: C=CC(=O)Nc1cc(Nc2ncnc(Nc3cc(Cl)c(F)cc3C(C)(C)O)n2)c(OC)cc1N1CC[C@@H](N(C)C)C1]
(R)-N-(5-(4-(5-chloro-4-fluoro-2-(2-hydroxypropan-2-yl)phenylamino)-1,3,5-triazin-2-ylamino)-2-(3-(dimethylamino)pyrrolidin-1-yl)-4-methoxyphenyl)acrylamide |

TABLE 1-continued

Exemplary Compounds 1-98

| Compound No. | Compound Structure and Nomenclature |
|---|---|
| 34 | 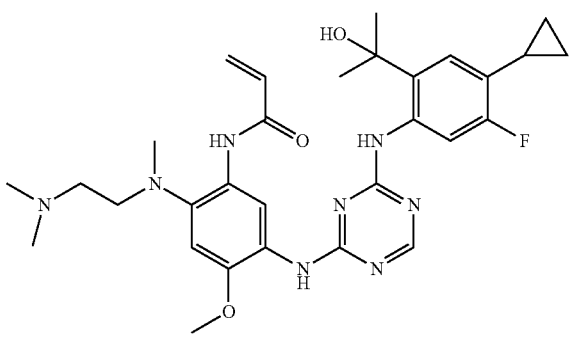 [SMILES: C=CC(=O)Nc1cc(Nc2ncnc(Nc3cc(F)c(C4CC4)cc3C(C)(C)O)n2)c(OC)cc1N(C)CCN(C)C]<br>N-(5-(4-(4-cyclopropyl-5-fluoro-2-(2-hydroxypropan-2-yl)phenylamino)-1,3,5-triazin-2-ylamino)-2-((2-(dimethylamino)ethyl)(methyl)amino)-4-methoxyphenyl)acrylamide |
| 35 | 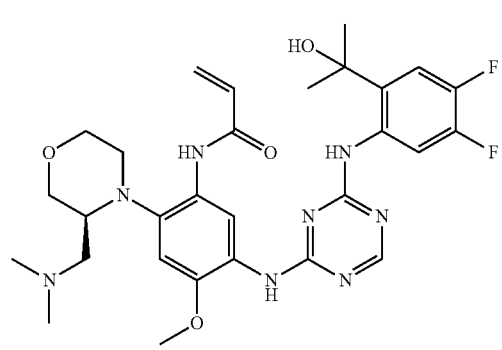 [SMILES: C=CC(=O)Nc1cc(Nc2ncnc(Nc3cc(F)c(F)cc3C(C)(C)O)n2)c(OC)cc1N1CCOC[C@@H]1CN(C)C]<br>(S)-N-(5-(4-(4,5-difluoro-2-(2-hydroxypropan-2-yl)phenylamino)-1,3,5-triazin-2-ylamino)-2-(3-((dimethylamino)methyl)morpholino)-4-methoxyphenyl)acrylamide |
| 36 | 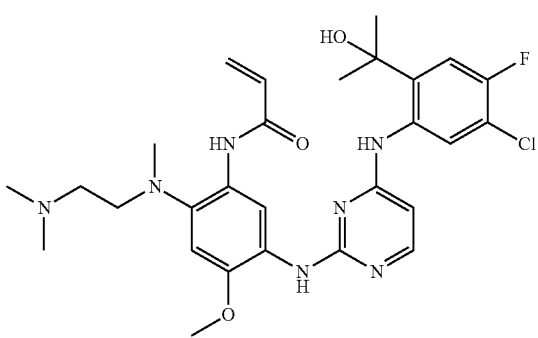 [SMILES: C=CC(=O)Nc1cc(Nc2nccc(Nc3cc(Cl)c(F)cc3C(C)(C)O)n2)c(OC)cc1N(C)CCN(C)C]<br>(N-(5-(4-(5-chloro-4-fluoro-2-(2-hydroxypropan-2-yl)phenylamino)pyrimidin-2-ylamino)-2-((2-(dimethylamino)ethyl)(methyl)amino)-4-methoxyphenyl)acrylamide) |

TABLE 1-continued

Exemplary Compounds 1-98

| Compound No. | Compound Structure and Nomenclature |
|---|---|
| 37 | 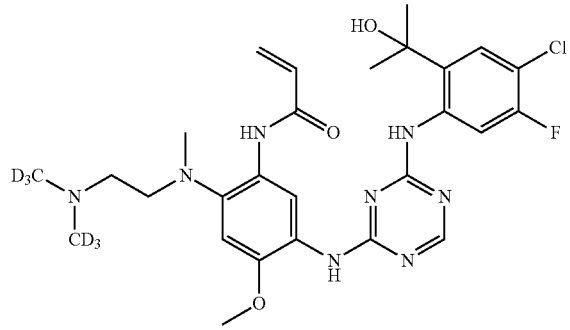 [SMILES: [2H]C([2H])([2H])N(CCN(C)c1cc(OC)c(Nc2ncnc(Nc3cc(F)c(Cl)cc3C(C)(C)O)n2)cc1NC(=O)C=C)C([2H])([2H])[2H]]<br>N-(2-((2-(bis(methyl-d$_3$)amino)ethyl)(methyl)amino)-5-((4-((4-chloro-5-fluoro-2-(2-hydroxypropan-2-yl)phenyl)amino)-1,3,5-triazin-2-yl)amino)-4-methoxyphenyl)acrylamide |
| 38 | 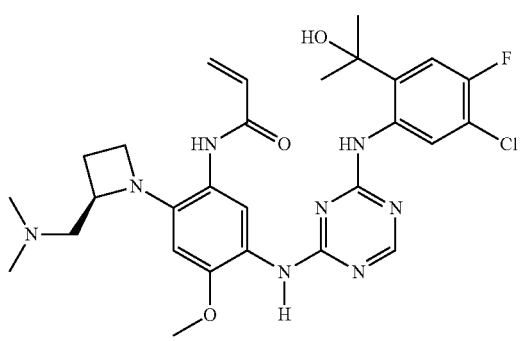 [SMILES: C=CC(=O)Nc1cc(Nc2ncnc(Nc3cc(Cl)c(F)cc3C(C)(C)O)n2)c(OC)cc1N1CC[C@@H]1CN(C)C]<br>(R)-N-(5-(4-(5-chloro-4-fluoro-2-(2-hydroxypropan-2-yl)phenylamino)-1,3,5-triazin-2-ylamino)-2-(2-((dimethylamino)methyl)azetidin-1-yl)-4-methoxyphenyl)acrylamide |
| 39 | 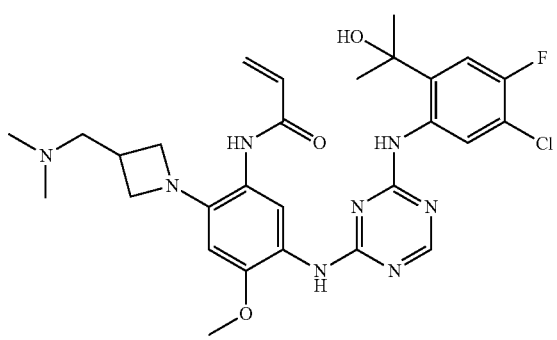 [SMILES: C=CC(=O)Nc1cc(Nc2ncnc(Nc3cc(Cl)c(F)cc3C(C)(C)O)n2)c(OC)cc1N1CC(CN(C)C)C1]<br>N-(5-(4-(5-chloro-4-fluoro-2-(2-hydroxypropan-2-yl)phenylamino)-1,3,5-triazin-2-ylamino)-2-(3-((dimethylamino)methyl)azetidin-1-yl)-4-methoxyphenyl)acrylamide |

TABLE 1-continued

Exemplary Compounds 1-98

| Compound No. | Compound Structure and Nomenclature |
|---|---|
| 40 | 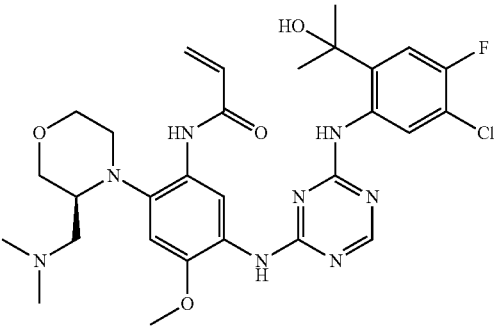 [SMILES: C=CC(=O)Nc1cc(Nc2ncnc(Nc3cc(Cl)c(F)cc3C(C)(C)O)n2)c(OC)cc1N1CCOC[C@@H]1CN(C)C]<br>(S)-N-(5-(4-(5-chloro-4-fluoro-2-(2-hydroxypropan-2-yl)phenylamino)-1,3,5-triazin-2-ylamino)-2-(3-((dimethylamino)methyl)morpholino)-4-methoxyphenyl)acrylamide |
| 41 | 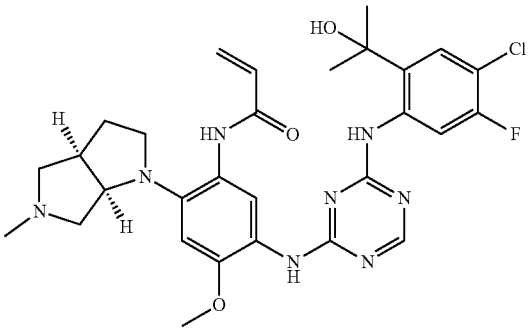 [SMILES: C=CC(=O)Nc1cc(Nc2ncnc(Nc3cc(F)c(Cl)cc3C(C)(C)O)n2)c(OC)cc1N1CC[C@@H]2CN(C)C[C@@H]21]<br>N-(5-(4-(4-chloro-5-fluoro-2-(2-hydroxypropan-2-yl)phenylamino)-1,3,5-triazin-2-ylamino)-4-methoxy-2-((3aR,6aR)-5-methylhexahydropyrrolo[3,4-b]pyrrol-1(2H)-yl)phenyl)acrylamide |
| 42 | 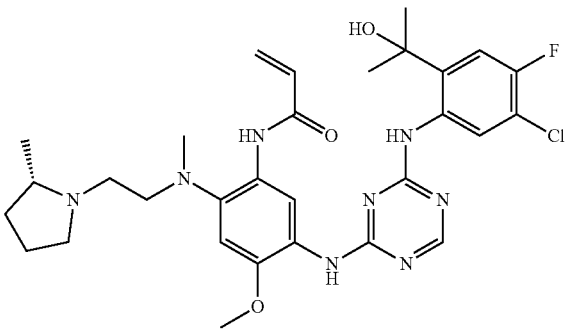 [SMILES: C=CC(=O)Nc1cc(Nc2ncnc(Nc3cc(Cl)c(F)cc3C(C)(C)O)n2)c(OC)cc1N(C)CCN1CCC[C@@H]1C]<br>(S)-N-(5-(4-(5-chloro-4-fluoro-2-(2-hydroxypropan-2-yl)phenylamino)-1,3,5-triazin-2-ylamino)-4-methoxy-2-(methyl(2-(2-methylpyrrolidin-1-yl)ethyl)amino)phenyl)acrylamide |

TABLE 1-continued

Exemplary Compounds 1-98

| Compound No. | Compound Structure and Nomenclature |
|---|---|
| 43 | 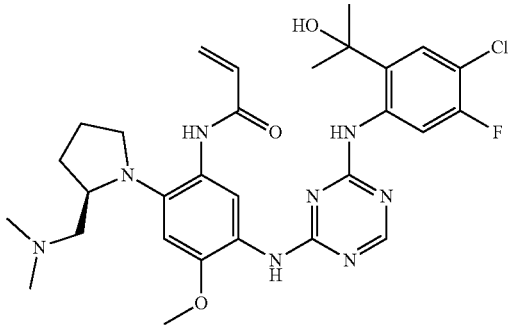 [SMILES: C=CC(=O)Nc1cc(Nc2ncnc(Nc3cc(F)c(Cl)cc3C(C)(C)O)n2)c(OC)cc1N1CCC[C@@H]1CN(C)C]<br>(R)-N-(5-(4-(4-chloro-5-fluoro-2-(2-hydroxypropan-2-yl)phenylamino)-1,3,5-triazin-2-ylamino)-2-(2-(((dimethylamino)methyl)pyrrolidin-1-yl)-4-methoxyphenyl)acrylamid |
| 44 | 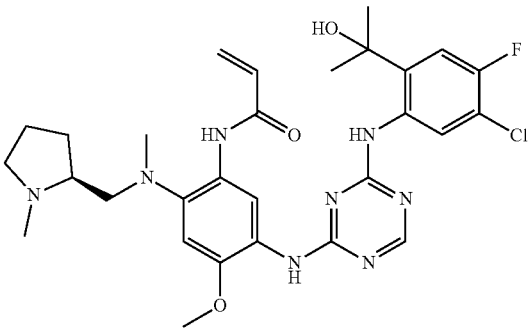 [SMILES: C=CC(=O)Nc1cc(Nc2ncnc(Nc3cc(Cl)c(F)cc3C(C)(C)O)n2)c(OC)cc1N(C)C[C@@H]1CCCN1C]<br>(S)-N-(5-(4-(5-chloro-4-fluoro-2-(2-hydroxypropan-2-yl)phenylamino)-1,3,5-triazin-2-ylamino)-4-methoxy-2-(methyl((1-methylpyrrolidin-2-yl)methyl)amino)phenyl)acrylamide |
| 45 | 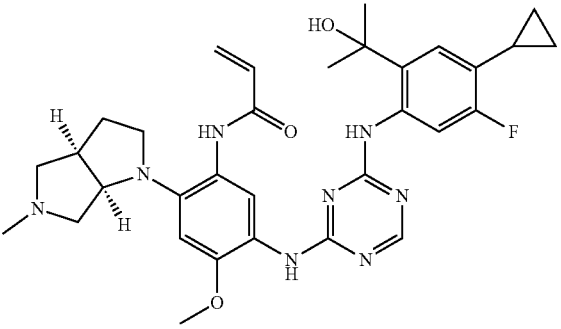 [SMILES: C=CC(=O)Nc1cc(Nc2ncnc(Nc3cc(F)c(C4CC4)cc3C(C)(C)O)n2)c(OC)cc1N1CC[C@@H]2CN(C)C[C@@H]21]<br>N-(5-(4-(4-cyclopropyl-5-fluoro-2-(2-hydroxypropan-2-yl)phenylamino)-1,3,5-triazin-2-ylamino)-4-methoxy-2-((3aR,6aR)-5-methylhexahydropyrrolo[3,4-b]pyrrol-1(2H)-yl)phenyl)acrylamide |

TABLE 1-continued

Exemplary Compounds 1-98

| Compound No. | Compound Structure and Nomenclature |
|---|---|
| 46 | 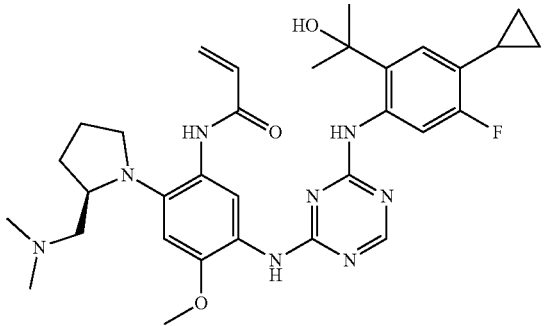 [SMILES: C=CC(=O)Nc1cc(Nc2ncnc(Nc3cc(F)c(C4CC4)cc3C(C)(C)O)n2)c(OC)cc1N1CCC[C@@H]1CN(C)C]<br>(R)-N-(5-(4-(4-cyclopropyl-5-fluoro-2-(2-hydroxypropan-2-yl)phenylamino)-1,3,5-triazin-2-ylamino)-2-(2-((dimethylamino)methyl)pyrrolidin-1-yl)-4-methoxyphenyl)acrylamide |
| 47 | 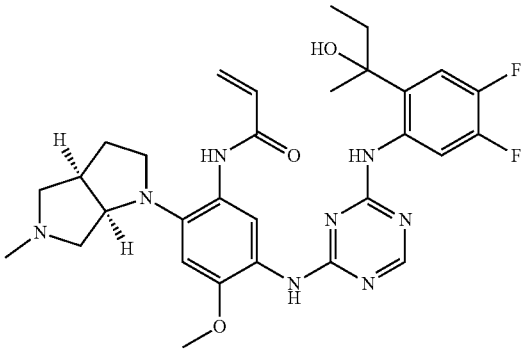 [SMILES: C=CC(=O)Nc1cc(Nc2ncnc(Nc3cc(F)c(F)cc3C(C)(O)CC)n2)c(OC)cc1N1CC[C@@H]2CN(C)C[C@@H]21]<br>N-(5-(4-(4,5-difluoro-2-(2-hydroxybutan-2-yl)phenylamino)-1,3,5-triazin-2-ylamino)-4-methoxy-2-((3aR,6aR)-5-methylhexahydropyrrolo[3,4-b]pyrrol-1(2H)-yl)phenyl)acrylamide |
| 48 | 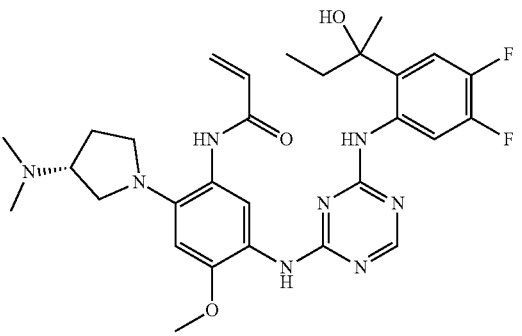 [SMILES: C=CC(=O)Nc1cc(Nc2ncnc(Nc3cc(F)c(F)cc3C(C)(O)CC)n2)c(OC)cc1N1CC[C@@H](N(C)C)C1]<br>N-(5-(4-(4,5-difluoro-2-(2-hydroxybutan-2-yl)phenylamino)-1,3,5-triazin-2-ylamino)-2-((R)-3-(dimethylamino)pyrrolidin-1-yl)-4-methoxyphenyl)acrylamide |

TABLE 1-continued

Exemplary Compounds 1-98

| Compound No. | Compound Structure and Nomenclature |
|---|---|
| 49 | 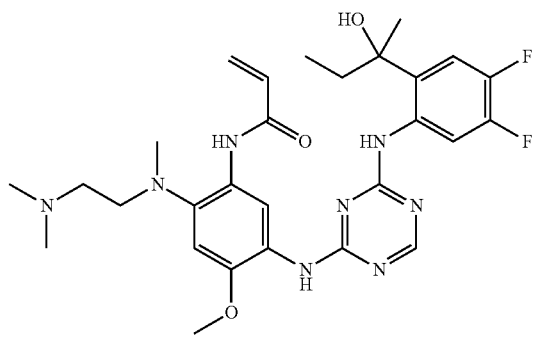 [SMILES: C=CC(=O)Nc1cc(Nc2ncnc(Nc3cc(F)c(F)cc3C(C)(O)CC)n2)c(OC)cc1N(C)CCN(C)C]<br>N-(5-(4-(4,5-difluoro-2-(2-hydroxybutan-2-yl)phenylamino)-1,3,5-triazin-2-ylamino)-2-((2-(dimethylamino)ethyl)(methyl)amino)-4-methoxyphenyl)acrylamide |
| 50 | 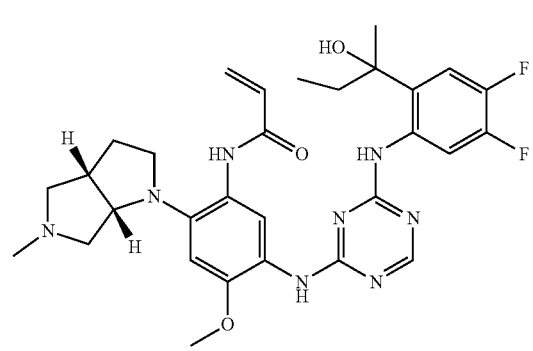 [SMILES: C=CC(=O)Nc1cc(Nc2ncnc(Nc3cc(F)c(F)cc3C(C)(O)CC)n2)c(OC)cc1N1CC[C@H]2CN(C)C[C@H]21]<br>N-(5-(4-(4,5-difluoro-2-(2-hydroxybutan-2-yl)phenylamino)-1,3,5-triazin-2-ylamino)-4-methoxy-2-((3aS,6aS)-5-methylhexahydropyrrolo[3,4-b]pyrrol-1(2H)-yl)phenyl)acrylamide |
| 51 | 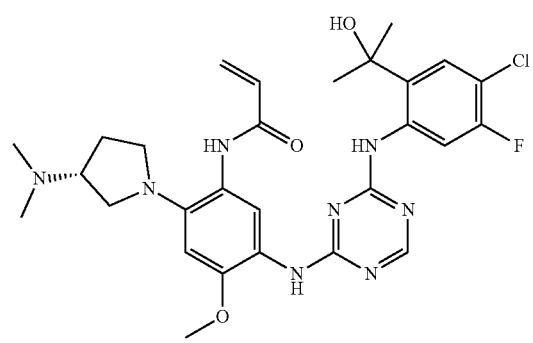 [SMILES: C=CC(=O)Nc1cc(Nc2ncnc(Nc3cc(F)c(Cl)cc3C(C)(C)O)n2)c(OC)cc1N1CC[C@@H](N(C)C)C1]<br>(R)-N-(5-(4-(4-chloro-5-fluoro-2-(2-hydroxypropan-2-yl)phenylamino)-1,3,5-triazin-2-ylamino)-2-(3-(dimethylamino)pyrrolidin-1-yl)-4-methoxyphenyl)acrylamide |

TABLE 1-continued

Exemplary Compounds 1-98

| Compound No. | Compound Structure and Nomenclature |
|---|---|
| 52 | 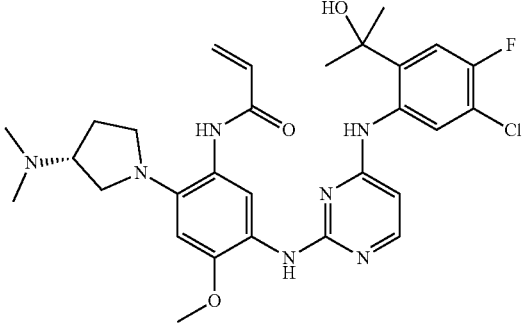 [SMILES: C=CC(=O)Nc1cc(Nc2nccc(Nc3cc(Cl)c(F)cc3C(C)(C)O)n2)c(OC)cc1N1CC[C@@H](N(C)C)C1]<br>(R)-N-(5-(4-(5-chloro-4-fluoro-2-(2-hydroxypropan-2-yl)phenylamino)pyrimidin-2-ylamino)-2-(3-(dimethylamino)pyrrolidin-1-yl)-4-methoxyphenyl)acrylamide |
| 53 | 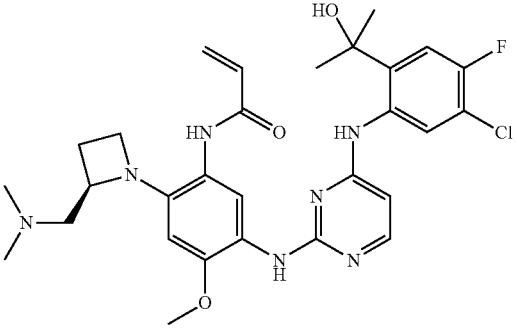 [SMILES: C=CC(=O)Nc1cc(Nc2nccc(Nc3cc(Cl)c(F)cc3C(C)(C)O)n2)c(OC)cc1N1CC[C@@H]1CN(C)C]<br>(R)-N-(5-(4-(5-chloro-4-fluoro-2-(2-hydroxypropan-2-yl)phenylamino)pyrimidin-2-ylamino)-2-(2-((dimethylamino)methyl)azetidin-1-yl)-4-methoxyphenyl)acrylamide |
| 54 | 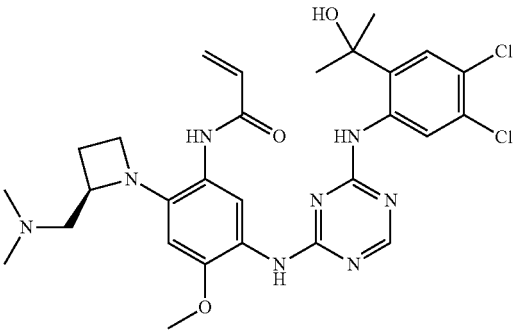<br>(R)-N-(5-(4-(4,5-dichloro-2-(2-hydroxypropan-2-yl)phenylamino)-1,3,5-triazin-2-ylamino)-2-(2-((dimethylamino)methyl)azetidin-1-yl)-4-methoxyphenyl)acrylamide |

TABLE 1-continued

Exemplary Compounds 1-98

| Compound No. | Compound Structure and Nomenclature |
| --- | --- |
| 55 | 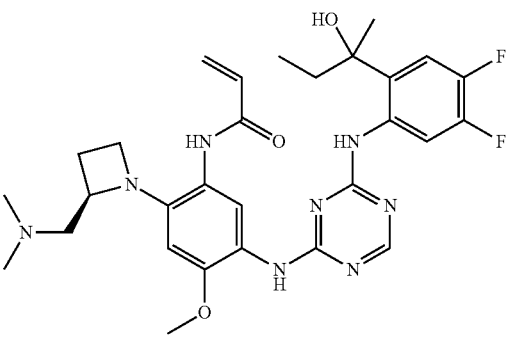 [SMILES: C=CC(=O)Nc1cc(Nc2ncnc(Nc3cc(F)c(F)cc3C(C)(O)CC)n2)c(OC)cc1N1CC[C@@H]1CN(C)C]<br>N-(5-(4-(4,5-difluoro-2-(2-hydroxybutan-2-yl)phenylamino)-1,3,5-triazin-2-ylamino)-2-((R)-2-((dimethylamino)methyl)azetidin-1-yl)-4-methoxyphenyl)acrylamide |
| 56 | 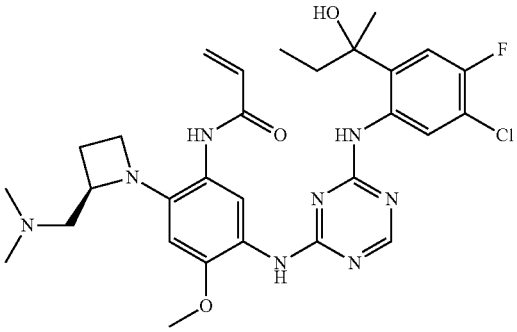 [SMILES: C=CC(=O)Nc1cc(Nc2ncnc(Nc3cc(Cl)c(F)cc3C(C)(O)CC)n2)c(OC)cc1N1CC[C@@H]1CN(C)C]<br>N-(5-(4-(5-chloro-4-fluoro-2-(2-hydroxybutan-2-yl)phenylamino)-1,3,5-triazin-2-ylamino)-2-((R)-2-((dimethylamino)methyl)azetidin-1-yl)-4-methoxyphenyl)acrylamide |
| 57 | 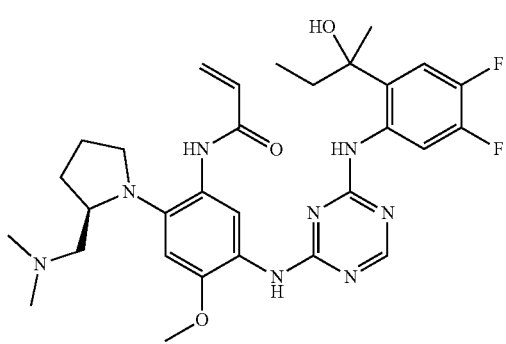 [SMILES: C=CC(=O)Nc1cc(Nc2ncnc(Nc3cc(F)c(F)cc3C(C)(O)CC)n2)c(OC)cc1N1CCC[C@@H]1CN(C)C]<br>N-(5-(4-(4,5-difluoro-2-(2-hydroxybutan-2-yl)phenylamino)-1,3,5-triazin-2-ylamino)-2-((R)-2-((dimethylamino)methyl)pyrrolidin-1-yl)-4-methoxyphenyl)acrylamide |

TABLE 1-continued

Exemplary Compounds 1-98

| Compound No. | Compound Structure and Nomenclature |
| --- | --- |
| 58 | 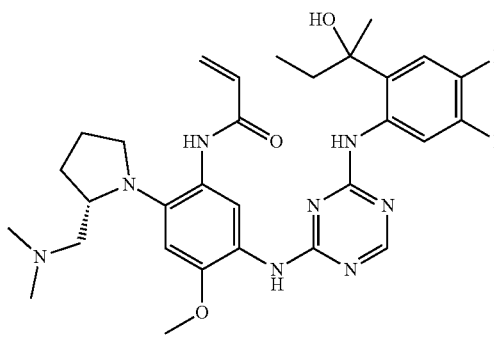<br>N-(5-(4-(4,5-difluoro-2-(2-hydroxybutan-2-yl)phenylamino)-1,3,5-triazin-2-ylamino)-2-((S)-2-((dimethylamino)methyl)pyrrolidin-1-yl)-4-methoxyphenyl)acrylamide |
| 59 | 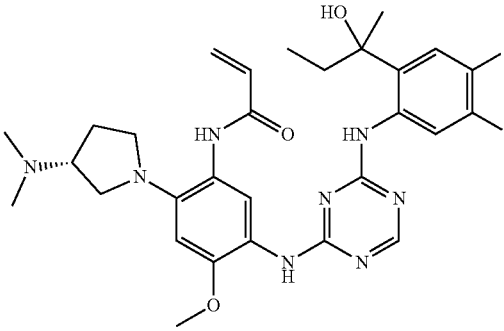<br>N-(5-(4-(5-chloro-4-fluoro-2-(2-hydroxybutan-2-yl)phenylamino)-1,3,5-triazin-2-ylamino)-2-((R)-3-(dimethylamino)pyrrolidin-1-yl)-4-methoxyphenyl)acrylamide |
| 60 | 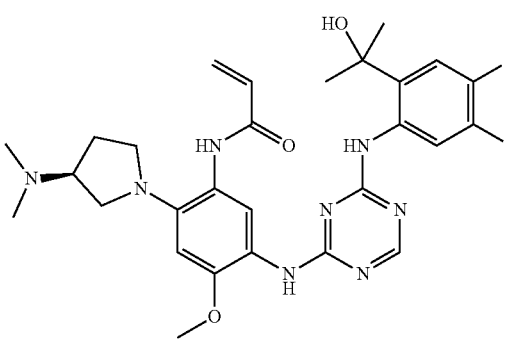<br>(S)-N-(5-(4-(5-chloro-4-fluoro-2-(2-hydroxypropan-2-yl)phenylamino)-1,3,5-triazin-2-ylamino)-2-(3-(dimethylamino)pyrrolidin-1-yl)-4-methoxyphenyl)acrylamide |

TABLE 1-continued

Exemplary Compounds 1-98

| Compound No. | Compound Structure and Nomenclature |
|---|---|
| 61 | 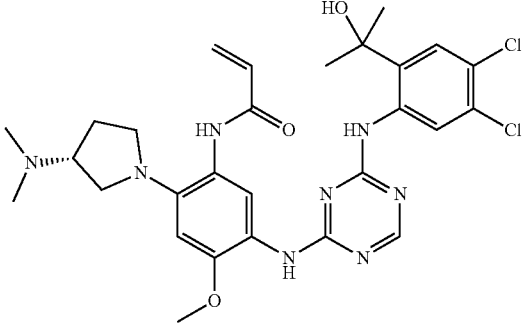 [SMILES: C=CC(=O)Nc1cc(Nc2ncnc(Nc3cc(Cl)c(Cl)cc3C(C)(C)O)n2)c(OC)cc1N1CC[C@@H](N(C)C)C1]<br>(R)-N-(5-(4-(4,5-dichloro-2-(2-hydroxypropan-2-yl)phenylamino)-1,3,5-triazin-2-ylamino)-2-(3-(dimethylamino)pyrrolidin-1-yl)-4-methoxyphenyl)acrylamide |
| 62 | 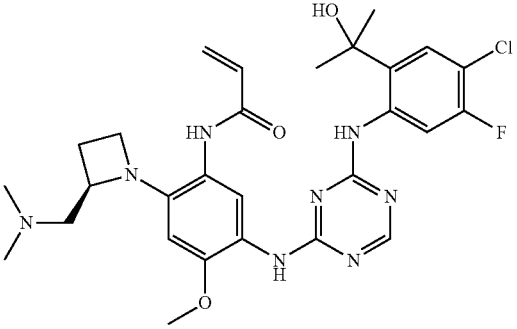 [SMILES: C=CC(=O)Nc1cc(Nc2ncnc(Nc3cc(F)c(Cl)cc3C(C)(C)O)n2)c(OC)cc1N1CC[C@@H]1CN(C)C]<br>(R)-N-(5-(4-(4-chloro-5-fluoro-2-(2-hydroxypropan-2-yl)phenylamino)-1,3,5-triazin-2-ylamino)-2-(2-((dimethylamino)methyl)azetidin-1-yl)-4-methoxyphenyl)acrylamide |
| 63 | 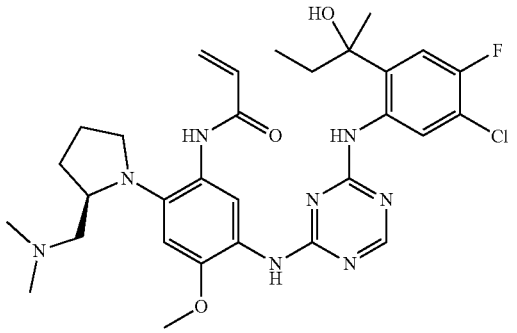 [SMILES: C=CC(=O)Nc1cc(Nc2ncnc(Nc3cc(Cl)c(F)cc3C(C)(O)CC)n2)c(OC)cc1N1CCC[C@@H]1CN(C)C]<br>N-(5-(4-(5-chloro-4-fluoro-2-(2-hydroxybutan-2-yl)phenylamino)-1,3,5-triazin-2-ylamino)-2-((R)-2-((dimethylamino)methyl)pyrrolidin-1-yl)-4-methoxyphenyl)acrylamide |

TABLE 1-continued

Exemplary Compounds 1-98

| Compound No. | Compound Structure and Nomenclature |
|---|---|
| 64 | 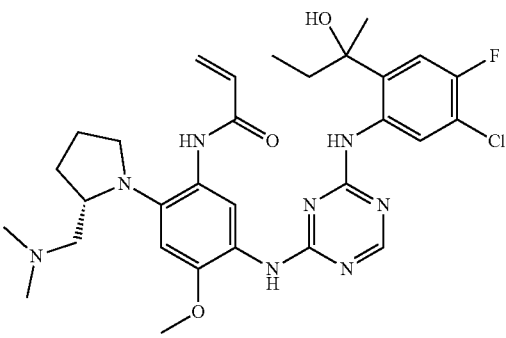 [SMILES: C=CC(=O)Nc1cc(Nc2ncnc(Nc3cc(Cl)c(F)cc3C(C)(O)CC)n2)c(OC)cc1N1CCC[C@H]1CN(C)C]<br>N-(5-(4-(5-chloro-4-fluoro-2-(2-hydroxybutan-2-yl)phenylamino)-1,3,5-triazin-2-ylamino)-2-((S)-2-((dimethylamino)methyl)pyrrolidin-1-yl)-4-methoxyphenyl)acrylamide |
| 65 | 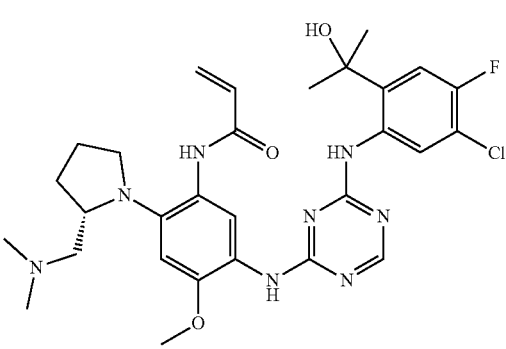 [SMILES: C=CC(=O)Nc1cc(Nc2ncnc(Nc3cc(Cl)c(F)cc3C(C)(C)O)n2)c(OC)cc1N1CCC[C@H]1CN(C)C]<br>(S)-N-(5-(4-(5-chloro-4-fluoro-2-(2-hydroxypropan-2-yl)phenylamino)-1,3,5-triazin-2-ylamino)-2-(2-((dimethylamino)methyl)pyrrolidin-1-yl)-4-methoxyphenyl)acrylamide |
| 66 | 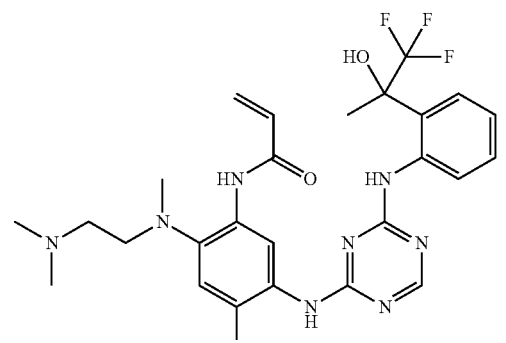<br>N-(2-((2-(dimethylamino)ethyl)(methyl)amino)-4-methoxy-5-(4-(2-(1,1,1-trifluoro-2-hydroxypropan-2-yl)phenylamino)-1,3,5-triazin-2-ylamino)phenyl)acrylamide |

TABLE 1-continued

Exemplary Compounds 1-98

| Compound No. | Compound Structure and Nomenclature |
|---|---|
| 67 | 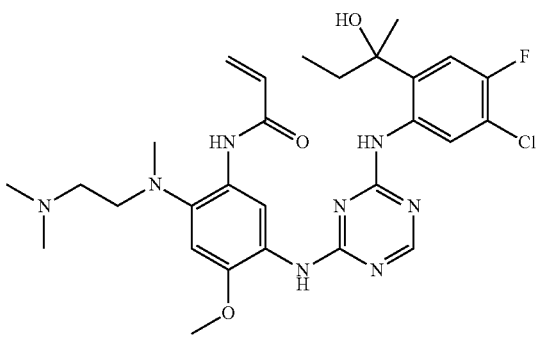 [SMILES: C=CC(=O)Nc1cc(Nc2ncnc(Nc3cc(Cl)c(F)cc3C(C)(O)CC)n2)c(OC)cc1N(C)CCN(C)C]<br>N-(5-(4-(5-chloro-4-fluoro-2-(2-hydroxybutan-2-yl)phenylamino)-1,3,5-triazin-2-ylamino)-2-((2-(dimethylamino)ethyl)(methyl)amino)-4-methoxyphenyl)acrylamide |
| 68 | 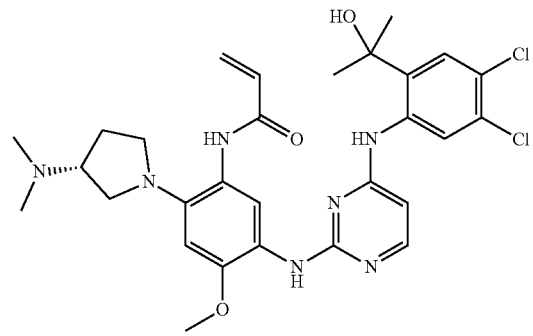 [SMILES: C=CC(=O)Nc1cc(Nc2nccc(Nc3cc(Cl)c(Cl)cc3C(C)(C)O)n2)c(OC)cc1N1CC[C@@H](N(C)C)C1]<br>(R)-N-(5-(4-(4,5-dichloro-2-(2-hydroxypropan-2-yl)phenylamino)pyrimidin-2-ylamino)-2-(3-(dimethylamino)pyrrolidin-1-yl)-4-methoxyphenyl)acrylamide |
| 69/70 | 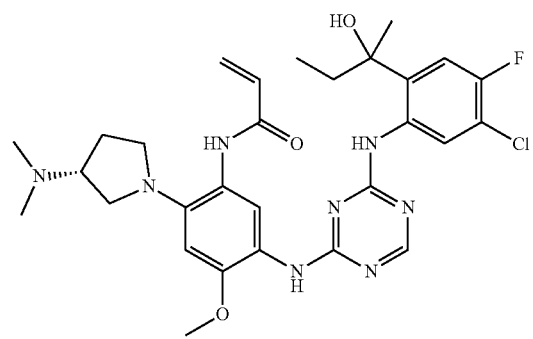 [SMILES: C=CC(=O)Nc1cc(Nc2ncnc(Nc3cc(Cl)c(F)cc3C(C)(O)CC)n2)c(OC)cc1N1CC[C@@H](N(C)C)C1]<br>N-(5-(4-(5-chloro-4-fluoro-2-((R)-2-hydroxybutan-2-yl)phenylamino)-1,3,5-triazin-2-ylamino)-2-((R)-3-(dimethylamino)pyrrolidin-1-yl)-4-methoxyphenyl)acrylamide<br>or N-(5-(4-(5-chloro-4-fluoro-2-((S)-2-hydroxybutan-2-yl)phenylamino)-1,3,5-triazin-2-ylamino)-2-((R)-3-(dimethylamino)pyrrolidin-1-yl)-4-methoxyphenyl)acrylamide |

TABLE 1-continued

Exemplary Compounds 1-98

| Compound No. | Compound Structure and Nomenclature |
|---|---|
| 71 | 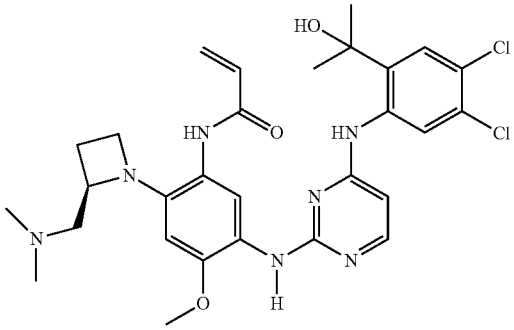 [SMILES: C=CC(=O)Nc1cc(Nc2nccc(Nc3cc(Cl)c(Cl)cc3C(C)(C)O)n2)c(OC)cc1N1CC[C@@H]1CN(C)C]<br>(R)-N-(5-(4-(4,5-dichloro-2-(2-hydroxypropan-2-yl)phenylamino)pyrimidin-2-ylamino)-2-(2-((dimethylamino)methyl)azetidin-1-yl)-4-methoxyphenyl)acrylamide |
| 72 | 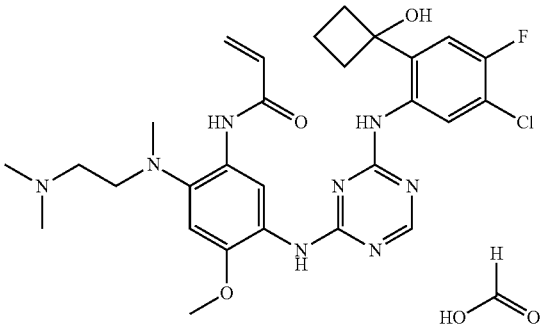 [SMILES: C=CC(=O)Nc1cc(Nc2ncnc(Nc3cc(Cl)c(F)cc3C3(O)CCC3)n2)c(OC)cc1N(C)CCN(C)C ; O=CO]<br>N-(5-(4-(5-chloro-4-fluoro-2-(1-hydroxycyclobutyl)phenylamino)-1,3,5-triazin-2-ylamino)-2-((2-(dimethylamino)ethyl)(methyl)amino)-4-methoxyphenyl)acrylamide formic acid salt |
| 73 | 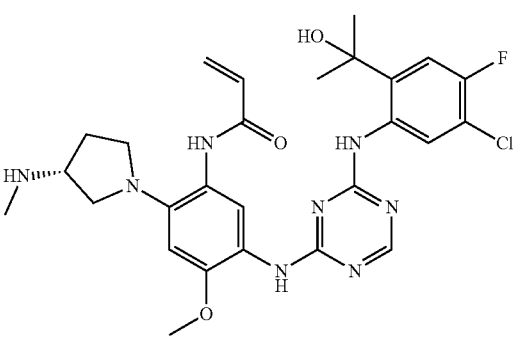 [SMILES: C=CC(=O)Nc1cc(Nc2ncnc(Nc3cc(Cl)c(F)cc3C(C)(C)O)n2)c(OC)cc1N1CC[C@@H](NC)C1]<br>(R)-N-(5-(4-(5-chloro-4-fluoro-2-(2-hydroxypropan-2-yl)phenylamino)-1,3,5-triazin-2-ylamino)-4-methoxy-2-(3-(methylamino)pyrrolidin-1-yl)phenyl)acrylamide |

TABLE 1-continued

Exemplary Compounds 1-98

| Compound No. | Compound Structure and Nomenclature |
|---|---|
| 74 | 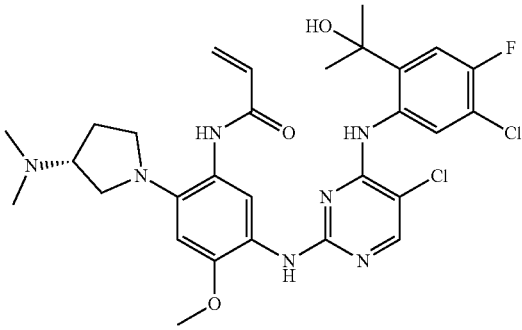 [SMILES: C=CC(=O)Nc1cc(Nc2ncc(Cl)c(Nc3cc(Cl)c(F)cc3C(C)(C)O)n2)c(OC)cc1N1CC[C@@H](N(C)C)C1]<br>(R)-N-(5-(5-chloro-4-(5-chloro-4-fluoro-2-(2-hydroxypropan-2-yl)phenylamino)pyrimidin-2-ylamino)-2-(3-(dimethylamino)pyrrolidin-1-yl)-4-methoxyphenyl)acrylamide |
| 75 | 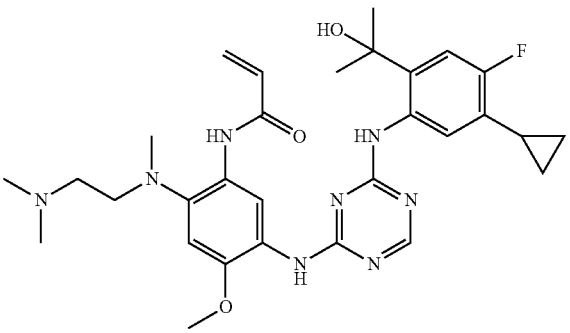 [SMILES: C=CC(=O)Nc1cc(Nc2ncnc(Nc3cc(C4CC4)c(F)cc3C(C)(C)O)n2)c(OC)cc1N(C)CCN(C)C]<br>N-(5-(4-(5-cyclopropyl-4-fluoro-2-(2-hydroxypropan-2-yl)phenylamino)-1,3,5-triazin-2-ylamino)-2-((2-(dimethylamino)ethyl)(methyl)amino)-4-methoxyphenyl)acrylamide |
| 76/77 | 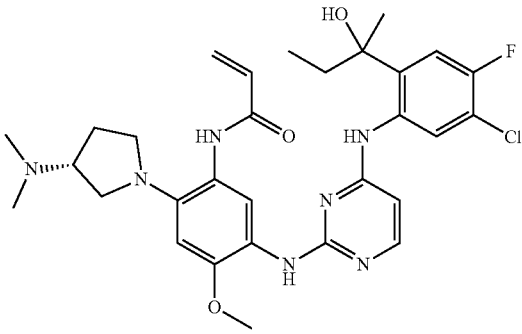 [SMILES: C=CC(=O)Nc1cc(Nc2nccc(Nc3cc(Cl)c(F)cc3C(C)(O)CC)n2)c(OC)cc1N1CC[C@@H](N(C)C)C1]<br>N-(5-(4-(5-chloro-4-fluoro-2-((R)-2-hydroxybutan-2-yl)phenylamino)pyrimidin-2-ylamino)-2-((R)-3-(dimethylamino)pyrrolidin-1-yl)-4-methoxyphenyl)acrylamide<br>or N-(5-(4-(5-chloro-4-fluoro-2-((S)-2-hydroxybutan-2-yl)phenylamino)pyrimidin-2-ylamino)-2-((R)-3-(dimethylamino)pyrrolidin-1-yl)-4-methoxyphenyl)acrylamide |

TABLE 1-continued

Exemplary Compounds 1-98

| Compound No. | Compound Structure and Nomenclature |
| --- | --- |
| 78 | 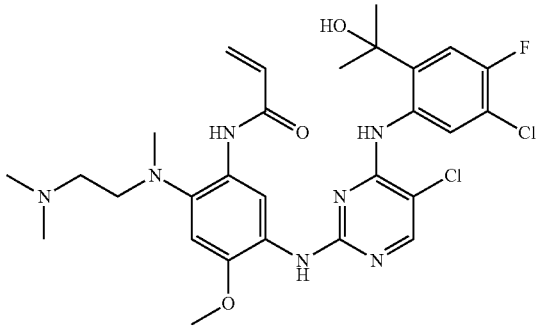 [SMILES: C=CC(=O)Nc1cc(Nc2ncc(Cl)c(Nc3cc(Cl)c(F)cc3C(C)(C)O)n2)c(OC)cc1N(C)CCN(C)C]  N-(5-(5-chloro-4-(5-chloro-4-fluoro-2-(2-hydroxypropan-2-yl)phenylamino)pyrimidin-2-ylamino)-2-((2-(dimethylamino)ethyl)(methyl)amino)-4-methoxyphenyl)acrylamide |
| 79 | 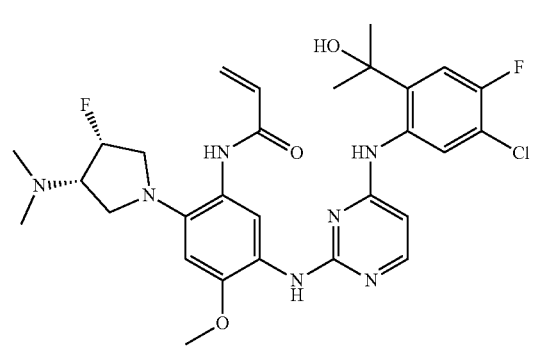 [SMILES: C=CC(=O)Nc1cc(Nc2nccc(Nc3cc(Cl)c(F)cc3C(C)(C)O)n2)c(OC)cc1N1C[C@@H](F)[C@@H](N(C)C)C1]  N-(5-(4-(5-chloro-4-fluoro-2-(2-hydroxypropan-2-yl)phenylamino)pyrimidin-2-ylamino)-2-((3S,4R)-3-(dimethylamino)-4-fluoropyrrolidin-1-yl)-4-methoxyphenyl)acrylamide |
| 80 | 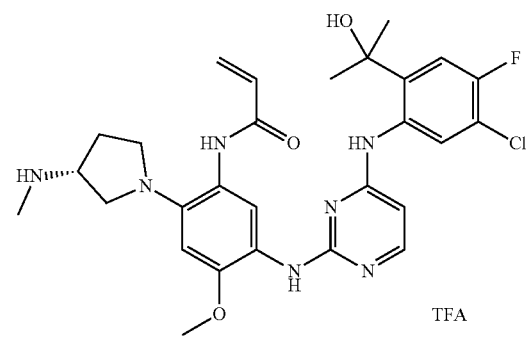 [SMILES: C=CC(=O)Nc1cc(Nc2nccc(Nc3cc(Cl)c(F)cc3C(C)(C)O)n2)c(OC)cc1N1CC[C@@H](NC)C1]  (R)-N-(5-(4-(5-chloro-4-fluoro-2-(2-hydroxypropan-2-yl)phenylamino)pyrimidin-2-ylamino)-4-methoxy-2-(3-(methylamino)pyrrolidin-1-yl)phenyl)acrylamide TFA salt |

TABLE 1-continued

Exemplary Compounds 1-98

| Compound No. | Compound Structure and Nomenclature |
|---|---|
| 81 | N-(5-(4-(5-chloro-4-fluoro-2-(2-hydroxypropan-2-yl)phenylamino)-5-methoxypyrimidin-2-ylamino)-2-((2-(dimethylamino)ethyl)(methyl)amino)-4-methoxyphenyl)acrylamide |
| 82 | (R)-N-(5-(4-(5-chloro-4-fluoro-2-(2-hydroxypropan-2-yl)phenylamino)pyrimidin-2-ylamino)-2-(2-((dimethylamino)methyl)-4,4-difluoropyrrolidin-1-yl)-4-methoxyphenyl)acrylamide |
| 83 | (R)-N-(5-(4-(5-chloro-4-fluoro-2-(2-hydroxypropan-2-yl)phenylamino)pyrimidin-2-ylamino)-2-(7-(dimethylamino)-5-azaspiro[2.4]heptan-5-yl)-4-methoxyphenyl)acrylamide formic acid salt |

TABLE 1-continued

Exemplary Compounds 1-98

| Compound No. | Compound Structure and Nomenclature |
|---|---|
| 84 | 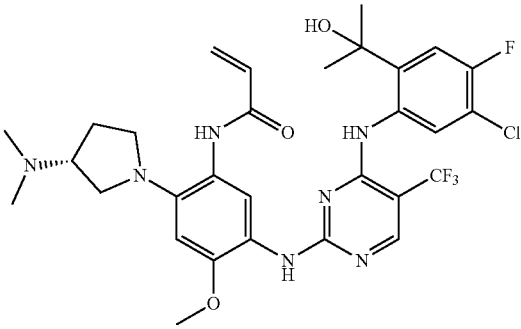 [SMILES: C=CC(=O)Nc1cc(Nc2ncc(C#N)c(Nc3cc(Cl)c(F)cc3C(C)(C)O)n2)c(OC)cc1N1CC[C@@H](N(C)C)C1]<br>(R)-N-(5-(4-(5-chloro-4-fluoro-2-(2-hydroxypropan-2-yl)phenylamino)-5-(trifluoromethyl)pyrimidin-2-ylamino)-2-(3-(dimethylamino)pyrrolidin-1-yl)-4-methoxyphenyl)acrylamide |
| 85 | 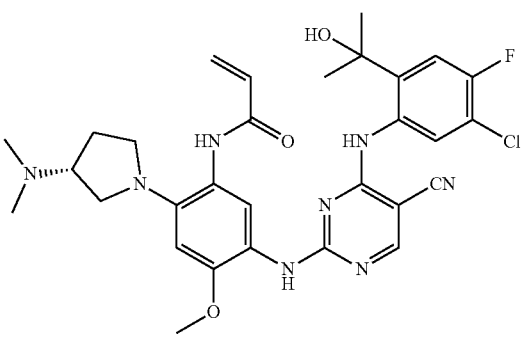<br>(R)-N-(5-(4-(5-chloro-4-fluoro-2-(2-hydroxypropan-2-yl)phenylamino)-5-cyanopyrimidin-2-ylamino)-2-(3-(dimethylamino)pyrrolidin-1-yl)-4-methoxyphenyl)acrylamide |
| 86 | 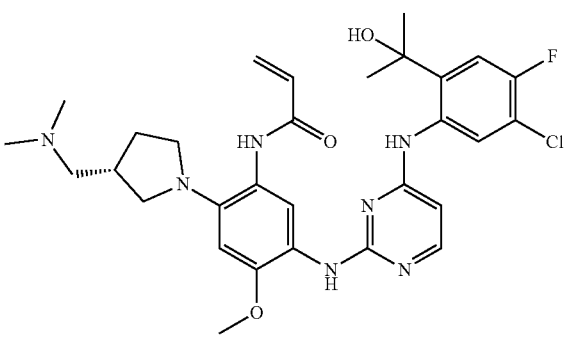 [SMILES: C=CC(=O)Nc1cc(Nc2nccc(Nc3cc(Cl)c(F)cc3C(C)(C)O)n2)c(OC)cc1N1CC[C@@H](CN(C)C)C1]<br>(S)-N-(5-(4-(5-chloro-4-fluoro-2-(2-hydroxypropan-2-yl)phenylamino)pyrimidin-2-ylamino)-2-(3-((dimethylamino)methyl)pyrrolidin-1-yl)-4-methoxyphenyl)acrylamide |

TABLE 1-continued

Exemplary Compounds 1-98

| Compound No. | Compound Structure and Nomenclature |
|---|---|
| 87 | 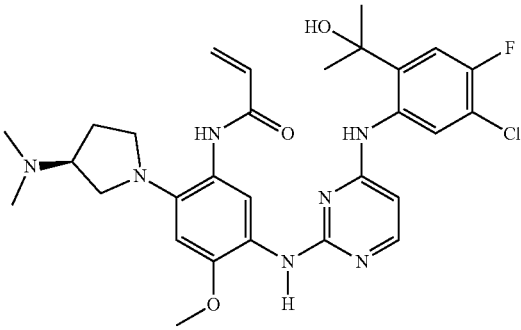 [SMILES: C=CC(=O)Nc1cc(Nc2nccc(Nc3cc(Cl)c(F)cc3C(C)(C)O)n2)c(OC)cc1N1CC[C@H](N(C)C)C1]<br>(S)-N-(5-(4-(5-chloro-4-fluoro-2-(2-hydroxypropan-2-yl)phenylamino)pyrimidin-2-ylamino)-2-(3-(dimethylamino)pyrrolidin-1-yl)-4-methoxyphenyl)acrylamide |
| 88 | 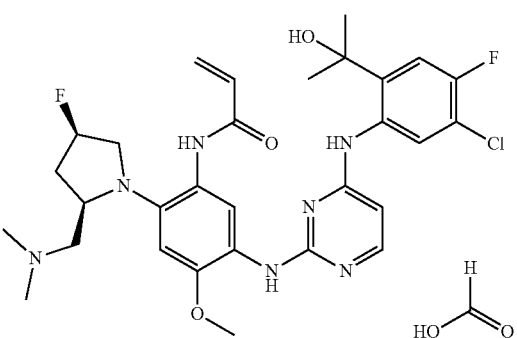 [SMILES: C=CC(=O)Nc1cc(Nc2nccc(Nc3cc(Cl)c(F)cc3C(C)(C)O)n2)c(OC)cc1N1C[C@H](F)C[C@@H]1CN(C)C ; O=CO]<br>N-(5-(4-(5-chloro-4-fluoro-2-(2-hydroxypropan-2-yl)phenylamino)pyrimidin-2-ylamino)-2-((2R,4R)-2-((dimethylamino)methyl)-4-fluoropyrrolidin-1-yl)-4-methoxyphenyl)acrylamide formic acid salt |
| 89 | 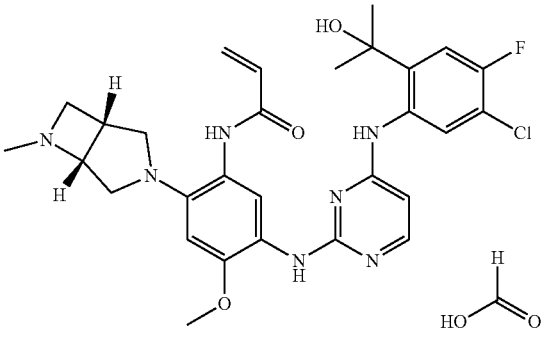 [SMILES: C=CC(=O)Nc1cc(Nc2nccc(Nc3cc(Cl)c(F)cc3C(C)(C)O)n2)c(OC)cc1N1C[C@H]2CN(C)[C@H]2C1 ; O=CO]<br>N-(5-(4-(5-chloro-4-fluoro-2-(2-hydroxypropan-2-yl)phenylamino)pyrimidin-2-ylamino)-4-methoxy-2-((1R,5R)-6-methyl-3,6-diazabicyclo[3.2.0]heptan-3-yl)phenyl)acrylamide formic acid salt |

TABLE 1-continued

Exemplary Compounds 1-98

| Compound No. | Compound Structure and Nomenclature |

90

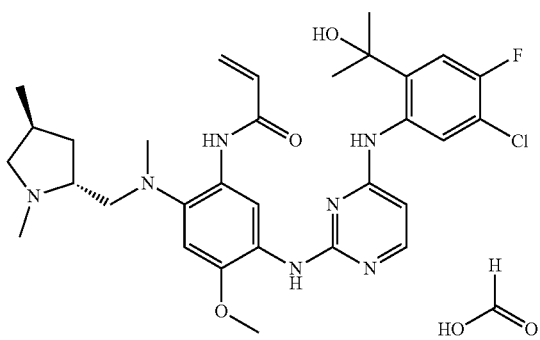 [SMILES: C=CC(=O)Nc1cc(Nc2nccc(Nc3cc(Cl)c(F)cc3C(C)(C)O)n2)c(OC)cc1N(C)C[C@H]1C[C@H](C)CN1C ; O=CO]

N-(5-(4-(5-chloro-4-fluoro-2-(2-hydroxypropan-2-yl)phenylamino)pyrimidin-2-ylamino)-2-((((2R,4S)-1,4-dimethylpyrrolidin-2-yl)methyl)(methyl)amino)-4-methoxyphenyl)acrylamide formic acid salt

91

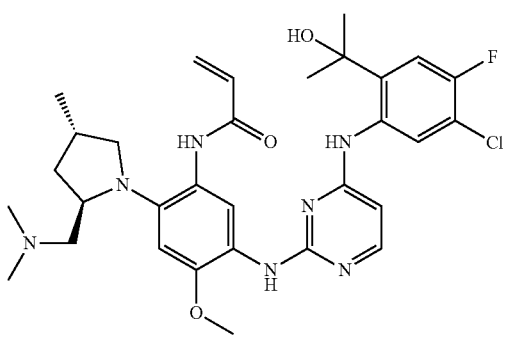 [SMILES: C=CC(=O)Nc1cc(Nc2nccc(Nc3cc(Cl)c(F)cc3C(C)(C)O)n2)c(OC)cc1N1C[C@@H](C)C[C@@H]1CN(C)C]

N-(5-(4-(5-chloro-4-fluoro-2-(2-hydroxypropan-2-yl)phenylamino)pyrimidin-2-ylamino)-2-((2R,4S)-2-((dimethylamino)methyl)-4-methylpyrrolidin-1-yl)-4-methoxyphenyl)acrylamide

92

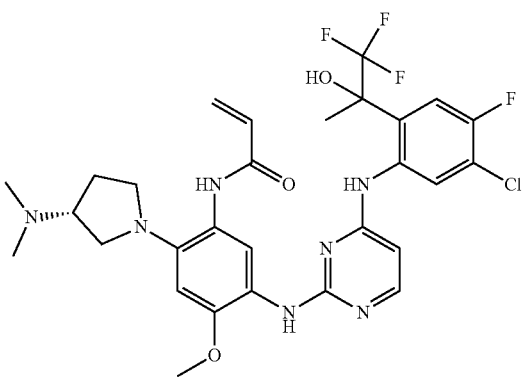 [SMILES: C=CC(=O)Nc1cc(Nc2nccc(Nc3cc(Cl)c(F)cc3C(C)(O)C(F)(F)F)n2)c(OC)cc1N1CC[C@@H](N(C)C)C1]

N-(5-(4-(5-chloro-4-fluoro-2-(1,1,1-trifluoro-2-hydroxypropan-2-yl)phenylamino)pyrimidin-2-ylamino)-2-((R)-3-(dimethylamino)pyrrolidin-1-yl)-4-methoxyphenyl)acrylamide TABLE 1-continued Exemplary Compounds 1-98

| Compound No. | Compound Structure and Nomenclature |
| --- | --- |
| 93 | 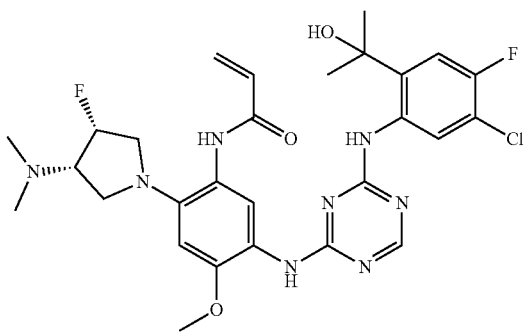 [SMILES: C=CC(=O)Nc1cc(Nc2ncnc(Nc3cc(Cl)c(F)cc3C(C)(C)O)n2)c(OC)cc1N1C[C@@H](F)[C@@H](N(C)C)C1]<br>N-(5-(4-(5-chloro-4-fluoro-2-(2-hydroxypropan-2-yl)phenylamino)-1,3,5-triazin-2-ylamino)-2-((3S,4R)-3-(dimethylamino)-4-fluoropyrrolidin-1-yl)-4-methoxyphenyl)acrylamide |
| 94 | 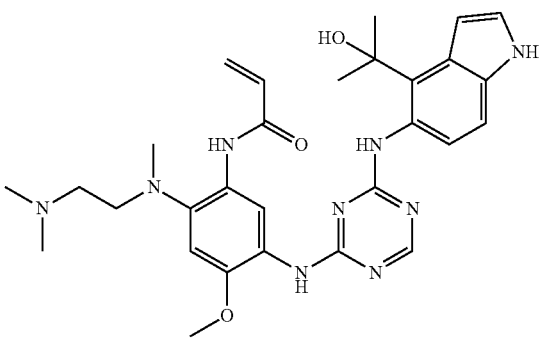 [SMILES: C=CC(=O)Nc1cc(Nc2ncnc(Nc3ccc4[nH]ccc4c3C(C)(C)O)n2)c(OC)cc1N(C)CCN(C)C]<br>N-(2-((2-(dimethylamino)ethyl)(methyl)amino)-5-(4-(4-(2-hydroxypropan-2-yl)-1H-indol-5-ylamino)-1,3,5-triazin-2-ylamino)-4-methoxyphenyl)acrylamide |
| 95 | 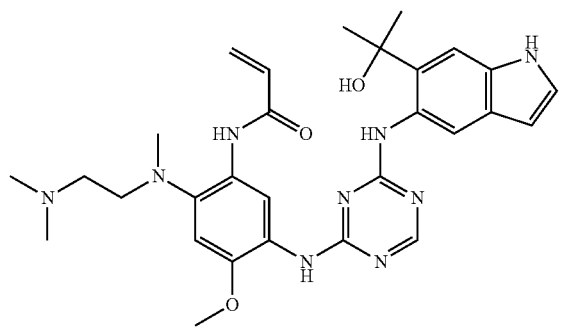 [SMILES: C=CC(=O)Nc1cc(Nc2ncnc(Nc3cc4cc[nH]c4cc3C(C)(C)O)n2)c(OC)cc1N(C)CCN(C)C]<br>N-(2-((2-(dimethylamino)ethyl)(methyl)amino)-5-(4-(6-(2-hydroxypropan-2-yl)-1H-indol-5-ylamino)-1,3,5-triazin-2-ylamino)-4-methoxyphenyl)acrylamide |

TABLE 1-continued

Exemplary Compounds 1-98

| Compound No. | Compound Structure and Nomenclature |
|---|---|
| 96 | 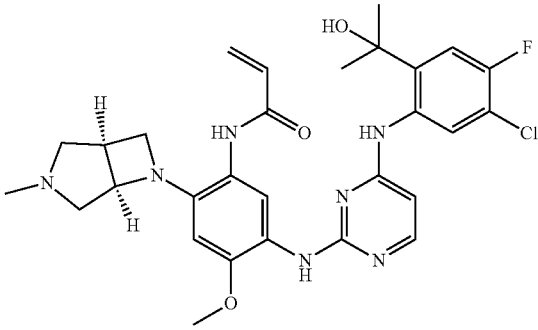 [SMILES: C=CC(=O)Nc1cc(Nc2nccc(Nc3cc(Cl)c(F)cc3C(C)(C)O)n2)c(OC)cc1N1C[C@@H]2CN(C)C[C@@H]21]<br>N-(5-(4-(5-chloro-4-fluoro-2-(2-hydroxypropan-2-yl)phenylamino)pyrimidin-2-ylamino)-4-methoxy-2-((1S,5R)-3-methyl-3,6-diazabicyclo[3.2.0]heptan-6-yl)phenyl)acrylamide |
| 97 | 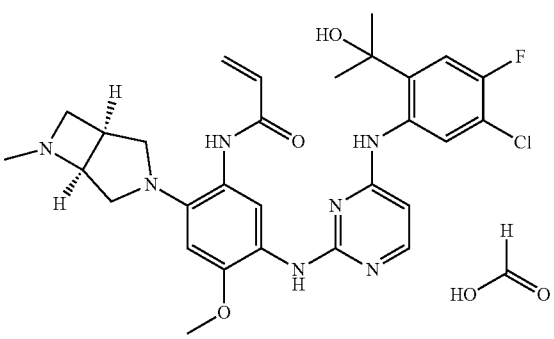 [SMILES: C=CC(=O)Nc1cc(Nc2nccc(Nc3cc(Cl)c(F)cc3C(C)(C)O)n2)c(OC)cc1N1C[C@@H]2CN(C)[C@@H]2C1 ; O=CO]<br>N-(5-(4-(5-chloro-4-fluoro-2-(2-hydroxypropan-2-yl)phenylamino)pyrimidin-2-ylamino)-4-methoxy-2-((1S,5S)-6-methyl-3,6-diazabicyclo[3.2.0]heptan-3-yl)phenyl)acrylamide formic acid salt |
| 98 | 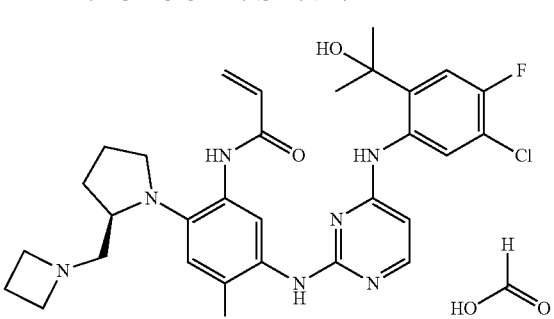<br>(R)-N-(2-(2-(azetidin-1-ylmethyl)pyrrolidin-1-yl)-5-(4-(5-chloro-4-fluoro-2-(2-hydroxypropan-2-yl)phenylamino)pyrimidin-2-ylamino)-4-methoxyphenyl)acrylamide formic acid salt |

It is appreciated that certain features of the present disclosure, which are, for clarity, described in the context of separate embodiments, can also be provided in combination in a single embodiment. Conversely, various features of the present disclosure, which are, for brevity, described in the context of a single embodiment, can also be provided separately or in any suitable subcombination.

At various places in the present disclosure, linking substituents are described. Where the structure clearly requires a linking group, the markush variables listed for that group are understood to be linking groups. For example, if the structure requires a linking group and the markush group definition for that variable lists "alkyl" then it is understood that the "alkyl" represents a linking alkylene group.

As used herein, the term "substituted", when refers to a chemical group, means the chemical group has one or more hydrogen atoms that is/are removed and replaced by substituents. As used herein, the term "substituent" has the ordinary meaning known in the art and refers to a chemical moiety that is covalently attached to, or if appropriate fused to, a parent group. As used herein, the term "optionally substituted" or "optionally . . . substituted" means that the chemical group may have no substituents (i.e. unsubstituted) or may have one or more substituents (i.e. substituted). It is to be understood that substitution at a given atom is limited by valency.

As used herein, the term "$C_{i\text{-}j}$" indicates a range of the carbon atoms numbers, wherein i and j are integers and the range of the carbon atoms numbers includes the endpoints (i.e. i and j) and each integer point in between, and wherein i∈{1, 2, 3, 4, 5, 6, 7, 8, 9, or 10}, j is greater than i,j∈{2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40}. For examples, $C_{1\text{-}6}$ indicates a range of one to six carbon atoms, including one carbon atom, two carbon atoms, three carbon atoms, four carbon atoms, five carbon atoms and six carbon atoms.

As used herein, the term "alkyl", whether as part of another term or used independently, refers to a saturated or unsaturated hydrocarbon chain, while the latter may be further subdivided into hydrocarbon chain having at least one double or triple bonds (alkenyl or alkynyl). The hydrocarbon chain mentioned above may be straight-chain or branched-chain. The term "$C_{i\text{-}j}$ alkyl" refers to an alkyl having i to j carbon atoms. In some embodiments, the alkyl group contains 1 to 12, 1 to 8, 1 to 6, 1 to 4, 1 to 3, or 1 to 2 carbon atoms. Examples of saturated alkyl group include, but are not limited to, methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2, 2-trimethylpropyl, and the like. Examples of unsaturated alkyl groups include, but are not limited to, ethenyl, n-propenyl, isopropenyl, n-butenyl, sec-butenyl, ethynyl, propyn-1-yl, propyn-2-yl, and the like.

As used herein the terms "halo" and "halogen" refer to an atom selected from fluorine, chlorine, bromine and iodine.

As used herein the terms "cyano" refers to a group of formula —CN.

As used herein, the term "hydroxyl" refers to a group of formula —OH.

As used herein, the term "alkoxy", whether as part of another term or used independently, refers to a group of formula —O-alkyl. The term "$C_{i\text{-}j}$ alkoxy" means that the alkyl moiety of the alkoxy group has i to j carbon atoms. In some embodiments, the alkyl moiety has 1 to 12, 1 to 10, 1 to 8, 1 to 6, 1 to 5, 1 to 4, 1 to 3 or 1 to 2 carbon atoms. Examples of alkoxy groups include, but are not limited to, methoxy, ethoxy, propoxy (e.g., n-propoxy and isopropoxy), t-butoxy, and the like.

As used herein, the term "carbocyclyl", whether as part of another term or used independently, refers to any ring in which all the ring atoms are carbon and which contains at least three ring forming carbon atoms. In some embodiments, the carbocyclyl may contain 3 to 12 ring forming carbon atoms, 3 to 10 ring forming carbon atoms, 3 to 8 ring forming carbon atoms or 4 to 8 ring forming carbon atoms. Carbocyclyl groups may be saturated or partially unsaturated. In some embodiments, the carbocyclyl group may be a saturated cyclic alkyl group. In some embodiments, the carbocyclyl group may be an unsaturated cyclic alkyl group that contains at least one double bond in its ring system. In some embodiments, an unsaturated carbocyclyl group may contains one or more aromatic rings.

Carbocyclyl groups can include mono- or poly-cyclic ring(s) (e.g., having 2, 3 or 4 fused, bridged or spiro rings). Examples of monocyclic carbocyclyl groups include, but are not limited to, cyclopropyl, cyclobutyl, cyclopentyl, cyclohexyl, cycloheptyl, cyclopentenyl, cyclohexenyl, cyclohexadienyl, cycloheptatrienyl, and the like. As used herein, the term "spiro rings" refers to ring systems having two rings connected through one single common atom; the term "fused rings" refers to ring systems having two rings sharing two adjacent atoms; and the term "bridged rings" refers to ring systems with two rings sharing three or more atoms. Examples of spiro carbocyclyl include, but are not limited to, spiro[5.5]undecane, spiro-pentadiene, spiro[3.6]-decan, and the like. Examples of fused carbocyclyl include, but are not limited to, naphthalene, benzopyrene, anthracene, acenaphthene, fluorene, nene and the like. Examples of bridged carbocyclyl include, but are not limited to, bicyclo[2,2,1]heptenyl, bicyclo[2.2.1]heptane, bicyclo[2.2.2]octane, bicyclo [3.3.1]nonane, bicyclo[3.3.3]undecane, and the like.

As used herein, the term "heterocyclyl" refers to a carbocyclyl group wherein one or more (e.g. 1, 2 or 3) ring atoms are replaced by heteroatoms which include, but are not limited to, oxygen, sulfur, nitrogen, phosphorus, and the like. In some embodiments, the heterocyclyl is a saturated heterocyclyl. In some embodiments, the heterocyclyl is an unsaturated heterocyclyl having one or more double bonds in its ring system. In some embodiments, an unsaturated heterocyclyl group may contains one or more aromatic rings.

Heterocyclyl groups can include mono- or poly-cyclic ring(s) (e.g., having 2, 3 or 4 fused, bridged or spiro rings). Exemplary monocyclic heterocyclyl groups include, but are not limited to, pyrrolidyl, tetrahydrofuran, piperidyl, piperazinyl, morpholinyl, and the like. Examples of spiro heterocyclyl include, but are not limited to, spiropyrans, spirooxazines, and the like. Examples of fused heterocyclyl include, but are not limited to, quinoline, isoquinoline, quinolizine, quinazoline, pteridine, chromene, isochromene, indole, isoindole, indolizine, indazole, purine, benzofuran, isobenzofuran, benzimidazole, benzothienyl, carbazole, phenazine, phenothiazine, phenanthridine groups, and the like. Examples of bridged heterocyclyl include, but are not limited to, morphan, hexamethylenetetramine, 1,4-diazabicyclo[2.2.2]octane (DABCO), and the like.

As used herein, the term "i-j membered" refers to carbocyclyl or heterocyclyl groups having i to j ring-forming atoms. For example, "3-8 membered carbocyclyl" refers to carbocyclyl groups having 3 to 10 (e.g., 3, 4, 5, 6, 7, 8, 9 or 10) ring-forming members; "3-10 membered heterocyclyl" refers to heterocyclyl having 3 to 10 (e.g., 3, 4, 5, 6, 7, 8, 9 or 10) ring-forming members. In some embodiments, carbocyclyl or heterocyclyl groups are 3-10 membered, 3-8 membered, 3-6 membered, or 4-6 membered. For example, piperidinyl is an example of a 6 membered heterocyclyl, pyrazolyl is an example of a 5 membered heterocyclyl, pyridyl is an example of a 6 membered heterocyclyl, and 1,2,3,4-tetrahydro-naphthalene is an example of a 10 membered carbocyclyl.

As used herein, the term "aromatic group" or "aromatic ring" refers to mono- or polycyclic carbocyclyl or heterocyclyl moiety having alternating double and single bonds between ring forming atoms in at least one ring. In some embodiments, the aromatic rings have 5 to 12, 5 to 10, 5 to 8, 6 to 12, 6 to 10, or 6 to 8 ring forming atoms (i.e., 5-12, 5-10, 5-8, 6-12, 6-10, or 6-8 membered). Examples of carbocyclic aromatic groups include, but are not limited to, phenyl, naphthyl, tetrahydronaphthyl, indanyl, idenyl and the like. In some embodiments, the heterocyclic aromatic group is 5 membered or 6 membered. Exemplary 5 membered heterocyclic aromatic groups are thienyl, furyl, pyrrolyl, imidazolyl, thiazolyl, oxazolyl, pyrazolyl, isothiazolyl, isoxazolyl, 1,2,3-triazolyl, 1,2,4-triazolyl, 1,3,4-triazolyl, tetrazolyl, 1,2,3-thiadiazolyl, 1,2,4-thiadiazolyl, 1,3,4-thiadiazolyl, 1,2,3-oxadiazolyl, 1,2,4-oxadiazolyl, 1,3,4-oxadiazolyl and the like. Exemplary 6 membered heterocyclic aromatic groups are pyridyl, pyrazinyl, pyrimidinyl, triazinyl and pyridazinyl.

The "compound" of present disclosure is intended to encompass all stereoisomers, geometric isomers, and tautomers of the structures depicted unless otherwise specified.

The term "stereoisomer" refers to any of the various stereoisomeric configurations (e.g., enantiomers, diastereomers and racemates) of an asymmetric compound (e.g., those having one or more asymmetrically substituted carbon atoms-"asymmetric centers"). Compounds of the present disclosure that contain asymmetric centers can be isolated in optically active (enantiomers or diastereomers) or optically inactive (racemic) forms. The term "enantiomer" includes pairs of stereoisomers that are non-superimposable mirror images of each other. A 1:1 mixture of a pair of enantiomers is a "racemic mixture". The terms "diastereomers" or "diastereoisomers" include stereoisomers that have at least two asymmetric atoms, but which are not mirror images of each other. Certain compounds containing one or more asymmetric centers may give rise to enantiomers, diastereomers or other stereoisomeric forms that may be defined, in terms of absolute configuration, as (R)- or (S)- at each asymmetric center according to the Cahn-Ingold-Prelog R-S system. Resolved compounds whose absolute configuration is unknown can be designated using the term "or" at the asymmetric center. Methods on how to prepare optically active forms from racemic mixtures are known in the art, such as resolution by HPLC or stereoselective synthesis.

The "geometric isomers" or "cis and trans isomers" refer to compounds with same formula but their functional groups are rotated into a different orientation in three-dimensional space. The term "tautomers" include prototropic tautomers which are isomeric protonation states of compounds having the same formula and total charge. Examples of prototropic tautomers include, but are not limited to, ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomers can be in equilibrium or sterically locked into one form by appropriate substitution. Compounds of the present disclosure identified by name or structure as one particular tautomeric form are intended to include other tautomeric forms unless otherwise specified.

The "compound" of the present disclosure is also intended to encompass all isotopes of atoms in the compounds. Isotopes of an atom include atoms having the same atomic number but different mass numbers. For example, hydrogen, carbon, nitrogen, oxygen, phosphorous, sulphur, fluorine, chlorine, bromide or iodine in the "compound" of present disclosure are meant to also include their isotopes such as but are not limited to: $^1H$, $^2H$, $^3H$, $^{11}C$, $^{12}C$, $^{13}C$, $^{14}C$, $^{14}N$, $^{15}N$, $^{16}O$, $^{17}O$, $^{18}O$, $^{31}P$, $^{32}P$, $^{32}S$, $^{33}S$, $^{34}S$, $^{36}S$, $^{17}F$, $^{19}F$, $^{35}Cl$, $^{37}Cl$, $^{79}Br$, $^{81}Br$, $^{127}I$ and $^{131}I$. In some embodiments, hydrogen includes protium, deuterium and tritium. In some embodiments, carbon includes $^{12}C$ and $^{13}C$.

It is also to be understood that the "compound" of present disclosure can exist in solvated as well as unsolvated forms, such as, for example, hydrated forms, solid forms, and the present disclosure is intended to encompass all such solvated and unsolvated forms.

It is further to be understood that the "compound" of present disclosure can exist in forms of pharmaceutically acceptable salts or esters.

As used herein, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments, compounds, materials, compositions, and/or dosage forms that are pharmaceutically acceptable refer to those approved by a regulatory agency (such as U.S. Food and Drug Administration, China Food and Drug Administration or European Medicines Agency) or listed in generally recognized pharmacopoeia (such as U.S. Pharmacopoeia, China Pharmacopoeia or European Pharmacopoeia) for use in animals, and more particularly in humans.

As used herein, "pharmaceutically acceptable salts" refers to derivatives of the compounds of present disclosure wherein the parent compound is modified by converting an existing acidic moiety (e.g., carboxyl and the like) or base moiety (e.g., amine, alkali and the like) to its salt form. In many cases, compounds of present disclosure are capable of forming acid and/or base salts by virtue of the presence of amino and/or carboxyl groups or groups similar thereto. And the "pharmaceutically acceptable salt" includes acid addition or base salts that retain biological effectiveness and properties of the parent compound, which typically are not biologically or otherwise undesirable.

As used herein, "pharmaceutically acceptable . . . esters" refers to esters which hydrolyze in vivo and include those that break down readily in the human body to leave the parent compound or a salt thereof. Such esters can act as a prodrug as defined herein. The esters can be formed with an amine, hydroxy, or carboxyl side chain on the compounds described herein. For example, if a disclosed compound contains an alcohol functional group, an ester can be formed by the replacement of the hydrogen atom of the alcohol group with an acidic group such as, including, but not limited to, carboxylic acids, phosphoric acids, phosphinic acids, sulfinic acids, sulfonic acids and boronic acids groups. The procedures and specific groups to make such esters are known to those of skill in the art and can readily be found in reference sources such as Greene and Wuts, Protective Groups in Organic Synthesis, 3rd Ed., John Wiley & Sons, New York, N.Y., 1999, which is incorporated herein by reference in its entirety.

Suitable pharmaceutically acceptable salts of a compound of the present disclosure includes, for example, an acid-addition salt, which can be derived from for example an inorganic acid (for example, hydrochloric, hydrobromic, sulfuric, nitric, phosphoric acid and the like) or organic acid (for example, formic, acetic, propionic, glycolic, oxalic, maleic, malonic, succinic, fumaric, tartaric, trimesic, citric, lactic, phenylacetic, benzoic, mandelic, methanesulfonic, napadisylic, ethanesulfonic, toluenesulfonic, trifluoroacetic, salicylic, sulfosalicylic acids and the like). In some embodiments, the pharmaceutically acceptable salt of the compound of the present disclosure is a formic acid salt. In some embodiments, the pharmaceutically acceptable salt of the compound of the present disclosure is a TFA salt. Suitable pharmaceutically acceptable salts of a compound of the present disclosure also includes, for example, an base-addition salt, which can be derived from for example an inorganic bases (for example, sodium, potassium, ammonium salts and hydroxide, carbonate, bicarbonate salts of metals from columns I to XII of the periodic table such as calcium, magnesium, iron, silver, zinc, copper and the like) or organic bases (for example, primary, secondary, and tertiary amines, substituted amines including naturally occurring substituted amines, cyclic amines, basic ion exchange resins, and the like). Certain organic amines include but are not limited to isopropylamine, benzathine, cholinate, diethanolamine, diethylamine, lysine, meglumine, piperazine and tromethamine. The skilled person would appreciate that additional acids or bases for forming acid/base-addition salts other than those shown in the examples may also be possible. Lists of additional suitable salts can be found, e.g., in "Remington's Pharmaceutical Sciences," 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

The present disclosure also includes active intermediates, active metabolites and prodrugs of the compounds of present disclosure. As used herein, an "active intermediate" refer to intermediate compound in the synthetic process, which exhibits the same or essentially the same biological activity as the final synthesized compound.

As used herein, an "active metabolite" refers to a breakdown or end product of a compound of the present disclosure or its salt or prodrug produced through metabolism or biotransformation in the animal or human body, which exhibits the same or essentially the same biological activity as the specified compound. Such metabolites may result from, for example, oxidation, reduction, hydrolysis, amidation, deamidation, esterification, deesterification, enzymatic cleavage, and the like, of the administered compound or salt or prodrug.

As used herein, "prodrugs" refer to any compounds or conjugates which release the active parent drug when administered to an animal or human subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl group is bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the present disclosure. Preparation and use of prodrugs is discussed in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are hereby incorporated by reference in their entirety.

Unless otherwise specified, "ErbB" or "wild-type ErbB" refers to normal ErbB family members. In one aspect, the present disclosure provides inhibitory compounds of ErbB family kinase (e.g., EGFR, Her2, Her3 and/or Her4). In some embodiments, the compounds of the present disclosure can inhibit both Wild-Type (WT) and mutant forms of ErbB family kinase. In some embodiments, the compounds of the present disclosure are selective inhibitors of at least one mutation of ErbB family kinase as compared to corresponding WT ErbB family kinase. As used herein, the term "mutations" refers to the any mutations to the ErbB protein, "mutant" or "mutated form" refers to the protein that contains said mutation. Exemplary mutations of ErbBs, include but are not limited to, L858R, T790M, G719S, G719X, delE746-A750, A763_Y764insFQEA, V769_D770insASV, H773_V774insNPH and the like in EGFR, and Exon 20 insYVMA in Her2. In some embodiments, the compounds of the present disclosure are selective inhibitors of at least one mutation of EGFR as compared to WT EGFR. In some embodiments, the compounds of the present disclosure are selective inhibitors of at least one mutation of Her2 as compared to WT Her2. In some embodiments, the at least one mutation of EGFR is a point mutation (e.g., L858R, T790M). In some embodiments, the at least one mutation of EGFR is a deletion mutation (e.g., delE746-A750). In some embodiments, the at least one mutation of EGFR is an insertion mutation (e.g., EGFR Exon 20 V769_D770insASV, Exon 20 H773_V774insNPH). In some embodiments, the at least one mutation of EGFR is an activating mutation (e.g., L858R, G719S or delE746-A750). In some embodiments, the at least one mutation of EGFR is a drug resistant mutation (e.g., Exon 20 T790M). In certain embodiments, an at least one mutation of EGFR is T790M. In some embodiments, a provided compound selectively inhibits T790M/L858R co-mutation, and is sparing as to WT EGFR inhibition.

As used herein, the term "selectively inhibits," as used in comparison to inhibition of WT EGFR/Her2, means that a provided compound is more potent as an inhibitor of at least one mutation of EGFR/Her2 (i.e., at least one point mutation, at least one deletion mutation, at least one insertion mutation, at least one activating mutation, at least one resistant mutation, or a combination of at least one deletion mutation and at least one point mutation) in at least one assay described herein (e.g., biochemical or cellular). In some embodiments, the term "selectively inhibits," as used in comparison to WT EGFR inhibition means that a provided compound is at least 100 times more potent, at least 50 times, at least 45 times, at least 40 times, at least 35 times, at least 30 times, at least 25 times, at least 20 times, at least 15 times, at least 10 times, at least 5 times, at least 4 times, at least 3 times, at least 2 times, at least 1.5 times, or at least 1.25 times more potent as an inhibitor of at least one mutation of EGFR, as defined and described herein, as compared to WT EGFR. In some embodiments, the term "selectively inhibits," as used in comparison to WT EGFR inhibition means that a provided compound is up to 1500 times more potent, up to 1200 times, up to 1000 times, up to 800 times, up to 600 times, up to 400 times, up to 200 times, up to 100 times, up to 50 times, up to 10 times more potent as an inhibitor of at least one mutation of EGFR, as defined and described herein, as compared to WT EGFR. As used herein, the term "sparing as to WT EGFR" means that said selective inhibitor of at least one mutation of EGFR, as defined and described above and herein, cannot inhibits WT EGFR within the upper limit of detection of at least one assay as described herein (e.g., biochemical or cellular as described in detail in Examples). In some embodiments, the term "sparing as to WT EGFR" means that a provided compound inhibits WT EGFR with an IC50 of at least 10 μM, at least 9 μM, at least 8 μM, at least 7 μM, at least 6 μM, at least 5 μM, at least 3 μM, at least 2 μM, or at least 1 μM.

In some embodiments, compounds of the present disclosure inhibit phosphorylation of WT EGFR and/or mutant EGFR with an $IC_{50}$ value of 0.1-1000 nM, preferably 0.1-600 nM, 1-600 nM, 0.1-500 nM, 1-500 nM, 0.1-400 nM, 1-400 nM, 0.1-300 nM, 1-300 nM, 0.1-200 nM, 1-200 nM, 0.1-100 nM, 1-100 nM, 0.1-80 nM, 0.1-50 nM, 0.1-40 nM, 0.1-30 nM, 0.1-20 mM, 0.1-10 nM, or 0.1-5 nM, more preferably 0.1-20 nM, 0.1-10 nM, or 0.1-5 nM.

In some embodiments, compounds of the present disclosure inhibit phosphorylation of WT Her2 and/or mutant Her2 with an $IC_{50}$ value of 0.1-1000 nM, preferably 0.1-600 nM, 1-600 nM, 0.1-500 nM, 1-500 nM, 0.1-400 nM, 1-400 nM, 0.1-300 nM, 1-300 nM, 0.1-200 nM, 1-200 nM, 0.1-100 nM, 1-100 nM, 0.1-80 nM, 0.1-50 nM, 0.1-40 nM, 0.1-30 nM, 0.1-20 mM, 0.1-10 nM, or 0.1-5 nM, more preferably 0.1-20 nM, 0.1-10 nM, or 0.1-5 nM.

In some embodiments, compounds of the present disclosure inhibit proliferation of WT EGFR and/or mutant EGFR bearing cells with an $GI_{50}$ value of 1-1000 nM, preferably 1-800 nM, 1-600 nM, 1-500 nM, 1-400 nM, 1-300 nM, 1-300 nM, 1-200 nM, 1-100 nM, 1-80 nM, 1-60 nM, 1-40 nM, 1-20 nM, or 1-10 nM more preferably 1-300 nM, 1-200 nM, 1-100 nM, 1-80 nM, 1-60 nM, 1-40 nM, 1-20 nM, or 1-10 nM.

In some embodiments, compounds of the present disclosure inhibit proliferation of WT Her2 and/or mutant Her2 bearing cells with an $GI_{50}$ value of 1-1000 nM, preferably 1-800 nM, 1-600 nM, 1-500 nM, 1-400 nM, 1-300 nM, 1-300 nM, 1-200 nM, 1-100 nM, 1-80 nM, 1-60 nM, 1-40 nM, 1-20 nM, or 1-10 nM more preferably 1-300 nM, 1-200 nM, 1-100 nM, 1-80 nM, 1-60 nM, 1-40 nM, 1-20 nM, or 1-10 nM.

In some embodiments, compounds of the present disclosure inhibit proliferation of BTK bearing cells with an $GI_{50}$ value of 1-1000 nM, more than 1000 nM, more than 2000 nM, or more than 3000 nM preferably 1-800 nM, 1-600 nM, 1-500 nM, 1-400 nM, 1-300 nM, 1-300 nM, 1-200 nM, 1-100 nM, 1-80 nM, 1-60 nM, 1-40 nM, 1-20 nM, or 1-10 nM more preferably 1-300 nM, 1-200 nM, 1-100 nM, 1-80 nM, 1-60 nM, 1-40 nM, 1-20 nM, or 1-10 nM.

In some embodiments, the $IC_{50}$ and/or $GI_{50}$ of the compounds to EGFR mutant is at least 2 times, 3 times, 4 times, 5 times, preferably 10 times, 20 times, 30 times, 50 times, or 100 times higher than the $IC_{50}$ and/or $GI_{50}$ of the compounds to wild-type EGFR.

Synthetic Method

Synthesis of the compounds provided herein, including salts, esters, hydrates, or solvates or stereoisomers thereof, are illustrated in the synthetic schemes in the examples. The compounds provided herein can be prepared using any known organic synthesis techniques and can be synthesized according to any of numerous possible synthetic routes, and thus these schemes are illustrative only and are not meant to limit other possible methods that can be used to prepare the compounds provided herein. Additionally, the steps in the Schemes are for better illustration and can be changed as appropriate. The embodiments of the compounds in examples were synthesized in China for the purposes of research and potentially submission to regulatory agencies.

The reactions for preparing compounds of the disclosure can be carried out in suitable solvents, which can be readily selected by one skilled in the art of organic synthesis. Suitable solvents can be substantially non-reactive with the starting materials (reactants), the intermediates, or products at the temperatures at which the reactions are carried out, e.g., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by a skilled artisan.

Preparation of compounds of the disclosure can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3rd Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("Preparative LC-MS Purification: Improved Compound Specific Method Optimization" Karl F. Blom, Brian Glass, Richard Sparks, Andrew P. Combs J. Combi. Chem. 2004, 6(6), 874-883, which is incorporated herein by reference in its entirety) and normal phase silica chromatography.

Abbreviations as used herein, are defined as follows: "1×" or "×1" for once, "2×" or "×2" for twice, "3×" or "×3" for thrice, "4×" or "×4" for four times, "5×" or "×5" for five times, "° C." for degrees Celsius, "eq" or "eq" for equivalent or equivalents, "g" for gram or grams, "mg" for milligram or milligrams, "L" for liter or liters, "mL" or "ml" for milliliter or milliliters, "μL" for microliter or microliters, "N" for normal, "M" for molar, "mmol" for millimole or millimoles, "min" for minute or minutes, "h" or "hr" for hour or hours, "r.t" or "it" for room temperature, "atm" for atmosphere, "psi" for pounds per square inch, "conc." for concentrate, "sat" or "sat'd" for saturated, "MS" or "Mass Spec" for mass spectrometry, "ESI" for electrospray ionization mass spectroscopy, "LCMS" for liquid chromatography mass spectrometry, "HPLC" for high pressure liquid chromatography, "RP" for reverse phase, "TLC" or "tlc" for thin layer chromatography, "SM" for starting material, "NMR" for nuclear magnetic resonance spectroscopy, "$^1H$" for proton, "δ" for delta, "s" for singlet, "d" for doublet, "t" for triplet, "q" for quartet, "m" for multiplet, "br" for broad, and "Hz" for hertz, "a", "P", "R", "S", "E", and "Z" are stereochemical designations familiar to one skilled in the art.

Abbreviations for chemicals used in the synthesis of the compounds provided herein are listed below:

| | |
|---|---|
| AcOH or HOAc | acetic acid |
| MeOH | Methanol |
| EtOH | Ethanol |
| t-BuOH | tert-butyl alcohol |
| t-BuOK | Potassium tert-butoxide |
| EtOAc or EA | ethyl acetate |
| Fe | Iron |
| FA | Formic acid |
| $NH_2Boc$ | tert-butyl carbamate |
| Boc | tert-butyloxycarbonyl |
| $BH_3 \cdot Me_2S$ or $BH_3 \cdot DMS$ | borane dimethyl sulfide complex |
| $CDCl_3$ | deuterated chloroform |
| $CH_2Cl_2$ | Dichloromethane |

| | -continued |
|---|---|
| CH₃CH₂I | ethyl iodide |
| CH₃CN or MeCN | Acetonitrile |
| Cs₂CO₃ | cesium carbonate |
| CuI | copper iodide |
| DCM | Dichloromethane |
| DEAD | diethyl azodicarboxylate |
| DIAD | diisopropyl azodicarboxylate |
| DIEA or DIPEA | N,N,-diisopropylethylamine |
| DMF | dimethyl formamide |
| DMSO | dimethyl sulfoxide |
| EDC (or EDC · HCl) or EDCI (or EDCI · HCl) or EDAC | 3-ethyl-3'-(dimethylamino)propyl-carbodiimide hydrochloride or 1-(3-dimethylaminopropyl)-3-ethylcarbodiimide hydrochloride |
| EDTA | ethylenediaminetetraacetic acid |
| HATU | O—(7-azabenzotriazol-1-yl)-N,N,N',N'-tetramethyluronium hexafluorophosphate |
| HCl | hydrochloric acid |
| Hex | Hexane |
| HOBt or HOBT | 1-hydroxybenzotriazole monohydrate |
| LiOH | lithium hydroxide |
| mCPBA or m-CPBA | meta-chloroperbenzoic acid |
| Pd/C | palladium on carbon |
| PE | petroleum ether |
| SOCl₂ | thionyl chloride |
| TEA or Et₃N | Triethylamine |
| TFA | trifluoroacetic acid |
| THF | Tetrahydrofuran |
| BH₃-THF | Borane tetrahydrofuran |
| TBAF | tetrabutylammonium fluoride |
| TRIS | tris(hydroxymethyl)aminomethane |
| K₃PO₄ | potassium phosphate |
| K₂CO₃ | potassium carbonate |
| KI | potassium iodide |
| KOH | potassium hydroxide |
| MgSO₄ | magnesium sulfate |
| NaCl | sodium chloride |
| AcONa or NaOAc | sodium acetate |
| MeONa | sodium methoxide |
| NaClO₂ | sodium chlorite |
| NaH₂PO₄ | Sodium dihydrogen phosphate |
| NaHCO₃ | sodium bicarbonate |
| NaIO₄ | sodium periodate |
| NaOH | sodium hydroxide |
| Na₂SO₃ | sodium sulfite |
| Na₂SO₄ | sodium sulfate |
| NH₄Cl | ammonium chloride |
| NMO | N-methylmorpholine-N-oxide |
| OsO₄ | Osmium tetroxide |
| PBr₃ | phosphorus tribromide |
| P(OEt)₃ | triethyl phosphate |
| PCl₅ | phosphorus pentachloride |
| POCl₃ | phosphorus oxychloride |
| Pd(dppf)Cl₂ or PdCl₂(dppf) | [1,1'-Bis(diphenylphosphino)ferrocene]dichloropalladium (II) |
| Pd₂(dba)₃ | tris(dibenzylideneacetone) dipalladium (0) |
| PPh₃ | Triphenylphosphine |
| Pd(PPh₃)₄ | tetrakis(triphenylphosphine) palladium (0) |
| Xantphos | 4,5-bis(diphenylphosphino)-9,9-dimethylxanthene |
| N₂H₄ · H₂O | hydrazine monohydrate |
| MTBE | methyl tert-butyl ether |
| NH₂NH₂ | hydrazine |

Pharmaceutical Composition

The present disclosure provides pharmaceutical compositions comprising at least one compound of the present disclosure. In some embodiments, the pharmaceutical composition comprises more than one compounds of the present disclosure. In some embodiments, the pharmaceutical composition comprises one or more compounds of the present disclosure, and a pharmaceutical acceptable carrier.

The pharmaceutically acceptable carriers are conventional medicinal carriers in the art which can be prepared in a manner well known in the pharmaceutical art. In some embodiments, the compounds of the present disclosure may be admixed with pharmaceutically acceptable carrier for the preparation of pharmaceutical composition.

The term "pharmaceutically acceptable carrier" as used herein refers to a pharmaceutically-acceptable material, composition or vehicle, such as a liquid or solid filler, diluent, excipient, solvent or encapsulating material, involved in carrying or transporting a compound provided herein from one location, body fluid, tissue, organ (interior or exterior), or portion of the body, to another location, body fluid, tissue, organ, or portion of the body. Pharmaceutically acceptable carriers can be vehicles, diluents, excipients, or other materials that can be used to contact the tissues of an animal without excessive toxicity or adverse effects. Exemplary pharmaceutically acceptable carriers include, sugars, starch, celluloses, malt, tragacanth, gelatin, Ringer's solution, alginic acid, isotonic saline, buffering agents, and the like. Pharmaceutically acceptable carrier that can be employed in present disclosure includes those generally known in the art, such as those disclosed in "Remington Pharmaceutical Sciences" Mack Pub. Co., New Jersey (1991), which is incorporated herein by reference.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) alcohol, such as ethyl alcohol and propane alcohol; (20) phosphate buffer solutions; and (21) other non-toxic compatible substances employed in pharmaceutical formulations such as acetone.

The pharmaceutical compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The form of pharmaceutical compositions depends on a number of criteria, including, but not limited to, route of administration, extent of disease, or dose to be administered.

The pharmaceutical compositions can be formulated for oral, nasal, rectal, percutaneous, intravenous, or intramuscular administration. In accordance to the desired route of administration, the pharmaceutical compositions can be formulated in the form of tablets, capsule, pill, dragee, powder, granule, sachets, cachets, lozenges, suspensions, emulsions, solutions, syrups, aerosols (as a solid or in a liquid medium), spray, ointment, paste, cream, lotion, gel, patche, inhalant, or suppository.

The pharmaceutical compositions can be formulated to provide quick, sustained or delayed release of the active ingredient after administration to the patient by employing procedures known in the art. In some embodiments, the pharmaceutical composition is formulated in a sustained released form. As used herein, the term "sustained released form" refers to release of the active agent from the pharmaceutical composition so that it becomes available for bio-absorption in the subject, primarily in the gastrointestinal tract of the subject, over a prolonged period of time (extended release), or at a certain location (controlled release). In some embodiments, the prolonged period of time can be about 1 hour to 24 hours, 2 hours to 12 hours, 3 hours to 8 hours, 4 hours to 6 hours, 1 to 2 days or more. In certain embodiments, the prolonged period of time is at least about 4 hours, at least about 8 hours, at least about 12 hours, or at least about 24 hours. The pharmaceutical composition can be formulated in the form of tablet. For example, release rate of the active agent can not only be controlled by dissolution of the active agent in gastrointestinal fluid and subsequent diffusion out of the tablet or pills independent of pH, but can also be influenced by physical processes of disintegration and erosion of the tablet. In some embodiments, polymeric materials as disclosed in "Medical Applications of Controlled Release," Langer and Wise (eds.), CRC Pres., Boca Raton, Fla. (1974); "Controlled Drug Bioavailability," Drug Product Design and Performance, Smolen and Ball (eds.), Wiley, New York (1984); Ranger and Peppas, 1983, J Macromol. Sci. Rev. Macromol Chem. 23:61; see also Levy et al., 1985, Science 228:190; During et al., 1989, Ann. Neurol. 25:351; Howard et al., 1989, J. Neurosurg. 71:105 can be used for sustained release. The above references are incorporated herein by reference in their entirety.

In certain embodiments, the pharmaceutical compositions comprise about 0.0001 mg to about 5000 mg of the compounds of the present disclosure (e.g. about 0.0001 mg to about 10 mg, about 0.001 mg to about 10 mg, about 0.01 mg to about 10 mg, about 0.1 mg to about 10 mg, about 1 mg to about 10 mg, about 5 mg to about 10 mg, about 5 mg to about 20 mg, about 5 mg to about 30 mg, about 5 mg to about 40 mg, about 5 mg to about 50 mg, about 10 mg to about 100 mg, about 20 mg to about 100 mg, about 30 mg to about 100 mg, about 40 mg to about 100 mg, about 50 mg to about 100 mg, about 50 mg to about 200 mg, about 50 mg to about 300 mg, about 50 mg to about 400 mg, about 50 mg to about 500 mg, about 100 mg to about 200 mg, about 100 mg to about 300 mg, about 100 mg to about 400 mg, about 100 mg to about 500 mg, about 200 mg to about 500 mg, about 300 mg to about 500 mg, about 400 mg to about 500 mg, about 500 mg to about 1000 mg, about 600 mg to about 1000 mg, about 700 mg to about 1000 mg, about 800 mg to about 1000 mg, about 900 mg to about 1000 mg, about 1000 mg to about 2000 mg, about 2000 mg to about 3000 mg, about 3000 mg to about 4000 mg, or about 4000 mg to about 5000 mg). Suitable dosages per subject per day can be from about 5 mg to about 500 mg, preferably about 5 mg to about 50 mg, about 50 mg to about 100 mg, or about 50 mg to about 500 mg.

In certain embodiments, the pharmaceutical compositions can be formulated in a unit dosage form, each dosage containing from about 0.0001 mg to about 10 mg, about 0.001 mg to about 10 mg, about 0.01 mg to about 10 mg, about 0.1 mg to about 10 mg, about 1 mg to about 10 mg, about 5 mg to about 10 mg, about 5 mg to about 20 mg, about 5 mg to about 30 mg, about 5 mg to about 40 mg, about 5 mg to about 50 mg, about 10 mg to about 100 mg, about 20 mg to about 100 mg, about 30 mg to about 100 mg, about 40 mg to about 100 mg, about 50 mg to about 100 mg, about 50 mg to about 200 mg, about 50 mg to about 300 mg, about 50 mg to about 400 mg, about 50 mg to about 500 mg, about 100 mg to about 200 mg, about 100 mg to about 300 mg, about 100 mg to about 400 mg, about 100 mg to about 500 mg, about 200 mg to about 500 mg, about 300 mg to about 500 mg, about 400 mg to about 500 mg, about 500 mg to about 1000 mg, about 600 mg to about 1000 mg, about 700 mg to about 1000 mg, about 800 mg to about 1000 mg, about 900 mg to about 1000 mg, about 1000 mg to about 2000 mg, about 2000 mg to about 3000 mg, about 3000 mg to about 4000 mg, or about 4000 mg to about 5000 mg of the compounds of the present disclosure. The term "unit dosage forms" refers to physically discrete units suitable as unitary dosages for human subjects and other mammals, each unit containing a predetermined quantity of active material calculated to produce the desired therapeutic effect, in association with a suitable pharmaceutical carrier. In some embodiments, the pharmaceutical compositions comprise one or more compounds of the present disclosure as a first active ingredient, and further comprise a second active ingredient. The second active ingredient can be any anticancer agent known in the art, for examples, cell signal transduction inhibitors, cell signal transduction inhibitors, alkylating agents, topoisomerase inhibitors, immunotherapeutic agents, mitosis inhibitors, antihormonal agents, chemotherapy drugs, EGFR inhibitors, BTK inhibitors, CTLA-4 inhibitors, MEK inhibitors, PD-L1 inhibitors; OX40 agonists, and the like. Representative examples of the anticancer agents for treating cancers or tumors may include, but are not limited to, sorafenib, sunitinib, dasatinib, vorinostat, temsirolimus, everolimus, pazopanib, trastuzumab, ado-trastuzumab emtansine, pertuzumab, bevacizumab, cetuximab, ranibizumab, pegaptanib, panitumumab, tremelimumab, pembrolizumab, nivolumab, ipilimumab, atezolizumab, avelumab, durvalumab, crizotinib, ruxolitinib, paclitaxel, vincristine, vinblastine, cisplatin, carboplatin, gemcitabine, tamoxifen, raloxifene, cyclophosphamide, chromabucil, carmustine, methotrexate, fluorouracil, actinomycin, doxorubicin, epirubicin, anthracycline, bleomycin, mitomycin-C, irinotecan, topotecan, teniposide interleukin, interferon, and the like. In some embodiments, the second active agent is one or more of bevacizumab, pembrolizumab, nivolumab, ipilimumab, atezolizumab, avelumab, durvalumab, crizotinib.

Method for Treatment

The present disclosure provides a method of treating a disease associated with ErbB (including, for example, EGFR or Her2), especially ErbB mutation, comprising administering to a subject an effective amount of one or more compounds, pharmaceutically acceptable salts, esters, hydrates, solvates or stereoisomers thereof or the pharmaceutical composition of the present disclosure.

The present disclosure also provides a method of treating a disease associated with BTK. In certain embodiments, the method comprises administering to a subject an effective amount of one or more compounds, pharmaceutically acceptable salts, esters, hydrates, solvates or stereoisomers thereof or the pharmaceutical composition of the present disclosure.

As used herein, the term "diseases associated with ErbB" or "ErbB associated diseases" refers to diseases whose onset or development or both are associated with the expression or activity of ErbB. Examples include but are not limited to, immune-related diseases, proliferative disorders, cancer, and other diseases.

As used herein, the term "diseases associated with EGFR" or "EGFR associated diseases" or "diseases associated with Her2" or "Her2 associated diseases" refers to diseases whose onset or development or both are associated with the genomic alterations, expression or activity of EGFR or Her2, as the case may be. Examples include but are not limited to, immune-related diseases, proliferative disorders, cancer, and other diseases.

As used herein, the term "diseases associated with BTK" or "BTK associated diseases" refers to diseases whose onset or development or both are associated with the genomic alterations, expression or activity of BTK, as the case may be. In certain embodiments, BTK associated diseases include oncology diseases and autoimmune diseases. Oncology diseases include but not limited to lymphoma and leukemia. Autoimmune diseases include but not limited to rheumatoid arthritis, systemic lupus erythematosus and Sjogren's syndrome.

As used herein, the terms "treatment", "treat" and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to present or delay their recurrence.

In some embodiments, the one or more compounds, pharmaceutically acceptable salts, esters, hydrates, solvates or stereoisomers thereof or the pharmaceutical composition provided herein is administered via a parenteral route or a non-parenteral route. In some embodiments, the one or more compounds pharmaceutically acceptable salts, hydrates, solvates or stereoisomers thereof or the pharmaceutical composition is administered orally, enterally, buccally, nasally, intranasally, transmucosally, epidermally, transdermally, dermally, ophthalmically, pulmonary, sublingually, rectally, vaginally, topically, subcutaneously, intravenously, intramuscularly, intraarterially, intrathecally, intracapsularly, intraorbitally, intracardiacally, intradermally, intraperitoneally, transtracheally, subcuticularly, intra-articularly, subcapsularly, subarachnoidly, intraspinally, or intrasternally.

The compounds provided herein can be administrated in pure form, in a combination with other active ingredients or in the form of pharmaceutically compositions of the present disclosure. In some embodiments, the compounds provided herein can be administered to a subject in need concurrently or sequentially in a combination with one or more anticancer agent(s) known in the art. In some embodiments, the administration is conducted once a day, twice a day, three times a day, or once every two days, once every three days, once every four days, once every five days, once every six days, once a week.

In some embodiments, the one or more compounds, pharmaceutically acceptable salts, esters, hydrates, solvates or stereoisomers thereof or the pharmaceutical composition provided herein is administered orally. For oral administration, any dose is appropriate that achieves the desired goals. In some embodiments, suitable daily dosages are between about 0.001-5000 mg, preferably between 0.1 mg and 5 g, more preferably between 5 mg and 1 g, more preferably between 10 mg and 500 mg, and the administration is conducted once a day, twice a day, three times a day, every day, or 3-5 days a week. In some embodiments, the dose of the one or more compounds, pharmaceutically acceptable salts, esters, hydrates, solvates or stereoisomers thereof or the pharmaceutical composition provided herein ranges between about 0.0001 mg, preferably, 0.001 mg, 0.01 mg, 0.1 mg, 1 mg, 10 mg, 50 mg, 100 mg, 200 mg, 250 mg, 500 mg, 750 mg, 1000 mg, 2000 mg, 3000 mg, 4000 mg or up to about 5000 mg per day.

Use of Compounds

In certain embodiments, the present disclosure provides use of the compounds, pharmaceutically acceptable salts, esters, hydrates, solvates or stereoisomers thereof, or pharmaceutical composition of the present disclosure in the manufacture of medicaments for treating diseases associated with ErbB (e.g., EGFR, Her2, Her3 or Her4). In certain embodiments, the present disclosure provides use of the compounds, pharmaceutically acceptable salts, esters, hydrates, solvates or stereoisomers thereof, or pharmaceutical composition of the present disclosure in the manufacture of medicaments for treating diseases associated with the mutant ErbB. In some embodiments, the mutant ErbB is mutant EGFR. In some embodiments, the mutant ErbB is mutant Her2. In certain embodiments, the diseases associated with ErbB are diseases associated with mutant ErbB, including cancers.

In certain embodiments, the present disclosure provides use of the compounds, pharmaceutically acceptable salts, esters, hydrates, solvates or stereoisomers thereof, or pharmaceutical composition of the present disclosure in the manufacture of medicaments for treating diseases associated with BTK. In certain embodiments, the present disclosure provides use of the compounds, pharmaceutically acceptable salts, esters, hydrates, solvates or stereoisomers thereof, or pharmaceutical composition of the present disclosure in the manufacture of medicaments for treating diseases associated with the BTK. In certain embodiments, the diseases associated with BTK includes cancers.

In particular, the cancers include but are not limited to, leukemia, glioblastoma, melanoma, chondrosarcoma, cholangiocarcinoma, osteosarcoma, lymphoma, lung cancer, adenoma, myeloma, hepatocellular carcinoma, adrenocortical carcinoma, pancreatic cancer, breast cancer, bladder cancer, prostate cancer, liver cancer, gastric cancer, colon cancer, colorectal cancer, ovarian cancer, cervical cancer, brain cancer, esophageal cancer, bone cancer, testicular cancer, skin cancer, kidney cancers, mesothelioma, neuroblastoma, thyroid cancer, head and neck cancers, esophageal cancers, eye cancers, prostate cancer, nasopharyngeal cancer, or oral cancer. In some embodiments, the cancers are lung cancer, breast cancer, ovarian cancer, bladder cancer, or glioblastoma. In some embodiments, the cancer is lung cancer (e.g., non-small cell lung cancer, small cell lung cancer, adenocarcinoma, squamous cell lung cancer and large cell lung cancer). In some embodiments, the cancer is metastatic lung cancer. In some embodiment, the cancer is cancer with one or more ErbB mutations (e.g., point mutations, deletion mutation, insertion mutations, activating mutations, or drug resistant mutations of EGFR or Her2).

The compounds and pharmaceutical compositions thereof in the present disclosure can be used in the prevention or treatment of the onset or development of any of the diseases or conditions associated with ErbB/BTK (expression or activities) in mammals especially in human. In some embodiments, the compounds and pharmaceutical compositions thereof in the present disclosure can be used in the prevention or treatment of the onset or development of any of the diseases or conditions associated with mutant ErbB in mammals especially in human.

In such situation, the present disclosure also provides a method of screening patient suitable for treating with the compounds or pharmaceutical composition of the present disclosure alone or combined with other ingredients (e.g. a second active ingredient, e.g. anticancer agent). The method includes sequencing the tumor samples from patients and detecting the accumulation of ErbB (e.g., EGFR or Her2) or BTK in the patient or detecting the mutations status of ErbB (e.g., EGFR or Her2) or BTK in the patient.

EXAMPLES

The followings further explain the general methods of the present disclosure. The compounds of the present disclosure may be prepared by the methods known in the art. The following illustrates the detailed preparation methods of the preferred compounds of the present disclosure. However, they are by no means limiting the preparation methods of the compounds of the present disclosure.

Synthetic Examples

The structures of the compounds in the following examples were characterized by nuclear magnetic resonance (NMR) or/and mass spectrometry (MS). NMR shift ($\delta$) was given in the unit of $10^{-6}$ (ppm). $^{1}$H-NMR spectra was recorded in dimethyl sulfoxide-$d_6$ (DMSO-$d_6$) or CDCl$_3$ or CD$_3$OD or D$_2$O (from Aldrich or Cambridge Isotope Lab., Inc.) on Bruker AVANCE NMR (400 MHz) spectrometers using ICON-NMR (under TopSpin program control), or Varian 400MR NMR or Varian VNMR400 NMR (400 MHz) spectrometers (under VnmrJ program control) with tetramethylsilane as an internal standard.

MS measurement was carried out using Shimadzu 2010 Mass Spectrometer or Agilent 6110A MSD or 1969A TOF mass spectrometer using electrospray, chemical and electron impact ionization methods from a range of instruments.

High Performance Liquid Chromatography (HPLC) measurement was carried out on Shimadzu LC-20A systems or Shimadzu LC-2010HT series, or Agilent 1200 LC or Agilent 1100 series using Ultimate XB-C18 column (3.0*50 mm, 3 um or 3.0*150 mm, 3 um), or Xbridge shieldRP18 column (5 um, 50 mm*2.1 mm), or Xtimate C18 column (3 um, 2.1*30 mm), or MERCK RP18 2.5-2 mm, or Agilent Zorbax Eclipse Plus C18 column (4.6 mm*150 mm, 5 m) etc.

Thin layer chromatography was carried out using Yantai Huanghai HSGF254 silica gel or Anhui Liang Chen Gui Yuan plates. The silica gel plates used for thin layer chromatography (TLC) were 0.15 mm~0.2 mm. The silica gel plates used for separating and purifying products by TLC were 0.4 mm~0.5 mm.

Purified chromatographic column uses the silica gel as the carrier (100~200, 200~300 or 300~400 mesh, produced by Yantai Huanghai co., or Anhui Liang Chen Gui Yuan co., etc.), or flash column (silica-CS flash column 40-60 um, or reversed phase C18 column 20-35 um, produced by Agela Technologies, etc.) or flash column silica-CS (40-60 um) or C18 column (20-40 um) by Agela Technologies in the Teledyne ISCO combi-flash or Biotage flash system. The size of columns was adjusted according to the amount of compounds.

The known starting materials of the present disclosure can be synthesized by using or according to the known methods in the art, or can be purchased from Alfa Aesar, Langcaster, TCI, Aldrich, Bepharm, and Scochem (or PharmaBlock, Bide, Amatek, Stru Chem, Firster Pharmaceutical, Titan (Adamas) etc.).

Unless otherwise specified, the reactions in the examples were all carried out under argon or nitrogen atmosphere. Argon or nitrogen atmosphere refers to that the reaction flask is connected to an argon or nitrogen balloon with a volume of about 1 L. Hydrogenation was usually carried out under pressure. Unless otherwise specified, the reaction temperature in the examples was ambient temperature, which was 20° C.-30° C.

The reaction progress in the examples was monitored by TLC. The eluent systems used for the reactions include dichloromethane-methanol system and petroleum ether-ethyl acetate system. The volume ratios of the solvents were adjusted according to the different polarities of compounds.

The elution system of column chromatography used for purifying compounds and eluent system of TLC include dichloromethane-methanol system and petroleum ether-ethyl acetate system. The volume ratios of the solvents were adjusted according to the different polarities of compounds. A small amount of alkaline or acidic agents (0.1%1%) such as formic acid, or acetic acid, or TFA, or ammonia can be added for adjustment.

Example 1

(R)—N-(2-(3-(dimethylamino)piperidin-1-yl)-5-(4-(2-(2-hydroxypropan-2-yl)phenylamino)-1,3,5-triazin-2-ylamino)-4-methoxyphenyl)acrylamide

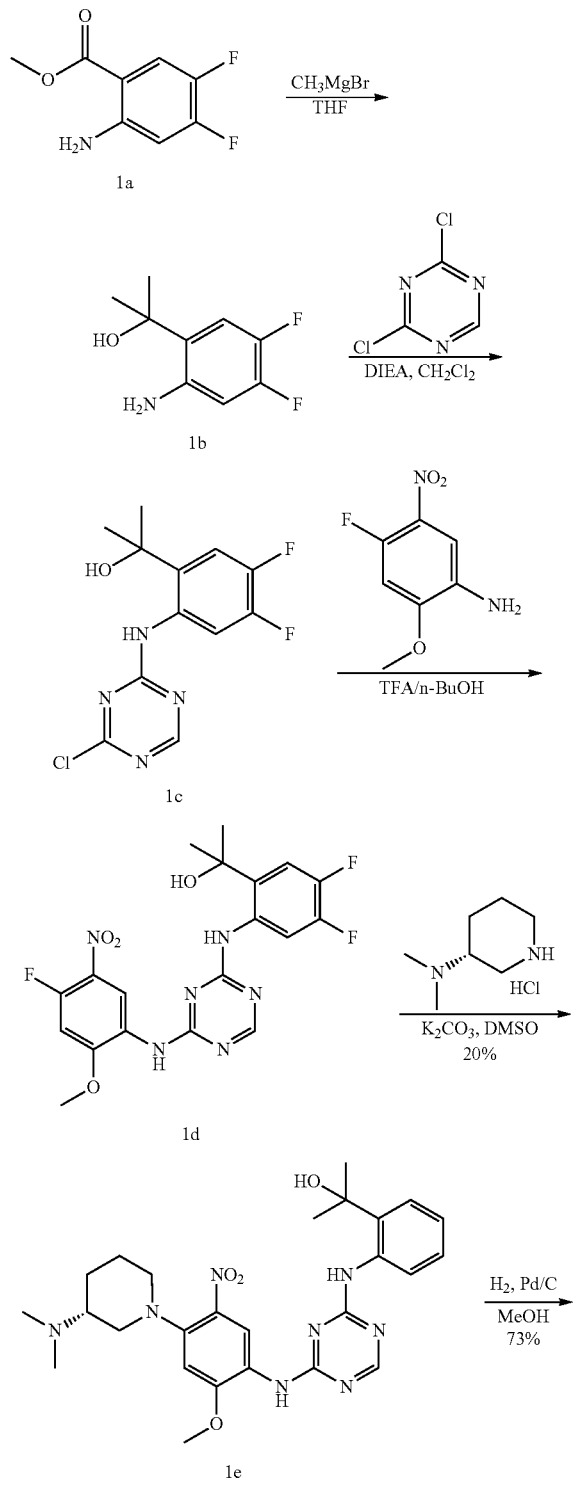

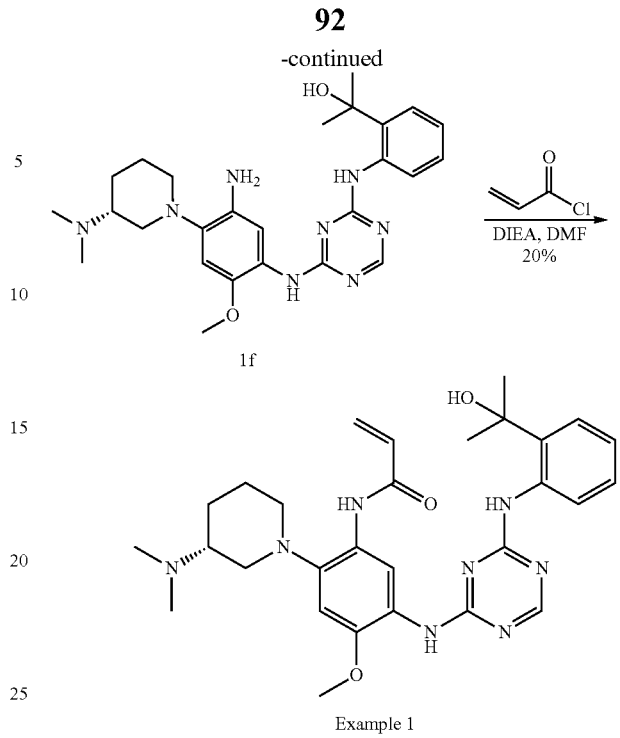

Example 1

Procedure for the Preparation of Compound 1b:

To a solution of compound 1a (25 g, 1.0 eq, 133.59 mmol) in THF (250 mL) was added CH$_3$MgBr (222.65 mL, 5.0 eq, 667.95 mmol) at 0-5° C. under ice-water bath. The resulting black mixture was stirred at 26-36° C. for 2 h until TLC (Petroleum ether/EtOAc=5/1 (v/v)) showed the starting material (R$_f$=0.70) was consumed. The reaction mixture was diluted with saturated aqueous NH$_4$Cl (500 mL) and extracted with EtOAc (2×300 mL). The combined organic layers was concentrated under reduced pressure and purified by column chromatography on silica gel (Petroleum ether/EtOAc=10/1 (v/v)) to give compound 1b (22 g, 88% yield) as yellow oil.

LCMS: R$_f$=0.678 min in 5-95AB_220&254.lcm chromatography (MERCK RP-18e 25-2 mm), MS (ESI) m/z=169.9 [M+H-18]$^+$.

$^1$H NMR (400 MHz, MeOH-d$_4$) δ 6.97 (dd, J=8.9, 12.7 Hz, 1H), 6.52 (dd, J=7.3, 12.8 Hz, 1H), 1.57 (s, 6H).

Procedure for the Preparation of Compound 1c:

A solution of compound 1b (1 g, 5.3 mmol) and DIEA (1 g, 7.9 mmol) in CH$_2$Cl$_2$ (10 mL) was added 2,4-dichloro-1,3,5-triazine (0.96 g, 6.4 mmol). The mixture was stirred at 26-34° C. for 12 hours. The reaction was purified by column chromatography on silica gel directly (20% EtOAc in petroleum ether (v/v)) to give the title product 1c as a white solid (900 mg, 56% yield).

LCMS: R$_f$=0.803 min in 5-95AB_220&254.lcm chromatography (MERCK RP-18e 25-2 mm), MS (ESI) m/z=300.9 [M+H]$^+$.

$^1$H NMR (400 MHz, DMSO-d$_6$) δ 10.84 (s, 1H), 8.68 (s, 1H), 8.10 (s, 1H), 7.46 (dd, J=8.8, 12.4 Hz, 1H), 6.35 (br s, 1H), 1.51 (s, 6H).

Procedure for the Preparation of Compound 1d:

To a solution of compound 1c (300 mg, 1.0 mmol) and 4-fluoro-2-methoxy-5-nitroaniline (185 mg, 1.0 mmol) in n-BuOH (10 mL) was added TFA (0.1 mL). The resulting mixture was stirred at 26-33° C. for 2 hours. The precipitated solid was collected by filtration and then dried under high vacuum to give the title product 1d as a yellow solid (400 mg, purity 99%, 88% yield).

LCMS: $R_t$=0.828 min in 5-95AB_220&254.lcm chromatography (MERCK RP-18e 25-2 mm), MS (ESI) m/z=451.1 [M+H]$^+$.

Procedure for the Preparation of Compound 1e:

A solution of compound d (1.144 g, 2.76 mmol), (R)—N,N-dimethylpiperidin-3-amine hydrochloride (500 mg, 3.04 mmol), and K$_2$CO$_3$ (764 mg, 5.52 mmol) in DMSO (30 mL) was stirred at 100° C. for 12 hours. The reaction mixture was added to cool water (200 mL). The yellow solid was precipitate out, then the residue was purified by column chromatography over silica gel (gradient eluent: CH$_2$Cl$_2$/MeOH from 100/0 to 90/10) to give the title product 1e as a yellow solid (298 mg, 84.0% purity, 20% yield).

LCMS: $R_t$=0.717 min in 5-95AB_220&254.lcm chromatography (MERCK RP-18e 25-2 mm), MS (ESI) m/z=523.5 [M+H]$^+$ Procedure for the Preparation of Compound 1f:

A solution of compound 1e (298 mg, 0.57 mmol) and Pd/C (30 mg, 0.1 eq) in MeOH (10 mL) was stirred under 1 atm of H$_2$ at 25° C. for 1 hour. The reaction mass was filtered through celite and washed with methanol (5 mL×3). Filtrates were combined and evaporated under vacuum to give the title product as brown oil (206 mg, 73% yield).

LCMS: $R_t$=0.630 min in 5-95AB_220&254.lcm chromatography (MERCK RP-18e 25-2 mm), MS (ESI) m/z=493.3 [M+H]$^+$ Procedure for the Preparation of Example 1:

A solution of if (194 mg, 0.39 mmol) and DIEA (78 mg, 1.5 eq, 0.59 mmol) in DMF (5 mL) was added acryloyl chloride (39 mg, 0.43 mmol) dropwise at 0° C. The mixture was stirred at 25° C. for 2 hours. The reaction was purified by prep-HPLC (Column: Phenomenex Gemini C18 150*25 mm*5 um; condition: 30-40% B (A: 0.05% ammonia in water; B: CH$_3$CN); Flow rate: 25 mL/min). Fractions containing the desired compound were lyophilized to give the Example 1 as a white solid (47.2 mg, 20% yield).

LCMS: $R_t$=2.100 min in 0-60AB_220&254.lcm chromatography (MERCK RP-18e 25-2 mm), MS (ESI) m/z=547.1 [M+H]$^+$.

HPLC: $R_t$=3.88 min in 0-60_AB_1.2ml.met.chromatography (Ultimate C18 3.0 um 3.0*50 mm); SFC: $R_t$=3.763 min, purity 96.5%.

$^1$H NMR (400 MHz, CDCl$_3$) δ 10.67 (br s, 1H), 9.91 (br s, 1H), 8.85 (s, 1H), 8.41 (s, 1H), 8.30 (d, J=8.0 Hz, 1H), 7.61 (br s, 1H), 7.35-7.30 (m, 2H), 7.04 (t, J=7.5 Hz, 1H), 6.72 (s, 1H), 6.50-6.27 (m, 2H), 5.82 (br d, J=11.0 Hz, 1H), 5.60 (s, 1H), 4.06-3.95 (m, 1H), 3.07 (br s, 1H), 2.89 (br s, 1H), 2.67 (br s, 2H), 2.45-2.38 (m, 1H), 2.34 (s, 6H), 1.98 (br s, 2H), 1.80 (s, 6H), 1.72-1.68 (m, 2H), 1.68-1.64 (m, 2H).

Example 2

N-(2-((2-(dimethylamino)ethyl)(methyl)amino)-5-(4-(2-(1-hydroxycyclopropyl) phenylamino)-1,3,5-triazin-2-ylamino)-4-methoxyphenyl)acrylamide

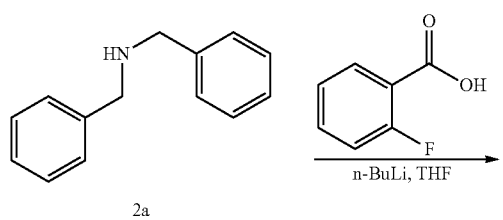

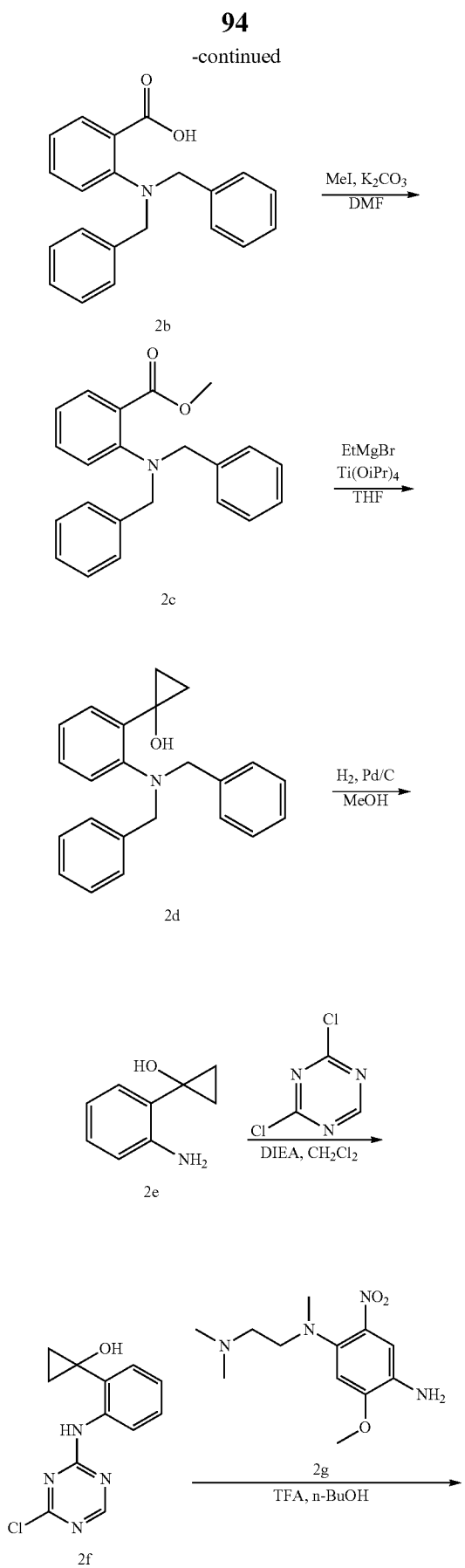

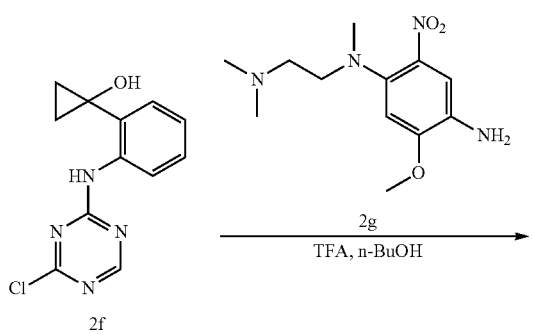

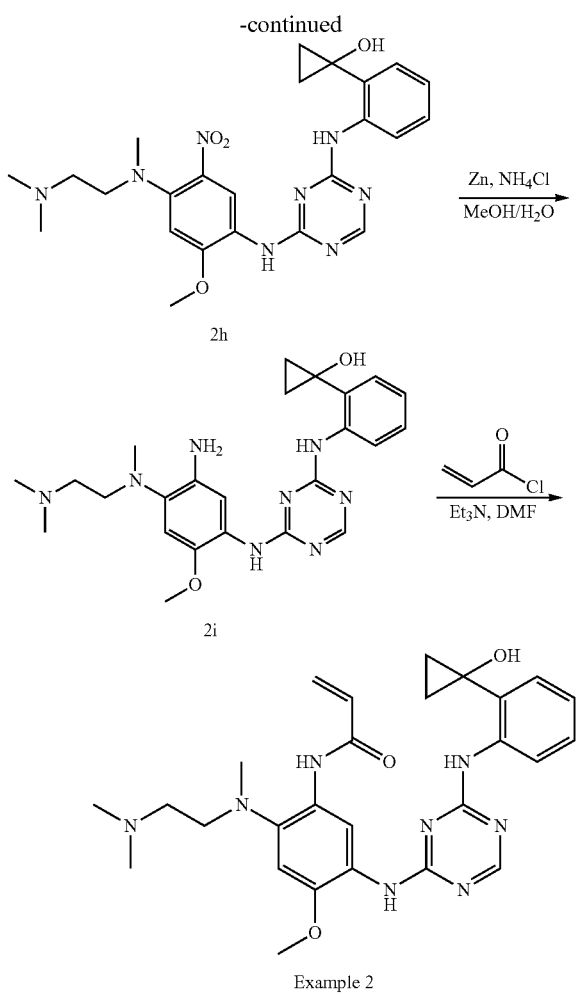

Example 2

Procedure for the Preparation of Compound 2b:

To a mixture of compound 2a (50 g, 253.5 mmol) in THF (500 mL) was added n-BuLi drop wise (140 mL, 2.5 M, 354.8 mmol) at −60° C. over 30 min, the mixture was stirred at −60° C. for 1 h. Then 2-fluorobenzoic acid (32 g, 228.1 mmol) was added and the resulting mixture was stirred at room temperature for 20 h. The reaction was quenched by aqueous NH$_4$Cl (1000 mL) at 0° C. The resulting mixture was extracted with EtOAc (300 mL×3). The combined organic layers were dried over Mg$_2$SO$_4$ and concentrated in vacuo. The residue was purified by column chromatography on silica gel (petroleum ether:EtOAc=3:1) to afford compound 2b (25 g, 31% yield) as colorless oil.

LCMS: R$_t$=0.753 min (MERCK RP18 2.5-2 mm), MS (ESI) m/z=318.0 [M+H].

$^1$H NMR (400 MHz, CDCl$_3$) δ 8.17 (dd, J=8.0, 1.6 Hz, 1H), 7.64-7.56 (m, 1H), 7.49 (d, J=7.6 Hz, 1H), 7.40-7.35 (m, 2H), 7.31-7.25 (m, 5H), 7.24-7.16 (m, 4H), 4.18 (s, 4H).

Procedure for the Preparation of Compound 2c:

To a mixture of compound 2b (25 g, 70.89 mmol) and K$_2$CO$_3$ (29.4 g, 212.67 mmol) in DMF (500 mL) was added MeI (20.1 g, 141.78 mmol). Then the reaction mixture was stirred at 25° C. for 1 h. The reaction mixture was poured into water (1200 mL), and extracted with EtOAc (400 mL×3). The combined organic layers were washed with brine (300 mL×3), dried over sodium sulfate, filtered, and the filtrate was concentrated to give compound 2c (27 g, crude) as yellow oil.

LCMS: R$_t$=0.822 min in 5-95AB_1.5min_220&254 chromatography (MERCK RP18 2.5-2 mm), MS (ESI) m/z=332.4 [M+H]$^+$.

$^1$H NMR (400 MHz, CDCl$_3$) δ 7.72 (dd, J=1.6 Hz, 8.0 Hz, 1H), 7.34-7.23 (m, 11H), 7.00-6.95 (m, 2H), 4.27 (s, 4H), 3.91 (s, 3H).

Procedure for the Preparation of Compound 2d:

To a mixture of compound 2c (27 g, 81.47 mmol) in THF (250 mL) was added dropwise Ti(OiPr)$_4$ (6.9 mg, 24.44 mmol) at 80° C. under N$_2$ balloon. Then EtMgBr (109 mL, 325.88 mmol) was added, and the reaction mixture was stirred at 80° C. for 1 h. The reaction mixture was poured into saturated NH$_4$Cl solution (200 mL), and extracted with EtOAc (80 mL×3). The combined organic layers were washed with brine (60 mL), dried over sodium sulfate, filtered, and the filtrate was concentrated to give the crude product, which was purified by column chromatography on silica gel (10% EtOAc in petroleum ether) to give compound 2d (17 g, 63% yield) as yellow oil.

LCMS: R$_t$=0.760 min in 5-95AB_1.5min_220&254 chromatography (MERCK RP18 2.5-2 mm), MS (ESI) m/z=330.1 [M+H]$^+$.

$^1$H NMR (400 MHz, CDCl$_3$) δ 7.87 (brs, 1H), 7.25-7.15 (m, 6H), 7.14-7.08 (m, 5H), 7.05-6.97 (m, 2H), 6.92 (dd, J=1.2 Hz, 8.0 Hz, 1H), 4.11 (s, 4H), 1.09-1.03 (m, 2H), 0.93-0.87 (m, 2H).

Procedure for the Preparation of Compound 2e:

To a mixture of compound 2d (0.5 g, 1.52 mmol) in MeOH (8 mL) was added Pd/C (wet) (100 mg) and AcOH (0.1 mL) under H$_2$ balloon. The reaction mixture was stirred at 20-25° C. for 40 h. The reaction mixture were filtered, and the filtrate was concentrated and purified by column chromatography on silica gel (petroleum ether:EtOAc=3:1) to compound 2e (200 mg, 29% yield) as colorless oil.

$^1$H NMR (400 MHz, CDCl$_3$) δ 7.19-7.12 (m, 2H), 6.75-6.70 (m, 2H), 4.30 (brs, 2H), 1.19-1.15 (m, 2H), 0.10-0.95 (m, 2H).

Procedure for the Preparation of Compound 2f:

To a mixture of compound 2e (200 mg, 1.34 mmol) and DIEA (346 mg, 2.68 mmol) in CH$_2$Cl$_2$ (8 mL) was added 2,4-dichloro-1,3,5-triazine (241 mg, 1.61 mmol). Then the reaction mixture was stirred at 25° C. for 12 h. The reaction mixture was concentrated, and purified by column chromatography on silica gel (30% EtOAc in petroleum ether) to give 1-(2-((4-chloro-1,3,5-triazin-2-yl)amino)phenyl) cyclopropanol 2f (220 mg, 62% yield) as yellow oil.

LCMS: R$_t$=0.718 min in 5-95AB_1.5min_220&254 chromatography (MERCK RP18 2.5-2 mm), MS (ESI) m/z=262.9 [M+H]$^+$.

$^1$H NMR (400 MHz, CDCl$_3$) δ 8.79 (brs, 1H), 8.55 (s, 1H), 8.19 (s, 1H), 7.41-7.33 (m, 1H), 7.33-7.30 (m, 1H), 7.18-7.13 (m, 1H), 1.28-1.24 (m, 2H), 1.03-0.99 (m, 2H).

Procedure for the Preparation of Compound 2g:

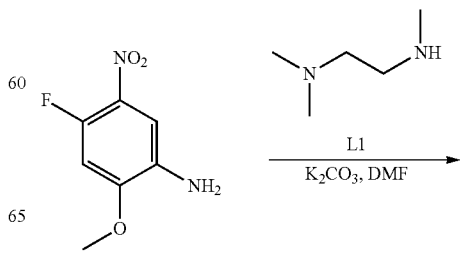

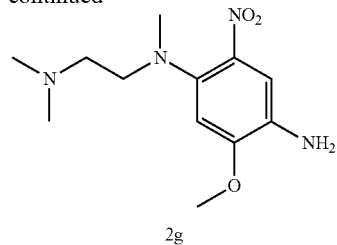

2g

A solution of 4-fluoro-2-methoxy-5-nitroaniline (20 g, 0.11 mol) and K₂CO₃ (29 g, 0.22 mol) in DMF (200 mL) was added N¹,N¹,N²-trimethylethane-1,2-diamine (13 g, 0.13 mol). The mixture was stirred at 25° C. for 48 hours. The reaction was treated with 1 L water and extracted with EtOAc (300 mL×3). The combined organic layers were washed with brine (500 mL×3). The organic layer was dried over sodium sulfate, filtered and the filtrate was concentrated in vacuum to give compound 2g (30 g, 100% yield) as red oil.

LCMS: $R_t$=0.125 min in 5-95AB_1.5min_220&254 chromatography (MERCK RP18 2.5-2 mm), MS (ESI) m/z=269.0 [M+H]⁺.

¹H NMR: (400 MHz, CDCl₃) δ 7.28 (s, 1H), 6.62 (s, 1H), 3.92 (s, 3H), 3.17 (t, J=7.2 Hz, 2H), 2.50 (t, J=7.2 Hz, 2H), 2.25 (s, 6H).

Procedure for the Preparation of Compound 2h:

To a mixture of compound 2f (140 mg, 0.53 mmol) and compound 2g (56 mg, 0.58 mmol) in n-BuOH (5 mL) was added TFA (0.5 ml). Then the reaction mixture was stirred at 22-28° C. for 12 h. The reaction mixture was concentrated and purified by column chromatography on silica gel (5% MeOH in CH₂Cl₂) to give compound 2h (160 mg, 61% yield) as a brown oil.

LCMS: $R_t$=0.682 min in 5-95AB_1.5min_220&254 chromatography (MERCK RP18 2.5-2 mm), MS (ESI) m/z=495.3 [M+H]⁺.

Procedure for the Preparation of Compound 2i:

To a mixture of compound 2h (110 mg, 0.22 mmol) and NH₄Cl (59 mg, 1.10 mmol) in MeOH (5 mL) and water (0.5 mL) was added Zn (72 mg, 1.10 mmol). Then the reaction mixture was stirred at 90° C. for 1 h. The reaction mixture was filtered, and the filtrate was concentrated to give compound 2i (140 mg, crude) as brown oil.

LCMS: $R_t$=0.636 min in 5-95AB_1.5min_220&254 chromatography (MERCK RP18 2.5-2 mm), MS (ESI) m/z=465.2 [M+H]⁺.

¹H NMR (400 MHz, CDCl₃) δ 8.24 (brs, 1H), 7.83 (brs, 1H), 7.60 (brs, 1H), 7.71-7.40 (m, 2H), 7.20-6.93 (m, 1H), 6.61 (s, 1H), 3.80 (s, 3H), 3.20-2.85 (m, 2H). 2.70-2.25 (m, 11H), 1.16-1.08 (m, 2H), 0.91-0.82 (m, 2H).

Procedure for the Preparation of Example 2:

To a mixture of compound 2i (140 mg, 0.21 mmol) and DIEA (54 mg, 0.42 mmol) in DMF (2 mL) was added acryloyl chloride (21 mg, 0.23 mmol) at 0° C. The reaction mixture was stirred at 24-27° C. for 0.5 h. The reaction mixture was purified by prep-HPLC: [Column: Phenomenex Gemini C18 250*50 mm*10 um; Condition: 35-65% B (A: 0.05% ammonia; B: CH₃CN); Flow rate: 30 ml/min]. Fractions containing the desired compound were lyophilized to afford Example 2 (32.0 mg, 6% yield) as a white solid.

LCMS: $R_t$=1.999 min in 10-80CD_3min_220&254 chromatography (B: XBrige Shield RP18 2.1*50 mm), MS (ESI) m/z=519.3 [M+H]⁺.

¹H NMR (400 MHz, CDCl₃) δ 10.34 (brs, 1H), 10.05 (brs, 1H), 8.78 (brs, 1H), 8.37-8.31 (m, 2H), 7.60 (brs, 1H), 7.30-7.24 (m, 2H), 6.95 (t, J=7.6 Hz, 1H), 6.71 (s, 1H), 6.23-6.21 (m, 2H), 5.64 (t, J=6.0 Hz, 1H), 3.81 (s, 3H), 2.81-2.78 (m, 2H), 2.63 (s, 3H), 2.23-2.18 (m, 9H), 1.31-1.22 (m, 2H), 0.97-0.94 (m, 2H).

HPLC: $R_t$=3.56 min in 10-80CD_1.2 ml chromatography (XBridge Shield RP 18 2.1*50 mm 5 um).

Example 3

N-(2-((2-(dimethylamino)ethyl)(methyl)amino)-5-(4-(6-fluoro-4-(2-hydroxypropan-2-yl)pyridin-3-ylamino)-1,3,5-triazin-2-ylamino)-4-methoxyphenyl)acrylamide

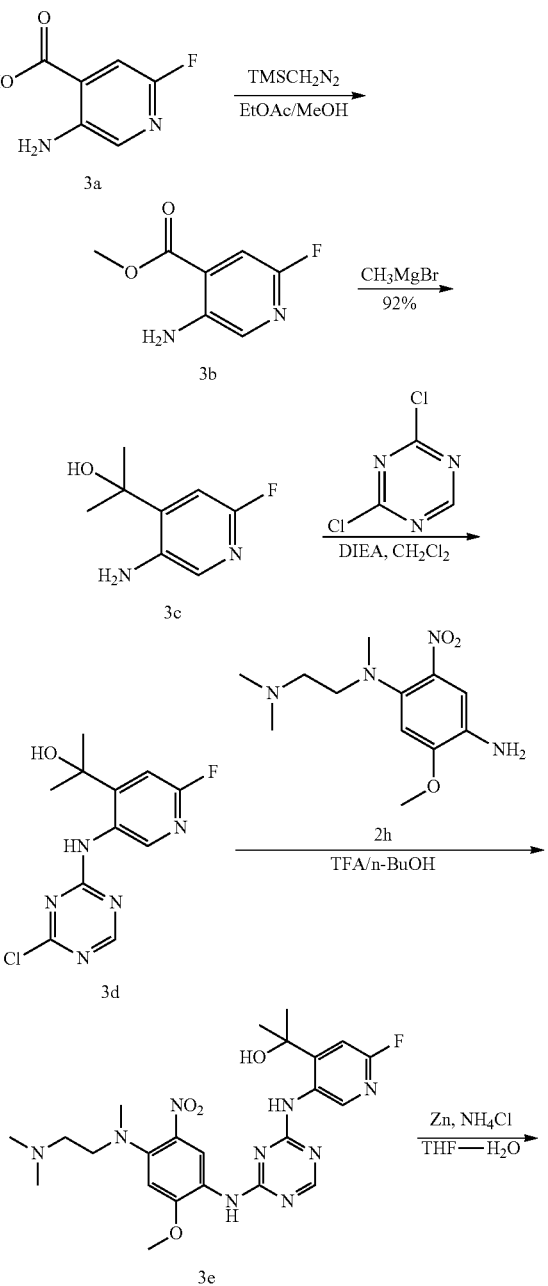

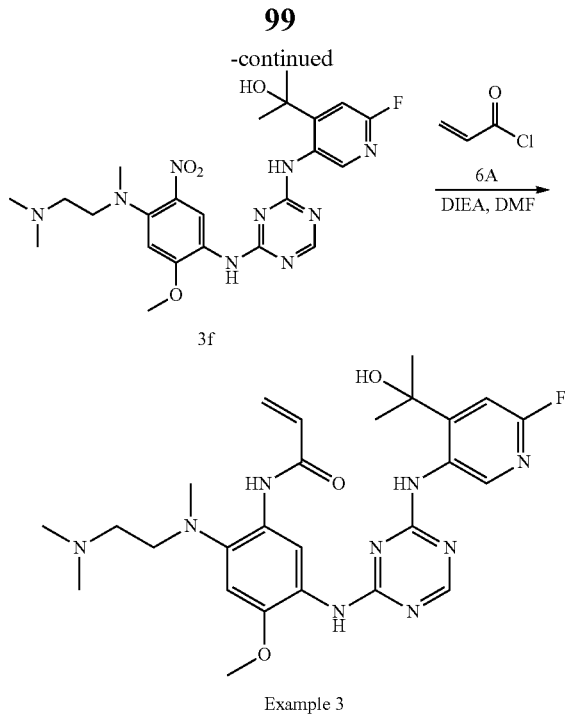

Example 3

Procedure for the Preparation of Compound 3b:

To a solution of compound 3a (700 mg, 4.48 mmol) in EtOAc (20 mL) and MeOH (20 mL) was added TMSCH$_2$N$_2$ (4.48 mL, 8.97 mmol, 2M in hexane). The mixture was stirred at 27-34° C. (room temperature) for 1.5 h. The reaction mixture was concentrated under reduced pressure and purified by column chromatography on silica gel (Petroleum ether/EtOAc=5/1) to afford compound 3b (650 mg: 85% yield) as white solid.

LCMS: R$_t$=0.576 min in 5-95AB_220&254.lcm chromatography (MERCK RP-18e 25-2 mm), MS (ESI) m/z=170.8 [M+H]$^+$.

$^1$H NMR (400 MHz, CDCl$_3$) δ 7.78 (s, 1H), 7.30 (d, J=2.6 Hz, 1H), 5.47 (br s, 2H), 3.94 (s, 3H).

Procedure for the Preparation of Compound 3c:

To a solution of compound 3b (650 mg, 3.82 mmol) in THF (40 mL) was added CH$_3$MgBr (5.1 mL, 3 M in ether) at 0~5° C. The mixture was stirred at 26-33° C. for 1.5 h. The reaction mixture was quenched by the addition of aqueous NH$_4$Cl (20 mL), then extracted with EtOAc (3×40 mL). The organic layers was washed with brine, and concentrated under reduced pressure and purified by column chromatography on silica gel (Petroleum ether/EtOAc=3/1) to afford compound 3c (600 mg, 92% yield) as light-yellow solid.

LCMS: R$_t$=1.572 min in 10-80-7min_220&254.lcm chromatography (MERCK RP-18e 25-2 mm), MS (ESI) m/z=283.9 [M+H]$^+$.

$^1$H NMR (400 MHz, CDCl$_3$) δ 7.47 (d, J=1.4 Hz, 1H), 6.58 (d, J=1.6 Hz, 1H), 1.62-1.58 (m, 6H).

Procedure for the Preparation of Compound 3d:

To a solution of compound 3c (600 mg, 3.52 mmol) and DIEA (683 mg, 5.95 mmol) in CH$_2$Cl$_2$ (40 mL) was added 2,4-dichloro-1,3,5-triazine (581 mg, 3.87 mmol). The resulting mixture was stirred at 26-33° C. (room temperature) for 2 h. The reaction was concentrated under reduced pressure and purified by column chromatography on silica gel (Petroleum ether/EtOAc=1/1) to afford compound 3d (650 m g, 65% yield) as a white solid.

LCMS: R$_t$=1.299 min in 10-80CD_3MIN_220&254.lcm chromatography (XBrige Shield RP18 2.1*50 mm), MS (ESI) m/z=283.9 [M+H]$^+$.

$^1$H NMR (400 MHz, CDCl$_3$) δ 9.85-9.51 (m, 1H), 8.97 (br s, 1H), 8.54 (br s, 1H), 6.85 (d, J=1.6 Hz, 1H), 2.97-2.37 (m, 1H), 1.70 (s, 6H).

Procedure for the Preparation of Compound 3e:

To a solution of compound 3d (600 mg, 2.11 mmol) and compound 2g (624 mg, 2.32 mmol) in n-BuOH (10 mL) was added TFA (0.1 mL). The resulting mixture was stirred at 26-32° C. for 18 h. The reaction mixture was quenched by the addition of aqueous NH$_4$Cl (20 mL), then extracted with EtOAc (3×40 mL). The organic layers were washed with brine (40 mL), dried and concentrated under reduced pressure to give the crude residue, which was purified by column chromatography on silica gel (CH$_2$Cl$_2$/MeOH=10/1) to afford compound 3e (80 mg, 7.3% yield) as red solid.

LCMS: R$_t$=0.662 min in 5-95AB_220&254.lcm chromatography (XBrige Shield RP18 2.1*50 mm), MS (ESI) m/z=516.2 [M+H]$^+$.

Procedure for the Preparation of Compound 3f:

To a solution of compound 3e (80 mg, 0.16 mmol) in THF (1 mL) and H$_2$O (1 mL) was added Zn (30 mg, 0.47 mmol) and NH$_4$Cl (25 mg, 0.47 mmol). The mixture was stirred at 50° C. for 1.5 h under N$_2$. The reaction mixture was quenched by the addition of aqueous NH$_4$Cl (20 mL), then extracted with EtOAc (3×40 mL). The organic layers were washed with brine, dried and concentrated under reduced pressure to afford compound 3f (35 mg) as brown solid.

LCMS: R$_t$=0.596 min in 5-95AB_220&254.lcm chromatography (XBrige Shield RP18 2.1*50 mm), MS (ESI) m/z=486.2 [M+H]$^+$.

Procedure for the Preparation of Example 3:

To a solution of compound 3f (35 mg, 0.07 mmol) and DIEA (14 mg, 0.11 mmol) in DMF (1 mL) was added acryloyl chloride (6.5 mg, 0.07 mmol) in DMF (1 mL). The resulting mixture was stirred at 0° C. for 30 min. The reaction was purified by prep-HPLC [Column: Phenomenex Gemini C18 250*50 mm*10 um; Condition: 43-53% B (A: 0.05% ammonia; B: CH3CN); Flow rate: 30 ml/min]. Fractions containing the desired compound were lyophilized to afford Example 3 (4.2 mg, 10.8% yield) as white solid.

LCMS: R$_t$=3.921 min in 10-80CD_7MIN_220&254.lcm chromatography (XBrige Shield RP18 2.1*50 mm), MS (ESI) m/z=540.3 [M+H]$^+$.

HPLC: R$_t$=3.26 min in 10-80_cd_1.2ML. MET.chromatography (XBridge Shield RP 18 2.1*50 mm 5 um).

$^1$H NMR (400 MHz, CDCl$_3$) δ 10.40 (br s, 1H), 10.11 (br s, 1H), 9.88 (br s, 1H), 9.01 (s, 1H), 8.34 (s, 1H), 7.62 (br s, 1H), 6.78 (s, 1H), 6.71 (s, 1H), 6.30 (br s, 3H), 5.75-5.63 (m, 1H), 3.81 (s, 3H), 2.81 (br s, 2H), 2.63 (s, 3H), 2.21 (br s, 8H), 1.71 (s, 6H).

Example 4

N-(5-(4-(4,5-difluoro-2-(2-hydroxypropan-2-yl)phenylamino)-1,3,5-triazin-2-ylamino)-2-((2-(dimethylamino)ethyl)(methyl)amino)-4-methoxyphenyl)acrylamide

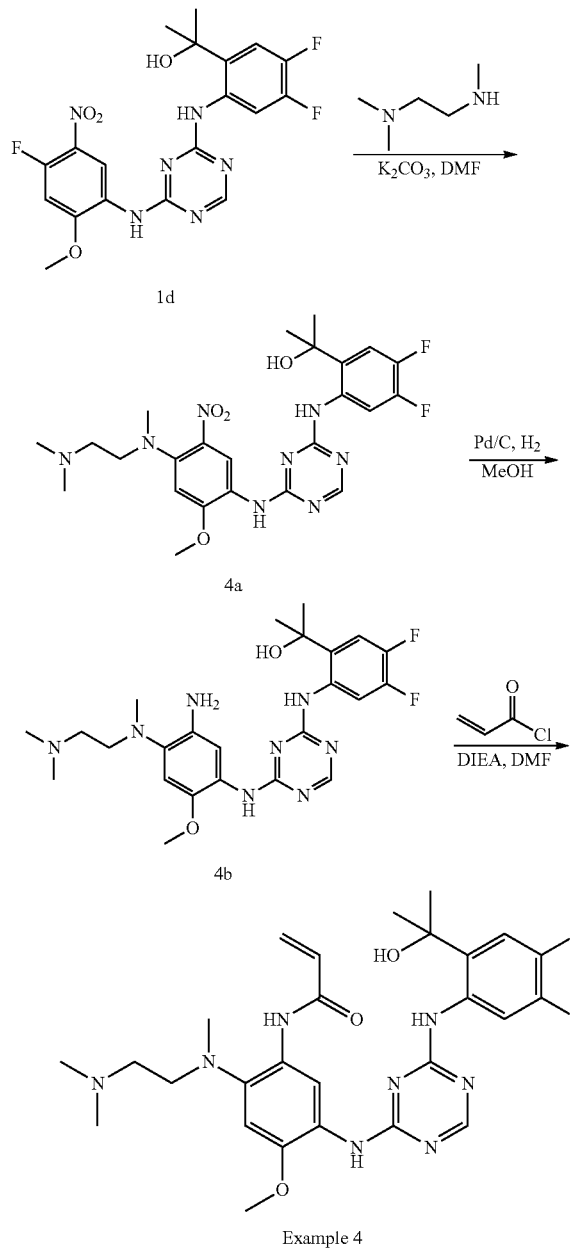

Example 4

Procedure for the Preparation of Compound 4a:

A solution of compound 1d (400 mg, 0.89 mmol), $N^1,N^1,N^2$-trimethylethane-1,2-diamine (91 mg, 0.89 mmol) and $K_2CO_3$ (184 mg, 1.45 mmol) in DMF (5 mL) was stirred at 27-34° C. under $N_2$ for 2 hours. The mixture was added drop wise to water (50 mL), and the resulting mixture was stirred at room temperature for 15 min. The precipitated solid was collected by filtration and then dried under high vacuum to give the title product 4a as an orange solid (270 mg, 57% yield).

LCMS: $R_t$=0.707 min in 5-95AB_220&254.lcm chromatography (MERCK RP-18e 25-2 mm), MS (ESI) m/z=533.1 [M+H]$^+$.

Procedure for the Preparation of Compound 4b:

A solution of compound 4a (270 mg, 0.50 mmol) and Pd/C (20 mg) in MeOH (10 mL) was purged and degassed with $H_2$ for 3 times, then stirred under $H_2$ (15 psi) at 27-34° C. for 2 hours. The reaction mass was filtered through Celite and washed with methanol (3×5 mL). Filtrates were combined and evaporated under vacuum to give the title product 4b as black oil (200 mg, 93% yield).

LCMS: $R_t$=1.224 min in 10-80AB_220&254.lcm chromatography (MERCK RP-18e 25-2 mm), MS (ESI) m/z=503.3 [M+H]$^+$.

$^1$H NMR (400 MHz, CDCl$_3$) δ 10.02 (s, 1H), 8.17-8.12 (m, 2H), 7.66 (s, 1H), 6.98 (dd, J=11.2, 8.8 Hz, 2H), 6.58 (s, 1H), 3.73 (s, 3H), 2.87-2.84 (m, 2H), 2.55 (s, 3H), 2.32 (t, J=6.8 Hz, 2H), 2.15 (s, 6H), 1.55 (s, 6H).

Procedure for the Preparation of Example 4:

A solution of compound 4b (100 mg, 0.20 mmol) and DIEA (38 mg, 0.30 mmol) in DMF (3 mL) was added acryloyl chloride (18 mg, 0.20 mmol) drop wise at 0° C. The mixture was stirred at 26-33° C. for 2 hours. The reaction was purified by prep-HPLC (Column: Phenomenex Gemini C18 150*25 mm*5 um; 45-75% B (A: 0.05% ammonia in water; B: CH$_3$CN); Flow rate: 30 mL/min). Fractions containing the desired compound were lyophilized to give Example 4 as a white solid (14.5 mg, purify 95.7%, 13% yield).

LCMS: $R_t$=2.053 min in 10-80CD_3min_220&254.lcm, chromatography (Xtimate C18, 2.1*30 mm3 um), MS (ESI) m/z=557.3 [M+H]$^+$.

HPLC: $R_t$=4.88 min in 10-80_CD_1.2ml.met.chromatography (Ultimate C18 3.0 um 3.0*50 mm).

$^1$H NMR (400 MHz, CDCl$_3$) δ 10.69 (s, 1H), 10.45 (s, 1H), 9.99 (s, 1H), 8.43 (s, 1H), 8.34 (dd, J=8.0, 12.8 Hz, 1H), 7.70 (s, 1H), 7.13 (dd, J=8.4, 12.0 Hz, 1H), 6.80 (s, 1H), 6.39 (s, 2H), 5.78 (d, J=11.2 Hz, 1H), 3.90 (s, 3H), 2.90 (s, 2H), 2.72 (s, 3H), 2.29 (s, 8H), 1.79 (s, 6H).

Example 5

(E)-N-(5-(4-(4,5-difluoro-2-(2-hydroxypropan-2-yl)phenylamino)-1,3,5-triazin-2-ylamino)-2-((2-(dimethylamino)ethyl)(methyl)amino)-4-methoxyphenyl)-4-(dimethylamino)but-2-enamide

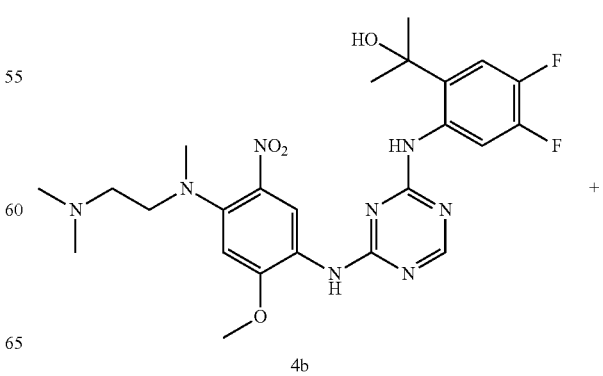

4b

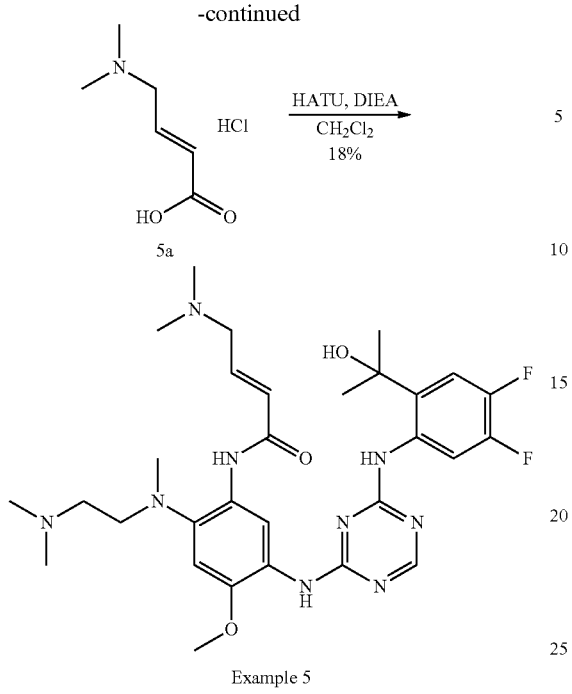

Example 5

Procedure for the Preparation of Example 5:

A mixture of compound 4b (80 mg, 0.16 mmol), compound 5a (31 mg, 0.19 mmol), HATU (91 mg, 0.24 mmol) and DIEA (62 mg, 0.48 mmol) in $CH_2Cl_2$ (4 mL) was stirred at 28-35° C. for 2 hours. The reaction was purified by prep-HPLC (Column: Phenomenex Gemini C18 150*25 mm*5 um; 55-85% B (A: 0.05% ammonia in water; B: $CH_3CN$); Flow rate: 30 mL/min). Fractions containing the desired compound were lyophilized to give Example 5 as a white solid (17.8 mg, 18% yield).

LCMS: $R_t$=1.755 min in 0-60AB_220&254.lcm chromatography (MERCK RP-18e 25-2 mm), MS (ESI) m/z=614.3 $[M+H]^+$.

HPLC: $R_t$=2.15 min in 0-60CD_1.2ml.met. chromatography (Ultimate C18 3.0 um 3.0*50 mm).

$^1$H NMR (400 MHz, $CDCl_3$) δ 10.69 (s, 1H), 10.29 (s, 1H), 9.98 (s, 1H), 8.42 (s, 1H), 8.33 (dd, J=13.2, 8.0 Hz, 1H), 7.69 (s, 1H), 7.12 (dd, J=12.0, 8.8 Hz, 1H), 6.92 (td, J=15.2, 6.0 Hz, 1H), 6.79 (s, 1H), 6.25 (s, 1H), 3.89 (s, 3H), 3.73 (s, 1H), 3.18 (d, J=5.6 Hz, 2H), 2.89 (t, J=5.2 Hz, 2H), 2.71 (s, 3H), 2.33 (s, 8H), 2.30 (s, 6H), 1.79 (s, 6H).

Example 6

N-(2-((2-(dimethylamino)ethyl)(methyl)amino)-5-(4-(4-(2-hydroxypropan-2-yl)-6-methylpyridin-3-ylamino)-1,3,5-triazin-2-ylamino)-4-methoxyphenyl)acrylamide

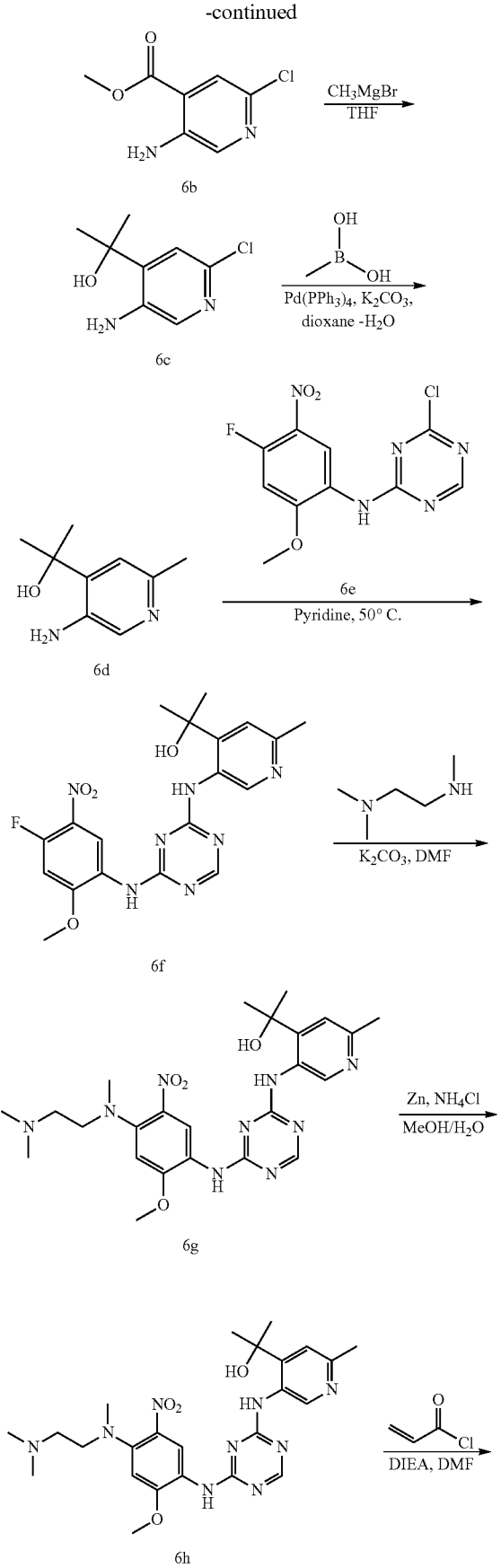

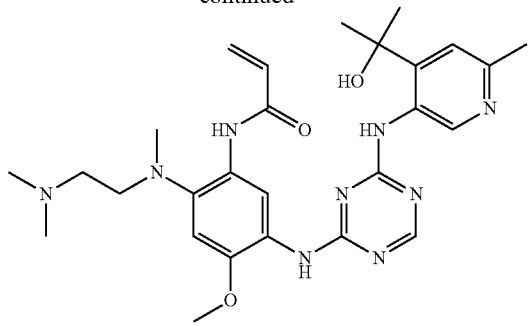

Example 6

Procedure for the Preparation of Compound 6b:

To a solution of compound 6a (4.0 g, 23.2 mmol) in EtOAc/MeOH=1:1 (60 mL) was added TMSCH$_2$N$_2$ (23.2 mL, 46.4 mmol, 2 M in hexane). The resulting mixture was stirred at 24-30° C. for 30 min. The reaction mixture was poured into H$_2$O (30 mL), and extracted with EtOAc (50 mL×3). The combined organic layers were washed with water (20 mL×3) and brine (20 mL), dried over Na$_2$SO$_4$ and concentrated in vacuo to give the title compound 6b (3.1 g, 67.7% yield) as a yellow solid.

LCMS: R$_t$=0.672 min in 5-95AB_220&254.lcm chromatography (ACSSH-LCMS-AB MERCK RP18 2.5-2 mm), MS (ESI) m/z=186.9 [M+H]$^+$.

$^1$H NMR (400 MHz, DMSO-d$_6$) δ 8.06 (s, 1H), 7.50 (s, 1H), 6.79 (br s, 2H), 3.84 (s, 3H).

Procedure for the Preparation of Compound 6c:

To a solution of compound 6b (3.1 g, 16.6 mmol) in THF (40 mL) was added dropwise CH$_3$MgBr (22.2 mL, 66.5 mmol, 3 M in ether) at 0° C. The resulting mixture was stirred at 26-34° C. for 1.5 h under N$_2$. The reaction mixture was poured into saturated NH$_4$Cl (100 mL), and then extracted with EtOAc (100 mL×3). The combined organic layers were washed with water (30 mL×3) and brine (30 mL), dried over Na$_2$SO$_4$ and concentrated in vacuo to give the title compound 6c (2.79 g, 85.6% yield) as a yellow solid.

LCMS: R$_t$=0.471 min in 5-95AB_220&254.lcm chromatography (ACSSH-LCMS-Q MERCK RP18 2.5-2 mm), MS (ESI) m/z=187.0 [M+H]$^+$.

$^1$H NMR (400 MHz, DMSO-d$_6$) δ 7.71 (s, 1H), 6.98 (s, 1H), 5.63 (s, 2H), 5.52 (s, 1H), 1.46 (s, 6H).

Procedure for the Preparation of Compound 6d:

To a solution of compound 6c (1.0 g, 5.36 mmol), methylboronic acid (1.28 g, 21.44 mmol) and K$_2$CO$_3$ (1.48 g, 10.72 mmol) in H$_2$O/dioxane=1:5 (20 mL) was added Pd(PPh$_3$)$_4$ (929 mg, 0.15 eq, 0.80 mmol). The reaction mixture was heated at 100° C. for 24 h under N$_2$. The reaction mixture was filtered, and the filtrate was concentrated in vacuo to give crude product, which was purified by column chromatography on silica gel (4% MeOH in CH$_2$Cl$_2$) to give compound 6d (235 mg, 26.1% yield) as a yellow solid.

LCMS: R$_t$=0.142 min in 5-95AB_220&254.lcm chromatography (ACSSH-LCMS-AB MERCK RP18 2.5-2 mm), MS (ESI) m/z=167.0 [M+H]$^+$.

$^1$H NMR (400 MHz, DMSO-d$_6$) δ 7.79 (s, 1H), 6.81 (s, 1H), 5.34 (s, 1H), 5.25 (br s, 2H), 2.26 (s, 3H), 1.46 (s, 6H).

Procedure for the Preparation of Compound 6e:

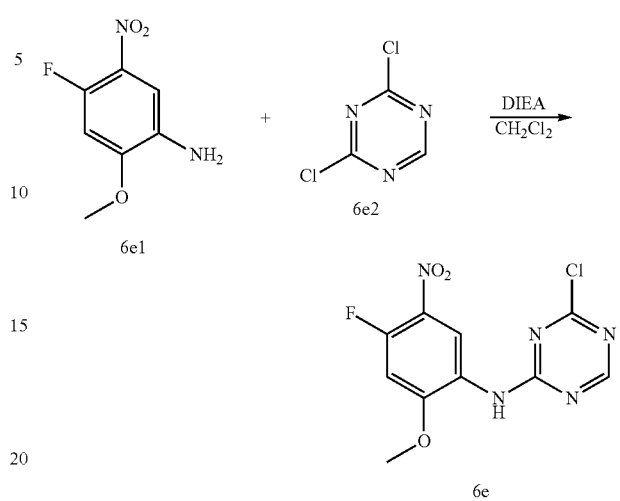

A stirred solution of compound 6e1 (100 g, 537.2 mmol) and DIEA (138.9 g, 1074.4 mmol) in CH$_2$Cl$_2$ (1500 mL) was added with compound 6e2 (96.7 g, 644.6 mmol) at 10° C., then stirred at 25° C. for 1 h. The reaction mixture was concentrated in vacuum directly to give the crude product, which was triturated with CH$_2$Cl$_2$ (800 mL) for 30 min, filtered and the solid cake was washed with CH$_2$Cl$_2$ (100 mL×2). The filter cake was dried in vacuum to give the title compound 6e (118 g, 73% yield) as a yellow solid.

LCMS: R$_t$=0.760 min in 5-95AB_1.5min_220&254 chromatography (MERCK RP18e 25-2 mm), MS (ESI) m/z=299.9 [M+H]$^+$.

$^1$H NMR: (400 MHz, DMSO-d$_6$) δ 10.27 (s, 1H), 8.60 (s, 1H), 8.37 (d, J=8.0 Hz, 1H), 7.41 (d, J=13.6 Hz, 1H), 3.95 (s, 3H).

Procedure for the Preparation of Compound 6f:

A mixture of compound 6d (200 mg, 1.20 mmol) and compound 6e (433 mg, 1.44 mmol) in pyridine (6 mL) was heated at 50° C. for 12 h. The reaction mixture was concentrated in vacuo to give crude product, which was purified by column chromatography on silica gel (5% MeOH in CH$_2$Cl$_2$) to give compound 6f (240 mg, 16% yield) as a puce solid.

LCMS: R$_t$=0.688 min in 5-95AB_220&254.lcm chromatography (ACSSH-LCMS-AB MERCK RP18 2.5-2 mm), MS (ESI) m/z=430.1 [M+H]$^+$.

Procedure for the Preparation of Compound 6g:

To a solution of compound 6f (240 mg, 0.191 mmol) and compound N$^1$,N$^1$,N$^2$-trimethylethane-1,2-diamine (29 mg, 0.286 mmol) in DMF (5 mL) was added K$_2$CO$_3$ (53 mg, 0.382 mmol). The reaction mixture was stirred at 27-34° C. for 12 h. The reaction mixture was poured into H$_2$O (30 mL), and extracted with EtOAc (30 mL×3). The combined organic layers were washed with water (20 mL×3) and brine (20 mL), dried over Na$_2$SO$_4$ and concentrated in vacuo to give compound 6g (120 mg, 91.8% yield) as orange oil.

LCMS: R$_t$=0.633 min in 5-95AB_220&254.lcm chromatography (ACSSH-LCMS-AB MERCK RP18 2.5-2 mm), MS (ESI) m/z=512.2 [M+H]$^+$.

Procedure for the Preparation of Compound 6h:

To a solution of compound 6g (90 mg, 0.131 mmol) in MeOH/H$_2$O=2/1 (9 mL) was added Zn (26 mg, 0.394 mmol) and NH$_4$Cl (21 mg, 0.394 mmol). The resulting mixture was heated at 90° C. for 3 h until TLC (CH$_2$Cl$_2$/MeOH=5/1 (v/v)) showed one main spot (R$_f$=0.25) and the starting material (R$_f$=0.5) was consumed completely. The reaction mixture was extracted with CHCl₃/isopropanol=3/1 (20 mL×3). The combined organic layers were dried over Na₂SO₄, then concentrated in vacuo to give compound 6h (85 mg, 94% yield) as a brown solid.

LCMS: $R_t$=0.571 min in 5-95AB_220&254.lcm chromatography (ACSSH-LCMS-AB MERCK RP18 2.5-2 mm), MS (ESI) m/z=482.3 [M+H]⁺.

Procedure for the Preparation of Example 6:

To a solution of compound 6h (85 mg, 0.123 mmol) and DIEA (24 mg, 0.185 mmol) in DMF (2 mL) was added acryloyl chloride (11 mg, 0.123 mmol) at 0° C. The resulting mixture was stirred at 0° C. for 1 h. The reaction mixture was filtered and the filtrate was purified by pre-HPLC (Column: Phenomenex Gemini C18 250*50 mm*10 um; Condition: 25-55% B (A: 0.05% ammonia, B: CH₃CN); Flow Rate: 30 ml/min) and lyophilized to give impure product as a white solid, which was further purified by pre-TLC (CH₂Cl₂: MeOH=7:1 (v/v)) to give Example 6 (18.4 mg, 27.9% yield) as a white solid.

LCMS: $R_t$=1.969 min in 10-80CD_3min_220&254 chromatography (ACSSH-LCMS-AS A: Xtimate C18, 2.1*30 mm, 3 um; B: XBrige Shield RP18 2.1*50 mm), MS (ESI) m/z=537.3 [M+H]⁺.

¹H NMR: (400 MHz, CDCl₃) δ 10.40 (br s, 1H), 10.20 (br s, 1H), 9.93 (br s, 1H), 9.32 (s, 1H), 8.39 (s, 1H), 7.67 (br s, 1H), 7.04 (s, 1H), 6.77 (s, 1H), 6.47-6.27 (m, 2H), 6.14 (br s, 1H), 5.80-5.69 (m, 1H), 3.87 (s, 3H), 2.90-2.84 (m, 2H), 2.69 (s, 3H), 2.53 (s, 3H), 2.31-2.25 (m, 8H), 1.75 (s, 6H).

Example 7

N-(2-((2-(dimethylamino)ethyl)(methyl)amino)-5-(4-(2-(2-hydroxypropan-2-yl)-6-methylpyridin-3-ylamino)-1,3,5-triazin-2-ylamino)-4-methoxyphenyl)acrylamide

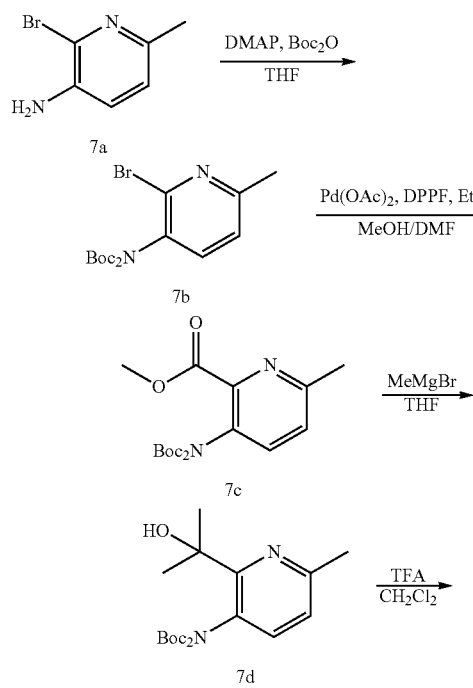

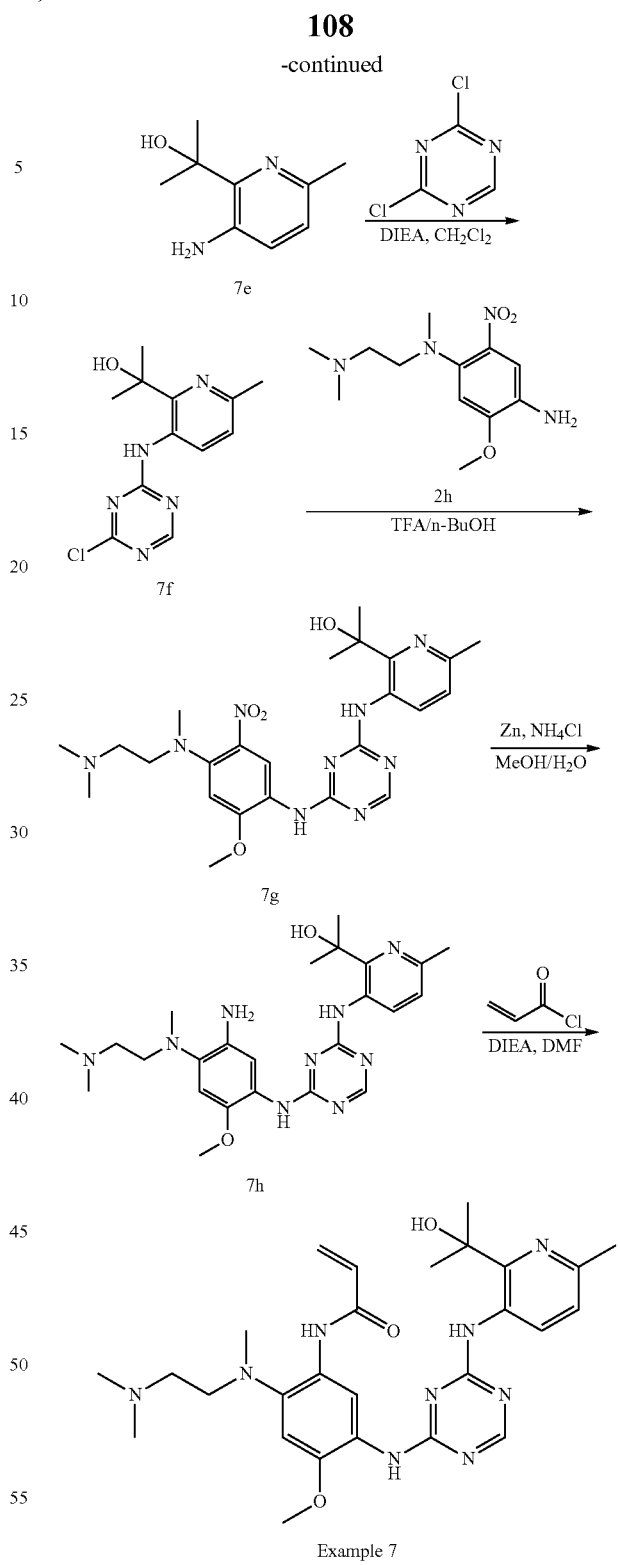

Example 7

Procedure for the Preparation of Compound 7b:

To a mixture of compound 7a (5 g, 26.73 mmol) in anhydrous THF (70 mL) was added DMAP (6.35 g, 53.46 mmol). The reaction mixture was stirred at room temperature for 10 minutes, (Boc)₂O (17.50 g, 80.19 mmol) was added, then stirred at room temperature for 1 hour. The reaction mixture was concentrated in vacuum to give the crude residue, which was purified by column chromatography on silica gel (510% EtOAc in petroleum ether) to afford the desired product 7b (10 g, 96.6% yield) as a light-yellow solid.

LCMS: $R_t$=0.875 min in 5-95AB_220&254.lcm chromatography (ACSSH-LCMS-Q MERCK RP18 2.5-2 mm), MS (ESI) m/z=388.9 [M+H]$^+$.

$^1$H NMR (400 MHz, CDCl$_3$) δ 7.40 (d, J=7.6 Hz, 1H), 7.14 (d, J=7.6 Hz, 1H), 2.57 (s, 3H), 1.41 (s, 18H)

Procedure for the Preparation of Compound 7c:

To a mixture of compound 7b (3.5 g, 9.04 mmol) in anhydrous MeOH (50 mL) and anhydrous DMF (150 mL) was added Pd(OAc)$_2$ (150 mg, 0.1 eq, 0.904 mmol) under nitrogen, followed with DPPF (501 mg, 0.904 mmol) and Et$_3$N (1.37 g, 13.56 mmol). The resulting mixture was stirred at 80° C. for 16 hours under CO atmosphere (50 Psi). The reaction mixture was filtered, and the filtrate was poured into water (10 mL), stirred for additional 10 minutes, extracted with EtOAc (20 mL×3). The combined organic layers were washed with brine (30 mL), dried over anhydrous Na$_2$SO$_4$ and concentrated in vacuum to give the crude residue, which was purified by column chromatography on silica gel (5-8% EtOAc in Petroleum ether) to afford compound 7c (2.0 g, 60.4% yield) as a white solid.

LCMS: $R_t$=0.812 min in 5-95AB_220&254.lcm chromatography (ACSSH-LCMS-Q MERCK RP18 2.5-2 mm), MS (ESI) m/z=367.1 [M+H]$^+$.

Procedure for the Preparation of Compound 7d:

To a mixture of compound 7c (2.0 g, 5.46 mmol) in anhydrous THF (20 mL) was added MeMgBr (9.1 mL, 27.3 mmol, 3 M in ether). The resulting mixture was stirred at 0° C. for 2.5 hours under N$_2$ atmosphere. The reaction mixture was poured into aqueous NH$_4$Cl (25 mL), stirred for 10 minutes, then extracted with EtOAc (30 mL×3). The combined organic layers were washed with brine (30 mL), dried over anhydrous Na$_2$SO$_4$ and concentrated under vacuum to give the title product 7d (1.4 g, 49.8% yield) as yellow oil, which was used in the next step directly without further purification.

LCMS: $R_t$=0.616 min in 5-95AB_220&254.lcm chromatography (ACSSH-LCMS-Q MERCK RP18 2.5-2 mm), MS (ESI) m/z=267.1 [M+H]$^+$.

Procedure for the Preparation of Compound 7e:

To a mixture of compound 7d (1.4 g, 1.13 mmol) in anhydrous CH$_2$Cl$_2$ (9 mL) was added TFA (3 mL). The resulting mixture was stirred at room temperature for 16 hours. The reaction mixture was poured into aqueous NaHCO$_3$ (25 mL) to adjust pH=8.0, stirred for 10 minutes, then extracted with EtOAc (25 mL×3). The combined organic layers were washed with brine (30 mL), dried over anhydrous Na$_2$SO$_4$ and concentrated in vacuum to give the crude residue, which was purified by column chromatography on silica gel (gradient eluent: Petroleum ether: Ethyl acetate=20/1 (v/v)) to afford compound 7e (230 mg, 26.3% yield) as a white solid.

LCMS: $R_t$=0.129 min in 5-95AB_220&254.lcm chromatography (ACSSH-LCMS-Q MERCK RP18 2.5-2 mm), MS (ESI) m/z=167.0 [M+H]$^+$.

$^1$H NMR (400 MHz, Methanol-d$_4$) δ 6.97 (d, J=8.4 Hz, 1H), 6.86 (d, J=8.0 Hz, 1H), 2.35 (s, 3H), 1.58 (s, 6H).

Procedure for the Preparation of Compound 7f:

To a mixture of compound 7e (311 mg, 2.076 mmol) in anhydrous CH$_2$Cl$_2$ (5 mL) was added DIEA (358 mg, 2.768 mmol), followed with compound 2,4-dichloro-1,3,5-triazine (230 mg, 1.0 eq, 1.384 mmol). The resulting mixture was stirred at 25° C. for 1.5 hours. The reaction mixture was poured into water (20 mL) and EtOAc (20 mL), stirred for 5 minute and then extracted with EtOAc (30 mL×3). The combined organic layers were washed with brine (40 mL), dried over anhydrous Na$_2$SO$_4$ and concentrated in vacuum to give the crude residue, which was purified by flash column chromatography on silica gel (1530% EtOAc in Petroleum ether) to afford compound 7f (290 mg, 74.9% yield) as an off-white solid.

LCMS: $R_t$=0.352 min in 5-95AB_220&254.lcm chromatography (ACSSH-LCMS-Q MERCK RP18 2.5-2 mm), MS (ESI) m/z=279.9 [M+H]$^+$.

$^1$H NMR (400 MHz, CDCl$_3$) δ 9.93-9.54 (m, 1H), 8.50 (s, 1H), 8.30 (br d, J=14.4 Hz, 1H), 7.12 (br d, J=8.4 Hz, 1H), 3.07-2.87 (m, 1H), 2.51 (s, 3H), 1.69 (s, 6H).

Procedure for the Preparation of Compound 7g:

To a mixture of compound 7f (290 mg, 1.038 mmol) in n-BuOH (10 mL) was added compound 2g (289 mg, 1.038 mmol) and TFA (0.1 mL). The resulting mixture was stirred at room temperature for 16 hours to afford a dark-red turbid solution. The mixture was concentrated in vacuum directly to give the crude residue, which was purified by flash column chromatography on silica gel (0 to 15% MeOH in CH$_2$Cl$_2$, with 1% ammonia) to afford compound 7g (110 mg, 20.7% yield) as a yellow solid.

LCMS: $R_t$=0.604 min in 5-95AB_220&254.lcm chromatography (ACSSH-LCMS-Q MERCK RP18 2.5-2 mm), MS (ESI) m/z=512.2 [M+H]$^+$.

$^1$H NMR (400 MHz, CDCl$_3$) δ 8.91 (br s, 1H), 8.36 (br s, 1H), 8.24 (br s, 1H), 7.47 (br s, 1H), 7.15 (br d, J=8.4 Hz, 1H), 6.66 (s, 1H), 3.96 (s, 3H), 3.29 (t, J=7.2 Hz, 2H), 2.89 (s, 3H), 2.54 (s, 3H), 2.28 (s, 6H), 1.69 (s, 8H).

Procedure for the Preparation of Compound 7h:

To a solution of compound 7g (110 mg, 0.215 mmol) in MeOH/H$_2$O=5/1 (6 mL) was added Zn (70 mg, 1.075 mmol) and NH$_4$Cl (58 mg, 5.0 eq, 1.075 mmol). The resulting mixture was heated at 90° C. for 3 h. The reaction mixture was filtered, and the filtrate was extracted with CH$_2$Cl$_2$ (20 mL×3). The combined organic layers were washed with water (10 mL×3) and brine (10 mL), dried over Na$_2$SO$_4$ and concentrated in vacuum to give the compound 7h (93 mg, 79.6% yield) as a brown solid.

LCMS: $R_t$=0.554 min in 5-95AB_220&254.lcm chromatography ((ACSSH-LCMS-AB MERCK RP18 2.5-2 mm), MS (ESI) m/z=482.1 [M+H]$^+$.

Procedure for the Preparation of Example 7:

To a solution of compound 7h (93 mg, 0.171 mmol) and DIEA (33 mg, 1.5 eq, 0.256 mmol) in DMF (2 mL) was added acryloyl chloride (15 mg, 1.0 eq, 0.171 mmol) at 0° C. The resulting mixture was stirred at 0° C. for 1 h. The reaction mixture was concentrated in vacuo to give the crude product which was purified by pre-TLC (CH$_2$Cl$_2$: MeOH=7:1 (v/v)) to give impure product as a yellow solid. The crude product was further purified by pre-HPLC (Column: Waters Xbridge 150*25 5 um; Condition: 30-55% B (A: 0.05% ammonia, B: CH$_3$CN); Flow Rate: 25 ml/min) and lyophilized to give Example 7 (20.3 mg, 22.2% yield) as a yellow solid.

LCMS: $R_t$=2.002 min in 10-80CD_3min_220&254 chromatography (ACSSH-LCMS-AS A: Xtimate C18, 2.1*30 mm, 3 um; B: XBrige Shield RP18 2.1*50 mm), MS (ESI) m/z=536.3 [M+H]$^+$.

$^1$H NMR (400 MHz, CDCl$_3$) δ 10.34 (br s, 2H), 9.95 (br s, 1H), 8.43 (d, J=8.4 Hz, 1H), 8.37 (br s, 1H), 7.64 (br s, 1H), 7.07 (d, J=8.4 Hz, 1H), 6.77 (s, 1H), 6.52-6.31 (m, 2H), 5.77 (br d, J=10.4 Hz, 1H), 3.87 (s, 3H), 2.88 (t, J=4.8 Hz, 2H), 2.70 (s, 3H), 2.49 (s, 3H), 2.28 (s, 8H), 1.78 (s, 6H).

Example 8

N-(2-((2-(dimethylamino)ethyl)(methyl)amino)-5-(4-(2-(2-hydroxypropan-2-yl)pyridin-3-ylamino)-1,3,5-triazin-2-ylamino)-4-methoxyphenyl)acrylamide

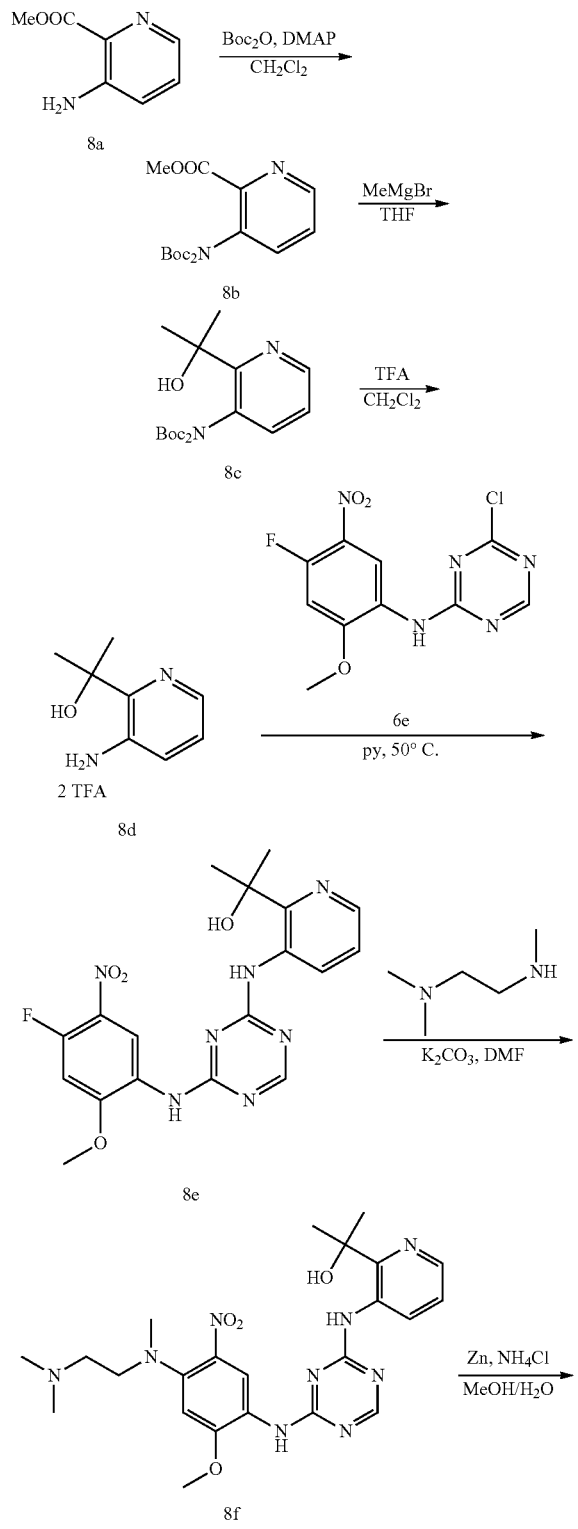

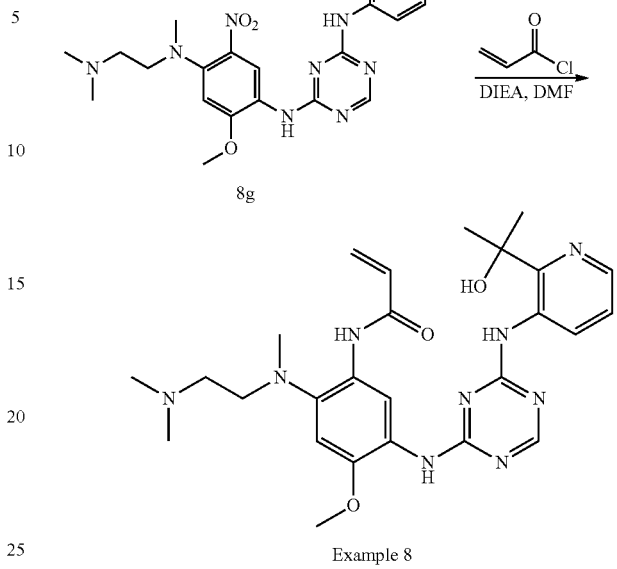

Procedure for the Preparation of Compound 8b:

To a solution of compound 8a (1.0 g, 6.57 mmol) in $CH_2Cl_2$ (20 mL) was added $(Boc)_2O$ (3.6 g, 16.42 mmol) and DMAP (1.2 g, 1.5 eq, 9.85 mmol). The resulting mixture was stirred at 28-38° C. for 4 h. The reaction mixture was concentrated under reduced pressure to give the crude residue, which was purified by column chromatography on silica gel (petroleum ether/EtOAc=50/1 (v/v)) to give compound 8b (2.5 g, 99% yield) as white solid.

LCMS: $R_t$=0.784 min in 5-95AB_220&254.lcm chromatography (MERCK RP-18e 25-2 mm), MS (ESI) m/z=353.0 $[M+H]^+$.

$^1$H NMR (400 MHz, Methanol-$d_4$) δ 8.63 (dd, J=1.4, 4.6 Hz, 1H), 7.85 (dd, J=1.5, 8.0 Hz, 1H), 7.69 (dd, J=4.8, 8.0 Hz, 1H), 3.94 (s, 3H), 1.36 (s, 18H).

Procedure for the Preparation of Compound 8c:

A solution of compound 8b (2.3 g, 6.52 mmol) in THF (30 mL) was purged and degassed with $N_2$ for 3 times and MeMgBr (10.87 mL) was added to it drop wise at 0° C. The resulting mixture was stirred at 29-34° C. for 1 h. The reaction mixture was diluted with saturated aqueous $NH_4Cl$ (10 mL) and extracted with EtOAc (2×20 mL). The combined organic layers was concentrated under reduced pressure and purified by chromatography column on silica gel (Petroleum ether/EtOAc=10/1) to give compound 8c (1 g, 61% yield) as white solid LCMS: $R_t$=0.697 min in 5-95AB_1.5min_220&254 chromatography (MERCK RP18e 25-2 mm), MS (ESI) m/z=253.0$[M+H]^+$.

Procedure for the Preparation of Compound 8d:

To a solution of compound 8c (1 g, 1.0 eq, 3.70 mmol) in $CH_2Cl_2$ (6 mL) was added TFA (2 mL). The resulting mixture was stirred at 29-36° C. for 1 h. The reaction mixture was concentrated under reduced pressure to give compound 8d (1.2 g, 94% yield) as yellow oil (TFA salt).

$^1$H NMR (400 MHz, Methanol-$d_4$) δ 7.85 (dd, J=1.0, 5.3 Hz, 1H), 7.72 (dd, J=1.3, 8.5 Hz, 1H), 7.61 (dd, J=5.5, 8.5 Hz, 1H), 1.70 (s, 6H).

Procedure for the Preparation of Compound 8e:

To a solution of compound 8d (200 mg, 1.0 eq, 0.67 mmol) in pyridine (5 mL) was added compound 6e (256 mg, 1.1 eq, 0.74 mmol). The resulting mixture was stirred at 28-36° C. for 6 h. The reaction mixture was concentrated under reduced pressure and purified by column chromatography on silica gel (CH$_2$Cl$_2$/MeOH=10/1) to give compound 8e (240 mg, 58% yield) as yellow solid.

LCMS: R$_t$=0.687 min in 5-95AB_1.5min_220&254 chromatography (MERCK RP18e 25-2 mm), MS (ESI) m/z=438.1[M+H]$^+$.

Procedure for the Preparation of Compound 8f:

To a solution of compound 8e (240 mg, 1.0 eq, 0.58 mmol) in DMF (10 mL) was added K$_2$CO$_3$ (160 mg, 2.0 eq, 1.16 mmol) and compound N$^1$,N$^1$,N$^2$-trimethylethane-1,2-diamine (118 mg, 2.0 eq, 1.16 mmol). The resulting mixture was stirred at 28-36° C. for 2 h. The reaction mixture was diluted with H$_2$O (200 mL) and extracted with EtOAc (2×100 mL). The combined organic layers was washed with brine (100 mL), dried over anhydrous Na$_2$SO$_4$ and concentrated under reduced pressure to give the crude residue, which was purified by column chromatography on silica gel (CH$_2$Cl$_2$/MeOH=10/1) to give compound 8f (170 mg, 59% yield) as yellow solid.

LCMS: R$_t$=0.643 min in 5-95AB_1.5min_220&254 chromatography (MERCK RP18e 25-2 mm), MS (ESI) m/z=498.2[M+H]$^+$.

Procedure for the Preparation of Compound 8g:

To a solution of compound 8f (170 mg, 1.0 eq, 0.34 mmol) in MeOH (10 mL) and H$_2$O (5 mL) was added Zn (111 mg, 5.0 eq, 1.70 mmol) and NH$_4$Cl (182 mg, 10.0 eq, 3.40 mmol). The resulting mixture was stirred at 80° C. for 2 h. The reaction mixture was concentrated under reduced pressure and extracted with EtOAc (2×10 mL). The combined organic layers was dried over anhydrous Na$_2$SO$_4$ and concentrated under reduced pressure to give compound 8g (140 mg, 88% yield) as white solid.

LCMS: R$_t$=0.554 min in 5-95AB_1.5min_220&254 chromatography (MERCK RP18e 25-2 mm), MS (ESI) m/z=468.2[M+H]$^+$.

Procedure for the Preparation of Example 8:

To a solution of compound 8g (140 mg, 1.0 eq, 0.30 mmol) and DIEA (58 mg, 1.5 eq, 0.45 mmol) in DMF (3 mL) was added acryloyl chloride (27 mg, 1.0 eq, 0.30 mmol). The resulting mixture was stirred at 0° C. for 30 min. The reaction mixture was purified by prep-HPLC [Column: Waters Xbridge 150*25 5 um; Condition: 28-58% B (A: 0.05% NH$_3$H$_2$O; B: CH$_3$CN); Flow rate: 25 ml/min]. Fractions containing the desired compound were lyophilized to afford Example 8 (58.7 mg, 37% yield) as white solid.

LCMS: R$_t$=1.844 min in 10-80CD_3min_220&254 chromatography (XBrige Shield RP18 2.1*50 mm), MS (ESI) m/z=522.3 [M+H]$^+$.

HPLC: R$_t$=3.65 min in 10-80_CD_1.2 ml chromatography (XBridge Shield RP 18 2.1*50 mm 5 um).

$^1$H NMR (400 MHz, CDCl$_3$) δ 10.85 (br s, 1H), 10.41 (br s, 1H), 9.99 (br s, 1H), 8.69 (d, J=7.0 Hz, 1H), 8.41 (s, 1H), 8.23 (dd, J=1.5, 4.5 Hz, 1H), 7.68 (br s, 1H), 7.23 (dd, J=4.9, 8.2 Hz, 1H), 6.79 (s, 1H), 6.48-6.41 (m, 1H), 6.37 (br d, J=10.0 Hz, 1H), 5.78 (br d, J=11.0 Hz, 1H), 3.88 (s, 3H), 2.88 (br s, 2H), 2.71 (s, 3H), 2.28 (s, 8H), 1.83 (s, 6H).

Example 9

N-(5-(4-(3,4-difluoro-2-(2-hydroxypropan-2-yl)phenylamino)-1,3,5-triazin-2-ylamino)-2-((2-(dimethylamino)ethyl)(methyl)amino)-4-methoxyphenyl)acrylamide

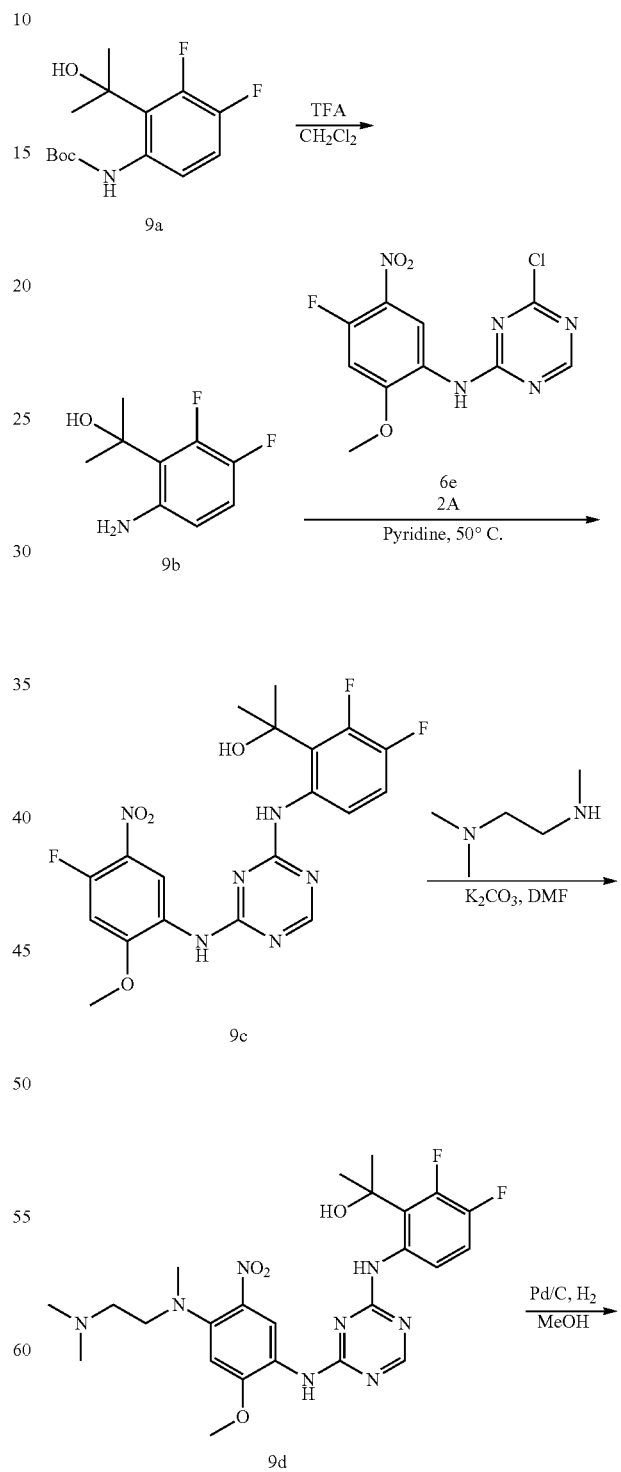

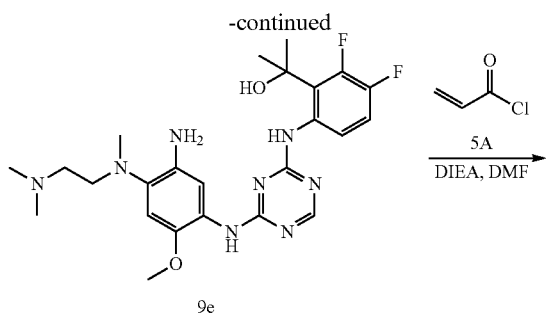

9e

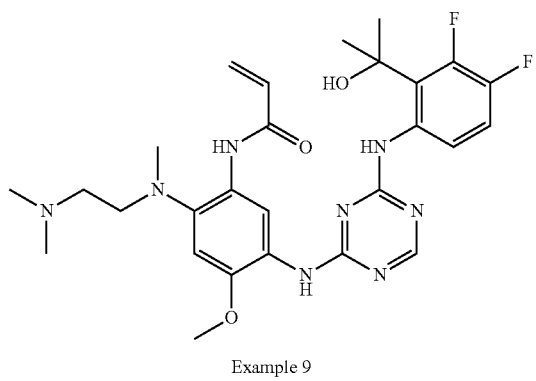 [SMILES: C=CC(=O)Nc1cc(Nc2ncnc(Nc3ccc(F)c(F)c3C(C)(C)O)n2)c(OC)cc1N(C)CCN(C)C]

Example 9

Procedure for the Preparation of Compound 9b:

To a solution of compound 9a (340 mg, 1.0 eq, 1.18 mmol) in CH$_2$Cl$_2$ (6 mL) was added TFA (2 mL). The resulting mixture was stirred at 26-32° C. for 2 h. The resulting mixture was concentrated under reduced pressure to give compound 9b in TFA salt (400 mg, 94% yield) as a yellow solid.

LCMS: R$_t$=0.698 min in 5-95AB_220&254.lcm chromatography (Agilent Pursit 5 C18 20*2.0 mm), MS (ESI) m/z=188.1 [M+H]$^+$.

Procedure for the Preparation of Compound 9c:

To a solution of compound 9b (286 mg, 1.0 eq, 0.95 mmol) in pyridine (10 mL) was added compound 6e (400 mg, 1.1 eq, 1.05 mmol). The resulting mixture was stirred at 50° C. for 6 h. The reaction mixture was concentrated under reduced pressure to give the crude residue, which was purified by column chromatography on silica gel (Petroleum ether/EtOAc=1/1 (v/v)) to give compound 9c (200 mg, 42% yield) as a yellow solid.

LCMS: R$_t$=0.946 min in 5-95AB_1.5min_220&254 chromatography (MERCK RP18 25-2 mm), MS (ESI) m/z=451.1 [M+H]$^+$.

Procedure for the Preparation of Compound 9d:

To a solution of compound 9c (200 mg, 0.44 mmol) in DMF (5 mL) was added K$_2$CO$_3$ (122 mg, 0.88 mmol) and compound N$^1$,N$^1$,N-trimethylethane-1,2-diamine (54 mg, 0.53 mmol). The resulting mixture was stirred at 26-33° C. for 2 h. The reaction mixture was poured to H$_2$O (50 mL) and filtered. The filter cake was concentrated under reduced pressure to give compound 9d (200 mg, 85% yield) as a yellow solid.

LCMS: R$_t$=0.807 min in 5-95AB_1.5min_220&254 chromatography (MERCK RP18 25-2 mm), MS (ESI) m/z=533.2 [M+H]$^+$.

Procedure for the Preparation of Compound 9e:

To a solution of compound 9d (200 mg, 0.38 mmol) in MeOH (5 mL) was added Pd/C (20 mg). The resulting mixture was purged and degassed with H$_2$ for 3 times, then stirred at 26-34° C. (room temperature) under H$_2$ (hydrogen balloon, 30 Psi) for 2 h. The reaction mixture was filtered and concentrated under reduced pressure to give compound 9e (150 mg, 78% yield) as a brown solid.

LCMS: R$_t$=0.752 min in 5-95AB_1.5min_220&254 chromatography (Xtimate C18 2.1*30 mm), MS (ESI) m/z=503.2 [M+H]$^+$.

Procedure for the Preparation of Example 9:

To a solution of compound 9e (150 mg, 0.30 mmol) and DIEA (58 mg, 0.45 mmol) in DMF (3 mL) was added compound acryloyl chloride (27 mg, 0.30 mmol). The resulting mixture was stirred at 0° C. for 30 min. The reaction mixture was purified by prep-HPLC [Column: Waters Xbridge 150*25 5um; Condition: 42-72% B (A: 0.05% NH$_3$H$_2$O; B: CH$_3$CN); Flow rate: 25 ml/min]. Fractions containing the desired compound were lyophilized to afford Example 9 (39.4 mg, 23% yield) as a white solid.

LCMS: R$_t$=1.784 min in 10-80AB_4min_220&254 chromatography (Xtimate C18 2.1*30 mm), MS (ESI) m/z=557.0 [M+H]$^+$.

HPLC: R$_t$=3.12 min in 10-80_ab_1.2ML chromatography (Ultimate C18 3*50 mm 3 um).

$^1$H NMR (400 MHz, CDCl$_3$) δ 11.29 (br s, 1H), 10.45 (br s, 1H), 9.89 (br s, 1H), 8.38 (s, 1H), 8.14 (br dd, J=5.2, 7.2 Hz, 1H), 7.65 (br s, 1H), 7.09 (q, J=9.2 Hz, 1H), 6.78 (s, 1H), 6.44-6.29 (m, 2H), 6.08 (br s, 1H), 5.81-5.74 (m, 1H), 3.88 (s, 3H), 2.92-2.84 (m, 2H), 2.70 (s, 3H), 2.35-2.20 (m, 8H), 1.88 (d, J=3.6 Hz, 6H).

Example 10

N-(2-((2-(dimethylamino)ethyl)(methyl)amino)-5-(4-(2-(3-hydroxyoxetan-3-yl)phenylamino)-1,3,5-triazin-2-ylamino)-4-methoxyphenyl)acrylamide

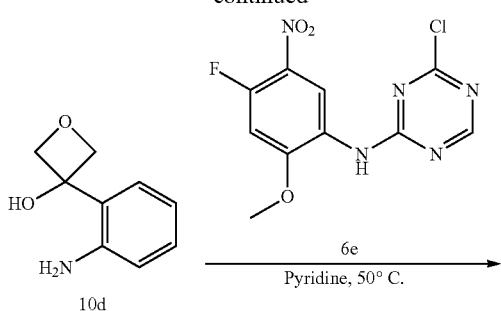

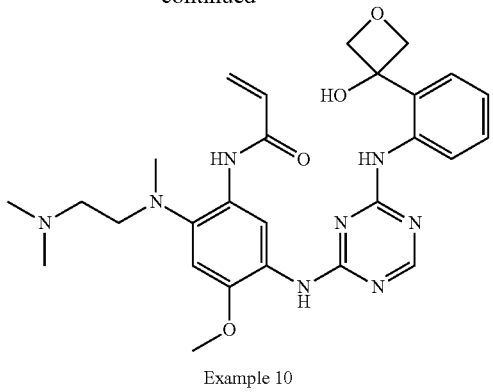

Example 10

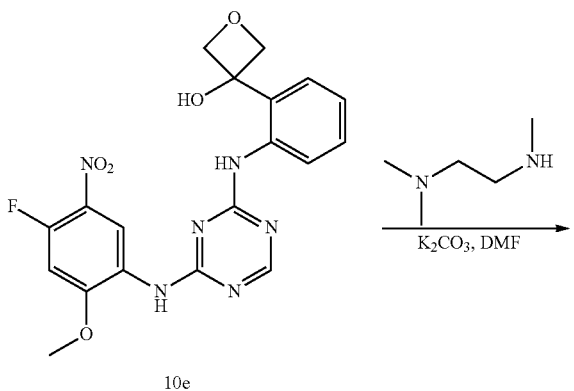

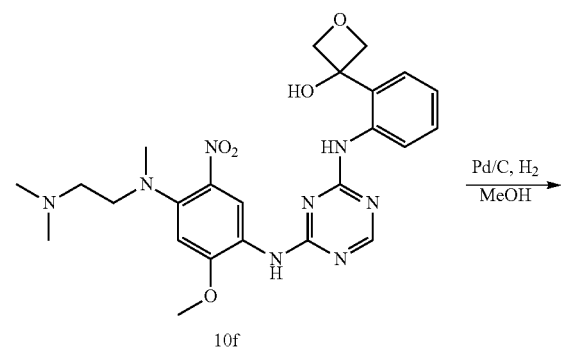

Procedure for the Preparation of Compound 10a:

To a mixture of compound aniline (5 g, 53.69 mmol) in $CHCl_3$ (80 mL) was added $Boc_2O$ (23.4 g, 107.38 mmol). The reaction mixture was stirred at 70° C. for 12 h. The reaction mixture was concentrated in vacuum directly to give the crude residue, which was purified by column chromatography on silica gel (2% EtOAc in petroleum ether) to give the title compound 10a (8 g, 100% yield) as a white solid. LCMS: $R_f$=0.793 min in 5-95AB_220&254 chromatography (MERCK RP18 2.5-2 mm), MS (ESI) m/z=137.9 [M+55]+.

$^1$H NMR (400 MHz, $CDCl_3$) δ 7.38 (d, J=8.0 Hz, 2H), 7.33-7.28 (m, 2H), 7.08-7.03 (m, 1H), 6.50 (brs, 1H), 1.54 (s, 9H).

Procedure for the Preparation of Compound 10b:

To a solution of compound 10a (3.0 g, 1.55 mmol) in THF (50 mL) was added dropwise t-BuLi (30 mL, 38.81 mmol) at −78° C. for 1 h. The reaction mixture was warmed to 0° C. for 15 mins and then cooled to −78° C. Oxetan-3-one (3.36 g, 46.61 mmol) was added drop wise at −78° C. for 15 mins. The resulting mixture was stirred at −78° C. for 1 h. The reaction was quenched by the addition of 100 mL of water and then extracted with EtOAc (3×100 mL).

The organic layers were washed with brine (3×100 mL), dried and concentrated in vacuum to give the crude residue, which was purified by column chromatography on silica gel (Petroleum ether:EtOAc=3/1 (v/v)) to afford compound 10b (580 mg, 14.1% yield) as a white solid.

LCMS: $R_f$=0.722 min in 5-95AB_1.5min_220&254 chromatography (MERCK RP18e 25-2 mm), MS (ESI) m/z=209.9 [M-55]+.

$^1$H NMR (400 MHz, DMSO-$d_6$) δ 8.09 (s, 1H), 7.65 (d, J=7.8 Hz, 1H), 7.40 (dd, J=1.4, 7.8 Hz, 1H), 7.34-7.29 (m, 1H), 7.16-7.11 (m, 1H), 4.88 (d, J=7.0 Hz, 2H), 4.71 (d, J=7.0 Hz, 2H), 1.45 (s, 9H).

Procedure for the Preparation of Compound 10c:

To a solution of compound 10b (500 mg, 1.89 mmol) in MeOH (20 mL) and $H_2O$ (10 mL) was added $K_2CO_3$ (780 mg, 5.66 mmol). The resulting mixture was stirred at 70° C. for 2 h. The reaction mixture was extracted with EtOAc (3×50 mL). The combined organic layers was washed with brine, dried and concentrated in vacuum to give the crude residue, which was purified by column chromatography on silica gel (Petroleum ether/EtOAc=3/1 (v/v)) to afford compound 10c (240 mg, 77.1% yield) as a brown solid.

LCMS: $R_f$=0.553 min in 10-80CD_3MIN_220&254; XBrige Shield RP18 2.1*50 mm, MS (ESI) m/z=166.1 [M+H]+.

$^1$H NMR (400 MHz, DMSO-d$_6$) δ 7.14 (d, J=7.8 Hz, 1H), 7.05-6.99 (m, 1H), 6.70 (d, J=7.8 Hz, 1H), 6.59 (dt, J=1.0, 7.4 Hz, 1H), 6.18 (brs, 1H), 4.89 (d, J=6.8 Hz, 2H), 4.79 (s, 2H), 4.71 (d, J=6.8 Hz, 2H).

Procedure for the Preparation of Compound 10d:

To a solution of compound 10c (500 mg, 1.89 mmol) in MeOH (20 mL) and H$_2$O (10 mL) was added K$_2$CO$_3$ (780 mg, 5.66 mmol). The resulting mixture was stirred at 70° C. for 2 h. The reaction mixture was extracted with EtOAc (3×50 mL). The combined organic layers was washed with brine, dried and concentrated in vacuum to give the crude residue, which was purified by column chromatography on silica gel (Petroleum ether/EtOAc=3/1 (v/v)) to afford compound 10d (240 mg, 77.1% yield) as a brown solid.

LCMS: R$_t$=0.553 min in 10-80CD_3MIN_220&254; XBrige Shield RP18 2.1*50 mm, MS (ESI) m/z=166.1 [M+H]$^+$.

$^1$H NMR (400 MHz, DMSO-d$_6$) δ 7.14 (d, J=7.8 Hz, 1H), 7.05-6.99 (m, 1H), 6.70 (d, J=7.8 Hz, 1H), 6.59 (dt, J=1.0, 7.4 Hz, 1H), 6.18 (brs, 1H), 4.89 (d, J=6.8 Hz, 2H), 4.79 (s, 2H), 4.71 (d, J=6.8 Hz, 2H).

Procedure for the Preparation of Compound 10e:

To a solution of compound 10d (220 mg, 1.33 mmol) in Pyridine (10 mL) was added compound 6e (439 mg, 1.47 mmol). The resulting mixture was stirred at 50° C. for 18 h. The mixture reaction was concentrated under reduced pressure and purified by prep-TLC (CH$_2$Cl$_2$/MeOH=15/1 (v/v)) on silica gel to afford compound 10e (150 mg, 26.3% yield) as a brown solid.

LCMS: R$_t$=0.723 min in 5-95AB_1.5min_220&254 chromatography (MERCK RP18 2.5-2 mm), MS (ESI) m/z=429.1 [M+H]$^+$.

Procedure for the Preparation of Compound 10f:

A solution of compound 10e (190 mg, 0.44 mmol) and K$_2$CO$_3$ (122 mg, 0.89 mmol) in DMF (2 mL) was added with compound N$^1$,N$^1$,N-trimethylethane-1,2-diamine (54 mg, 0.53 mmol). The mixture was stirred at 25-33° C. for 2 hours. The reaction was added 10 mL water, and the mixture was extracted with EtOAc (10 mL×3). The combined organic layers was washed with brine (10 mL×3), dried and concentrated in vacuum to give the crude residue, which was purified by prep-TLC (CH$_2$Cl$_2$/MeOH=15/1 (v/v)) on silica gel to afford compound 10f (140 mg, 62% yield) as a brown solid.

LCMS: R$_t$=0.714 min in 5-95AB_1.5min_220&254 chromatography (MERCK RP18 2.5-2 mm), MS (ESI) m/z=511.3 [M-OH]$^+$.

Procedure for the Preparation of Compound 10g:

To a solution of compound 10f (130 mg, 0.25 mmol) in MeOH (3 mL) was added Pd/C (13 mg) under N$_2$. The mixture was stirred at 26-31° C. under H$_2$ (15 Psi) for 1 h. The reaction mixture was filtered and concentrated under reduced pressure to afford compound 10g (95 mg, 78% yield) as brown oil.

LCMS: R$_t$=0.669 min in 5-95AB_1.5min_220&254 chromatography (5-95AB_1.5MIN_1500), MS (ESI) m/z=481.3 [M+H]$^+$.

Procedure for the Preparation of Example 10:

To a solution of compound 10h (85 mg, 0.18 mmol) and DIEA (34 mg, 0.26 mmol) in DMF (1 mL) was added acryloyl chloride (16 mg, 0.18 mmol) in DMF (1 mL). The resulting mixture was stirred at 0° C. for 30 min. The reaction was purified by prep-HPLC [Column: Waters Xbridge 150*25 5 um; Condition: 25-50% B (A: 0.05% ammonia; B: CH$_3$CN); Flow rate: 25 ml/min]. Fractions containing the desired compound were lyophilized to afford Example 10 (25.2 mg, 26.7% yield) as a brown solid.

LCMS: R$_t$=3.452 min in 10-80CD_7MIN_220&254 chromatography (XBrige Shield RP18 2.1*50 mm), MS (ESI) m/z=535.3 [M+H]$^+$.

HPLC: R$_t$=2.91 min in 10-80_CD_1.2ML chromatography (XBridge Shield RP 18 2.1*50 mm 5 um).

$^1$H NMR (400 MHz, DMSO-d$_6$) δ 10.08 (s, 1H), 8.85 (br s, 1H), 8.47-8.33 (m, 2H), 8.23 (s, 1H), 7.92 (br s, 1H), 7.38 (brd, J=6.6 Hz, 1H), 7.08 (br s, 1H), 6.98 (s, 1H), 6.83 (br s, 1H), 6.47-6.33 (m, 1H), 6.27-6.17 (m, 1H), 5.75 (br d, J=11.4 Hz, 1H), 4.86 (br d, J=6.8 Hz, 2H), 4.70 (brd, J=7.0 Hz, 2H), 3.76 (s, 3H), 2.85 (br t, J=5.6 Hz, 2H), 2.71 (s, 3H), 2.34-2.28 (m, 2H), 2.20 (s, 6H).

Example 11

N-(5-(4-(5-chloro-4-fluoro-2-(2-hydroxypropan-2-yl)phenylamino)-1,3,5-triazin-2-ylamino)-2-((2-(dimethylamino)ethyl)(methyl)amino)-4-methoxyphenyl)acrylamide

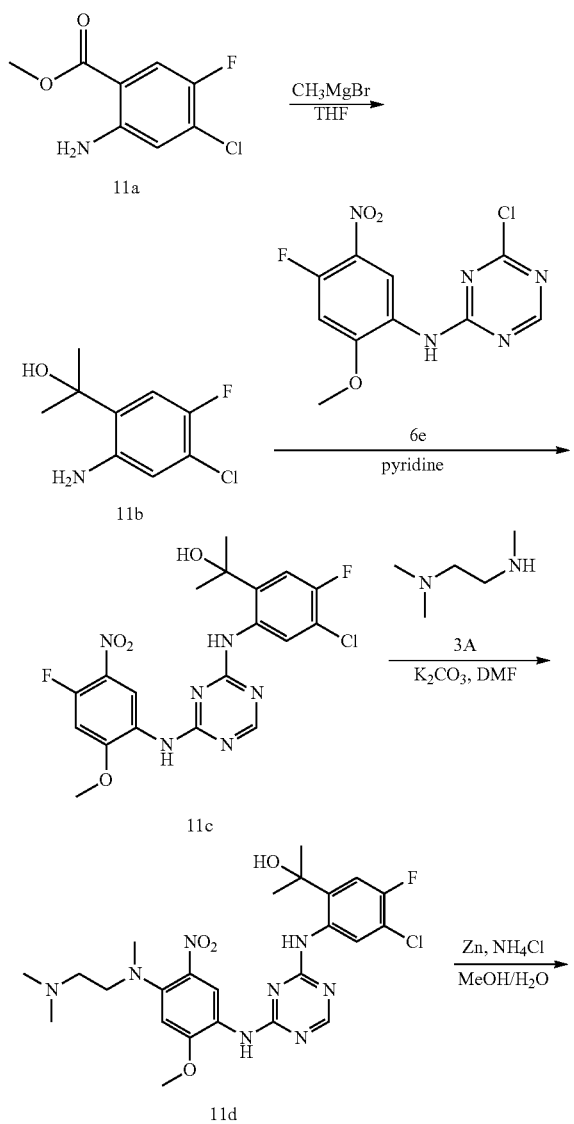

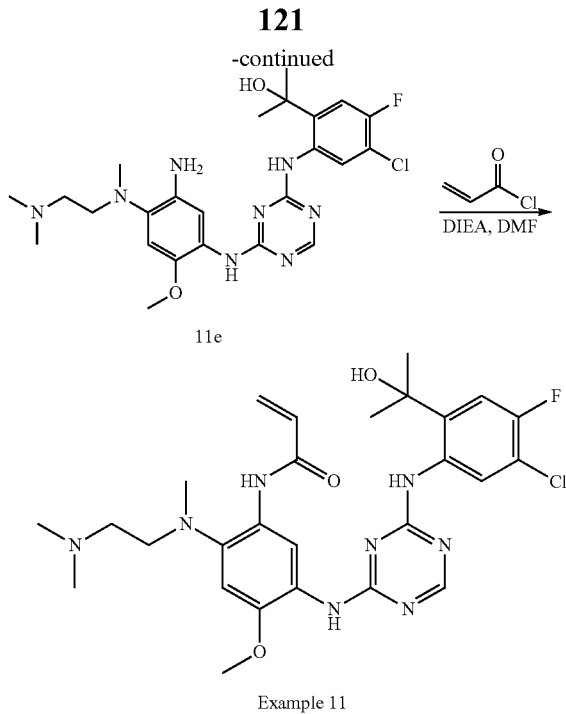

Example 11

Procedure for the Preparation of Compound 11b:

To a solution of compound 11a (2.0 g, 9.83 mmol) in TH (20 mL) was added dropwise CH₃MgBr (16.4 mL, 49.2 mmol, 3 Min ether) at 0° C. The resulting mixture was stirred at 27-34° C. for 2 h under N₂. The reaction mixture was poured into saturated NH₄Cl (100 mL), and extracted with EtOAc (30 mL×3). The combined organic layers were washed with water (20 mL×3) and brine (20 mL), dried over Na₂SO₄ and concentrated in vacuo to give compound 11b (2.0 g, 95% yield) as brown oil.

LCMS: $R_f$=0.558 min in 5-95AB_220&254.lcm chromatography (ACSSH-LCMS-AB MERCK RP18 2.5-2 mm), MS (ESI) m/z=185.9 [M-OH]⁺.

¹H NMR (400 MHz, CDCl₃) δ 6.91 (d, J=10.8 Hz, 1H), 6.63 (d, J=6.4 Hz, 1H), 1.64 (s, 6H).

Procedure for the Preparation of Compound 11c:

A mixture of compound 11b (1.9 g, 9.3 mmol) and compound 6e (2.8 g, 9.3 mmol) in pyridine (20 mL) was heated at 50° C. for 12 h. The reaction mixture was concentrated in vacuo to give crude product, which was purified by column chromatography on silica gel (50% EtOAc in petroleum ether) to give compound 11c (2.6 g, 60% yield) as a light yellow solid.

LCMS: $R_f$=0.821 min in 5-95AB_220&254.lcm chromatography (MERCK RP18 2.5-2 mm), MS (ESI) m/z=467.1 [M+H]⁺.

¹H NMR (400 MHz, CDCl₃) δ 9.73 (br s, 1H), 9.42 (br s, 1H), 8.49 (s, 1H), 8.33 (br s, 1H), 7.54 (s, 1H), 7.09 (d, J=10.4 Hz, 1H), 6.78 (d, J=12.0 Hz, 1H), 4.03 (s, 3H), 2.51 (br s, 1H), 1.71 (s, 6H).

Procedure for the Preparation of Compound 11d:

To a solution of compound 11d (740 mg, 1.59 mmol) and K₂CO₃ (439 mg, 3.18 mmol) in DMF (10 mL) was added N¹,N¹,N-trimethylethane-1,2-diamine (244 mg, 2.39 mmol). The reaction mixture was stirred at 26-31° C. for 4 h. The reaction mixture was added dropwise into H₂O (100 mL) under ice water bath, then filtered, the filter cake was washed with H₂O (15 mL×3), and dried in high vacuum to give compound 11e (800 mg, 91.65% yield) as an orange solid.

LCMS: $R_f$=0.717 min in 5-95AB_220&254.lcm chromatography (MERCK RP18 2.5-2 mm), MS (ESI) m/z=549.1 [M+H]⁺.

¹H NMR (400 MHz, CDCl₃) δ 9.70 (br s, 1H), 9.00 (br s, 1H), 8.39 (br s, 2H), 7.42 (br s, 1H), 7.08 (d, J=10.5 Hz, 1H), 6.64 (s, 1H), 3.95 (s, 3H), 3.28 (t, J=7.2 Hz, 2H), 2.88 (s, 3H), 2.57 (t, J=7.2 Hz, 2H), 2.25 (s, 6H), 1.69 (s, 6H).

Procedure for the Preparation of Compound 11e:

To a solution of compound 11d (200 mg, 0.364 mmol) in 8 mL MeOH/H₂O=5/1 (v/v) was added Zn (119 mg, 1.82 mmol) and NH₄Cl (97 mg, 1.82 mmol). The resulting mixture was heated at 90° C. for 1 h. The reaction mixture was filtered, and the filtrate was concentrated in vacuo to give the residue, which was dissolved with CH₂Cl₂ (30 mL), washed with water (20 mL×3) and brine (20 mL), dried over Na₂SO₄ and concentrated in vacuo to give compound 11e (180 mg, 95.3% yield) as brown oil.

LCMS: $R_f$=0.679 min in 5-95AB_220&254.lcm chromatography (MERCK RP18 2.5-2 mm), MS (ESI) m/z=519.1 [M+H]⁺.

Procedure for the Preparation of Example 11:

To a solution of compound 11e (180 mg, 0.35 mmol) and DIEA (68 mg, 0.53 mmol) in DMF (3 mL) was added acryloyl chloride (32 mg, 0.35 mmol) at 0° C. The resulting mixture was stirred at 0° C. for 1 h. The reaction was quenched by H₂O (0.1 mL) and then filtered. The filtrate was purified by pre-HPLC (Column: Waters Xbridge 150*25 5 um; Condition: 52-82% B (A: 0.05% ammonia, B: CH₃CN); Flow Rate: 25 ml/min) and lyophilized to give Example 11 (52.9 mg, 26.4% yield) as a white solid.

LCMS: $R_f$=2.124 min in 10-80CD_3min_220&254 chromatography (XBrige Shield RP18 2.1*50 mm), MS (ESI) m/z=573.3 [M+H]⁺.

¹H NMR (400 MHz, CDCl₃) δ 10.60 (br s, 1H), 10.44 (br s, 1H), 9.96 (br s, 1H), 8.47 (d, J=7.6 Hz, 1H), 8.42 (s, 1H), 7.69 (br s, 1H), 7.10 (d, J=10.8 Hz, 1H), 6.78 (s, 1H), 6.49-6.28 (m, 2H), 6.18 (br s, 1H), 5.91-5.65 (m, 1H), 3.88 (s, 3H), 2.88 (t, J=5.6 Hz, 2H), 2.70 (s, 3H), 2.27 (s, 8H), 1.77 (s, 6H).

Example 12

N-(5-(4-(4-chloro-5-fluoro-2-(2-hydroxypropan-2-yl)phenylamino)-1,3,5-triazin-2-ylamino)-2-((2-(dimethylamino)ethyl)(methyl)amino)-4-methoxyphenyl)acrylamide

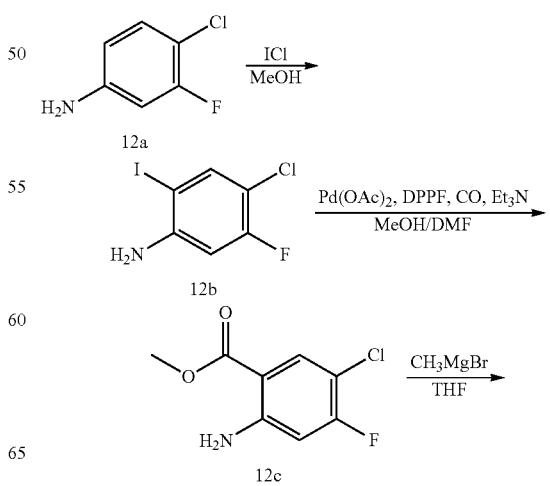

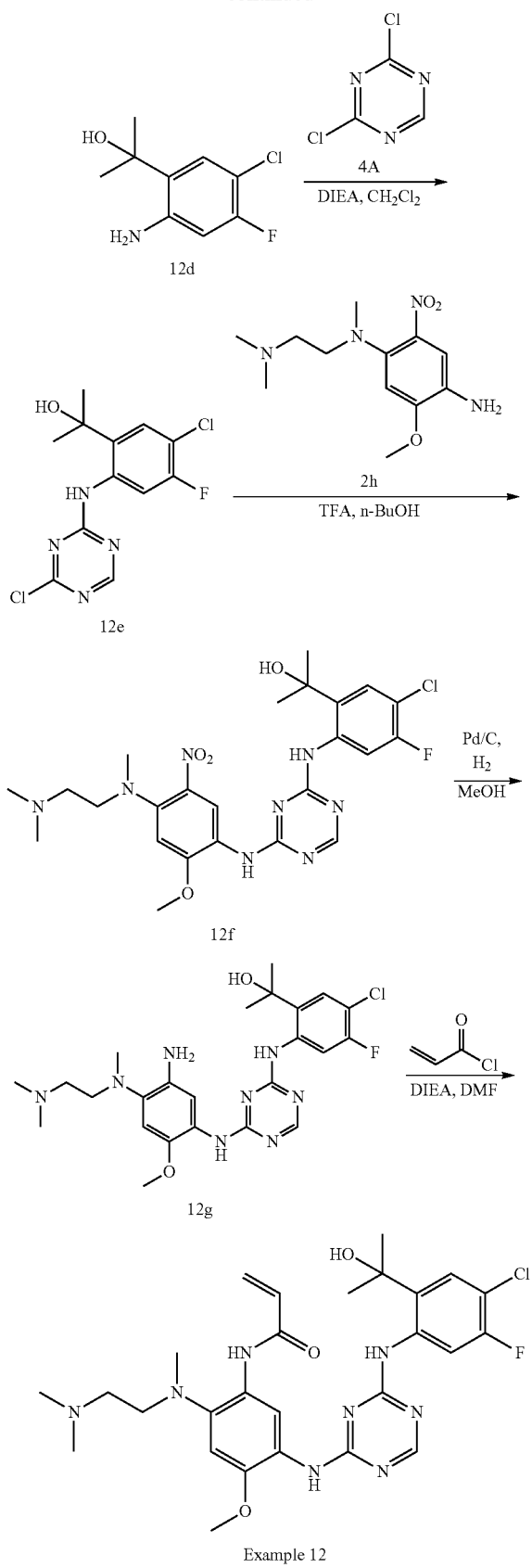

Example 12

Procedure for the Preparation of Compound 12b:
To a solution of compound 12a (2 g, 13.74 mmol) in CH$_2$Cl$_2$ (20 mL) was added IC (3.3 g, 20.61 mmol) at 0° C. The resulting mixture was stirred at 27-34° C. for 2 h. The reaction mixture was concentrated under reduced pressure and purified by column chromatography on silica gel (Petroleum ether/EtOAc=100/1) to give compound 12b (2.5 g, 67% yield) as a brown solid.
LCMS: R$_t$=0.811 min in 5-95AB_220&254.lcm chromatography (MERCK RP-18 25-2 mm), MS (ESI) m/z=271.8 [M+H]$^+$.
$^1$H NMR (400 MHz, Methanol-d$_4$) δ 7.59 (d, J=8.0 Hz, 1H), 6.62 (d, J=11.6 Hz, 1H).

Procedure for the Preparation of Compound 12c:
To a solution of compound 12b (450 mg, 1.66 mmol) in MeOH (10 mL) and DMF (20 mL) was added Pd(OAc)$_2$ (38 mg, 0.17 mmol), DPPF (94 mg, 0.17 mmol) and Et$_3$N (504 mg, 4.98 mmol). The resulting mixture was purged and degassed with CO for 3 times, then stirred at 80° C. under CO (50 Psi) for 24 h. The reaction mixture was filtered and diluted with EtOAc (50 mL). The organic layer was washed with brine (50 mL), dried and concentrated under reduced pressure to give the crude residue, which was purified by column chromatography on silica gel (petroleum ether/EtOAc=50/1 (v/v)) to give compound 12c (320 mg, 95% yield) as a white solid.
LCMS: R$_t$=0.941 min in 5-95AB_1.5min_220&254 chromatography (MERCK RP18 25-2 mm), MS (ESI) m/z=203.9[M+H]$^+$.
$^1$H NMR (400 MHz, MeOH-d$_4$) δ 7.83 (d, J=8.4 Hz, 1H), 6.59 (d, J=11.6 Hz, 1H), 3.85 (s, 3H).

Procedure for the Preparation of Compound 12d:
To a solution of compound 12c (320 mg, 1.57 mmol) in THF (10 mL) was added CH$_3$MgBr (2.62 mL, 7.85 mmol) at 0° C. The resulting mixture was stirred at 26-31° C. for 2 h. The reaction mixture was diluted with sat aq NH$_4$Cl (10 mL) and extracted with EtOAc (2×20 mL). The combined organic layers were concentrated under reduced pressure and purified by column chromatography on silica gel (Petroleum ether/EtOAc=10/1 (v/v)) to give compound 12d (250 mg, 78% yield) as colorless oil.
LCMS: R$_t$=0.826 min in 5-95AB_1.5min_220&254 chromatography (MERCK RP18 25-2 mm), MS (ESI) m/z=185.9 [M+H-18]$^+$.
$^1$H NMR (400 MHz, MeOH-d$_4$) δ 7.08 (d, J=8.4 Hz, 1H), 6.49 (d, J=11.6 Hz, 1H), 1.57 (s, 6H).

Procedure for the Preparation of Compound 12e:
To a solution of compound 12d (200 mg, 0.98 mmol) in CH$_2$Cl$_2$ (10 mL) was added DIEA (253 mg, 1.96 mmol) and 2,4-dichloro-1,3,5-triazine (162 mg, 1.08 mmol). The resulting mixture was stirred at 26-32° C. for 2 h. The reaction was concentrated under reduced pressure and purified by column chromatography on silica gel (Petroleum ether/EtOAc=10/1 (v/v)) to give compound 12e (210 mg, 67% yield) as a white solid.
LCMS: R$_t$=0.971 min in 5-95AB_1.5min_220&254 chromatography (MERCK RP18 25-2 mm), MS (ESI) m/z=316.9 [M+H]$^+$.

Procedure for the Preparation of Compound 12f:
To a solution of compound 12e (210 mg, 0.66 mmol) and compound 2g (177 mg, 0.66 mmol) in n-BuOH (5 mL) was added TFA (0.05 mL). The resulting mixture was stirred at 26-33° C. for 1 h. The reaction mixture was concentrated under reduced pressure and purified by column chromatography on silica gel (CH$_2$Cl$_2$/MeOH=10/1 (v/v)) to give compound 12f (150 mg, 41% yield) as brown oil.

LCMS: $R_t$=0.821 min in 5-95AB_1.5min_220&254 chromatography (MERCK RP18 25-2 mm), MS (ESI) m/z=549.1[M+H]$^+$.

Procedure for the Preparation of Compound 12g:

To a solution of compound 12f (150 mg, 0.27 mmol) in MeOH (5 mL) was added 10% Pd/C (15 mg). The resulting mixture was purged and degassed with H$_2$ for 3 times, then stirred at 26-34° C. (room temperature) under H$_2$ (30 Psi) for 2 h. The reaction mixture was filtered and concentrated under reduced pressure to give compound 12g (110 mg, 78% yield) as a brown solid.

LCMS: $R_t$=0.771 min in 5-95AB_1.5min_220&254 chromatography (Xtimate C18 2.1*30 mm), MS (ESI) m/z=519.1 [M+H]$^+$.

Procedure for the Preparation of Example 12:

To a solution of compound 12g (110 mg, 0.21 mmol) and DIEA (41 mg, 0.32 mmol) in DMF (3 mL) was added acryloyl chloride (19 mg, 0.21 mmol). The resulting mixture was stirred at 0° C. for 30 min. The reaction mixture was purified by prep-HPLC [Column: Waters Xbridge 150*25 5 um; Condition: 50-80% B (A: 0.05% NH$_3$H$_2$O; B: CH$_3$CN); Flow rate: 25 ml/min]. Fractions containing the desired compound were lyophilized to afford Example 12 (13.5 mg, 11% yield) as a white solid.

LCMS: $R_t$=2.167 min in 10-80AB_4min_220&254 chromatography (Xtimate C18 2.1*30 mm), MS (ESI) m/z=573.0 [M+H]$^+$.

HPLC: $R_t$=3.38 min in 10-80_ab_1.2ML chromatography (Ultimate C18 3*50 mm 3 um).

$^1$H NMR (400 MHz, CDCl$_3$) δ 10.85 (br s, 1H), 10.45 (br s, 1H), 9.96 (br s, 1H), 8.43 (s, 1H), 8.39 (d, J=11.8 Hz, 1H), 7.72 (br s, 1H), 7.29 (d, J=8.4 Hz, 1H), 6.78 (s, 1H), 6.43-6.32 (m, 2H), 6.10 (br s, 1H), 5.81-5.73 (m, 1H), 3.88 (s, 3H), 2.91-2.85 (m, 2H), 2.70 (s, 3H), 2.35-2.20 (m, 8H), 1.78 (s, 6H).

Example 13

N-(2-((2-(dimethylamino)ethyl)(methyl)amino)-5-(4-(2-(2-hydroxypropan-2-yl)-4-(trifluoromethyl)phenylamino)-1,3,5-triazin-2-ylamino)-4-methoxyphenyl)acrylamide

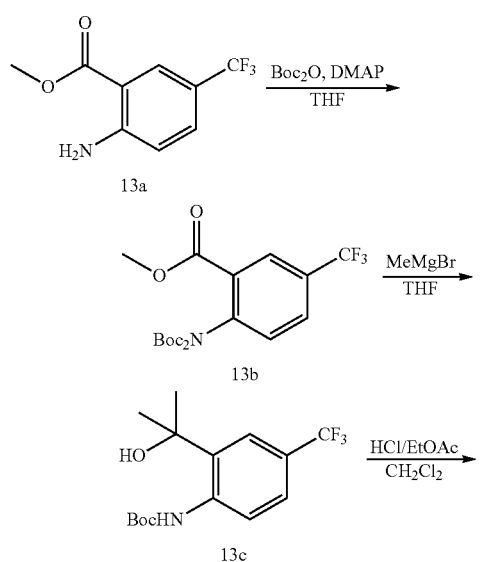

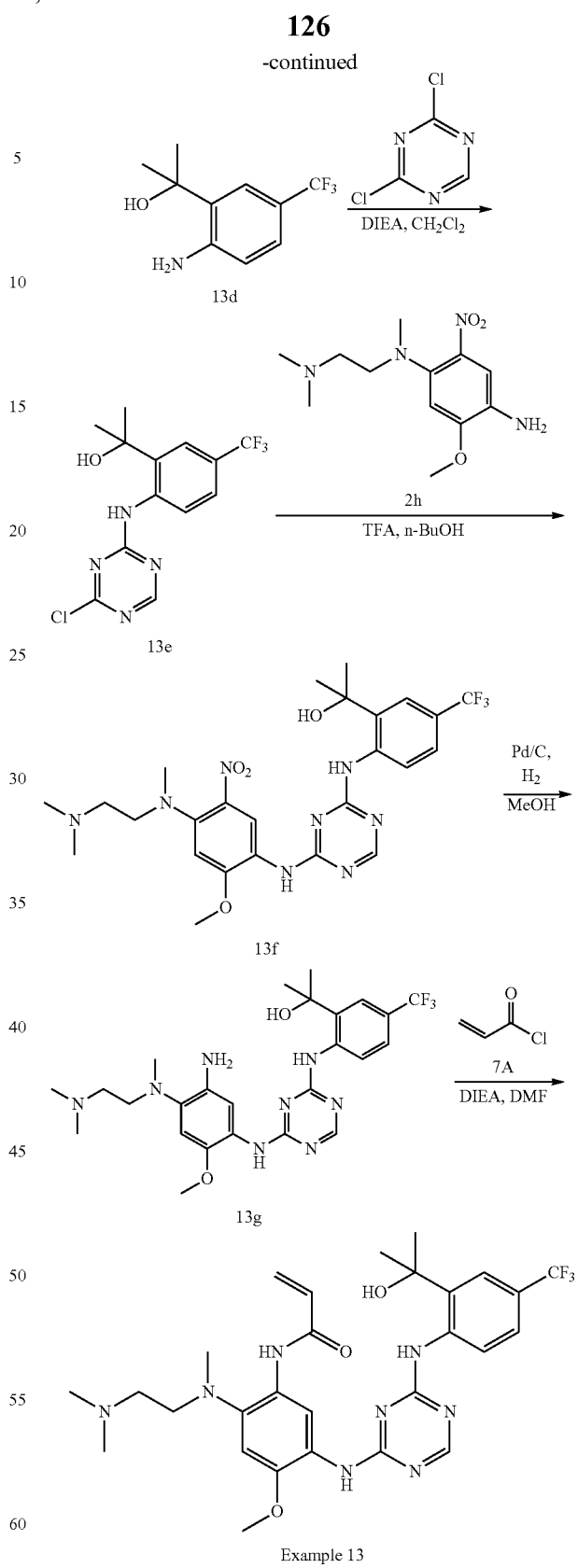

Procedure for the Preparation of Compound 13b:

To a solution of compound 13a (0.92 g, 4.2 mmol) and Boc$_2$O (3.17 g, 14.7 mmol) in THF (15 mL) was added DMAP (256 mg, 2.1 mmol) at 26-32° C. The reaction was stirred at 26-32° C. for 4 h. The reaction solution was concentrated in vacuum to give the crude residue, which was purified by column chromatography on silica gel (0-10% EtOAc in petroleum ether) to afford the desired product compound 13b (1.43 g, 81.2% yield) as an off-white solid.

LCMS: $R_t$=1.078 min in 5-95AB_220&254.lcm chromatography (MERCK RP-18e 25-2 mm), MS (ESI) m/z=442.1 [M+23]$^+$.

$^1$H NMR (400 MHz, CDCl$_3$) δ 8.28 (d, J=1.6 Hz, 1H), 7.95 (dd, J=2.0, 8.4 Hz, 1H), 7.53 (d, J=8.4 Hz, 1H), 3.93 (s, 3H), 1.36 (s, 18H).

Procedure for the Preparation of Compound 13c:

To a solution of compound 13b (1.43 g, 3.41 mmol) in THF (25 mL) was added dropwise MeMgBr (4.54 mL, 13.63 mmol, 3 M in ether) at ice water bath. The mixture was stirred for 3 hr at 26-32° C. To the reaction was added saturated NH$_4$Cl (30 mL) and the aqueous was extracted with EtOAc (50 mL×3). The combined organic layer was washed with brine (30 mL) and dried over Na$_2$SO$_4$, filtered and concentrated in vacuum to give the crude residue, which was purified by column chromatography on silica gel (3-30% EtOAc in petroleum ether) to afforded the desired product compound 13c (0.84 g, 77.8% yield) as a yellow solid.

LCMS: $R_t$=0.889 min in 5-95AB_220&254.lcm chromatography (MERCK RP-18e 25-2 mm), MS (ESI) m/z=246.0 [M+H]$^+$.

$^1$H NMR (400 MHz, Methanol-d$_4$): δ 8.22 (d, J=8.8 Hz, 1H), 7.54-7.51 (m, 2H), 1.64 (s, 6H), 1.54 (s, 9H).

Procedure for the Preparation of Compound 13d:

To a solution of compound 13c (640 mg, 2.0 mmol) in CH$_2$Cl$_2$ (10 mL) was added dropwise HCl/EtOAc (20 mL, 4 M) at ice water bath. The mixture was stirred for 6 hr at 26-34° C. The reaction mixture was basified with saturated NaHCO$_3$ to pH=8 and extracted with EtOAc (70 mL×3). The combined organic layer was washed with brine (50 mL) and dried over Na$_2$SO$_4$, filtered and concentrated in vacuum to give the crude, which was purified by flash column chromatography (3-30% EtOAc in petroleum ether) to afforded the desired product compound 13d (260 mg, 45.1% yield) as a yellow oil.

LCMS: $R_t$=0.726 min in 5-95AB_220&254.lcm chromatography (MERCK RP-18e 25-2 mm), MS (ESI) m/z=202.0 [M-17]$^+$.

$^1$H NMR (400 MHz, Methanol-d$_4$): δ 7.33 (s, 1H), 7.23 (d, J=8.8 Hz, 1H), 6.74 (d, J=8.4 Hz, 1H), 1.63 (s, 6H).

Procedure for the Preparation of Compound 13e:

To a solution of compound 13d (260 mg, 1.18 mmol) and DIEA (304 mg, 2.56 mmol) was added 2,4-dichloro-1,3,5-triazine (267 mg, 1.78 mmol) at 0° C. After the reaction was stirred at 28-34° C. for 4 h, the reaction was quenched with saturated NH$_4$Cl (5 mL) and the aqueous was extracted with EtOAc (50 ml×3). The combined organic layer was washed with brine (50 mL) and dried over Na$_2$SO$_4$, filtered and concentrated in vacuum give the crude (320 mg), which was purified by flash column chromatography (3-30% EtOAc in petroleum ether) to afforded compound 13e (200 mg, 50.8% yield) as a white solid.

LCMS: $R_t$=0.832 min in 5-95AB_220&254.lcm chromatography (MERCK RP-18e 25-2 mm), MS (ESI) m/z=332.9 [M+H]$^+$.

Procedure for the Preparation of Compound 13f:

To a solution of compound 13e (200 mg, 0.61 mmol) and compound 2g (183 mg, 0.68 mmol) in n-BuOH (10 mL) was added dropwise TFA (0.8 mL) at ice water bath. The mixture was stirred for 2 hr at 28-34° C. The reaction solution was directly concentrated in vacuum to give the crude residue, which was purified by flash column chromatography on silica gel (eluting with 0-15% MeOH in dichloromethane) to give the impure (350 mg), it was further purified by prep-TLC (MeOH/CH$_2$Cl$_2$=10/1) to give compound 13f (80 mg, 50.8% yield) as a brown solid.

LCMS: $R_t$=0.755 min in 5-95AB_220&254.lcm chromatography (MERCK RP-18e 25-2 mm), MS (ESI) m/z=565.1 [M+H]$^+$.

$^1$H NMR (400 MHz, CDCl$_3$): δ ppm 8.48-8.43 (m, 2H), 7.63 (d, J=8.4 Hz, 1H), 7.52-7.48 (m, 2H), 6.96 (s, 1H), 4.00 (s, 3H), 3.40 (t, J=6.4 Hz, 2H), 2.90 (s, 3H), 2.65 (t, J=6.4 Hz, 2H), 2.30 (s, 6H), 1.75 (s, 6H).

Procedure for the Preparation of Compound 13g:

The mixture of compound 13f (80 mg, 0.14 mmol) and Pd/C (70 mg, 10%) in EtOAc (30 mL) was stirred at H$_2$ (15 psi) for 30 min. The reaction was filtered and the cake was washed with EtOAc (50 mL). The filtrate was concentrated in vacuum to give compound 13g (60 mg, 80.0% yield) as a grey solid.

LCMS: $R_t$=0.712 min in 5-95AB_220&254.lcm chromatography (MERCK RP-18e 25-2 mm), MS (ESI) m/z=535.2 [M+H]$^+$.

$^1$H NMR (400 MHz, CDCl$_3$) δ 9.83-9.80 (m, 1H), 8.39 (d, J=8.8 Hz, 1H), 8.27-8.25 (m, 1H), 7.77 (s, 1H), 7.68-7.49 (m, 2H), 7.41 (s, 1H), 6.59 (s, 1H), 3.95 (s, 3H), 2.88 (t, J=6.8 Hz, 2H), 2.59 (s, 3H), 2.37 (t, J=6.8 Hz, 2H), 2.35-2.34 (m, 2H), 2.25 (s, 6H), 2.21-2.20 (m, 1H), 1.67 (s, 6H).

Procedure for the Preparation of Example 13:

To the mixture of compound 12g (60 mg, 0.112 mmol) and DIEA (29 mg, 0.224 mmol) in DMF (1 mL) was added dropwise compound acryloyl chloride (16.5 mg in 1 mL of DMF) over 30 min at ice water bath. After the reaction was stirred for 30 min at 0-5° C., the reaction was turned to the brown solution. The reaction was quenched with H$_2$O (45 mg) and then purified by prep-TLC directly (CH$_2$Cl$_2$/MeOH=10/1) to give Example 13 (18.2 mg, 27.5% yield) as a white solid.

LCMS: $R_t$=2.698 min in 0-60AB_4.0min_220&254 chromatography (Xtimate C18 2.1*30 mm), MS (ESI) m/z=589.0 [M+H]$^+$.

$^1$H NMR (400 MHz, CDCl$_3$): δ 10.88 (br s, 1H), 10.37 (br s, 1H), 9.89 (br s, 1H), 8.46 (d, J=8.4 Hz, 1H), 8.36 (s, 1H), 7.64 (br s, 1H), 7.54-7.43 (m, 2H), 6.71 (s, 1H), 6.39-6.22 (m, 2H), 5.71 (br d, J=11.2 Hz, 1H), 3.81 (s, 3H), 2.81 (m, 2H), 2.63 (s, 3H), 2.21 (m, 8H), 1.75 (s, 6H).

Example 14

N-(5-(4-(4-chloro-3-fluoro-2-(2-hydroxypropan-2-yl)phenylamino)-1,3,5-triazin-2-ylamino)-2-((2-(dimethylamino)ethyl)(methyl)amino)-4-methoxyphenyl)acrylamide

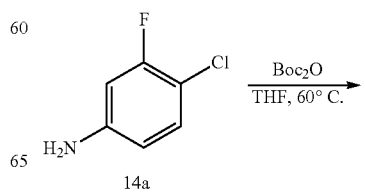

-continued

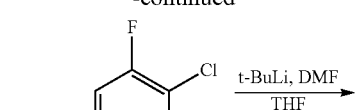
14b

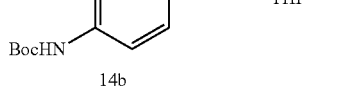
14c

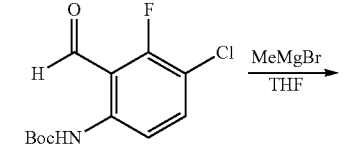
14d

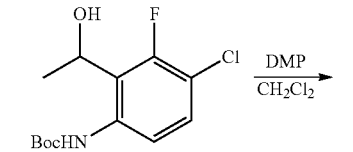
14e

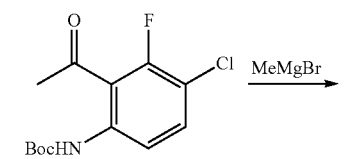
14f

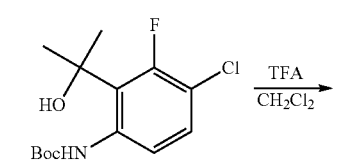

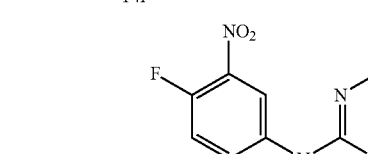
14g

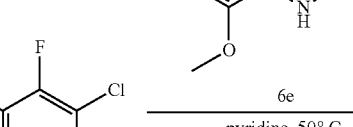
14h

-continued

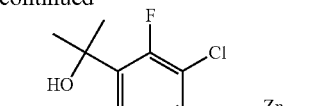
14i

14j

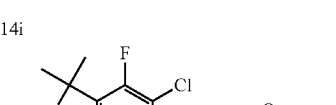
Example 14

Procedure for the Preparation of Compound 14b:

A solution of compound 14a (5 g, 34.35 mmol) and Boc₂O (15 g, 68.70 mmol) in THF (80 mL) was stirred at 60° C. for 12 h. The reaction mixture was concentrated in vacuo directly to give the crude product, which was purified by column chromatography on silica gel (2% EtOAc in petroleum ether) to give compound 14b (8.2 g, 69% yield) as yellow solid.

LCMS: $R_t$=0.866 min in 5-95AB_1.5min_220&254 chromatography (MERCK RP18 2.5-2 mm).

$^1$H NMR (400 MHz, CDCl₃) δ 7.36 (d, J=9.6 Hz, 1H), 7.19 (t, J=6.8 Hz, 1H), 6.87 (d, J=7.6 Hz, 1H), 6.45 (s, 1H), 1.45 (s, 9H).

Procedure for the Preparation of Compound 14c:

To a solution of compound 14b (8 g, 32.56 mmol) in THF (120 mL) was added t-BuLi (1.3 M) (50 mL, 65.12 mmol) at −78° C. under N₂. After 1 h stirring, DMF (3.6 g, 48.84 mmol) was added, and the reaction mixture was stirred at −78 to 33° C. for 16 h. The reaction mixture was quenched with saturated NH₄Cl solution (300 mL), then extracted with EtOAc (200 mL×3). The combined organic layers were washed with brine (100 mL), dried over sodium sulfate, and concentrated in vacuo to give compound 14c (8.2 g, 92% yield) as a yellow solid.

LCMS: $R_t$=0.929 min in 5-95AB_1.5min_220&254 chromatography (MERCK RP18e 25-2 mm).

¹H NMR (400 MHz, Methanol-d₄) δ 10.49 (brs, 1H), 10.28 (s, 1H), 8.18 (dd, J=0.8 Hz, 9.2 Hz, 1H), 7.48 (t, J=8.8 Hz, 1H), 1.46 (s, 9H).

Procedure for the Preparation of Compound 14d:

To a solution of compound 14c (4 g, 14.62 mmol) in THF (40 mL) was added MeMgBr (3.0 M) (19.5 mL, 58.48 mmol) at 0° C. under $N_2$. The reaction mixture was stirred at 0° C. for 2 h. The reaction mixture was quenched with saturated $NH_4Cl$ solution (80 mL), and extracted with EtOAc (30 mL×3). The combined organic layers were washed with brine (30 mL), dried over sodium sulfate, and concentrated in vacuo to give compound 14d (4 g, 94% yield) as yellow oil, which was used in the next step directly without further purification.

LCMS: $R_t$=0.871 min in 5-95AB_1.5min_220&254 chromatography (MERCK RP18e 25-2 mm).

Procedure for the Preparation of Compound 14e:

To a solution of compound 14d (4 g, 14.62 mmol) in $CH_2Cl_2$ (40 mL) was added DMP (9.3 g, 21.93 mmol) at 0° C. under $N_2$. The reaction mixture was stirred at 0° C. for 2 h. Saturated $NaHCO_3$ solution (40 mL), and saturated $Na_2SO_3$ solution (30 mL) were added, and the mixture was stirred at 25-33° C. for 30 min, the organic layer was separated and extracted with $CH_2Cl_2$ (30 mL). The combined organic layers were washed brine (20 mL), dried over sodium sulfate, and concentrated in vacuo to give the crude product, which was purified by column chromatography on silica gel (1% EtOAc in petroleum ether) to give compound 14e (2.5 g, 59% yield) as a yellow solid.

LCMS: $R_t$=0.924 min in 5-95AB_1.5min_220&254 chromatography (MERCK RP18e 25-2 mm), MS (ESI) m/z=187.9 $[M-101+H]^+$.

¹H NMR (400 MHz, $CDCl_3$) δ 10.20 (brs, 1H), 8.19 (d, J=9.6 Hz, 1H), 7.47 (t, J=9.2 Hz, 1H), 2.67 (d, J=8.0 Hz, 1H), 1.52 (s, 9H).

Procedure for the Preparation of Compound 14f:

To a solution of compound 14e (2.5 g, 8.69 mmol) in THF (40 mL) was added MeMgBr (3.0 M) (10 mL, 30.42 mmol) at 0° C. under $N_2$. The reaction mixture was stirred at 0° C. for 2 h. The reaction mixture was quenched with saturated $NH_4Cl$ solution (80 mL), and extracted with EtOAc (30 mL×3). The combined organic layers were washed with brine (30 mL), dried over sodium sulfate, and concentrated in vacuo to give the crude product, which was purified by column chromatography on silica gel (0.5% EtOAc in petroleum ether) to recover the compound 14e (1.2 g), followed by eluting with 2% EtOAc in petroleum ether to give the title product 14f (1.5 g, 57% yield) as a yellow solid.

LCMS: $R_t$=1.066 min in 5-95AB_1.5min_220&254 chromatography (MERCK RP18e 25-2 mm), MS (ESI) m/z=270.1 $[M-55+Na]^+$.

¹H NMR (400 MHz, $CDCl_3$) δ 9.67 (brs, 1H), 7.94 (d, J=9.2 Hz, 1H), 7.23 (t, J=8.4 Hz, 1H), 1.75 (d, J=3.6 Hz, 6H), 1.51 (s, 9H).

Procedure for the Preparation of Compound 14g:

To a solution of compound 14f (1.5 g, 4.94 mmol) in $CH_2Cl_2$ (15 mL) was added TFA (5 mL) at 0° C. under $N_2$. The reaction mixture was stirred at 36-34° C. for 1 h. The reaction mixture was concentrated in vacuo to give compound 14g (700 mg, 94% yield) as yellow oil.

LCMS: $R_t$=0.652 min in 5-95AB_1.5min_220&254 chromatography (MERCK RP18e 25-2 mm), MS (ESI) m/z=185.9 $[M-OH]^+$.

¹H NMR (400 MHz, $CDCl_3$) δ 6.92 (t, J=8.0 Hz, 1H), 6.24 (dd, J=1.2 Hz, 8.4 Hz, 1H), 1.65 (d, J=3.6 Hz, 6H).

Procedure for the Preparation of Compound 14h:

A solution of compound 14g (200 mg, 0.98 mmol) and compound 6e (294 mg, 0.98 mmol) in pyridine (1.5 mL) was stirred at 50° C. for 4 h. The reaction mixture was concentrated in vacuo directly to give the crude product, which was purified by column chromatography on silica gel (EtOAc: petroleum ether=7:3 (v/v)) to give the title product 14 h (150 mg, 21% yield) as a brown solid.

LCMS: $R_t$=0.864 min in 5-95AB_1.5min_220&254 chromatography (MERCK RP18e 25-2 mm), MS (ESI) m/z=467.0 $[M+H]^+$.

Procedure for the Preparation of Compound 14i:

To a solution of compound 14h (150 mg, 0.32 mmol) and $K_2CO_3$ (89 mg, 0.64 mmol) in DMF (3 mL) was added $N^1,N^1$,N-trimethylethane-1,2-diamine (39 mg, 0.39 mmol). The reaction mixture was stirred at 28-33° C. for 2 h. The reaction mixture was poured into water (10 mL), and stirred for 30 min. The mixture was filtered, and the filter cake was washed with water (10 mL×3). The filter cake was dried in high vacuum to give compound 14i (240 mg, crude) as a yellow solid.

LCMS: $R_t$=0.738 min in 5-95AB_220&254 chromatography (B: XBrige Shield RP18 2.1*50 mm), MS (ESI) m/z=549.1 $[M+H]^+$.

Procedure for the Preparation of Compound 14j:

To a solution of compound 14i (200 mg, 0.35 mmol) and $NH_4Cl$ (95 mg, 1.75 mmol) in MeOH (4 mL) and water (0.5 mL) was added Zn (115 mg, 1.75 mmol). The reaction mixture was stirred at 90° C. for 2 h. The reaction mixture was filtered, and the filtrate was poured into water (50 mL), extracted with EtOAc (25 mL×3). The combined organic layers were washed with brine (20 mL), dried over sodium sulfate, filtered and the filtrate was concentrated in vacuo to give compound 14j (180 mg, crude) as a black solid.

LCMS: $R_t$=0.699 min in 5-95AB_1.5min_220&254 chromatography (MERCK RP18e 25-2 mm), MS (ESI) m/z=519.1 $[M+H]^+$.

Procedure for the Preparation of Example 14:

To a mixture of 14j (180 mg, crude, 0.35 mmol) and DIEA (90 mg, 0.70 mmol) in DMF (3 mL) was added acryloyl chloride (32 mg, 0.35 mmol) at 0° C. The reaction mixture was stirred at 26-32° C. for 0.5 h. The reaction mixture was purified by prep-HPLC: [Column: Waters Xbridge 150*25 5 um; Condition: 65-95% B (A: 0.05% ammonia; B: $CH_3CN$); Flow rate: 30 ml/min]. Fractions containing the desired compound were lyophilized to afford Example 14 (24.5 mg, 12% yield) as a white solid.

LCMS: $R_t$=2.204 min in 10-80CD_3min_220&254 chromatography (B: XBrige Shield RP18 2.1*50 mm), MS (ESI) m/z=573.2 $[M+H]^+$.

¹H NMR (400 MHz, $CDCl_3$) δ 11.61 (brs, 1H), 10.30 (brs, 1H), 9.86 (s, 1H), 8.40 (s, 1H), 8.27 (d, J=8.8 Hz, 1H), 7.66 (brs, 1H), 7.35-7.26 (m, 1H), 6.75 (brs, 1H), 6.40 (d, J=16.0 Hz, 1H), 6.01 (brs, 1H), 5.78 (d, J=11.2 Hz, 1H), 3.88 (s, 3H), 3.07-2.87 (m, 2H), 2.71 (s, 3H), 2.58-2.13 (m, 8H), 1.87 (d, J=3.6 Hz, 6H).

HPLC: $R_t$=3.86 min in 10-80CD_1.2 ml chromatography (XBridge Shield RP 18 2.1*50 mm 5 um).

Example 15

N-(5-(4-(4,5-dichloro-2-(2-hydroxypropan-2-yl)phenylamino)-1,3,5-triazin-2-ylamino)-2-((2-(dimethylamino)ethyl)(methyl)amino)-4-methoxyphenyl)acrylamide

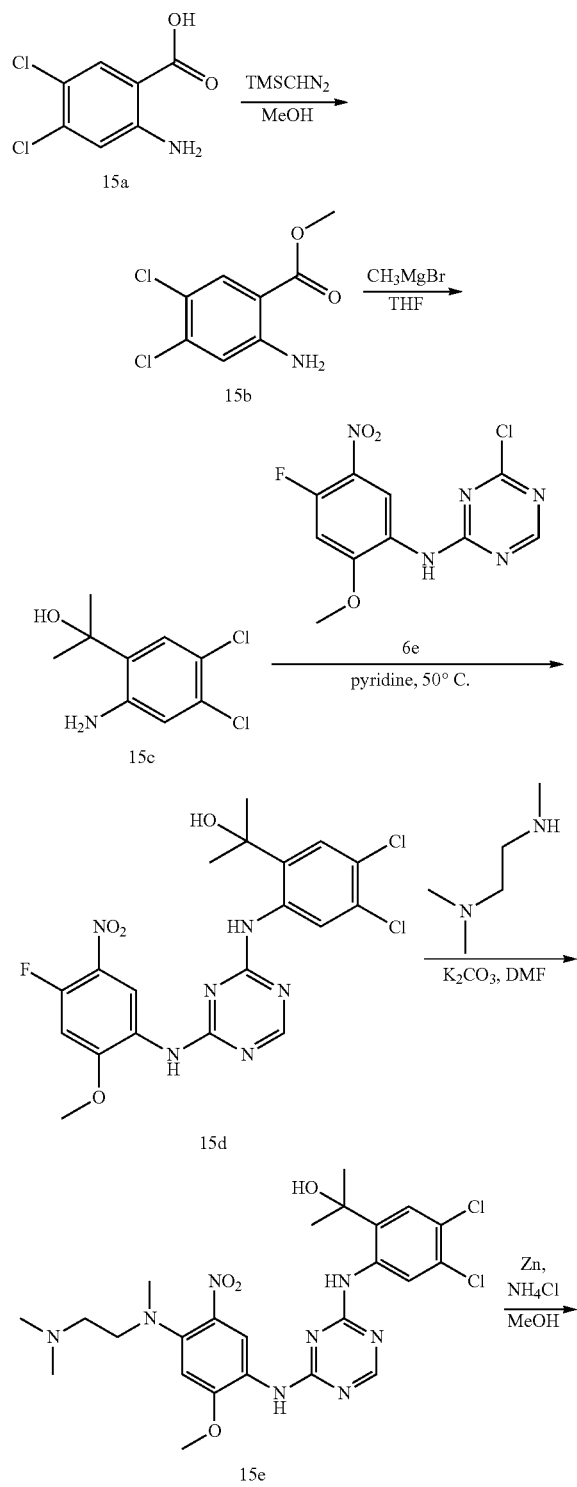

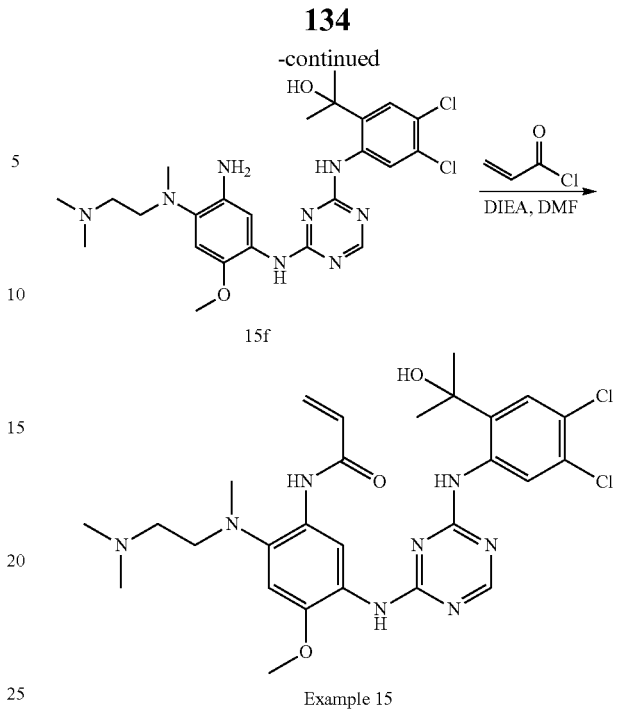

Procedure for the Preparation of Compound 15b:

To a solution of compound 15a (2.0 g, 9.71 mmol) in EtOAc (40 mL) and MeOH (40 mL) was added TMSCHN$_2$ (9.7 mL, 25.78 mmol, 2M in hexane). The mixture was stirred at 26-33° C. for 1.5 h. The reaction mixture was concentrated under reduced pressure to afford compound 15b (2.0 g, 94.1% yield) as a white solid.

LCMS: R$_t$=0.988 min in 5-95AB_1.5min_220&254 chromatography (MERCK RP18e 25-2 mm), MS (ESI) m/z=187.8 [M-31]$^+$.

$^1$H NMR (400 MHz, CDCl$_3$) δ 7.85 (s, 1H), 6.72 (s, 1H), 5.71 (br s, 2H), 3.80 (s, 3H).

Procedure for the Preparation of Compound 15c:

To a solution of compound 15b (1.0 g, 4.54 mmol) in THF (30 mL) was added CH$_3$MgBr (6 mL, 3 M in ether) at 0~5° C. The mixture was stirred at 26-34° C. for 1.5 h (yellow solution). The reaction mixture was quenched by the addition of aqueous NH$_4$Cl (20 mL), then extracted with EtOAc (3×100 mL). The organic layers were washed with brine (3×100 mL), and concentrated under reduced pressure to afford compound 15c (950 mg, 95% yield) as a white solid.

LCMS: R$_t$=0.867 min in 5-95AB_1.5min_220&254 chromatography (MERCK RP18e 25-2 mm), MS (ESI) m/z=201.8 [M-OH]$^+$.

$^1$H NMR (400 MHz, CDCl$_3$) δ 7.13 (s, 1H), 6.70 (s, 1H), 1.64 (s, 6H).

Procedure for the Preparation of Compound 15d:

To a solution of compound 15c (500 mg, 2.27 mmol) in Pyridine (5 mL) was added compound 6e (749 mg, 2.50 mmol). The resulting mixture was stirred at 50° C. for 18 h. The mixture reaction was concentrated under reduced pressure and purified by Prep-TLC on silica gel (CH$_2$Cl$_2$/MeOH=15/1 (v/v)) to afford compound 15d (300 mg, 29.2% yield) as a brown solid.

LCMS: R$_t$=0.991 min in 5-95AB_1.5min_220&254 chromatography (MERCK RP18e 25-2 mm), MS (ESI) m/z=483.1 [M+H]$^+$.

Procedure for the Preparation of Compound 15e:

A solution of compound 15d (300 mg, 0.62 mmol) and K$_2$CO$_3$ (171 mg, 1.24 mmol) in DMF (4 mL) was added $N^1,N^1,N$-trimethylethane-1,2-diamine (76 mg, 0.74 mmol). The mixture was stirred at 28-33° C. for 2 hours. The reaction was added with 10 mL water and extracted with EtOAc (10 mL×3). The combined organic layers were washed with brine (10 mL×3), dried over sodium sulfate and concentrated in vacuo to give the crude, which was purified by prep-TLC on silica gel ($CH_2Cl_2$/MeOH=15/1 (v/v)) to afford compound 15e (250 mg, 71% yield) as a brown solid.

LCMS: $R_t$=0.745 min in 5-95AB_1.5min_220&254 chromatography (MERCK RP18e 25-2 mm), MS (ESI) m/z=565.1 $[M+H]^+$.

Procedure for the Preparation of Compound 15f:

To a solution of compound 15e (220 mg, 0.39 mmol) in MeOH (5 mL) and $H_2O$ (1 mL) was added Zn (127 mg, 1.95 mmol) and $NH_4Cl$ (208 mg, 3.89 mmol). The mixture was stirred at 70° C. for 1.5 h under $N_2$ (turned to brown mixture). The reaction mixture was quenched by the addition of aqueous $NH_4Cl$ (20 mL), then extracted with EtOAc (3×10 mL). The organic layer was washed with brine (3×10 mL), dried and concentrated in vacuum to give compound 15f (190 mg, 91.4% yield).

LCMS: $R_t$=0.799 min in 5-95AB_1.5min_220&254 chromatography (MERCK RP18e 25-2 mm), MS (ESI) m/z=535.1 $[M+H]^+$.

Procedure for the Preparation of Example 15:

To a solution of compound 15f (190 mg, 0.35 mmol) and DIEA (69 mg, 0.53 mmol) in DMF (1 mL) was added acryloyl chloride (32 mg, 0.35 mmol) in DMF (1 mL). The resulting mixture was stirred at 0° C. for 30 min. The reaction was purified by prep-HPLC [Column: Waters Xbridge 150*25 5 um; Condition: 25-55% B (A: 0.05% ammonia; B: $CH_3CN$); Flow rate: 25 ml/min]. Fractions containing the desired compound were lyophilized to afford Example 15 (37.8 mg, 12.2% yield) as a white solid.

LCMS: $R_t$=5.084 min in 10-80CD_7MIN_220&254 chromatography (XBrige Shield RP18 2.1*50 mm), MS (ESI) m/z=589.3 $[M+H]^+$.

HPLC: $R_t$=4.32 min in 10-80_CD_1.2ML chromatography (XBridge Shield RP 18 2.1*50 mm 5 um).

$^1$H NMR (400 MHz, DMSO-$d_6$) δ 10.32 (br s, 1H), 10.03 (s, 1H), 9.15 (br s, 1H), 8.42 (br s, 1H), 8.29 (br d, J=14.8 Hz, 2H), 7.38 (br s, 1H), 7.03 (br s, 1H), 6.43-6.34 (m, 1H), 6.33 (s, 1H), 6.25-6.13 (m, 1H), 5.73 (br d, J=11.6 Hz, 1H), 3.78 (s, 3H), 2.86 (br t, J=5.6 Hz, 2H), 2.72 (s, 3H), 2.37-2.30 (m, 2H), 2.21 (s, 6H), 1.52 (s, 6H).

Example 16

N-(5-(4-(4-chloro-3,5-difluoro-2-(2-hydroxypropan-2-yl)phenylamino)-1,3,5-triazin-2-ylamino)-2-((2-(dimethylamino)ethyl)(methyl)amino)-4-methoxyphenyl)acrylamide

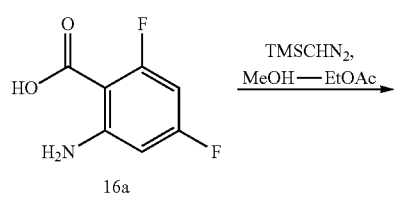

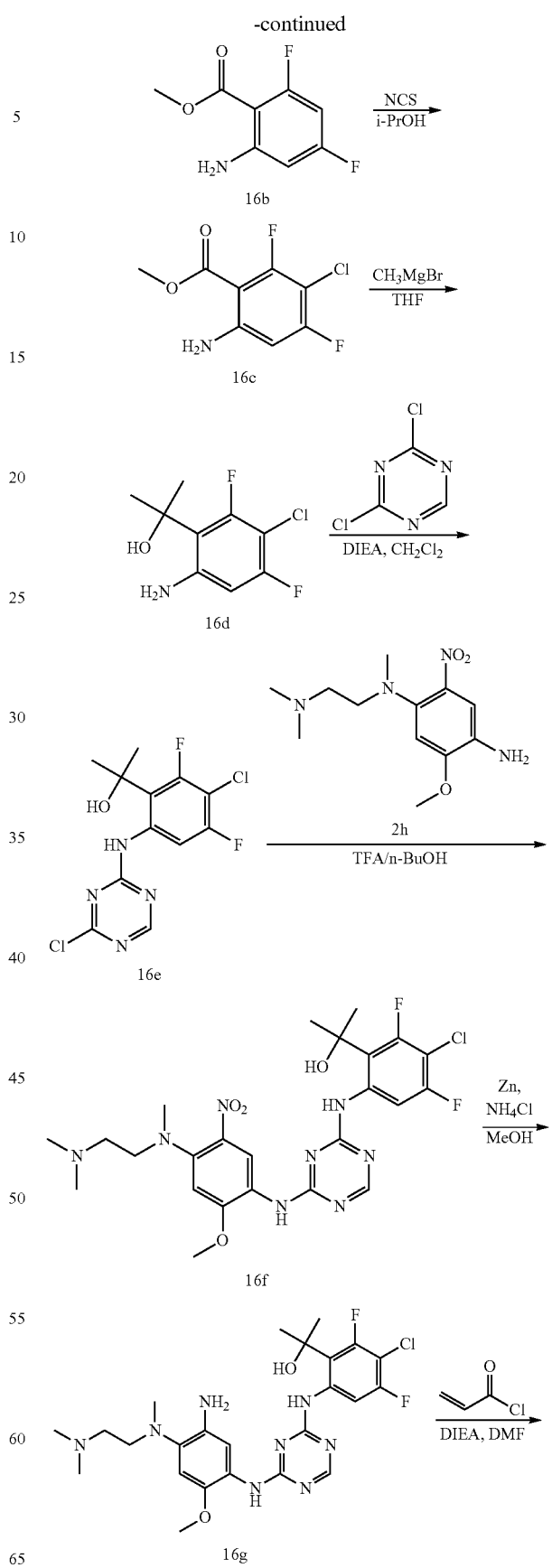

-continued

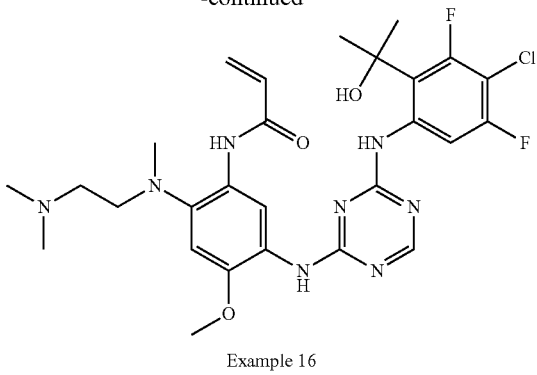

Example 16

Procedure for the Preparation of Compound 16b:

To a solution of compound 16a (5.0 g, 28.89 mmol) in EtOAc (50 mL) and MeOH (50 mL) was added TMSCHN$_2$ (29 mL, 57.76 mmol, 2M in hexane) at 0-5° C. The mixture was stirred at 28-36° C. (room temperature) for 1.5 h. The reaction mixture was concentrated under reduced pressure to afford compound 16b (4.8 g, 82.5% yield) as a brown solid.

LCMS: R$_t$=0.882 min in 5-95AB_1.5min_220&254 chromatography (MERCK RP18e 25-2 mm), MS (ESI) m/z=187.8 [M+H]$^+$.

$^1$H NMR: (400 MHz, CDCl$_3$) δ 6.05-5.94 (m, 2H), 5.93-5.72 (m, 2H), 3.76 (s, 3H).

Procedure for the Preparation of Compound 16c: A stirred solution of compound 16b (2.70 g, 14.42 mmol) in i-PrOH (50 mL) was cooled to 0° C. and added with NCS (2.02 g, 15.15 mmol) in portions, the resulting yellow suspension was stirred at 0° C. to 30° C. for 12 h while monitoring with LCMS (turned to clean gradually). The reaction mixture was concentrated in vacuum directly to give the crude product, which was purified by flash column chromatography on silica gel (Condition: 65-75% B (A: 0.05% TFA in water; B: MeOH); Flow rate: 40 ml/min)) to give compound 16c (1000 mg purity 87.20%, and 500 mg starting material) as a white solid.

LCMS: R$_t$=0.905 min in 5-95AB_1.5min_220&254 chromatography (MERCK RP18e 25-2 mm), MS (ESI) m/z=189.9 [M-32]$^+$.

$^1$H NMR (400 MHz, DMSO-d$_6$) δ 7.04 (br s, 2H), 6.61 (dd, J=1.8, 11.8 Hz, 1H), 3.82 (s, 3H).

Procedure for the Preparation of Compound 16d:

To a solution of compound 16c (500 mg, 2.26 mmol) in THF (10 mL) was added CH$_3$MgBr (3 mL, 3 M in ether) at 0~5° C. The yellow solution was stirred at 24-29° C. for 1.5 h (yellow solution). The reaction mixture was quenched by the addition of aqueous NH$_4$Cl (20 mL), then extracted with EtOAc (3×10 mL). The organic layers were washed with brine (3×10 mL), and concentrated in vacuum directly to give compound 16d (450 mg, 74% yield) as a white solid.

LCMS: R$_t$=0.900 min in 5-95AB_1.5min_220&254 chromatography (MERCK RP18e 25-2 mm), MS (ESI) m/z=203.9 [M-OH]$^+$.

Procedure for the Preparation of Compound 16e:

To a solution of compound 16d (450 mg, 2.03 mmol) and DIEA (394 mg, 3.05 mmol) in CH$_2$Cl$_2$ (10 mL) was added 2,4-dichloro-1,3,5-triazine (335 mg, 2.23 mmol). The resulting white mixture was stirred at 24-29° C. (room temperature) for 2 h. The reaction mixture was quenched by the addition of aqueous NH$_4$Cl (20 mL), then extracted with EtOAc (3×10 mL). The organic layers were washed with brine (3×10 mL), and concentrated in vacuum directly to give compound 16e (500 mg, 30% yield) as a white solid.

LCMS: R$_t$=0.927 min in 5-95AB_1.5min_220&254 chromatography (MERCK RP18e 25-2 mm), MS (ESI) m/z=334.9 [M+H]$^+$.

Procedure for the Preparation of Compound 16f:

To three separated solutions of compound 16e (100 mg×3, 0.90 mmol) and compound 2g (80 mg, 0.30 mmol) in n-BuOH (2 mL) was added TFA (0.02 mL). The resulting mixture was stirred at 25-33° C. for 3 h (red mixture). The reaction mixture was concentrated in vacuum directly to give the crude product, which was purified by flash column chromatography on silica gel (Condition: 87-89% B (A: 0.05% TFA in water; B: MeOH); Flow rate: 40 ml/min)) to give compound 16f (150 mg purity 97.18%, 30% yield) as a red solid.

LCMS: R$_t$=0.792 min in 5-95AB_1.5min_220&254 chromatography (MERCK RP18e 25-2 mm), MS (ESI) m/z=567.3[M+H]$^+$.

Procedure for the Preparation of Compound 16g:

To a solution of compound 16f (150 mg, 0.26 mmol) in MeOH (5 mL) and H$_2$O (1 mL) was added Zn (87 mg, 1.32 mmol) and NH$_4$Cl (142 mg, 2.65 mmol). The mixture was stirred at 70° C. for 1.5 h under N$_2$ (black mixture). The reaction mixture was quenched by the addition of aqueous NH$_4$Cl (20 mL), then extracted with EtOAc (3×10 mL). The organic layers were washed with brine (3×10 mL), dried and concentrated in vacuum directly to give compound 16g (120 mg, 84.6% yield) as brown oil.

LCMS: R$_t$=0.802 min in 5-95AB_1.5min_220&254 chromatography (MERCK RP18e 25-2 mm), MS (ESI) m/z=537.1 [M+H]$^+$.

Procedure for the Preparation of Example 16:

To a solution of compound 16g (120 mg, 0.22 mmol) and DIEA (43 mg, 0.33 mmol) in DMF (1 mL) was added acryloyl chloride (20 mg, 0.22 mmol) in DMF (1 mL). The brown resulting mixture was stirred at 0° C. for 30 min. The reaction was purified by prep-HPLC [Column: Waters Xbridge 150*25 5 um; Condition: 62-92% B (A: 0.05% ammonia; B: CH$_3$CN); Flow rate: 25 ml/min]. Fractions containing the desired compound were lyophilized to afford Example 16 (27.6 mg, 21% yield) as a white solid.

LCMS: R$_t$=2.310 min in 10-80CD_3MIN_220&254 chromatography (XBrige Shield RP18 2.1*50 mm), MS (ESI) m/z=591.2 [M+H]$^+$.

HPLC: R$_t$=4.78 min in 10-80_CD_1.2ML chromatography (XBridge Shield RP 18 2.1*50 mm.

$^1$H NMR (400 MHz, DMSO-d$_6$) δ 11.23 (br s, 1H), 10.05 (br s, 1H), 9.24 (brs, 1H), 8.35-8.27 (m, 2H), 7.01 (s, 1H), 6.82 (br s, 1H), 6.42 (br s, 1H), 6.18 (br d, J=16.8 Hz, 1H), 5.72 (br d, J=10.8 Hz, 1H), 3.77 (s, 3H), 2.90 (br s, 2H), 2.77-2.68 (m, 3H), 2.45-2.31 (m, 2H), 2.24 (br s, 6H), 1.61 (br s, 6H).

Example 17

N-(5-(4-(4,5-difluoro-2-(2-hydroxypropan-2-yl)phenylamino)-1,3,5-triazin-2-ylamino)-4-methoxy-2-((3aR,6aR)-5-methylhexahydropyrrolo[3,4-b]pyrrol-1(2H)-yl)phenyl) acrylamide

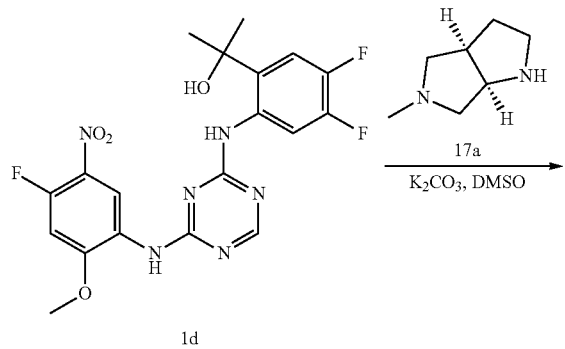

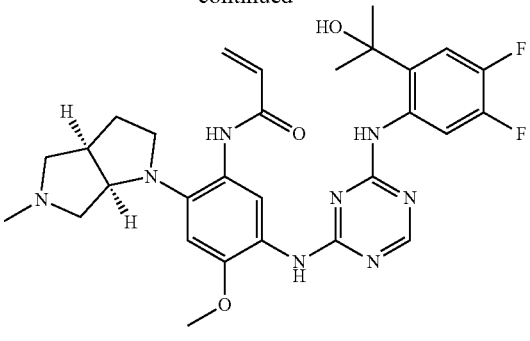

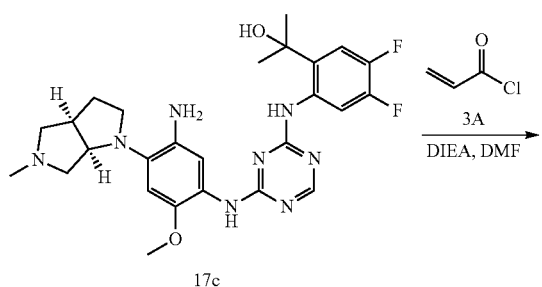

Procedure for the Preparation of Compound 17b:

To a solution of compound 1d (200 mg, 0.444 mmol) and K$_2$CO$_3$ (123 mg, 0.888 mmol) in DMSO (6 mL) was added compound 17a (67 mg, 0.533 mmol). The reaction mixture was stirred at 85° C. for 1 h (changed from pale yellow to orange). The reaction mixture was added dropwise into H$_2$O (80 mL) under ice water bath and the precipitated solid was collected by filtration, the filter cake was washed with H$_2$O (15 mL×3), and then dried in high vacuum to give compound 17b (200 mg, 81% yield) as an orange solid.

LCMS: R$_t$=0.717 min in 5-95AB_220&254.lcm chromatography (MERCK RP18 2.5-2 mm), MS (ESI) m/z=557.1 [M+H]$^+$.

$^1$H NMR (400 MHz, Methanol-d$_4$) δ 8.24 (br s, 2H), 8.03 (br s, 1H), 7.21 (dd, J=8.4, 12.0 Hz, 1H), 6.58 (s, 1H), 4.56-4.39 (m, 1H), 3.96 (s, 3H), 3.61 (dt, J=6.8, 10.4 Hz, 1H), 3.18 (t, J=8.8 Hz, 1H), 3.07 (quin, J=7.6 Hz, 1H), 2.83 (t, J=8.8 Hz, 1H), 2.79-2.69 (m, 1H), 2.39 (dd, J=7.2, 9.6 Hz, 1H), 2.26 (s, 3H), 2.20 (dd, J=3.2, 10.0 Hz, 1H), 2.14-2.02 (m, 1H), 1.92 (dd, J=6.4, 12.4 Hz, 1H), 1.60 (s, 6H).

Procedure for the Preparation of Compound 17c:

To a solution of compound 17b (200 mg, 0.36 mmol) in MeOH (15 mL) was added Pd/C (10%, 20 mg). The reaction mixture was stirred at 25-31° C. for 3 h under H$_2$ balloon (15 Psi). The reaction mixture was filtered, and the filtrate was concentrated in vacuo to give compound 17c (168 mg, 88.6% yield) as a grayish-green solid.

LCMS: R$_t$=0.675 min in 5-95AB_220&254.lcm chromatography (MERCK RP18 2.5-2 mm), MS (ESI) m/z=527.3 [M+H]$^+$.

$^1$H NMR (400 MHz, Methanol-d$_4$) δ 8.21 (br s, 2H), 7.47 (br s, 1H), 7.22 (dd, J=9.0, 12.4 Hz, 1H), 6.86 (s, 1H), 4.15-4.03 (m, 1H), 3.79 (s, 3H), 3.48-3.38 (m, 1H), 3.00-2.88 (m, 1H), 2.74-2.65 (m, 2H), 2.62 (d, J=10.0 Hz, 1H), 2.45 (dd, J=7.8, 9.2 Hz, 1H), 2.33 (s, 3H), 2.19-2.09 (m, 2H), 1.85-1.71 (m, 1H), 1.60 (s, 6H).

Procedure for the Preparation of Example 17:

To a solution of compound 17c (155 mg, 0.294 mmol) and DIEA (57 mg, 0.441 mmol) in DMF (2 mL) was added acryloyl chloride (27 mg, 0.294 mmol) under ice water bath. The resulting mixture was stirred at 5-10° C. for 0.5 h. The reaction was quenched by H$_2$O (0.1 mL) and then filtered. The filtrate was purified by pre-HPLC (Column: Waters Xbridge 150*25 5 um; Condition: 30-60% B (A: 0.05% ammonia, B: CH$_3$CN); Flow Rate: 25 ml/min) and lyophilized to give Example 17 (39.1 mg, 22.90% yield) as a white solid.

LCMS: R$_t$=1.990 min in 10-80CD_3min_220&254. lcm chromatography (XBrige Shield RP18 2.1*50 mm), MS (ESI) m/z=581.3 [M+H]$^+$.

¹H NMR (400 MHz, CDCl₃) δ 10.65 (br s, 1H), 9.90 (br s, 1H), 9.59 (br s, 1H), 8.40 (s, 1H), 8.32 (dd, J=8.0, 12.8 Hz, 1H), 7.67 (br s, 1H), 7.10 (dd, J=8.8, 12.0 Hz, 1H), 6.78 (s, 1H), 6.56-6.44 (m, 1H), 6.44-6.33 (m, 1H), 6.00 (br s, 1H), 5.76 (d, J=10.0 Hz, 1H), 3.87 (s, 3H), 3.68 (dd, J=4.4, 7.8 Hz, 1H), 3.22 (t, J=7.2 Hz, 1H), 2.93-2.78 (m, 3H), 2.72 (d, J=10.0 Hz, 1H), 2.29 (s, 5H), 1.90 (dd, J=4.4, 10.4 Hz, 1H), 1.87-1.80 (m, 1H), 1.76 (s, 6H).

Example 18

N-(5-(4-(4,5-difluoro-2-(2-hydroxypropan-2-yl)phenylamino)-1,3,5-triazin-2-ylamino)-4-methoxy-2-(methyl(2-(pyrrolidin-1-yl)ethyl)amino)phenyl)acrylamide

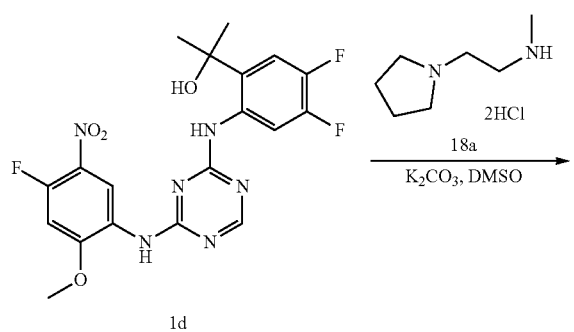

1d

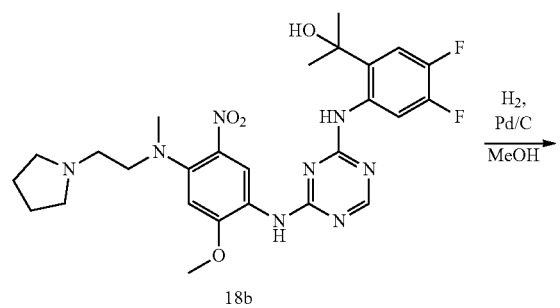

18b

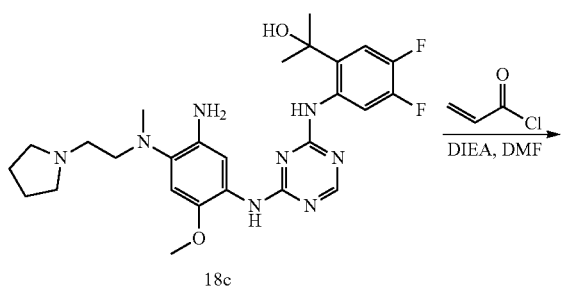

18c

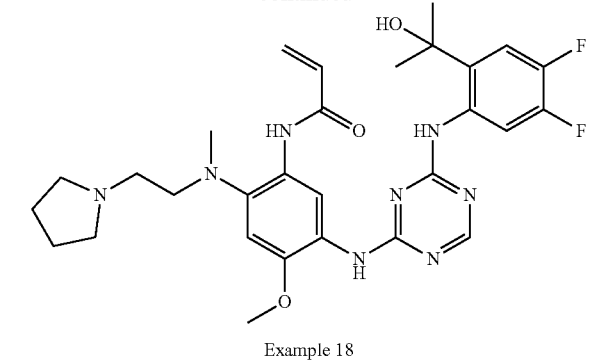

Example 18

Procedure for the Preparation of Compound 18b:

To a solution of compound 1d (200 mg, 1.0 eq, 0.44 mmol) and K₂CO₃ (243 mg, 4.0 eq, 1.76 mmol) in DMSO (5 mL) was added compound 18a (133 mg, 1.5 eq, 0.66 mmol). The resulting mixture was stirred at 85° C. for 4 h while the colour changes from pale yellow to deep yellow. The reaction mixture was pour into ice water (50 mL) and yellow solid was precipitated. The yellow precipitated solid was collected by filtration and then dissolved with CH₂Cl₂ (30 mL), dried over anhydrous Na₂SO₄ and concentrated under reduced pressure to give compound 18b (230 mg, 93% yield) as yellow solid.

LCMS: R$_t$=0.754 min in 5-95AB_220&254.lcm chromatography (MERCK RP-18e 25-2 mm), MS (ESI) m/z=559.3 [M+H]⁺.

Procedure for the Preparation of Compound 18c:

To a solution of compound 18b (230 mg, 1.0 eq, 0.41 mmol) in MeOH (10 mL) was added Pd/C (23 mg). The resulting mixture was purged and degassed with H₂ for 3 times, then stirred at 25-28° C. (room temperature) under hydrogen balloon (15 psi) for 1 h. The reaction mixture was filtered and concentrated under reduced pressure to give compound 18c (200 mg, 92% yield) as brown solid.

LCMS: R$_t$=0.678 min in 5-95AB_1.5min_220&254 chromatography (MERCK RP18e 25-2 mm), MS (ESI) m/z=529.1 [M+H]⁺.

Procedure for the Preparation of Example 18:

To a solution of compound 18c (200 mg, 1.0 eq, 0.38 mmol) and DIEA (98 mg, 2.0 eq, 0.76 mmol) in DMF (2.5 mL) was added acryloyl chloride (34 mg, 1.0 eq, 0.38 mmol) in DMF (0.5 mL). The resulting mixture was stirred at 0° C. under ice-water bath for 30 min. The reaction mixture was purified by RP-HPLC (reverse phase HPLC) [Column: reversed-phase Column; Condition: 50-70% B (A: 0.25% NH₃HCO₃; B: MeOH); Flow rate: 40 ml/min], the fractions were concentrated under reduced pressure and lyophilized to afford compound Example 18 (45.7 mg, 20% yield) as white solid.

LCMS: R$_t$=1.716 min in 10-80AB_4min_220&254 chromatography (Xtimate C18 2.1*30 mm), MS (ESI) m/z=583.2 [M+H]⁺.

HPLC: R$_t$=3.24 min in 10-80_ab_1.2ML chromatography (Ultimate C18 3*50 mm 3 um).

¹H NMR (400 MHz, CDCl₃) δ 10.65 (br s, 1H), 9.89 (br s, 2H), 8.40 (s, 1H), 8.32 (dd, J=8.0, 12.8 Hz, 1H), 7.67 (br s, 1H), 7.10 (dd, J=8.4, 12.0 Hz, 1H), 6.74 (s, 2H), 6.38 (d, J=16.8 Hz, 1H), 5.77 (br d, J=10.8 Hz, 1H), 3.88 (s, 3H), 3.06 (br s, 2H), 2.91-2.74 (m, 4H), 2.70 (s, 5H), 1.94 (br s, 4H), 1.76 (s, 6H).

Example 19

(R)—N-(5-(4-(4,5-difluoro-2-(2-hydroxypropan-2-yl)phenylamino)-1,3,5-triazin-2-ylamino)-2-(2-((dimethylamino)methyl)azetidin-1-yl)-4-methoxyphenyl)acrylamide

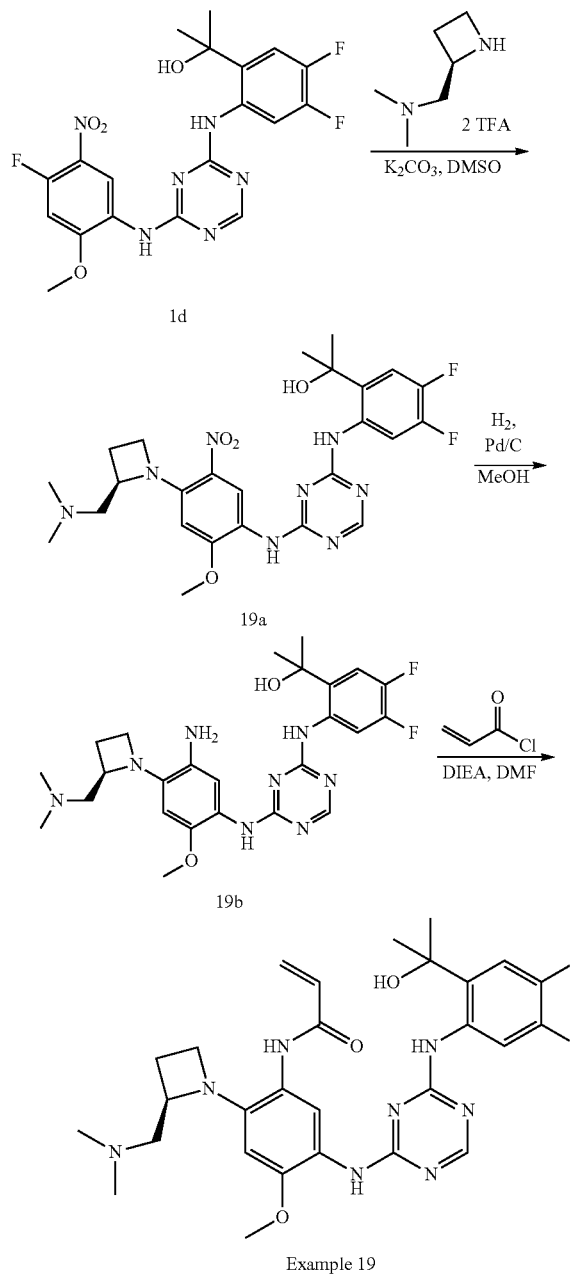

Procedure for the Preparation of Compound 19a:

To a solution of compound 1d (300 mg, 1.0 eq, 0.67 mmol) and K$_2$CO$_3$ (926 mg, 10.0 eq, 6.70 mmol) in DMSO (5 mL) was added (R)-1-(azetidin-2-yl)-N,N-dimethylmethanamine TFA salt (2.0 g, 10.0 eq, 6.70 mmol). The resulting mixture was stirred at 85° C. for 4 h while the colour changes from pale yellow to deep yellow. The reaction mixture was pour into ice water (50 mL) and yellow solid was precipitated. The precipitated solid was collected by filtration and dissolved with CH$_2$Cl$_2$ (20 mL), dried over anhydrous Na$_2$SO$_4$ and concentrated under reduced pressure to give compound 19a (300 mg) as yellow solid.

LCMS: R$_t$=0.734 min in 5-95AB_1.5min_220&254 chromatography (MERCK RP18e 25-2 mm), MS (ESI) m/z=567.2[M+Na]$^+$.

Procedure for the Preparation of Compound 19b:

To a solution of compound 19a (300 mg, 1.0 eq, 0.55 mmol) in MeOH (10 mL) was added Pd/C (30 mg). The resulting mixture was purged and degassed with H$_2$ for 3 times, then stirred at 24-29° C. under H$_2$ (hydrogen balloon, 15 Psi) for 2 h. The reaction mixture was filtered and concentrated under reduced pressure to give compound 19b (270 mg) as brown solid.

LCMS: R$_t$=0.679 min in 5-95AB_1.5min_220&254 chromatography (MERCK RP18e 25-2 mm), MS (ESI) m/z=515.3[M+H]$^+$.

Procedure for the Preparation of Example 19:

To a solution of compound 19b (270 mg, 1.0 eq, 0.52 mmol) and DIEA (134 mg, 2.0 eq, 1.04 mmol) in DMF (2.5 mL) was added acryloyl chloride (47 mg, 1.0 eq, 0.52 mmol) in DMF (0.5 mL). The resulting mixture was stirred at 0° C. under ice-water bath for 30 min. The reaction mixture was purified by prep-HPLC [Column: Waters Xbridge 150*25 5 um; Condition: 20-50% B (A: 0.05% NH3H2O; B: CH3CN); Flow rate: 25 ml/min]. Fractions containing the desired compound were lyophilized to afford Example 19 (77.5 mg) as white solid.

LCMS: R$_t$=1.658 min in 10-80AB_4min_220&254 chromatography (Xtimate C18 2.1*30 mm), MS (ESI) m/z=568.8 [M+H]$^+$.

HPLC: R$_t$=2.89 min in 10-80_ab_1.2ML chromatography (Ultimate C18 3*50 mm 3 um).

$^1$H NMR (400 MHz, CDCl$_3$) δ 10.49 (br s, 1H), 9.40 (br s, 1H), 8.94 (br s, 1H), 8.38 (s, 1H), 8.30 (dd, J=7.9, 12.9 Hz, 1H), 7.67-7.44 (m, 1H), 7.09 (dd, J=8.7, 12.2 Hz, 1H), 6.63 (s, 1H), 6.43-6.29 (m, 2H), 5.80 (br d, J=10.3 Hz, 1H), 4.30-4.17 (m, 1H), 3.90 (s, 3H), 3.86 (br s, 1H), 3.58 (q, J=8.0 Hz, 1H), 2.66 (dd, J=5.9, 12.9 Hz, 1H), 2.49-2.37 (m, 2H), 2.26 (s, 6H), 2.15-2.05 (m, 1H), 1.74 (s, 6H).

Example 20

(R)—N-(5-(4-(4,5-difluoro-2-(2-hydroxypropan-2-yl)phenylamino)-1,3,5-triazin-2-ylamino)-4-methoxy-2-(methyl((1-methylpyrrolidin-2-yl)methyl)amino) phenyl)acrylamide

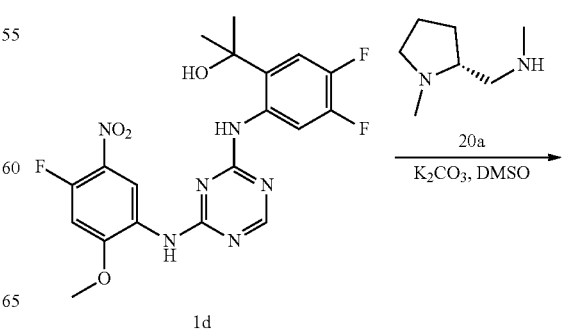

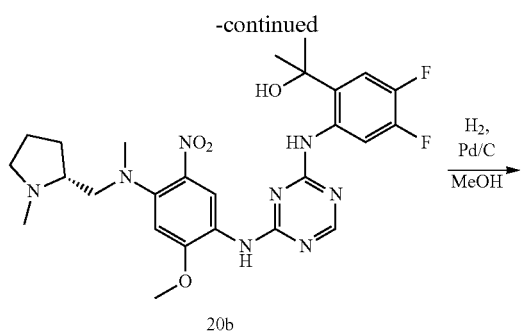

20b

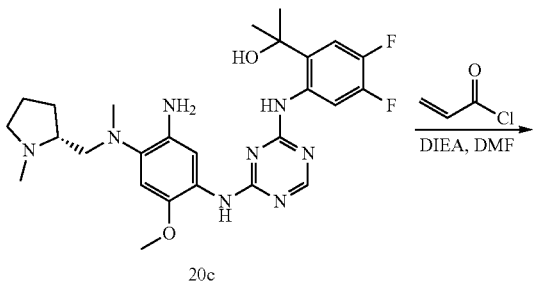

20c

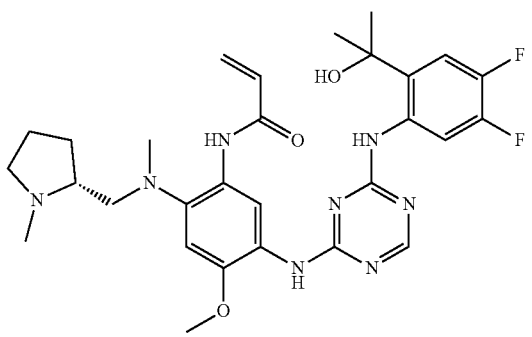

Example 20

Procedure for the Preparation of Compound 20b:

To a solution of compound 1d (300 mg, 0.666 mmol) and K$_2$CO$_3$ (184 mg, 1.332 mmol) in DMSO (6 mL) was added compound 20a (160 mg, 0.793 mmol). The reaction mixture was stirred at 85° C. for 6 h while changed from pale yellow to orange. The reaction mixture was added drop wise into H$_2$O (80 mL) under ice water bath and solid was precipitated out, it was collected by filtration and the filter cake was washed with H$_2$O (15 mL×3), dried under vacuum to give compound 20b (300 mg, 81% yield) as an orange solid.

LCMS: R$_f$=0.731 min in 5-95AB_220&254.lcm chromatography (MERCK RP18 2.5-2 mm), MS (ESI) m/z=559.1 [M+H]$^+$.

$^1$H NMR (400 MHz, Methanol-d$_4$) δ 8.37 (br s, 1H), 8.27 (br s, 1H), 8.05 (br s, 1H), 7.22 (dd, J=8.8, 12.4 Hz, 1H), 6.83 (s, 1H), 3.97 (s, 3H), 3.54 (dd, J=5.2, 13.6 Hz, 1H), 3.23-3.00 (m, 2H), 2.90 (s, 3H), 2.67-2.54 (m, 1H), 2.44 (s, 3H), 2.29 (q, J=9.2 Hz, 1H), 2.12-1.97 (m, 1H), 1.81-1.68 (m, 2H), 1.60 (s, 6H), 1.57-1.47 (m, 1H).

Procedure for the Preparation of Compound 20c:

To a solution of compound 20b (300 mg, 0.537 mmol) in MeOH (15 mL) was added Pd/C (10%, 30 mg). The reaction mixture was stirred at 25-31° C. for 3 h under H$_2$ balloon (15 Psi). The reaction mixture was filtered, and the filtrate was concentrated in vacuo to give compound 20c (260 mg, 79.4% yield) as a brown solid.

LCMS: R$_f$=0.686 min in 5-95AB_220&254.lcm chromatography (MERCK RP18 2.5-2 mm), MS (ESI) m/z=529.2 [M+H]$^+$.

Procedure for the Preparation of Example 20:

To a solution of compound 20c (260 mg, 0.427 mmol) and DIEA (83 mg, 0.64 mmol) in DMF (3 mL), was added acryloyl chloride (39 mg, 0.427 mmol) in ice water bath. The resulting mixture was stirred at 5-10° C. for 0.5 h. The reaction was quenched by H$_2$O (0.1 mL) and then filtered, the filtrate was purified by pre-HPLC (Column: Waters Xbridge 150*25 5 um; Condition: 50-80% B (A: 0.05% ammonia, B: CH$_3$CN); Flow Rate: 25 ml/min) and lyophilized to give Example 20 (44.4 mg, 17.9% yield) as a white solid.

LCMS: R$_f$=2.208 min in 10-80CD_3min_220&254. lcm chromatography (XBrige Shield RP18 2.1*50 mm), MS (ESI) m/z=583.3 [M+H]$^+$.

HPLC: R$_f$=4.39 min in 10-80_CD_1.2ML chromatography (XBridge Shield RP 18 2.1*50 mm 5 um).

$^1$H NMR (400 MHz, CDCl$_3$) δ 10.58 (br s, 1H), 10.08 (br s, 1H), 10.01 (br s, 1H), 8.40 (s, 1H), 8.31 (dd, J=8.0, 13.2 Hz, 1H), 7.65 (br s, 1H), 7.10 (dd, J=8.8, 12.0 Hz, 1H), 6.71 (s, 1H), 6.39 (br s, 1H), 6.38 (br s, 1H), 6.04 (br s, 1H), 5.77 (t, J=5.6 Hz, 1H), 3.88 (s, 3H), 3.18-3.03 (m, 1H), 2.87-2.80 (m, 1H), 2.74 (s, 3H), 2.71-2.64 (m, 2H), 2.56 (s, 3H), 2.41-2.33 (m, 1H), 1.97 (qd, J=8.8, 12.4 Hz, 1H), 1.79-1.72 (m, 8H), 1.43-1.35 (m, 1H).

Example 21

(R)—N-(5-(4-(4,5-difluoro-2-(2-hydroxypropan-2-yl)phenylamino)-1,3,5-triazin-2-ylamino)-2-(2-((dimethylamino)methyl)pyrrolidin-1-yl)-4-methoxyphenyl)acrylamide

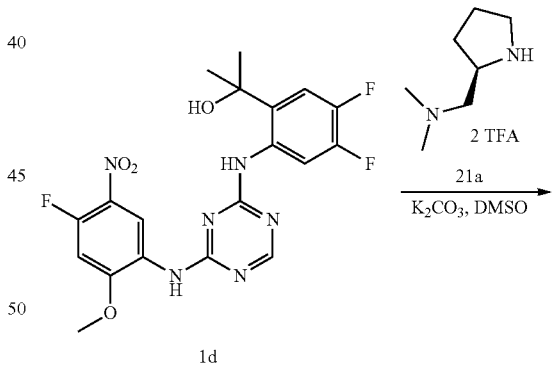

1d

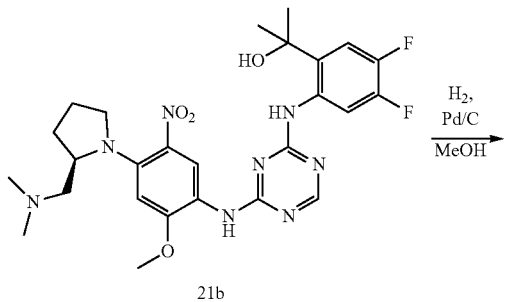

21b

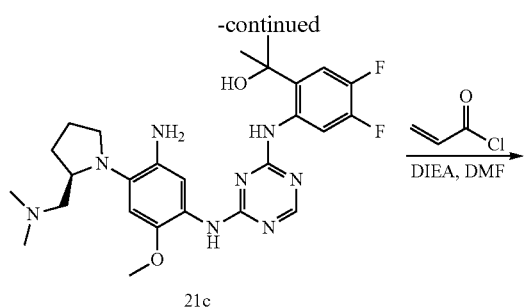

21c

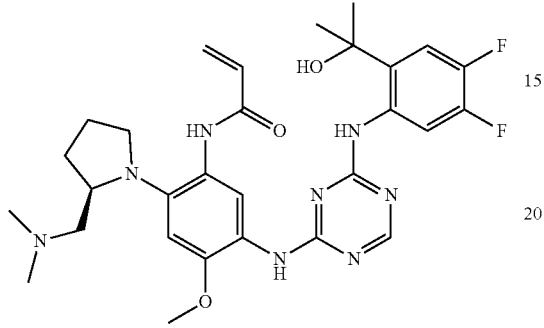

Example 21

Procedure for the Preparation of Compound 21b:

A solution of compound 1d (150 mg, 0.33 mmol), compound 21a (101 mg, 0.50 mmol), and K$_2$CO$_3$ (91 mg, 0.66 mmol) in DMSO (3 mL) was stirred at 90° C. for 3 h. The reaction mixture was poured into ice water (15 mL), then stirred for 30 min, the precipitated solid was collected and the filter cake was dissolved into CH$_2$Cl$_2$ (35 mL), dried over sodium sulfate, filtered and the filtrate was concentrated in vacuum to give compound 21b (220 mg, crude) as a yellow solid.

$^1$H NMR (400 MHz, CDCl$_3$) δ 9.75 (brs, 1H), 8.88 (brs, 1H), 8.30 (s, 1H), 8.17 (s, 1H), 7.26 (s, 1H), 7.01 (dd, J=8.4 Hz, 12.0 Hz, 1H), 6.63 (s, 1H), 3.88 (s, 3H), 3.58-3.50 (m, 1H), 2.61-2.56 (m, 2H), 2.36-2.28 (m, 1H), 2.26-2.19 (m, 7H), 1.96-1.91 (m, 1H), 1.83-1.65 (m, 3H), 1.62 (s, 6H).

Procedure for the Preparation of Compound 21c:

A solution of compound 21b (200 mg crude, 0.33 mmol) and Pd/C (20 mg) in MeOH (3 mL) was stirred under H$_2$ balloon at 25-31° C. for 1 h (dark mixture). The reaction mixture was filtered, and the filtrate was concentrated in vacuum to give compound 21c (180 mg, crude) as a green solid.

$^1$H NMR (400 MHz, CDCl$_3$) δ 9.75 (brs, 1H), 8.29-8.15 (m, 2H), 7.80-7.50 (m, 2H), 7.01 (dd, J=9.2 Hz, 12.4 Hz, 1H), 6.64 (s, 1H), 3.74 (s, 3H), 3.36-3.31 (m, 2H), 2.60-2.53 (m, 1H), 2.25-2.15 (m, 2H), 2.13 (s, 6H), 1.87-1.82 (m, 2H), 1.68-1.63 (m, 1H), 1.61-1.56 (m, 7H).

Procedure for the Preparation of Example 21:

To a solution of compound 21c (180 mg, crude, 0.33 mmol) and DIEA (85 mg, 0.66 mmol) in DMF (3 mL) was added acryloyl chloride (30 mg, 0.33 mmol) drop wise at 0° C.

The black mixture was stirred at 0° C. for 1 h. The reaction mixture was purified by prep-HPLC: [Column: Waters Xbridge 150*25 5 um; Condition: 40-70% B (A: 0.05% ammonia; B: CH$_3$CN); Flow rate: 25 ml/min]. Fractions containing the desired compound were lyophilized to afford Example 21 (40.6 mg, 21% over 3 steps) as a white solid.

LCMS: R$_t$=1.856 min in 10-80AB_4min_220&254 chromatography (Xtimate C18 2.1*30 mm), MS (ESI) m/z=583.0 [M+H]$^+$.

$^1$H NMR (400 MHz, CDCl$_3$) δ 11.65 (brs, 1H), 10.06 (brs, 1H), 9.88 (s, 1H), 8.40 (s, 1 H), 8.32 (dd, J=8.0 Hz, 12.8 Hz, 1H), 7.68 (s, 1H), 7.10 (dd, J=8.8 Hz, 12.4 Hz, 1H), 6.71 (s, 1H), 6.41-6.30 (m, 2H), 6.05 (brs, 1H), 5.78 (dd, J=3.2 Hz, 8.0 Hz, 1H), 3.86 (s, 3H), 3.33-3.28 (m, 2H), 3.02-2.93 (m, 1H), 2.29 (dd, J=8.0 Hz, 12.4 Hz, 1H), 2.17-2.07 (m, 7H), 2.01-1.84 (m, 3H), 1.76 (s, 6H), 1.72-1.64 (m, 1H).

HPLC: R$_t$=3.26 min in 10-80AB_1.2 ml chromatography (Ultimate C18 3*50 mm 3 um).

Example 22

N-(2-((2-(bis(methyl-d$_3$)amino)ethyl)(methyl)amino)-5-((4-((4,5-difluoro-2-(2-hydroxypropan-2-yl)phenyl)amino)-1,3,5-triazin-2-yl)amino)-4-methoxyphenyl) acrylamide

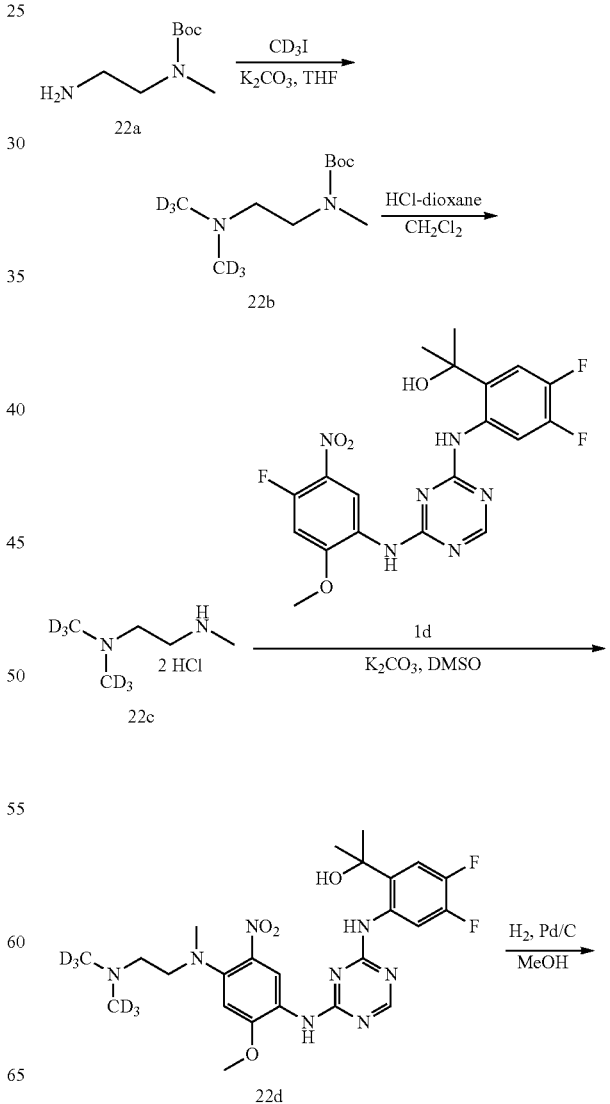

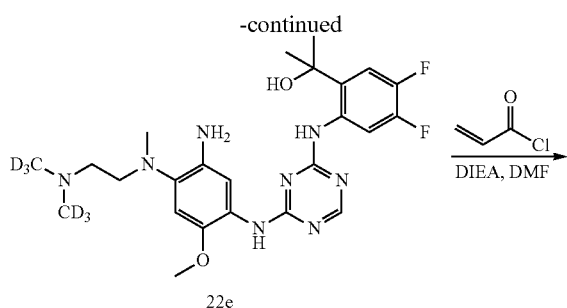

22e

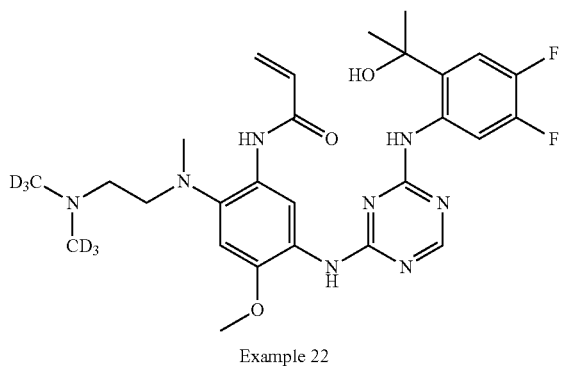

Example 22

Procedure for the Preparation of Compound 22b:

To a solution of compound 22a (500 mg, 2.87 mmol) and K₂CO₃ (793 mg, 5.74 mmol) in THF (20 mL) was added CD₃I (624 mg, 4.30 mmol). The mixture was stirred at 26-33° C. for 1 h while white solid was precipitate out. Then CD₃I (208 mg, 0.5 eq, 1.43 mmol) was added to the mixture and stirred at 26-33° C. for another 1 h. The reaction mixture was filtered and the organic layer was concentrated under reduced pressure to give compound 22b (300 mg, 50% yield) as a colorless solid. LCMS: R$_t$=0.743 min in 0-60AB_2MIN_E.M chromatography (Xtimate C18, 2.1×30 mm, 3 um), MS (ESI) m/z=209.2 [M+H]⁺.

¹H NMR (400 MHz, DMSO-d₆) δ 3.24-3.18 (m, 1H), 3.12 (t, J=6.8 Hz, 1H), 2.78 (br s, 3H), 2.62 (br t, J=6.7 Hz, 1H), 2.34-2.26 (m, 1H), 1.38 (s, 9H).

Procedure for the Preparation of Compound 22c:

To a solution of compound 22b (300 mg, 1.0 eq, 1.44 mmol) in CH₂Cl₂ (5 mL) was added HCl-dioxane (5 mL, 4 M). The resulting mixture was stirred at 22-27° C. for 2 h. The reaction mixture was concentrated under reduced pressure to give compound 22c (250 mg, 95% yield) as yellow oil.

LCMS: R$_t$=0.098 min in 0-60AB_2MIN_E.M chromatography (Xtimate C18, 2.1×30 mm, 3 um), MS (ESI) m/z=109.2 [M+H]⁺.

¹H NMR (400 MHz, DMSO-d₆) δ 3.43-3.37 (m, 1H), 3.36-3.22 (m, 1H), 3.16 (br s, 2H), 2.56 (br s, 3H).

Procedure for the Preparation of Compound 22d:

To a solution of compound 22c (250 mg, 0.55 mmol) and K₂CO₃ (304 mg, 2.20 mmol) in DMSO (5 mL) was added compound 6d (250 mg, 1.38 mmol). The resulting mixture was stirred at 22-27° C. for 12 h while the colour changes from pale brown to deep yellow. The reaction mixture was diluted with EtOAc (20 mL) and washed with brine (2×30 mL). The organic layer was dried over anhydrous Na₂SO₄ and concentrated under reduced pressure to give the crude residue, which was purified by column chromatography on silica gel (CH₂Cl₂/MeOH=10/1) to give compound 22d (90 mg, 30% yield) as a yellow solid.

LCMS: R$_t$=2.414 min in 10-80AB_7min_220&254.lcm chromatography (Xtimate C18 2.1×30 mm), MS (ESI) m/z=539.0 [M+H]⁺.

Procedure for the Preparation of Compound 22e:

To a solution of compound 22d (90 mg, 1.0 eq, 0.17 mmol) in MeOH (10 mL) was added Pd/C (9 mg). The resulting mixture was purged and degassed with H₂ for 3 times, then stirred at 23-28° C. under hydrogen balloon (15 Psi) for 2 h. The reaction mixture was filtered and concentrated under reduced pressure to give compound 22e (70 mg, 81% yield) as colorless oil. The structure and purity were confirmed by LCMS(R$_t$=0.698 min, 509.4 [M+H]⁺).

LCMS: R$_t$=0.698 min in 5-95AB_1.5min_220&254 chromatography (MERCK RP18e 25-2 mm), MS (ESI) m/z=509.4 [M+H]⁺.

Procedure for the Preparation of Example 22:

To a solution of compound 22e (70 mg, 0.14 mmol) and DIEA (36 mg, 0.28 mmol) in DMF (2.5 mL) was added a solution of compound acryloyl chloride (13 mg, 0.14 mmol) in DMF (0.5 mL) drop wise at 0° C. The resulting mixture was stirred at 0° C. under ice-water bath for 30 min. The reaction mixture was purified by prep-HPLC [Column: Waters Xbridge 150×25 5 um; Condition: 38-68% B (A: 0.05% NH₃H₂O; B: CH₃CN); Flow rate: 25 ml/min]. Fractions containing the desired compound were lyophilized to afford Example 22 (21.9 mg, 28% yield) as a white solid.

LCMS: R$_t$=1.790 min in 10-80AB_4min_220&254 chromatography (Xtimate C18 2.1×30 mm), MS (ESI) m/z=563.0 [M+H]⁺.

HPLC: R$_t$=3.06 min in 10-80_ab_1.2ML chromatography (Ultimate C18 3×50 mm 3 um).

¹H NMR (400 MHz, CDCl₃) δ 10.68 (br s, 1H), 10.46 (br s, 1H), 9.97 (br s, 1H), 8.41 (s, 1H), 8.32 (dd, J=8.0, 12.8 Hz, 1H), 7.69 (br s, 1H), 7.11 (dd, J=8.8, 12.2 Hz, 1H), 6.78 (s, 1H), 6.44-6.30 (m, 2H), 6.11 (br s, 1H), 5.80-5.73 (m, 1H), 3.88 (s, 3H), 2.88 (br s, 2H), 2.71 (s, 3H), 2.29 (br s, 2H), 1.77 (s, 6H).

Example 23

N-(5-(4-(4,5-difluoro-2-(2-hydroxypropan-2-yl)phenylamino)-1,3,5-triazin-2-ylamino)-2-(3-((dimethylamino)methyl)azetidin-1-yl)-4-methoxyphenyl)acrylamide

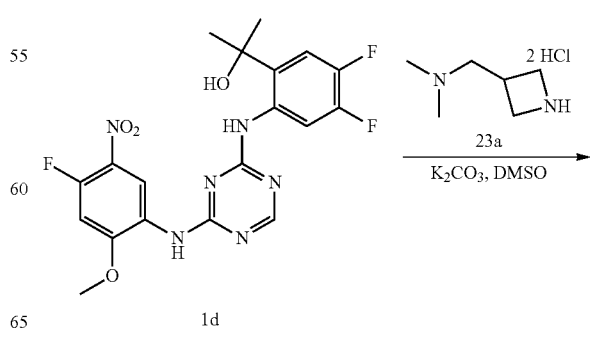

1d

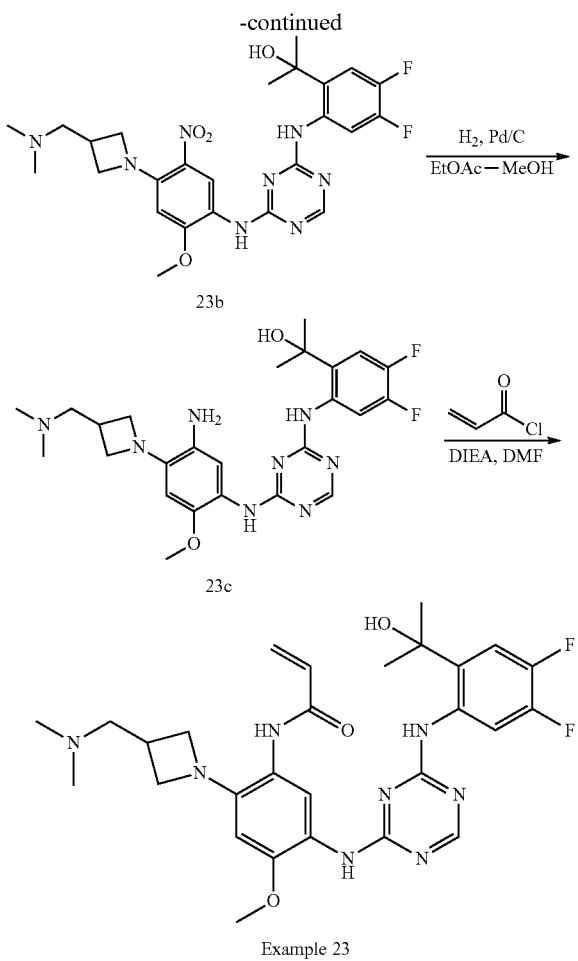

Example 23

Procedure for the Preparation of Compound 23b:

A mixture of compound 1d (150 mg, 0.318 mmol), compound 23a (60 mg, 0.318 mmol) and K$_2$CO$_3$ (175 mg, 1.27 mmol) in DMSO (2 mL) was stirred at 90° C. for 3 h (brown suspension). The reaction was quenched with ice water (8 mL), then filtered, and the cake was washed with H$_2$O (5 mL), dried in high vacuo to afforded compound 23b (180 mg, 74.3% yield) as a yellow solid.

LCMS: R$_t$=0.710 min in 5-95AB_220&254.lcm chromatography (MERCK RP-18e 25-2 mm), MS (ESI) m/z=545.2 [M+H]$^+$.

$^1$H NMR (400 MHz, CDCl$_3$) δ 10.05 (brs, 1H), 8.98 (brs, 1H), 8.37 (s, 1H), 8.24 (s, 1H), 7.28 (m, 1H), 7.11-7.05 (m, 1H), 5.97 (s, 1H), 4.17 (d, J=8.0 Hz, 2H), 3.93 (s, 3H), 3.67-3.63 (m, 2H), 2.95-2.88 (m, 1H), 2.57 (d, J=7.6 Hz, 2H), 2.43 (s, 6H), 1.69 (s, 6H).

Procedure for the Preparation of Compound 23c:

The mixture of compound 23b (180 mg, 0.33 mmol) and Pd/C (180 mg, 10%) in EtOAc (20 mL) and MeOH (5 mL) under H$_2$ balloon was stirred for 3 h at 23-28° C. (turned to the black mixture). The reaction was filtered and the cake was rinsed with EtOAc (50 mL), the filtrate was concentrated in vacuo to give compound 23c (140 mg, 82.3% yield) as a yellow solid.

LCMS: R$_t$=0.660 min in 5-95AB_220&254.lcm chromatography (MERCK RP-18e 25-2 mm), MS (ESI) m/z=515.2 [M+H]$^+$.

$^1$H NMR (400 MHz, CDCl$_3$): δ ppm 9.63 (brs, 1H), 8.23-8.17 (m, 2H), 7.59 (s, 1H), 7.49 (s, 1H), 7.04-6.98 (m, 1H), 6.17 (m, 1H), 3.94 (t, J=7.2 Hz, 2H), 3.50 (s, 3H), 3.41 (t, J=7.6 Hz, 2H), 2.85-2.77 (m, 1H), 2.55-2.48 (m, 2H), 2.17 (s, 6H), 1.59 (s, 6H).

Procedure for the Preparation of Example 23:

To the mixture of compound 23c (140 mg, 0.27 mmol) and DIEA (105 mg, 0.81 mmol) in DMF (3 mL) was added drop wise a solution of acryloyl chloride (29.9 mg, 0.33 mmol) in DMF (1 mL) under ice water bathe over 1 h. After the reaction was stirred for 30 min at 0-5° C. (brown solution), the reaction was quenched with H$_2$O (0.1 mL) and the resulting solution was directly purified by prep-HPLC [Waters Xbridge 150*25.5 um; Condition: 37-57% B (A: 0.05% ammonia; B: CH$_3$CN); Flow rate: 25 ml/min]. Fractions containing the desired compound were lyophilized to afford Example 23 (32.4 mg, 20.9% yield) as a yellow solid.

LCMS: R$_t$=2.172 min in 0-60AB_4.0min_220&254 chromatography (Xtimate C18 2.1*30 mm), MS (ESI) m/z=569.0 [M+H]$^+$.

$^1$H NMR (400 MHz, CDCl$_3$) δ 8.35-8.27 (m, 2H), 7.50 (s, 1H), 7.30-7.27 (m, 1H), 7.10-7.25 (m, 1H), 6.41-6.27 (m, 3H), 5.80 (d, J=10.0 Hz, 2H), 3.99 (t, J=7.6 Hz, 2H), 3.87 (s, 3H), 3.50 (t, J=7.2 Hz, 2H), 2.94-2.87 (m, 1H), 2.54 (d, J=8.0 Hz, 2H), 2.23 (s, 6H), 1.71 (s, 6H).

HPLC: R$_t$=2.24 min. HPLC-P Venusil XBP C18 3*50 mm, method\0-60AB_1.2 ML.MET

Example 24

N-(5-(4-(4,5-difluoro-2-(2-hydroxypropan-2-yl)phenylamino)-1,3,5-triazin-2-ylamino)-4-methoxy-2-(methyl(2-(piperidin-1-yl)ethyl)amino)phenyl)acrylamide

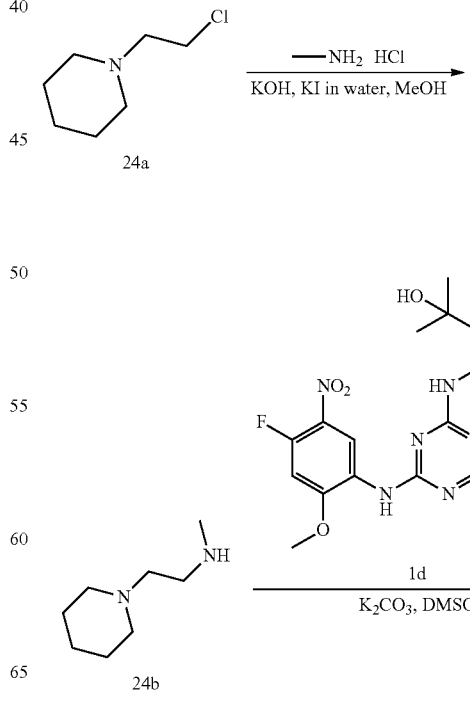

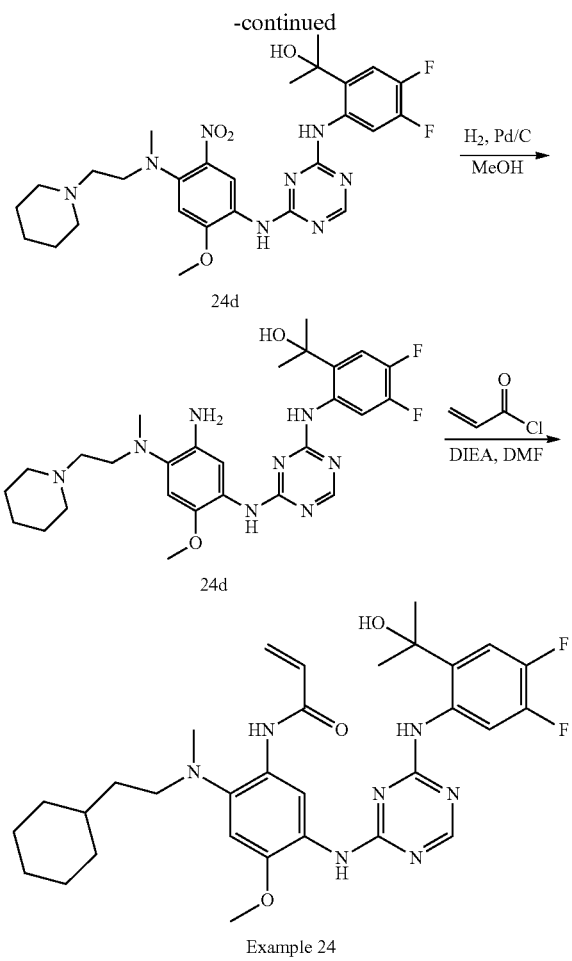

Example 24

Procedure for the Preparation of Compound 24b:

To a solution of compound 24a (1.0 g, 6.77 mmol) and methanamine (1.4 g, 20.31 mmol) in MeOH (10 mL) was added KOH (760 mg, 13.55 mmol) in 5 ml water with catalytic amount of KI (225 mg, 1.35 mmol). The resulting mixture was heated at 50° C. to 80° C. for 18 h. The reaction was treated with HCl (1M) to adjust pH=7, then extracted with EtOAc (3×10 mL). The organic layers were washed with brine (3×10 mL), dried and concentrated under reduced pressure to give the crude residue, which was purified by column chromatography on silica gel (CH$_2$Cl$_2$/MeOH=10/1 (v/v)) to afford compound 24b (120 mg, 12.5 yield) as colorless oil.

LCMS: R$_t$=1.688 min (MSD TIC) in 10-80CD_4MIN (XBrige Shield RP18 2.1×50 mm), MS (ESI) m/z=143.2 [M+H]$^+$.

$^1$H NMR (400 MHz, CDCl$_3$) δ 2.57-2.47 (m, 2H), 2.46-2.30 (m, 8H), 2.28-2.15 (m, 2H), 1.59-1.54 (m, 5H), 1.42 (br d, J=5.2 Hz, 2H).

Procedure for the Preparation of Compound 24c:

A solution of compound 1d (190 mg, 0.42 mmol) and K$_2$CO$_3$ (116 mg, 0.84 mmol) in DMSO (2 mL) was added compound 24b (60 mg, 0.42 mmol). The mixture was stirred at 28-33° C. for 2 hours. The reaction mixture was purified by flash column chromatography on silica gel (Condition: 65-75% B (A: 0.05% TFA in water; B: MeOH); Flow rate: 40 ml/min)) to give compound 24c (90 mg, 37.3% yield) as a red solid.

LCMS: R$_t$=0.805 min in 5-95AB_1.5min_220&254 chromatography (MERCK RP18e 25-2 mm), MS (ESI) m/z 573.2 [M+H]$^+$.

Procedure for the Preparation of Compound 24d:

To a solution of compound 24c (90 mg, 0.16 mmol) in MeOH (3 mL) was added Pd/C (10 mg) under N$_2$ protect. The black mixture was stirred at 26-33° C. under H$_2$ balloon (15 Psi) for 1 h. The reaction mixture was filtered and concentrated under reduced pressure to afford compound 24d (70 mg, 82.1% yield) as brown oil.

LCMS: R$_t$=0.764 min in 5-95AB_1.5min_220&254 chromatography (MERCK RP18e 25-2 mm), MS (ESI) m/z 543.1 [M-OH]$^+$.

Procedure for the Preparation of Example 24:

To a solution of compound 24d (70 mg, 0.13 mmol) and DIEA (25 mg, 0.19 mmol) in DMF (1 mL) was added a solution of acryloyl chloride (12 mg, 0.13 mmol) in DMF (1 mL).

The resulting brown mixture was stirred at 0° C. for 30 min. The reaction was purified by prep-HPLC [Column: Waters Xbridge 150×25 5um; Condition: 40-70% B (A: 0.05% ammonia; B: CH$_3$CN); Flow rate: 25 ml/min]. Fractions containing the desired compound were lyophilized to afford Example 24 (12.9 mg, 16.8% yield) as a white solid.

LCMS: R$_t$=5.224 min in 10-80CD_7MIN_220&254 chromatography (XBrige Shield RP18 2.1*50 mm), MS (ESI) m/z 597.3 [M+H]$^+$.

HPLC, R$_t$=4.81 purity 96.87% (220 nm); 10-80_CD_1.2 mL.MET (XBridge Shield RP 18 2.1×50 mm 5 um).

$^1$H NMR (400 MHz, DMSO-d$_6$) δ 10.26 (br s, 1H), 9.33 (s, 1H), 9.14 (br s, 1H), 8.25 (s, 1H), 8.14 (s, 1H), 7.26 (br s, 1H), 6.96 (br s, 1H), 6.59 (dd, J=10.4, 16.8 Hz, 1H), 6.31-6.12 (m, 2H), 5.72 (br d, J=10.4 Hz, 1H), 3.77 (s, 3H), 2.98 (br t, J=6.4 Hz, 2H), 2.70 (s, 3H), 2.40-2.22 (m, 6H), 1.57-1.44 (m, 10H), 1.37 (br d, J=4.0 Hz, 2H), 1.24 (br s, 1H).

Example 25

N-(5-(4-(4,5-difluoro-2-(2-hydroxypropan-2-yl)phenylamino)-1,3,5-triazin-2-ylamino)-4-methoxy-2-((3aS,6aS)-5-methylhexahydropyrrolo[3,4-b]pyrrol-1(2H)-yl)phenyl) acrylamide

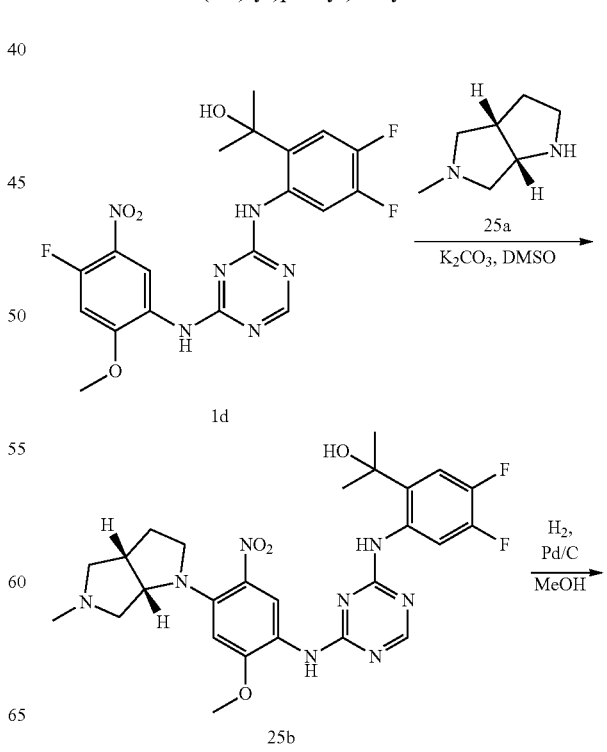

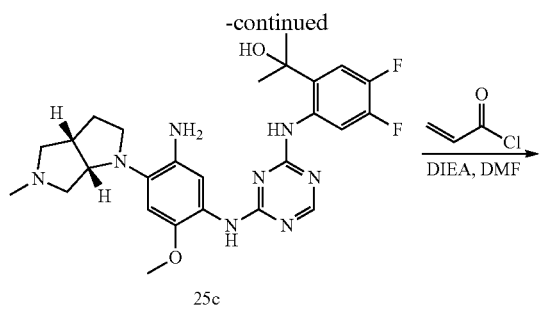

25c

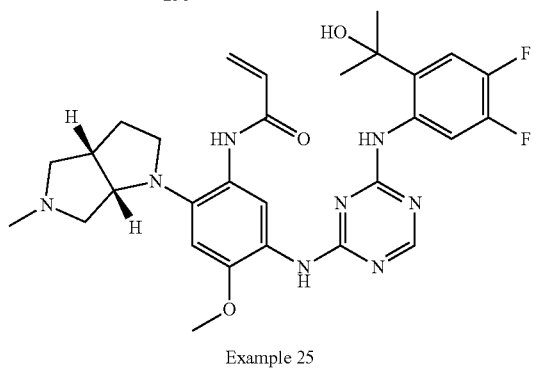

Example 25

Procedure for the Preparation of Compound 25b.

To a solution of compound 1d (200 mg, 0.444 mmol) and K$_2$CO$_3$ (123 mg, 0.888 mmol) in DMSO (4 mL) was added compound 25a (196 mg, 1.554 mmol). The pale yellow reaction mixture was stirred at 85° C. for 3 h (changed from brown to orange). The reaction mixture was added drop wise into H$_2$O (40 mL) under ice water bath while solid was precipitate out. The precipitated solid was collected by filtration and washed with H$_2$O (15 mL×3), then dried in high vacuo to give compound 25b (230 mg, 89.8% yield) as an orange solid.

LCMS: R$_t$=0.709 min in 5-95AB_220&254.lcm chromatography (MERCK RP18 2.5-2 mm), MS (ESI) m/z=557.2 [M+H]$^+$.

$^1$H NMR (400 MHz, CDCl$_3$) δ 10.04 (br s, 1H), 8.30 (br s, 1H), 8.19 (s, 1H), 7.48 (br s, 1H), 7.06 (dd, J=8.4, 12.0 Hz, 1H), 6.37 (s, 1H), 4.45-4.33 (m, 1H), 3.92 (s, 3H), 3.53 (dt, J=6.4, 10.4 Hz, 1H), 3.15 (t, J=8.4 Hz, 1H), 3.01 (quin, J=7.2 Hz, 1H), 2.67 (t, J=8.8 Hz, 1H), 2.61-2.51 (m, 1H), 2.39 (br dd, J=6.4, 9.2 Hz, 1H), 2.23 (d, J=9.2 Hz, 1H), 2.19 (s, 3H), 2.12-1.99 (m, 1H), 1.86 (dd, J=6.0, 12.4 Hz, 1H), 1.65 (s, 6H).

Procedure for the Preparation of Compound 25c:

To a solution of compound 25b (230 mg, 0.338 mmol) in MeOH (15 mL) was added Pd/C (10%, 25 mg). The reaction mixture was stirred at 22-28° C. for 3 h under H$_2$ balloon (15 Psi). The reaction mixture was filtered, and the filtrate was concentrated in vacuo to give compound 25c (180 mg, 82% yield) as greyish-green oil.

LCMS: R$_t$=0.667 min in 5-95AB_220&254.lcm chromatography (ACSSH-LCMS-AB MERCK RP18 2.5-2 mm), MS (ESI) m/z=527.2 [M+H]$^+$.

Procedure for the Preparation of Example 25:

To a solution of compound 25c (170 mg, 0.33 mmol) and DIEA (64 mg, 0.50 mmol) in DMF (2 mL) was added acryloyl chloride (29 mg, 0.33 mmol) under ice water bath. The resulting mixture was stirred at 5-10° C. for 0.5 h. The reaction was quenched by H$_2$O (0.1 mL) and then filtered, the filtrate was purified by pre-HPLC (Column: Waters Xbridge 150*25 5 um; Condition: 30-60% B (A: 0.05% ammonia, B: CH$_3$CN); Flow Rate: 25 ml/min) and lyophilized to give Example 25 (48.0 mg, 25.1% yield) as a white solid.

LCMS: R$_t$=1.982 min in 10-80CD_3min_220&254 (XBrige Shield RP18 2.1*50 mm), MS (ESI) m/z=581.3 [M+H]$^+$.

HPLC: R$_t$=3.94 purity 96.04% (220 nm); 10-80_CD_1.2 mL.MET (XBridge Shield RP 18 2.1*50 mm 5 um).

$^1$H NMR (400 MHz, CDCl$_3$) δ 10.66 (br s, 1H), 9.92 (br s, 1H), 9.59 (br s, 1H), 8.40 (s, 1H), 8.33 (dd, J=8.0, 12.8 Hz, 1H), 7.68 (br s, 1H), 7.10 (dd, J=8.8, 12.0 Hz, 1H), 6.78 (s, 1H), 6.53-6.34 (m, 2H), 5.99 (br s, 1H), 5.76 (d, J=9.6 Hz, 1H), 3.87 (s, 3H), 3.72-3.60 (m, 1H), 3.21 (t, J=7.2 Hz, 1H), 2.92-2.78 (m, 3H), 2.71 (d, J=10.0 Hz, 1H), 2.33-2.31 (m, 1H), 2.29 (s, 3H), 2.23-2.17 (m, 1H), 1.90 (dd, J=4.0, 10.0 Hz, 1H), 1.87-1.80 (m, 1H), 1.76 (br s, 6H).

Example 26

N-(5-(4-(5-chloro-4-fluoro-2-(2-hydroxypropan-2-yl)phenylamino)-1,3,5-triazin-2-ylamino)-4-methoxy-2-(methyl(2-(piperidin-1-yl)ethyl)amino)phenyl)acrylamide

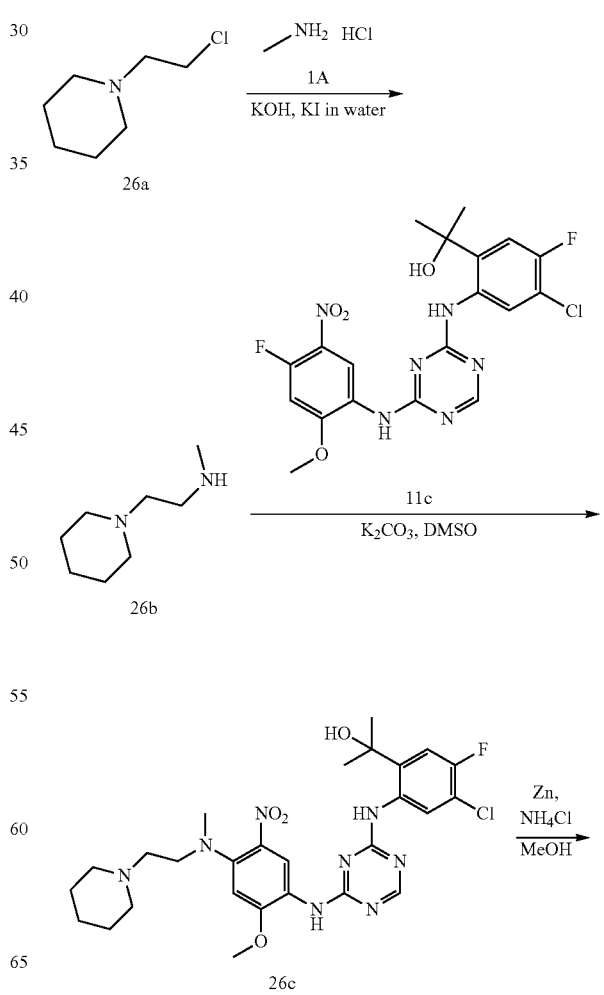

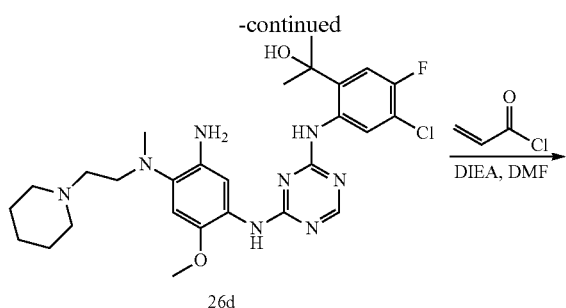

26d

Example 26

Procedure for the Preparation of Compound 26b:

To a solution of compound 26a (1.0 g, 6.77 mmol) in MeOH (10 mL) was added DIEA (1.8 g, 13.55 mmol) and methanamine hydrochloride (10 mL, 20.31 mmol, 2M in THF). The resulting mixture was stirred for 18 h. The reaction was treated with HCl (1M) to adjust pH=7, then extracted with EtOAc (3×10 mL). The organic layers were washed with brine (3×10 mL), dried and concentrated under reduced pressure to give the crude residue, which was purified by column chromatography on silica gel ($CH_2Cl_2$/MeOH=10/1 (v/v)) to afford compound 26b (120 mg, 12.5% yield) as colorless oil.

LCMS: $R_t$=1.688 min in 10-80CD_4MIN (XBrige Shield RP18 2.1×50 mm), MS (ESI) m/z=143.2 $[M+H]^+$.

$^1$H NMR (400 MHz, $CDCl_3$) δ 2.57-2.47 (m, 2H), 2.46-2.30 (m, 8H), 2.28-2.15 (m, 2H), 1.59-1.54 (m, 5H), 1.42 (br d, J=5.0 Hz, 2H).

Procedure for the Preparation of Compound 26c:

A solution of compound 26b (197 mg, 0.42 mmol) and $K_2CO_3$ (116 mg, 0.84 mmol) in DMSO (2 mL) was added with compound 11c (60 mg, 0.42 mmol). The mixture was stirred at 23-28° C. for 2 hours. It was purified by Biotage flash reversed-phase C-18 column chromatography eluting with MeOH/$H_2O$ (MeOH in water from 55% to 60%) to give compound 26c (150 mg, 60.4% yield) as a red solid.

LCMS: $R_t$=0.826 min in 5-95AB_1.5min_220&254 chromatography (MERCK RP18e 25-2 mm), MS (ESI) m/z=589.1 $[M+H]^+$.

Procedure for the Preparation of Compound 26d:

To a solution of compound 26c (150 mg, 0.26 mmol) in MeOH (5 mL) and $H_2O$ (1 mL) was added Zn (87 mg, 1.32 mmol) and $NH_4Cl$ (142 mg, 2.65 mmol). The mixture was stirred at 70° C. for 1.5 h under $N_2$ (black mixture). The reaction mixture was quenched by the addition of aqueous $NH_4Cl$ (20 mL), then extracted with EtOAc (3×10 mL). The organic layers were washed with brine (3×10 mL), dried and concentrated in vacuum directly to give compound 26d (120 mg, 84.4% yield) as brown oil.

LCMS: $R_t$=0.783 min in 5-95AB_1.5min_220&254 chromatography (MERCK RP18e 25-2 mm), MS (ESI) m/z=559.1 $[M-OH]^+$.

Procedure for the Preparation of Example 26:

To a solution of compound 26d (120 mg, 0.21 mmol) and DIEA (42 mg, 0.32 mmol) in DMF (1 mL) was added a solution of acryloyl chloride (19 mg, 0.21 mmol) in DMF (1 mL) drop-wise at 0° C. The brown resulting mixture was stirred at 0° C. for 30 min. The reaction was purified by Biotage flash reversed-phase C-18 column chromatography [Condition: 75-80% B (A: 0.05% aqueous $NH_4HCO_3$; B: $CH_3CN$); Flow rate: 40 ml/min].

Fractions containing the desired compound were lyophilized to afford Example 26 (47.2 mg, 35.9% yield) as a white solid.

LCMS: $R_t$=5.365 min in 10-80CD_7MIN_220&254 chromatography (XBrige Shield RP18 2.1*50 mm), MS (ESI) m/z=613.3 $[M+H]^+$.

HPLC: $R_t$=4.83 purity 97.09% (220 nm), 10-80_CD_1.2 mL.MET (XBridge Shield RP 18 2.1×50 mm 5 um).

$^1$H NMR (400 MHz, DMSO-$d_6$) δ 10.19 (br s, 1H), 9.34 (br s, 1H), 9.08 (br s, 1H), 8.25 (s, 1H), 8.12 (s, 1H), 7.26 (br s, 1H), 6.97 (br s, 1H), 6.60 (br s, 1H), 6.30 (s, 1H), 6.19 (br d, J=17.1 Hz, 1H), 5.72 (br d, J=10.3 Hz, 1H), 3.79 (s, 3H), 2.98 (br s, 2H), 2.69 (s, 3H), 2.34 (br s, 6H), 1.57-1.31 (m, 13H).

Example 27

(R)—N-(5-(4-(4,5-difluoro-2-(2-hydroxypropan-2-yl)phenylamino)-1,3,5-triazin-2-ylamino)-2-(3-(dimethylamino)pyrrolidin-1-yl)-4-methoxyphenyl)acrylamide Id 27a

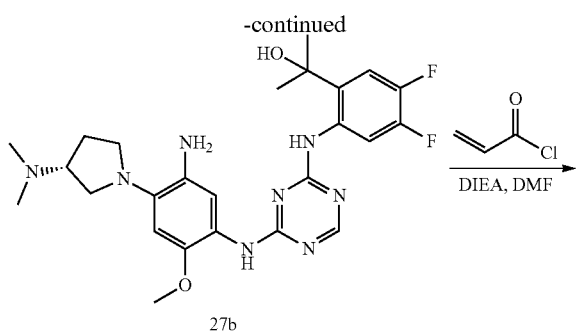

27b

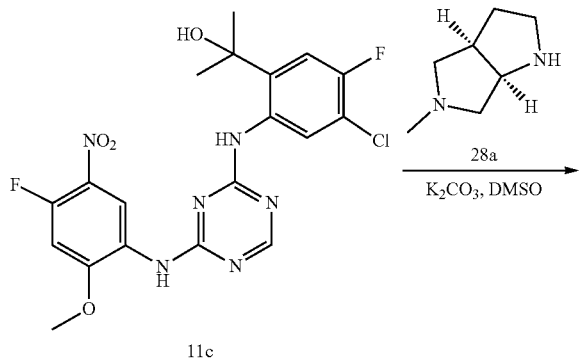

Example 27

Procedure for the Preparation of Compound 27a:

To a solution of compound 1d (180 mg, 0.40 mmol), K₂CO₃ (110.6 mg, 0.80 mmol) in DMSO (4 mL) was added (R)—N,N-dimethylpyrrolidin-3-amine (54.8 mg, 0.48 mmol). The resulting mixture was stirred at 24-27° C. for 2 h. The reaction mixture was combined with that of bath 1359-035 and poured into water (50 mL) carefully with stirring, yellow solid was precipitated. The precipitated solid was collected by filtration and dissolved with CH₂Cl₂ (20 mL), dried over anhydrous Na₂SO₄ and concentrated under reduced pressure to give compound 27a (210 mg, 87% yield) as a yellow solid.

LCMS: $R_t$=0.705 min in 5-95AB_1.5min_220&254 chromatography (MERCK RP18e 25-2 mm), MS (ESI) m/z=545.1 [M+H]⁺.

Procedure for the Preparation of Compound 27b:

To a solution of compound 27a (210 mg, 0.39 mmol) in MeOH (5 mL) was added Pd/C (35 mg). The resulting mixture was purged and degassed with H₂ for 3 times, then stirred at 23-29° C. under H₂ balloon, (15 Psi) for 2 h. The reaction mixture was filtered and concentrated under reduced pressure to give compound 27b (170 mg, 84.7% yield) as a brown solid.

LCMS: $R_t$=0.667 min in 5-95AB_1.5min_220&254 chromatography (MERCK RP18e 25-2 mm), MS (ESI) m/z=515.2 [M+H]⁺.

Procedure for the Preparation of Example 27:

To a solution of compound 27b (100 mg, 0.19 mmol) and DIEA (50 mg, 0.38 mmol) in DMF (2 mL) was added acryloyl chloride (17 mg, 0.19 mmol) in DMF (1 mL). The resulting mixture was stirred at 0° C. under ice-water bath for 20 min. The reaction mixture was quenched by three drops of water and purified by prep-TLC (CH₂Cl₂/MeOH=7/1 (v/v)) to afford the impure product (100 mg) as a white solid, which was further purified by prep-HPLC (column: Waters Xbridge 150*25 5 um: 30-60% B (A: water (0.05% ammonia hydroxide v/v), B: CH₃CN), flow rate: 25 mL/min) to afford Example 27 (15 mg, 13.9% yield) as a white solid.

LCMS: $R_t$=1.651 min in 10-80AB_4min_220&254 chromatography (Xtimate C18 2.1*30 mm), MS (ESI) m/z=568.9 [M+H]⁺.

HPLC: $R_t$=3.17 min in 10-80_CD_1.2ML chromatography (Ultimate C18 3*50 mm 3 um).

¹H NMR (400 MHz, CDCl₃) δ 10.59 (br s, 1H), 9.80 (br s, 1H), 8.49 (br s, 1H), 8.40 (s, 1H), 8.33 (dd, J=8.0, 13.2 Hz, 1H), 7.64 (br s, 1H), 7.10 (dd, J=8.4, 12.2 Hz, 1H), 6.76 (s, 1H), 6.40-6.36 (m, 2H), 5.84-5.78 (m, 1H), 3.88 (s, 3H), 3.15-3.07 (m, 4H), 2.90 (br t, J=7.2 Hz, 1H), 2.31 (s, 6H), 2.19 (dt, J=7.2, 12.8 Hz, 1H), 2.00-1.90 (m, 1H), 1.76 (s, 6H), 3.87 (s, 3H), 2.40 (s, 6H).

Example 28

N-(5-(4-(5-chloro-4-fluoro-2-(2-hydroxypropan-2-yl)phenylamino)-1,3,5-triazin-2-ylamino)-4-methoxy-2-((3aR,6aR)-5-methylhexahydropyrrolo[3,4-b]pyrrol-1(2H)-yl)phenyl)acrylamide

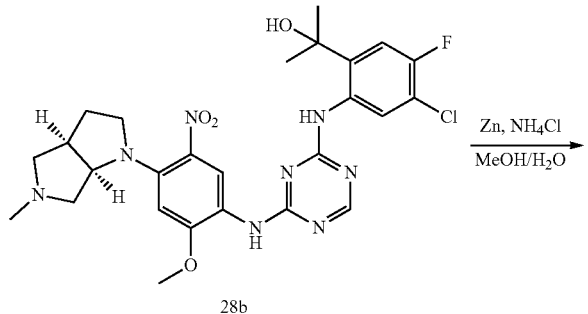

11c

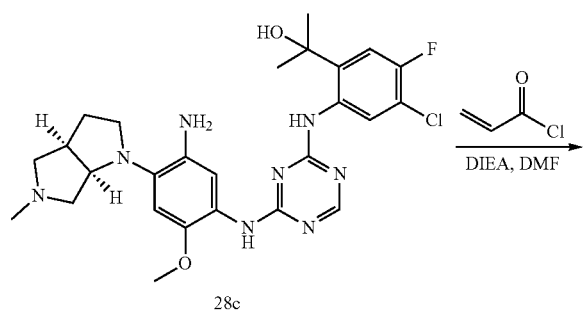

28b

28c

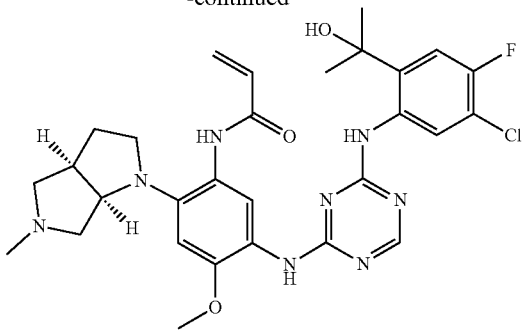

Example 28

Procedure for the Preparation of Compound 28b:

To a solution of compound 11c (300 mg, 0.64 mmol) in DMSO (5 mL) was added potassium carbonate (450 mg, 3.25 mmol) and compound 28a (120 mg, 0.95 mmol). The mixture was stirred at 85° C. for 3 h. The mixture was poured into ice water (30 mL) and the solid was precipitated out. The solid was separated by suction filtration and dried in vacuo to afford compound 28b (320 mg, 87% yield) as orange solid.

LCMS: $R_t$=1.868 min in 10-80AB_4min_220&254 chromatography (Xtimate C18, 2.1×30 mm, 3 um), MS (ESI) m/z=573.2 [M+H]$^+$.

$^1$H NMR: (400 MHz, CDCl$_3$) δ 9.60 (s, 1H), 8.85 (s, 1H), 8.30 (s, 1H), 7.32 (s, 1H), 7.00 (d, J=10.4 Hz, 1H), 6.32 (s, 1H), 4.40-4.29 (m, 1H), 3.88 (s, 3H), 3.53-3.43 (m, 1H), 3.18-3.08 (m, 1H), 3.01-2.90 (m, 1H), 2.61-2.55 (m, 1H), 2.47-2.40 (m, 1H), 2.39-2.33 (m, 1H), 2.24-2.17 (m, 1H), 2.13 (s, 3H), 2.05-1.95 (m, 1H), 1.86-1.75 (m, 1H), 1.62 (s, 6H).

Procedure for the Preparation of Compound 28c:

To a solution of compound 28b (200 mg, 0.35 mmol) in methanol/water (5 mL/1 mL) was added NH$_4$Cl (112 mg, 2.09 mmol) and Zn (114 mg, 1.75 mmol). The resulting mixture was stirred at 90° C. for 1 h under nitrogen. The mixture was poured into water (20 mL) and extracted with dichloromethane (15 mL×4). The combined organic layers were dried over sodium sulfate, filtered and concentrated in vacuo to afford a brown gum, which was purified by flash column chromatography on silica gel (0 to 10% methanol in CH$_2$Cl$_2$) to afford compound 28c (110 mg, 57.8% yield) as green solid.

LCMS: $R_t$=0.716 min in 5-95AB_220&254 chromatography (MERCK RP18 2.5-2 mm), MS (ESI) m/z=543.0 [M+H]$^+$.

$^1$H NMR: (400 MHz, DMSO-d$_6$) δ 10.15 (s, 1H), 8.82 (br. s, 1H), 8.42 (s, 1H), 8.24 (s, 1H), 7.27 (d, J=10.4 Hz, 1H), 6.80 (br. s, 3H), 6.29 (s, 1H), 4.28-4.20 (m, 1H), 3.69 (s, 3H), 3.07-2.95 (m, 2H), 2.70-2.59 (m, 2H), 2.53 (s, 3H), 2.49-2.36 (m, 2H), 2.32-2.18 (m, 1H), 2.15-2.02 (m, 1H), 1.85-1.72 (m, 1H), 1.52 (s, 6H).

Procedure for the Preparation of Example 28:

To a solution of compound 28c (90 mg, 0.17 mmol) in DMF (3 mL) was added DIEA (43 mg, 0.33 mmol), followed with acryloyl chloride (15 mg, 0.17 mmol) in three times at 0° C. The mixture was quenched with water and combined with previous batch for further purification by pre-HPLC (column: Waters Xbridge 150×25, 5um, condition: 46%-66% B (A: water/10 mM NH$_4$HCO$_3$, B: CH$_3$CN), flow rare: 25 mL/min) to afford Example 28 (29.4 mg, 23.8% yield) as white solid.

LCMS: $R_t$=1.870 min in 10-80AB_4min_220&254 chromatography (Xtimate C18 2.1×30 mm), MS (ESI) m/z=597.1 [M+H]$^+$.

HPLC: $R_t$=3.84 min in 10-80_CD_1.2 ml chromatography (XBridge Shield RP 18 2.1×50 mm 5 um).

$^1$H NMR (400 MHz, CDCl$_3$) δ 10.53 (s, 1H), 9.85 (s, 1H), 9.52 (s, 1H), 8.40 (d, J=7.2 Hz, 1H), 8.34 (s, 1H), 7.60 (s, 1H), 7.02 (d, J=10.8 Hz, 1H), 6.70 (s, 1H), 6.42 (br. s, 1H), 6.35-6.26 (m, 1H), 5.98 (br. s, 1H), 5.69 (d, J=10.8 Hz, 1H), 3.79 (s, 3H), 3.65-3.53 (m, 1H), 3.19-3.09 (m, 1H), 2.85-2.73 (m, 3H), 2.72-2.56 (m, 1H), 2.31-2.08 (m, 5H), 1.84-1.75 (m, 2H), 1.69 (s, 6H).

Example 29

N-(5-(4-(5-chloro-4-fluoro-2-(2-hydroxypropan-2-yl)phenylamino)-1,3,5-triazin-2-ylamino)-4-methoxy-2-(methyl(2-(pyrrolidin-1-yl)ethyl)amino)phenyl)acrylamide

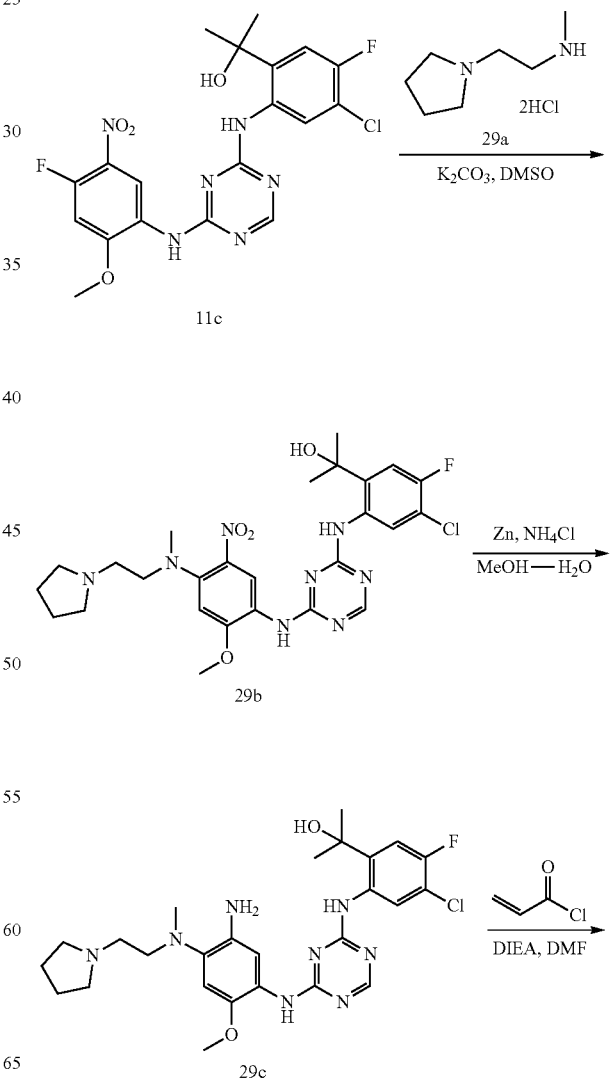

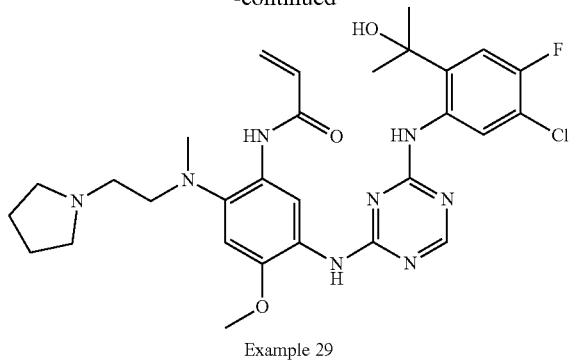

Example 29

Procedure for the Preparation of Compound 29b:

To a solution of compound 11c (200 mg, 0.43 mmol) and K$_2$CO$_3$ (119 mg, 0.86 mmol) in DMSO (5 mL) was added compound 29a (105 mg, 0.52 mmol). The resulting mixture was stirred at 85° C. for 4 h while the colour changes from pale yellow to deep yellow. The reaction mixture was pour into ice water (50 mL) and yellow solid was precipitated. The precipitated solid was collected by filtration and dissolved with CH$_2$Cl$_2$ (30 mL), dried over anhydrous Na$_2$SO$_4$ and concentrated under reduced pressure to give compound 29b (230 mg, 93% yield) as yellow solid.

LCMS: R$_t$=0.814 min in 5-95AB_220&254.lcm chromatography (MERCK RP-18e 25-2 mm), MS (ESI) m/z=575.1 [M+H]$^+$.

Procedure for the Preparation of Compound 29c:

To a solution of compound 29b (230 mg, 0.40 mmol) in MeOH (10 mL) and H$_2$O (2 mL) was added Zn (130 mg, 2.00 mmol) and NH$_4$Cl (214 mg, 4.00 mmol). The resulting mixture was stirred at 80° C. for 2 h. The reaction mixture was filtered and the filtrate was concentrated under reduced pressure to give the residue, which was partitioned between EtOAc (2×10 mL) and water (10 mL). The combined organic layers was dried over anhydrous Na$_2$SO$_4$, filtered and concentrated under reduced pressure to give compound 29c (180 mg, 82% yield) as white solid.

LCMS: R$_t$=0.766 min in 5-95AB_1.5min_220&254 chromatography (MERCK RP18e 25-2 mm), MS (ESI) m/z=545.1 [M+H]$^+$.

Procedure for the Preparation of Example 29:

To a solution of compound 29c (180 mg, 0.33 mmol) and DIEA (85 mg, 0.66 mmol) in DMF (2.5 mL) was added a solution of acryloyl chloride (30 mg, 0.33 mmol) in DMF (0.5 mL). The resulting mixture was stirred at 0° C. under ice-water bath for 30 min. The reaction mixture was purified by RP-HPLC (reverse phase HPLC) [Column: reversed-phase Column; Condition: 42-72% B (A: 0.25% NH$_3$HCO$_3$; B: MeOH); Flow rate: 40 ml/min]. The fractions were concentrated under reduced pressure and lyophilized to afford Example 29 (47.4 mg, 20% yield) as white solid.

LCMS: R$_t$=1.912 min in 10-80AB_4min_220&254 chromatography (Xtimate C18 2.1×30 mm), MS (ESI) m/z=599.0 [M+H]$^+$.

HPLC: R$_t$=3.41 min in 10-80_ab_1.2ML chromatography (Ultimate C18 3×50 mm 3 um).

$^1$H NMR (400 MHz, CDCl$_3$) δ 10.61 (br s, 1H), 10.06 (br s, 1H), 9.96 (br s, 1H), 8.48 (d, J=7.6 Hz, 1H), 8.43 (s, 1H), 7.69 (br s, 1H), 7.10 (d, J=10.8 Hz, 1H), 6.78 (s, 1H), 6.38 (br d, J=4.8 Hz, 2H), 6.13 (br s, 1H), 5.80-5.72 (m, 1H), 3.88 (s, 3H), 2.95 (br s, 2H), 2.69 (s, 3H), 2.55 (br s, 4H), 2.42 (br s, 2H), 1.83 (br s, 4H), 1.78 (s, 6H).

Example 30

(R)—N-(5-(4-(5-chloro-4-fluoro-2-(2-hydroxypropan-2-yl)phenylamino)-1,3,5-triazin-2-ylamino)-4-methoxy-2-(methyl((1-methylpyrrolidin-2-yl)methyl)amino)phenyl) acrylamide

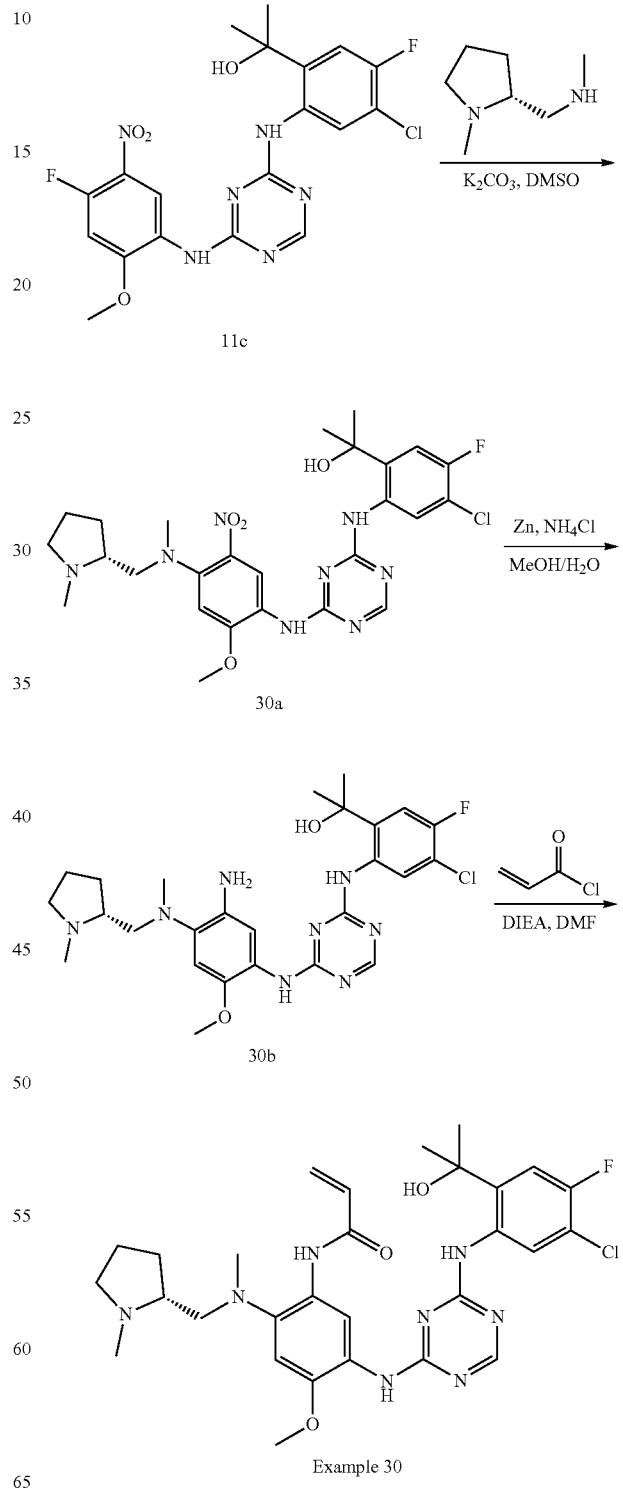

Example 30

Procedure for the Preparation of Compound 30a:

To a solution of compound 11c (180 mg, 0.386 mmol) and K$_2$CO$_3$ (107 mg, 0.772 mmol) in DMSO (3 mL) was added (R)—N-methyl-1-(1-methylpyrrolidin-2-yl)methanamine (93 mg, 0.463 mmol). The reaction mixture was stirred at 85° C. for 1 h (changed from yellow to deep orange). The reaction mixture was added drop wise into H$_2$O (40 mL) under ice water bath and solid was precipitated out. The solid was collected by filtration and washed with H$_2$O (15 mL×3), then dried in vacuo to give compound 30a (227 mg, 82% yield) as an orange solid.

LCMS: R$_t$=0.743 min in 5-95AB_220&254.lcm chromatography (ACSSH-LCMS-AB MERCK RP18 2.5-2 mm), MS (ESI) m/z=575.1 [M+H]$^+$.

$^1$H NMR (400 MHz, CDCl$_3$) δ 9.96 (br s, 1H), 8.88 (br s, 1H), 8.29 (br s, 2H), 7.51 (br s, 1H), 7.02 (d, J=10.4 Hz, 1H), 6.62 (s, 1H), 3.89 (s, 3H), 3.48-3.39 (m, 1H), 3.07 (dd, J=7.6, 13.2 Hz, 1H), 3.01-2.95 (m, 1H), 2.80 (s, 3H), 2.54-2.43 (m, 1H), 2.34 (s, 3H), 2.22-2.15 (m, 1H), 2.02-1.91 (m, 1H), 1.75-1.65 (m, 2H), 1.63 (s, 6H), 1.54-1.46 (m, 1H).

Procedure for the Preparation of Compound 30b:

To a solution of compound 30a (227 mg, 0.316 mmol) in MeOH/H$_2$O=5/1 (5 mL) was added Zn (124 mg, 6.0 eq, 1.896 mmol) and NH$_4$Cl (101 mg, 1.896 mmol). The resulting mixture was heated at 90° C. for 1 h (changed from orange to brown). The reaction mixture was filtered, and the filtrate was concentrated in vacuo to give the crude residue, which was dissolved with CH$_2$Cl$_2$ (20 mL), washed with water (15 mL×3), then dried over Na$_2$SO$_4$ and concentrated in vacuo to give compound 30b (170 mg, 98% yield) as a brown solid.

LCMS: R$_t$=0.700 min in 5-95AB_220&254.lcm chromatography (ACSSH-LCMS-AB MERCK RP18 2.5-2 mm), MS (ESI) m/z=545.2 [M+H]$^+$.

Procedure for the Preparation of Example 30:

To a solution of compound 30b (170 mg, 0.312 mmol) and DIEA (60 mg, 0.468 mmol) in DMF (2 mL) was added acryloyl chloride (28 mg, 0.312 mmol) under ice water bath. The resulting mixture was stirred at 5-10° C. for 10 min. The reaction was quenched by H$_2$O (0.1 mL) and then filtered, the filtrate was purified by pre-HPLC (Column: Waters Xbridge 150*25 5 um; Condition: 50-80% B (A: 0.05% ammonia, B: CH$_3$CN); Flow Rate: 25 ml/min) and then lyophilized to give Example 30 (78.1 mg, 41.8% yield).

LCMS: R$_t$=1.983 min in 10-80AB_4min_220&254. lcm chromatography (ACSSH-LCMS-D Xtimate C18 2.1*30 mm), MS (ESI) m/z=599.0 [M+H]$^+$.

$^1$H NMR (400 MHz, CDCl$_3$) δ 10.52 (br s, 1H), 10.09 (br s, 1H), 10.02 (br s, 1H), 8.46 (d, J=7.2 Hz, 1H), 8.41 (s, 1H), 7.65 (br s, 1H), 7.09 (d, J=10.8 Hz, 1H), 6.71 (s, 1H), 6.39 (br s, 1H), 6.38 (br s, 1H), 6.11 (br s, 1H), 5.77 (t, J=5.6 Hz, 1H), 3.88 (s, 3H), 3.20-3.02 (m, 1H), 2.89-2.78 (m, 1H), 2.74 (s, 3H), 2.71-2.63 (m, 2H), 2.56 (s, 3H), 2.45-2.30 (m, 1H), 2.06-1.88 (m, 1H), 1.77 (br s, 6H), 1.73-1.69 (m, 2H), 1.45-1.32 (m, 1H).

Example 31

(R)—N-(5-(4-(5-chloro-4-fluoro-2-(2-hydroxypropan-2-yl)phenylamino)-1,3,5-triazin-2-ylamino)-2-(2-((dimethylamino)methyl)pyrrolidin-1-yl)-4-methoxyphenyl)acrylamide

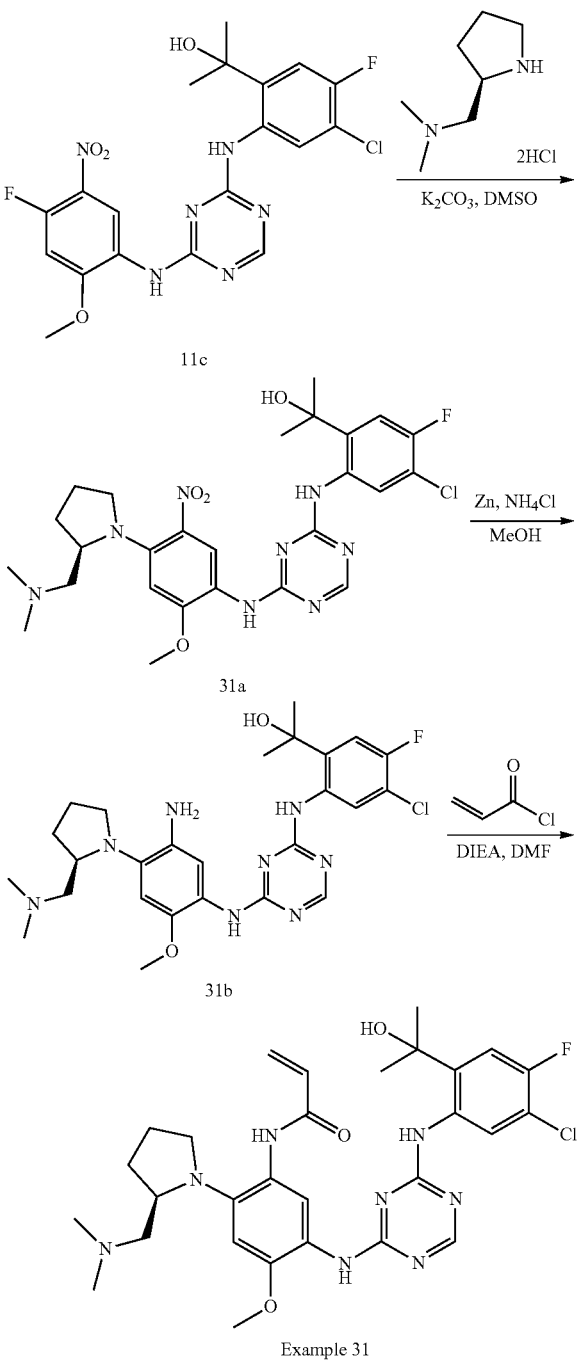

Example 31

Procedure for the Preparation of Compound 31a:

A solution of compound 11c (180 mg, 0.38 mmol), (R)—N,N-dimethyl-1-(pyrrolidin-2-yl)-methanamine dihydrochloride (74 mg, 0.58 mmol) and K$_2$CO$_3$ (106.6 mg, 0.77 mmol) in DMSO (2 mL) was stirred at 85° C. for 1 h. The reaction mixture was added into H$_2$O (10 mL) in ice water bath with stirring, the precipitated solid was collected by filtration and then dissolved with DCM (30 mL), dried over Na₂SO₄ and concentrated in vacuum to give the product 31a (310 mg, 88% yield) as orange oil.

LCMS: $R_t$=0.758 min in 5-95AB_220&254.lcm chromatography (ACSSH-LCMS-AB MERCK RP18 2.5-2 mm), MS (ESI) m/z=575.4 [M+H]⁺.

¹H NMR (400 MHz, CDCl₃) δ 9.79 (br s, 1H), 8.86 (br s, 1H), 8.34 (br s, 2H), 7.33 (br s, 1H), 7.05 (d, J=10.4 Hz, 1H), 6.68 (s, 1H), 4.13-3.98 (m, 1H), 3.93 (s, 4H), 3.70-3.58 (m, 1H), 3.58 (dt, J=6.0, 10.4 Hz, 2H), 2.46-2.31 (m, 2H), 2.05-1.93 (m, 1H), 1.92-1.79 (m, 9H), 1.73-1.62 (m, 6H).

Procedure for the Preparation of Compound 31b:

To a solution of compound 31a (300 mg, 0.52 mmol) in MeOH/H₂O=5/1 (9 mL) was added Zn (170.55 mg, 2.61 mmol) and NH₄Cl (139.5 mg, 2.61 mmol). The resulting mixture was heated at 90° C. for 1 h. The reaction mixture was filtered, and the filtrate was concentrated in vacuo to give the crude residue, which was dissolved with CH₂Cl₂ (30 mL), washed with water (30 mL×2) and brine (30 mL), then dried over Na₂SO₄ and concentrated in vacuo to give the product 31b (160 mg, 56% yield) as brown solid.

LCMS: $R_t$=0.693 min in 5-95AB_220&254.lcm chromatography (ACSSH-LCMS-AB MERCK RP18 2.5-2 mm), MS (ESI) m/z=545.1 [M+H]⁺.

¹H NMR (400 MHz, CDCl₃) δ 9.58 (br s, 1H), 8.35 (br d, J=7.2 Hz, 1H), 7.81 (br s, 1H), 7.71-7.48 (m, 1H), 7.07 (br d, J=10.4 Hz, 1H), 6.71 (br s, 1H), 5.30 (s, 1H), 4.05-3.85 (m, 2H), 3.81 (br s, 3H), 3.52-3.33 (m, 2H), 2.69-2.59 (m, 2H), 2.29-2.15 (m, 8H), 1.68 (br d, J=4.4 Hz, 6H).

Procedure for the Preparation of Example 31:

To a solution of compound 31b (90 mg, 0.165 mmol) and DIEA (31.9 mg, 0.53 mmol) in DMF (2 mL) was added acryloyl chloride (14.9 mg, 0.165 mmol) drop wise at 0° C. The resulting mixture was stirred at 0° C. for 1 h. The reaction was quenched by H₂O (0.1 mL) and then filtered, the filtrate was combined and further purified by prep-HPLC (Column: Gemini 150*25 5 um; Mobile A: water 0.05% ammonia hydroxide v/v Mobile B: DMF Flow rate: 25 ml/min Gradient Time: 10 min Profile Descriptive: 35%-65%) to give Example 31 (20.1 mg, 11.4% yield) as a yellow solid.

LCMS: $R_t$=1.826 min in 10-80AB_4min_220&254 chromatography (ACSSH-LCMS-AS A: Xtimate C18, 2.1*30 mm, 3 um; B: XBrige Shield RP18 2.1*50 mm), MS (ESI) m/z=599.3 [M+H]⁺.

HPLC: $R_t$=3.98 10-80_CD_1.2ml.met XBridge Shield RP 18 2.1*50 mm 5 um.

¹H NMR (400 MHz, CDCl₃) δ 10.59 (br s, 1H), 10.05 (br s, 1H), 9.89 (br s, 1H), 8.56-8.32 (m, 2H), 7.67 (br s, 1H), 7.09 (d, J=10.8 Hz, 1H), 6.69 (s, 1H), 6.37 (br s, 2H), 6.08 (br s, 1H), 5.86-5.72 (m, 1H), 3.86 (s, 3H), 3.31 (br s, 2H), 3.08-2.86 (m, 1H), 2.39 (br s, 1H), 2.29-2.13 (m, 6H), 2.09-1.91 (m, 3H), 1.76 (s, 8H).

Example 32

N-(2-((2-(dimethylamino)ethyl)(methyl)amino)-5-(4-(6-(2-hydroxypropan-2-yl)-1-methyl-1H-indol-5-ylamino)-1,3,5-triazin-2-ylamino)-4-methoxyphenyl)acrylamide

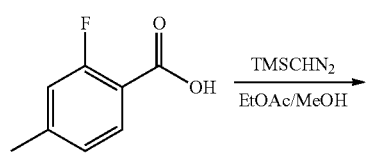

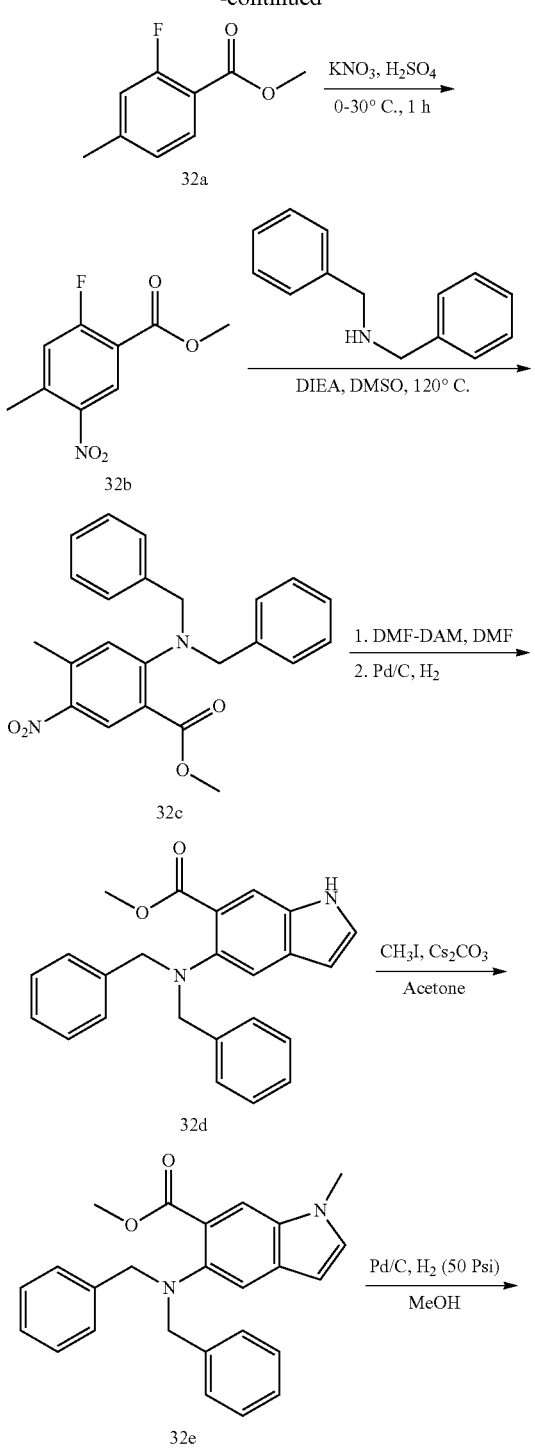

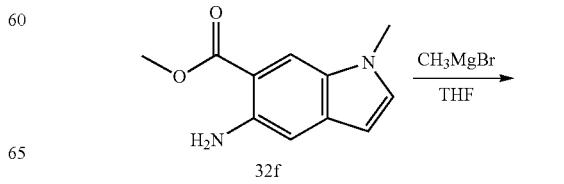

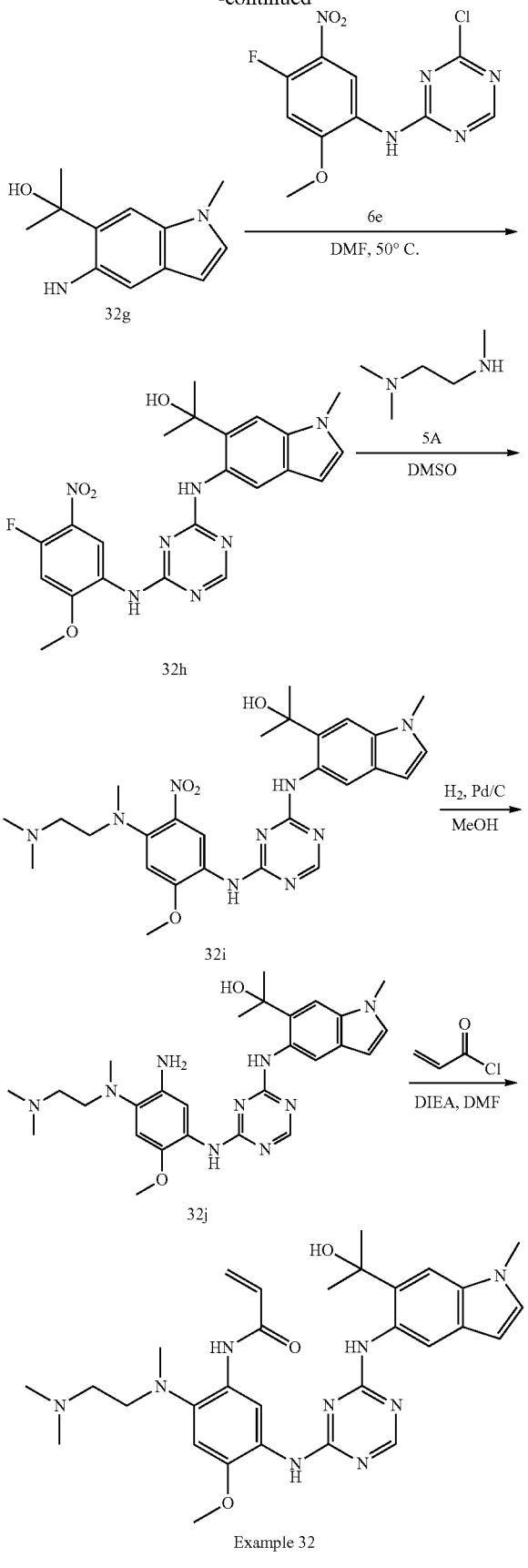

Procedure for the Preparation of Compound 32a:

To a solution of 2-fluoro-4-methylbenzoic acid (10.0 g, 64.87 mmol) in EtOAc (100 mL) and MeOH (100 mL) was added TMSCHN$_2$ (64.87 mL, 129.75 mmol, 2M in hexane). The mixture was stirred at 28-36° C. (room temperature) for 1.5 h. The reaction mixture was concentrated under reduced pressure to give the crude residue, which was purified by column chromatography on silica gel (Petroleum ether/EtOAc=10/1 (v/v)) to afford compound 32a (9 g, 82.5% yield) as a white solid.

LCMS: $R_t$=0.780 min in 5-95AB_1.5min_220&254 chromatography (MERCK RP18e 25-2 mm), MS (ESI) m/z=169.0 [M+H]$^+$.

$^1$H NMR (400 MHz, CDCl$_3$) δ 7.76 (t, J=7.8 Hz, 1H), 6.93 (d, J=7.4 Hz, 1H), 6.88 (d, J=12.0 Hz, 1H), 3.84 (s, 3H), 2.32 (s, 3H).

Procedure for the Preparation of Compound 32b:

To a solution of compound 32a (9.0 g, 53.52 mmol) in H$_2$SO$_4$ (100 mL), Then KNO$_3$ (10.8 g, 107.04 mmol) was added in several portions at 0-5° C. The resulting mixture was stirred at 28-36° C. for 1 h. The reaction mixture was concentrated under reduced pressure to give the crude residue, which was purified by column chromatography on silica gel (Petroleum ether/EtOAc=10/1) to afford compound 32b (10 g, 87% yield) as a brown solid.

LCMS: $R_t$=0.781 min in 5-95AB_1.5min_220&254 chromatography (MERCK RP18e 25-2 mm), MS (ESI) m/z NA.

$^1$H NMR (400 MHz, CDCl$_3$) δ 8.66 (d, J=6.6 Hz, 1H), 7.16 (d, J=10.6 Hz, 1H), 3.98 (s, 3H), 2.69 (s, 3H).

Procedure for the Preparation of Compound 32c:

To a solution of compound 32b (6.0 g, 28.15 mmol) in DMSO (100 mL) was added compound dibenzylamine (8.3 g, 42.22 mmol) and DIEA (7.3 g, 56.29 mmol). The mixture was stirred at 120° C. (room temperature) for 1.5 h. The reaction mixture was concentrated under reduced pressure to give the crude residue, which was purified by column chromatography on silica gel (Petroleum ether/EtOAc=10/1 (v/v)) to afford compound 32c (4.8 g, 44% yield) as a brown solid.

LCMS: $R_t$=0.947 min in 5-95AB_1.5min_220&254 chromatography (MERCK RP18e 25-2 mm), MS (ESI) m/z=391.1 [M+H]$^+$.

$^1$H NMR (400 MHz, Methanol-d$_4$) δ 8.46 (s, 1H), 7.33-7.22 (m, 10H), 6.96 (s, 1H), 4.44 (s, 4H), 3.91 (s, 3H), 2.54 (s, 3H).

Procedure for the Preparation of Compound 32d:

To a solution of compound 32c (4.8 g, 12.30 mmol) in DMF (20 mL) was added DMF-DMA (4.4 g, 36.88 mmol), the mixture was stirred at 150° C. for 2 h. The reaction mixture was concentrated under reduced pressure, then CH$_2$Cl$_2$ (20 mL) and Pd/C (480 mg) were added and the mixture was stirred under a hydrogen atmosphere (15 Psi) for 2 h. The reaction was filtered, and CH$_2$Cl$_2$ (100 mL) and H$_2$O (300 mL) were added to the filtrated.

The organic was separated and washed with brine (3×100 mL), dried and concentrated in vacuum to give the crude residue, which was purified by column chromatography on silica gel (petroleum ether/EtOAc=5/1 (v/v)) to give compound 32d (3.0 g, 66.7% yield) as a brown solid.

LCMS: $R_t$=1.395 min in 10-80AB_3MIN_220&254 chromatography (XBrige Shield RP18 2.1*50 mm), MS (ESI) m/z=371.2 [M+H]$^+$.

$^1$H NMR (400 MHz, DMSO-d$_6$) δ 11.18 (br s, 1H), 7.98-7.93 (m, 1H), 7.63 (s, 1H), 7.42 (t, J=2.8 Hz, 1H), 7.35 (s, 2H), 7.34 (s, 2H), 7.31 (s, 1H), 7.27 (s, 1H), 7.25 (s, 2H), 7.23 (s, 1H), 7.18 (s, 1H), 6.31 (br s, 1H), 4.12 (s, 4H), 3.86 (s, 3H).

Procedure for the Preparation of Compound 32e:

To a solution of compound 32d (2.7 g, 7.29 mmol) and $Cs_2CO_3$ (7.1 g, 21.87 mmol) in Acetone (50 mL) was added $CH_3I$ (1.6 g, 10.93 mmol). The resulting suspension was stirred at 18-25° C. for 18 h. The reaction mixture was filtered and the filtrate was treated with aqueous $NH_4Cl$ (20 mL), then extracted with $CH_2Cl_2$ (25 mL×2). The combined organic layer was dried and concentrated under reduced pressure to give compound 32e (2.6 g, 92.9% yield) as a brown solid.

LCMS: $R_t$=0.849 min in 5-95AB_1.5MIN_220&254.lcm; chromatography (MERCK RP18 2.5-2 mm), MS (ESI) m/z=385.2 [M+H]$^+$.

Procedure for the Preparation of Compound 32f:

To a solution of compound 32e (3.5 g, 9.10 mmol) in MeOH (50 mL) was added Pd/C (10%, 300 mg). The resulting mixture was purged and degassed with $H_2$ for three times, then stirred at 29-40° C. under $H_2$ balloon (15 Psi) for 18 h. The reaction mixture was filtered and the filtrate was concentrated under reduced pressure to afford compound 32f (1.6 g, 86.5% yield) as a brown solid.

LCMS: $R_t$=0.536 min in 5-95AB_1.5MIN_220&254.lcm chromatography (Xtimate C18 2.1*30 mm), MS (ESI) m/z=205.0 [M+H]$^+$.

$^1$H NMR (400 MHz, $CDCl_3$) δ 7.91 (s, 1H), 7.11 (d, J=3.2 Hz, 1H), 6.87 (s, 1H), 6.24 (d, J=2.4 Hz, 1H), 5.31 (br s, 2H), 3.93 (s, 3H), 3.76 (s, 3H).

Procedure for the Preparation of Compound 32g:

To a solution of compound 32f (1.0 g, 4.90 mmol) in THF (50 mL) was added $CH_3MgBr$ (8.2 mL, 3 M in ether) drop wise at 0~5° C. The mixture was stirred at 17-21° C. for 1.5 h. The reaction mixture was quenched by the addition of aqueous $NH_4Cl$ (100 mL), then extracted with EtOAc (3×100 mL). The combined organic layers was washed with brine (3×100 mL), dried and concentrated under reduced pressure to give the crude residue, which was purified by column chromatography on silica gel (Petroleum ether/EtOAc=20/1 (v/v)) to afford compound 32g (700 mg, 70% yield) as brown solid.

LCMS: $R_t$=0.865 min in 10-80AB_7min_220&254.lcm chromatography (Xtimate C18 2.1*30 mm), MS (ESI) m/z=186.9 [M-17]$^+$.

$^1$H NMR (400 MHz, $CDCl_3$) δ 7.14 (s, 1H), 6.98-6.96 (m, 2H), 6.27 (d, J=2.4 Hz, 2H), 4.11-3.80 (m, 2H), 3.74 (s, 3H), 1.77 (s, 6H).

Procedure for the Preparation of Compound 32h:

To a solution of compound 32g (200 mg, 0.98 mmol) in DMF (3 mL) was added compound 6e (323 mg, 1.08 mmol). The resulting mixture was stirred at 50° C. for 2 h. The reaction was pour into ice water (50 mL) with stirring and yellow solid was precipitated out.

The solid was collected by filtration and dissolved with $CH_2Cl_2$ (20 mL), then dried over anhydrous $Na_2SO_4$ and concentrated under reduced pressure to give compound 32h (380 mg, 83.1% yield) as a yellow solid.

LCMS: $R_t$=0.796 min in 5-95AB_1.5min_220&254 chromatography (MERCK RP18 2.5-2 mm), MS (ESI) m/z=490.1 [M+Na]$^+$.

Procedure for the Preparation of Compound 32i:

A solution of compound 32h (300 mg, 0.64 mmol) in DMSO (4 mL) was added $N^1,N^1,N^2$-trimethylethane-1,2-diamine (131 mg, 1.28 mmol), then stirred at 14-19° C. for 2 hours. The reaction was poured into ice water (50 mL) with stirring and yellow solid was precipitated out. The solid was collected by filtration and dissolved with $CH_2Cl_2$ (60 mL), then dried over anhydrous $Na_2SO_4$ and concentrated under reduced pressure to give compound 32i (280 mg, 80% yield) as a yellow solid.

LCMS: $R_t$=0.703 min in 5-95AB_1.5min_220&254 chromatography (MERCK RP18 2.5-2 mm), MS (ESI) m/z=550.2 [M+H]$^+$.

Procedure for the Preparation of Compound 32j:

To a solution of compound 32i (250 mg, 0.45 mmol) in MeOH (5 mL) was added Pd/C (25 mg, 10%) under $N_2$. The resulting black mixture was stirred at 15-21° C. under $H_2$ balloon (15 Psi) for 1 h. The reaction mixture was filtered and concentrated under reduced pressure to afford compound 32j (200 mg, 84.7% yield) as brown oil.

LCMS: $R_t$=0.653 min in 5-95AB_1.5min_220&254 chromatography (MERCK RP18 2.5-2 mm), MS (ESI) m/z=520.1 [M+H]$^+$.

$^1$H NMR (400 MHz, $CDCl_3$) δ 9.47 (br s, 1H), 8.24 (s, 2H), 7.96 (br s, 1H), 7.73 (br s, 1H), 7.07 (d, J=2.4 Hz, 1H), 6.67-6.64 (m, 1H), 6.50 (d, J=2.4 Hz, 1H), 3.81-3.79 (m, 6H), 3.49 (s, 3H), 2.91 (br t, J=6.8 Hz, 2H), 2.62 (s, 4H), 2.37 (br t, J=6.8 Hz, 2H), 2.26-2.22 (m, 6H), 1.77 (s, 6H).

Procedure for the Preparation of Example 32:

To a solution of compound 32j (200 mg, 0.38 mmol) and DIEA (75 mg, 0.58 mmol) in DMF (1 mL) was added acryloyl chloride (35 mg, 0.38 mmol) in DMF (1 mL) drop wise at 0° C. The resulting brown mixture was stirred at 0° C. for 30 min. The reaction was purified by prep-HPLC [Column: Waters Xbridge 150*25 5 um; Condition: 30-50% B (A: 0.05% ammonia; B: $CH_3CN$); Flow rate: 25 ml/min] and then lyophilized to afford Example 32 (57.8 mg, 26.2% yield) as a white solid. LCMS: $R_t$=4.478 min in 10-80CD_7MIN_220&254 chromatography (XBrige Shield RP18 2.1*50 mm), MS (ESI) m/z=574.3 [M+H]$^+$.

HPLC: $R_t$=3.90 min in 10-80_CD_1.2 mL.MET (XBridge Shield RP 18 2.1*50 mm Sum).

$^1$H NMR (400 MHz, $CDCl_3$) δ 10.61 (br s, 1H), 10.42 (br s, 1H), 10.03 (br s, 1H), 8.41-8.39 (m, 2H), 7.59 (br s, 1H), 7.02 (d, J=2.8 Hz, 1H), 6.78 (s, 1H), 6.48-6.44 (m, 2H), 6.37-6.30 (m, 1H), 6.00 (br s, 1H), 5.78 (br d, J=10.8 Hz, 1H), 3.88 (s, 3H), 3.79 (s, 3H), 2.88 (br t, J=5.2 Hz, 2H), 2.71 (s, 3H), 2.27 (s, 8H), 1.90 (s, 6H).

Example 33

(R)—N-(5-(4-(5-chloro-4-fluoro-2-(2-hydroxypropan-2-yl)phenylamino)-1,3,5-triazin-2-ylamino)-2-(3-(dimethylamino)pyrrolidin-1-yl)-4-methoxyphenyl)acrylamide

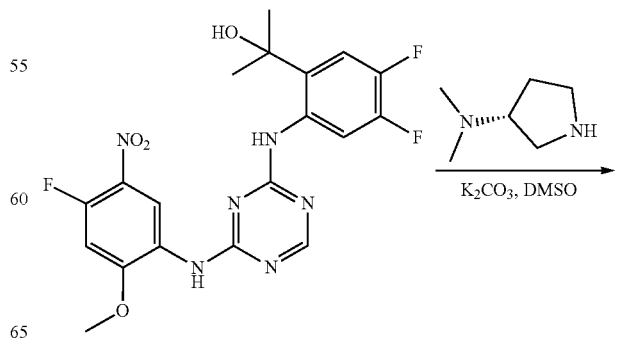

11c

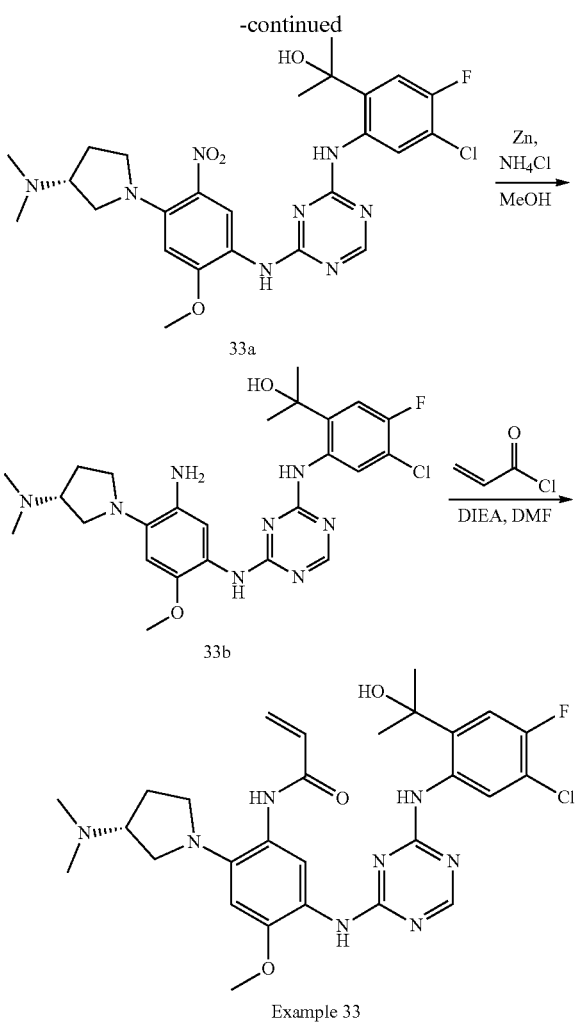

Example 33

Procedure for the Preparation of Compound 33a:

To a solution of compound 11c (200 mg, 0.43 mmol) and K$_2$CO$_3$ (119 mg, 0.86 mmol) in DMSO (4 mL) was added compound (R)—N,N-dimethylpyrrolidin-3-amine (59 mg, 0.51 mmol). The resulting mixture was stirred at 24-27° C. for 1 h. The reaction mixture was pour into water (50 mL) and yellow solid was precipitated. The yellow solid was collected by filtration and dissolved with CH$_2$Cl$_2$ (20 mL), dried over anhydrous Na$_2$SO$_4$ and concentrated under reduced pressure to give the title product 33a (220 mg, 91% yield) as yellow solid.

LCMS: R$_t$=0.789 min in 5-95AB_1.5min_220&254 chromatography (MERCK RP18e 25-2 mm), MS (ESI) m/z=583.1[M+Na]$^+$.

$^1$H NMR (400 MHz, CDCl$_3$) δ 9.69 (br s, 1H), 8.91 (br s, 1H), 8.38 (br s, 2H), 7.35 (br s, 1H), 7.08 (d, J=10.4 Hz, 1H), 6.28 (s, 1H), 3.92 (s, 3H), 3.59-3.51 (m, 1H), 3.37-3.31 (m, 1H), 3.23-3.18 (m, 1H), 3.15-3.07 (m, 1H), 2.86-2.75 (m, 1H), 2.29 (s, 6H), 2.25-2.15 (m, 1H), 1.99-1.88 (m, 1H), 1.69 (s, 6H).

Procedure for the Preparation of Compound 33b:

To a solution of compound 33a (220 mg, 0.39 mmol), Zn (224 mg, 4.19 mmol) in MeOH/H$_2$O (6 mL, 5/1) was added NH$_4$Cl (236 mg, 3.6 mmol). The resulting mixture was stirred at 90° C. for 2 h. The reaction mixture was filtered and concentrated under vacuum to give the residue, which was dissolved with CH$_2$Cl$_2$ (20 mL), washed with water (15 mL×3), dried over Na$_2$SO$_4$ and concentrated under reduced pressure to give the title product 33b (180 mg, 87% yield) as a brown solid.

LCMS: R$_t$=0.732 min in 5-95AB_1.5min_220&254 chromatography (MERCK RP18e 25-2 mm), MS (ESI) m/z=531.2[M+H]$^+$.

Procedure for the Preparation of Example 33:

To a solution of Compound 33b (180 mg, 0.34 mmol) and DIEA (66 mg, 0.51 mmol) in DMF (2 mL) was added a solution of acryloyl chloride (31 mg, 0.34 mmol) in DMF (0.5 mL) drop wise. The resulting mixture was stirred at 0° C. under ice-water bath for 20 min. The reaction mixture was quenched by three drops of water and purified by prep-HPLC (column: Waters Xbridge 150*25 5 um: 30-60% B (A: water (0.05% ammonia hydroxide v/v), B: CH$_3$CN), flow rate: 25 mL/min) to afford the title product Example 33 (53.6 mg, 27% yield) as white solid.

LCMS: R$_t$=1.726 min in 10-80AB_4min_220&254 chromatography (Xtimate C18 2.1*30 mm), MS (ESI) m/z=584.9 [M+H]$^+$.

HPLC: R$_t$=2.85 min in 10-80_CD_1.2ML chromatography (Ultimate C18 3*50 mm 3 um).

$^1$H NMR (400 MHz, CDCl$_3$) δ 10.53 (br s, 1H), 9.79 (br s, 1H), 8.54-8.45 (m, 2H), 8.41 (s, 1H), 7.64 (br s, 1H), 7.09 (d, J=10.8 Hz, 1H), 6.75 (s, 1H), 6.40-6.35 (m, 2H), 5.84-5.79 (m, 1H), 3.87 (s, 3H), 3.14-3.06 (m, 4H), 2.93-2.84 (m, 1H), 2.30 (s, 6H), 2.23-2.13 (m, 1H), 2.00-1.90 (m, 1H), 1.76 (s, 6H).

Example 34

N-(5-(4-(4-cyclopropyl-5-fluoro-2-(2-hydroxypropan-2-yl)phenylamino)-1,3,5-triazin-2-ylamino)-2-((2-(dimethylamino)ethyl)(methyl)amino)-4-methoxyphenyl)acrylamide

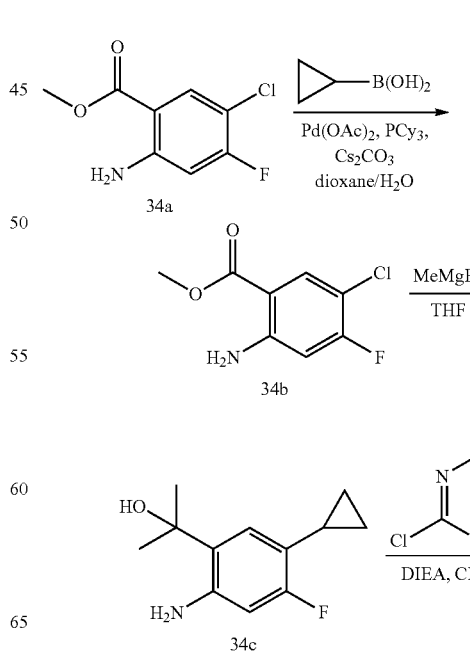

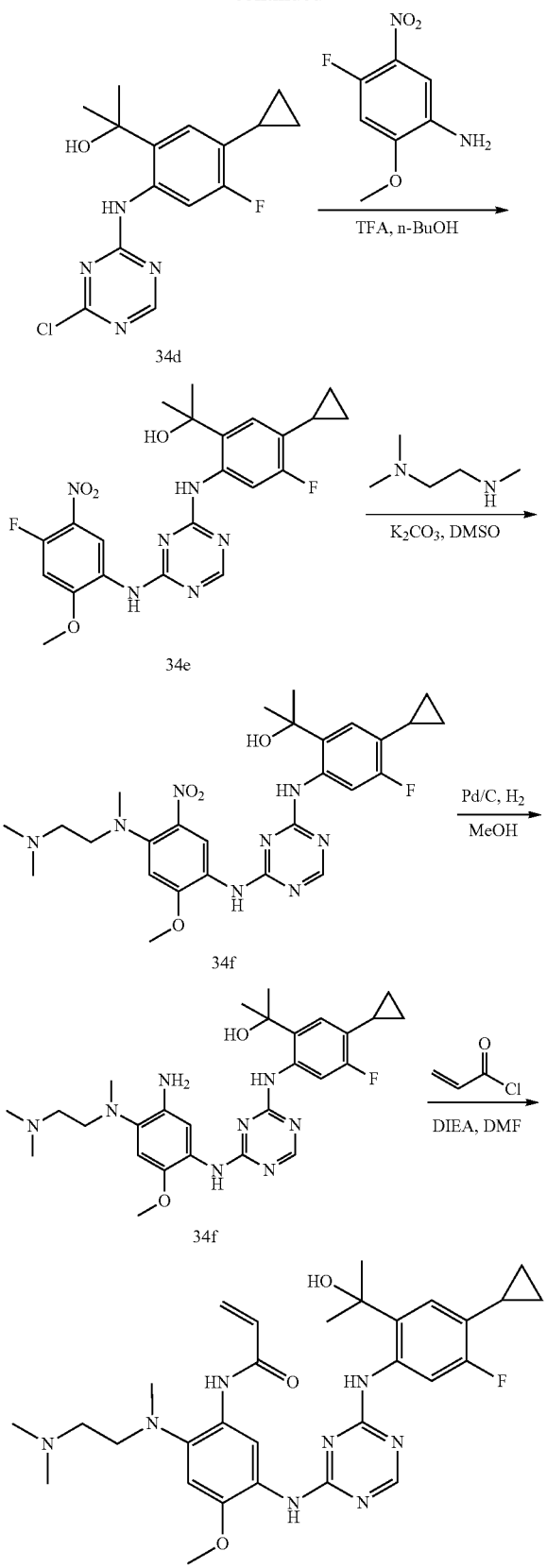

Procedure for the Preparation of Compound 34b:

To a solution of compound 34a (1.0 g, 4.91 mmol) in dioxane (20 mL) and H$_2$O (4 mL) was added cyclopropylboronic acid (1.1 g, 12.28 mmol), followed with Pd(OAc)$_2$ (772 mg, 3.44 mmol), PCy$_3$ (1.9 g, 6.87 mmol) and Cs$_2$CO$_3$ (4.8 g, 3.0 eq, 14.73 mmol) under N$_2$ atmosphere. The resulting mixture was degassed with N$_2$ for 1 min and stirred at 100° C. under microwave for 1 h. The reaction mixture was filtered and diluted with EtOAc (50 mL), washed with brine (50 mL), dried over anhydrous Na$_2$SO$_4$, concentrated under reduced pressure to give the residue, which was purified by column chromatography on silica gel (petroleum ether/EtOAc=100/1 (v/v)) to give compound 34b (700 mg, 68% yield) as brown solid.

LCMS: R$_t$=0.797 min in 5-95AB_1.5min_220&254 chromatography (MERCK RP18e 25-2 mm), MS (ESI) m/z=209.9 [M+H]$^+$.

$^1$H NMR (400 MHz, Methanol-d$_4$) δ 7.45 (d, J=8.8 Hz, 1H), 6.41 (d, J=12.4 Hz, 1H), 3.82 (s, 3H), 1.88-1.81 (m, 1H), 0.89-0.81 (m, 2H), 0.60-0.50 (m, 2H).

Procedure for the Preparation of Compound 34c:

To a solution of compound 34b (700 mg, 3.35 mmol) in THF (10 mL) was added CH$_3$MgBr (5.58 mL, 16.75 mmol) at 0° C. The resulting mixture was stirred at 24-26° C. for 2 h. The reaction mixture was diluted with saturated aqueous NH$_4$Cl (10 mL) and extracted with EtOAc (2×20 mL), the combined organic layers was concentrated under reduced pressure and purified by column chromatography on silica gel (Petroleum ether/EtOAc=10/1) to give compound 34c (450 mg, 64% yield) as colorless oil.

LCMS: R$_t$=0.672 min in 5-95AB_1.5min_220&254 chromatography (MERCK RP18e 25-2 mm), MS (ESI) m/z=191.9 [M+H-18]$^+$.

$^1$H NMR (400 MHz, DMSO-d$_6$) δ 6.65-6.56 (m, 1H), 6.34 (d, J=12.8 Hz, 1H), 1.84-1.72 (m, 1H), 1.44 (s, 6H), 0.82-0.75 (m, 2H), 0.55-0.48 (m, 2H).

Procedure for the Preparation of Compound 34d:

To a solution of compound 34c (400 mg, 1.91 mmol) in CH$_2$Cl$_2$ (10 mL) was added DIEA (494 mg, 3.82 mmol) and 2,4-dichloro-1,3,5-triazine (315 mg, 2.10 mmol). The resulting mixture was stirred at 24-27° C. for 2 h. The reaction was concentrated under reduced pressure and purified by column chromatography on silica gel (Petroleum ether/EtOAc=10/1 (v/v)) to give compound 34d (450 mg, 73% yield) as colorless oil.

LCMS: R$_t$=0.999 min in 5-95AB_1.5min_220&254 chromatography (MERCK RP18e 25-2 mm), MS (ESI) m/z=323.0 [M+H]$^+$.

$^1$H NMR (400 MHz, Methanol-d$_4$) δ 8.69-8.44 (m, 1H), 7.99 (br d, J=14.0 Hz, 1H), 6.93 (d, J=8.4 Hz, 1H), 2.08-2.02 (m, 1H), 1.59 (s, 6H), 1.02-0.93 (m, 2H), 0.77-0.68 (m, 2H).

Procedure for the Preparation of Compound 34e:

To a solution of compound 34d (450 mg, 1.39 mmol) and B (259 g, 1.39 mmol) in n-BuOH (5 mL) was added TFA (0.05 mL). The resulting mixture was stirred at 25-30° C. for 3 h while grey solid was precipitated out. The reaction mixture was filtered and the filter cake was washed with 30 mL of petroleum ether, dried under reduced pressure to give compound 34e (450 mg, 68% yield) as grey solid.

LCMS: R$_t$=0.890 min in 5-95AB_1.5min_220&254 chromatography (MERCK RP18e 25-2 mm), MS (ESI) m/z=473.2 [M+H]$^+$.

$^1$H NMR (400 MHz, Methanol-d$_4$) δ 8.80 (s, 1H), 8.31 (br s, 1H), 8.16-7.58 (m, 1H), 7.15 (d, J=12.8 Hz, 1H), 6.91 (d, J=8.4 Hz, 1H), 4.02 (s, 3H), 1.99 (br s, 1H), 1.59 (s, 6H), 0.95 (br d, J=7.2 Hz, 2H), 0.74-0.67 (m, 2H).

Procedure for the Preparation of Compound 34f:

To a solution of compound 34e (150 mg, 0.32 mmol) and K₂CO₃ (88 mg, 0.64 mmol) in DMSO (5 mL) was added N¹,N¹,N-trimethylethane-1,2-diamine (49 mg, 0.48 mmol). The resulting mixture was stirred at 22-32° C. for 12 h while the colour changes from pale brown to deep yellow. The reaction mixture was pour into ice water (50 mL) and yellow solid was precipitated out. The precipitated solid was filtered and dissolved with CH₂Cl₂ (30 mL), dried over anhydrous Na₂SO₄ and concentrated under reduced pressure to give compound 34f (150 mg, 84% yield) as yellow solid.

LCMS: $R_t$=0.831 min in 5-95AB_1.5min_220&254 chromatography (MERCK RP18e 25-2 mm), MS (ESI) m/z=555.2 [M+H]⁺.

Procedure for the Preparation of Compound 34g:

To a solution of compound 34f (150 mg, 0.27 mmol) in MeOH (10 mL) was added Pd/C (15 mg). The resulting mixture was purged and degassed with H₂ for 3 times, then stirred at 23-29° C. under H₂ balloon, (15 Psi) for 2 h. The reaction mixture was filtered and concentrated under reduced pressure to give compound 34g (130 mg, 92% yield) as brown oil.

LCMS: $R_t$=0.765 min in 5-95AB_1.5min_220&254 chromatography (MERCK RP18e 25-2 mm), MS (ESI) m/z=525.1 [M+H]⁺.

Procedure for the Preparation of Example 34:

To a solution of compound 34g (130 mg, 0.25 mmol) and DIEA (85 mg, 0.66 mmol) in DMF (2.5 mL) was added acryloyl chloride (30 mg, 0.33 mmol) in DMF (0.5 mL). The resulting mixture was stirred at 0° C. under ice-water bath for 30 min. The reaction mixture was purified by RP-HPLC (reverse phase HPLC) [Column: reversed-phase Column; Condition: 0-30% B (A: 0.25% NH₃HCO₃; B: MeOH); Flow rate: 40 ml/min] and then lyophilized to afford Example 34 (24.4 mg, 17% yield) as white solid.

LCMS: $R_t$=1.994 min in 10-80AB_4min_220&254 chromatography (Xtimate C18 2.1*30 mm), MS (ESI) m/z=601.3 [M+Na]⁺.

HPLC: $R_t$=3.41 min in 10-80_ab_1.2ML chromatography (Ultimate C18 3*50 mm 3 um).

¹H NMR (400 MHz, CDCl₃) δ 10.72 (br s, 1H), 10.39 (br s, 1H), 9.97 (br s, 1H), 8.41 (s, 1H), 8.11 (d, J=12.4 Hz, 1H), 7.66 (br s, 1H), 6.86 (d, J=8.4 Hz, 1H), 6.78 (s, 1H), 6.45-6.30 (m, 2H), 5.93 (br s, 1H), 5.79-5.72 (m, 1H), 3.88 (s, 3H), 2.92-2.83 (m, 2H), 2.70 (s, 3H), 2.33-2.23 (m, 8H), 2.06-1.97 (m, 1H), 1.76 (s, 6H), 0.97-0.86 (m, 2H), 0.73-0.65 (m, 2H).

Example 35

(S)—N-(5-(4-(4,5-difluoro-2-(2-hydroxypropan-2-yl)phenylamino)-1,3,5-triazin-2-ylamino)-2-(3-((dimethylamino)methyl)morpholino)-4-methoxyphenyl)acrylamide

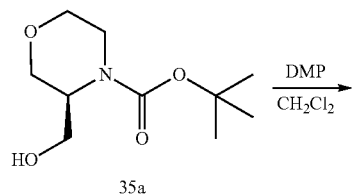

35a

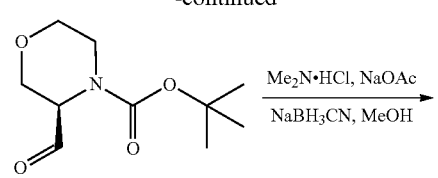

35b

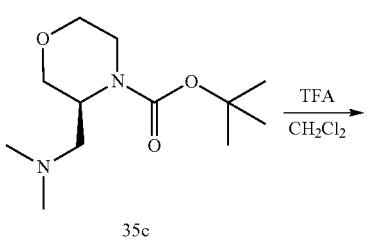

35c

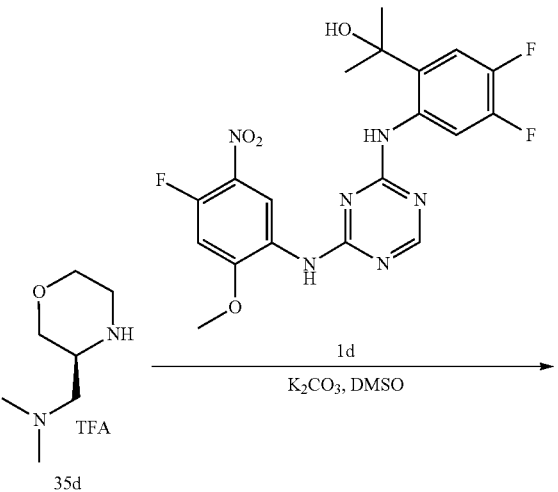

35d

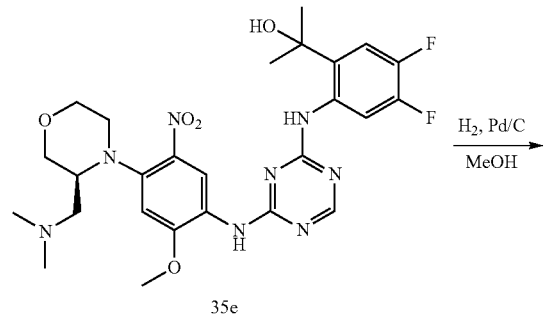

35e

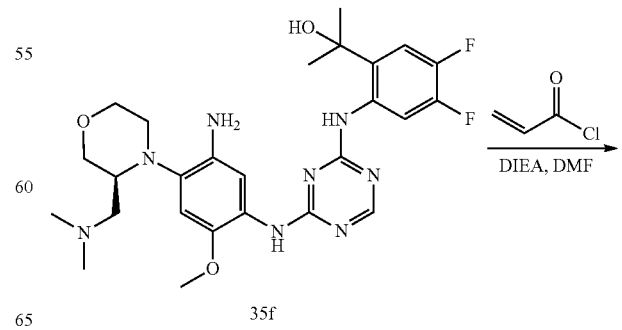

35f

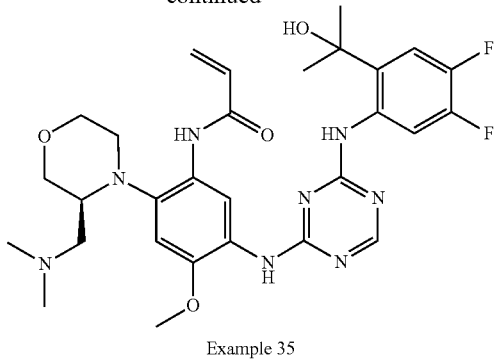

Example 35

Procedure for the Preparation of Compound 35b:

To a solution of compound 35a (1.4 g, 6.44 mmol) in CH$_2$Cl$_2$ (40 mL) was added DMP (4.1 g, 9.67 mmol) in portions at 0-5° C. The resulting white mixture was stirred at 0~5° C. for 1 h. The reaction was treated with aqueous NaHCO$_3$ (30 mL), extracted with EtOAc (3×20 mL). The combined organic layers was washed with brine (3×20 mL), dried and concentrated under reduced pressure to give the crude, which was purified by column chromatography on silica gel (Petroleum ether/EtOAc=5/1 (v/v)) to afford compound 35b (1.1 g, 79.7% yield) as light yellow oil.

$^1$H NMR (400 MHz, DMSO-d$_6$) δ 9.60 (br d, J=10.0 Hz, 1H), 4.52-4.36 (m, 2H), 3.94-3.67 (m, 2H), 3.60 (dd, J=4.4, 12.2 Hz, 2H), 3.05-2.79 (m, 1H), 1.43-1.36 (m, 9H).

Procedure for the Preparation of Compound 35c:

To a solution of compound 35b (1.0 g, 4.65 mmol) in MeOH (10 mL) was added Me$_2$N.HCl (1.1 g, 13.94 mmol), NaOAc (572 mg, 6.97 mmol), the white mixture was stirred at 24-26° C. for 2 h, then NaBH$_3$CN (584 mg, 9.29 mmol) was added, the resulting mixture was stirred at 22-27° C. for 18 h. The reaction mixture was quenched by the addition of aqueous NH$_4$Cl (20 mL), extracted with EtOAc (3×10 mL). The combined organic layers was washed with brine (3×10 mL), dried and concentrated in vacuum to give compound 35c (800 mg, 70.5% yield) as colorless oil.

LCMS: R$_f$=2.519 min in 10-80CD_4MIN_E.M, XBrige Shield RP18 2.1*50 mm, MS (ESI) m/z=245.1 [M+H]$^+$.

$^1$H NMR (400 MHz, CDCl$_3$) δ 3.99-3.63 (m, 2H), 3.46-3.33 (m, 1H), 2.98 (br s, 1H), 2.71 (br t, J=10.8 Hz, 1H), 2.31-2.18 (m, 6H), 1.41 (s, 9H).

Procedure for the Preparation of Compound 35d:

To a solution of compound 35c (500 mg, 2.30 mmol) in CH$_2$Cl$_2$ (6 mL) was added TFA (2 mL). The resulting colorless solution was stirred at 22-32° C. for 3 h. The reaction solution was concentrated in vacuum directly to give compound 35d in TFA salt (300 mg, 61.1% yield) as colorless oil.

LCMS: R$_f$=0.306 min in 10-80CD_4MIN_E.M; XBrige Shield RP18 2.1*50 mm, MS (ESI) m/z=145.2 [M-OH]$^+$.

Procedure for the Preparation of Compound 35e:

A solution of compound 35d (187 mg, 0.42 mmol) and K$_2$CO$_3$ (116 mg, 0.84 mmol) in DMSO (2 mL) was added compound 1d (60 mg, 0.42 mmol). The mixture was stirred at 28-33° C. for 2 hours. It was purified by Biotage flash reversed-phase C-18 column chromatography directly eluting with MeOH/H$_2$O (MeOH in water from 56% to 60%) to give desired product 35e (50 mg, 20.9% yield) as a red solid, which was used in the next step directly.

Procedure for the Preparation of Compound 35f:

To a solution of compound 35e (90 mg, 0.16 mmol) in MeOH (3 mL) was added Pd/C (10 mg) under N$_2$ protect. The black mixture was stirred at 26-33° C. under hydrogen balloon (15 Psi) for 1 h. The reaction mixture was filtered and concentrated under reduced pressure to afford compound 35f (70 mg, 82.1% yield) as brown oil.

LCMS: R$_f$=1.791 min in 10-80CD_3MIN_220&254; XBrige Shield RP18 2.1*50 mm MS (ESI) m/z=545.3 [M+H]$^+$.

Procedure for the Preparation of Example 35:

To a solution of compound 35f (70 mg, 0.13 mmol) and DIEA (25 mg, 0.19 mmol) in DMF (1 mL) was added a solution of acryloyl chloride (12 mg, 0.13 mmol) in DMF (1 mL) drop wise. The resulting brown mixture was stirred at 0° C. for 30 min. The reaction was purified by prep-HPLC [Column: Waters Xbridge 150*25 5 um; Condition: 35-65% B (A: 0.05% ammonia; B: CH$_3$CN); Flow rate: 25 ml/min]. Fractions containing the desired compound were lyophilized to afford Example 35 (11.9 mg, 16.8% yield) as a white solid.

LCMS: R$_f$=1.816 min in 10-80CD_3MIN_220&254; XBrige Shield RP18 2.1*50 mm, MS (ESI) m/z=599.3 [M+H]$^+$.

HPLC, R$_f$=3.45 purity 92.56% (220 nm), 10-80_CD_1.2 mL.MET (XBridge Shield RP 18 2.1*50 mm 5 um).

$^1$H NMR (400 MHz, DMSO-d$_6$) δ 10.29 (br s, 1H), 9.14 (s, 2H), 8.31 (s, 1H), 8.27 (s, 1H), 7.26 (br s, 1H), 7.11 (s, 1H), 6.64 (br dd, J=10.4, 17.1 Hz, 1H), 6.27 (s, 1H), 6.18 (br d, J=16.8 Hz, 1H), 5.73 (br d, J=10.4 Hz, 1H), 4.02 (br d, J=9.2 Hz, 1H), 3.78 (s, 5H), 3.55-3.48 (m, 1H), 3.28 (br s, 1H), 2.85 (br s, 2H), 2.68 (br s, 1H), 2.34 (s, 1H), 2.25 (br t, J=11.2 Hz, 1H), 2.01 (s, 6H), 1.92 (br d, J=9.2 Hz, 1H), 1.52 (br s, 6H).

Example 36

(N-(5-(4-(5-chloro-4-fluoro-2-(2-hydroxypropan-2-yl)phenylamino)pyrimidin-2-ylamino)-2-((2-(dimethylamino)ethyl)(methyl)amino)-4-methoxyphenyl)acrylamide)

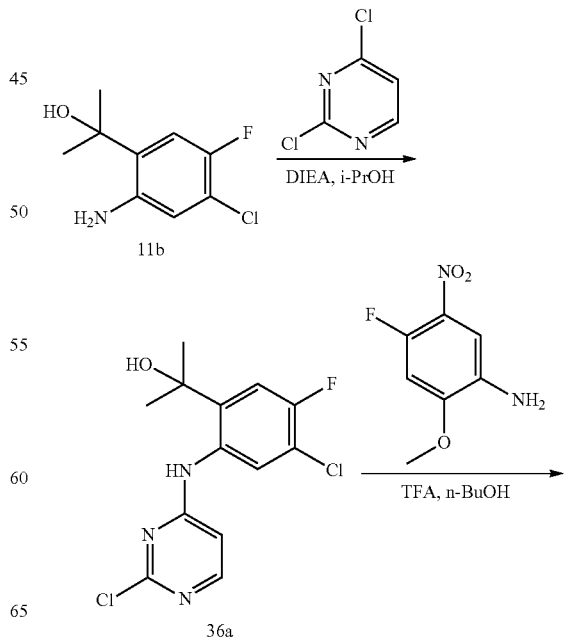

36a

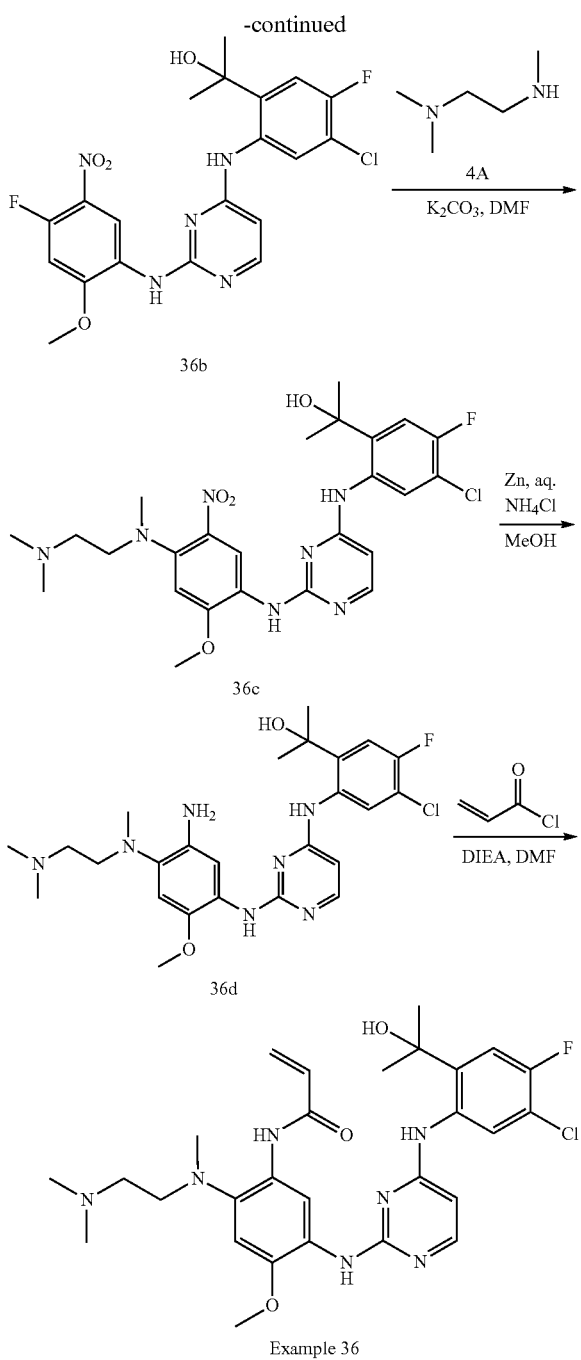

Procedure for the Preparation of Compound 36a:

To a solution of compound 11b (500 mg, 2.46 mmol) and DIEA (634 mg, 4.92 mmol) in isopropanol (10 mL) was added 2,4-dichloropyrimidine (442 mg, 2.95 mmol). The resulting mixture was heated at 90° C. for 27 h. The reaction mixture was concentrated in vacuo to give the crude product, which was purified by column chromatography on silica gel (25-40% EtOAc in petroleum ether) to give compound 36a (390 mg, 50.14% yield) as an off-white solid.

LCMS: $R_f$=0.796 min in 5-95AB_220&254.lcm chromatography (ACSSH-LCMS-AB MERCK RP18 2.5-2 mm), MS (ESI) m/z=315.9 [M+H]$^+$.

$^1$H NMR (400 MHz, Methanol-d$_4$) δ 8.12 (d, J=6.0 Hz, 1H), 8.08 (br d, J=6.8 Hz, 1H), 7.31 (d, J=10.8 Hz, 1H), 6.70 (d, J=6.0 Hz, 1H), 1.57 (s, 6H).

Procedure for the Preparation of Compound 36b:

A solution of compound 36a (760 mg, 2.4 mmol) and 4-fluoro-2-methoxy-5-nitroaniline (448 mg, 2.4 mmol) in TFA/n-BuOH=1/10 (11 mL) was heated at 50° C. for 4 h, additional 30 mg of compound 4-fluoro-2-methoxy-5-nitroaniline as added and prolong the reaction time at 50° C. for another 22 h. The reaction mixture was filtered and the solid cake was washed with petroleum ether (20 mL×3), then dried in high vacuo to give compound 36b (960 mg, 86% yield) as an off-white solid.

LCMS: $R_f$=0.753 min in 5-95AB_220&254.lcm chromatography (ACSSH-LCMS-AB MERCK RP18 2.5-2 mm), MS (ESI) m/z=466.1 [M+H]$^+$.

$^1$H NMR (400 MHz, Methanol-d$_4$) δ 8.52 (d, J=8.0 Hz, 1H), 7.96 (d, J=6.8 Hz, 1H), 7.84 (d, J=7.2 Hz, 1H), 7.33 (d, J=10.8 Hz, 1H), 7.20 (d, J=12.8 Hz, 1H), 6.48 (d, J=7.2 Hz, 1H), 4.00 (s, 3H), 1.59 (s, 6H).

Procedure for the Preparation of Compound 36c:

To a solution of compound 36b (200 mg, 0.43 mmol) and K$_2$CO$_3$ (119 mg, 0.86 mmol) in DMF (3 mL) was added N$^1$,N$^1$,N-trimethylethane-1,2-diamine (66 mg, 0.644 mmol). The reaction mixture was stirred at 22-32° C. for 15 h (changed from brown to deep orange). The reaction mixture was added drop wise into H$_2$O (40 mL) under ice water bath with stirring and solid precipitated out. The solid was collected by filtration and washed with H$_2$O (15 mL×3), then dried in high vacuo to give compound 36c (210 mg, 89% yield) as an orange solid.

LCMS: $R_f$=0.669 min in 5-95AB_220&254.lcm chromatography (ACSSH-LCMS-AB MERCK RP18 2.5-2 mm), MS (ESI) m/z=548.1 [M+H]$^+$.

$^1$H NMR (400 MHz, Methanol-d$_4$) δ 8.60 (s, 1H), 7.99 (d, J=6.0 Hz, 1H), 7.95 (d, J=7.6 Hz, 1H), 7.26 (d, J=10.8 Hz, 1H), 6.82 (s, 1H), 6.20 (d, J=6.0 Hz, 1H), 3.99 (s, 3H), 3.24 (t, J=7.4 Hz, 2H), 2.85 (s, 3H), 2.59 (t, J=7.2 Hz, 2H), 2.28 (s, 6H), 1.59 (s, 6H).

Procedure for the Preparation of Compound 36d:

To a solution of compound 36c (200 mg, 0.365 mmol) in MeOH/H$_2$O=5/1 (5 mL) was added Zn (143 mg, 2.190 mmol) and NH$_4$Cl (117 mg, 2.190 mmol). The resulting mixture was heated at 90° C. for 2 h (changed from orange to brown). The reaction mixture was filtered, and the filtrate was concentrated in vacuo to give the crude residue, which was dissolved with CH$_2$Cl$_2$ (20 mL) and washed with water (15 mL×3), dried over Na$_2$SO$_4$ and concentrated in vacuo to give compound 36d (170 mg, 89.9% yield) as a brown solid.

LCMS: $R_f$=0.646 min in 5-95AB_220&254.lcm chromatography (ACSSH-LCMS-AB MERCK RP18 2.5-2 mm), MS (ESI) m/z=518.2 [M+H]$^+$.

Procedure for the Preparation of Example 36:

To a solution of compound 36d (170 mg, 0.329 mmol) and DIEA (64 mg, 0.494 mmol) in DMF (2 mL) was added acryloyl chloride (30 mg, 1.0 eq, 0.329 mmol) in ice water bath. The resulting mixture was stirred at 5-10° C. for 10 min. The reaction was quenched by H$_2$O (0.1 mL) and then filtered, the filtrate was purified by pre-HPLC (Column: Xtimate C18 150*25 mm*5 um; Condition: 53-83% B (A: 0.04% NH$_3$.H$_2$O+10 mM NH$_4$HCO$_3$, B: CH$_3$CN); Flow Rate: 25 ml/min) and then lyophilized to give Example 36 (17.0 mg, 8.1% yield) as an off-white solid.

LCMS: $R_f$=2.356 min in 10-80CD_3min_220&254 chromatography (ACSSH-LCMS-AS A: Xtimate C18, 2.1*30 mm, 3 um; B: XBrige Shield RP18 2.1*50 mm), MS (ESI) m/z=572.2 [M+H]$^+$.

$^1$H NMR (400 MHz, CDCl$_3$) δ 10.34 (br s, 1H), 9.72 (s, 1H), 9.43 (s, 1H), 8.02 (d, J=6.0 Hz, 1H), 7.46 (s, 1H), 7.41 (d, J=7.2 Hz, 1H), 7.08 (d, J=10.8 Hz, 1H), 6.69 (s, 1H), 6.36-6.21 (m, 3H), 6.02 (br s, 1H), 5.70-5.63 (m, 1H), 3.79 (s, 3H), 2.85-2.78 (m, 2H), 2.61 (s, 3H), 2.20 (s, 8H), 1.66 (s, 6H).

Example 37

N-(2-((2-(bis(methyl-$d_3$)amino)ethyl)(methyl)amino)-5-((4-((4-chloro-5-fluoro-2-(2-hydroxypropan-2-yl)phenyl)amino)-1,3,5-triazin-2-yl)amino)-4-methoxyphenyl) acrylamide

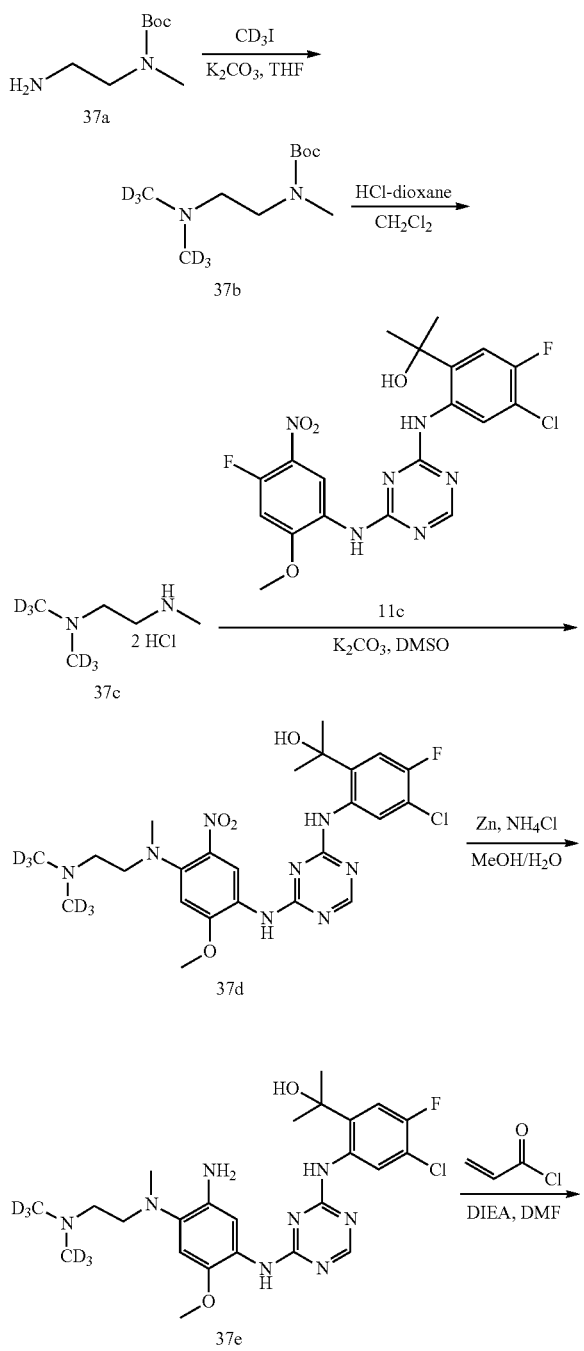

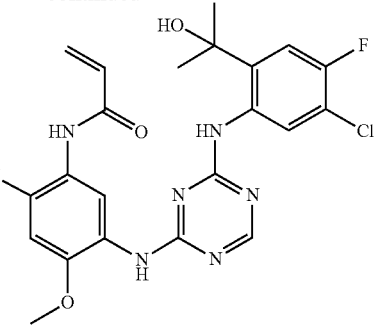

Example 37

Procedure for the Preparation of Compound 37b:

To three separated solution of compound 37a (500 mg, 2.87 mmol) and $K_2CO_3$ (793 mg, 5.74 mmol) in THF (10 mL) was added $CD_3I$ (624 mg, 4.30 mmol). The mixture was stirred at 24-26° C. for 1 h while white solid was precipitate out. The three reaction mixtures were filtered and the organic layer was concentrated under reduced pressure to give the crude residue, which was diluted with EtOAc (20 ml) and washed with $H_2O$ (20 mL), then dried over anhydrous $Na_2SO_4$ and concentrated under reduced pressure to give compound 37b (350 mg, 19% yield) as colorless oil.

LCMS: $R_t$=0.744 min in 0-60AB_2MIN_E.M chromatography (Xtimate C18, 2.1*30 mm, 3 um), MS (ESI) m/z=209.2 $[M+H]^+$.

$^1$H NMR (400 MHz, DMSO-$d_6$) δ 3.19-3.13 (m, 1H), 3.13-3.10 (m, 1H), 2.68 (br d, J=6.4 Hz, 3H), 2.56 (t, J=6.8 Hz, 1H), 2.32-2.24 (m, 1H), 1.30-1.23 (m, 9H).

Procedure for the Preparation of Compound 37c:

To a solution of compound 37b (300 mg, 1.44 mmol) in $CH_2Cl_2$ (5 mL) was added HCl/dioxane (5 mL, 4 M) at 0° C. The resulting mixture was stirred at 22-32° C. for 2 h. The reaction mixture was concentrated under reduced pressure to give compound 37c (260 mg, crude) as white solid.

LCMS: $R_t$=0.097 min in 0-60AB_2MIN_E.M chromatography (Xtimate C18, 2.1*30 mm, 3 um), MS (ESI) m/z=109.1 $[M+H]^+$.

$^1$H NMR (400 MHz, DMSO-$d_6$) δ 3.38 (s, 1H), 3.35 (br d, J=4.0 Hz, 1H), 3.27-3.11 (m, 2H), 2.58 (br d, J=4.4 Hz, 3H).

Procedure for the Preparation of Compound 37d:

To a solution of compound 37c (250 mg, 0.54 mmol) and $K_2CO_3$ (149 mg, 1.08 mmol) in DMSO (5 mL) was added compound 11d (230 mg, 1.27 mmol). The resulting mixture was stirred at 22-29° C. for 12 h while the color changes from pale brown to deep yellow. The reaction mixture was diluted with EtOAc (20 mL) and washed with brine (2×30 mL).

The organic layer was dried over anhydrous $Na_2SO_4$ and concentrated under reduced pressure to give the crude residue, which was purified by column chromatography on silica gel ($CH_2Cl_2$/MeOH=10/1) to give compound 37d (90 mg, 30% yield) as yellow solid.

LCMS: $R_t$=0.820 min in 5-95AB_1.5min_220&254 chromatography (MERCK RP18e 25-2 mm), MS (ESI) m/z=555.2 $[M+H]^+$.

Procedure for the Preparation of Compound 37e:

To a solution of compound 37d (90 mg, 0.16 mmol) in MeOH (4 mL) and $H_2O$ (2 mL) was added Zn (52 mg, 0.80 mmol) and $NH_4Cl$ (85 mg, 1.60 mmol). The resulting mixture was purged and degassed with $N_2$ for 3 times, then stirred at 80° C. for 1 h. The reaction mixture was filtered and concentrated under reduced pressure, the residue was dissolved with EtOAc (20 mL) and washed with H$_2$O (10 mL), dried over anhydrous Na$_2$SO4 and concentrated under reduced pressure to give compound 37e (80 mg, 95% yield) as brown solid.

LCMS: R$_t$=0.709 min in 5-95AB_1.5min_220&254 chromatography (MERCK RP18e 25-2 mm), MS (ESI) m/z=525.0 [M+H]$^+$.

Procedure for the Preparation of Example 37:

To a solution of compound 37e (80 mg, 0.15 mmol) and DIEA (39 mg, 0.30 mmol) in DMF (2.5 mL) was added a solution of acryloyl chloride (14 mg, 0.15 mmol) in DMF (0.5 mL) drop wise. The resulting mixture was stirred at 0° C. under ice-water bath for 30 min. The reaction mixture was purified by prep-HPLC [Column: Waters Xbridge 150*25 5 um; Condition: 43-73% B (A: 0.05% NH$_3$H$_2$O; B: CH$_3$CN); Flow rate: 25 ml/min]. Fractions containing the desired compound were lyophilized to afford Example 37 (35.0 mg, 40% yield) as white solid.

LCMS: R$_t$=1.882 min in 10-80AB_4min_220&254 chromatography (Xtimate C18 2.1*30 mm), MS (ESI) m/z=579.3 [M+H]$^+$.

HPLC: R$_t$=3.23 min in 10-80_ab_1.2ML chromatography (Ultimate C18 3*50 mm 3 um).

$^1$H NMR (400 MHz, CDCl$_3$) δ 10.60 (br s, 1H), 10.46 (br s, 1H), 9.96 (br s, 1H), 8.47 (d, J=7.6 Hz, 1H), 8.42 (s, 1H), 7.69 (br s, 1H), 7.10 (d, J=10.8 Hz, 1H), 6.78 (s, 1H), 6.45-6.30 (m, 2H), 6.18 (br s, 1H), 5.81-5.70 (m, 1H), 3.88 (s, 3H), 2.87 (br d, J=4.8 Hz, 2H), 2.70 (s, 3H), 2.29 (br s, 2H), 1.78 (s, 6H).

Example 38

(R)—N-(5-(4-(5-chloro-4-fluoro-2-(2-hydroxypropan-2-yl)phenylamino)-1,3,5-triazin-2-ylamino)-2-(2-((dimethylamino)methyl)azetidin-1-yl)-4-methoxyphenyl)acrylamide

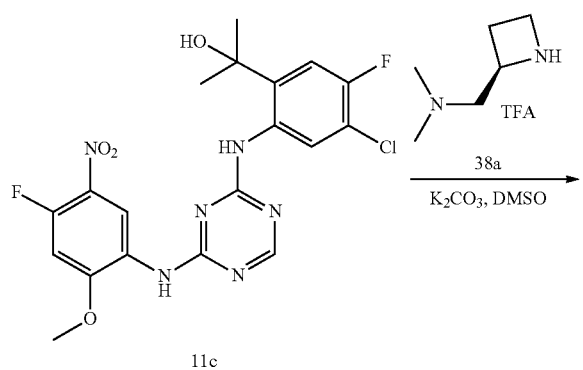

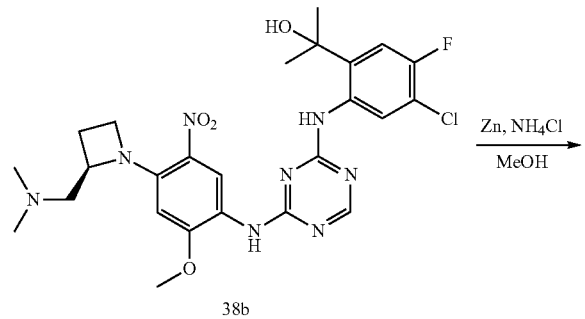

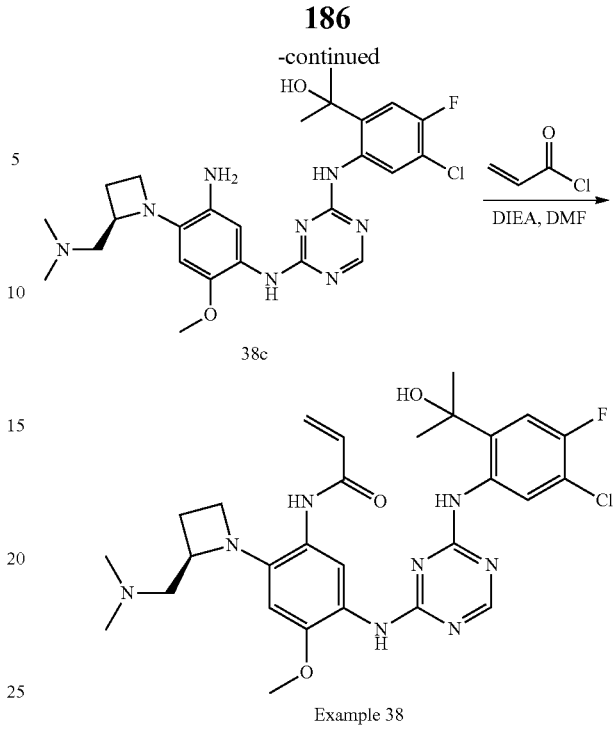

Example 38

Procedure for the Preparation of Compound 38b:

A solution of compound 11c (180 mg, 0.385 mmol), compound 38a (440.3 mg, 3.86 mmol) and K$_2$CO$_3$ (532.9 mg, 3.86 mmol) in DMSO (2 mL) was stirred at 85° C. for 2 h. The reaction mixture was added into H$_2$O (10 mL) in ice water bath with stirring, the solid precipitated was filtered and the filter cake was dissolved with DCM (30 mL), then dried and concentrated in vacuum to give the product 38b (230 mg, 95.7% yield) as orange solid.

LCMS: R$_t$=0.718 min in 5-95AB_220&254.lcm chromatography (ACSSH-LCMS-AB MERCK RP18 2.5-2 mm), MS (ESI) m/z=560.1, 583.1 [M+H, M+Na]$^+$.

$^1$H NMR (400 MHz, CDCl$_3$) δ 9.71 (br s, 1H), 8.98 (br s, 1H), 8.37 (br s, 2H), 7.35 (br s, 1H), 7.06 (d, J=10.4 Hz, 1H), 6.83 (s, 1H), 4.45-4.35 (m, 1H), 4.30 (dt, J=5.1, 9.2 Hz, 1H), 3.93 (s, 3H), 3.33-3.24 (m, 1H), 2.80 (m, 1H), 2.49 (dd, J=5.6, 13.2 Hz, 1H), 2.46-2.36 (m, 1H), 2.30 (s, 6H), 2.20-2.08 (m, 1H), 1.69 (s, 6H).

Procedure for the Preparation of Compound 38c:

To a solution of compound 38b (230 mg, 0.410 mmol) in 6 mL MeOH/H$_2$O=5/1 (v/v) was added Zn (134.02 mg, 2.05 mmol) and NH$_4$Cl (109.65 mg, 2.05 mmol). The resulting mixture was heated at 90° C. for 1 h. The reaction mixture was filtered, and the filtrate was concentrated in vacuo to give the crude, which was dissolved with CH$_2$Cl$_2$ (30 mL), washed with water (20 mL×2) and brine (20 mL), then dried over Na$_2$SO$_4$ and concentrated in vacuo to give the product 38c (197 mg, 90.5% yield) as brown solid.

LCMS: R$_t$=0.657 min in 5-95AB_220&254.lcm chromatography (ACSSH-LCMS-AB MERCK RP18 2.5-2 mm), MS (ESI) m/z=531.3 [M+H]$^+$.

Procedure for the Preparation of Example 38:

To a solution of compound 38c (197 mg, 0.351 mmol) and DIEA (67.9 mg, 0.527 mmol) in DMF (3 mL) was added acryloyl chloride (31.7 mg, 0.351 mmol) at 0° C. The resulting mixture was stirred at 0° C. for 1 h. The reaction was quenched by H$_2$O (0.1 mL) and purified by preparative HPLC (Instrument: DB Column: Gemini 150*25 5 um. Mobile A: water 0.05% ammonia hydroxide v/v Mobile B:

DMF Flow rate: 25 ml/min Gradient Time: 10 min Profile Descriptive: 30%-60% to give Example 38 (36.6 mg, 18% yield) as a light-yellow solid.

LCMS: $R_t$=1.295 min in 10-80AB_4min_220&254 chromatography (ACSSH-LCMS-AS A: Xtimate C18, 2.1*30 mm, 3 um; B: XBrige Shield RP18 2.1*50 mm), MS (ESI) m/z=585.3 [M+H]+.

HPLC: $R_t$=3.37 min in 10-80_CD_1.2ml. met XBridge Shield RP 18 2.1*50 mm 5 um.

1H NMR (400 MHz, CDCl3) δ 10.41 (br s, 1H), 9.38 (br s, 1H), 8.95 (br s, 1H), 8.38 (m, 1H), 7.56 (m, 1H), 7.08 (m, 1H), 6.62 (m, 1H), 6.37 (m, 1H), 6.82-6.21 (m, 2H), 5.80 (br s, 1H), 4.23 (m, 1H), 3.89 (m, 5H), 3.56 (m, 1H), 2.64 (m, 1H), 2.39 (m, 1H), 2.25 (m, 7H), 1.90-1.73 (s, 6H).

Example 39

N-(5-(4-(5-chloro-4-fluoro-2-(2-hydroxypropan-2-yl)phenylamino)-1,3,5-triazin-2-ylamino)-2-(3-((dimethylamino)methyl)azetidin-1-yl)-4-methoxyphenyl)acrylamide

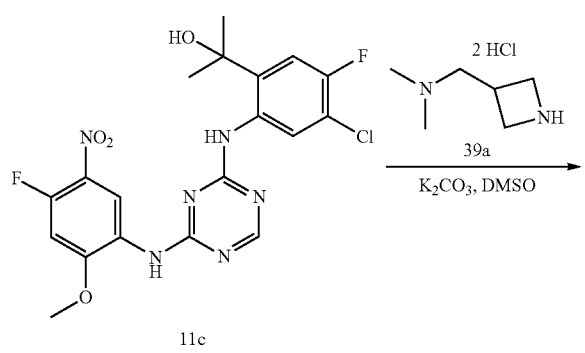

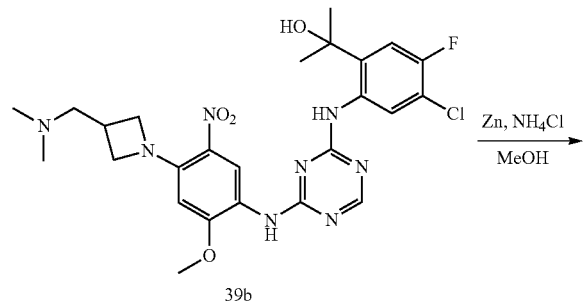

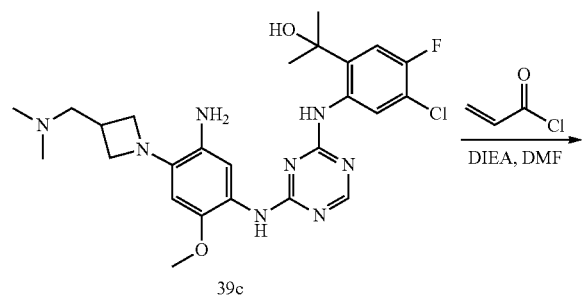

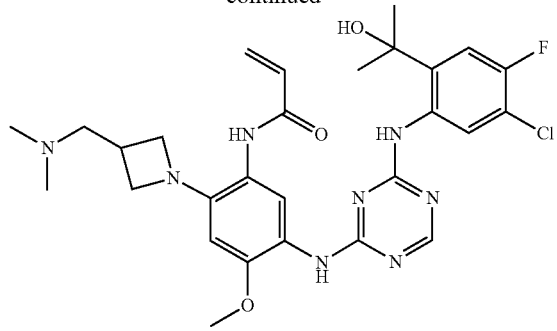

Example 39

Procedure for the Preparation of Compound 39b:

A mixture of compound 11c (100 mg, 0.22 mmol), compound 39a (40 mg, 0.22 mmol) and K2CO3 (110 mg, 0.85 mmol) in DMSO (2 mL) was stirred at 90° C. for 3 h (the yellow suspension). After completion, the ice water (10 mL) was added into the mixture. A solid precipitated was filtered and the filtered cake was washed with H2O (10 mL), dried in high vacuum to give compound 39b (150 mg, 83.4% yield) as a yellow solid.

LCMS: $R_t$=0.710 min in 5-95AB_220&254.lcm chromatography (MERCK RP-18e 25-2 mm), MS (ESI) m/z=583.1 [M+Na]+.

1H NMR: (400 MHz, DMSO-d6) δ ppm 10.23 (br s, 1H), 9.27-8.91 (m, 1H), 8.27 (s, 1H), 7.90 (s, 1H), 7.29 (s, 1H), 6.30 (br s, 1H), 6.21 (s, 1H), 4.09 (t, J=8.4 Hz, 2H), 3.86 (s, 3H), 3.62 (t, J=8.4 Hz, 2H), 2.91-2.82 (m, 1H), 2.55 (s, 2H), 2.15 (s, 6H), 1.51 (s, 6H).

Procedure for the Preparation of Compound 39c:

To a mixture of compound 39b (150 mg, 0.267 mmol) in MeOH/H2O (50/10 mL) was added Zn (87 mg, 1.34 mmol) and NH4Cl (71 mg, 1.34 mmol). The resulting suspension was stirred at 85° C. for 3 hr. The reaction was filtered and the filtrate was concentrated in vacuum to give the crude residue, which was treated with water (20 mL) and extracted with CH2Cl2 (30 mL×3). The combined organic layers were washed with brine (20 mL), dried over Na2SO4 and concentrated in vacuum to give the product 39c (120 mg, 85.1% yield) as a yellow solid.

LCMS: $R_t$=0.665 min in 5-95AB_220&254.lcm chromatography (MERCK RP18 2.5-2 mm), MS (ESI) m/z=529.1 [M+H-2]+.

1H NMR: (400 MHz, DMSO-d6) δ 10.11 (br s, 1H), 8.84 (br s, 1H), 8.33 (s, 1H), 8.19 (s, 1H), 7.26 (s, 1H), 6.53 (br s, 1H), 6.27-6.21 (m, 2H), 4.05-3.91 (m, 4H), 3.67 (s, 3H), 3.46-3.39 (m, 2H), 2.76-2.67 (m, 1H), 2.16 (s, 6H), 1.51 (s, 6H).

Procedure for the Preparation of Example 39:

To a mixture of compound 39c (120 mg, 0.225 mmol) and DIEA (87 mg, 0.675 mmol) in DMF (3 mL) was added drop wise acryloyl chloride (26.6 mg, 0.293 mmol) in DMF (1 mL) with ice water bathe over 1 h. The resulting mixture was stirred for 30 min at 0-5° C. (brown solution), then quenched with H2O (0.05 mL) and purified by prep-HPLC directly [Waters Xbridge 150*25.5 um; Condition: 28-58% B (A: 0.05% ammonia; B: CH3CN); Flow rate: 25 ml/min]. Fractions containing the desired compound were lyophilized to afford Example 39 (48.0 mg, 20.9% yield) as a white solid.

LCMS: $R_t$=2.325 min in 0-60AB_4.0min_220&254 chromatography (Xtimate C18 2.1*30 mm), MS (ESI) m/z=585.1 [M+H]+.

HPLC: $R_t$=4.92 min in 0-60_CD_1.2 ml chromatography (XBridge Shield RP 18 2.1*50 mm 5 um).

$^1$H NMR: (400 MHz, CDCl$_3$) δ ppm 10.23 (brs, 1H), 9.07 (brs, 1H), 8.36-8.28 (m, 2H), 743-7.32 (m, 2H), 6.99 (d, J=10.8 Hz, 1H), 6.34-6.19 (m, 3H), 5.72 (d, J=9.2 Hz, 1H), 3.90 (t, J=7.2 Hz, 2H), 3.80 (s, 3H), 3.42 (t, J=6.4 Hz, 2H), 2.86-2.79 (m, 1H), 2.45 (d, J=7.2 Hz, 2H), 2.16 (s, 6H), 1.64 (s, 6H).

Example 40

(S)—N-(5-(4-(5-chloro-4-fluoro-2-(2-hydroxypropan-2-yl)phenylamino)-1,3,5-triazin-2-ylamino)-2-(3-((dimethylamino)methyl)morpholino)-4-methoxyphenyl)acrylamide

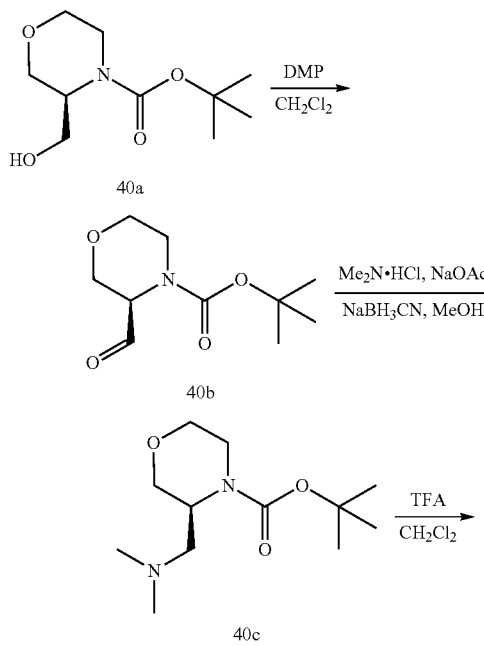

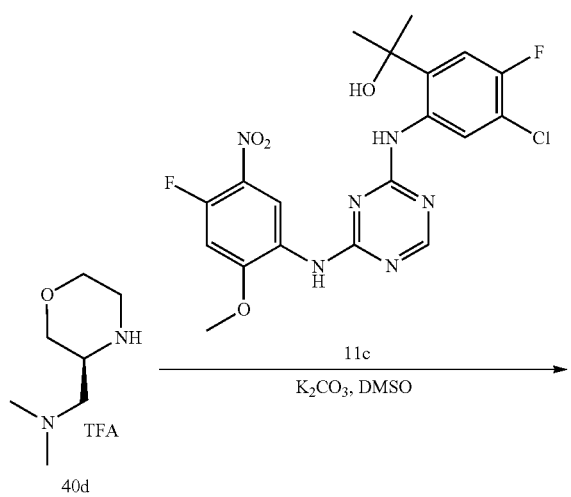

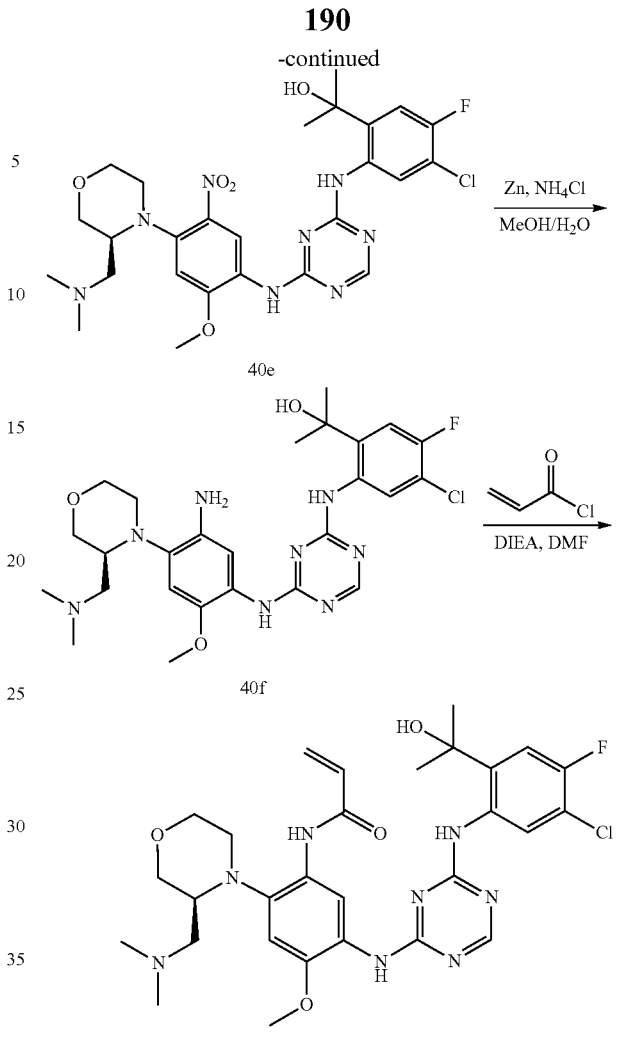

Procedure for the Preparation of Compound 40b:

To a solution of compound 40a (1.4 g, 6.44 mmol) in CH$_2$Cl$_2$ (40 mL) was added DMP (4.1 g, 9.67 mmol) in portions at 0-5° C. The resulting white mixture was stirred at 0-5° C. for 1 h. The reaction was treated with aqueous NaHCO$_3$ (30 mL), extracted with EtOAc (3×20 mL). The combined organic layers was washed with brine (3×20 mL), dried and concentrated under reduced pressure to give the crude, which was purified by column chromatography on silica gel (Petroleum ether/EtOAc=5/1 (v/v)) to afford compound 40b (1.1 g, 79.7% yield) as light yellow oil.

LCMS: $R_t$=1.300-1.400 min in 10-80CD_3MIN_220&254, chromatography (XBrige Shield RP18 2.1×50 mm).

$^1$H NMR: (400 MHz, DMSO-d$_6$) δ 9.60 (br d, J=10.0 Hz, 1H), 4.52-4.36 (m, 2H), 3.94-3.67 (m, 2H), 3.63-3.52 (m, 2H), 3.08-2.79 (m, 1H), 1.43-1.36 (m, 9H).

Procedure for the Preparation of Compound 40c:

To a solution of compound 40b (1.0 g, 4.65 mmol) in MeOH (10 mL) was added Me$_2$N.HCl (1.1 g, 13.94 mmol) and NaOAc (572 mg, 6.97 mmol), the white mixture was stirred at 24-26° C. for 2 h, then NaBH$_3$CN (584 mg, 9.29 mmol) was added, the resulting mixture was stirred at 22-27° C. for 18 h. The reaction mixture was quenched by the addition of aqueous NH$_4$Cl (20 mL), extracted with EtOAc (3×10 mL). The combined organic layers were washed with brine (3×10 mL), dried and concentrated in vacuum to give compound 40c (800 mg, 70.5% yield) as colorless oil.

LCMS: $R_t$=2.475 min in 10-80CD_7MIN_220&254, chromatography (XBrige Shield RP18 2.1×50 mm), MS (ESI) m/z=245.1 [M+H]$^+$.

$^1$H NMR: (400 MHz, CDCl$_3$) δ 4.15-3.40 (m, 5H), 3.53-3.44 (m, 2H), 3.06 (br s, 1H), 2.79 (br t, J=10.8 Hz, 1H), 2.32 (br s, 6H), 1.48 (s, 9H).

Procedure for the Preparation of Compound 40d:

To a solution of compound 40c (500 mg, 2.30 mmol) in CH$_2$Cl$_2$ (6 mL) was added TFA (2 mL). The resulting colorless solution was stirred at 22-32° C. for 3 h. The reaction solution was concentrated in vacuum directly to give compound 40d in TFA salt (300 mg, 61.1% yield) as colorless oil.

LCMS: $R_t$=0.561 min in 10-80CD_4MIN_E, chromatography (XBrige Shield RP18 2.1×50 mm), MS (ESI) m/z=145.2 [M+H]$^+$.

Procedure for the Preparation of Compound 40e:

A solution of compound 40d (375 mg, 0.42 mmol) and K$_2$CO$_3$ (230 mg, 1.67 mmol) in DMSO (2 mL) was added compound 11c (120 mg, 0.83 mmol). The mixture was stirred at 28-33° C. for 8 hours. It was purified by Biotage flash reversed-phase C-18 column chromatography eluting with MeOH/H$_2$O (MeOH in water from 56% to 60%) to give compound 40e (120 mg, 20.9% yield) as a red solid.

LCMS: $R_t$=0.809 min in 5-95AB_1.5MIN_220&254, chromatography (MERCK RP18 2.5-2 mm). MS (ESI) m/z=591.3 [M+H]$^+$.

Procedure for the Preparation of Compound 40f:

To a solution of compound 40e (120 mg, 0.20 mmol) in MeOH (5 mL) and H$_2$O (1 mL) was added Zn (67 mg, 1.02 mmol) and NH$_4$Cl (109 mg, 2.04 mmol). The black suspension was stirred at 70° C. for 1.5 h under N$_2$. The reaction mixture was quenched by the addition of aqueous NH$_4$Cl (20 mL), extracted with EtOAc (10 mL×3). The organic layers were washed with brine (10 mL×3), dried and concentrated in vacuum directly to give compound 40f (70 mg, 82.1% yield) as brown oil.

LCMS: $R_t$=0.760 min in 5-95AB_1.5MIN_220&254.lcm, chromatography (MERCK RP18 2.5-2 mm), MS (ESI) m/z=561.2 [M+H]$^+$.

Procedure for the Preparation of Example 40:

To a solution of compound 40f (70 mg, 0.12 mmol) and DIEA (24 mg, 0.19 mmol) in DMF (1 mL) was added a solution of acryloyl chloride (11 mg, 0.12 mmol) in DMF (1 mL) drop wise. The resulting brown mixture was stirred at 0° C. for 30 min. The reaction was purified by prep-HPLC [Column: Waters Xbridge 150×25 Sum; Condition: 35-65% B (A: 0.05% ammonia; B: CH$_3$CN); Flow rate: 25 ml/min]. Fractions containing the desired compound were lyophilized to afford Example 40 (10.2 mg, 15.5% yield) as a white solid.

LCMS: $R_t$=4.015 min in 10-80CD_7MIN_220&254, chromatography (XBrige Shield RP18 2.1×50 mm), MS (ESI) m/z=615.3 [M+H]$^+$.

HPLC: $R_t$=3.76 min, 10-80_CD_1.2 mL.MET (XBridge Shield RP 18 2.1×50 mm Sum).

$^1$H NMR: (400 MHz, DMSO-d$_6$) δ 10.20 (br s, 1H), 9.15-9.00 (m, 2H), 8.29 (br d, J=15.6 Hz, 2H), 7.26 (br s, 1H), 7.12 (br s, 1H), 6.63 (dd, J=10.0, 16.8 Hz, 1H), 6.30 (s, 1H), 6.17 (br d, J=16.8 Hz, 1H), 5.73 (br d, J=11.0 Hz, 1H), 4.01 (br d, J=9.4 Hz, 1H), 3.82-3.77 (m, 5H), 3.55-3.49 (m, 1H), 3.32-3.23 (m, 1H), 2.84 (br s, 2H), 2.29-2.18 (m, 1H), 2.02 (s, 6H), 1.91 (br d, J=9.4 Hz, 1H), 1.51 (d, J=7.2 Hz, 6H).

Example 41

N-(5-(4-(4-chloro-5-fluoro-2-(2-hydroxypropan-2-yl)phenylamino)-1,3,5-triazin-2-ylamino)-4-methoxy-2-((3aR,6aR)-5-methylhexahydropyrrolo[3,4-b]pyrrol-1(2H)-yl)phenyl)acrylamide

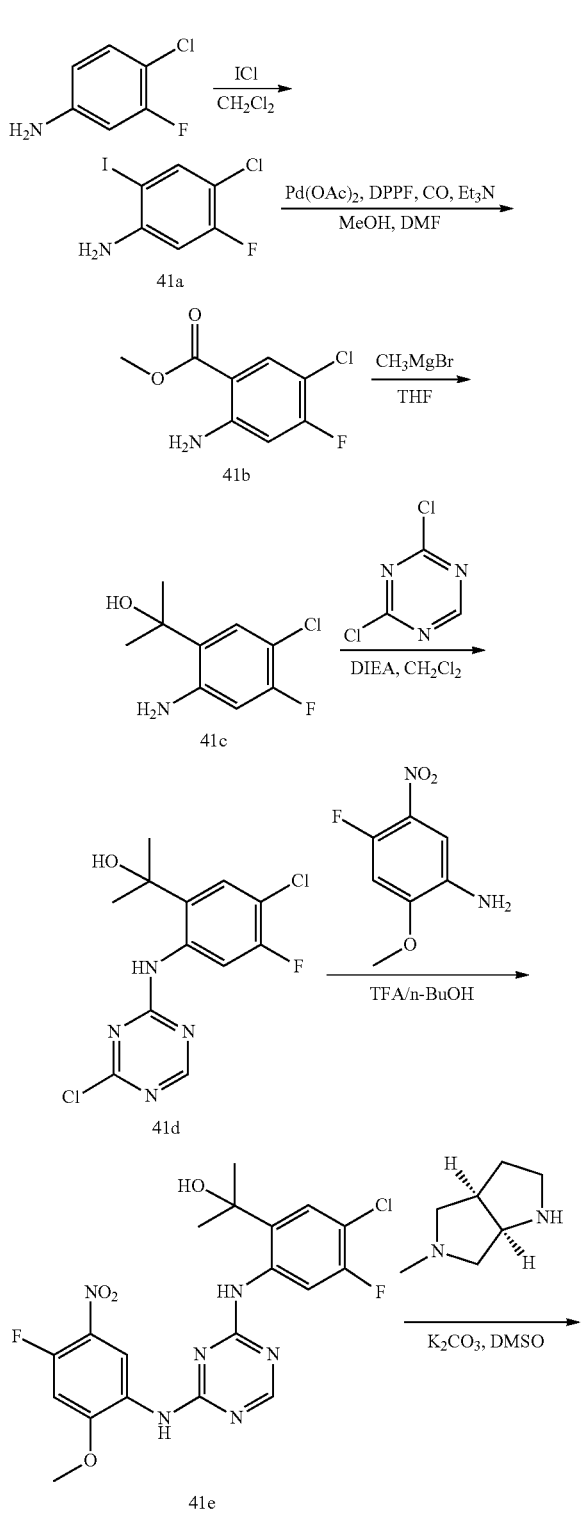

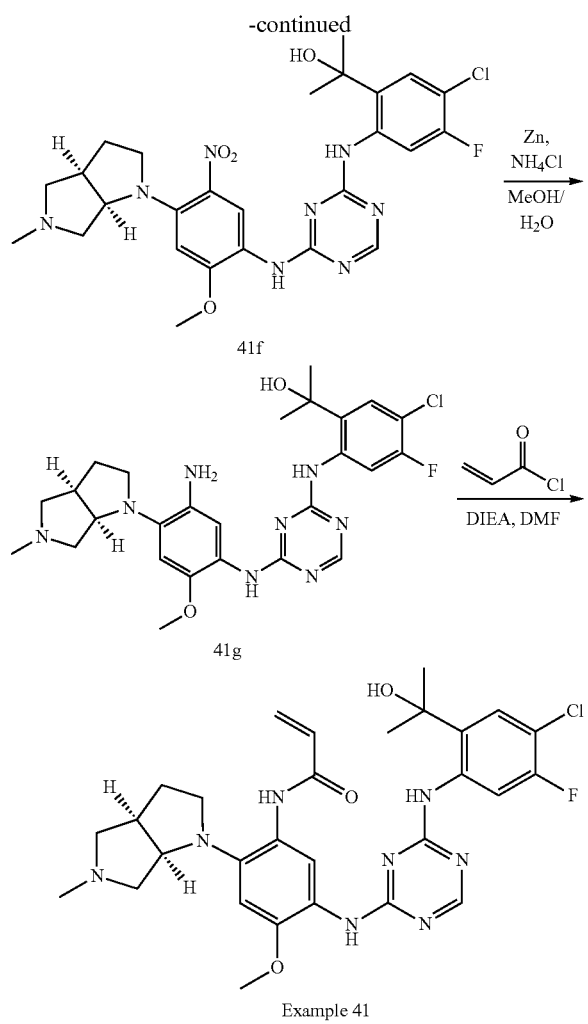

41f

41g

Example 41

Procedure for the Preparation of Compound 41a:

To a solution of 4-chloro-3-fluoroaniline (15 g, 103.05 mmol) in dichloromethane (150 mL) was added ICl (25 g, 154.57 mmol) drop wise. The resulting black mixture was stirred at 24-29° C. for 2 h. The mixture was diluted with 100 mL dichloromethane and washed with saturated solution of sodium bicarbonate (200 mL). The organic layer was concentrated to give the crude residue, which was purified by flash column chromatography on silica gel (0 to 0.5% ethyl acetate in Petroleum ether) to afford compound 41a (8 g brown solid and 12 g black solid, 71.5% yield in total).

LCMS: $R_t$=0.974 min in 5-95AB_220&254 chromatography (MERCK RP18 2.5-2 mm), MS (ESI) m/z=271.8 [M+H]$^+$.

$^1$H NMR: (400 MHz, CDCl$_3$) δ 7.53 (d, J=8.0 Hz, 1H), 6.46 (d, J=10.4 Hz, 1H), 4.12 (s, 2H).

Procedure for the Preparation of Compound 41b:

To a solution of compound 41a (20 g, 73.67 mmol) in DMF (60 mL) and methanol (120 mL) was added DPPF (4.08 g, 7.37 mmol), Et$_3$N (31 mL, 221.03 mmol) and Pd(OAc)$_2$ (1.65 g, 7.37 mmol) under nitrogen. The reaction mixture was purged and degassed with CO for three times and stirred at 80° C. under CO (50 psi) for 24 h. The mixture was filtered and methanol was removed in vacuum to give the residue, which was poured into brine (300 mL) and black solid was precipitated out. The solid was collected by filtration and further purified by flash column chromatography on silica gel (0 to 1% ethyl acetate in Petroleum ether) to afford compound 41b (11.8 g, 78.6% yield) as pink solid.

$^1$H NMR: (400 MHz, CDCl$_3$) δ 7.83 (d, J=8.4 Hz, 1H), 6.36 (d, J=10.8 Hz, 1H), 5.80 (s, 2H), 3.79 (s, 3H).

Procedure for the Preparation of Compound 41c:

To a solution of compound 41b (6 g, 29.47 mmol) in THF (100 mL) was added CH$_3$MgBr (49.1 mL, 147.35 mmol) drop wise at 0° C. under nitrogen. The resulting brown mixture was stirred at 24-31° C. for 2 h. The mixture was quenched with saturated solution of NH$_4$Cl (300 mL) and extracted with ethyl acetate (200 mL×3). The combined organic layers were dried over sodium sulfate, filtered and concentrated to give the crude product, which was purified by flash column chromatography on silica gel (0 to 15% ethyl acetate in Petroleum ether) to afford compound 41c (5.17 g, 84% yield) as yellow oil.

LCMS: $R_t$=0.821 min in 5-95AB_220&254 chromatography (MERCK RP18 2.5-2 mm), MS (ESI) m/z=185.9 [M+H]$^+$.

$^1$H NMR: (400 MHz, CDCl$_3$) δ 7.09 (d, J=8.4 Hz, 1H), 6.42 (d, J=11.2 Hz, 1H), 4.84 (s, 2H), 1.66 (s, 6H).

Procedure for the Preparation of Compound 41d:

To a solution of compound 41c (5.17 g, 25.39 mmol) in dichloromethane (100 mL) was added DIEA (6.56 g, 50.78 mmol) and 2,4-dichloro-1,3,5-triazine (4.19 g, 27.93 mmol). The resulting solution was stirred at 23-29° C. for 3 h. The solution was concentrated in vacuum to give the crude product, which was purified by flash column chromatography on silica gel (0 to 10% ethyl acetate in Petroleum ether) to afford compound 41d (5.74 g, 71.3% yield) as white solid.

LCMS: $R_t$=2.614 min in 10-80AB_4min_220&254 chromatography (Xtimate C18 2.1*30 mm), MS (ESI) m/z=316.7 [M+H]$^+$.

$^1$H NMR: (400 MHz, CDCl$_3$) δ 10.20 (s, 1H), 8.49 (s, 1H), 8.16 (d, J=10.8 Hz, 1H), 7.22 (d, J=7.6 Hz, 1H), 2.24 (s, 1H), 1.62 (s, 6H).

Procedure for the Preparation of Compound 41e:

To a yellow solution of compound 41d (4.74 g, 14.95 mmol) in n-BuOH/TFA (50 mL/0.5 mL) was added 4-fluoro-2-methoxy-5-nitroaniline (2.8 g, 15.04 mmol). The resulting mixture was stirred at 21-24° C. for 1 h while color changed to brown and yellow solid was precipitated out. The solid was collected by filtration and washed with Petroleum ether (20 mL), the solid was dried in vacuum to afford compound 41e (5.42 g, 77.7% yield).

LCMS: $R_t$=0.971 min in 5-95AB_220&254 chromatography (MERCK RP18 2.5-2 mm), MS (ESI) m/z=467.1 [M+H]$^+$.

$^1$H NMR: (400 MHz, DMSO-d$_6$) δ 10.56 (s, 1H), 9.49 (s, 1H), 8.45 (s, 1H), 8.39 (s, 1H), 7.45-7.34 (m, 1H), 3.95 (s, 3H), 1.53 (s, 6H).

Procedure for the Preparation of Compound 41f:

To a solution of compound 41e (200 mg, 0.43 mmol) and K$_2$CO$_3$ (119 mg, 0.86 mmol) in DMSO (5 mL) was added (3aR,6aR)-5-methyloctahydropyrrolo[3,4-b]pyrrole (65 mg, 0.52 mmol). The resulting mixture was stirred at 85° C. for 4 h while the colour changes from pale yellow to deep yellow. The reaction mixture was pour to ice water (50 mL) and yellow solid was precipitated. The yellow precipitate was filtered and dissolved with CH$_2$Cl$_2$ (20 mL), then dried over anhydrous Na$_2$SO$_4$ and concentrated under reduced pressure to give compound 41f (230 mg, 93% yield) as a yellow solid.

LCMS: $R_t$=0.755 min in 5-95AB_220&254.lcm chromatography (Xtimate C18 2.1*30 mm), MS (ESI) m/z=572.9 [M+H]$^+$.

195

Procedure for the Preparation of Compound 41g:

To a solution of compound 41f (230 mg, 0.40 mmol) in MeOH (10 mL) and $H_2O$ (5 mL) was added Zn (131 mg, 2.00 mmol) and $NH_4Cl$ (214 mg, 4.00 mmol). The resulting mixture was purged and degassed with $N_2$ for 3 times, then stirred at 80° C. for 1 h. The reaction mixture was filtered and concentrated under reduced pressure to give the residue, which was dissolved with EtOAc (20 mL) and washed with $H_2O$ (10 mL), dried over anhydrous $Na_2SO_4$ and concentrated under reduced pressure to give compound 41g (190 mg, 87% yield) as a brown solid.

LCMS: $R_t$=0.701 min in 5-95AB_1.5min_220&254 chromatography (Xtimate C18 2.1*30 mm), MS (ESI) m/z=542.9 [M+H]$^+$.

Procedure for the Preparation of Example 41:

To a solution of compound 41g (190 mg, 0.35 mmol) and DIEA (90 mg, 0.70 mmol) in DMF (2.5 mL) was added acryloyl chloride (32 mg, 0.35 mmol) in DMF (0.5 mL) drop wise. The resulting mixture was stirred at 0° C. under ice-water bath for 30 min. The reaction mixture was purified by prep-HPLC [Column: Waters Xbridge 150*25 5 um; Condition: 40-70% B (A: 0.05% $NH_3H_2O$; B: $CH_3CN$); Flow rate: 25 ml/min]. Fractions containing the desired compound were lyophilized to afford Example 41 (74.4 mg, 36% yield) as a white solid.

LCMS: $R_t$=1.924 min in 10-80AB_4min_220&254 chromatography (Xtimate C18 2.1*30 mm), MS (ESI) m/z=597.1 [M+H]$^+$.

HPLC: $R_t$=3.30 min in 10-80_ab_1.2ML chromatography (Ultimate C18 3*50 mm 3 um).

$^1$H NMR: (400 MHz, CDCl$_3$) δ 10.83 (br s, 1H), 9.91 (br s, 1H), 9.60 (br s, 1H), 8.42 (s, 1H), 8.40 (d, J=11.6 Hz, 1H), 7.70 (br s, 1H), 7.29 (s, 1H), 6.78 (s, 1H), 6.56-6.33 (m, 2H), 5.96 (br s, 1H), 5.77 (br d, J=10.8 Hz, 1H), 3.87 (s, 3H), 3.73-3.64 (m, 1H), 3.22 (br t, J=7.6 Hz, 1H), 2.93-2.79 (m, 3H), 2.72 (br d, J=10.4 Hz, 1H), 2.33 (br s, 1H), 2.30 (s, 3H), 2.25-2.16 (m, 1H), 1.95-1.86 (m, 2H), 1.78 (s, 6H).

Example 42

(S)—N-(5-(4-(5-chloro-4-fluoro-2-(2-hydroxypropan-2-yl)phenylamino)-1,3,5-triazin-2-ylamino)-4-methoxy-2-(methyl(2-(2-methylpyrrolidin-1-yl)ethyl)amino)phenyl) acrylamide

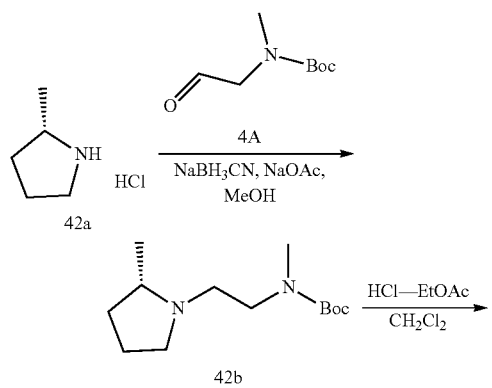

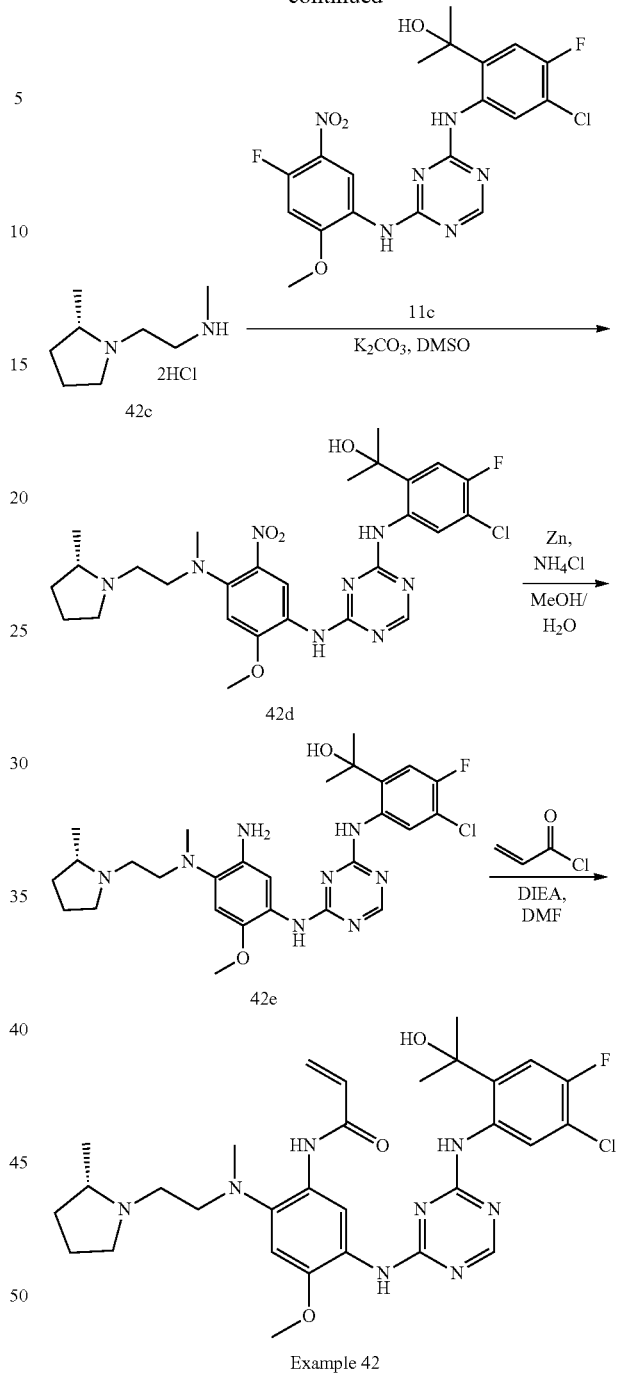

Procedure for the Preparation of Compound 42b:

To a solution of compound 42a (300 mg, 2.47 mmol) in MeOH (8 mL) was added NaOAc (404.74 mg, 4.93 mmol). The mixture was stirred at 23-28° C. for 10 min and tert-butyl methyl(2-oxoethyl)carbamate (512.76 mg, 2.96 mmol) was added. The resulting mixture was stirred at 23-28° C. for 1 h and then NaBH$_3$CN (310.05 mg, 4.93 mmol) was added to the above mixture. The mixture was stirred at 23-28° C. for 15 h. The mixture was concentrated in vacuum to give the residue, which was dissolved with CH$_2$Cl$_2$ (15 mL) and washed with water (6 mL), brine (6 mL), dried over Na$_2$SO4 and concentrated in vacuum to give the crude product. It was purified by column chromatography on silica gel (0.5% MeOH in CH$_2$Cl$_2$) to give compound 42b (350 mg, 58.5% yield) as yellow oil.

$^1$H NMR: (400 MHz, CDCl$_3$) δ 3.65-2.93 (m, 5H), 2.89 (s, 3H), 2.75-2.32 (m, 2H), 2.20 (br s, 1H), 2.06-1.65 (m, 3H), 1.46 (s, 9H), 1.26-1.06 (m, 3H).

Procedure for the Preparation of Compound 42c:

To a solution of compound 42b (350 mg, 1.44 mmol) in CH$_2$Cl$_2$ (3 mL) was added HCl-EtOAc (4 mL). The resulting mixture was stirred at 22-32° C. for 12 h. The reaction mixture was concentrated in vacuum to give compound 42c (200 mg, 64% yield) as a white solid.

LCMS: R$_t$=0.101 min in 0-60AB_2MIN_50_E.lcm chromatography (Xtimate C18, 2.1*30 mm, 3 um), MS (ESI) m/z=143.1 [M+H]$^+$.

$^1$H NMR: (400 MHz, D$_2$O) δ 3.81-3.61 (m, 2H), 3.60-3.33 (m, 4H), 3.24-3.12 (m, 1H), 2.77 (s, 3H), 2.39-2.23 (m, 1H), 2.17-2.04 (m, 1H), 2.03-1.94 (m, 1H), 1.79-1.63 (m, 1H), 1.41 (d, J=6.4 Hz, 3H).

Procedure for the Preparation of Compound 42d:

To a solution of compound 11c (200 mg, 0.428 mmol) and K$_2$CO$_3$ (118 mg, 0.856 mmol) in DMSO (3 mL) was added compound 42c (111 mg, 0.514 mmol). The reaction mixture was heated at 50° C. for 3 h while color changed from brown to orange. The reaction mixture was added drop wise into H$_2$O (40 mL) in ice water bath with stirring while solid was precipitated out, then filtered. The filter cake was washed with H$_2$O (15 mL×3), dried in high vacuum to give compound 42d (210 mg, 83% yield) as an orange solid.

LCMS: R$_t$=0.748 min in 5-95AB_220&254.lcm chromatography (MERCK RP18 2.5-2 mm), MS (ESI) m/z=589.1 [M+H]$^+$.

$^1$H NMR: (400 MHz, CD$_3$OD) δ 8.53 (br s, 1H), 8.26 (br s, 1H), 8.18 (br s, 1H), 7.21 (d, J=10.8 Hz, 1H), 6.81 (s, 1H), 3.96 (s, 3H), 3.42-3.33 (m, 2H), 3.19-3.08 (m, 2H), 2.90 (s, 3H), 2.51-2.34 (m, 2H), 2.24 (q, J=9.2 Hz, 1H), 2.04-1.91 (m, 1H), 1.81-1.70 (m, 2H), 1.60 (s, 6H), 1.40 (qd, J=8.4, 12.4 Hz, 1H), 1.12 (d, J=6.0 Hz, 3H).

Procedure for the Preparation of Compound 42e:

To a solution of compound 42d (200 mg, 0.34 mmol) in MeOH/H$_2$O (5 mL, 5/1) was added Zn (133 mg, 2.04 mmol) and NH$_4$Cl (109 mg, 2.04 mmol). The resulting mixture was heated at 90° C. for 3 h while color changed from orange to brown. The reaction mixture was filtered, and then the filtrate was concentrated in vacuum to give the crude residue, which was dissolved with CH$_2$Cl$_2$ (20 mL), and washed with water (15 mL×3), then dried over Na$_2$SO$_4$ and concentrated in vacuum to give compound 42e (118 mg, 62% yield) as a brown solid.

LCMS: R$_t$=0.703 min in 5-95AB_220&254.lcm chromatography (MERCK RP18 2.5-2 mm), MS (ESI) m/z=559.1 [M+H]$^+$.

Procedure for the Preparation of Example 42:

To a solution of compound 42e (115 mg, 0.206 mmol) and DIEA (40 mg, 0.309 mmol) in DMF (2 mL), was added acryloyl chloride drop wise (19 mg, 0.206 mmol) in ice water bath. The resulting mixture was stirred at 5-10° C. for 15 min. The reaction was quenched by H$_2$O (0.1 mL) and then filtered, the filtrate was purified by pre-HPLC (Column: Waters Xbridge 150*25 5 um; Condition: 42-72% B (A: 0.05% ammonia, B: CH$_3$CN); Flow Rate: 25 ml/min) and lyophilized to give Example 42 (23.7 mg, 16.8% yield) as an off-white solid.

LCMS: R$_t$=4.638 min in 30-90CD_7min_220&254. lcm chromatography (Xtimate 2.1*30 mm 3 um), MS (ESI) m/z=613.3 [M+H]$^+$.

HPLC: R$_t$=4.56 min in 10-80CD_1.2 ml chromatography (XBridge Shield RP 18 2.1*50 mm 5 um).

$^1$H NMR: (400 MHz, CDCl$_3$) δ 10.60 (br s, 1H), 9.92 (br s, 1H), 9.73 (br s, 1H), 8.48 (d, J=7.2 Hz, 1H), 8.42 (s, 1H), 7.69 (br s, 1H), 7.10 (d, J=10.8 Hz, 1H), 6.78 (s, 1H), 6.53-6.30 (m, 2H), 6.10 (br s, 1H), 5.84-5.70 (m, 1H), 3.88 (s, 3H), 3.22-3.18 (m, 1H), 3.02-2.90 (m, 2H), 2.88-2.77 (m, 1H), 2.67 (s, 3H), 2.37-2.28 (m, 1H), 2.16-1.91 (m, 3H), 1.77 (s, 6H), 1.66 (br s, 1H), 1.49-1.40 (m, 1H), 1.36-1.20 (m, 1H), 1.04 (d, J=5.6 Hz, 3H).

Example 43

(R)—N-(5-(4-(4-chloro-5-fluoro-2-(2-hydroxypropan-2-yl)phenylamino)-1,3,5-triazin-2-ylamino)-2-(2-((dimethylamino)methyl)pyrrolidin-1-yl)-4-methoxyphenyl)acrylamide

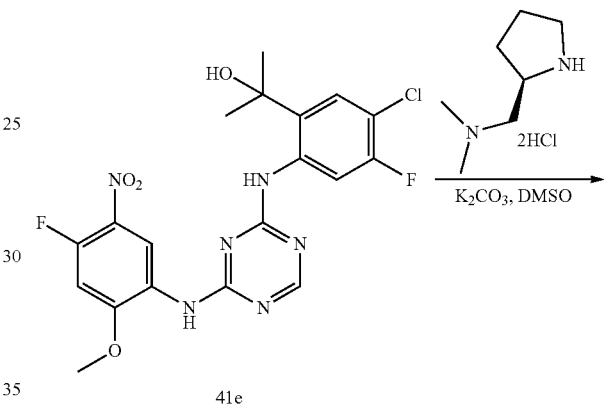

41e

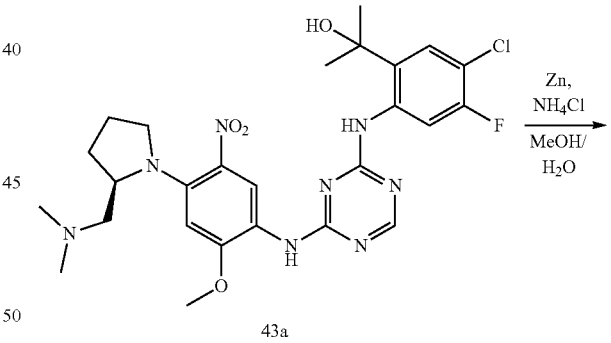

43a

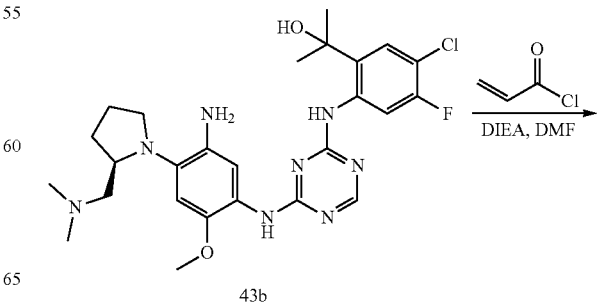

43b

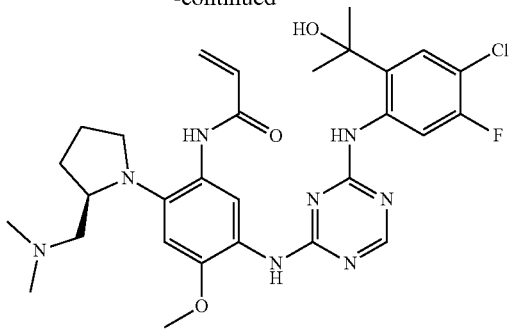

Example 43

Procedure for the Preparation of Compound 43a:

To a solution of compound 41e (200 mg, 0.428 mmol) and K₂CO₃ (118 mg, 0.856 mmol) in DMSO (3 mL) was added (R)—N,N-dimethyl-1-(pyrrolidin-2-yl)methanamine (103 mg, 0.514 mmol). The reaction mixture was heated at 85° C. for 2.5 h while color changed from brown to orange. The reaction mixture was added drop wise into H₂O (40 mL) under ice water bath with stirring while solid was precipitated out, then filtered. The filter cake was washed with H₂O (15 mL×3), then dried in high vacuum to give compound 43a (200 mg, 73.7% yield) as an orange solid.

LCMS: R$_t$=0.745 min in 5-95AB_220&254.lcm chromatography (MERCK RP18 2.5-2 mm), MS (ESI) m/z=575.2 [M+H]⁺.

Procedure for the Preparation of Compound 43b:

To a solution of compound 43a (200 mg, 0.348 mmol) in MeOH/H₂O=5/1 (5 mL) was added Zn (136 mg, 2.087 mmol) and NH₄Cl (112 mg, 2.087 mmol). The resulting mixture was heated at 90° C. for 1.5 h while color changed from orange to brown. The reaction mixture was filtered, the filtrate was concentrated in vacuum to give the residue, which was dissolved with CH₂Cl₂ (20 mL) and washed with water (15 mL×3), then dried over Na₂SO₄ and concentrated in vacuum to give compound 43b (175 mg, 92.3% yield) as a brown solid.

LCMS: R$_t$=0.725 min in 5-95AB_220&254.lcm chromatography (Xtimate C18 2.1*30 mm), MS (ESI) m/z=545.0 [M+H]⁺.

Procedure for the Preparation of Example 43:

To a solution of compound 43b (175 mg, 0.321 mmol) and DIEA (62 mg, 0.482 mmol) in DMF (2 mL) was added acryloyl chloride (29 mg, 0.321 mmol) in ice water bath. The resulting mixture was stirred at 5-10° C. for 15 min. The reaction was quenched by H₂O (0.1 mL) and then filtered, the filtrate was purified by pre-HPLC (Column: Waters Xbridge 150*25 5 um; Condition: 42-72% B (A: 0.05% ammonia, B: CH₃CN); Flow Rate: 25 ml/min) and then lyophilized to give Example 43 (46.0 mg, 21.44% yield) as a white solid.

LCMS: R$_t$=2.066 min in 10-80AB_4min_220&254. lcm chromatography (Xtimate C18 2.1*30 mm), MS (ESI) m/z=599.2 [M+H]⁺.

HPLC: R$_t$=4.12 min in 10-80CD_1.2 ml chromatography (XBridge Shield RP 18 2.1*50 mm 5 um).

¹H NMR: (400 MHz, CDCl₃) δ 10.82 (br s, 1H), 10.07 (br s, 1H), 9.88 (br s, 1H), 8.41 (s, 1H), 8.39 (d, J=12.0 Hz, 1H), 7.70 (br s, 1H), 7.32-7.25 (m, 1H), 6.71 (s, 1H), 6.44-6.28 (m, 2H), 6.03 (br s, 1H), 5.84-5.71 (m, 1H), 3.86 (s, 3H), 3.39-3.25 (m, 2H), 3.03-2.92 (m, 1H), 2.37 (dd, J=7.8, 12.0 Hz, 1H), 2.33-2.21 (m, 1H), 2.19 (s, 6H), 2.06 (dd, J=5.4, 12.0 Hz, 1H), 2.02-1.92 (m, 2H), 1.78 (s, 6H), 1.70-1.65 (m, 1H).

Example 44

(S)—N-(5-(4-(5-chloro-4-fluoro-2-(2-hydroxypropan-2-yl)phenylamino)-1,3,5-triazin-2-ylamino)-4-methoxy-2-(methyl((1-methylpyrrolidin-2-yl)methyl)amino)phenyl) acrylamide

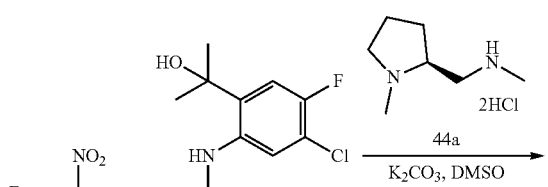

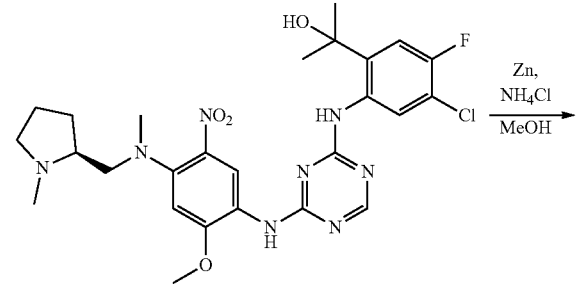

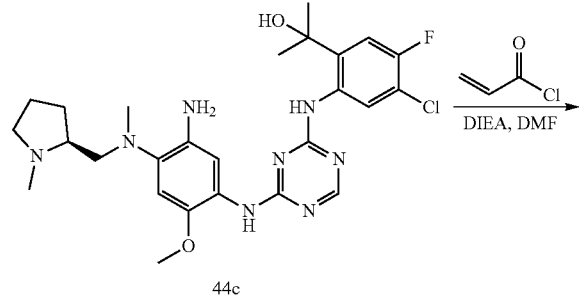

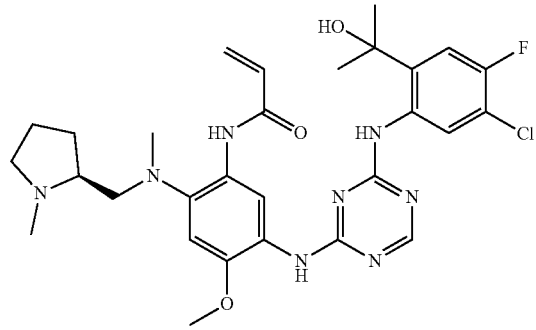

Example 44

Procedure for the Preparation of Compound 44b:

To a solution of compound 36b (180 mg, 0.39 mmol), $K_2CO_3$ (216 mg, 1.56 mmol) in DMSO (10 mL) was added compound 44a (117 mg, 0.58 mmol). The resulting mixture was stirred at 50° C. for 12 h. The reaction mixture was combined with previous batch and added drop wise into $H_2O$ (100 mL) under ice water bath with stirring, the precipitated solid was filtered and the filter cake was dissolved with $CH_2Cl_2$ (15 mL×3), then dried and concentrated in vacuum to give target compound 44b (220 mg, average 89.0% yield) as an orange solid.

LCMS: $R_t$=0.738 min in 5-95AB_1.5min_220&254 chromatography (MERCK RP18e 25-2 mm), MS (ESI) m/z=575.1 [M+Na]$^+$.

$^1$H NMR (400 MHz, CDCl$_3$) δ 9.64 (s, 1H), 9.04 (s, 1H), 8.40 (br s, 1H), 8.38-8.30 (m, 1H), 7.42 (br s, 1H), 7.08 (d, J=10.4 Hz, 1H), 6.68 (s, 1H), 3.95 (s, 3H), 3.50 (dd, J=4.8, 13.6 Hz, 1H), 3.17-3.05 (m, 2H), 2.86 (s, 3H), 2.63 (s, 2H), 2.59-2.52 (m, 1H), 2.42 (s, 3H), 2.30-2.21 (m, 1H), 2.07-1.96 (m, 1H), 1.80-1.74 (m, 1H), 1.70 (s, 6H).

Procedure for the Preparation of Compound 44c:

To a solution of compound 44b (220 mg, 0.38 mmol), Zn (125 mg, 1.9 mmol) in 6 mL methanol/water=5:1 (v/v) was added $NH_4Cl$ (102 mg, 1.9 mmol). The resulting mixture was stirred at 75° C. for 2 h. The reaction mixture was filtered and concentrated under vacuum to give the residue, which was treated with water (10 mL) and extracted with $CH_2Cl_2$ (15 mL). The combined organic layers was dried over $Na_2SO_4$, filtered and concentrated in vacuum to afford compound 44c (90 mg, 43.4% yield) as a brown solid.

LCMS: $R_t$=0.701 min in 5-95AB_1.5min_220&254 chromatography (MERCK RP18e 25-2 mm), MS (ESI) m/z=545.1[M+H]$^+$.

Procedure for the Preparation of Example 44:

To a solution of compound 44c (90 mg, 0.17 mmol) and DIEA (33 mg, 0.26 mmol) in DMF (2.5 mL) was added acryloyl chloride (31 mg, 0.34 mmol) in DMF (0.5 mL) drop wise. The resulting mixture was stirred at 0° C. (ice-water bath) for 20 min. The reaction mixture was quenched by three drops of water and then purified directly by prep-HPLC (column: Waters Xbridge 150*25 5 um: 53-83% B (A: water (0.05% ammonia hydroxide v/v), B: $CH_3CN$), flow rate: 25 mL/min) to give Example 44 (11.1 mg, 10.9% yield) as a white solid.

LCMS: $R_t$=1.994 min in 10-80AB_4min_220&254 chromatography (Xtimate C18 2.1*30 mm) MS (ESI) m/z=599.1 [M+H]$^+$.

HPLC: $R_t$=4.42 min in 10-80_CD_1.2ML chromatography (XBridge Shield RP 18 2.1*50 mm 5 um).

$^1$H NMR (400 MHz, CDCl$_3$) δ 10.53 (br s, 1H), 10.10 (br s, 1H), 10.03 (br s, 1H), 8.47 (d, J=7.2 Hz, 1H), 8.41 (s, 1H), 7.64 (br s, 1H), 7.10 (d, J=10.8 Hz, 1H), 6.71 (s, 1H), 6.43-6.32 (m, 2H), 6.12 (br s, 1H), 5.81-5.74 (m, 1H), 3.88 (s, 3H), 3.14-3.08 (m, 1H), 2.88-2.78 (m, 1H), 2.74 (s, 3H), 2.71-2.63 (m, 2H), 2.56 (s, 3H), 2.41-2.32 (m, 1H), 2.06-1.90 (m, 1H), 1.81-1.72 (m, 7H), 1.45-1.23 (m, 2H).

Example 45

N-(5-(4-(4-cyclopropyl-5-fluoro-2-(2-hydroxypropan-2-yl)phenylamino)-1,3,5-triazin-2-ylamino)-4-methoxy-2-((3aR,6aR)-5-methylhexahydropyrrolo[3,4-b]pyrrol-1(2H)-yl)phenyl)acrylamide

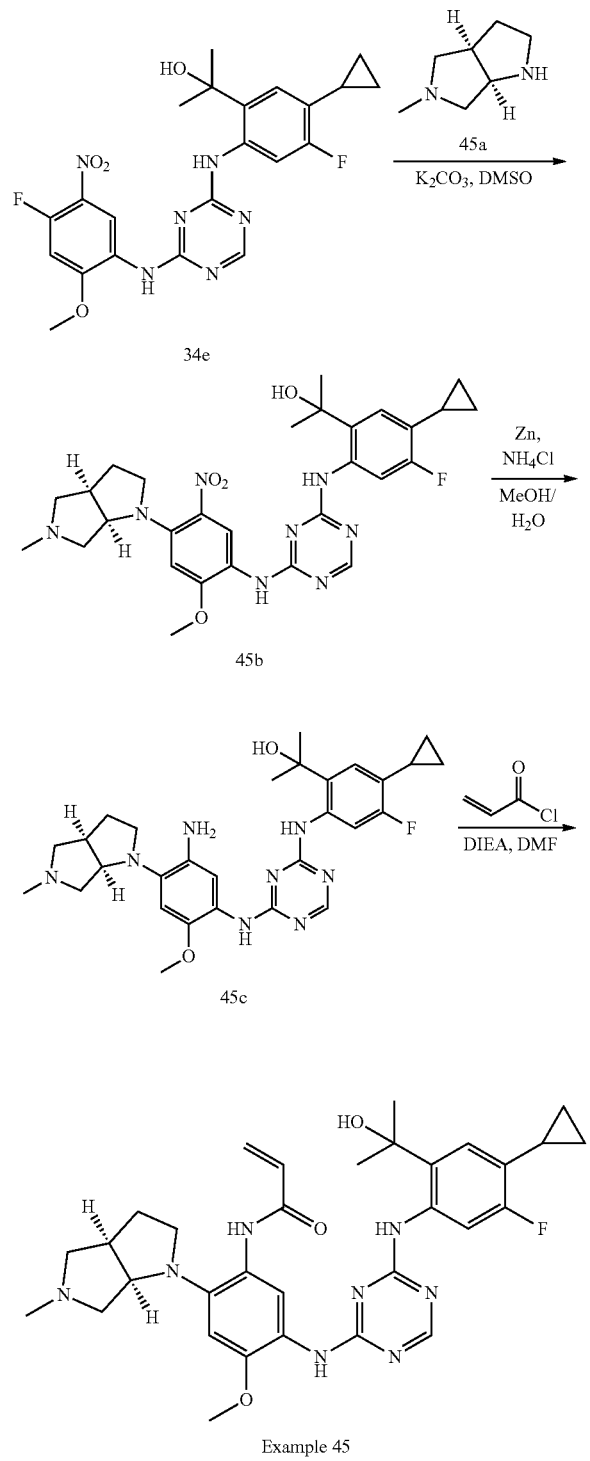

Example 45

Procedure for the Preparation of Compound 45b:

To a solution of compound 34e (150 mg, 0.32 mmol) and K$_2$CO$_3$ (88 mg, 0.64 mmol) in DMSO (5 mL) was added compound 45a (48 mg, 0.38 mmol). The resulting mixture was stirred at 85° C. for 4 h while the colour changes from pale yellow to deep yellow. The reaction mixture was pour to ice water (50 mL) and yellow solid was precipitated. The solid was filtered and filter cake was dissolved with CH$_2$Cl$_2$ (20 mL), then dried over anhydrous Na$_2$SO$_4$ and concentrated under reduced pressure to give compound 45b (150 mg, 82% yield) as yellow solid.

LCMS: R$_t$=0.834 min in 5-95AB_220&254.lcm chromatography (MERCK RP-18e 25-2 mm), MS (ESI) m/z=579.3 [M+H]$^+$.

Procedure for the Preparation of Compound 45c:

To a solution of compound 45b (150 mg, 0.26 mmol) in MeOH (10 mL) and H$_2$O (5 mL) was added Zn (85 mg, 1.30 mmol) and NH$_4$Cl (139 mg, 2.60 mmol). The resulting mixture was purged and degassed with N$_2$ for 3 times, then stirred at 80° C. for 2 h. The reaction mixture was filtered and concentrated under reduced pressure, then extracted with EtOAc (10 mL×2), the combined organic layers was washed with H$_2$O (10 mL), dried over anhydrous Na$_2$SO$_4$ and concentrated under reduced pressure to give compound 45c (130 mg, 91% yield) as brown solid.

LCMS: R$_t$=0.715 min in 5-95AB_1.5min_220&254 chromatography (MERCK RP18e 25-2 mm), MS (ESI) m/z=549.1 [M+H]$^+$.

Procedure for the Preparation of Example 45:

To a solution of compound 45c (130 mg, 0.24 mmol) and DIEA (62 mg, 0.48 mmol) in DMF (2.5 mL) was added acryloyl chloride (22 mg, 0.24 mmol) in DMF (0.5 mL) drop wise. The resulting mixture was stirred at 0° C. under ice-water bath for 30 min. The reaction mixture was purified by prep-HPLC [Column: Waters Xbridge 150*25 5 um; Condition: 35-65% B (A: 0.05% NH$_3$H$_2$O; B: CH$_3$CN); Flow rate: 25 ml/min]. Fractions containing the desired compound were lyophilized to afford Example 45 (28.1 mg, 19% yield) as white solid.

LCMS: R$_t$=1.778 min in 10-80AB_4min_220&254 chromatography (Xtimate C18 2.1*30 mm), MS (ESI) m/z=603.3 [M+H]$^+$.

HPLC: R$_t$=2.79 min in 10-80_ab_1.2ML chromatography (Ultimate C18 3*50 mm 3 um).

$^1$H NMR: (400 MHz, CDCl$_3$) δ 10.72 (br s, 1H), 9.93 (br s, 1H), 9.56 (br s, 1H), 8.41 (s, 1H), 8.12 (d, J=12.4 Hz, 1H), 7.64 (br s, 1H), 6.86 (d, J=8.4 Hz, 1H), 6.78 (s, 1H), 6.55-6.45 (m, 1H), 6.44-6.35 (m, 1H), 5.76 (br d, J=11.2 Hz, 1H), 3.87 (s, 3H), 3.67 (br s, 1H), 3.22 (br t, J=7.6 Hz, 1H), 2.96-2.79 (m, 3H), 2.73 (br d, J=10.0 Hz, 1H), 2.30 (br s, 4H), 2.25-2.17 (m, 1H), 2.08-1.94 (m, 2H), 1.89 (br s, 1H), 1.76 (s, 6H), 1.05-0.88 (m, 2H), 0.75-0.55 (m, 2H).

Example 46

(R)—N-(5-(4-(4-cyclopropyl-5-fluoro-2-(2-hydroxypropan-2-yl)phenylamino)-1,3,5-triazin-2-ylamino)-2-(2-((dimethylamino)methyl)pyrrolidin-1-yl)-4-methoxyphenyl)acrylamide

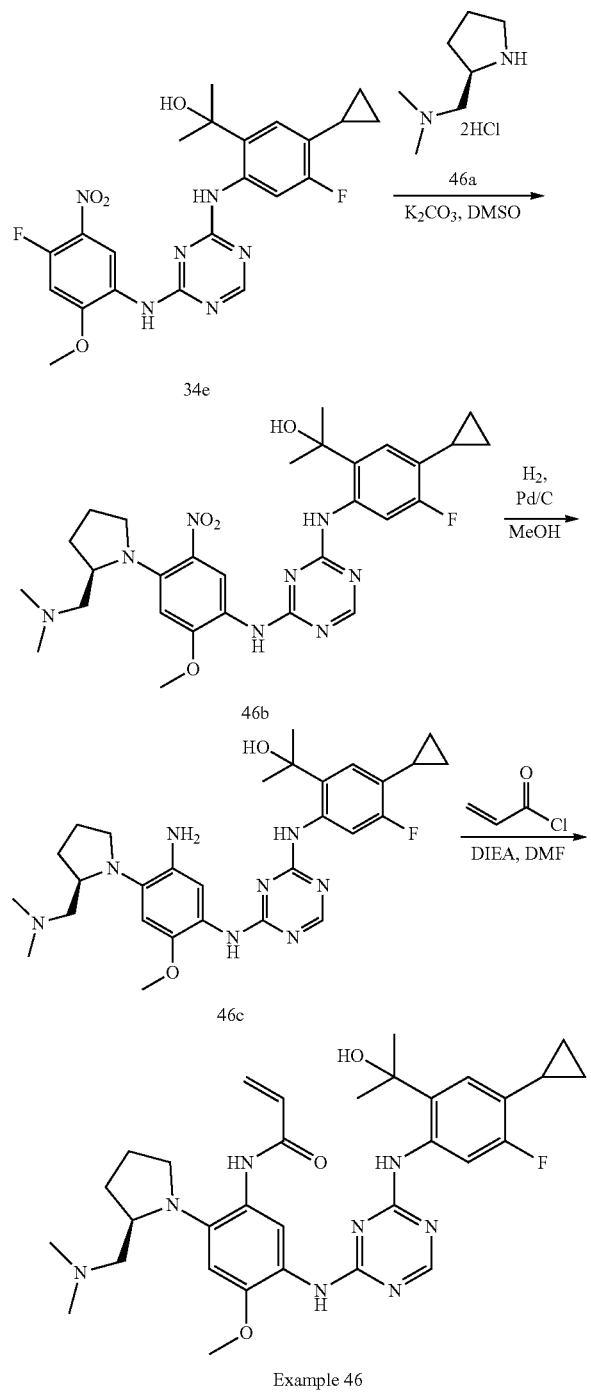

Example 46

Procedure for the Preparation of Compound 46b:

To a solution of compound 34e (150 mg, 0.32 mmol) and K$_2$CO$_3$ (88 mg, 0.64 mmol) in DMSO (5 mL) was added compound 46a (96 mg, 0.48 mmol). The resulting mixture was stirred at 85° C. for 4 h while the colour changes from pale yellow to deep yellow. The reaction mixture was pour to ice water (50 mL) and yellow solid was precipitated. The yellow solid was filtered and the filter cake was diluted with CH$_2$Cl$_2$ (20 mL), dried over anhydrous Na$_2$SO$_4$ and concentrated under reduced pressure to give compound 46b (140 mg, 75% yield) as yellow solid.

LCMS: R$_t$=0.766 min in 5-95AB_220&254.lcm chromatography (MERCK RP-18e 25-2 mm), MS (ESI) m/z=581.1 [M+H]$^+$.

Procedure for the Preparation of Compound 46c:

To a solution of compound 46b (140 mg, 0.24 mmol) in MeOH (5 mL) was added Pd/C (15 mg). The resulting mixture was purged and degassed with H$_2$ for 3 times, then stirred at 21-24° C. under H$_2$ balloon (15 Psi) for 2 h. The reaction mixture was filtered and concentrated under reduced pressure to give compound 46c (130 mg, 98% yield) as brown oil.

LCMS: R$_t$=0.738 min in 5-95AB_1.5min_220&254 chromatography (MERCK RP18e 25-2 mm), MS (ESI) m/z=551.1 [M+H]$^+$.

Procedure for the Preparation of Example 46:

To a solution of compound 46c (130 mg, 0.24 mmol) and DIEA (62 mg, 0.48 mmol) in DMF (2.5 mL) was added acryloyl chloride (22 mg, 0.24 mmol) in DMF (0.5 mL) drop wise. The resulting mixture was stirred at 0° C. under ice-water bath for 30 min. The reaction mixture was purified by prep-HPLC [Column: Waters Xbridge 150*25 5 um; Condition: 42-72% B (A: 0.05% NH$_3$H$_2$O; B: CH$_3$CN); Flow rate: 25 ml/min]. Fractions containing the desired compound were lyophilized to afford Example 46 (32.5 mg, 22% yield) as white solid.

LCMS: R$_t$=1.883 min in 10-80AB_4min_220&254 chromatography (Xtimate C18 2.1*30 mm), MS (ESI) m/z=605.3 [M+H]$^+$.

HPLC: R$_t$=3.00 min in 10-80_ab_1.2ML chromatography (Ultimate C18 3*50 mm 3 um).

$^1$H NMR: (400 MHz, CDCl$_3$) δ 10.71 (br s, 1H), 10.00 (br s, 1H), 9.91 (br s, 1H), 8.41 (s, 1H), 8.11 (d, J=12.4 Hz, 1H), 7.65 (br s, 1H), 6.86 (d, J=8.4 Hz, 1H), 6.70 (s, 1H), 6.44-6.30 (m, 2H), 5.77 (br d, J=11.2 Hz, 1H), 3.86 (s, 3H), 3.39-3.24 (m, 2H), 3.03-2.90 (m, 1H), 2.41-2.31 (m, 1H), 2.25-2.15 (m, 7H), 2.10-1.96 (m, 4H), 1.76 (s, 6H), 1.69 (br d, J=4.4 Hz, 1H), 0.98-0.88 (m, 2H), 0.73-0.66 (m, 2H).

Example 47

N-(5-(4-(4,5-difluoro-2-(2-hydroxybutan-2-yl)phenylamino)-1,3,5-triazin-2-ylamino)-4-methoxy-2-((3aR,6aR)-5-methylhexahydropyrrolo[3,4-b]pyrrol-1(2H)-yl)phenyl) acrylamide

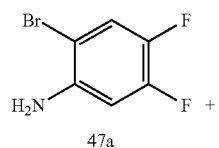

47a

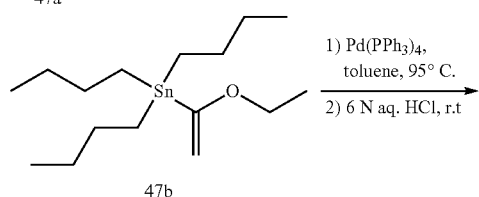

1) Pd(PPh$_3$)$_4$, toluene, 95° C.
2) 6 N aq. HCl, r.t

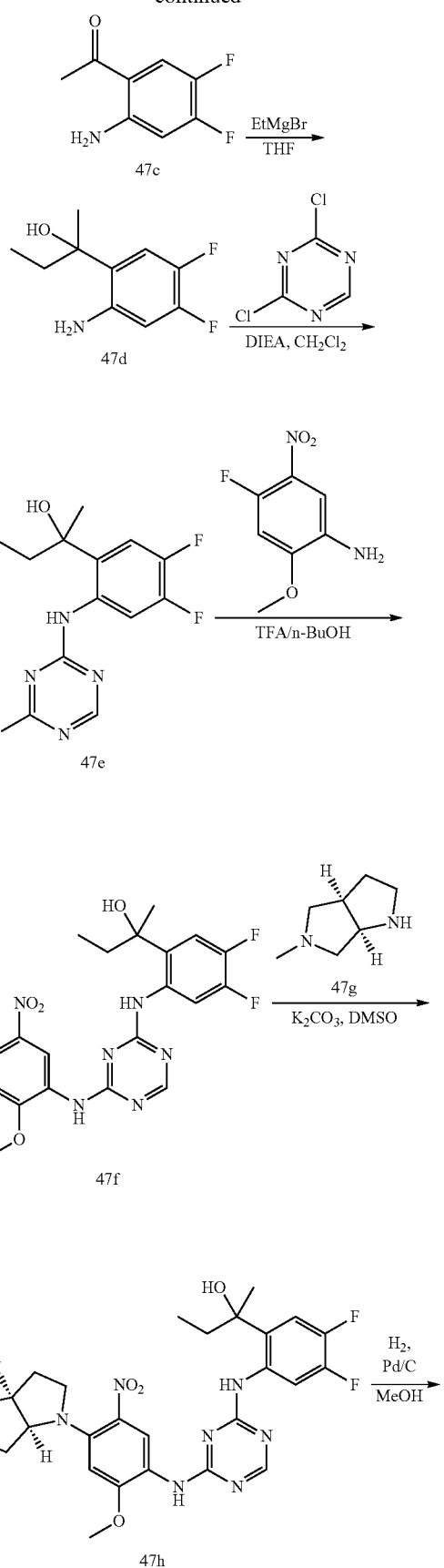

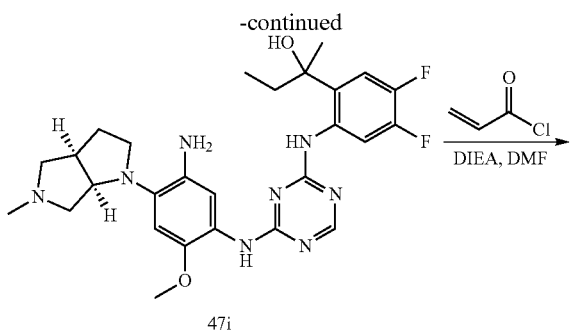

47i

Example 47

Procedure for the Preparation of Compound 47c:

To a mixture of compound 47a (10 g, 48.08 mmol) and compound 47b (20.84 g, 57.69 mmol) in toluene (200 mL) was added Pd(PPh$_3$)$_4$ (2.78 g, 2.4 mmol) in one portion under N$_2$. The resulting black mixture was stirred at 100° C. for 12 h under N$_2$. The reaction was cooled to 25° C. and then treated with 6N HCl (10 mL) with stirring at 25° C. for 1 h. It was diluted with water (400 mL) and extracted with EtOAc (120 mL×3). The combined organic layers was washed with 20% KF solution (200 mL) and brine (100 mL) successively, dried over sodium sulfate and concentrated in vacuum to give the crude product, which was purified by column chromatography on silica gel (5% EtOAc in petroleum ether) to give compound 47c (4.2 g, 51% yield) as a yellow solid.

LCMS: R$_f$=0.709 min in 5-95AB_220&254.lcm chromatography (MERCK RP18 2.5-2 mm), MS (ESI) m/z=171.9 [M+H]$^+$.

$^1$H NMR: (400 MHz, CDCl$_3$) δ 7.50 (dd, J=8.8 Hz, 11.2 Hz, 1H), 6.41 (dd, J=6.8 Hz, 12.0 Hz, 1H), 6.37-6.17 (m, 2H), 2.52 (s, 3H).

Procedure for the Preparation of Compound 47d:

To a solution of compound 47c (2 g, 11.68 mmol) in THF (100 mL) was added EtMgBr (3.0 M) (16 mL, 46.72 mmol) at 0° C. under N$_2$. The reaction mixture was stirred at 23-27° C. for 2 h. The reaction mixture was quenched with saturated NH$_4$Cl solution (50 mL), and extracted with EtOAc (30 mL×3). The combined organic layers was dried over Na$_2$SO$_4$, filtered, and the filtrate was concentrated under reduced pressure to give crude product, which was purified by column chromatography on silica gel (0-30% EtOAc in petroleum ether (v/v)) to give compound 47d (1.7 g, 72% yield) as yellow oil.

LCMS: R$_f$=0.559 min in 5-95AB_220&254.lcm chromatography MERCK RP18 2.5-2 mm, MS (ESI) m/z=184.0 [M+H-18]$^+$.

$^1$H NMR: (400 MHz, MeOD-d$_4$) δ 6.91 (dd, J=8.8 Hz, 12.8 Hz, 1H), 6.51 (dd, J=7.6 Hz, 12.8 Hz, 1H), 2.07-2.01 (m, 1H), 1.86-1.76 (m, 1H), 1.53 (s, 3H), 0.80 (t, J=7.6 Hz, 3H).

Procedure for the Preparation of Compound 47e:

To a solution of compound 47d (1.68 g, 8.4 mmol) in CH$_2$Cl$_2$ (15 mL) was added DIEA (1.6 g, 12.6 mmol) and 2,4-dichloropyrimidine (1.5 g, 10.0 mmol). The resulting mixture was stirred at 22-30° C. for 0.5 h. The reaction mixture were concentrated under reduced pressure and purified by column chromatography on silica gel (0-20% EtOAc in petroleum ether) to give compound 47e (1.58 g, 60% yield) as a yellow solid.

LCMS: R$_f$=0.825 min in 5-95AB_220&254.lcm chromatography (MERCK RP18 2.5-2 mm), MS (ESI) m/z=314.9 [M+H]$^+$.

Procedure for the Preparation of Compound 47f:

To a solution of compound 47e (1.58 g, 5.0 mmol) and 4-fluoro-2-methoxy-5-nitroaniline (935 mg, 5.0 mmol) in n-BuOH (10 mL) was added TFA (0.1 mL). The resulting mixture was stirred at 18-25° C. for 2 h while grey solid was precipitated out. The reaction mixture was filtered and the filter cake was collected and dried under reduced pressure to give compound 47f (1.5 g, 97% yield) as a pale solid.

LCMS: R$_f$=0.911 min in 5-95AB_220&254.lcm chromatography (Xtimate C18 2.1*30 mm), MS (ESI) m/z=464.9 [M+H]$^+$.

$^1$H NMR: (400 MHz, DMSO-d$_6$) δ 10.55 (br s, 1H), 9.46 (br s, 1H), 8.46 (br s, 1H), 8.37 (s, 1H), 7.39 (d, J=13.6 Hz, 1H), 7.33-7.29 (m, 1H), 7.18 (s, 1H), 7.05 (s, 1H), 3.94 (s, 3H), 1.82-1.70 (m, 2H), 1.51 (s, 3H), 0.71 (br t, J=7.6 Hz, 3H).

Procedure for the Preparation of Compound 47h:

To a solution of compound 47f (150 mg, 0.32 mmol) and K$_2$CO$_3$ (88 mg, 0.64 mmol) in DMSO (3 mL) was added compound 47g (48 mg, 0.38 mmol). The resulting mixture was stirred at 85° C. for 2 h while the colour changes from pale yellow to deep yellow. The reaction mixture was pour into ice water (50 mL) and the yellow precipitated solid was filtered, the filter cake was dissolved with CH$_2$Cl$_2$ (20 mL), then dried over anhydrous Na$_2$SO$_4$ and concentrated under reduced pressure to give compound 47h (160 mg, 88% yield) as yellow solid.

LCMS: R$_f$=0.766 min in 5-95AB_220&254.lcm chromatography (MERCK RP-18e 25-2 mm), MS (ESI) m/z=571.0 [M+H]$^+$.

Procedure for the Preparation of Compound 47i:

To a solution of compound 47h (160 mg, 0.28 mmol) in MeOH (5 mL) was added Pd/C (16 mg). The resulting mixture was purged and degassed with H$_2$ for 3 times, then stirred at 22-30° C. under H$_2$ (hydrogen balloon, 15 Psi) for 1 h. The reaction mixture was filtered and concentrated under reduced pressure to give the title compound 47i (140 mg, 92% yield) as colorless solid.

LCMS: R$_f$=0.732 min in 5-95AB_1.5min_220&254 chromatography (MERCK RP18e 25-2 mm), MS (ESI) m/z=541.0 [M+H]$^+$.

Procedure for the Preparation of Example 47:

To a solution of compound 47i (140 mg, 0.26 mmol) and DIEA (67 mg, 0.52 mmol) in DMF (2.5 mL) was added acryloyl chloride (24 mg, 0.26 mmol) in DMF (0.5 mL) drop wise. The resulting mixture was stirred at 0° C. under ice-water bath for 30 min. The reaction mixture was purified by prep-HPLC [Column: Waters Xbridge 150*25 5 um; Condition: 45-75% B (A: 0.05% NH$_3$H$_2$O; B: CH$_3$CN); Flow rate: 25 ml/min]. Fractions containing the desired compound were lyophilized to afford Example 47 (50.6 mg, 33% yield) as white solid.

LCMS: R$_f$=1.855 min in 10-80AB_4min_220&254 chromatography (Xtimate C18 2.1*30 mm), MS (ESI) m/z=595.1 [M+H]$^+$.

HPLC: R*f*=2.69 min in 10-80_ab_1.2ML chromatography (Ultimate C18 3*50 mm 3 um).

¹H NMR: (400 MHz, CDCl₃) δ 10.91 (br s, 1H), 9.94 (br s, 1H), 9.57 (br s, 1H), 8.45-8.35 (m, 2H), 7.69 (br s, 1H), 7.03 (dd, J=8.8, 12.4 Hz, 1H), 6.79 (s, 1H), 6.49-6.33 (m, 2H), 5.78-5.73 (m, 1H), 3.96-3.81 (m, 3H), 3.62 (br dd, J=4.4, 7.6 Hz, 1H), 3.19 (br t, J=7.6 Hz, 1H), 2.98-2.76 (m, 3H), 2.70 (br d, J=10.4 Hz, 1H), 2.36-2.26 (m, 4H), 2.26-2.10 (m, 2H), 2.09-2.00 (m, 1H), 1.89 (br dd, J=4.0, 10.2 Hz, 1H), 1.86-1.78 (m, 1H), 1.70 (s, 3H), 0.89 (td, J=7.2, 11.2 Hz, 3H).

Example 48

N-(5-(4-(4,5-difluoro-2-(2-hydroxybutan-2-yl)phenylamino)-1,3,5-triazin-2-ylamino)-2-((R)-3-(dimethylamino)pyrrolidin-1-yl)-4-methoxyphenyl)acrylamide

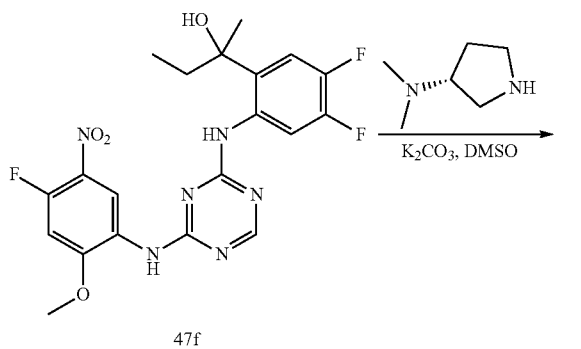

47f

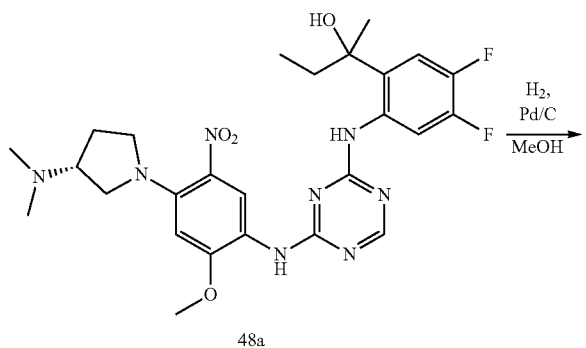

48a

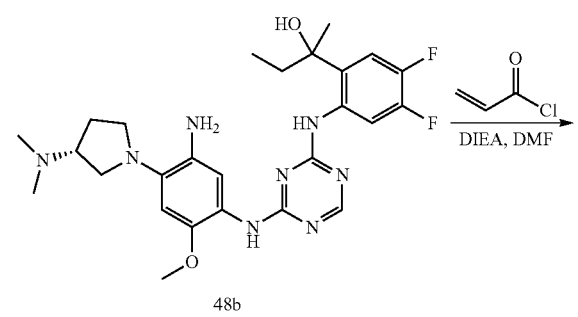

48b

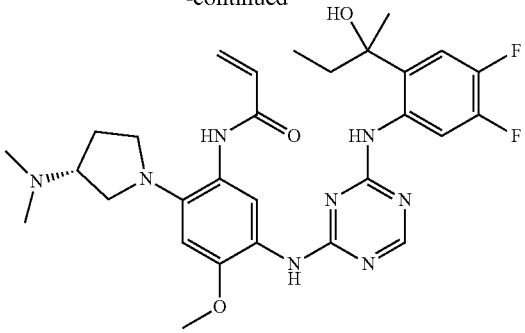

Example 48

Procedure for the Preparation of Compound 48a:

To a solution of compound 48a (200 mg, 0.43 mmol) and K₂CO₃ (119 mg, 0.86 mmol) in DMSO (5 mL) was added compound (R)—N,N-dimethylpyrrolidin-3-amine (60 mg, 0.52 mmol). The resulting mixture was stirred at 23-29° C. for 0.5 h. The reaction mixture was added drop wise into H₂O (100 mL) under ice water bath with stirring, the precipitated solid was filtered and the filter cake was dissolved with CH₂Cl₂ (45 mL), then dried and concentrated in vacuum to give compound 48b (230 mg, 96% yield) as an orange solid.

LCMS: R*f*=0.722 min in 5-95AB_220&254.lcm chromatography (MERCK RP18 2.5-2 mm), MS (ESI) m/z=559.2 [M+H]⁺.

Procedure for the Preparation of Compound 48b:

To a solution of 48a (230 mg, 0.41 mmol) in MeOH (10 mL) was added Pd/C (35 mg). The resulting mixture was purged and degassed with H₂ for 3 times, then stirred at 23-30° C. under H₂ balloon (15 Psi) for 0.5 h. The reaction mixture was filtered and the filtrate was concentrated under reduced pressure to give compound 48b (205 mg, 94% yield) as a brown solid.

LCMS: R*f*=0.680 min in 5-95AB_220&254.lcm chromatography (MERCK RP18 2.5-2 mm), MS (ESI) m/z=529.2 [M+H]⁺.

Procedure for the Preparation of Example 48:

To a solution of compound 48b (205 mg, 0.4 mmol) and DIEA (78 mg, 0.4 mmol) in DMF (2.5 mL) was added acryloyl chloride (37 mg, 0.4 mmol) in DMF (0.5 mL) drop wise. The resulting mixture was stirred at 0° C. under ice-water bath for 20 min. The reaction mixture was quenched by three drops of water and then purified by prep-HPLC directly (column: Waters Xbridge 150*25 5 um: 40-70% B (A: water (0.05% ammonia hydroxide v/v), B: CH₃CN), flow rate: 25 mL/min) to give Example 48 (65.1 mg, 28% yield) as a white solid.

LCMS: R*f*=1.795 min in 10-80CD_4min_220&254 chromatography (Xtimate C18 2.1*30 mm, MS (ESI) m/z=583.1 [M+H]⁺.

HPLC: R*f*=3.45 min in 10-80_CD_1.2ML chromatography (XBridge Shield RP 18 2.1*50 mm 5 um).

¹H NMR: (400 MHz, CDCl₃) δ 10.84 (br s, 1H), 9.78 (br s, 1H), 8.43-8.35 (m, 2H), 7.64 (br s, 1H), 7.02 (dd, J=8.4 Hz, 12.0 Hz, 1H), 6.76 (s, 1H), 6.37-6.32 (m, 2H), 5.82-5.77 (m, 1H), 3.87 (s, 3H), 3.16-3.04 (m, 4H), 2.94-2.85 (m, 1H), 2.30 (s, 6H), 2.24-2.08 (m, 2H), 2.05-1.90 (m, 2H), 1.69 (s, 3H), 0.92-0.86 (m, 3H).

Example 49

N-(5-(4-(4,5-difluoro-2-(2-hydroxybutan-2-yl)phenylamino)-1,3,5-triazin-2-ylamino)-2-((2-(dimethylamino)ethyl)(methyl)amino)-4-methoxyphenyl)acrylamide

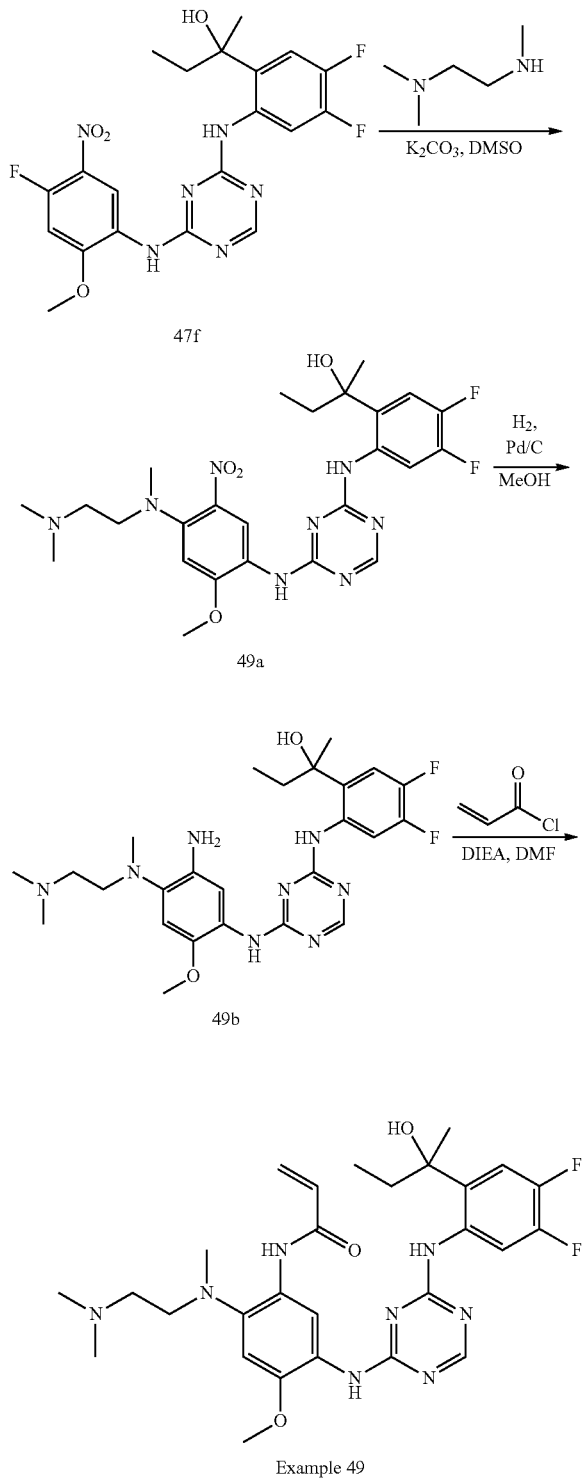

Procedure for the Preparation of Compound 49a:

To a solution of compound 47f (200 mg, 0.43 mmol) and K₂CO₃ (119 mg, 0.86 mmol) in DMSO (5 mL) was added compound $N^1,N^1$,N-trimethylethane-1,2-diamine (53 mg, 0.52 mmol). The resulting mixture was stirred at 18-25° C. for 0.5 h. The reaction mixture was added drop wise into H₂O (50 mL) in ice water bath with stirring, the precipitated solid was filtered and the filter cake was dissolved with CH₂Cl₂ (50 mL), dried and concentrated under reduced pressure to give compound 49a (230 mg, 97% yield) as an orange solid.

LCMS: $R_t$=0.778 min in 5-95AB_220&254.lcm chromatography (Xtimate C18 2.1*30 mm), MS (ESI) m/z=547.0 [M+H]⁺.

Procedure for the Preparation of Compound 49b:

To a solution of compound 49a (230 mg, 0.42 mmol) in MeOH (10 mL) was added Pd/C (35 mg). The resulting mixture was purged and degassed with H₂ for 3 times, then stirred at 18-20° C. under H₂ balloon (15 Psi) for 0.5 h. The reaction mixture was filtered and the filtrate was concentrated under reduced pressure to give compound 49b (150 mg, 69% yield) as a burgundy solid.

LCMS: $R_t$=0.691 min in 5-95AB_220&254.lcm chromatography (MERCK RP18 2.5-2 mm), MS (ESI) m/z=517.2 [M+H]⁺.

¹H NMR: (400 MHz, MeOH-d₄) δ 8.20 (br s, 2H), 7.16 (dd, J=8.8 Hz, 12.0 Hz, 1H), 6.83 (s, 1H), 3.80 (s, 3H), 3.07-3.01 (m, 2H), 2.65 (s, 3H), 2.48 (t, J=7.2 Hz, 2H), 2.27 (s, 6H), 1.90-1.83 (m, 2H), 1.58 (s, 3H), 0.81 (t, J=7.2 Hz, 3H).

Procedure for the Preparation of Example 49:

To a solution of compound 49b (150 mg, 0.29 mmol) and DIEA (56 mg, 0.44 mmol) in DMF (2.5 mL) was added acryloyl chloride (26 mg, 029 mmol) in DMF (0.5 mL) drop wise. The resulting mixture was stirred at 0° C. under ice-water bath for 20 min. The reaction mixture was quenched by three drops of water and purified by prep-HPLC directly (column: Xbridge BEH C18, 250*50 mm, 10 um, Condition: 44-84% B (A: water (0.04% NH₃H₂O+10 mM NH₄HCO₃)), B: CH₃CN), flow rate: 25 mL/min) to give Example 49 (31.3 mg, 20% yield) as a pale yellow solid.

LCMS: $R_t$=1.877 min in 10-80AB_4min_220&254 chromatography (Xtimate C18 2.1*30 mm), MS (ESI) m/z=571.1 [M+H]⁺.

HPLC: $R_t$=2.72 min in 10-80_CD_1.2ML chromatography (Ultimate C18 3*50 mm 3 um).

¹H NMR: (400 MHz, CDCl₃) δ 10.91 (br s, 1H), 10.42 (br s, 1H), 9.94 (br s, 1H), 8.40 (s, 1H), 8.39-8.33 (m, 1H), 7.70 (br s, 1H), 7.02 (dd, J=8.4 Hz, 12.0 Hz, 1H), 6.78 (s, 1H), 6.44-6.26 (m, 2H), 5.93 (br s, 1H), 5.78-5.72 (m, 1H), 3.88 (s, 3H), 2.87 (br t, J=4.8 Hz, 2H), 2.70 (s, 3H), 2.35-2.20 (m, 8H), 2.19-2.09 (m, 1H), 2.07-1.99 (m, 1H), 1.70 (s, 3H), 0.88 (t, J=7.6 Hz, 3H).

Example 50

N-(5-(4-(4,5-difluoro-2-(2-hydroxybutan-2-yl)phenylamino)-1,3,5-triazin-2-ylamino)-4-methoxy-2-((3aS,6aS)-5-methylhexahydropyrrolo[3,4-b]pyrrol-1(2H)-yl)phenyl) acrylamide

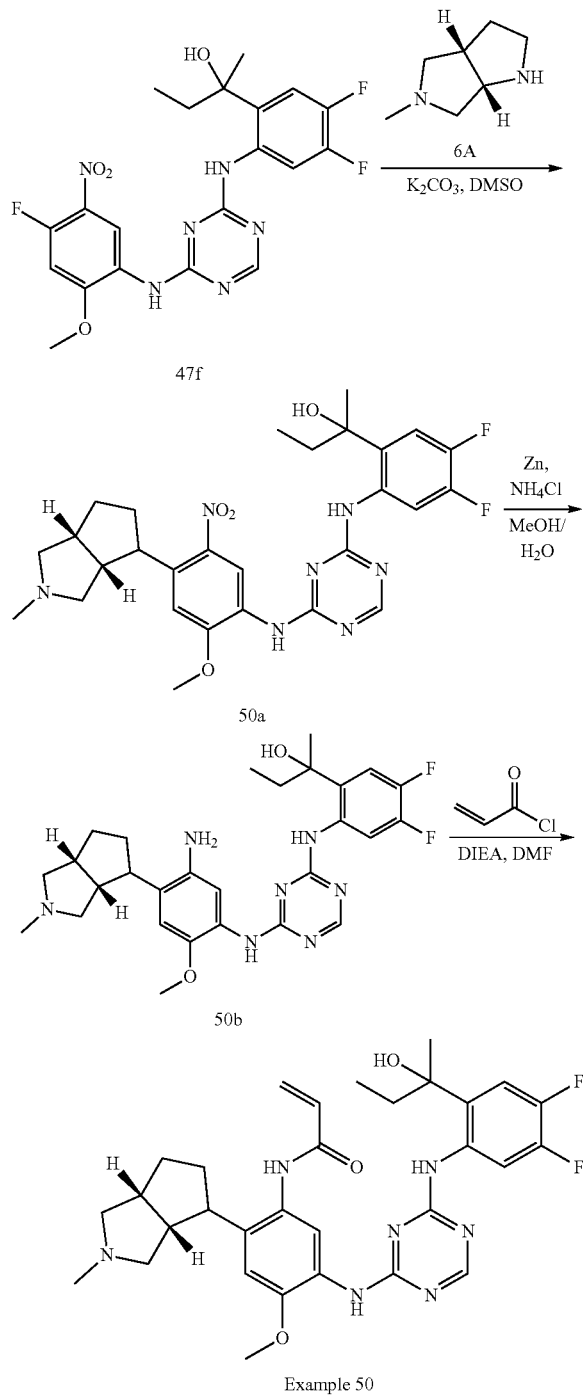

Example 50

Procedure for the Preparation of Compound 50a:

To a mixture of compound 47f (150 mg, 0.32 mmol) in DMSO (3 mL) was added K$_2$CO$_3$ (134 mg, 0.97 mmol) and (3aS,6aS)-5-methyloctahydropyrrolo[3,4-b]pyrrole (60 mg, 0.48 mmol). The resulting mixture was stirred at 50° C. for 12 h, then 80° C. for 2 h. The reaction mixture was poured into water (15 mL) while orange solid was precipitated out. The solid was collected by suction filtration and dried in vacuum to afford compound 50a (190 mg, 91.7% yield).

LCMS: R$_f$=2.019 min in 10-80AB_4min_220&254 chromatography (Xtimate C18 2.1*30 mm), MS (ESI) m/z=571.1 [M+H]$^+$.

$^1$H NMR: (400 MHz, CDCl$_3$) δ 9.83 (br. s, 1H), 8.45-8.05 (m, 2H), 7.29 (br. s, 1H), 7.02-6.88 (m, 1H), 6.33 (s, 1H), 4.39-4.31 (m, 1H), 3.89 (s, 3H), 3.54-3.41 (m, 1H), 3.19-3.10 (m, 1H), 3.02-2.92 (m, 1H), 2.63-2.55 (m, 1H), 2.48-2.42 (m, 1H), 2.40-2.34 (m, 1H), 2.24-2.18 (m, 1H), 2.15 (d, J=2.4 Hz, 3H), 2.07-1.99 (m, 1H), 1.90-1.87 (m, 1H), 1.82-1.76 (m, 2H), 1.59 (s, 3H), 0.81 (t, J=7.2 Hz, 3H).

Procedure for the Preparation of Compound 50b:

To a yellow solution of compound 50a (190 mg, 0.33 mmol) in methanol/water (5 mL/1 mL) was added NH$_4$Cl (125 mg, 2.33 mmol) and Zn (109 mg, 1.66 mmol). The resulting mixture was stirred at 90° C. for 1 h. The reaction mixture was poured into water (15 mL) and extracted with dichloromethane/methanol (3/1, 10 mL×4). The combined organic layers were dried and concentrated in vacuum to afford compound 50b (170 mg, 95.2% yield) as black solid.

LCMS: R$_f$=1.526 min in 10-80AB_4min_220&254 chromatography (Xtimate C18 2.1*30 mm), MS (ESI) m/z=541.2 [M+H]$^+$.

$^1$H NMR: (400 MHz, CDCl$_3$) δ 9.86 (br. s, 1H), 8.29-8.15 (m, 2H), 7.78-7.42 (m, 2H), 7.01-6.88 (m, 1H), 6.62 (s, 1H), 4.06-3.96 (m, 1H), 3.74 (s, 3H), 3.42-3.32 (m, 1H), 2.88-2.79 (m, 1H), 2.77-2.68 (m, 1H), 2.63-2.55 (m, 1H), 2.54-2.48 (m, 1H), 2.47-2.38 (m, 1H), 2.22 (s, 3H), 2.15-2.07 (m, 1H), 2.06-1.97 (m, 1H), 1.85 (q, J=7.2 Hz, 2H), 1.77-1.73 (m, 1H), 1.57 (s, 3H), 0.79 (t, J=7.2 Hz, 3H).

Procedure for the Preparation of Example 50:

To a solution of compound 50b (170 mg, 0.31 mmol) in DMF (3 mL) was added DIEA (81 mg, 0.63 mmol), followed with acryloyl chloride (28 mg, 0.31 mmol) at 0° C. in three times and then stirred for 2 h. The mixture was quenched with 3 drops of water and purified by pre-HPLC (column: Waters Xbridge 150*25 5 um, condition: 45%-75% B (A: water/10 mM NH$_4$HCO$_3$, B: CH$_3$CN), flow rate: 25 mL/min) to afford Example 50 (39.8 mg, 21.6% yield) as white solid.

LCMS: R$_f$=1.697 min in 10-80AB_4min_220&254 chromatography (Xtimate C18 2.1*30 mm), MS (ESI) m/z=595.1 [M+H]$^+$.

HPLC: R$_f$=3.94 min in 10-80_CD_1.2 ml chromatography (XBridge Shield RP 18 2.1*50 mm 5 um).

$^1$H NMR (400 MHz, CDCl$_3$) δ 10.84 (br. s, 1H), 9.87 (s, 1H), 9.49 (s, 1H), 8.37-8.25 (m, 2H), 7.60 (br. s, 1H), 6.95 (dd, J 8.8, 12.4 Hz, 1H), 6.71 (s, 1H), 6.46-6.22 (m, 1H), 5.68 (d, J=11.6 Hz, 1H), 3.79 (s, 3H), 3.60-3.53 (m, 1H), 3.17-3.08 (m, 1H), 2.88-2.78 (m, 2H), 2.77-2.72 (m, 1H), 2.68-2.60 (m, 1H), 2.28-2.24 (m, 1H), 2.22 (s, 3H), 2.18-2.03 (m, 2H), 2.00-1.89 (m, 1H), 1.85-1.72 (m, 2H), 1.65 (s, 3H), 0.86-0.77 (m, 3H).

Example 51

(R)—N-(5-(4-(4-chloro-5-fluoro-2-(2-hydroxypropan-2-yl)phenylamino)-1,3,5-triazin-2-ylamino)-2-(3-(dimethylamino)pyrrolidin-1-yl)-4-methoxyphenyl)acrylamide

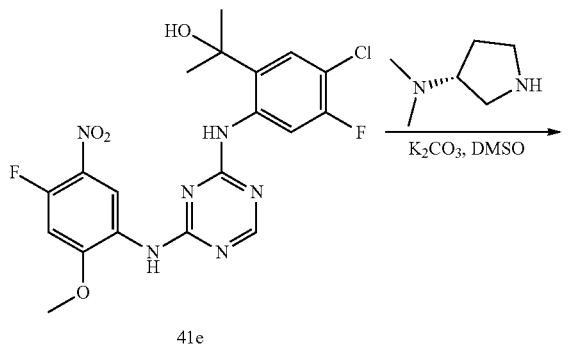

41e

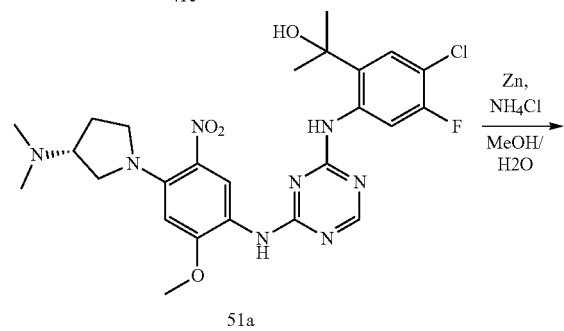

51a

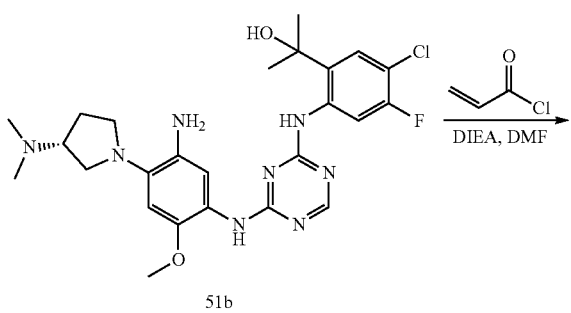

51b

Example 51

Procedure for the Preparation of Compound 51a:

To a mixture of compound 41e (200 mg, 0.43 mmol) in DMSO (5 mL) was added K$_2$CO$_3$ (178 mg, 1.29 mmol) and (R)—N,N-dimethylpyrrolidin-3-amine (59 mg, 0.51 mmol).

The resulting orange mixture was stirred at 23-29° C. for 4 h. The mixture was poured into water (25 mL) and the orange precipitated solid was collected by suction filtration. The solid was dried in vacuum to afford compound 51a (230 mg, 95% yield).

LCMS: R$_t$=0.778 min in 5-95AB_220&254 chromatography (MERCK RP18 2.5-2 mm), MS (ESI) m/z=583.0 [M+Na]$^+$.

$^1$H NMR: (400 MHz, CDCl$_3$) δ 10.06 (br. s, 1H), 8.92 (br. s, 1H), 8.46-8.25 (m, 2H), 7.35 (br. s, 1H), 7.26 (s, 1H), 6.31 (s, 1H), 3.95 (s, 3H), 3.61-3.52 (m, 1H), 3.39-3.32 (m, 1H), 3.25-3.12 (m, 2H), 2.89-2.78 (m, 1H), 2.31 (s, 6H), 2.02-1.81 (m, 2H), 1.71 (d, J=5.2 Hz, 6H).

Procedure for the Preparation of Compound 51b:

To a yellow solution of compound 51a (230 mg, 0.41 mmol) in methanol/water (5 mL/1 mL) was added NH$_4$Cl (154 mg, 2.87 mmol) and Zn (134 mg, 2.05 mmol). The resulting mixture was stirred at 90° C. for 1 h. The mixture was poured into water (20 mL) and extracted with dichloromethane (15 mL×5). The combined organic layers were dried over sodium sulfate, filtered and concentrated in vacuum to afford compound 51b (180 mg, 82.7% yield) as green solid.

LCMS: R$_t$=0.713 min in 10-80AB_4min_220&254 chromatography (Xtimate C18 2.1*30 mm), MS (ESI) m/z=531.0 [M+H]$^+$.

$^1$H NMR: (400 MHz, CDCl$_3$) δ 9.86 (br. s, 1H), 8.30-8.16 (m, 2H), 7.79-7.39 (m, 2H), 7.18 (s, 1H), 6.59 (s, 1H), 3.75 (s, 3H), 3.16-2.98 (m, 4H), 2.95-2.84 (m, 1H), 2.29 (s, 6H), 1.88-1.79 (m, 2H), 1.61 (s, 6H).

Procedure for the Preparation of Example 51:

To a solution of compound 51b (160 mg, 0.3 mmol) in DMF (2 mL) was added DIEA (78 mg, 0.6 mmol) and stirred at 0° C., followed with acryloyl chloride (27 mg, 0.3 mmol) at 0° C. in three times and stirred for 0.5 h. The reaction mixture was combined with that of previous batch and purified by pre-HPLC (column: Waters Xbridge 150*25 5 um, condition: 42%-72% B (A: water/10 mM NH$_4$HCO$_3$, B: CH$_3$CN), flow rate: 25 mL/min) to afford Example 51 (91.4 mg, 46% yield) as white solid.

LCMS: R$_t$=1.660 min in 10-80AB_4min_220&254 chromatography (Xtimate C18 2.1*30 mm), MS (ESI) m/z=585.2 [M+H]$^+$.

HPLC: R$_t$=3.46 min in 10-80_CD_1.2 ml chromatography (XBridge Shield RP 18 2.1*50 mm 5 um).

$^1$H NMR (400 MHz, CDCl$_3$) δ 10.67 (br. s, 1H), 9.63 (s, 1H), 8.53 (s, 1H), 8.38-8.26 (m, 2H), 7.57 (s, 1H), 7.22-7.16 (m, 1H), 6.63 (s, 1H), 6.51-6.38 (m, 1H), 6.35-6.25 (m, 1H), 5.73 (d, J=10.0 Hz, 1H), 3.79 (s, 3H), 3.15-3.06 (m, 2H), 3.04-2.96 (m, 2H), 2.94-2.85 (m, 1H), 2.30 (s, 6H), 2.15-2.10 (m, 1H), 1.99-1.94 (m, 1H), 1.68 (s, 6H).

Example 52

(R)—N-(5-(4-(5-chloro-4-fluoro-2-(2-hydroxypropan-2-yl)phenylamino)pyrimidin-2-ylamino)-2-(3-(dimethylamino)pyrrolidin-1-yl)-4-methoxyphenyl)acrylamide

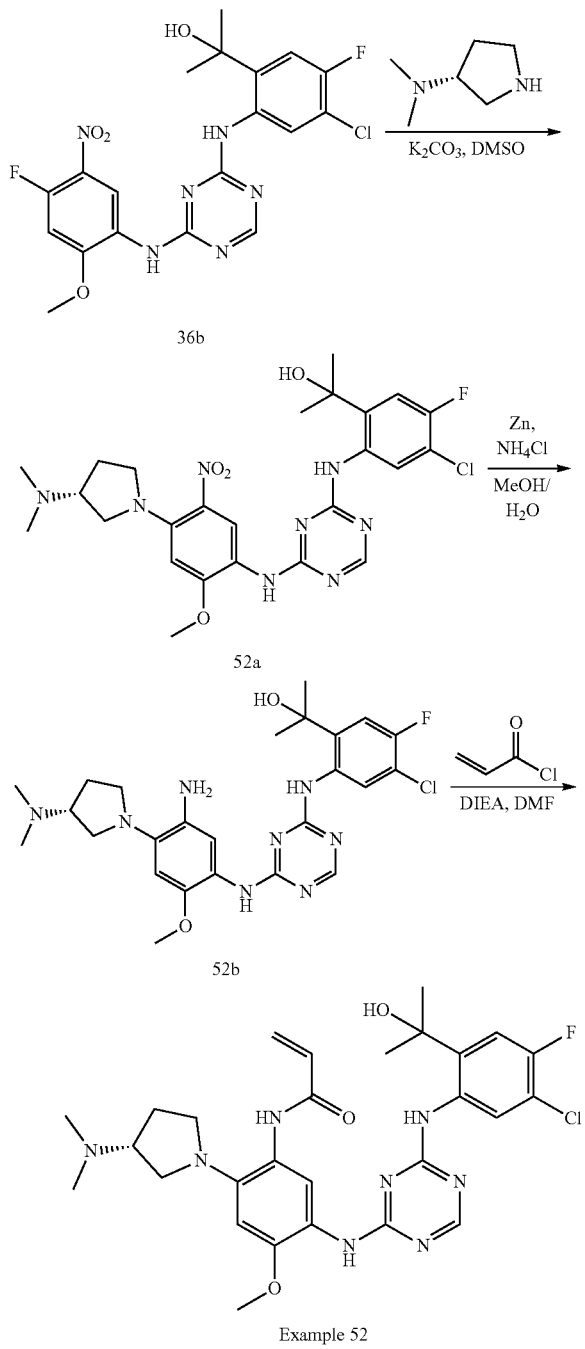

36b

52a

52b

Example 52

Procedure for the Preparation of Compound 52a:

To a solution of compound 36b (200 mg, 0.429 mmol) and K$_2$CO$_3$ (119 mg, 0.858 mmol) in DMSO (3 mL) was added (R)—N,N-dimethylpyrrolidin-3-amine (59 mg, 0.515 mmol). The reaction mixture was stirred at 22-30° C. for 4 h, then 50° C. for 1 h while color changed from brown to deep orange. The reaction mixture was added drop wise into H$_2$O (40 mL) under ice water bath. The precipitated solid was collected by filtration and washed with H$_2$O (15 mL×3), the filter cake was dissolved with CH$_2$Cl$_2$ (20 mL), dried over Na$_2$SO$_4$ and concentrated in vacuum to give compound 52a (210 mg, 87.4% yield) as an orange solid.

LCMS: R$_f$=0.677 min in 5-95AB_220&254.lcm chromatography (MERCK RP18 2.5-2 mm), MS (ESI) m/z=559.9 [M+H]$^+$.

$^1$H NMR (400 MHz, Methanol-d$_4$) δ 8.42 (s, 1H), 7.99 (d, J=7.6 Hz, 1H), 7.96 (d, J=5.6 Hz, 1H), 7.24 (d, J=10.8 Hz, 1H), 6.50 (s, 1H), 6.15 (d, J=5.6 Hz, 1H), 3.96 (s, 3H), 3.54 (dt, J=6.4, 10.4 Hz, 1H), 3.36 (t, J=9.2 Hz, 1H), 3.28-3.24 (m, 1H), 3.09 (dd, J=6.8, 10.0 Hz, 1H), 2.93-2.81 (m, 1H), 2.33 (s, 6H), 2.30-2.25 (m, 1H), 1.97-1.82 (m, 1H), 1.59 (d, J=3.6 Hz, 6H).

Procedure for the Preparation of Compound 52b:

To a solution of compound 52a (210 mg, 0.375 mmol) in 5 mL MeOH/H$_2$O=5/1 (v/v) was added Zn (147 mg, 2.25 mmol) and NH$_4$Cl (120 mg, 2.25 mmol). The resulting mixture was heated at 90° C. for 2 h while color changed from orange to brown. The reaction mixture was filtered, and the filtrate was concentrated in vacuum to give the crude residue, which was dissolved with CH$_2$Cl$_2$ (20 mL), washed with water (15 mL×3), then dried over Na$_2$SO$_4$ and concentrated in vacuum to give compound 52b (125 mg, 63% yield) as a brown solid.

LCMS: R$_f$=0.629 min in 5-95AB_220&254.lcm chromatography (MERCK RP18 2.5-2 mm), MS (ESI) m/z=530.1 [M+H]$^+$.

$^1$H NMR (400 MHz, CDCl$_3$) δ 8.85 (s, 1H), 8.15 (d, J=7.2 Hz, 1H), 8.03 (d, J=6.0 Hz, 1H), 7.87 (s, 1H), 7.43 (s, 1H), 7.08 (d, J=10.4 Hz, 1H), 6.66 (s, 1H), 6.05 (d, J=5.6 Hz, 1H), 3.81 (s, 3H), 3.20-3.11 (m, 2H), 3.06-2.97 (m, 2H), 2.91-2.83 (m, 1H), 2.28 (s, 6H), 2.17-2.09 (m, 1H), 1.92-1.81 (m, 1H), 1.65 (s, 6H).

Procedure for the Preparation of Example 52:

To a solution of compound 52b (125 mg, 0.236 mmol) and DIEA (46 mg, 0.354 mmol) in DMF (1.5 mL) was added acryloyl chloride (21 mg, 0.236 mmol) in ice water bath. The resulting mixture was stirred at 5-10° C. for 15 min. The reaction was quenched by H$_2$O (0.1 mL) and then filtered, the filtrate was purified by pre-HPLC directly (Column: Xtimate C18 150*25 mm*5 um; Condition: 35-65% B (A: 0.04% NH$_3$.H$_2$O+10 mM NH$_4$HCO$_3$, B: CH$_3$CN); Flow Rate: 30 ml/min) and then lyophilized to give Example 52 (14.5 mg, 10.5% yield) as an off-white solid.

LCMS: R$_f$=2.028 min in 10-80CD_3min_220&254. lcm chromatography (XBrige Shield RP18 2.1*50 mm, Sum), MS (ESI) m/z=584.3 [M+H]$^+$.

$^1$H NMR (400 MHz, CDCl$_3$) δ 9.62 (s, 1H), 9.43 (br s, 1H), 8.59 (br s, 1H), 8.08 (d, J=5.2 Hz, 1H), 7.53 (d, J=6.8 Hz, 1H), 7.47 (br s, 1H), 7.14 (d, J=10.8 Hz, 1H), 6.75 (s, 1H), 6.41-6.31 (m, 3H), 5.77 (t, J=5.4 Hz, 1H), 3.86 (s, 3H), 3.15-3.02 (m, 4H), 2.97-2.84 (m, 1H), 2.30 (s, 6H), 2.21-2.14 (m, 1H), 1.99-1.94 (m, 1H), 1.72 (s, 6H).

Example 53

(R)—N-(5-(4-(5-chloro-4-fluoro-2-(2-hydroxypropan-2-yl)phenylamino)pyrimidin-2-ylamino)-2-(2-((dimethylamino)methyl)azetidin-1-yl)-4-methoxyphenyl)acrylamide

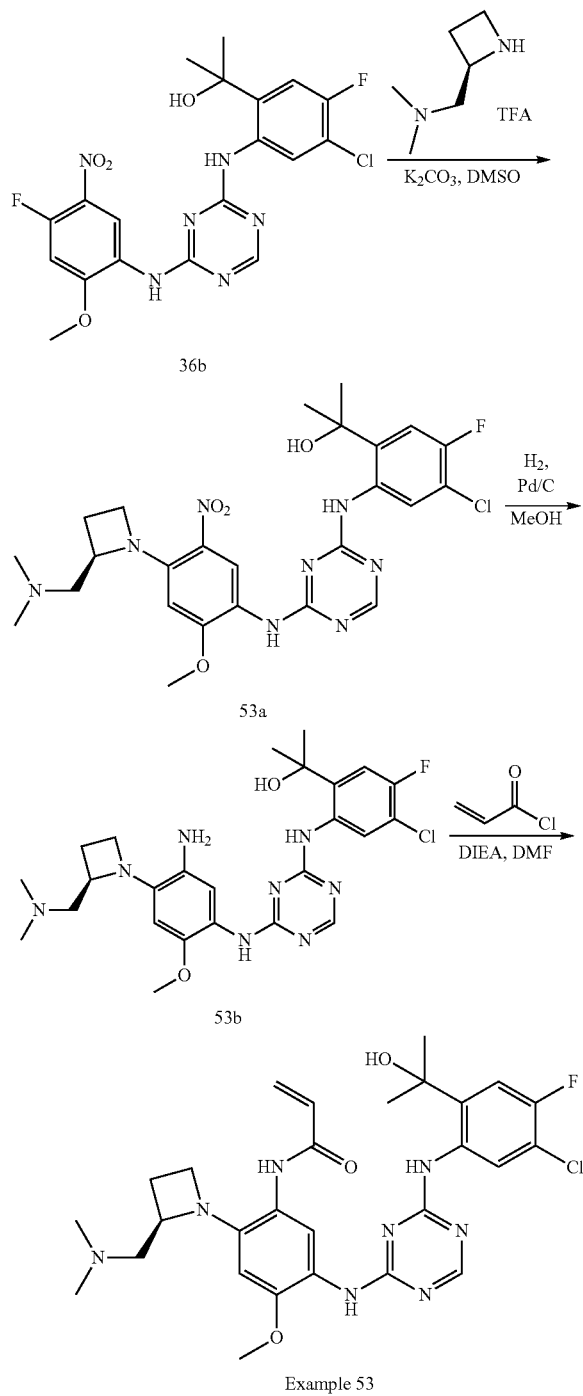

Procedure for the Preparation of Compound 53a:
To a solution of compound 36b (150 mg, 0.32 mmol) and K₂CO₃ (442 mg, 3.20 mmol) in DMSO (5 mL) was added (R)-1-(azetidin-2-yl)-N,N-dimethylmethanamine TFA salt (986 mg, 3.20 mmol). The resulting mixture was stirred at 85° C. for 4 h while the colour changes from pale yellow to deep yellow. The reaction mixture was pour into ice water (50 mL) and yellow solid was precipitated. The solid was filtered and dissolved with CH₂Cl₂ (20 mL), then dried over anhydrous Na₂SO₄ and concentrated under reduced pressure to give compound 53a (150 mg, 84% yield) as yellow solid.

LCMS: R$_f$=0.692 min in 5-95AB_220&254.lcm chromatography (MERCK RP-18e 25-2 mm), MS (ESI) m/z=559.9 [M+H]⁺.

Procedure for the Preparation of Compound 53b:
To a solution of compound 53a (150 mg, 0.27 mmol) in MeOH (5 mL) was added Pd/C (15 mg). The resulting mixture was purged and degassed with H₂ for 3 times, then stirred at 22-30° C. under hydrogen balloon (15 Psi) for 1 h. The reaction mixture was filtered and concentrated under reduced pressure to give compound 53b (100 mg, 70% yield) as black solid.

LCMS: R$_f$=0.663 min in 5-95AB_1.5min_220&254 chromatography (MERCK RP18e 25-2 mm), MS (ESI) m/z=530.0 [M+H]⁺.

Procedure for the Preparation of Example 53:
To a solution of compound 53b (100 mg, 0.19 mmol) and DIEA (49 mg, 2.0 eq, 0.38 mmol) in DMF (2.5 mL) was acryloyl chloride (17 mg, 0.19 mmol) in DMF (0.5 mL). The resulting mixture was stirred at 0° C. under ice-water bath for 30 min. The reaction mixture was purified by prep-HPLC [Column: Waters Xbridge 150*25 5 um; Condition: 36-66% B (A: 0.05% NH₃H₂O; B: CH₃CN); Flow rate: 25 ml/min]. Fractions containing the desired compound were lyophilized to afford Example 53 (12.2 mg, 11% yield) as white solid.

LCMS: R$_f$=1.378 min in 10-80AB_4min_220&254 chromatography (Xtimate C18 2.1*30 mm), MS (ESI) m/z=584.1 [M+H]⁺.

HPLC: R$_f$=2.74 min in 10-80_ab_1.2ML chromatography (Ultimate C18 3*50 mm 3 um).

¹H NMR: (400 MHz, CDCl₃) δ 9.41-9.33 (m, 2H), 8.95 (br s, 1H), 8.08 (d, J=6.0 Hz, 1H), 7.52 (br d, J=6.8 Hz, 1H), 7.44 (s, 1H), 7.15 (d, J=10.4 Hz, 1H), 6.68 (s, 1H), 6.38 (d, J=2.8 Hz, 1H), 6.36-6.30 (m, 2H), 5.81-5.75 (m, 1H), 5.62-5.36 (m, 1H), 4.19 (br d, J=6.8 Hz, 1H), 3.90 (s, 3H), 3.83-3.78 (m, 1H), 3.56 (q, J=8.4 Hz, 1H), 2.65 (br dd, J=5.6, 12.4 Hz, 1H), 2.45 (br dd, J=6.8, 12.8 Hz, 1H), 2.37 (br d, J=7.6 Hz, 1H), 2.26 (s, 6H), 2.16-2.08 (m, 1H), 1.71 (d, J=2.8 Hz, 6H).

Example 54

(R)—N-(5-(4-(4,5-dichloro-2-(2-hydroxypropan-2-yl)phenylamino)-1,3,5-triazin-2-ylamino)-2-(2-((dimethylamino)methyl)azetidin-1-yl)-4-methoxyphenyl)acrylamide

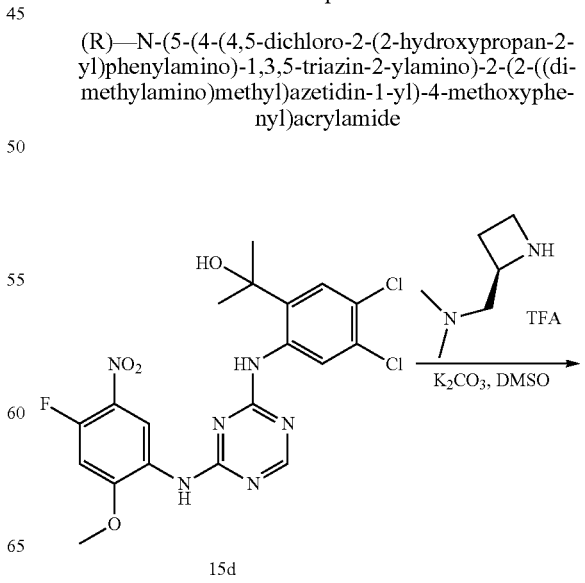

221

-continued

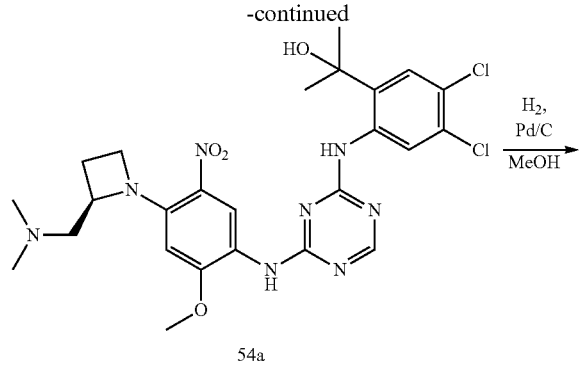

54a

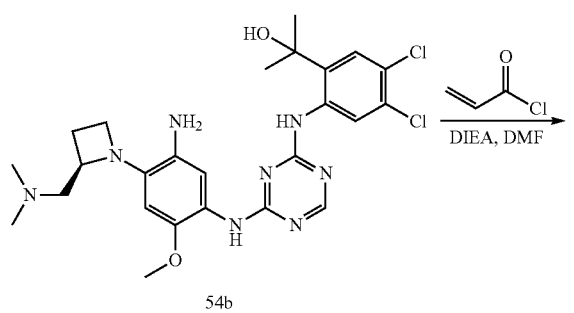

54b

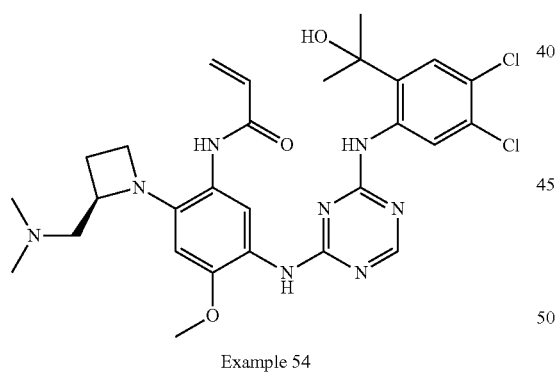

Example 54

The synthesis followed a similar experimental procedure as Example 19 to afford Example 54 as pale white solid.

LCMS: $R_t$=4.386 min in 10-80CD_7min_220&254.lcm; XBrige Shield RP18 2.1*50 mm MS (ESI) m/z=601.3 [M+H]$^+$.

HPLC: $R_t$=3.72 min in 10-80_ab_1.2ML chromatography (Ultimate C18 3*50 mm 3 um).

$^1$H NMR (400 MHz, DMSO-d$_6$) δ 10.54 (br s, 1H), 9.32 (br s, 1H), 8.84 (br s, 1H), 8.51 (s, 1H), 8.33 (s, 1H), 7.52 (br s, 1H), 7.25 (s, 1H), 6.59-6.52 (m, 1H), 6.34-6.26 (m, 2H), 5.76-5.68 (m, 1H), 4.22-4.12 (m, 1H), 3.82 (s, 3H), 3.78 (br s, 1H), 3.48 (q, J=8.0 Hz, 1H), 2.60 (br dd, J=5.6, 12.8 Hz, 1H), 2.45-2.26 (m, 2H), 2.20 (s, 6H), 2.09-1.90 (m, 2H), 1.67 (br s, 6H).

222

Example 55

N-(5-(4-(4,5-difluoro-2-(2-hydroxybutan-2-yl)phenylamino)-1,3,5-triazin-2-ylamino)-2-((R)-2-((dimethylamino)methyl)azetidin-1-yl)-4-methoxyphenyl) acrylamide

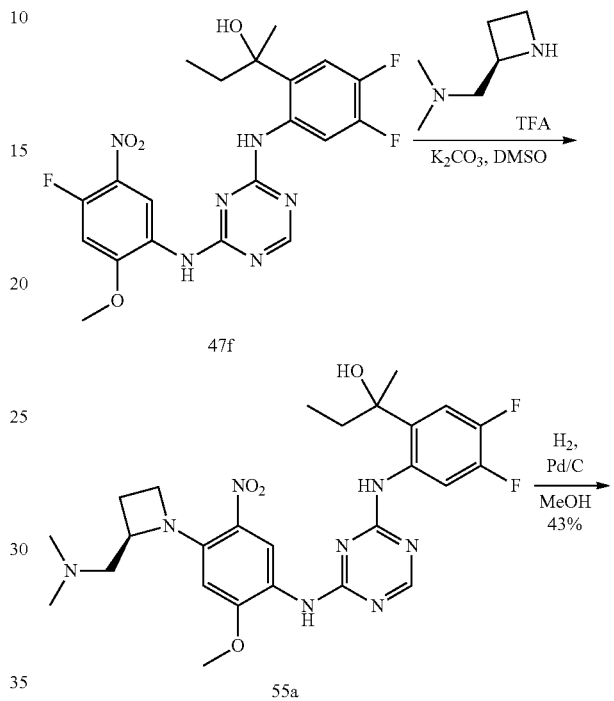

47f

55a

55b

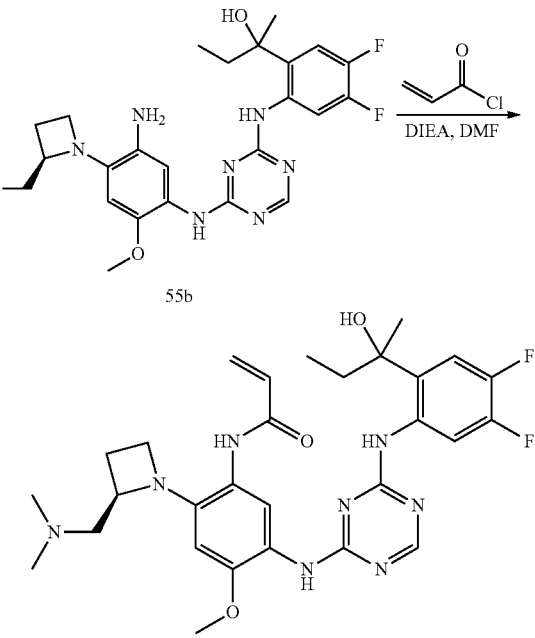

Example 55

The synthesis followed a similar experimental procedure as Example 47 to afford Example 55 as a white solid. LCMS:

R=1.741 min in 10-80AB_4min_220&254 chromatography (Xtimate C18 2.1*30 mm), MS (ESI) m/z=583.1 [M+H].

HPLC: $R_t$=3.49 min in 10-80_CD_1.2ML chromatography (XBridge Shield RP18 2.1*50 mm 5 um).

$^1$H NMR: (400 MHz, CDCl$_3$) δ 10.70 (br s, 1H), 9.43 (br s, 1H), 8.87 (br s, 1H), 8.39-8.26 (m, 2H), 7.62-7.48 (m, 1H), 6.99 (dd, J=8.8 Hz, 12.4 Hz, 1H), 6.61 (br d, J=6.0 Hz, 1H), 6.40-6.26 (m, 2H), 5.80-5.74 (m, 1H), 4.27-4.16 (m, 1H), 3.88 (s, 3H), 3.84-3.79 (m, 1H), 3.60-3.51 (m, 1H), 2.65 (br dd, J=5.6 Hz, 13.6 Hz, 1H), 2.49-2.32 (m, 2H), 2.24 (s, 6H), 2.16-1.91 (m, 3H), 1.66 (s, 3H), 0.86 (q, J=7.6 Hz, 3H).

Example 56

N-(5-(4-(5-chloro-4-fluoro-2-(2-hydroxybutan-2-yl)phenylamino)-1,3,5-triazin-2-ylamino)-2-((R)-2-((dimethylamino)methyl)azetidin-1-yl)-4-methoxyphenyl)acrylamide

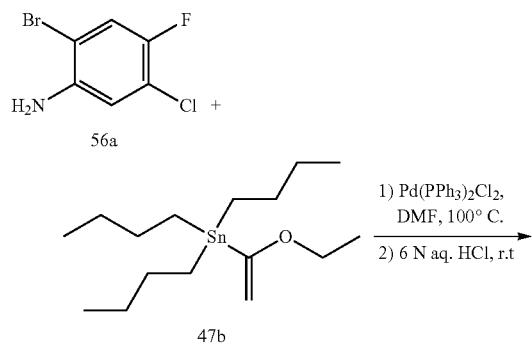

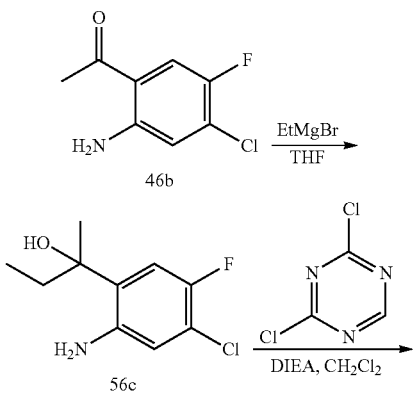

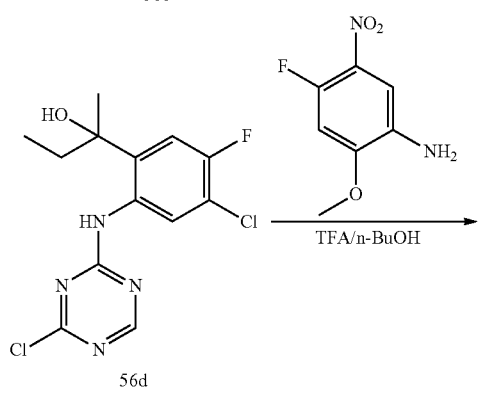

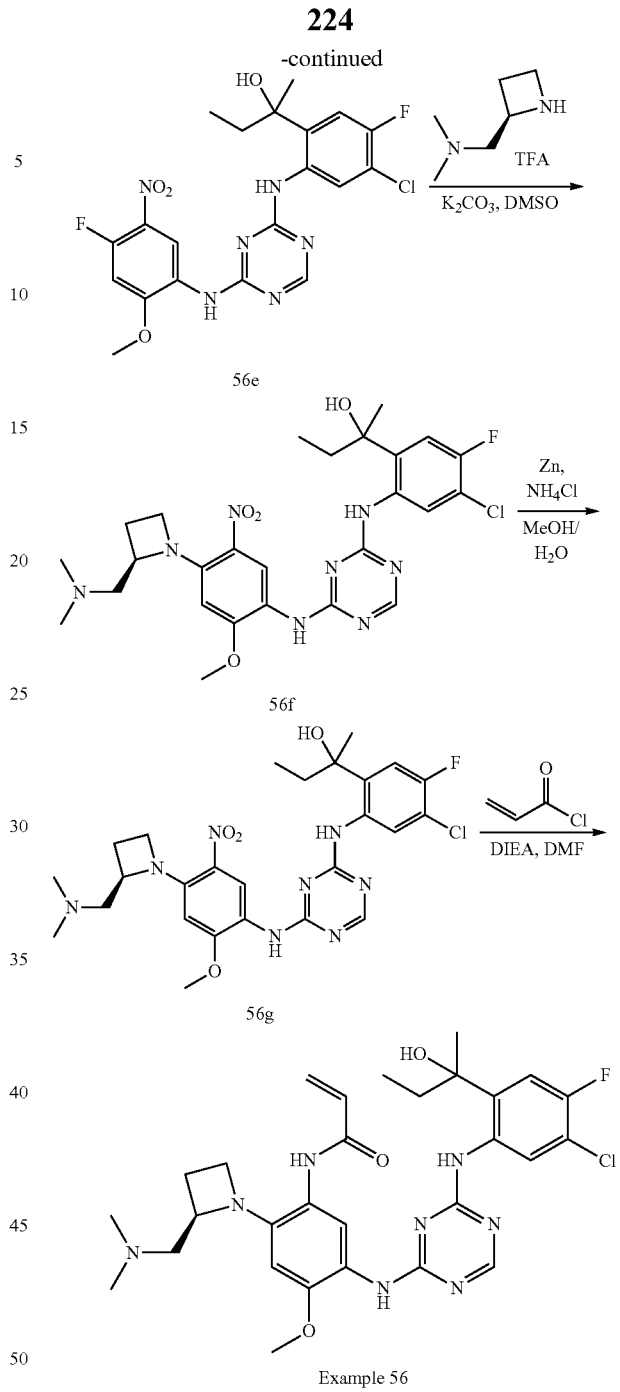

Example 56

Procedure for the Preparation of Compound 56b:

To a solution of compound 56a (5 g, 22.28 mmol) in DMF (50 mL) was added Pd(PPh$_3$)$_2$Cl$_2$ (1.0 g, 1.42 mmol) and compound 47b (8.85 g, 24.5 mmol) under nitrogen. The mixture was stirred at 100° C. under nitrogen for 12 h, then cooled to room temperature, aqueous HCl (6 M, 8 mL) was added to the mixture and stirred at 25° C. for additional 3 h. The mixture was diluted with water (250 mL) and extracted with ethyl acetate (200 mL×3). The combined organic layers were washed with water (300 mL), dried over sodium sulfate, filtered and concentrated in vacuum to give the crude product, which was purified by column chromatography on silica gel (0 to 10% EtOAc in PE (v/v)) to afford compound 56b (1.89 g, 45% yield).

LCMS: R$_t$=2.071 min in 10-80AB_4min_220&254 chromatography (Xtimate C18 2.1*30 mm), MS (ESI) m/z=187.9 [M+H]$^+$.

$^1$H NMR (400 MHz, CDCl$_3$) δ 7.39 (d, J=10.0 Hz, 1H), 6.65 (d, J=4.0 Hz, 1H), 2.47 (s, 3H).

Procedure for the Preparation of Compound 56c:

To a yellow solution of compound 56b (1.69 g, 9.01 mmol) in THF (20 mL) was added EtMgBr (12 mL, 36.03 mmol) drop wise under nitrogen at 0° C. The resulting mixture was stirred at 19-24° C. for 3 h. The mixture was quenched with saturated solution of NH$_4$Cl (100 mL) and extracted with EtOAc (30 mL×3). The combined organic layers were combined with previous batch and concentrated in vacuum to give the crude product, which was purified by column chromatography on silica gel (0 to 10% EtOAc in PE) to afford compound 56c (1.1 g, 50% yield) as yellow oil.

LCMS: R$_t$=1.429 min in 10-80AB_4min_220&254 chromatography (Xtimate C18 2.1*30 mm), MS (ESI) m/z=199.9 [M–H$_2$O+H]$^+$.

$^1$H NMR (400 MHz, DMSO-d$_6$) δ 6.94 (d, J=11.6 Hz, 1H), 6.71 (d, J=6.8 Hz, 1H), 5.50 (s, 2H), 1.88-1.72 (m, 2H), 1.43 (s, 3H), 0.72 (t, J=7.2 Hz, 3H).

Procedure for the Preparation of Compound 56d:

To a yellow solution of compound 56c (1.34 g, 6.16 mmol) in dichloromethane (20 mL) was added DIEA (1.59 g, 12.31 mmol) and 2,4-dichloro-1,3,5-triazine (1.02 g, 6.77 mmol) successively. The resulting yellow solution was stirred at 21-29° C. for 2 h. The mixture was concentrated in vacuum to give the crude product, which was purified by column chromatography on silica gel (0 to 10% EtOAc in PE) to afford compound 56d (1.28 g, 58% yield) as yellow solid.

LCMS: R$_t$=0.922 min in 5-95AB_220&254 chromatography (MERCK RP18 2.5-2 mm), MS (ESI) m/z=330.7 [M+H]$^+$.

$^1$H NMR (400 MHz, CDCl$_3$) δ 10.35-10.03 (m, 1H), 8.62-8.44 (m, 1H), 8.35 (d, J=7.2 Hz, 1H), 7.02 (d, J=10.4 Hz, 1H), 2.44 (br. s, 1H), 1.95-1.88 (m, 2H), 1.66 (s, 3H), 0.87 (t, J=7.2 Hz, 3H).

Procedure for the Preparation of Compound 56e:

To a mixture of compound 56d (1.28 g, 3.87 mmol) in n-BuOH/TFA (10 mL/0.1 mL) was added 4-fluoro-2-methoxy-5-nitroaniline (720 mg, 3.87 mmol). The mixture was stirred at 23-29° C. for 4 h while grey solid was precipitated out. The solid was collected by suction filtration and dried in high vacuo to afford compound 56e (1.07 g, 57.5% yield).

LCMS: R$_t$=0.984 min in 5-95AB_220&254 chromatography (MERCK RP18 2.5-2 mm), MS (ESI) m/z=481.1 [M+H]$^+$.

$^1$H NMR: (400 MHz, DMSO-d$_6$) δ 10.46 (br s, 1H), 8.36 (s, 1H), 7.40 (d, J=13.6 Hz, 1H), 7.30 (s, 1H), 7.26 (br d, J=10.8 Hz, 1H), 7.17 (s, 1H), 7.05 (s, 1H), 3.93 (s, 3H), 1.85-1.68 (m, 2H), 1.51 (s, 3H), 0.72 (t, J=7.2 Hz, 3H).

Procedure for the Preparation of Compound 56f:

To a mixture of compound 56e (150 mg, 0.31 mmol) in DMSO (3 mL) was added K$_2$CO$_3$ (474 mg, 3.43 mmol) and (R)-1-(azetidin-2-yl)-N,N-dimethylmethanamine TFA salt (1.07 mg, 3.12 mmol). The resulting mixture was stirred at 85° C. for 1 h. The reaction mixture was combined with previous batch and poured into ice water (20 mL), the orange precipitated solid was collected by suction filtration and washed with water (10 mL), then dried in vacuo to afford compound 7 (160 mg, 79% yield).

LCMS: R$_t$=2.003 min in 10-80AB_4min_220&254 chromatography (Xtimate C18 2.1*30 mm), MS (ESI) m/z=575.1 [M+H]$^+$.

$^1$H NMR: (400 MHz, CDCl$_3$) δ 9.66 (s, 1H), 8.90 (s, 1H), 8.45-8.18 (m, 2H), 7.28 (br. s, 1H), 6.93 (d, J=10.4 Hz, 1H), 6.75 (br. s, 1H), 4.35 (br. s, 1H), 4.29-4.18 (m, 1H), 3.87 (s, 3H), 3.28-3.15 (m, 1H), 2.82-2.74 (m, 1H), 2.68-2.60 (m, 1H), 2.50-2.23 (m, 2H), 2.26 (s, 3H), 2.14-2.02 (m, 1H), 1.92-1.85 (m, 2H), 1.54 (s, 6H), 0.81 (t, J=7.2 Hz, 3H).

Procedure for the Preparation of Compound 56g:

To a yellow solution of compound 56f (160 mg, 0.28 mmol) in methanol/water (5 mL/1 mL) was added NH$_4$Cl (89 mg, 1.67 mmol) and Zn (90 mg, 1.39 mmol). The resulting mixture was stirred at 90° C. for 1 h. The reaction mixture was poured into water (20 mL) and extracted with dichloromethane/methanol=3:1 (v/v) (10 mL×3). The combined organic layers were dried and concentrated in vacuum to afford compound 56g (150 mg, 98% yield) as black solid.

LCMS: R$_t$=2.144 min in 0-60AB_4min_220&254 chromatography (Xtimate C18 2.1*30 mm), MS (ESI) m/z=545.2 [M+H]$^+$.

$^1$H NMR: (400 MHz, CDCl$_3$) δ 9.66 (br. s, 1H), 8.30 (br. s, 1H), 8.21 (br. s, 1H), 7.78-7.37 (m, 2H), 6.93 (d, J=10.4 Hz, 1H), 6.45 (s, 1H), 4.21-4.09 (m, 1H), 4.00-3.88 (m, 1H), 3.76 (s, 3H), 3.34-3.20 (m, 1H), 2.43-2.30 (m, 1H), 2.22-2.17 (m, 5H), 2.14-2.00 (m, 2H), 1.89-1.83 (m, 2H), 1.61-1.51 (m, 6H), 0.82-0.77 (m, 3H).

Procedure for the Preparation of Example 56:

To a black solution of compound 56g (150 mg, 0.27 mmol) in DMF (2 mL) was added DIEA (71 mg, 0.55 mmol), followed with acryloyl chloride (25 mg, 0.27 mmol) at 0° C. in three times and stirred at 0° C. for 1 h. The mixture was quenched with 3 drops of water and purified by pre-HPLC directly (column: Waters Xbridge 150*25 um, condition: 41%-61% B (A: water/10 mM NH$_4$HCO$_3$, B: CH$_3$CN), flow rate: 25 mL/min) to afford Example 56 (31.9 mg, 19.7% yield) as grey solid, 11.6 mg was delivered and the rest batch of 20.3 mg was further purified by SFC separation.

LCMS: R$_t$=1.709 min in 10-80AB_4min_220&254 chromatography (Xtimate C18 2.1*30 mm), MS (ESI) m/z=621.1 [M+Na]$^+$.

HPLC: R$_t$=3.65 min in 10-80_CD_1.2 ml chromatography (XBridge Shield RP 18 2.1*50 mm 5 um).

$^1$H NMR (400 MHz, CDCl$_3$) δ 10.68 (br s, 1H), 9.41 (br s, 1H), 8.90 (br s, 1H), 8.61-8.25 (m, 2H), 7.59 (br s, 1H), 7.02 (d, J=9.6 Hz, 1H), 6.64 (br s, 1H), 6.39 (br s, 2H), 5.80 (br s, 1H), 4.41-4.16 (m, 1H), 4.02-3.78 (m, 4H), 3.66-3.45 (m, 1H), 2.83-2.62 (m, 1H), 2.58-2.46 (m, 1H), 2.44-2.37 (m, 1H), 2.30 (s, 6H), 2.21-2.05 (m, 3H), 1.69 (s, 3H), 0.94-0.83 (m, 3H).

Example 57

N-(5-(4-(4,5-difluoro-2-(2-hydroxybutan-2-yl)phenylamino)-1,3,5-triazin-2-ylamino)-2-((R)-2-((dimethylamino)methyl)pyrrolidin-1-yl)-4-methoxyphenyl)acrylamide

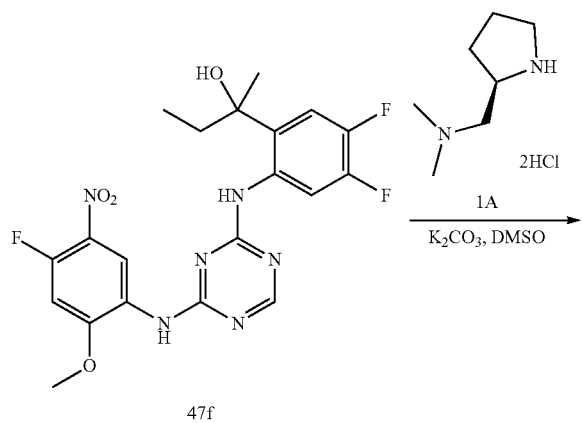

The synthesis followed a similar experimental procedure as Example 47 to afford Example 57 as a pale yellow solid.

LCMS: $R_t$=1.928 min in 10-80AB_4min_220&254 chromatography (Xtimate C18 2.1*30 mm, MS (ESI) m/z=597.1 [M+H]$^+$.

HPLC: $R_t$=4.09 min in 10-80_CD_1.2ML chromatography (XBridge Shield RP 18 2.1*50 mm 5 um).

$^1$H NMR: (400 MHz, CDCl$_3$) δ 10.92 (br s, 1H), 10.14-9.97 (m, 1H), 9.95-9.80 (m, 1H), 8.40 (s, 1H), 8.39-8.34 (m, 1H), 7.68 (br d, J=9.6 Hz, 1H), 7.03 (dd, J=8.4 Hz, 12.4 Hz, 1H), 6.71 (s, 1H), 6.36 (br d, J=5.2 Hz, 2H), 6.04-5.63 (m, 2H), 3.86 (s, 3H), 3.39-3.26 (m, 2H), 3.01-2.92 (m, 1H), 2.42-2.32 (m, 1H), 2.19 (s, 6H), 2.13-1.91 (m, 5H), 1.70 (s, 3H), 1.68-1.63 (m, 2H), 0.94-0.84 (m Hz, 3H).

Example 58

N-(5-(4-(4,5-difluoro-2-(2-hydroxybutan-2-yl)phenylamino)-1,3,5-triazin-2-ylamino)-2-((S)-2-((dimethylamino)methyl)pyrrolidin-1-yl)-4-methoxyphenyl)acrylamide

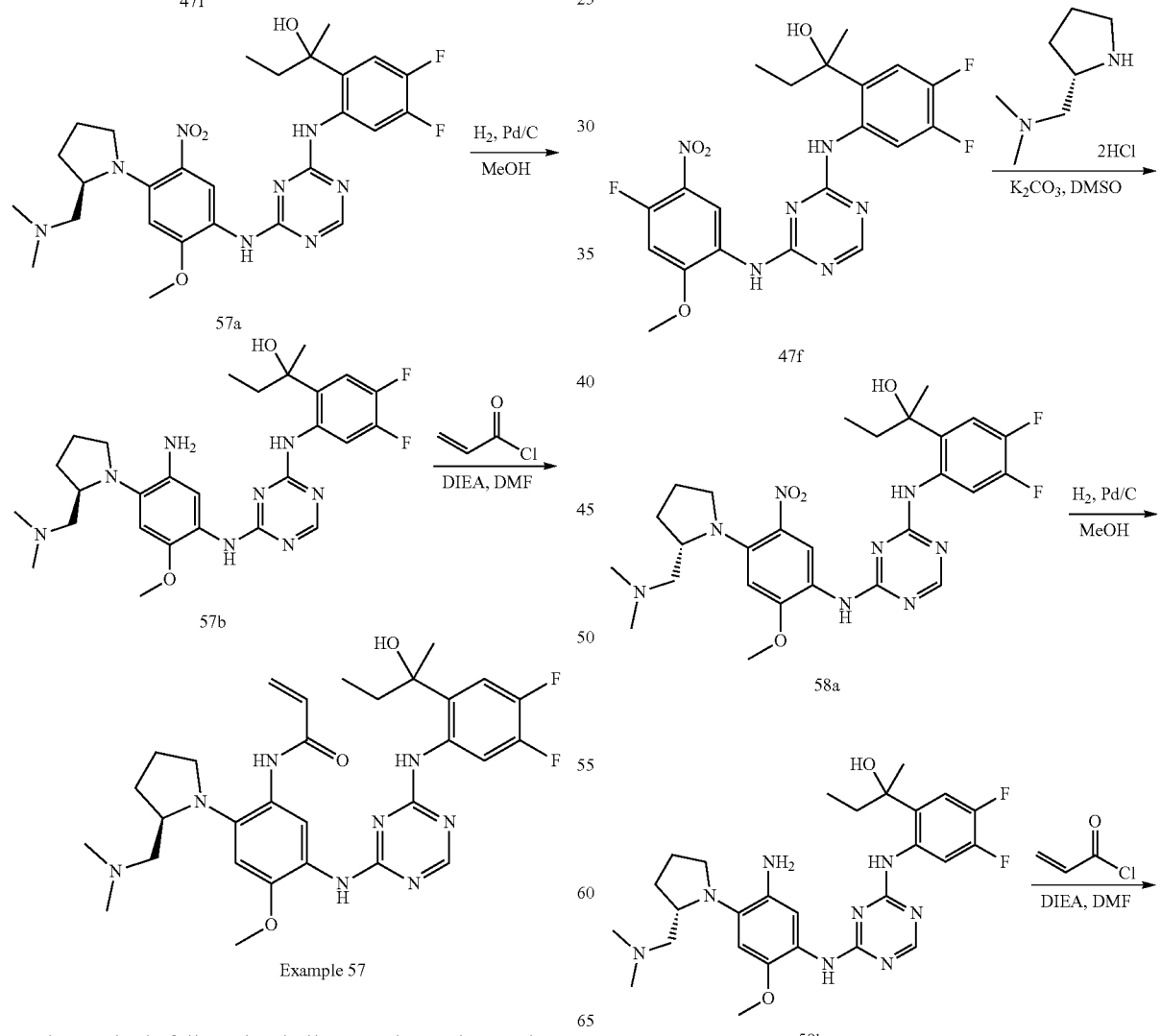

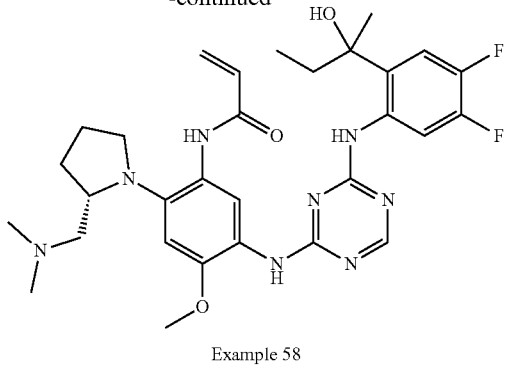

Example 58

The synthesis followed a similar experimental procedure as Example 47 to afford Example 58 as white solid.

LCMS: $R_t$=1.959 min in 10-80AB_4min_220&254 chromatography (Xtimate C18 2.1*30 mm), MS (ESI) m/z=619.1 [M+Na]$^+$.

HPLC: $R_t$=2.74 min in 10-80_ab_1.2ML chromatography (Ultimate C18 3*50 mm 3 um).

$^1$H NMR: (400 MHz, CDCl$_3$) δ 10.91 (br s, 1H), 10.24-9.80 (m, 2H), 8.48-8.33 (m, 2H), 7.68 (br d, J=10.4 Hz, 1H), 7.03 (dd, J=8.8, 12.4 Hz, 1H), 6.71 (s, 1H), 6.36 (br d, J=4.4 Hz, 2H), 5.79-5.75 (m, 1H), 3.87 (s, 3H), 3.32 (br d, J=10.8 Hz, 2H), 3.02-2.91 (m, 1H), 2.44-2.32 (m, 1H), 2.23-2.16 (m, 7H), 2.14-1.86 (m, 6H), 1.70 (s, 3H), 0.89 (td, J=7.6, 12.0 Hz, 3H).

Example 59

N-(5-(4-(5-chloro-4-fluoro-2-(2-hydroxybutan-2-yl)phenylamino)-1,3,5-triazin-2-ylamino)-2-((R)-3-(dimethylamino)pyrrolidin-1-yl)-4-methoxyphenyl)acrylamide

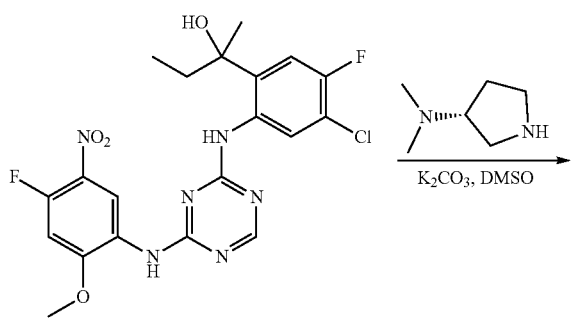

56e

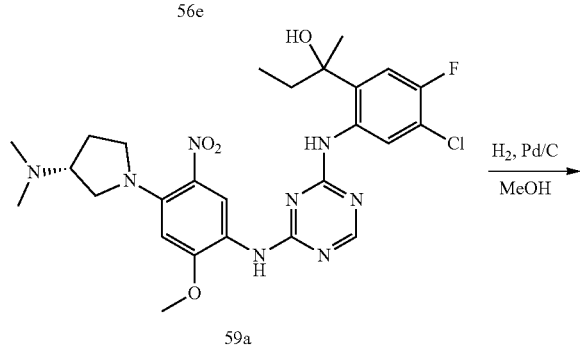

59a

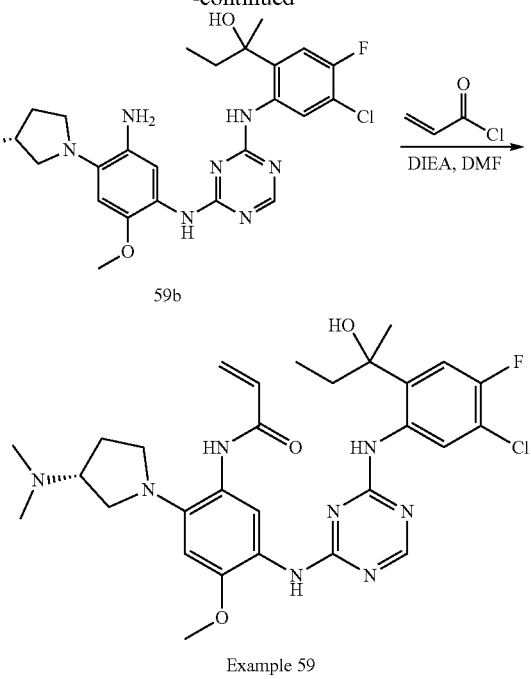

59b

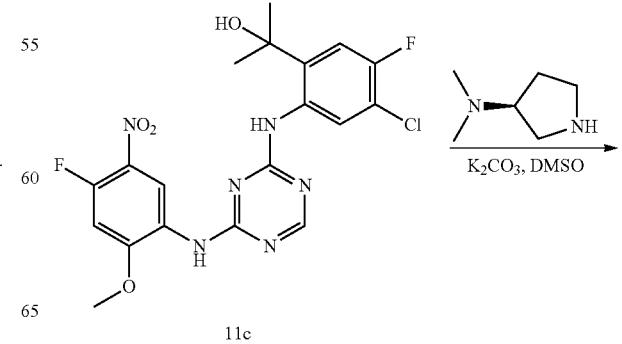

Example 59

The synthesis followed a similar experimental procedure as Example 56 to afford Example 59 as a white solid.

LCMS: $R_t$=1.713 min in 10-80AB_4min_220&254. lcm chromatography (Xtimate C18 2.1*30 mm), MS (ESI) m/z=599.1 [M+H]$^+$.

$^1$H NMR (400 MHz, CDCl$_3$) δ 10.78 (br s, 1H), 9.77 (br s, 1H), 8.54 (br s, 1H), 8.53 (br s, 1H), 8.41 (s, 1H), 7.64 (br s, 1H), 7.01 (d, J=10.8 Hz, 1H), 6.74 (s, 1H), 6.48-6.29 (m, 2H), 5.86-5.76 (m, 1H), 5.62 (br s, 1H), 3.87 (s, 3H), 3.17-3.03 (m, 4H), 2.98-2.86 (m, 1H), 2.33 (s, 6H), 2.24-2.15 (m, 1H), 2.14-2.07 (m, 1H), 2.05-1.95 (m, 2H), 1.69 (s, 3H), 0.89 (dt, J=3.2, 7.6 Hz, 3H).

Example 60

(S)—N-(5-(4-(5-chloro-4-fluoro-2-(2-hydroxypropan-2-yl)phenylamino)-1,3,5-triazin-2-ylamino)-2-(3-(dimethylamino)pyrrolidin-1-yl)-4-methoxyphenyl)acrylamide 11c

231
-continued

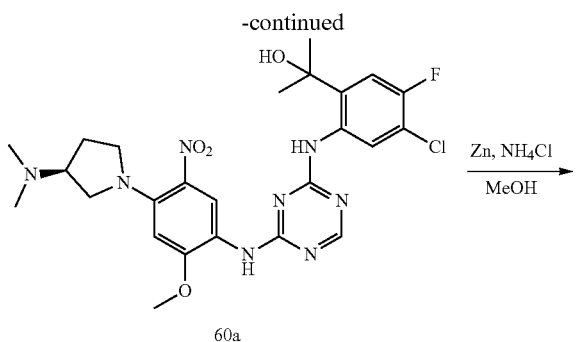
60a

60b

Example 60

The synthesis followed a similar experimental procedure as Example 33 to afford Example 60 as a white solid.

LCMS: $R_t$=1.568 min in 10-80AB_4min_220&254. lcm chromatography (Xtimate C18 2.1*30 mm), MS (ESI) m/z=585.2 [M+H]$^+$.

$^1$H NMR (400 MHz, CDCl$_3$) δ 10.51 (br s, 1H), 9.72 (br s, 1H), 8.56 (br s, 1H), 8.47 (d, J=7.2 Hz, 1H), 8.40 (s, 1H), 7.63 (br s, 1H), 7.08 (d, J=10.8 Hz, 1H), 6.71 (s, 1H), 6.55-6.26 (m, 2H), 5.88 (br s, 1H), 5.79 (d, J=9.2 Hz, 1H), 3.86 (s, 3H), 3.20-2.99 (m, 4H), 2.90 (quin, J=6.8 Hz, 1H), 2.31 (s, 6H), 2.23-2.12 (m, 1H), 2.03-1.90 (m, 1H), 1.75 (br s, 6H).

232
Example 61

(R)—N-(5-(4-(4,5-dichloro-2-(2-hydroxypropan-2-yl)phenylamino)-1,3,5-triazin-2-ylamino)-2-(3-(dimethylamino)pyrrolidin-1-yl)-4-methoxyphenyl)acrylamide

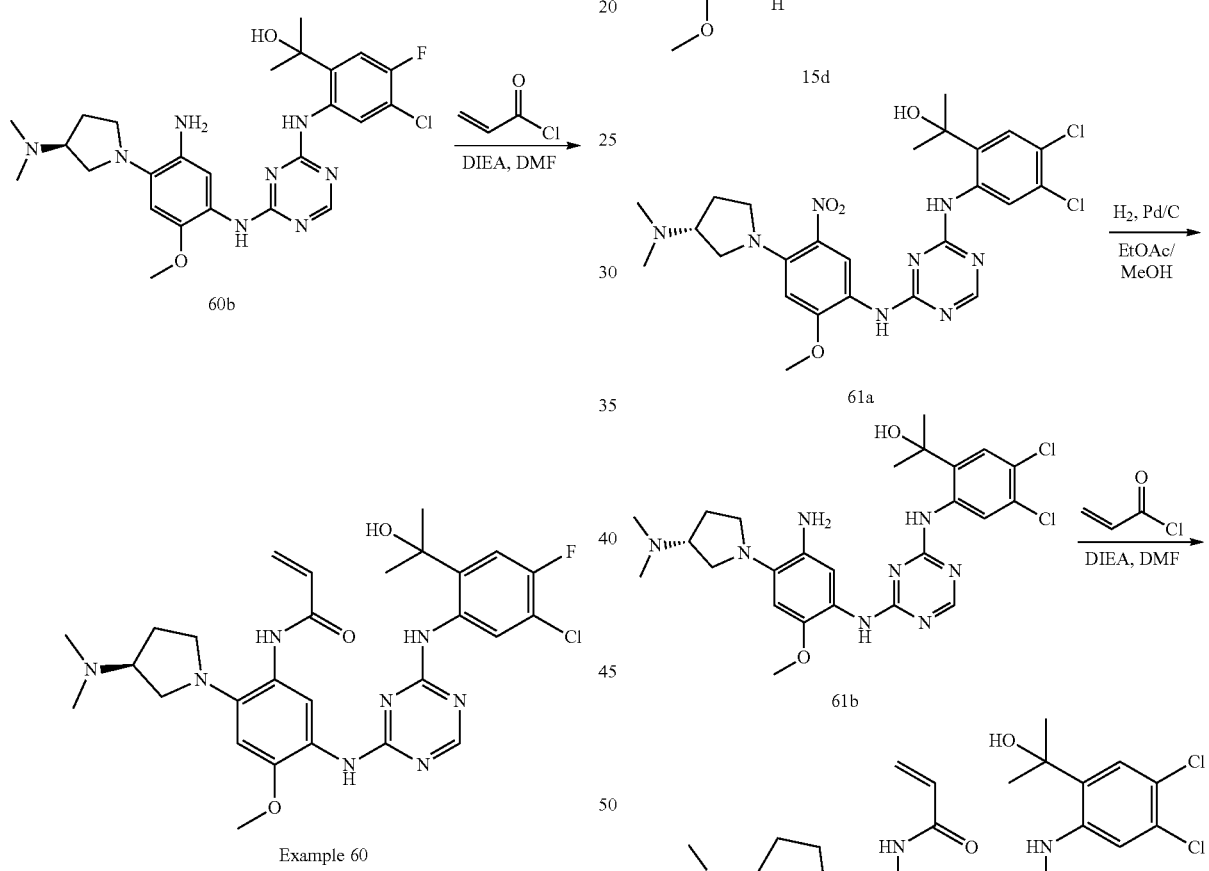

15d

61a

61b

Example 61

The synthesis followed a similar experimental procedure as Example 33 to afford Example 61 as a white solid.

LCMS: $R_t$=2.535 min in 0-60AB_4.0min_220&254 chromatography (Xtimate C18 2.1*30 mm), MS (ESI) m/z=601.1 [M+H]$^+$.

233

$^1$H NMR (400 MHz, CDCl$_3$) δ 10.71 (br s, 1H), 9.80 (br s, 1H), 8.63 (s, 1H), 8.52 (br s, 1H), 8.44 (s, 1H), 7.67 (br s, 1H), 7.35 (s, 1H), 6.76 (s, 1H), 6.39-6.38 (m, 2H), 5.95-5.70 (m, 2H), 3.89 (s, 3H), 3.15-3.08 (m, 4H), 2.94-2.87 (m, 1H), 2.32 (s, 6H), 2.24-2.13 (m, 1H), 1.96-1.93 (m, 1H), 1.78 (s, 6H).

Example 62

(R)—N-(5-(4-(4-chloro-5-fluoro-2-(2-hydroxypropan-2-yl)phenylamino)-1,3,5-triazin-2-ylamino)-2-(2-((dimethylamino)methyl)azetidin-1-yl)-4-methoxyphenyl)acrylamide

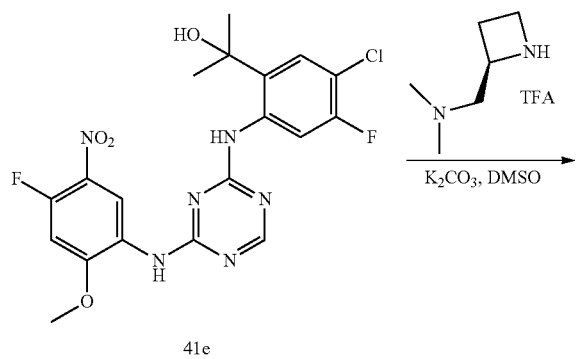

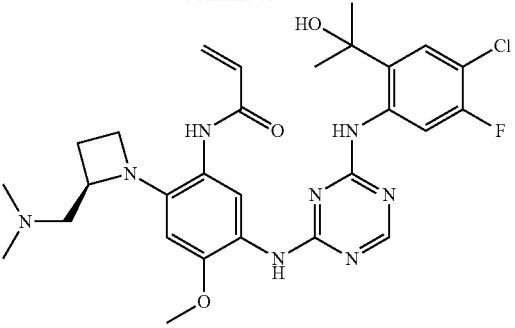

Example 62

234

The synthesis followed a similar experimental procedure as Example 41 to afford Example 62 as a white solid.

LCMS: R$_t$=1.493 min in 10-80AB_3min_220&254 chromatography (Xtimate C18, 2.1*30 mm, 3 um), MS (ESI) m/z=585.3 [M+H]$^+$.

HPLC: R$_t$=3.52 min in 10-80_CD_1.2ml. met XBridge Shield RP 18 2.1*50 mm 5 um.

$^1$H NMR (400 MHz, CDCl$_3$) δ 10.66 (br s, 1H), 9.50-9.19 (m, 1H), 8.93 (br s, 1H), 8.50-8.28 (m, 2H), 7.58 (br s, 1H), 7.26 (br s, 1H), 6.62 (s, 1H), 6.44-6.28 (m, 2H), 5.80 (br d, J=9.6 Hz, 1H), 4.29-4.17 (m, 1H), 3.90 (s, 3H), 3.87-3.79 (m, 1H), 3.58 (q, J=8.4 Hz, 1H), 2.73-2.62 (m, 1H), 2.56-2.40 (m, 2H), 2.26 (s, 6H), 2.18-2.00 (m, 1H), 1.75 (s, 6H).

Example 63

N-(5-(4-(5-chloro-4-fluoro-2-(2-hydroxybutan-2-yl)phenylamino)-1,3,5-triazin-2-ylamino)-2-((R)-2-((dimethylamino)methyl)pyrrolidin-1-yl)-4-methoxyphenyl)acrylamide

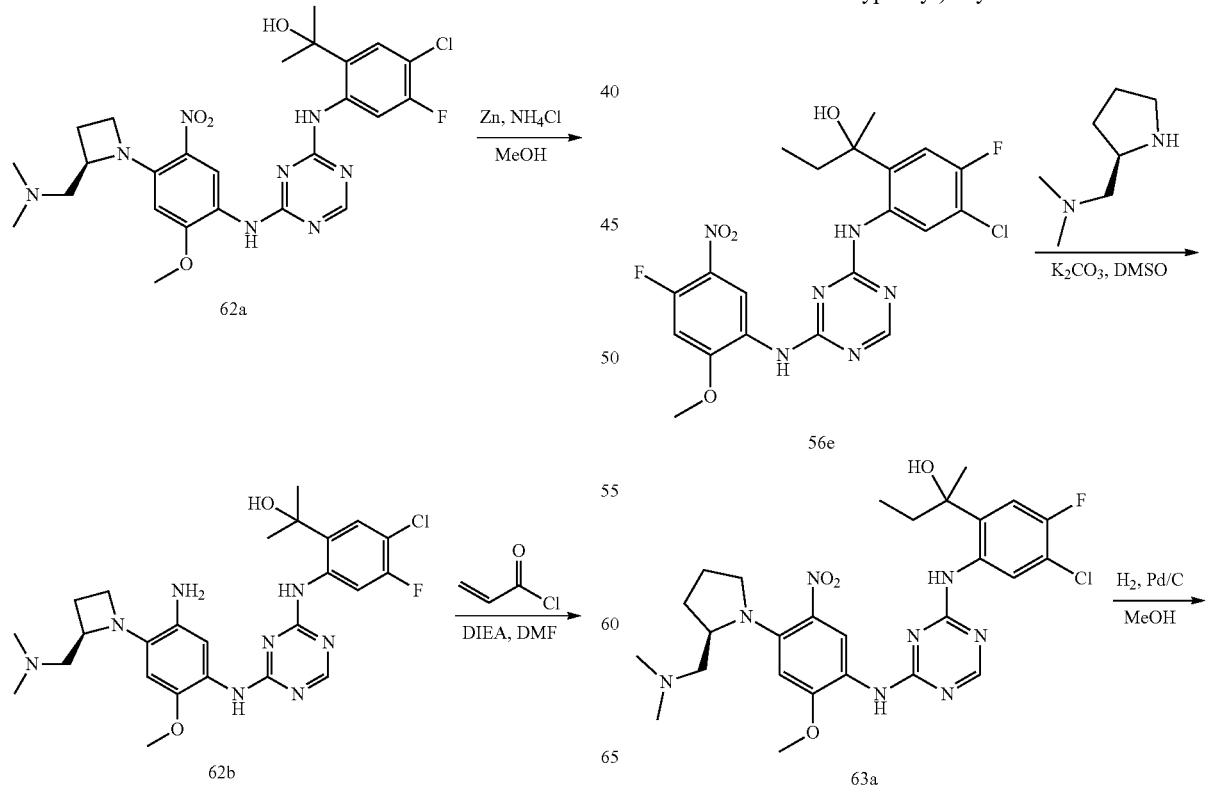

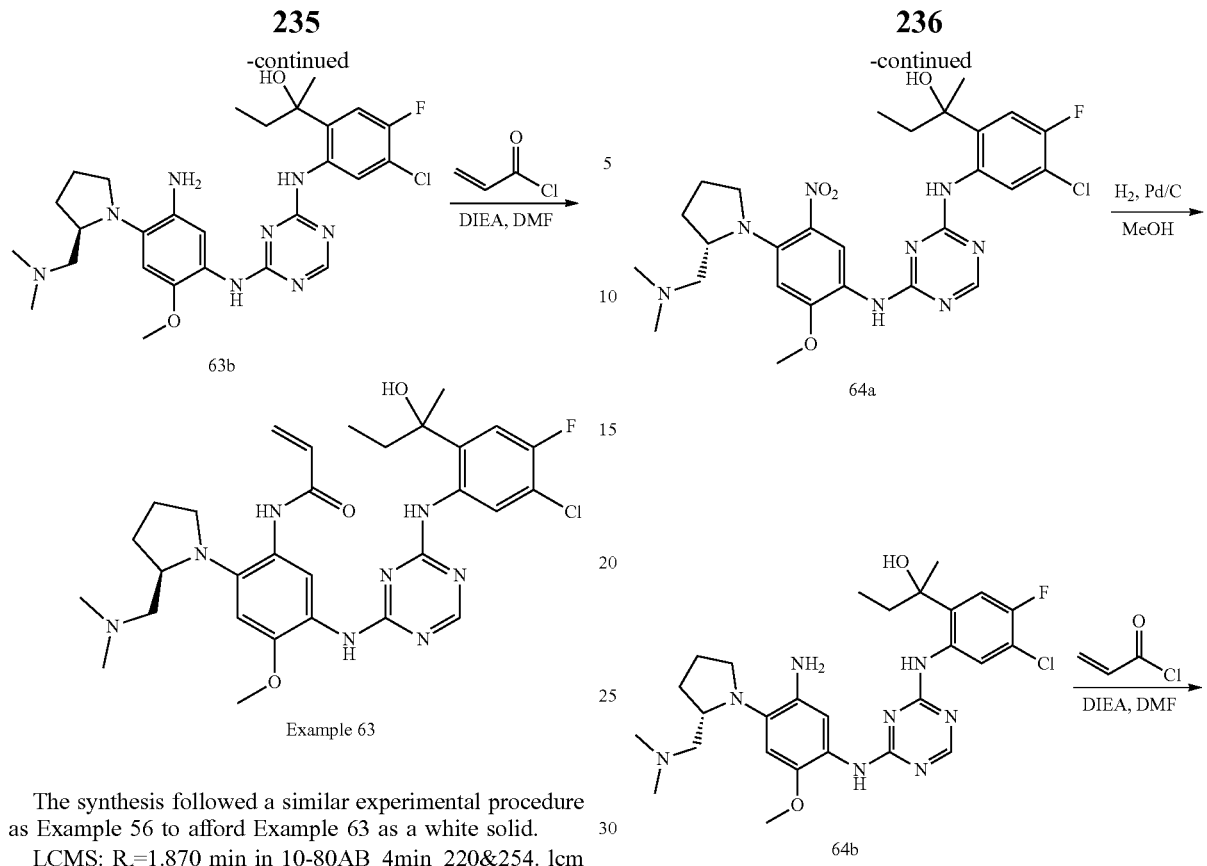

Example 63

The synthesis followed a similar experimental procedure as Example 56 to afford Example 63 as a white solid.

LCMS: $R_t$=1.870 min in 10-80AB_4min_220&254. lcm chromatography (Xtimate C18 2.1*30 mm), MS (ESI) m/z=613.1 [M+H]$^+$.

$^1$H NMR (400 MHz, CDCl$_3$) δ 10.86 (br s, 1H), 10.04 (d, J=27.6 Hz, 1H), 9.89 (br d, J=20.0 Hz, 1H), 8.53 (dd, J=2.8, 7.2 Hz, 1H), 8.41 (s, 1H), 7.69 (d, J=8.8 Hz, 1H), 7.02 (d, J=10.8 Hz, 1H), 6.70 (s, 1H), 6.36 (s, 1H), 6.35 (br s, 1H), 5.92 (br s, 1H), 5.77 (t, J=5.8 Hz, 1H), 3.86 (s, 3H), 3.39-3.24 (m, 2H), 3.02-2.92 (m, 1H), 2.37 (dd, J=7.8, 12.0 Hz, 1H), 2.23-2.16 (m, 7H), 2.13-1.88 (m, 5H), 1.70 (s, 3H), 1.69-1.64 (m, 1H), 0.89 (td, J=7.4, 20.0 Hz, 3H).

Example 64

N-(5-(4-(5-chloro-4-fluoro-2-(2-hydroxybutan-2-yl)phenylamino)-1,3,5-triazin-2-ylamino)-2-((S)-2-((dimethylamino)methyl)pyrrolidin-1-yl)-4-methoxyphenyl)acrylamide

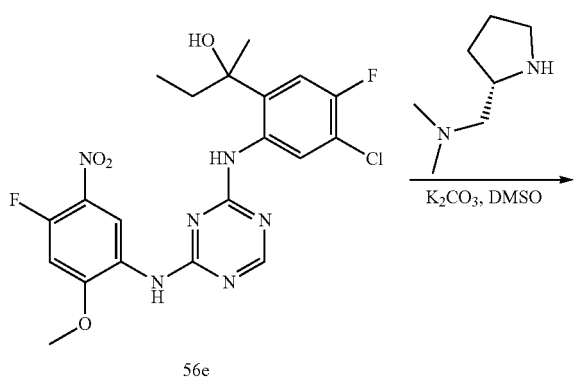

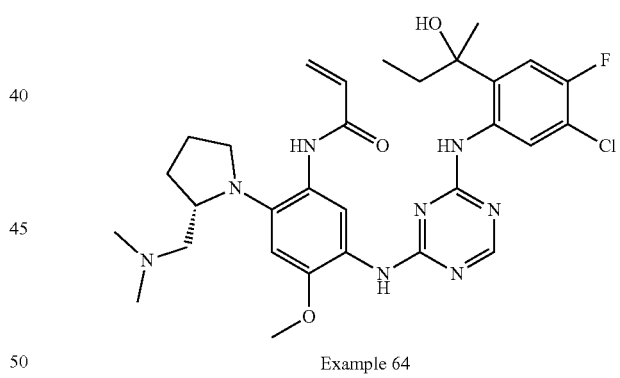

Example 64

The synthesis followed a similar experimental procedure as Example 56 to afford Example 64 as a light-yellow solid.

LCMS: $R_t$=1.473 min in 10-80AB_3min_220&254 chromatography (Xtimate C18, 2.1*30 mm, 3 um), MS (ESI) m/z=613.3 [M+H]$^+$.

HPLC: $R_t$=4.27 min, 10-80_CD_1.2ml.met XBridge Shield RP 18 2.1*50 mm 5 um.

$^1$H NMR: (400 MHz, CDCl$_3$) δ 10.86 (br s, 1H), 10.15-9.97 (m, 1H), 9.93-9.79 (m, 1H), 8.53 (br d, J=7.4 Hz, 1H), 8.41 (s, 1H), 7.73-7.63 (m, 1H), 7.02 (d, J=10.8 Hz, 1H), 6.71 (s, 1H), 6.36 (br d, J=5.2 Hz, 2H), 5.91 (br s, 1H), 5.82-5.73 (m, 1H), 3.87 (s, 3H), 3.40-3.22 (m, 2H), 2.97 (q, J=7.2 Hz, 1H), 2.46-2.30 (m, 2H), 2.22-2.16 (m, 7H), 2.13-1.89 (m, 6H), 1.71 (s, 3H), 0.94-0.85 (m, 3H).

Example 65

(S)—N-(5-(4-(5-chloro-4-fluoro-2-(2-hydroxypropan-2-yl)phenylamino)-1,3,5-triazin-2-ylamino)-2-(2-((dimethylamino)methyl)pyrrolidin-1-yl)-4-methoxyphenyl)acrylamide

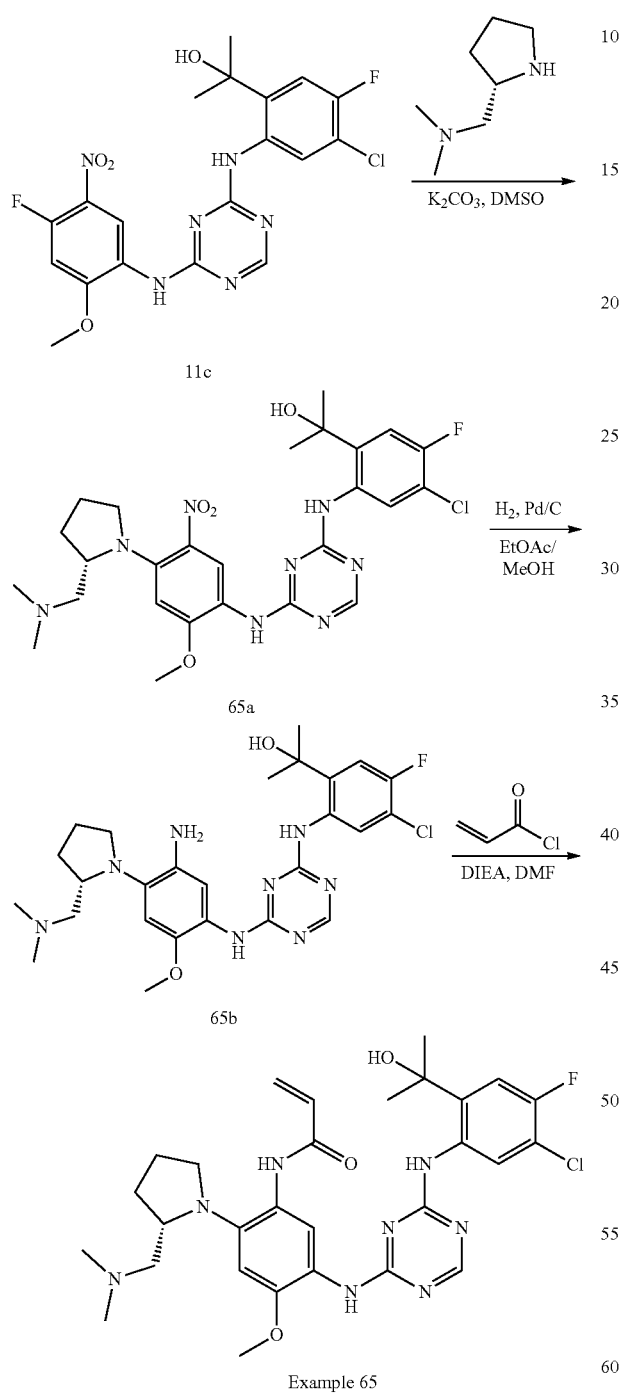

The synthesis followed a similar experimental procedure as Example 31 to afford Example 65 as a white solid.

LCMS: $R_t$=2.553 min in 0-60AB_4.0min_220&254 chromatography (Xtimate C18 2.1*30 mm), MS (ESI) m/z=621.0 [M+Na]+.

$^1$H NMR (CDCl$_3$ 400 MHz) δ 10.60 (br s, 1H), 10.09 (br s, 1H), 9.91 (br s, 1H), 8.48 (d, J=7.2 Hz, 1H), 8.42 (s, 1H), 7.68 (br s, 1H), 7.10 (d, J=10.8 Hz, 1H), 6.70 (s, 1H), 6.45-6.29 (m, 2H), 6.11 (br s, 1H), 5.85-5.73 (m, 1H), 3.87 (s, 3H), 3.38-3.25 (m, 2H), 3.02-2.93 (m, 1H), 2.42-2.34 (m, 1H), 2.24-2.16 (m, 7H), 2.16-1.91 (m, 4H), 1.77 (s, 6H).

Example 66

N-(2-((2-(dimethylamino)ethyl)(methyl)amino)-4-methoxy-5-(4-(2-(1,1,1-trifluoro-2-hydroxypropan-2-yl)phenylamino)-1,3,5-triazin-2-ylamino)phenyl)acrylamide

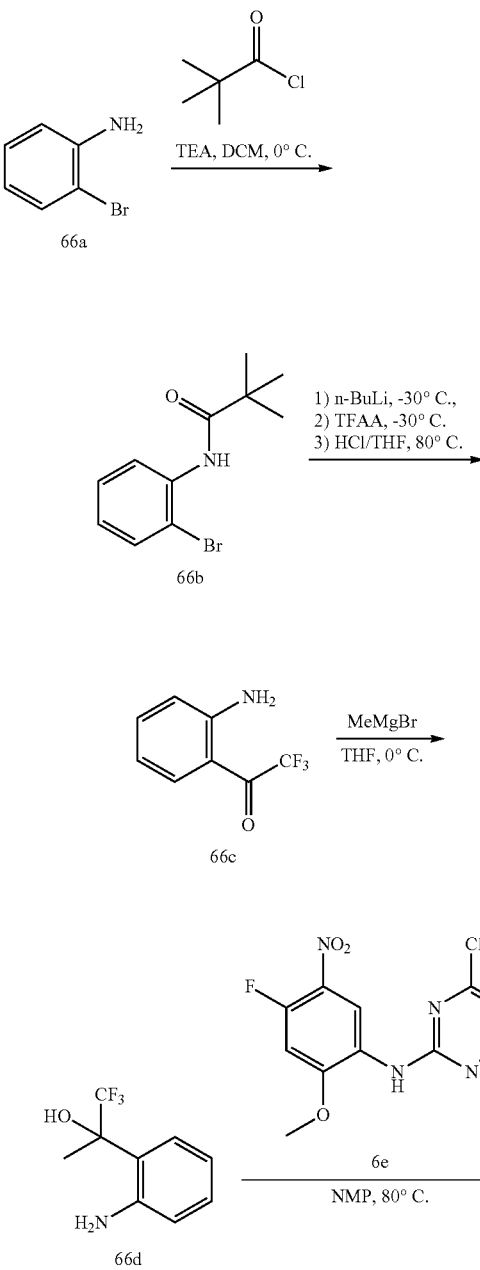

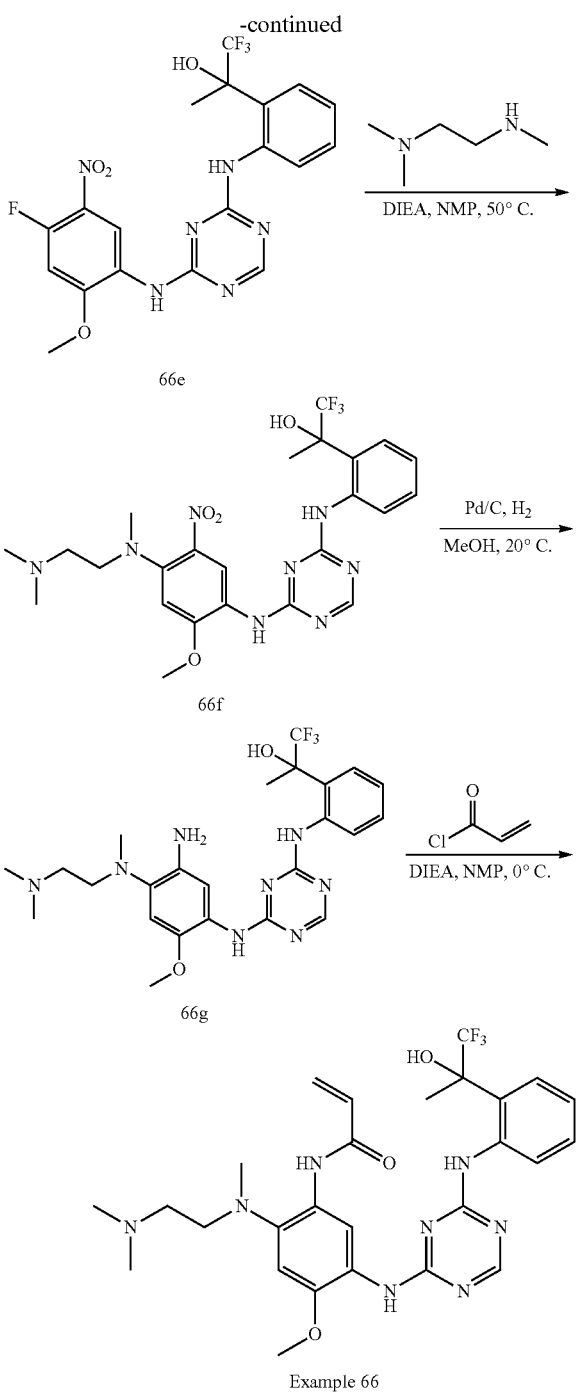

Example 66

Procedure for the Preparation of Compound 66b:

A solution of compound 66a (5.0 g, 29 mmol) and triethylamine (3.82 g, 38 mmol) in DCM (125 mL) was added pivaloyl chloride (3.855 g, 32 mmol) at 0° C. The resulting mixture was stirred at 20° C. for 16 h. The reaction mixture was diluted with water (100 mL) and the organic phase was separated. The aqueous phase was extracted with DCM (50 mL×3), and the combined organic layers were washed with brine (200 mL×1), dried over anhydrous $Na_2SO_4$, filtered and evaporated under reduced pressure. The residue was purified by flash silica chromatography, gradient elution from 10% to 30% EtOAc in petroleum ether (v/v). Pure fractions were evaporated to dryness to afford compound 66b (7.271 g, 98% yield) as a white solid.

LCMS: $R_f$=1.44 min in 3 min chromatography (3 min-5-95% MeCN in water (6 mmol/L $NH_4HCO_3$), Waters Acquity UPLC BEH C18 1.7 um, 2.1*50 mm, 40° C.), MS (ESI) m/z 257.2 $[M+H]^+$.

Procedure for the Preparation of Compound 66c:

To a solution of compound 66b (2.0 g, 7.8 mmol) in THF (46 mL) was added n-BuLi (12 mL, 1.6 M in hexane) at −30° C., the resulting mixture was stirred at −30° C. for 1 h. TFAA (2.5 g, 12 mmol) was added at −30° C., then the mixture was stirred at 20° C. for further 16 h. The mixture was quenched with 1 M HCl solution (32 mL) and extracted with EA (20 mL×5). The combined organics were dried over anhydrous sodium sulfate, filtered and concentrated under reduced pressure. The residue was treated with con. HCl (20 mL) and THF (20 mL), then the resulting mixture was heated at 80° C. for 16 h. The reaction mixture was diluted with saturated $NaHCO_3$ solution (100 mL), extracted with EA (50 mL×5). The combined organics were washed with brine (200 mL×1) and evaporated under reduced pressure. The residue was purified by silica gel flash chromatography, elution gradient from 0% to 30% EtOAc in petroleum ether. Pure fractions were evaporated to dryness to afford compound 66c (863 mg, 58% yield) as a brown oil.

$^1$H NMR (500 MHz, $CDCl_3$) δ ppm 6.4 (br s, 2H) 6.7-6.8 (m, 2H) 7.3-7.4 (m, 1H) 7.7-7.8 (m, 1H).

Procedure for the Preparation of Compound 66d:

To a solution of compound 66c (850 mg, 4.5 mmol) in THF (17 mL) was added methylmagnesium bromide (7.48 mL, 3M in THF) at 0° C. The resulting reaction was stirred at 20° C. for 1 h. The reaction was quenched with saturated $NH_4Cl$ solution (50 mL) and extracted with EA (50 mL×3). The combined organics were washed with brine, dried over anhydrous sodium sulfate, filtered and evaporated under reduced pressure. The residue was purified by silica gel flash chromatography, elution gradient from 10% to 50% EtOAc in petroleum ether. Pure fractions were evaporated to dryness to afford compound 66d (342 mg, 21% yield) as a brown oil.

LCMS: $R_f$=1.16 min in 3 min chromatography (3 min-5-95% MeCN in water (6 mmol/L $NH_4HCO_3$), Waters Acquity UPLC BEH C18 1.7 um, 2.1*50 mm, 40° C.), MS (ESI) m/z 206.1 $[M+H]^+$.

$^1$H NMR (500 MHz, DMSO-$d_6$) δ 1.7 (s, 3H) 5.5 (s, 2H) 6.5-6.5 (m, 1H) 6.6 (dd, J=7.9, 1.3 Hz, 1H) 6.9 (s, 1H) 7.0-7.0 (m, 1H) 7.1 (d, J=8.2 Hz, 1H).

Procedure for the Preparation of Compound 66e:

A solution of compound 6e (174 mg, 0.58 mmol) and compound 66d (120 mg, 0.58 mmol) in NMP (1 mL) was sealed and heated at 80° C. for 40 min. The reaction was diluted by water (50 mL) and extracted with EA (20 mL×5). The combined organic layers were washed with brine, dried over anhydrous sodium sulfate, filtered and evaporated under reduced pressure. The residue was purified by silica gel flash chromatography, elution gradient from 30% to 100% EtOAc in petroleum ether. Pure fractions were evaporated to dryness to afford compound 66e (235 mg, 85% yield) as a brown solid.

LCMS: $R_f$=1.90 min in 3 min chromatography (3 min-5-95% MeCN in water (6 mmol/L $NH_4HCO_3$), Waters Acquity UPLC BEH C18 1.7 um, 2.1*50 mm, 40° C.) MS (ESI) m/z 469.3 $[M+H]^+$.

Procedure for the Preparation of Compound 66f:

A solution of compound 66e (235 mg, 0.50 mmol), $N^1,N^1,N^2$-trimethylethane-1,2-diamine (72 mg, 0.70 mmol), and DIEA (194 mg, 1.5 mmol) in NMP (3.0 mL) was heated at 50° C. for 80 min. The reaction mixture was diluted with water (100 mL) and extracted with EA (20 mL×5). The combined organics was washed with brine, dried over anhydrous sodium sulfate, filtered and evaporated under reduced pressure. The residue was purified by silica gel flash chromatography, elution gradient from 0% to 10% MeOH in DCM. Pure fractions were evaporated to dryness to afford compound 66f (191 mg, 69% yield) as a light brown solid.

LCMS: $R_t$=1.28 min in 3 min chromatography (3 min-5-95% MeCN in water (6 mmol/L $NH_4HCO_3$), Waters Acquity UPLC BEH C18 1.7 um, 2.1*50 mm, 40° C.), MS (ESI) m/z 551.2 $[M+H]^+$.

Procedure for the Preparation of Compound 66g:

Palladium on carbon (37 mg) was added to a solution of compound 66f (95 mg, 0.17 mmol) in MeOH (10 mL). The resulting reaction was stirred at 20° C. under hydrogen atmosphere for 30 min. The mixture was filtered and the filtrate was evaporated under reduced pressure to afford compound 66 (90 mg, crude) as a light brown solid.

LCMS: $R_t$=1.19 min in 3 min chromatography (3 min-5-95% MeCN in water (6 mmol/L $NH_4HCO_3$), Waters Acquity UPLC BEH C18 1.7 um, 2.1*50 mm, 40° C.), MS (ESI) m/z 521.3 $[M+H]^+$.

Procedure for the Preparation of Example 66:

To a solution of compound 66g (90 mg, 0.17 mmol) and DIEA (67 mg, 0.52 mmol) in NMP (3 mL) was added a solution of acryloyl chloride (21 mg, 0.23 mmol) in NMP (0.5 mL) at 0° C. The reaction mixture was stirred at 0° C. for 30 min. Then the solution was purified by C18-flash chromatography, elution gradient from 0% to 60% MeCN in water (0.02% ammonia). Pure fractions were lyophilized to dryness to afford Example 66 (23 mg, 23% yield) as a light yellow solid.

LCMS: $R_t$=1.24 min in 3 min chromatography (3 min-5-95% MeCN in water (6 mmol/L $NH_4HCO_3$), Waters Acquity UPLC BEH C18 1.7 um, 2.1*50 mm, 40° C.), MS (ESI) m/z 575.3 $[M+H]^+$.

$^1$H NMR: (500 MHz, DMSO-$d_6$) δ 1.8 (br s, 3H) 2.2 (s, 6H) 2.3 (br t, J=5.7 Hz, 2H) 2.7 (s, 3H) 2.9 (br d, J=5.0 Hz, 2H) 3.8 (s, 3H) 5.7 (br d, J=10.7 Hz, 1H) 6.2 (br d, J=17.3 Hz, 1H) 6.4 (br dd, J=16.7, 10.1 Hz, 1H) 7.0 (s, 2H) 7.0-7.3 (m, 1H) 7.3-7.4 (m, 1H) 8.4 (s, 1H) 8.2 (s, 1H) 8.2-8.4 (m, 1H) 8.9 (brs, 1H) 10.1 (brs, 1H).

Example 67

N-(5-(4-(5-chloro-4-fluoro-2-(2-hydroxybutan-2-yl)phenylamino)-1,3,5-Rtiazin-2-ylamino)-2-((2-(dimethylamino)ethyl)(methyl)amino)-4-methoxyphenyl)acrylamide

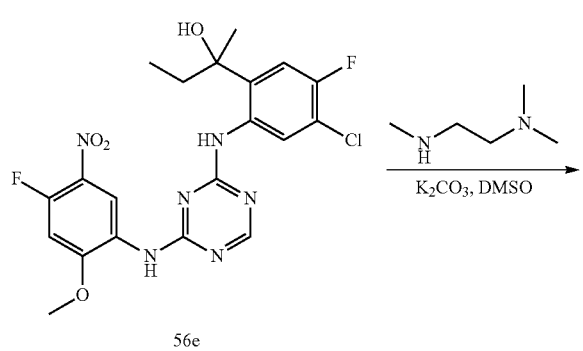

The synthesis followed a similar experimental procedure as Example 56 to afford Example 67 as a white solid.

LCMS: $R_t$=1.585 min in 10-80AB_3min_220&254 chromatography (Xtimate C18, 2.1*30 mm), MS (ESI) m/z=609.1 $[M+Na]^+$.

HPLC: $R_t$=3.45 10-80AB_1.2ml.met (Ultimate C18 3*50 mm 3 um).

$^1$H NMR: (400 MHz, $CDCl_3$) δ 10.84 (br s, 1H), 10.42 (br s, 1H), 9.94 (br s, 1H), 8.52 (br d, J=7.4 Hz, 1H), 8.41 (s, 1H), 7.70 (br s, 1H), 7.02 (d, J=10.8 Hz, 1H), 6.78 (s, 1H), 6.42-6.29 (m, 2H), 5.97 (br s, 1H), 5.82-5.72 (m, 1H), 3.88 (s, 3H), 2.92-2.82 (m, 2H), 2.70 (s, 3H), 2.42-2.31 (m, 8H), 2.18-2.02 (m, 2H), 1.70 (s, 3H), 0.88 (br t, J=7.6 Hz, 3H).

Example 68

(R)—N-(5-(4-(4,5-dichloro-2-(2-hydroxypropan-2-yl)phenylamino)pyrimidin-2-ylamino)-2-(3-(dimethylamino)pyrrolidin-1-yl)-4-methoxyphenyl)acrylamide

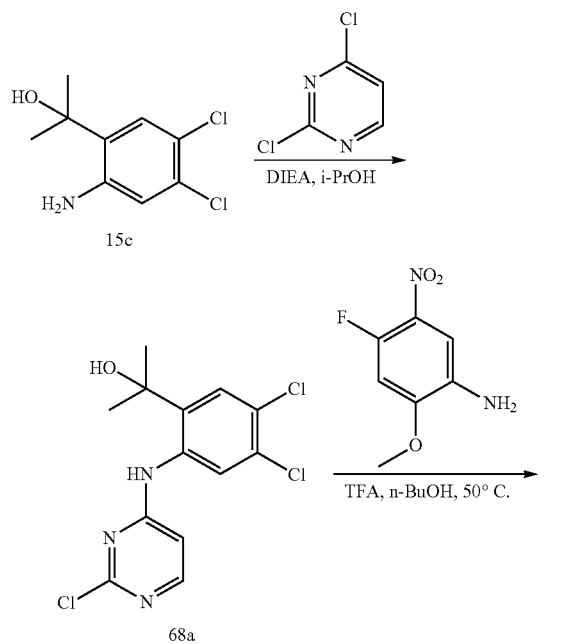

68a

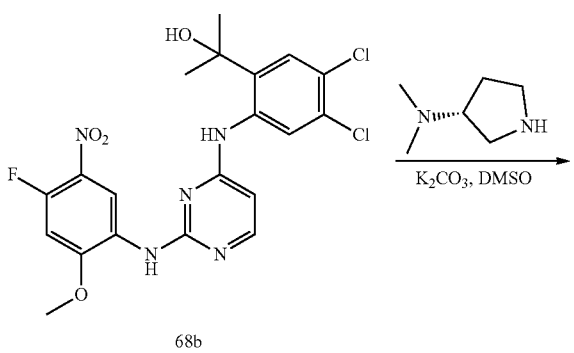

68b

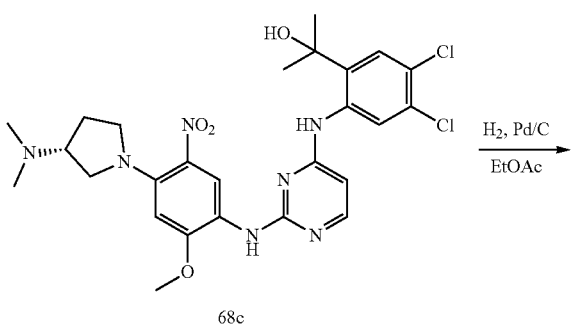

68c

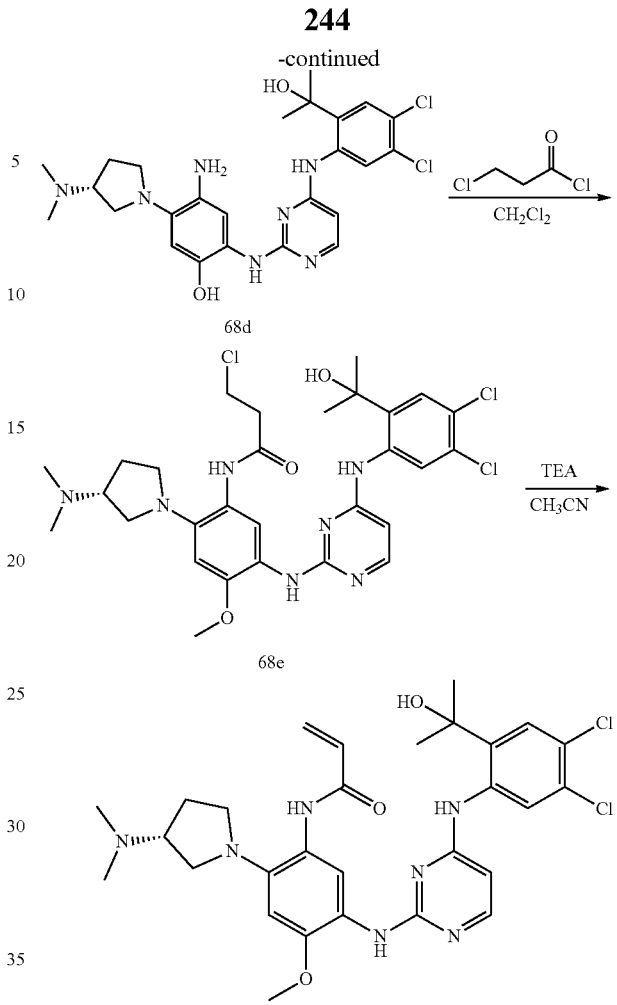

Example 68

Procedure for the Preparation of Compound 68a:
To a solution of compound 15c (900 mg, 4.09 mmol) and DIEA (1.1 g, 8.18 mmol) in isopropanol (2 mL) was added 2,4-dichloropyrimidine (730 mg, 4.90 mmol). The resulting mixture was heated at 90° C. for 48 h. The reaction mixture was concentrated in vacuum to give the crude product, which was purified by column chromatography on silica gel (25-35% EtOAc in petroleum ether) to give compound 68a (1.1 g, 81% yield) as white solid.
LCMS: $R_f$=0.883 min in 5-95AB_220&254.lcm chromatography (MERCK RP-18e 25-2 mm), MS (ESI) m/z=331.8/333.8 [M+H]$^+$.
$^1$H NMR (400 MHz, Methanol-$d_4$) δ 8.27 (s, 1H), 8.14 (d, J=6.0 Hz, 1H), 7.50 (s, 1H), 6.74 (d, J=6.0 Hz, 1H), 1.58 (s, 6H).

Procedure for the Preparation of Compound 68b:
To a solution of compound 68a (1.1 g, 3.31 mmol) and 4-fluoro-2-methoxy-5-nitroaniline (616 mg, 3.31 mmol) in n-BuOH (10 mL) was added TFA (0.1 mL). The resulting mixture was stirred at 50° C. for 12 h. The reaction mixture was filtered and the filtered cake was dried under reduced pressure to give compound 68b (1.3 g, 81% yield) as white solid.
LCMS: $R_f$=0.807 min in 5-95AB_1.5min_220&254 chromatography (MERCK RP18e 25-2 mm), MS (ESI) m/z=482.0 [M+H]$^+$.
$^1$H NMR (400 MHz, CDCl$_3$) δ 8.53 (br d, J=8.8 Hz, 1H), 8.02-7.92 (m, 2H), 7.53 (s, 1H), 7.22 (d, J=12.8 Hz, 1H), 6.49 (d, J=7.3 Hz, 1H), 4.00 (s, 3H), 1.59 (s, 6H).

245

Procedure for the Preparation of Compound 68c:

To a solution of compound 68b (200 mg, 0.41 mmol) and K$_2$CO$_3$ (113 mg, 0.82 mmol) in DMSO (5 mL) was added (R)—N,N-dimethylpyrrolidin-3-amine (56 mg, 0.49 mmol). The resulting mixture was stirred at 16-21° C. for 12 h while the color changes from pale yellow to deep yellow. The reaction mixture was pour into ice water (50 mL) and yellow solid was precipitated out. The solid was collected by filtration and dissolved with CH$_2$Cl$_2$ (20 mL), then dried over anhydrous Na$_2$SO$_4$ and concentrated under reduced pressure to give compound 68c (200 mg, 85% yield) as yellow solid.

LCMS: R$_t$=0.867 min in 5-95AB_1.5min_220&254 chromatography (MERCK RP18e 25-2 mm), MS (ESI) m/z=576.0 [M+H]$^+$.

Procedure for the Preparation of Compound 68d:

To a solution of compound 68c (200 mg, 0.35 mmol) in EtOAc (5 mL) was added Pd/C (40 mg). The resulting mixture was purged and degassed with H$_2$ for 3 times, then stirred at 12-17° C. under H$_2$ balloon, (15 Psi) for 1 h. The reaction mixture was filtered and concentrated under reduced pressure to give compound 68d (150 mg, 78% yield) as yellow solid.

LCMS: R$_t$=0.670 min in 5-95AB_1.5min_220&254 chromatography (MERCK RP18e 25-2 mm), MS (ESI) m/z=546.1 [M+H]$^+$.

$^1$H NMR (400 MHz, CDCl$_3$) δ 8.96 (s, 1H), 8.30 (s, 1H), 8.07 (d, J=5.6 Hz, 1H), 7.87 (s, 1H), 7.45 (s, 1H), 7.33 (s, 1H), 6.68 (s, 1H), 6.09 (d, J=5.6 Hz, 1H), 3.82 (s, 3H), 3.15 (br d, J=6.8 Hz, 2H), 3.05 (br d, J=6.4 Hz, 2H), 2.89 (s, 1H), 2.31 (s, 6H), 2.14 (br s, 1H), 1.90 (br s, 1H), 1.68 (s, 6H).

Procedure for the Preparation of Compound 68e:

To a solution of compound 68d (150 mg, 0.27 mmol) in CH$_2$Cl$_2$ (3 mL) was added 3-chloropropanoyl chloride (35 mg, 0.27 mmol) in ice water bath. The resulting mixture was stirred at 5-10° C. for 5 min while the color changed from brown to yellow. The reaction mixture was poured into saturated NaHCO$_3$ (5 mL) and extracted with CH$_2$Cl$_2$ (15 mL×2). The combined organic layers were dried over Na$_2$SO$_4$ and concentrated under reduced pressure to give the crude residue, which was purified by column chromatography on silica gel (10% MeOH in CH$_2$Cl$_2$) to give compound 68e (90 mg, 52% yield) as white solid.

LCMS: R$_t$=0.709 min in 5-95AB_1.5min_220&254 chromatography (MERCK RP18e 25-2 mm), MS (ESI) m/z=636.1/638.1 [M+H]$^+$.

$^1$H NMR (400 MHz, CDCl$_3$) δ 9.60-9.43 (m, 2H), 8.63-8.45 (m, 1H), 8.11 (d, J=5.6 Hz, 1H), 7.67 (s, 1H), 7.49 (s, 1H), 7.40 (s, 1H), 6.76 (s, 1H), 6.37 (s, 1H), 3.91 (br d, J=6.4 Hz, 2H), 3.86 (s, 3H), 3.10 (br s, 4H), 2.91 (br s, 2H), 2.33 (br s, 8H), 2.06 (s, 1H), 1.77-1.70 (m, 6H).

Procedure for the Preparation of Example 68:

To a solution of compound 68e (90 mg, 0.14 mmol) in CH$_3$CN (3 mL) was added TEA (42 mg, 0.42 mmol). The resulting mixture was stirred at 80° C. for 18 h. The reaction mixture was concentrated under reduced pressure and purified by flash column chromatography on silica gel (5% MeOH in CH$_2$Cl$_2$), the eluents were concentrated under reduced pressure and then lyophilized to afford Example 68 (33.1 mg, 31% yield) as light yellow solid.

LCMS: R$_t$=1.589 min in 10-80AB_4min_220&254 chromatography (Xtimate C18 2.1*30 mm), MS (ESI) m/z=600.0 [M+H]$^+$.

HPLC: R$_t$=2.42 min in 10-80_ab_1.2ML chromatography (Ultimate C18 3*50 mm 3 um).

$^1$H NMR (400 MHz, CDCl$_3$) δ 9.57 (br d, J=11.8 Hz, 2H), 8.04 (d, J=5.8 Hz, 1H), 7.52 (s, 1H), 7.41 (s, 1H), 7.32 (s,

246

1H), 6.65 (br s, 1H), 6.37-6.27 (m, 2H), 5.71 (br d, J=11.2 Hz, 1H), 3.79 (s, 3H), 3.12 (br d, J=12.8 Hz, 2H), 3.07-2.98 (m, 2H), 2.98-2.92 (m, 1H), 2.39 (br s, 6H), 2.15 (br s, 2H), 1.66 (s, 6H).

Example 69/Example 70

N-(5-(4-(5-chloro-4-fluoro-2-((R)-2-hydroxybutan-2-yl)phenylamino)-1,3,5-triazin-2-ylamino)-2-((R)-3-(dimethylamino)pyrrolidin-1-yl)-4-methoxyphenyl)acrylamide and N-(5-(4-(5-chloro-4-fluoro-2-((S)-2-hydroxybutan-2-yl)phenylamino)-1,3,5-triazin-2-ylamino)-2-((R)-3-(dimethylamino)pyrrolidin-1-yl)-4-methoxyphenyl)acrylamide

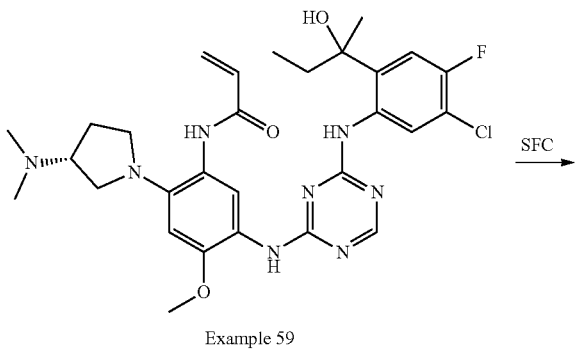

Example 59

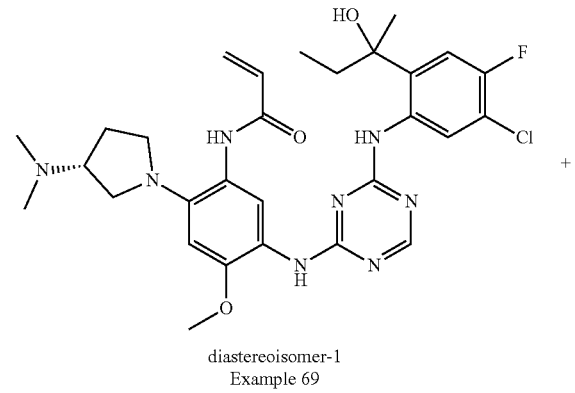

diastereoisomer-1
Example 69

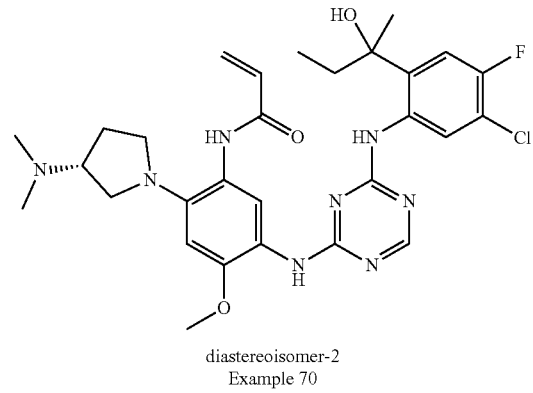

diastereoisomer-2
Example 70

Example 59 (50 mg, 0.0835 mmol) was separated by SFC to give Example 69 (21.0 mg, 42% yield) as a white solid and Example 70 (24.6 mg, 49.2% yield) as a white solid.

Example 69

LCMS: R$_t$=1.840 min in 10-80AB_4min_220&254 chromatography (Xtimate C18 2.1*30 mm), MS (ESI) m/z=621.0 [M+Na]$^+$.

HPLC: R$_t$=3.88 min in 10-80_CD_1.2 ml chromatography (XBridge Shield RP 18 2.1*50 mm 5 um).

$^1$H NMR (400 MHz, CDCl$_3$) δ 10.79 (br s, 1H), 9.69 (br s, 1H), 8.79 (br s, 1H), 8.53 (d, J=7.2 Hz, 1H), 8.40 (s, 1H), 7.61 (br s, 1H), 7.01 (d, J=10.8 Hz, 1H), 6.73 (br s, 1H), 6.67 (s, 1H), 6.37 (d, J=16.4 Hz, 1H), 5.79 (d, J=10.8 Hz, 1H), 5.70 (br s, 1H), 3.87 (s, 3H), 3.41-3.24 (m, 2H), 3.18 (br s, 1H), 3.07 (dd, J=6.4, 10.0 Hz, 1H), 2.98 (q, J=8.0 Hz, 1H), 2.55 (s, 6H), 2.30-2.20 (m, 2H), 2.14-2.08 (m, 1H), 2.04-1.99 (m, 1H), 1.69 (s, 3H), 0.88 (t, J=7.6 Hz, 3H).

SFC: R$_t$=6.855 min in AD-3_IPA(DEA)_5-40-2.5ML.

Example 70

LCMS: R$_t$=1.850 min in 10-80AB_4min_220&254 chromatography (Xtimate C18 2.1*30 mm), MS (ESI) m/z=599.0 [M+H]$^+$.

HPLC: R$_t$=3.85 min in 10-80_CD_1.2 ml chromatography (XBridge Shield RP 18 2.1*50 mm 5 um).

$^1$H NMR (400 MHz, CDCl$_3$) δ 10.79 (br s, 1H), 9.68 (br s, 1H), 8.86 (br s, 1H), 8.52 (d, J=7.2 Hz, 1H), 8.41 (s, 1H), 7.61 (br s, 1H), 7.01 (d, J=10.8 Hz, 1H), 6.84 (br s, 1H), 6.66 (s, 1H), 6.37 (d, J=16.4 Hz, 1H), 5.80 (d, J=11.2 Hz, 1H), 5.71 (br s, 1H), 3.87 (s, 3H), 3.45-3.31 (m, 2H), 3.25 (br s, 1H), 3.06 (dd, J=6.6, 10.4 Hz, 1H), 2.96 (q, J=8.0 Hz, 1H), 2.60 (br s, 6H), 2.35-2.19 (m, 2H), 2.15-2.09 (m, 1H), 2.04-2.00 (m, 1H), 1.69 (s, 3H), 0.87 (t, J=7.6 Hz, 3H).

SFC: R$_t$=7.292 min in AD-3IPA(DEA)_540-2.5ML.

Example 71

(R)—N-(5-(4-(4,5-dichloro-2-(2-hydroxypropan-2-yl)phenylamino)pyrimidin-2-ylamino)-2-(2-((dimethylamino)methyl)azetidin-1-yl)-4-methoxyphenyl)acrylamide

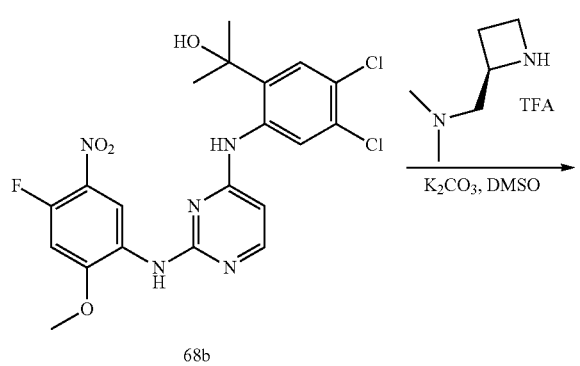

68b

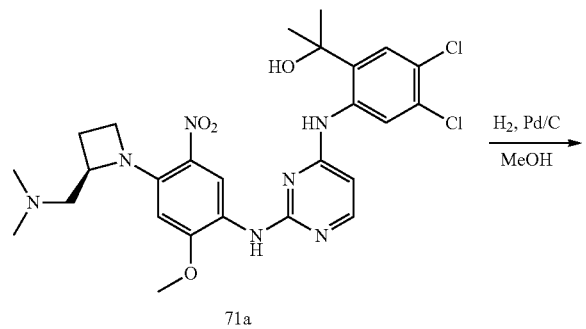

71a

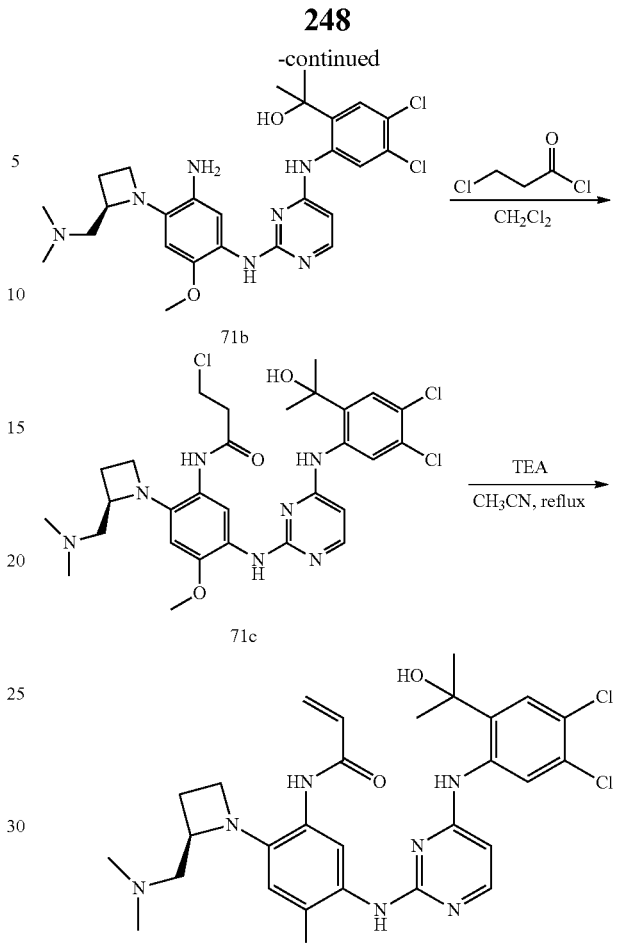

Example 71

Procedure for the Preparation of Compound 71a:

To a solution of compound 68b (200 mg, 0.42 mmol) and K$_2$CO$_3$ (1.2 g, 8.4 mmol) in DMSO (5 mL) was added (R)-1-(azetidin-2-yl)-N,N-dimethylmethanamine TFA salt (887 mg, 4.2 mmol). The resulting mixture was stirred at 50° C. for 1 h. The reaction mixture was added drop wise into H$_2$O (100 mL) under ice water bath with stirring, the precipitated solid was filtered and the filter cake was dissolved with CH$_2$Cl$_2$ (45 mL), then dried and concentrated in vacuum to give crude product, which was further purified by flash reversed-phase C-18 column chromatography eluting with MeOH/TFA/H$_2$O (MeOH in water from 10% to 100%) to give compound 71a (180 mg, 74% yield) as a yellow solid.

LCMS: R$_t$=0.710 min in 5-95AB_1.5min_220&254 chromatography (Xtimate C18 2.1*30 mm), MS (ESI) m/z=576.1 [M+H]$^+$.

Procedure for the Preparation of Compound 71b:

To a solution of 71a (180 mg, 0.31 mmol) in MeOH (10 mL) was added Pd/C (40 mg). The resulting mixture was purged and degassed with H$_2$ for 3 times, then stirred at 15-21° C. under H$_2$ balloon (15 Psi) for 1 h. The reaction mixture was filtered and the filtrate was concentrated under reduced pressure to give compound 71b (140 mg, 73% yield) as a black solid.

LCMS: R$_t$=0.689 min in 5-95AB_1.5min_220&254 chromatography (Xtimate C18 2.1*30 mm), MS (ESI) m/z=546.1[M+H]$^+$.

Procedure for the Preparation of Compound 71c:

To a solution of compound 71b (110 mg, 0.2 mmol) in CH$_2$Cl$_2$ (3 mL) was added 3-chloropropanoyl chloride (26 mg, 0.2 mmol) under ice water bath. The resulting mixture was stirred at 5-10° C. for 45 min while the color changed from black to brown. The reaction mixture was poured into saturated NaHCO$_3$ (5 mL), extracted with CH$_2$Cl$_2$ (15 mL×2). The combined organic layers were washed with water (10 mL×2) and brine (10 mL) successively, dried and concentrated in vacuum to give the crude residue, which was purified by column chromatography on silica gel (0-5% MeOH in CH$_2$Cl$_2$) to give compound 71c (50 mg, 39% yield) as a brown solid.

LCMS: R$_t$=0.883 min in 10-80AB_2min_220&254 chromatography (Xtimate C18 2.1*30 mm), MS (ESI) m/z=636.1 [M+H]$^+$.

Procedure for the Preparation of Example 71:

To a solution of compound 71c (50 mg, 0.078 mmol) in CH$_3$CN (5 mL) was added Et$_3$N (32 mg, 0.31 mmol). The resulting mixture was stirred at 80° C. for 12 h. The reaction mixture was concentrated in vacuum to give the crude, which was purified by column chromatography on silica gel (0-5% MeOH in CH$_2$Cl$_2$) and then dried and lyophilized to afford Example 71 (24.1 mg, 51% yield) as an off-white solid.

LCMS: R$_t$=1.648 min in 10-80AB_4min_220&254 chromatography (Xtimate C18 2.1*30 mm), MS (ESI) m/z=600.0 [M+H]$^+$.

HPLC: R$_t$=2.42 min in 10-80AB_1.2ML chromatography (Ultimate C18 3*50 mm 3 um).

$^1$H NMR (400 MHz, CDCl$_3$) δ 9.76 (br s, 1H), 9.40 (br s, 1H), 8.76 (br s, 1H), 8.06 (d, J=5.6 Hz, 1H), 7.86-7.55 (m, 2H), 7.39 (s, 1H), 6.86 (br s, 1H), 6.67 (s, 1H), 6.43-6.35 (m, 2H), 5.80 (d, J=11.6 Hz, 1H), 5.70-5.43 (m, 1H), 4.69 (br s, 1H), 4.09 (br s, 1H), 3.95 (s, 3H), 3.45-3.33 (m, 1H), 3.16-3.08 (m, 2H), 2.75 (br s, 6H), 2.56-2.45 (m, 1H), 2.43-2.34 (m, 1H), 1.71 (s, 6H).

Example 72

N-(5-(4-(5-chloro-4-fluoro-2-(1-hydroxycyclobutyl)phenylamino)-1,3,5-triazin-2-ylamino)-2-((2-(dimethylamino)ethyl)(methyl)amino)-4-methoxyphenyl)acrylamide formic Acid Salt

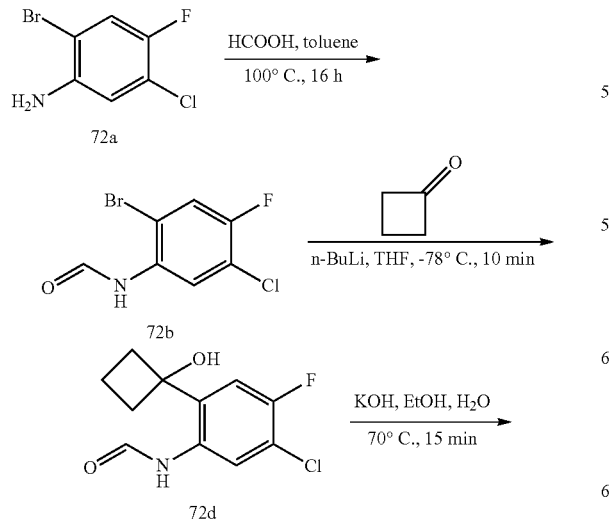

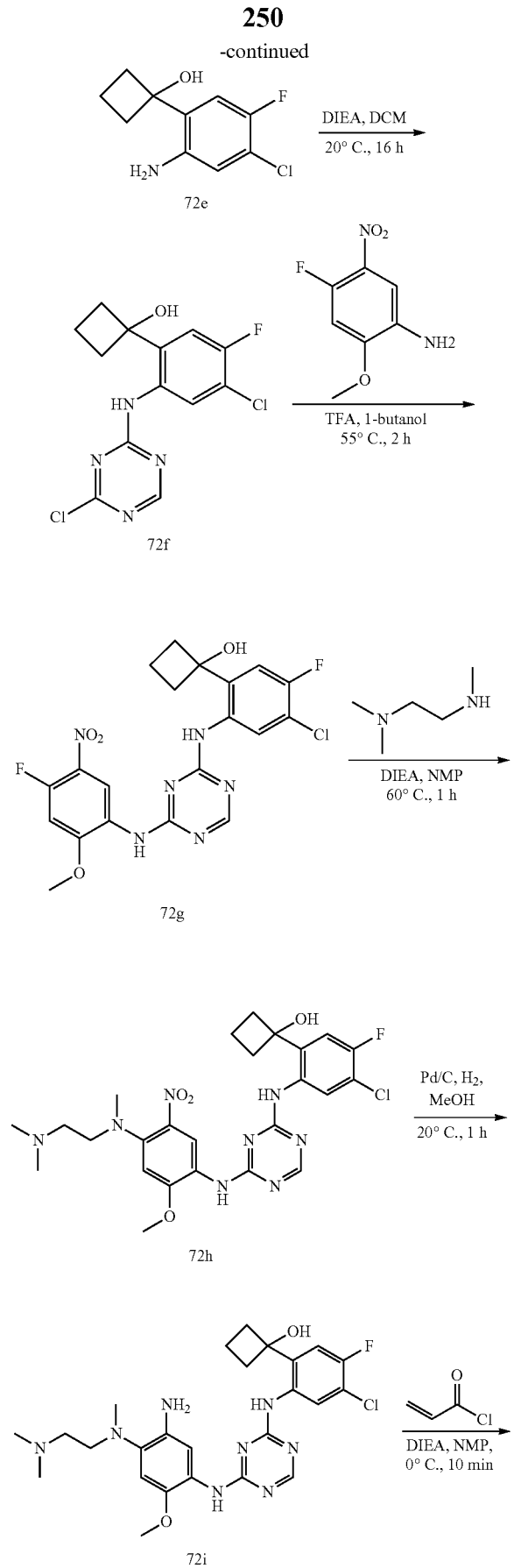

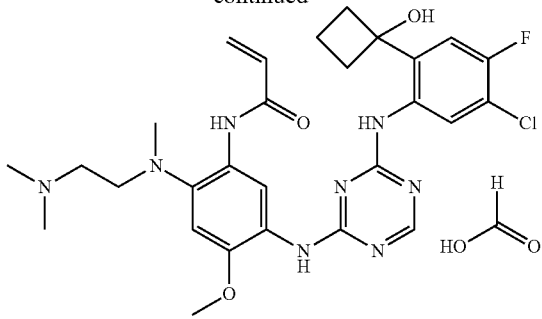

Example 72

Procedure for the Preparation of Compound 72b:

To a mixture of compound 72a (2.0 g, 9.0 mmol) in toluene (15 mL) was added formic acid (1.0 g, 22 mmol), the resulting mixture was refluxed for 8 hours. The mixture was concentrated in vacuum and the crude product was washed with methanol (10 mL), and then filtered. The solid was dried in vacuum to afford compound 72b (1.6 g, 71% yield) as a white solid.

LCMS: $R_f$=1.12 min in 3 min chromatography (3 min-5-95% MeCN in water (0.02% FA), Waters Acquity UPLC BEH C18 1.7 um, 2.1*50 mm, 40° C.), MS (ESI) m/z 252.0, 254.0 [M+H]$^+$.

Procedure for the Preparation of Compound 72c:

To a mixture of compound 72b (1.6 g, 6.3 mmol) was added n-BuLi (10 mL, 1.6M in hexane) at −78° C. under nitrogen atmosphere in 3 min followed by cyclobutanone (1 g, 14 mmol). The resulting mixture was stirred at −78° C. for 10 min under nitrogen atmosphere. The mixture was quenched by saturated NH$_4$Cl aqueous solution (50 mL) and extracted with EtOAc (50 mL). The organic layer was concentrated in vacuum to afford compound 2c (500 mg, 32% yield) as a yellow oil.

LCMS: $R_f$=1.06 min in 3 min chromatography (3 min-5-95% MeCN in water (0.02% FA), Waters Acquity UPLC BEH C18 1.7 um, 2.1*50 mm, 40° C.), MS (ESI) m/z 226.0 [M+H]$^+$.

Procedure for the Preparation of Compound 72d:

To a mixture of compound 72c (500 mg, 2.1 mmol) in ethanol (3 mL) was added potassium hydroxide (200 mg, 3.6 mmol) and water (2 mL), the resulting mixture was heated at 70° C. for 15 min under nitrogen atmosphere. The mixture was diluted with saturated NH$_4$Cl aqueous solution (50 mL) and extracted with EtOAc (50 mL). The organic layer was concentrated in vacuum, the residue was purified by C18-flash chromatography, elution gradient from 5% to 60% MeCN in water (0.02% FA). Pure fractions were evaporated to dryness to afford compound 72d (320 mg, 72% yield) as a yellow solid.

LCMS: $R_f$=1.12 min in 3 min chromatography (3 min-5-95% MeCN in water (0.02% FA), Waters Acquity UPLC BEH C18 1.7 um, 2.1*50 mm, 40° C.), MS (ESI) m/z 198.2 [M+H]$^+$.

Procedure for the Preparation of Compound 72e:

To a mixture of compound 72d (302 mg, 1.4 mmol) in DCM (5 mL) was added 2,4-dichloro-1,3,5-triazine (300 mg, 2.0 mmol) and DIEA (300 mg, 2.3 mmol), the resulting mixture was stirred at 20° C. for 16 hours. The mixture was then purified by flash silica chromatography, elution gradient from 5% to 50% EtOAc in petroleum ether. Pure fractions were evaporated to dryness to afford compound 72e (350 mg, 77% yield) as a yellow solid.

LCMS: $R_f$=1.39 min in 3 min chromatography (3 min-5-95% MeCN in water (0.02% FA), Waters Acquity UPLC BEH C18 1.7 um, 2.1*50 mm, 40° C.), MS (ESI) m/z 329.1 [M+H]$^+$.

Procedure for the Preparation of Compound 72f:

To a mixture of compound 72e (160 mg, 0.49 mmol) in 1-butanol (8 mL) was added 4-fluoro-2-methoxy-5-nitroaniline (80 mg, 0.54 mmol) and TFA (20 mg, 0.21 mmol), the resulting mixture was stirred at 55° C. for 2 hours. The mixture was then purified by C18-flash chromatography, elution gradient from 5% to 70% MeCN in water (0.02% FA). Pure fractions were evaporated to dryness to afford compound 72f (150 mg, 64% yield) as a yellow solid.

LCMS: $R_f$=1.40 min in 3 min chromatography (3 min-5-95% MeCN in water (0.02% FA), Waters Acquity UPLC BEH C18 1.7 um, 2.1*50 mm, 40° C.), MS (ESI) m/z 479.1 [M+H]$^+$.

Procedure for the Preparation of Compound 72g:

To a mixture of compound 72f (80 mg, 0.17 mmol) in NMP (5 mL) was added N,N,N'-Trimethylethylenediamine (30 mg, 0.29 mmol) and DIEA (40 mg, 0.31 mmol), the resulting mixture was stirred at 60° C. for 1 hour. The mixture was then purified by C18-flash chromatography, elution gradient from 5% to 60% MeCN in water (0.02% FA). Pure fractions were evaporated to dryness to afford compound 72g (70 mg, 75% yield) as a yellow solid.

LCMS: $R_f$=1.00 min in 3 min chromatography (3 min-5-95% MeCN in water (0.02% FA), Waters Acquity UPLC BEH C18 1.7 um, 2.1*50 mm, 40° C.), MS (ESI) m/z 560.2 [M+H]$^+$.

Procedure for the Preparation of Compound 72h:

To a mixture of compound 72g (70 mg, 0.13 mmol) in methanol (5 mL) was added palladium on carbon (20 mg), the resulting mixture was stirred at 20° C. for 1 hour under hydrogen atmosphere. The mixture was then filter and the filtrate were concentrated in vacuum to afford compound 72h (50 mg, 76% yield) as a white solid.

LCMS: $R_f$=0.92 min in 3 min chromatography (3 min-5-95% MeCN in water (0.02% FA), Waters Acquity UPLC BEH C18 1.7 um, 2.1*50 mm, 40° C.), MS (ESI) m/z 531.3 [M+H]$^+$.

Procedure for the Preparation of Example 72:

To a mixture of compound 72h (50 mg, 0.094 mmol) in NMP (2 mL) was added acryloyl chloride (10 mg, 0.11 mmol) and DIEA (30 mg, 0.23 mmol) at 0° C., the resulting solution was stirred at 0° C. for 10 min. The mixture was purified by C18-flash chromatography, elution gradient from 5% to 60% MeCN in water (0.02% FA). Pure fractions were evaporated to dryness to afford Example 72 in the form of formic acid salt (28 mg, 51% yield) as a white solid.

LCMS: $R_f$=0.97 min in 3 min chromatography (3 min-5-95% MeCN in water (0.02% FA), Waters Acquity UPLC BEH C18 1.7 um, 2.1*50 mm, 40° C.), MS (ESI) m/z 585.3 [M+H]$^+$.

$^1$H NMR: (500 MHz, DMSO-d$_6$) δ 1.46 (br d, J=7.57 Hz, 1H) 1.83 (br s, 1H) 2.23-2.32 (m, 2H) 2.35-2.44 (m, 2H) 2.51-2.57 (m, 2H) 2.59 (s, 3H) 2.79 (s, 3H) 2.80 (s, 3H) 3.26-3.27 (m, 2H) 3.81 (s, 3H) 5.76 (br d, J=10.40 Hz, 1H) 6.25 (br d, J=17.34 Hz, 1H) 6.52 (br s, 1H) 6.64 (br dd, J=17.18, 10.25 Hz, 1H) 7.00 (br s, 1H) 7.40 (br s, 1H) 8.04 (br s, 1H) 8.26 (s, 1H) 8.81-9.22 (m, 2H) 9.24-9.51 (m, 2H).

Example 73

(R)—N-(5-(4-(5-chloro-4-fluoro-2-(2-hydroxypropan-2-yl)phenylamino)-1,3,5-triazin-2-ylamino)-4-methoxy-2-(3-(methylamino)pyrrolidin-1-yl)phenyl)acrylamide

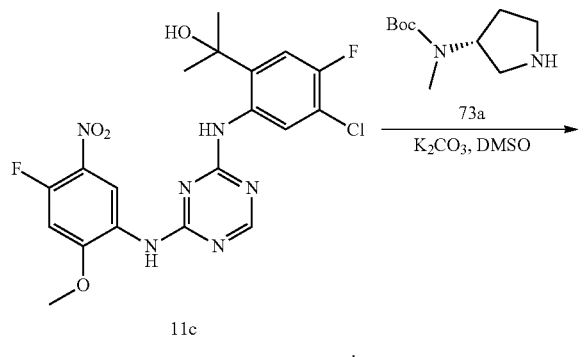

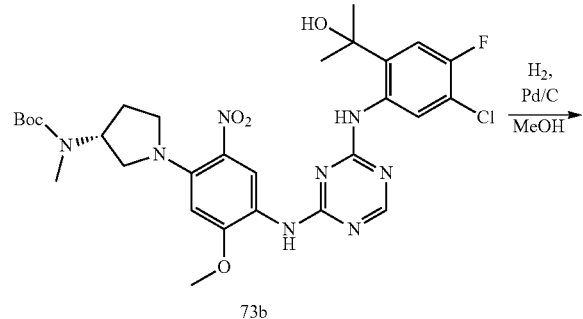

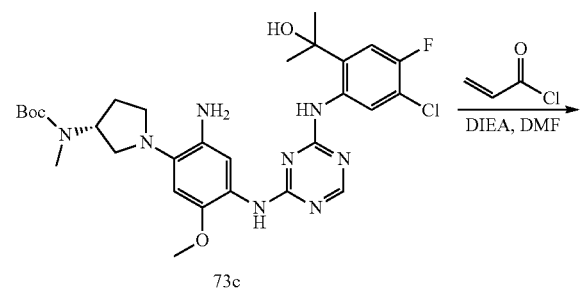

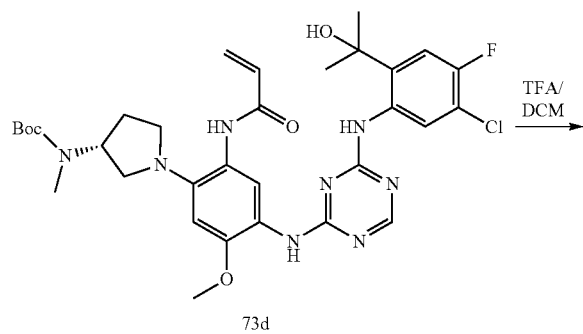

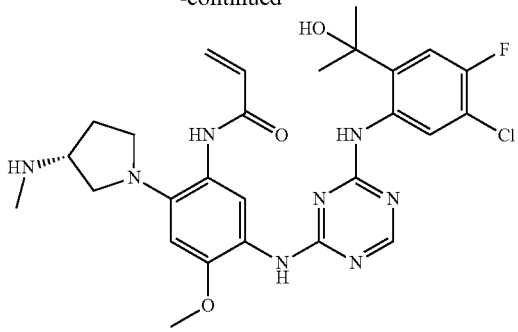

Example 73

Procedure for the Preparation of Compound 73b:

A solution of compound 11c (200 mg, 0.428 mmol), compound 73a (128.71 mg, 0.642 mmol) and K$_2$CO$_3$ (118.4 mg, 0.856 mmol) in DMSO (2 mL) was stirred at 85° C. for 2 h. The reaction was combined with previous batch and added into H$_2$O (20 mL) under ice water bath with stirring, the precipitated solid was filtered and the filter cake was dissolved with CH$_2$Cl$_2$ (50 mL), dried and concentrated in vacuum to give compound 73b (430 mg, 88.6% yield) as an orange solid.

LCMS: R$_f$=0.873 min in 5-95AB_220&254.lcm chromatography (MERCK RP18 2.5-2 mm), MS (ESI) m/z=647.1 [M+H]$^+$.

$^1$H NMR (400 MHz, CDCl$_3$) δ 9.71 (br s, 1H), 8.96 (br s, 1H), 8.38 (m, 2H), 7.36 (s, 1H), 7.08 (d, J=10.4 Hz, 1H), 6.32 (s, 1H), 4.82 (m, 1H), 3.96 (s, 3H), 3.43-3.28 (m, 3H), 3.14-3.04 (m, 1H), 2.86 (s, 3H), 2.22-2.10 (m, 2H), 1.70 (s, 6H), 1.47 (s, 9H).

Procedure for the Preparation of Compound 73c:

To a solution of compound 73b (380 mg, 0.587 mmol) in MeOH (5 mL) was added Pd/C (200 mg). The resulting mixture was stirred at 16-21° C. for 3 h under H2 balloon (15 Psi). The reaction mixture was filtered, the filtrate was combined with previous batch and concentrated in vacuum to give compound 73c (380 mg, 92.7% yield) as a brown solid.

LCMS: R$_f$=0.823 min in 5-95AB_220&254.lcm chromatography (MERCK RP18 2.5-2 mm), MS (ESI) m/z=617.2 [M+H]$^+$.

$^1$H NMR: (400 MHz, CDCl$_3$) δ 9.61 (br s, 1H), 8.33 (m, 2H), 7.87-7.33 (m, 2H), 7.09 (d, J=10.4 Hz, 1H), 6.63 (s, 1H), 4.91 (br s, 1H), 3.83 (s, 3H), 3.80-3.55 (m, 2H), 3.20 (m, 1H), 3.12-3.06 (m, 2H), 2.92 (s, 3H), 2.32-2.21 (m, 1H), 1.98-1.87 (m, 1H), 1.68 (s, 6H), 1.48 (s, 9H).

Procedure for the Preparation of Compound 73d:

To a solution of compound 73c (280.0 mg, 0.453 mmol) and DIEA (87.65 mg, 0.679 mmol) in DMF (2 mL) was added acryloyl chloride (41.07 mg, 0.453 mmol) drop wise at 0° C. The resulting mixture was stirred at 0° C. for 1 h. The reaction mixture was quenched with H$_2$O (0.2 mL), it was combined with previous batch and purified by C18-reverse flash column chromatography (MeOH and water) to give compound 73d (114 mg, 27.6% yield).

LCMS: R$_f$=0.868 min in 5-95AB_220&254.lcm chromatography (MERCK RP18 2.5-2 mm), MS (ESI) m/z=671.3 [M+H]$^+$.

$^1$H NMR (400 MHz, CDCl$_3$) δ 10.55 (br s, 1H), 9.87 (br s, 1H), 8.72-8.51 (m, 1H), 8.49 (br d, J=7.6 Hz, 1H), 8.42 (s, 1H), 7.66 (br s, 1H), 7.10 (d, J=10.8 Hz, 1H), 6.72 (s, 1H), 6.39 (br s, 2H), 6.02-5.63 (m, 2H), 4.71 (br s, 1H), 3.89 (s,

3H), 3.19-3.11 (m, 2H), 3.05-2.99 (m, 2H), 2.95 (s, 3H), 2.38-2.25 (m, 1H), 2.10-2.00 (m, 1H), 1.77 (s, 6H), 1.50 (s, 9H).

Procedure for the Preparation of Example 73:

To a solution of compound 73d (94 mg, 0.146 mmol) in CH₂Cl₂ (3 mL) was added TFA (1 mL) at 15-21° C. The resulting mixture was then stirred at this temperature for 12 h. The reaction was combined with previous batch and purified by preparative HPLC (Instrument: BH Column: Gemini 150*25 5 um. Mobile A: water 0.05% ammonia hydroxide v/v Mobile B: CH₃CN Flow rate: 25 ml/min Gradient Time: 7 min Profile Descriptive: 42%-72%) to give Example 73 (27.0 mg, 27.8% yield) as a white solid.

LCMS: $R_t$=1.317 min in 10-80AB_4min_220&254 chromatography (A: Xtimate C18, 2.1*30 mm, 3 um; B: XBrige Shield RP18 2.1*50 mm), MS (ESI) m/z=571.2 [M+H]⁺.

HPLC: $R_t$=3.02 min in 10-80_CD_1.2ml. met, XBridge Shield RP 18 2.1*50 mm 5 um.

¹H NMR: (400 MHz, CDCl₃) δ 10.54 (br s, 1H), 9.77 (br s, 1H), 8.72 (br s, 1H), 8.48 (d, J=7.2 Hz, 1H), 8.41 (s, 1H), 7.63 (br s, 1H), 7.09 (d, J=10.4 Hz, 1H), 6.72 (s, 1H), 6.51-6.30 (m, 2H), 5.80 (br d, J=11.4 Hz, 1H), 6.04-5.68 (m, 1H), 3.87 (s, 3H), 3.73 (m, 1H), 3.72-3.66 (m, 1H), 3.49 (s, 1H), 2.98 (m, 3H), 2.48 (s, 3H), 2.32-2.24 (m, 1H), 1.85-1.79 (m, 1H), 1.76 (s, 6H).

Example 74

(R)—N-(5-(5-chloro-4-(5-chloro-4-fluoro-2-(2-hydroxypropan-2-yl)phenylamino) pyrimidin-2-ylamino)-2-(3-(dimethylamino)pyrrolidin-1-yl)-4-methoxyphenyl) acrylamide

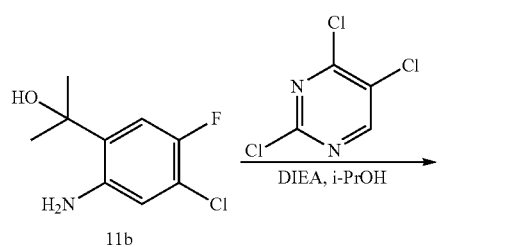

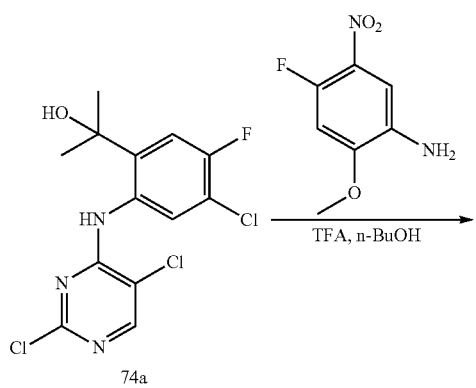

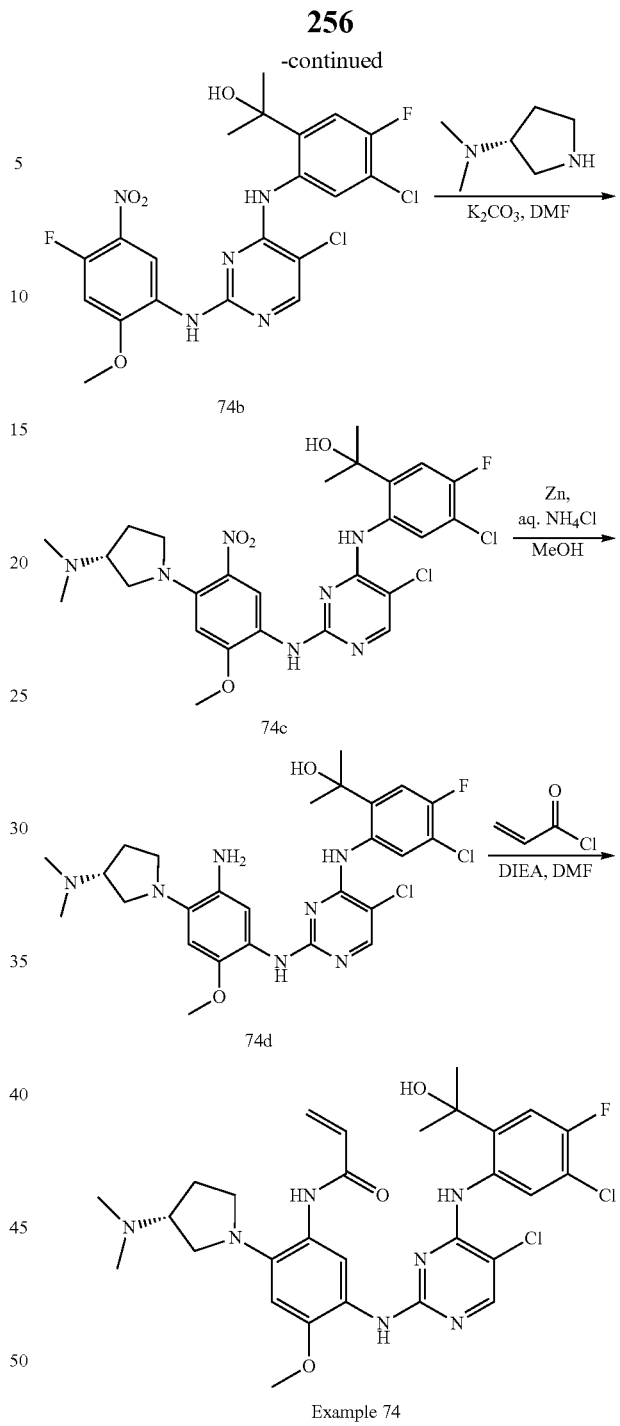

Procedure for the Preparation of Compound 74a:

The mixture of compound 11b (350 mg, 1.72 mmol), 2,4,5-trichloropyrimidine (314.5 mg, 1.72 mmol) and DIEA (444 mg, 3.44 mmol) in i-PrOH (5 mL) was stirred at 80° C. for 5 hr. The reaction mixture was combined with previous batch and concentrated in vacuum to give the crude residue, which was purified by flash column chromatography on silica gel twice (0-10% EtOAc in petroleum ether) to afford compound 74a (580 mg, 84.6% yield) as an off-white solid.

LCMS: $R_t$=0.870 min in 5-95AB_220&254.lcm chromatography (MERCK RP18 2.5-2 mm), MS (ESI) m/z=351.8 [M+H+2]⁺.

¹H NMR: (400 MHz, CDCl₃) δ 8.45 (d, J=7.2 Hz, 1H), 8.17 (s, 1H), 7.09 (d, J=10.4 Hz, 1H), 2.77 (br s, 1H), 1.68 (s, 6H).

Procedure for the Preparation of Compound 74b:

The mixture of compound 74a (500 mg, 1.43 mmol), 4-fluoro-2-methoxy-5-nitroaniline (345 mg, 1.85 mmol) and TFA (350 uL) in n-BuOH (3.5 mL) was stirred at 100° C. for 5 hr. The reaction was combined with previous batch and then filtered, the filtered cake was washed with n-BuOH (2 mL) and dried in vacuo to give compound 74b (560 mg, 71.4% yield) as a grey solid.

LCMS: $R_t$=0.836 min in 5-95AB_220&254.lcm chromatography (MERCK RP-18e 25-2 mm), MS (ESI) m/z=500.1 [M+H]⁺.

Procedure for the Preparation of Compound 74c:

The mixture of compound 74b (150 mg, 0.3 mmol), (R)—N,N-dimethylpyrrolidin-3-amine (41.1 mg, 0.36 mmol) and K₂CO₃ (83.0 mg, 0.6 mmol) in DMSO (2 mL) was stirred at 80° C. for 5 h (brown suspension). The reaction was combined with previous batch and added into H₂O (10 mL) while solid was precipitated out. The solid was collected by filtration and washed with H₂O (5 mL), dried in high vacuum to give compound 74c (220 mg, 92.8% yield) as a brown solid.

LCMS: $R_t$=0.709 min in 5-95AB_220&254.lcm chromatography (MERCK RP-18e 25-2 mm), MS (ESI) m/z=594.1 [M+H]⁺.

Procedure for the Preparation of Compound 74d:

The mixture of compound 74c (180 mg, 0.3 mmol), Zn (98.4 mg, 1.5 mmol) and NH₄Cl (81 mg, 1.5 mmol) in MeOH/H₂O (5.0/2.0 mL) was stirred at 80° C. for 3 hr (black suspension). The reaction mixture was filtered and the filter cake was washed with CH₂Cl₂ (20 mL) and H₂O (5 mL) successively, the filtrate was extracted with CH₂Cl₂ (30 mL×3). The combined organic layer was washed with brine (20 mL), dried over Na₂SO₄ and concentrated in vacuum to give the crude residue, which was purified by flash column chromatography on silica gel (eluting with MeOH/CH₂Cl₂=10/1 (v/v)) to give compound 74d (130 mg, 76.0% yield) as a grey solid.

LCMS: $R_t$=0.708 min in 5-95AB_220&254.lcm chromatography (MERCK RP-18e 25-2 mm), MS (ESI) m/z=564.1 [M+H]⁺.

Procedure for the Preparation of Example 74:

To the mixture of compound 74d (130 mg, 0.23 mmol) and DIEA (89.1 mg, 0.69 mmol) in DMF (3 mL) was added acryloyl chloride (31.0 mg, 0.34 mmol) drop wise under ice water bath. After the reaction was stirred at 0-5° C. for 4 hr, the brown solution was quenched with MeOH (0.05 mL) and purified by prep-HPLC directly [Xtimate C18 150*25 mm*5 um Condition: 44-74% B (A: 0.04% ammonia+10 mM NH₄HCO₃ B: CH₃CN); Flow rate: 30 ml/min]. Fractions containing the desired compound were lyophilized to afford Example 74 (32.4 mg, 22.8% yield) as a white solid.

LCMS: $R_t$=2.266 min in 0-60AB_4.0min_220&254 chromatography (Xtimate C18 2.1*30 mm), MS (ESI) m/z=618.0 [M+H]⁺.

HPLC: $R_t$=5.68 min in 0-60_CD_1.2ML chromatography (XBridge Shield RP 18 2.1*50 mm 5 um).

¹H NMR: (400 MHz, CDCl₃) δ 9.76 (br s, 1H), 8.93 (br s, 1H), 8.46 (d, J=7.2 Hz, 1H), 8.20 (br s, 1H), 8.11 (s, 1H), 7.18 (s, 1H), 6.87 (d, J=10.4 Hz, 1H), 6.68 (s, 1H), 6.40-6.20 (m, 2H), 5.72 (d, J=10.8 Hz, 1H), 3.85 (s, 3H), 3.70-3.47 (m, 1H), 3.20-3.04 (m, 4H), 2.95-2.84 (m, 1H), 2.34 (s, 6H), 2.22-2.10 (m, 1H), 1.98-1.86 (m, 1H), 1.61 (d, J=2.0 Hz, 6H).

Example 75

N-(5-(4-(5-cyclopropyl-4-fluoro-2-(2-hydroxypropan-2-yl)phenylamino)-1,3,5-triazin-2-ylamino)-2-((2-(dimethylamino)ethyl)(methyl)amino)-4-methoxyphenyl)acrylamide

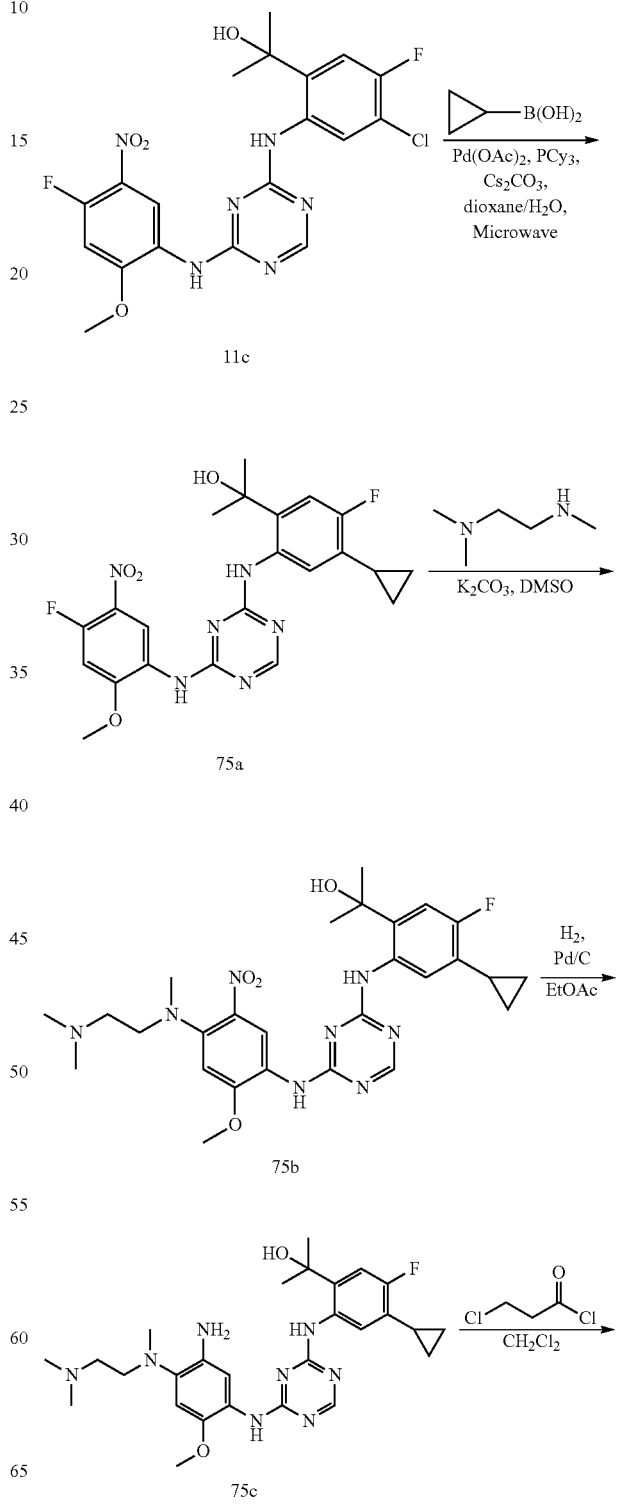

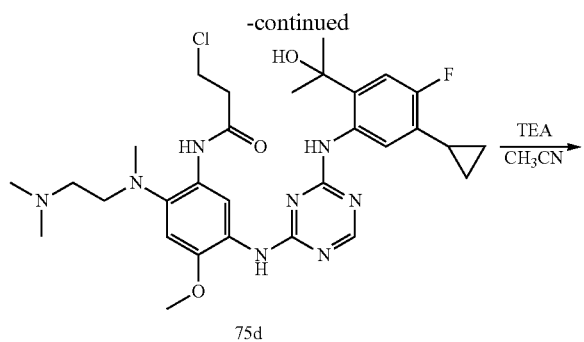

75d

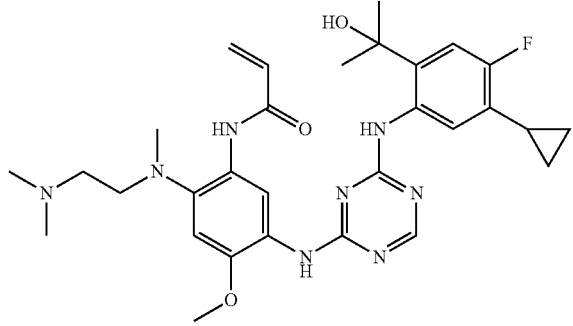

Example 75

Procedure for the Preparation of Compound 75a:

To a solution of compound 11c (500 mg, 1.07 mmol) in dioxane (10 mL) and $H_2O$ (2 mL) was added cyclopropylboronic acid (229 mg, 2.67 mmol), $Pd(OAc)_2$ (168 mg, 0.75 mmol), $PCy_3$ (420 mg, 1.50 mmol) and $Cs_2CO_3$ (1.1 g, 3.21 mmol). The resulting mixture was degassed with $N_2$ for 1 min and stirred at 130° C. under microwave for 1 h. The reaction mixture was filtered and concentrated under reduced pressure to give the crude product, which was purified by column chromatography on silica gel (Petroleum ether/EtOAc=2/1 (v/v)) to give compound 75a (300 mg, 59% yield) as brown solid.

LCMS: $R_t$=0.878 min in 5-95AB_220&254.lcm chromatography (MERCK RP-18e 25-2 mm), MS (ESI) m/z=473.1 $[M+H]^+$.

$^1$H NMR: (400 MHz, $CDCl_3$) δ 9.32 (s, 1H), 8.55-8.28 (m, 1H), 7.72 (s, 1H), 7.51 (br d, J=13.6 Hz, 1H), 7.26-7.23 (m, 1H), 6.97 (br d, J=11.2 Hz, 1H), 6.76 (d, J=12.0 Hz, 1H), 4.02 (s, 3H), 2.16 (br d, J=7.2 Hz, 1H), 1.69-1.64 (m, 6H), 0.96 (br s, 2H), 0.73 (br s, 2H).

Procedure for the Preparation of Compound 75b:

To a solution of compound 75a (300 mg, 0.64 mmol) and $K_2CO_3$ (177 mg, 1.28 mmol) in DMSO (5 mL) was added $N^1,N^1,N^2$-trimethylethane-1,2-diamine (79 mg, 0.77 mmol). The resulting mixture was stirred at 14-23° C. for 4 h while the color changes from brown to deep yellow. The reaction mixture was diluted with EtOAc (20 mL) and washed with water (30 mL). The organic layer was dried and concentrated under reduced pressure to give the crude, which was purified by column chromatography on silica gel (5% MeOH in $CH_2Cl_2$) to give compound 75b (200 mg, 56% yield) as yellow solid.

LCMS: $R_t$=0.760 min in 5-95AB_1.5min_220&254 chromatography (MERCK RP18e 25-2 mm), MS (ESI) m/z=555.1 $[M+H]^+$.

$^1$H NMR: (400 MHz, $CDCl_3$) δ 9.47-8.93 (m, 1H), 8.38 (br s, 1H), 7.86-7.51 (m, 1H), 7.40 (br s, 1H), 7.21 (s, 1H), 7.04-6.88 (m, 1H), 6.65 (s, 1H), 3.96 (s, 3H), 3.28 (br t, J=7.2 Hz, 2H), 2.87 (s, 3H), 2.58 (br t, J=7.2 Hz, 2H), 2.27 (s, 7H), 1.73-1.65 (m, 6H), 1.00-0.90 (m, 4H).

Procedure for the Preparation of Compound 75c:

To a solution of compound 75b (200 mg, 0.36 mmol) in EtOAc (10 mL) was added Pd/C (40 mg). The resulting mixture was purged and degassed with $H_2$ for 3 times, then stirred at 12-21° C. under $H_2$ balloon (15 Psi) for 12 h. The reaction mixture was filtered and concentrated under reduced pressure to give compound 75c (160 mg, 85% yield) as light-yellow solid.

LCMS: $R_t$=1.799 min in 10-80AB_4min_220&254 chromatography (Xtimate C18 2.1*30 mm), MS (ESI) m/z=525.2 $[M+H]^+$.

$^1$H NMR: (400 MHz, $CDCl_3$) δ 9.12 (s, 1H), 8.34 (br s, 1H), 7.85 (s, 1H), 7.62 (s, 1H), 7.26-7.23 (m, 1H), 7.06-6.90 (m, 1H), 6.67 (s, 1H), 3.82 (s, 3H), 3.00-2.93 (m, 2H), 2.69-2.64 (m, 3H), 2.43 (br s, 2H), 2.29 (br s, 6H), 2.10 (br s, 1H), 1.67 (s, 6H), 0.96 (br s, 2H), 0.77 (br s, 2H).

Procedure for the Preparation of Compound 75d:

To a solution of compound 75c (160 mg, 0.30 mmol) in $CH_2Cl_2$ (5 mL) was added compound 3-chloropropanoyl chloride (42 mg, 0.33 mmol) under ice water bath. The resulting mixture was stirred at 0-5° C. for 30 min while little undissolved oil was precipitated out. The reaction mixture was poured into saturated $NaHCO_3$ (10 mL) and stirred at 15-22° C. for 30 min, then extracted with $CH_2Cl_2$ (15 mL×2). The combined organic layers were dried over $Na_2SO_4$ and concentrated under reduced pressure to give the crude residue, which was purified by column chromatography on silica gel (5% MeOH in $CH_2Cl_2$) to give compound 75d (150 mg, 81% yield) as light-yellow solid.

LCMS: $R_t$=0.751 min in 5-95AB_1.5min_220&254 chromatography (Xtimate C18 2.1*30 mm), MS (ESI) m/z=615.2 $[M+H]^+$.

$^1$H NMR: (400 MHz, $CDCl_3$) δ 10.31 (br s, 1H), 10.08 (s, 1H), 9.86 (s, 1H), 8.38 (s, 1H), 7.80 (br d, J=8.0 Hz, 1H), 7.65 (br s, 1H), 7.32 (s, 1H), 7.02-6.90 (m, 1H), 6.74 (s, 1H), 3.92 (t, J=6.4 Hz, 2H), 3.87 (s, 3H), 3.80 (t, J=6.8 Hz, 1H), 2.98 (br s, 3H), 2.80 (t, J=6.8 Hz, 1H), 2.68 (s, 3H), 2.41 (br s, 8H), 1.74 (s, 6H), 1.03-0.94 (m, 2H), 0.82 (br d, J=6.0 Hz, 2H).

Procedure for the Preparation of Example 75:

To a solution of compound 75d (150 mg, 0.24 mmol) in $CH_3CN$ (5 mL) was added TEA (97 mg, 4.0 eq, 0.96 mmol). The resulting mixture was stirred at 80° C. for 12 h. The reaction mixture was purified by prep-HPLC [Column: Waters Xbridge 150*25 5 um; Condition: 55-85% B (A: 0.05% $NH_3H_2O$; B: $CH_3CN$); Flow rate: 25 ml/min]. Fractions containing the desired compound were lyophilized to afford Example 75 (51.6 mg, 43% yield) as white solid.

LCMS: $R_t$=1.867 min in 10-80AB_4min_220&254 chromatography (Xtimate C18 2.1*30 mm), MS (ESI) m/z=579.0 $[M+H]^+$.

HPLC: $R_t$=3.29 min in 10-80_ab_1.2ML chromatography (Ultimate C18 3*50 mm 3 um).

$^1$H NMR (400 MHz, $CDCl_3$) δ 10.43 (br s, 2H), 9.98 (br s, 1H), 8.38 (s, 1H), 7.83 (br d, J=7.6 Hz, 1H), 7.63 (br s, 1H), 6.96 (d, J=11.6 Hz, 1H), 6.78 (s, 1H), 6.44-6.28 (m, 2H), 6.05 (br s, 1H), 5.80-5.73 (m, 1H), 3.87 (s, 3H), 2.91-2.84 (m, 2H), 2.70 (s, 3H), 2.27 (s, 7H), 2.14-2.04 (m, 1H), 1.76 (s, 6H), 1.04-0.94 (m, 2H), 0.86-0.73 (m, 2H).

Example 76/Example 77
N-(5-(4-(5-chloro-4-fluoro-2-((R)-2-hydroxybutan-2-yl)phenylamino)pyrimidin-2-ylamino)-2-((R)-3-(dimethylamino)pyrrolidin-1-yl)-4-methoxyphenyl)acrylamide and N-(5-(4-(5-chloro-4-fluoro-2-((S)-2-hydroxybutan-2-yl)phenylamino)pyrimidin-2-ylamino)-2-((R)-3-(dimethylamino)pyrrolidin-1-yl)-4-methoxyphenyl)acrylamide
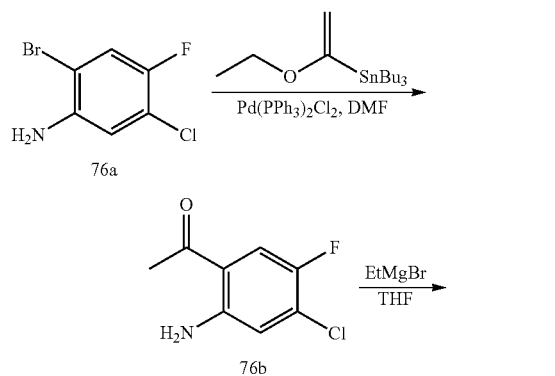
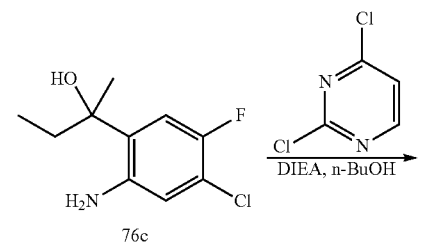
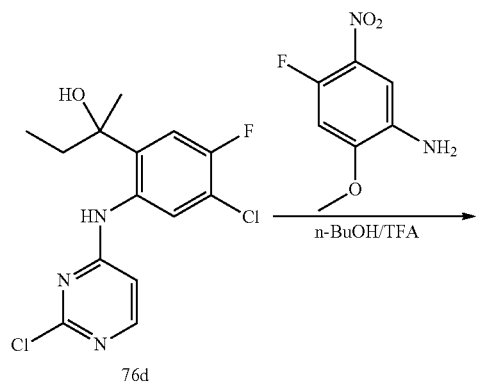
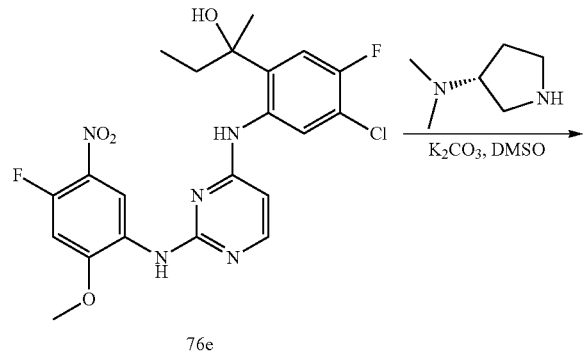
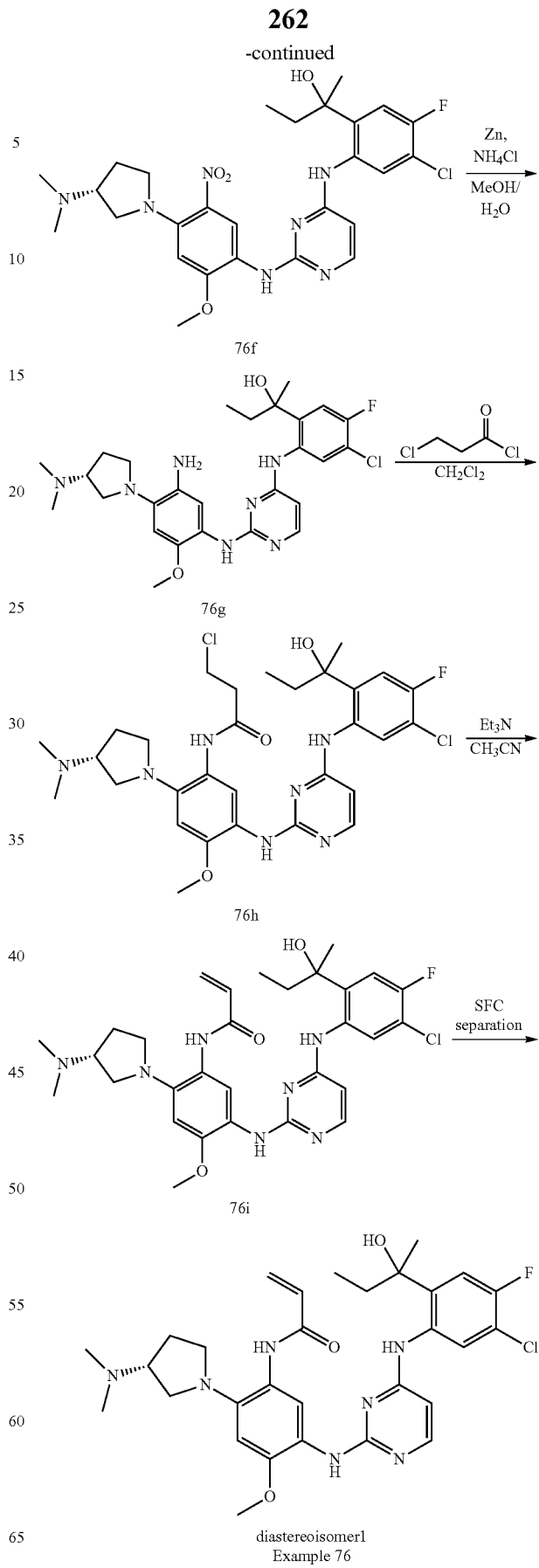

-continued

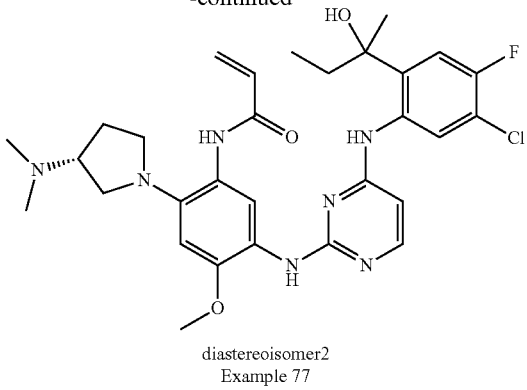

diastereoisomer2
Example 77

Procedure for the Preparation of Compound 76b:

To a solution of compound 76a (5.0 g, 22.28 mmol) in DMF (50 mL) was added bis(triphenylphosphine)palladium (II) (1.0 g, 1.42 mmol) and tributyl(1-ethoxyvinyl)tin (8.85 g, 24.51 mmol) under nitrogen. The resulting mixture was stirred at 110° C. under nitrogen for 12 h. After cooled to room temperature, the reaction mixture was treated with aqueous HCl (6 M, 10 mL) and stirred at 25° C. for another 4 h. The mixture was poured into water (300 mL) and extracted with ethyl acetate (100 mL×3). The combined organic layers were washed with a solution of KF (20%, 100 mL×2) and brine (100 mL) successively, dried over sodium sulfate and concentrated to afford a black crude product, which was purified by column chromatography on silica gel (0 to 5% ethyl acetate in PE) to afford compound 76b (1.7 g, 40.6% yield) as yellow solid.

LCMS: $R_t$=2.030 min in 10-80AB_4min_220&254 chromatography (Xtimate C18 2.1*30 mm), MS (ESI) m/z=187.9 [M+H]$^+$.

$^1$H NMR (400 MHz, DMSO-d$_6$) δ 7.74 (d, J=10.4 Hz, 1H), 7.20 (s, 2H), 6.92 (d, J=6.4 Hz, 1H), 2.48 (s, 3H).

Procedure for the Preparation of Compound 76c:

To a yellow solution of compound 76b (1.7 g, 9.06 mmol) in THF (20 mL) was added EtMgBr (12 mL, 36.25 mmol) drop wise under nitrogen at 0° C. The resulting mixture was stirred at 19-21° C. for 2 h. The mixture was quenched with saturated solution of NH$_4$Cl (100 mL) and extracted with EtOAc (50 mL×3). The combined organic layers were dried and concentrated in vacuum to afford the crude product, which was purified by column chromatography on silica gel (0 to 10% EtOAc in PE (v/v)) to afford compound 76c (1.2 g, 60.8% yield) as yellow oil.

LCMS: $R_t$=0.758 min in 10-80AB_4min_220&254 chromatography (Xtimate C18 2.1*30 mm), MS (ESI) m/z=199.8 [M−H$_2$O+H]$^+$.

$^1$H NMR (400 MHz, CDCl$_3$) δ 6.76 (d, J=10.8 Hz, 1H), 6.55 (d, J 6.4 Hz, 1H), 4.53 (brs, 2H), 1.95-1.80 (m, 2H), 1.51 (s, 3H), 0.79 (t, J=7.2 Hz, 3H).

Procedure for the Preparation of Compound 76d:

To a light-yellow solution of compound 76c (1.0 g, 4.59 mmol) in n-BuOH (15 mL) was added DIEA (1.19 g, 9.19 mmol) and 2,4-dichloropyrimidine (753 mg, 5.05 mmol). The resulting mixture was stirred at 120° C. for 10 h. The mixture was concentrated in vacuum and purified by column chromatography on silica gel (0 to 20% EtOAc in PE) to afford compound 76d (780 mg, 51.5% yield) as light-yellow solid.

LCMS: $R_t$=0.872 min in 5-95AB_220&254 chromatography (MERCK RP18 2.5-2 mm), MS (ESI) m/z=330.0 [M+H]$^+$.

$^1$H NMR (400 MHz, CDCl$_3$) δ 9.18 (s, 1H), 8.05 (d, J=6.0 Hz, 1H), 7.89 (d, J=6.8 Hz, 1H), 6.98 (d, J=10.4 Hz, 1H), 6.47 (d, J=6.0 Hz, 1H), 2.36 (s, 1H), 1.81 (q, J=7.6 Hz, 2H), 1.56 (s, 3H), 0.76 (t, J=7.6 Hz, 3H).

Procedure for the Preparation of Compound 76e:

To a mixture of compound 76d (700 mg, 2.12 mmol) in n-BuOH/TFA (5 mL/0.05 mL) was added 4-fluoro-2-methoxy-5-nitroaniline (415 mg, 2.23 mmol). The resulting mixture was stirred at 50° C. for 3 h and 80° C. for 3 h. The mixture was cooled to 25° C. while a grey solid was precipitated, the solid was collected by suction filtration and then dried in vacuum to afford compound 76e (680 mg, 62.9% yield) as grey solid.

LCMS: $R_t$=0.755 min in 5-95AB_220&254 chromatography (MERCK RP18 2.5-2 mm), MS (ESI) m/z=480.1 [M+H]$^+$.

$^1$H NMR: (400 MHz, DMSO-d$_6$) δ 10.28 (br s, 1H), 8.60-8.47 (m, 1H), 8.08 (d, J=6.4 Hz, 1H), 7.85-7.76 (m, 1H), 7.45-7.34 (m, 2H), 6.47 (br. s, 1H), 5.89 (s, 1H), 3.97 (s, 3H), 1.84-1.65 (m, 2H), 1.49 (s, 3H), 0.67 (t, J=7.2 Hz, 3H).

Procedure for the Preparation of Compound 76f:

To an orange solution of compound 76e (160 mg, 0.33 mmol) in DMSO (3 mL) was added K$_2$CO$_3$ (92 mg, 0.67 mmol) and (R)—N,N-dimethylpyrrolidin-3-amine (46 mg, 0.40 mmol). The resulting mixture was stirred at 50° C. for 3 h. The mixture was poured into ice water (30 mL) and an orange solid was precipitated out, it was separated by suction filtration and dried in vacuo to afford compound 76f (130 mg, 68.6% yield).

LCMS: $R_t$=0.674 min in 5-95AB_220&254 chromatography (MERCK RP18 2.5-2 mm), MS (ESI) m/z=574.1 [M+H]$^+$.

$^1$H NMR: (400 MHz, CDCl$_3$) δ 8.98 (d, J=4.8 Hz, 1H), 8.88 (d, J=10.8 Hz, 1H), 7.98 (dd, J=6.0, 1.6 Hz, 1H), 7.90-7.82 (m, 1H), 7.11 (d, J=7.6 Hz, 1H), 6.96 (dd, J=10.8, 2.0 Hz, 1H), 6.22 (s, 1H), 6.06 (dd, J=6.0, 3.6 Hz, 1H), 3.85 (s, 3H), 3.52-3.42 (m, 1H), 3.30-3.23 (m, 1H), 3.12-3.02 (m, 2H), 2.78-2.69 (m, 1H), 2.22 (d, J=3.2 Hz, 6H), 2.16-2.07 (m, 1H), 1.90-1.75 (m, 3H), 1.55 (s, 3H), 0.78 (t, J=7.2 Hz, 3H).

Procedure for the Preparation of Compound 76g:

To a mixture of compound 76f (200 mg, 0.36 mmol) in methanol/water (5 mL/1 mL) was added Zn (114 mg, 1.74 mmol) and NH$_4$Cl (186 mg, 3.48 mmol). The mixture was stirred at 90° C. for 1 h. The mixture was poured into water (30 mL) and extracted with dichloromethane/methanol (3/1, 20 mL×4). The combined organic layers were dried and concentrated to afford compound 76g (220 mg, 95% yield) as black solid.

LCMS: $R_t$=1.345 min in 10-80AB_4min_220&254 chromatography (Xtimate C18 2.1*30 mm), MS (ESI) m/z=544.1 [M+H]$^+$.

$^1$H NMR: (400 MHz, CDCl$_3$) δ 8.87 (s, 1H), 8.06 (d, J=7.2 Hz, 1H), 7.93 (d, J=6.0 Hz, 1H), 7.77 (s, 1H), 7.34 (s, 1H), 6.94 (d, J=10.8 Hz, 1H), 6.58 (s, 1H), 5.95 (d, J=5.2 Hz, 1H), 3.73 (s, 3H), 3.15-3.01 (m, 2H), 2.99-2.87 (m, 2H), 2.84-2.74 (m, 1H), 2.20 (s, 6H), 2.11-1.99 (m, 1H), 1.88-1.77 (m, 3H), 1.54 (s, 3H), 0.78 (t, J=7.6 Hz, 3H).

Procedure for the Preparation of Compound 76h:

To a brown solution of compound 76g (200 mg, 0.31 mmon) in dichloromethane (5 mL) was added 3-chloropropionyl chloride (40 mg, 0.31 mmol). The resulting mixture was stirred at 5-10° C. under ice bath for 1 h. The mixture was quenched with saturation solution of sodium bicarbonate (30 mL) and extracted with dichloromethane (10 mL×3). The combined organic layers were dried over sodium sulfate, filtered and concentrated in vacuum to afford compound 76h (200 mg, 86% yield) as brown gum.

LCMS: $R_t$=0.715 min in 5-95AB_220&254 chromatography (MERCK RP18 2.5-2 mm), MS (ESI) m/z=634.5 [M+H]$^+$.

$^1$H NMR: (400 MHz, CDCl$_3$) δ 9.48 (d, J=5.2 Hz, 1H), 9.31 (br. s, 1H), 8.49 (br. s, 1H), 8.00 (d, J=6.0 Hz, 1H), 7.52-7.46 (m, 1H), 7.42-7.38 (m, 1H), 7.34 (s, 1H), 7.01 (d, J=10.8 Hz, 1H), 6.67 (s, 1H), 6.24 (d, J=6.4 Hz, 1H), 3.84-3.75 (m, 5H), 3.12-2.92 (m, 4H), 2.88-2.76 (m, 3H), 2.26 (s, 6H), 2.16-2.06 (m, 2H), 1.93-1.85 (m, 2H), 1.59 (s, 3H), 1.19-1.17 (m, 3H).

Procedure for the Preparation of Compound 76i:

To a brown mixture of compound 76h (200 mg, 0.27 mmol) in CH$_3$CN (5 mL) was added Et$_3$N (81 mg, 0.80 mmol). The resulting mixture was stirred at 80° C. for 2 h. The reaction mixture was purified by prep-HPLC (column: Waters Xbridge 150*25, 5um, condition: 42%-62% B (A: water/10 mM NH$_4$HCO$_3$, B: CH$_3$CN), flow rate: 25 mL/min) and then lyophilized to afford compound 76i (73.2 mg, 44.7% yield) as yellow solid. It was further purified by SFC separation.

LCMS: $R_t$=1.595 min in 10-80AB_4min_220&254 chromatography (Xtimate C18 2.1*30 mm), MS (ESI) m/z=597.9 [M+H]$^+$.

HPLC: $R_t$=4.12 min in 10-80_CD_1.2 ml chromatography (XBridge Shield RP 18 2.1*50 mm 5 um).

$^1$H NMR (400 MHz, CDCl$_3$) δ 9.53 (s, 1H), 9.46 (s, 1H), 8.69 (s, 1H), 8.00 (d, J=5.6 Hz, 1H), 7.47-7.35 (m, 2H), 7.01 (d, J=10.8 Hz, 1H), 6.69-6.48 (m, 2H), 6.35-6.34 (m, 2H), 5.70 (d, J=10.8 Hz, 1H), 5.42 (br s, 1H), 3.79 (s, 3H), 3.28-2.84 (m, 5H), 2.44 (s, 6H), 2.23-2.09 (m, 2H), 2.06-1.99 (m, 1H), 1.95-1.88 (m, 1H), 1.58 (s, 3H), 0.77 (t, J=7.2 Hz, 3H).

Chiral SFC: $R_t$=6.233 min and 6.903 min in IC-3_MeOH (DEA)_40-2.5ML.

Procedure for the Preparation of Example 76 and Example 77: Compound 76i (73.2 mg) was separated by SFC (column: DAICEL CHIRALPAK IC 250 mm*30 mm 5 um, condition: 40% B (A: CO$_2$, B: 0.1% ammonia/methanol), flow rate: 60 mL/min) to afford Example 76 (13.5 mg, 18.4% yield) and Example 77 (18.2 mg, 24.9% yield) as white solid.

Example 76

LCMS: $R_t$=1.588 min in 10-80AB_4min_220&254 chromatography (Xtimate C18 2.1*30 mm), MS (ESI) m/z=598.0 [M+H]$^+$.

HPLC: $R_t$=4.15 min in 10-80_CD_1.2 ml chromatography (XBridge Shield RP 18 2.1*50 mm 5 um).

$^1$H NMR (400 MHz, CDCl$_3$) δ 9.55 (s, 1H), 9.43 (s, 1H), 8.53 (s, 1H), 8.00 (d, J=6.0 Hz, 1H), 7.44 (d, J=6.8 Hz, 1H), 7.39 (s, 1H), 7.01 (d, J=10.8 Hz, 1H), 6.66 (s, 1H), 6.42-6.32 (m, 1H), 6.30 (s, 1H), 6.26 (d, J=5.2 Hz, 1H), 5.69 (d, J=10.8 Hz, 1H), 5.35 (br s, 1H), 3.79 (s, 3H), 3.13-2.95 (m, 4H), 2.93-2.82 (m, 1H), 2.29 (s, 6H), 2.18-2.09 (m, 1H), 2.06-1.99 (m, 1H), 1.98-1.88 (m, 2H), 1.58 (s, 3H), 0.78 (t, J=7.2 Hz, 3H).

Chiral SFC: $R_t$=6.292 min in IC-3_MeOH(DEA)_40-2.5ML.

Example 77

LCMS: $R_t$=1.599 min in 10-80AB_4min_220&254 chromatography (Xtimate C18 2.1*30 mm), MS (ESI) m/z=597.9 [M+H]$^+$.

HPLC: $R_t$=4.14 min in 10-80_CD_1.2 ml chromatography (XBridge Shield RP 18 2.1*50 mm 5 um).

$^1$H NMR (400 MHz, CDCl$_3$) δ 9.56 (s, 1H), 9.44 (s, 1H), 8.56 (s, 1H), 8.00 (d, J=6.0 Hz, 1H), 7.43 (d, J=7.2 Hz, 1H), 7.40 (s, 1H), 7.01 (d, J=10.8 Hz, 1H), 6.65 (s, 1H), 6.48-6.35 (m, 1H), 6.30 (s, 1H), 6.26 (d, J=5.6 Hz, 1H), 5.69 (d, J=11.2 Hz, 1H), 5.38 (br s, 1H), 3.78 (s, 3H), 3.14-3.04 (m, 2H), 3.03-2.96 (m, 2H), 2.95-2.88 (m, 1H), 2.32 (s, 6H), 2.19-2.10 (m, 1H), 2.07-2.00 (m, 1H), 1.98-1.88 (m, 2H), 1.58 (s, 3H), 0.77 (t, J=7.2 Hz, 3H).

Chiral SFC: $R_t$=6.980 min in IC-3_MeOH(DEA)_40-2.5ML.

Example 78

N-(5-(5-chloro-4-(5-chloro-4-fluoro-2-(2-hydroxy-propan-2-yl)phenylamino)pyrimidin-2-ylamino)-2-((2-(dimethylamino)ethyl)(methyl)amino)-4-methoxyphenyl)acrylamide

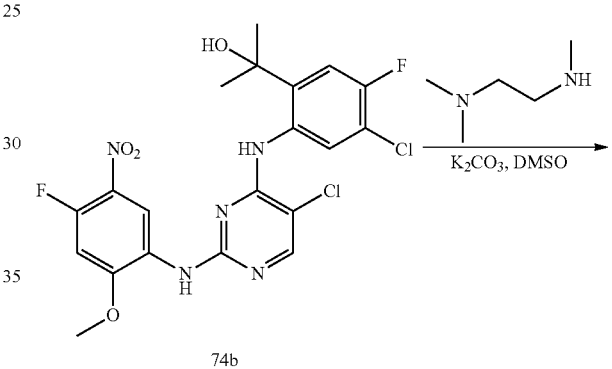

74b

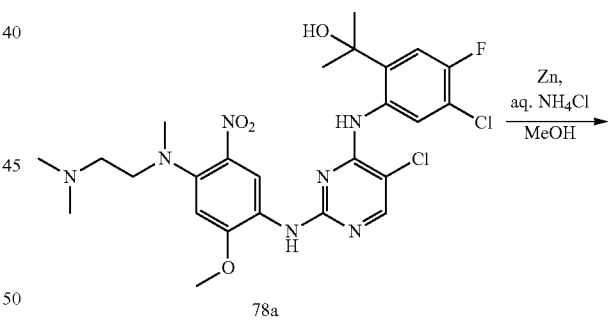

78a

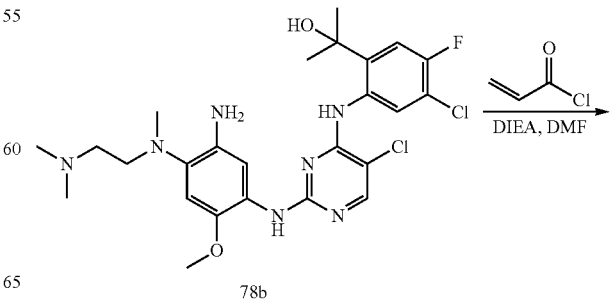

78b

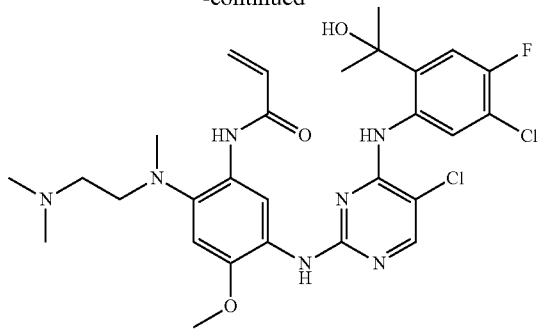

Example 78

The synthesis followed a similar experimental procedure as Example 74 to afford Example 78 as a white solid.

LCMS: $R_t$=1.336 min in 10-80AB_3min_220&254 chromatography (Xtimate C18, 2.1*30 mm, 3 um), MS (ESI) m/z=606.2 [M+H]⁺.

HPLC: $R_t$=3.13 min in 10-80_AB_1.2ml. met Ultimate C18 3*50 mm 3 um.

¹H NMR: (400 MHz, CDCl₃) δ 10.15 (br s, 1H), 9.66 (br s, 1H), 9.16 (s, 1H), 8.44 (br d, J=7.4 Hz, 1H), 8.15 (s, 1H), 7.24 (s, 1H), 6.87 (d, J=10.8 Hz, 1H), 6.72 (s, 1H), 6.43-6.17 (m, 2H), 5.69 (d, J=11.2 Hz, 1H), 3.86 (s, 3H), 3.78-3.66 (m, 1H), 2.88 (br s, 2H), 2.70 (s, 3H), 2.33-2.21 (m, 8H), 1.60 (s, 6H).

Example 79

N-(5-(4-(5-chloro-4-fluoro-2-(2-hydroxypropan-2-yl)phenylamino)pyrimidin-2-ylamino)-2-((3S,4R)-3-(dimethylamino)-4-fluoropyrrolidin-1-yl)-4-methoxyphenyl)acrylamide

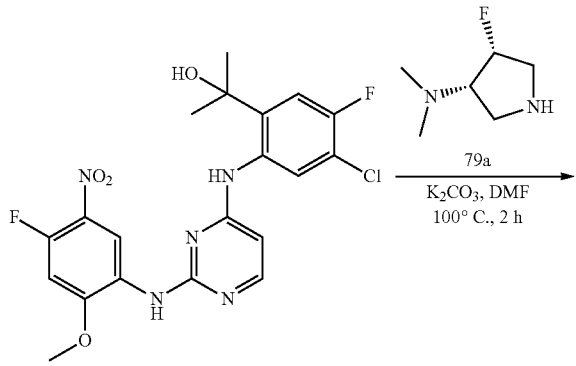

36b

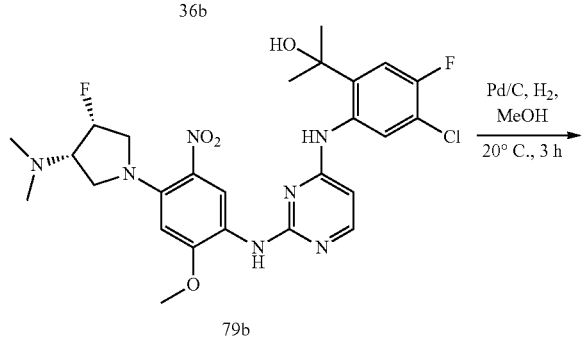

79b

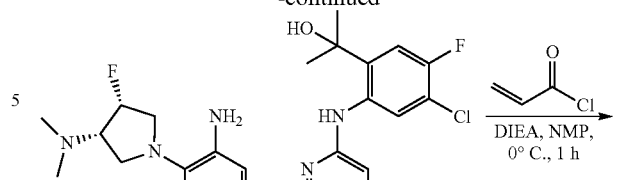

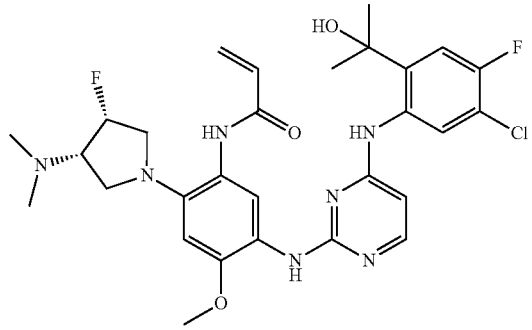

Example 79

Procedure for the Preparation of Compound 79a:

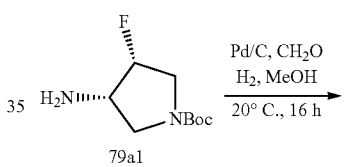

79a1

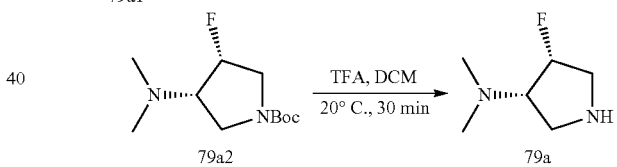

To a mixture of compound 79a1 (120 mg, 0.59 mmol) in methanol (3 mL) was added palladium on carbon (40 mg) and formaldehyde (0.3 mL, 37% aqueous solution), the resulting mixture was stirred at 20° C. for 16 hours under hydrogen atmosphere. The mixture was filtered, the filtrate was concentrated in vacuum to afford compound 79a2 (120 mg, 88% yield) as a white solid.

LCMS: $R_t$=1.10 min in 3 min chromatography (3 min-5-95% MeCN in water (0.02% FA), Waters Acquity UPLC BEH C18 1.7 um, 2.1*50 mm, 40° C.), MS (ESI) m/z 233.2 [M+H]⁺.

To a mixture of compound 79a2 (120 mg, 0.52 mmol) in DCM (1 mL) was added TFA (1 mL), the resulting mixture was stirred at 20° C. for 30 min. The mixture was then concentrated in vacuum and diluted with water (2 mL). The mixture was lyophilized to afford compound 79a (110 mg, 86% yield) as a white solid (TFA salt).

LCMS: $R_t$=0.27 min in 3 min chromatography (3 min-5-95% MeCN in water (0.02% FA), Waters Acquity UPLC BEH C18 1.7 um, 2.1*50 mm, 40° C.), MS (ESI) m/z 133.2 [M+H]⁺

Procedure for the Preparation of Compound 79b:

To a mixture of compound 79a (40 mg, 0.30 mmol) in DMF (3 mL) was added compound 36b (100 mg, 0.21 mmol) and potassium carbonate (90 mg, 0.65 mmol), the resulting mixture was stirred at 100° C. for 2 hours. The mixture was then purified by C18-flash chromatography, elution gradient from 5 to 50% CH$_3$CN in water (0.02% FA). Pure fractions were evaporated to dryness to afford compound 79b (95 mg, 77% yield) as an orange solid.

LCMS: R$_t$=0.64 min in 3 min chromatography (3 min-5-95% MeCN in water (0.02% FA), Waters Acquity UPLC BEH C18 1.7 um, 2.1*50 mm, 40° C.), MS (ESI) m/z 578.1 [M+H]$^+$.

Procedure for the Preparation of Compound 79c:

To a mixture of compound 79b (95 mg, 0.16 mmol) in methanol (5 mL) was added palladium on carbon (30 mg), the resulting mixture was stirred at 20° C. for 3 hours under hydrogen atmosphere. The mixture was then filter and the filtrate was concentrated in vacuum to afford compound 79c (75 mg, 83% yield) as a white solid.

LCMS: R$_t$=0.99 min in 3 min chromatography (3 min-5-95% MeCN in water (0.02% FA), Waters Acquity UPLC BEH C18 1.7 um, 2.1*50 mm, 40° C.), MS (ESI) m/z 548.2 [M+H]$^+$.

Procedure for the Preparation of Example 79:

To a mixture of compound 79c (70 mg, 0.13 mmol) in NMP (2 mL) was added acryloyl chloride (12 mg, 0.13 mmol) and DIEA (40 mg, 0.31 mmol) at 0° C., the resulting solution was stirred at 0° C. for 1 hour. The mixture was purified by C18-flash chromatography, elution gradient from 5% to 60% CH$_3$CN in water (6 mmol/L NH$_4$HCO$_3$). Pure fractions were evaporated to dryness to afford Example 79 (22 mg, 29% yield) as a white solid.

LCMS: R$_t$=1.31 min in 3 min chromatography (3 min-5-95% MeCN in water (6 mmol/L NH$_4$HCO$_3$), Waters Acquity UPLC BEH C18 1.7 um, 2.1*50 mm, 40° C.), MS (ESI) m/z 602.3 [M+H]$^+$.

$^1$H NMR: (500 MHz, DMSO-d$_6$) δ 1.49 (s, 6H) 2.24 (s, 6H) 2.53-2.65 (m, 1H) 3.21-3.33 (m, 2H) 3.41-3.45 (m, 1H) 3.64-3.78 (m, 1H) 3.80 (s, 3H) 5.17-5.35 (m, 1H) 5.68 (dd, J=10.25, 1.73 Hz, 1H) 6.05 (d, J=5.67 Hz, 1H) 6.12-6.23 (m, 2H) 6.39-6.55 (m, 2H) 7.29 (d, J=11.03 Hz, 1H) 7.47 (br s, 1H) 7.82 (br s, 1H) 7.95 (d, J=5.67 Hz, 1H) 8.14 (br d, J=7.25 Hz, 1H) 9.34 (s, 1H) 9.57 (s, 1H).

Example 80

(R)—N-(5-(4-(5-chloro-4-fluoro-2-(2-hydroxypropan-2-yl)phenylamino)pyrimidin-2-ylamino)-4-methoxy-2-(3-(methylamino)pyrrolidin-1-yl)phenyl)acrylamide TFA salt

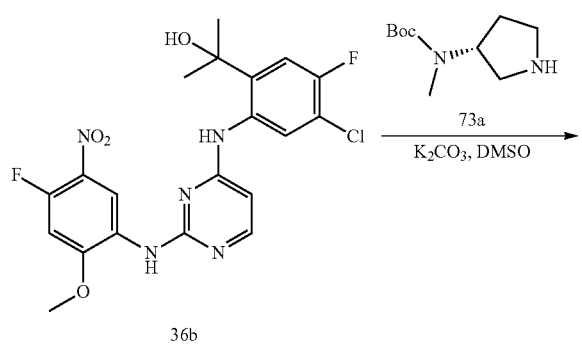

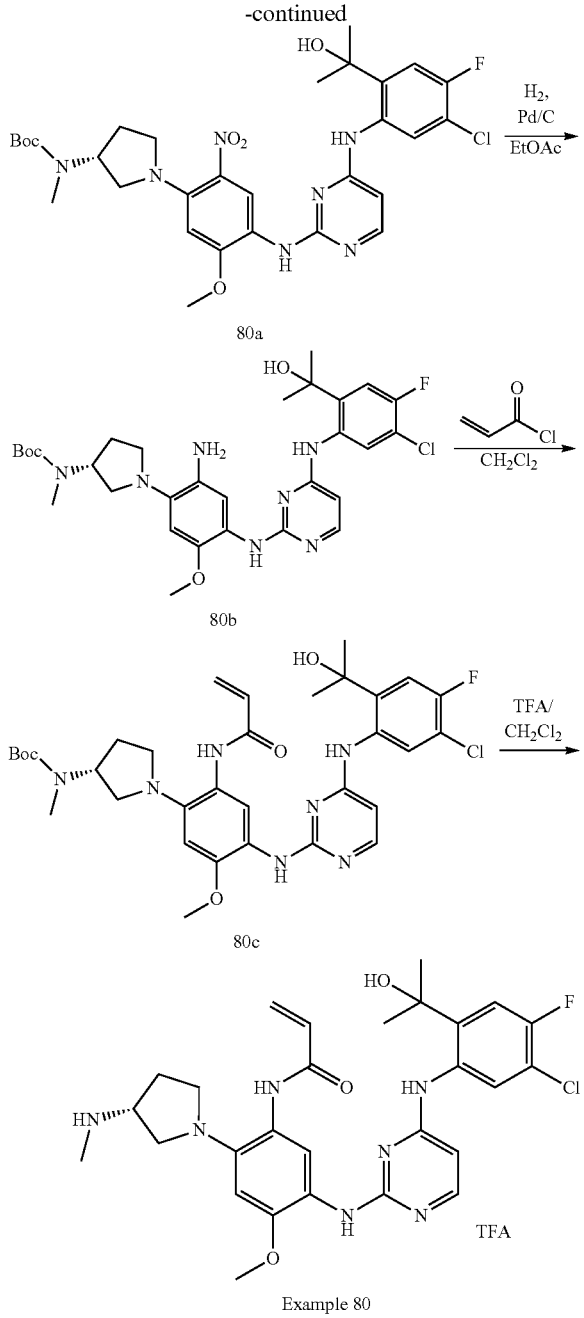

Procedure for the Preparation of Compound 80a:

To a solution of compound 36b (300 mg, 0.644 mmol) and K$_2$CO$_3$ (178 mg, 1.29 mmol) in DMSO (3 mL) was added compound 73a (155 mg, 0.644 mmol). The resulting mixture was stirred at 85° C. for 2 h while the color was changed from pale yellow to deep yellow. The reaction mixture was poured into ice water (20 mL) with stirring and yellow solid was precipitated. The precipitated solid was collected by filtration and then dissolved into CH$_2$Cl$_2$ (50 mL), dried over anhydrous Na$_2$SO$_4$ and concentrated under reduced pressure to give compound 80a (380 mg, 71% yield) as a yellow solid.

LCMS: R$_t$=0.800 min in 5-95AB_220&254.lcm chromatography (MERCK RP-18e 25-2 mm), MS (ESI) m/z=646.1 [M+H]$^+$.

Procedure for the Preparation of Compound 80b:

To a solution of compound 80a (350 mg, 0.542 mmol) in EtOAc (5 mL) was added Pd/C (200 mg, 10% wet). The resulting mixture was purged and degassed with $H_2$ for 3 times, then stirred at 13-20° C. under $H_2$ balloon (15 Psi) for 2 h. The reaction mixture was filtered and concentrated under reduced pressure to give compound 80b (300 mg, 70% yield) as a light yellow solid.

LCMS: $R_t$=0.758 min in 5-95AB_1.5min_220&254 chromatography (MERCK RP18e 25-2 mm), MS (ESI) m/z=616.2 $[M+H]^+$.

Procedure for the Preparation of Compound 80c:

To a solution of compound 80b (300 mg, 0.377 mmol) in $CH_2Cl_2$ (5 mL) was added acryloyl chloride (47.9 mg, 0.377 mmol) drop wise under ice water bath. The resulting mixture was stirred at 0-5° C. for 30 min. The reaction mixture was poured into saturated $NaHCO_3$ (5 mL) and stirred at 12-17° C. for 2 h, then extracted with $CH_2Cl_2$ (5 mL×2). The combined organic layers were dried over $Na_2SO_4$ and concentrated under reduced pressure to give the crude product, which was purified by column chromatography on silica gel (8% MeOH in $CH_2Cl_2$) to give compound 80c (200 mg, 60% yield) as a yellow solid.

LCMS: $R_t$=0.825 min in 5-95AB_1.5min_220&254 chromatography (Agilent Pursit 5 C18 20*2.0 mm), MS (ESI) m/z=670.5 $[M+H]^+$.

$^1$H NMR: (400 MHz, $CDCl_3$) δ 9.68-9.56 (m, 1H), 9.37 (s, 1H), 8.49 (br s, 1H), 8.01 (d, J=6.0 Hz, 1H), 7.43 (s, 1H), 7.37-7.27 (m, 1H), 7.08 (d, J=10.8 Hz, 1H), 6.64 (s, 1H), 6.32-6.26 (m, 2H), 5.74-5.65 (m, 1H), 4.68 (br s, 1H), 3.80 (s, 3H), 3.20-3.12 (m, 2H), 2.97-2.90 (m, 2H), 2.87 (s, 3H), 2.27-2.18 (m, 1H), 1.97-1.89 (m, 1H), 1.63 (s, 8H), 1.40 (s, 9H).

Procedure for the Preparation of Example 80:

To a solution of compound 80c (200 mg, 2.12 mmol) in $CH_2Cl_2$ (10 mL) was added TFA (1.57 g, 21.2 mmol) at 0° C. The mixture was stirred at 18-22° C. for 6 h. The mixture was concentrated in vacuum to give the crude product as brown oil, which was purified by preparative HPLC (Instrument: BH Column: Gemini 150*25 5 um. Mobile A: water 0.05% ammonia hydroxide v/v Mobile B: DMF Flow rate: 25 ml/min Gradient Time: 7 min Profile Descriptive: 42%-72%) to give Example 80 in TFA salt form (90 mg, 78% yield) as a yellow solid.

LCMS: $R_t$=1.455 min in 10-80AB_4min_220&254 chromatography (Xtimate C18 2.1*30 mm), MS (ESI) m/z=570.1 $[M+H]^+$.

HPLC: $R_t$=2.15 min in 10-80_ab_1.2ML chromatography (Ultimate C18 3*50 mm 3 um).

$^1$H NMR: (400 MHz, DMSO-$d_6$) δ 10.53 (br s, 1H), 9.86 (br s, 1H), 9.14 (br s, 1H), 8.90 (br s, 2H), 7.90 (br s, 2H), 7.68 (br s, 1H), 7.40 (br s, 1H), 6.71 (s, 1H), 6.55 (dd, J=10.4 Hz, 17.2 Hz, 1H), 6.43 (br s, 1H), 6.28-6.01 (m, 2H), 5.76-5.70 (m, 1H), 3.82-3.77 (m, 4H), 3.39-3.25 (m, 3H), 3.10-3.01 (m, 1H), 2.68-2.62 (m, 3H), 2.37-2.28 (m, 1H), 2.09-1.98 (m, 1H), 1.47 (s, 6H).

Example 81

N-(5-(4-(5-chloro-4-fluoro-2-(2-hydroxypropan-2-yl)phenylamino)-5-methoxypyrimidin-2-ylamino)-2-((2-(dimethylamino)ethyl)(methyl)amino)-4-methoxyphenyl)acrylamide

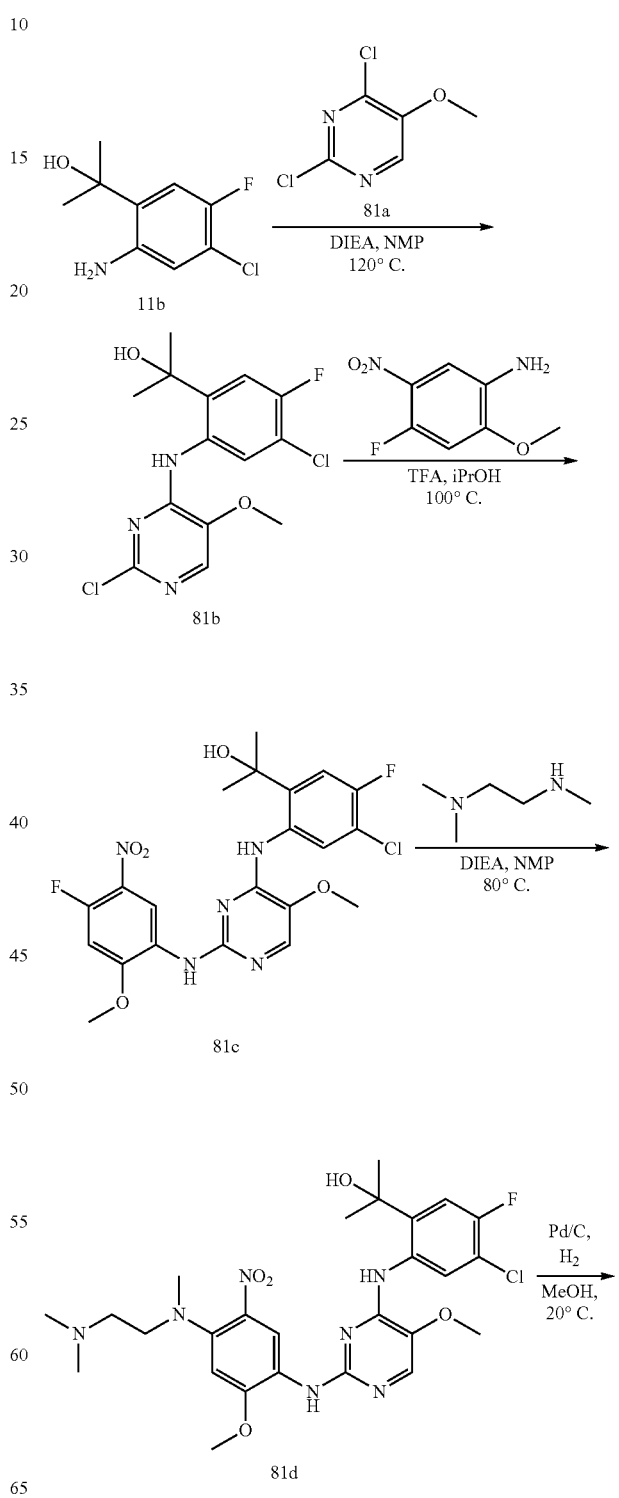

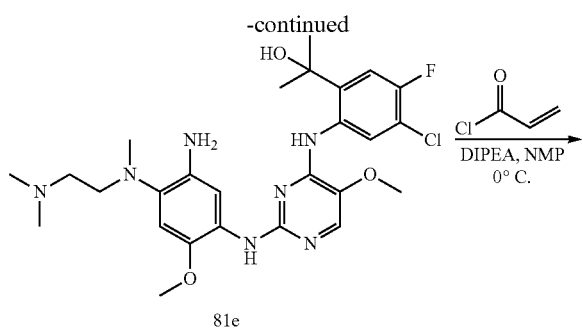

81e

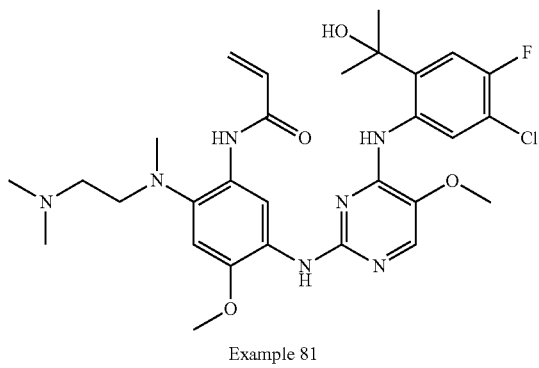 [SMILES: C=CC(=O)Nc1cc(Nc2ncc(OC)c(Nc3cc(Cl)c(F)cc3C(C)(C)O)n2)c(OC)cc1N(C)CCN(C)C]

Example 81

Procedure for the Preparation of Compound 81b:

A solution of compound 81a (200 mg, 1.1 mmol), compound 11b (240 mg, 1.2 mmol) and DIEA (434 mg, 3.4 mmol) in NMP (6 mL) was sealed and heated at 120° C. for 2 h. The reaction was diluted with water (100 mL) and extracted with EA (20 mL×5). The combined organics were washed with brine, dried over anhydrous sodium sulfate, filtered and the filtrate was evaporated under reduced pressure. The residue was purified by silica gel flash chromatography, elution gradient from 30% to 100% EtOAc in petroleum ether. Pure fractions were evaporated to dryness to afford compound 81b (50 mg, 13% yield) as a light yellow solid.

LCMS: $R_t$=1.53 min in 3 min chromatography (3 min-5-95% MeCN in water (6 mmol/L $NH_4HCO_3$), Waters Acquity UPLC BEH C18 1.7 um, 2.1*50 mm, 40° C.) MS (ESI) m/z 346.1 [M+H]$^+$.

$^1$H NMR: (500 MHz, DMSO-$d_6$) δ 1.5 (s, 6H) 3.9 (s, 3H) 6.4 (s, 1H) 7.3 (d, J=11.0 Hz, 1H) 8.0 (s, 1H) 8.5 (d, J=7.3 Hz, 1H) 10.8 (s, 1H).

Procedure for the Preparation of Compound 81c:

A solution of compound 81b (47 mg, 0.14 mmol), 4-fluoro-2-methoxy-5-nitroaniline (28 mg, 0.15 mmol), and TFA (15 mg, 0.136 mmol) in propan-2-ol (2.0 mL) was sealed and heated at 100° C. for 48 h. The reaction mixture was evaporated under reduced pressure. The residue was purified by silica gel flash chromatography, elution gradient from 0% to 10% MeOH in DCM. Pure fractions were evaporated to dryness to afford compound 81c (67 mg, 79% yield) as a brown solid.

LCMS: $R_t$=1.20 min in 3 min chromatography (3 min-5-95% MeCN in water (6 mmol/L $NH_4HCO_3$), Waters Acquity UPLC BEH C18 1.7 um, 2.1*50 mm, 40° C.), MS (ESI) m/z 496.1 [M+H]$^+$.

Procedure for the Preparation of Compound 81d:

A solution of compound 81c (67 mg, 0.14 mmol), $N^1,N^1,N^2$-trimethylethane-1,2-diamine (28 mg, 0.27 mmol) and DIEA (52 mg, 0.41 mmol) in NMP (0.6 mL) was heated at 80° C. for 2 h. The reaction mixture was diluted with water (50 mL) and extracted with EA (10 mL×5). The combined organics was washed with brine, dried over anhydrous sodium sulfate, filtered and the filtrate was evaporated under reduced pressure. The residue was purified by silica gel flash chromatography, elution gradient from 0% to 10% MeOH in DCM. Pure fractions were evaporated to dryness to afford compound 81d (30 mg, 38% yield) as a brown solid.

LCMS: $R_t$=1.46 min in 3 min chromatography (3 min-5-95% MeCN in water (6 mmol/L $NH_4HCO_3$), Waters Acquity UPLC BEH C18 1.7 um, 2.1*50 mm, 40° C.), MS (ESI) m/z 578.1 [M+H]$^+$.

Procedure for the Preparation of Compound 81e:

Palladium on carbon (11 mg) was added to a solution of compound 81d (30 mg, 0.050 mmol) in MeOH (5 mL). The reaction was stirred at 20° C. for 30 min under hydrogen atmosphere. The resulting mixture was filtered and the filtrate was evaporated under reduced pressure to afford compound 81e (22 mg, crude) as a light brown solid.

LCMS: $R_t$=1.22 min in 3 min chromatography (3 min-5-95% MeCN in water (6 mmol/L $NH_4HCO_3$), Waters Acquity UPLC BEH C18 1.7 um, 2.1*50 mm, 40° C.), MS (ESI) m/z 548.2 [M+H]$^+$.

Procedure for the Preparation of Example 81:

To a solution of compound 81e (22 mg, 0.04 mmol) and DIEA (16 mg, 0.12 mmol) in NMP (0.8 mL) was added a solution of acryloyl chloride (21 mg, 0.23 mmol) in NMP (0.2 mL) at 0° C. The reaction mixture was stirred at 0° C. for 30 min. The solution was purified by C18-flash chromatography, elution gradient from 0% to 80% MeCN in water (0.02% ammonia). Pure fractions were lyophilized to dryness to afford Example 81 (3.8 mg, 16% yield) as a off-white solid.

LCMS: $R_t$=1.34 min in 3 min chromatography (3 min-5-95% MeCN in water (6 mmol/L $NH_4HCO_3$), Waters Acquity UPLC BEH C18 1.7 um, 2.1*50 mm, 40° C.), MS (ESI) m/z 602.1 [M+H]$^+$.

$^1$H NMR: (500 MHz, DMSO-$d_6$) δ 1.5 (s, 6H) 2.2 (s, 6H) 2.3 (br t, J=5.7 Hz, 2H) 2.7 (s, 3H) 2.8 (brt, J=5.5 Hz, 2H) 3.8 (s, 3H) 3.8 (s, 3H) 5.7-5.7 (m, 1H) 6.1 (dd, J=16.9, 1.7 Hz, 1H) 6.2 (s, 1H) 6.3 (dd, J=16.9, 10.2 Hz, 1H) 7.0 (s, 1H) 7.2 (d, J=11.0 Hz, 1H) 7.6 (s, 1H) 7.8 (s, 1H) 8.6 (d, J=7.6 Hz, 1H) 8.7 (s, 1H) 10.0 (s, 1H) 10.4 (s, 1H).

Example 82

(R)—N-(5-(4-(5-chloro-4-fluoro-2-(2-hydroxypropan-2-yl)phenylamino)pyrimidin-2-ylamino)-2-(2-((dimethylamino)methyl)-4,4-difluoropyrrolidin-1-yl)-4-methoxyphenyl)acrylamide

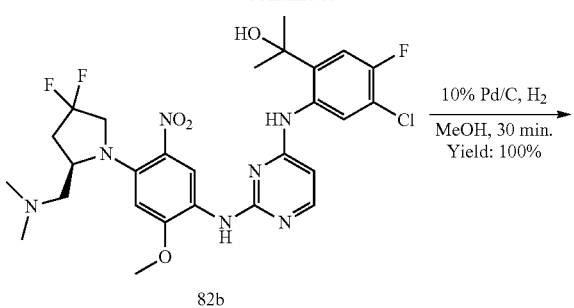

82b

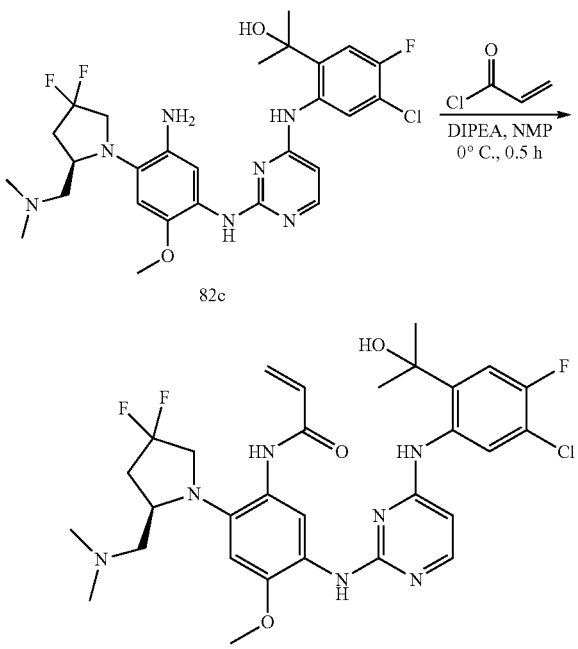

82c

Example 82

Procedure for the Preparation of Compound 82a:

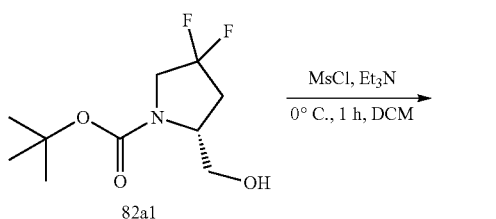

82a1

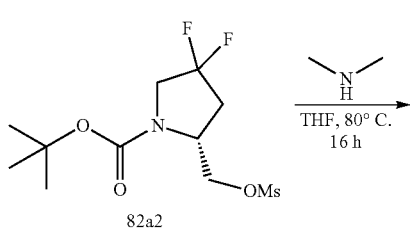

82a2

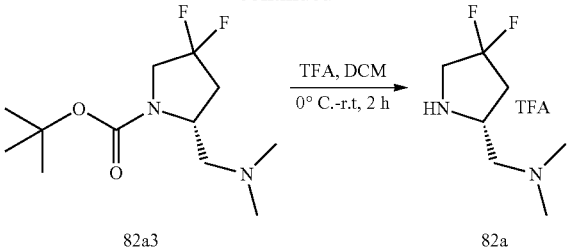

82a3 → 82a

To a stirred solution of compound 82a1 (250 mg, 1.054 mmol) and TEA (213 mg, 2.108 mmol) in DCM (5 mL) at 0° C. by ice/water bath was dropwise added MsCl (127 mg, 1.106 mmol, 1.05 equiv.) over 2 min. Then the reaction mixture was stirred at this temperature for 1 h. Then the reaction mixture was diluted with 50 ml of saturated NaHCO₃ solution, extracted with DCM (20 mL×3). The combined organic layer was washed with brine (60 mL×1), dried over anhydrous sodium sulfate, filtered and evaporated under reduced pressure to afford compound 82a2 (330 mg, crude) as a brown oil.

LCMS: $R_f$=1.21 min in 3 min chromatography (3 min-5-95% MeCN in water (6 mmol/L NH₄HCO₃, Waters Acquity UPLC BEH C18 1.7 um, 2.1*50 mm, 40° C.), MS (ESI) m/z 216.1 [M-Boc]⁺.

To a solution of compound 82a2 (330 mg, 1.05 mmol) in THF was added 40% Wt dimethylamine water solution (3 mL). The resulting mixture was sealed and heated at 80° C. for 16 h. The reaction was diluted with saturated NaHCO₃ solution (50 mL), extracted with EA (20 mL×3), washed with brine (50 mL×1), dried over anhydrous sodium sulfate, filtered and evaporated under reduced pressure to afford of compound 82a3 (275 mg, crude) as a brown oil.

LCMS: $R_f$=0.64 min in 3 min chromatography (3 min-5-95% MeCN in water (0.02% FA, Waters Acquity UPLC BEH C18 1.7 um, 2.1*50 mm, 40° C.), MS (ESI) m/z 208.7 [M-55]⁺.

A stirred solution of compound 82a3 (275 mg, 1.04 mmol) in DCM (3 mL) was cooled to 0° C. by ice/water bath. Then TFA was added dropwise into the reaction mixture. The resulting mixture was stirred and warmed slowly to room temperature for 2 h. After completion, the reaction solution was concentrated under reduced pressure to afford compound 82a (270 mg, crude) as a brown oil.

LCMS: $R_f$=0.25 min in 3 min chromatography (3 min-5-95% MeCN in water (0.02% FA, Waters Acquity UPLC BEH C18 1.7 um, 2.1*50 mm, 40° C.), MS (ESI) m/z 165.1 [M+1].

Procedure for the Preparation of Compound 82b:

A solution of compound 36b (152 mg, 0.270 mmol), compound 82a (106 mg, 0.404 mmol) and DIPEA (105 mg, 0.810 mmol) in NMP (2.5 mL) was sealed and heated at 100° C. for 5 days. The reaction mixture was diluted with 100 mL of water, extracted with EA (20 mL×5), the combined organic layer was washed with brine (100 mL×1), dried over anhydrous sodium sulfate, filtered and evaporated under reduced pressure. The residue was purified by silica gel flash column (MeOH/DCM=0%-10%) to afford compound 82b (84 mg, 51% Yield) as a light brown solid.

LCMS: $R_f$=1.63 min in 3 min chromatography (3 min-5-95% MeCN in water (6 mmol/L NH₄HCO₃, Waters Acquity UPLC BEH C18 1.7 um, 2.1*50 mm, 40° C.), MS (ESI) m/z 610.1 [M+H]⁺.

Procedure for the Preparation of Compound 82c:

10% of Pd/C (29 mg, 0.028 mmol) was added into a solution of compound 82b (84 mg, 0.138 mmol) in 7 mL of MeOH under nitrogen, the reaction was stirred at room temperature under atmosphere of hydrogen for 30 min. After completion of the reaction, the resulting mixture was filtered through Celite, and was washed with methanol. The filtrate was evaporated under reduced pressure to afford compound 82c (80 mg, crude) as a light brown solid.

LCMS: R$_t$=1.51 min in 3 min chromatography (3 min-5-95% MeCN in water (6 mmol/L NH$_4$HCO$_3$, Waters Acquity UPLC BEH C18 1.7 um, 2.1*50 mm, 40° C.), MS (ESI) m/z 580.2 [M+H]$^+$.

Procedure for the Preparation of Example 82:

A solution of compound 82c (54 mg, 0.093 mmol) and DIPEA (36 mg, 0.279 mmol) in NMP (2 mL) was cooled and stirred at 0° C. by ice/water bath. then added a solution of acryloyl chloride (8.4 mg, 0.093, 1.00 equiv.) in NMP (0.2 mL) dropwise into the reaction. The reaction mixture was stirred at 0° C. for 30 min. Then the solution was purified by C18/40 G (MeCN/Water=0%-80%, 0.02% ammonium hydroxide solution in water) and lyophilized to afford of Example 82 (8.50 mg, 14% yield) as an off-white solid.

LCMS: R$_t$=1.56 min in 3 min chromatography (3 min-5-95% MeCN in water (6 mmol/L NH$_4$HCO$_3$, Waters Acquity UPLC BEH C18 1.7 um, 2.1*50 mm, 40° C.), MS (ESI) m/z 634.2 [M+H]$^+$.

HPLC: R$_t$=10.203 min. (15 min-5-95% MeCN in water (6 mmol/L NH$_4$HCO$_3$, Agilent Eclipse Plus C18, Sum, 4.6*150 mm, 30° C.).

$^1$H NMR (500 MHz, DMSO-d$_6$) δ 1.4 (s, 6H) 2.0 (s, 6H) 2.1-2.4 (m, 4H) 2.5-2.7 (m, 1H) 3.6-3.7 (m, 1H) 3.7 (s, 3H) 3.8 (br d, J=6.3 Hz, 1H) 5.6 (br d, J=10.1 Hz, 1H) 6.0-6.1 (m, 3H) 6.5 (br dd, J=16.7, 10.4 Hz, 1H) 6.8 (s, 1H) 7.2 (br d, J=11.0 Hz, 1H) 7.8 (br s, 1H) 7.9 (br d, J=5.7 Hz, 1H) 8.1 (br d, J=6.9 Hz, 1H) 8.2 (s, 1H) 9.2 (s, 1H) 9.5 (br s, 1H).

Example 83

(R)—N-(5-(4-(5-chloro-4-fluoro-2-(2-hydroxypropan-2-yl)phenylamino)pyrimidin-2-ylamino)-2-(7-(dimethylamino)-5-azaspiro[2.4]heptan-5-yl)-4-methoxyphenyl) acrylamide formic Acid Salt

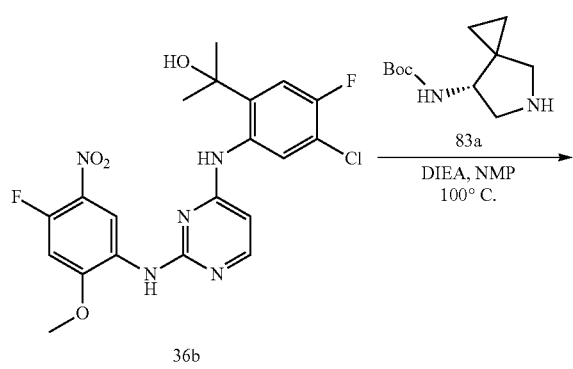

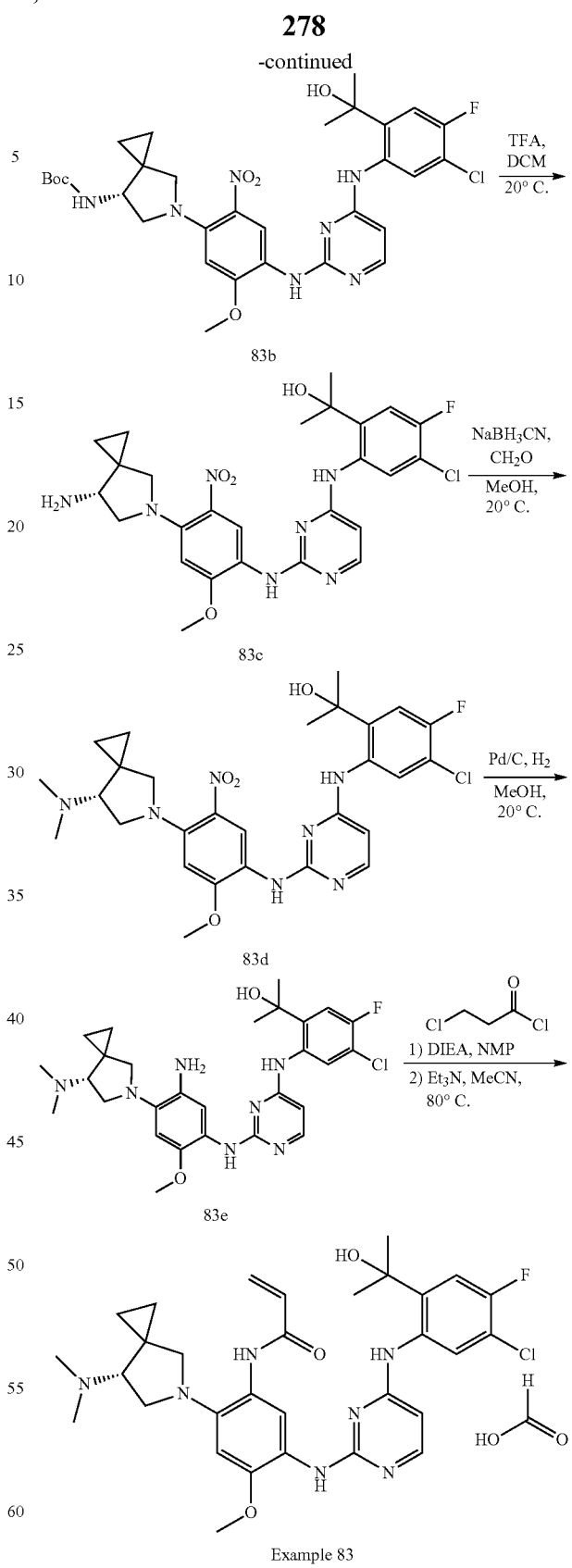

Procedure for the Preparation of Compound 83b:

To a mixture of compound 36b (120 mg, 0.26 mmol) in NMP (3 mL) was added compound 83a (55 mg, 0.26 mmol)

and DIEA (74 mg, 0.57 mmol). The resulting mixture was heated at 100° C. for 2 hours. The mixture was purified by C18-flash chromatography, elution gradient from 5% to 70% CH₃CN in water (0.02% FA). Pure fractions were evaporated to dryness to afford compound 83b (120 mg, 70% yield) as a yellow solid.

LCMS: $R_t$=1.19 min in 3 min chromatography (3 min-5-95% MeCN in water (0.02% FA), Waters Acquity UPLC BEH C18 1.7 um, 2.1*50 mm, 40° C.), MS (ESI) m/z 658.1 [M+H]⁺.

Procedure for the Preparation of Compound 83c:

To a mixture of compound 83b (120 mg, 0.18 mmol) in DCM (1 mL) was added TFA (1 mL). The resulting mixture was stirred at 20° C. for 30 min. The mixture was diluted with saturated sodium carbonate aqueous solution (50 mL) and EtOAc (50 mL). The organic layer was washed with brine, dried over sodium sulfate, concentrated in vacuum to afford compound 83c (96 mg, 94% yield) as a yellow solid.

LCMS: $R_t$=1.34 min in 3 min chromatography (3 min-5-95% MeCN in water (6 mmol/L NH₄HCO₃), Waters Acquity UPLC BEH C18 1.7 um, 2.1*50 mm, 40° C.), MS (ESI) m/z 558.1 [M+H]⁺.

Procedure for the Preparation of Compound 83d:

To a mixture of compound 83c (95 mg, 0.17 mmol) in methanol (3 mL) was added formaldehyde (1 mL) and NaBH₃CN (54 mg, 0.85 mmol). The resulting mixture was stirred at 20° C. for 1 hour. The mixture was purified by C18-flash chromatography, elution gradient from 5% to 70% CH₃CN in water (0.02% FA). Pure fractions were evaporated to dryness to afford compound 83d (82 mg, 82% yield) as a yellow solid.

LCMS: $R_t$=1.55 min in 3 min chromatography (3 min-5-95% MeCN in water (6 mmol/L NH₄HCO₃), Waters Acquity UPLC BEH C18 1.7 um, 2.1*50 mm, 40° C.), MS (ESI) m/z 586.0 [M+H]⁺.

Procedure for the Preparation of Compound 83e:

To a mixture of compound 83d (81 mg, 0.15 mmol) in methanol (3 mL) was added palladium on carbon (20 mg), the resulting mixture was stirred at 20° C. for 1 hour under hydrogen atmosphere. The mixture was then filter and the filtrate was concentrated in vacuum to afford compound 83e (67 mg, 87% yield) as a yellow solid.

LCMS: $R_t$=1.44 min in 3 min chromatography (3 min-5-95% MeCN in water (6 mmol/L NH₄HCO₃), Waters Acquity UPLC BEH C18 1.7 um, 2.1*50 mm, 40° C.), MS (ESI) m/z 556.1 [M+H]⁺.

Procedure for the Preparation of Example 83:

To a mixture of compound 83e (67 mg, 0.12 mmol) in NMP (2 mL) was added 3-chloropropionyl chloride (17 mg, 0.13 mmol) and DIEA (19 mg, 0.15 mmol) at 0° C., the resulting solution was stirred at 0° C. for 1 hour. MeCN (2 mL) and TEA (0.5 mL) were added. The mixture was heated at 80° C. for 16 hours. The mixture was diluted with water (30 mL) and EA (30 mL). The organic layer was concentrated, the residue was purified by C18-flash chromatography, elution gradient from 5% to 60% CH₃CN in water (0.02% FA). Pure fractions were evaporated to dryness to afford Example 83 in the form of formic acid (38 mg, 52% yield) as a white solid.

LCMS: $R_t$=0.74 min in 3 min chromatography (3 min-5-95% MeCN in water (0.02% FA), Waters Acquity UPLC BEH C18 1.7 um, 2.1*50 mm, 40° C.), MS (ESI) m/z 610.2 [M+H]⁺.

¹H NMR (500 MHz, DMSO-d₆) δ 0.53-0.59 (m, 2H) 0.66-0.72 (m, 1H) 0.91-0.96 (m, 1H) 1.49 (s, 6H) 2.23 (s, 6H) 2.77 (br dd, J=5.36, 2.84 Hz, 1H) 2.80 (d, J=8.83 Hz, 1H) 3.35-3.37 (m, 3H) 3.79 (s, 3H) 5.63-5.73 (m, 1H) 6.06 (d, J=5.67 Hz, 1H) 6.16 (dd, J=17.18, 2.05 Hz, 1H) 6.48 (dd, J=17.02, 10.40 Hz, 1H) 6.56 (s, 1H) 7.29 (d, J=11.03 Hz, 1H) 7.65 (s, 1H) 7.84 (br s, 1H) 7.96 (d, J=5.67 Hz, 1H) 8.14 (d, J=7.25 Hz, 1H) 8.21 (s, 1H) 9.21 (s, 1H) 9.58 (s, 1H).

Example 84

(R)—N-(5-(4-(5-chloro-4-fluoro-2-(2-hydroxypropan-2-yl)phenylamino)-5-(trifluoromethyl)pyrimidin-2-ylamino)-2-(3-(dimethylamino)pyrrolidin-1-yl)-4-methoxyphenyl)acrylamide

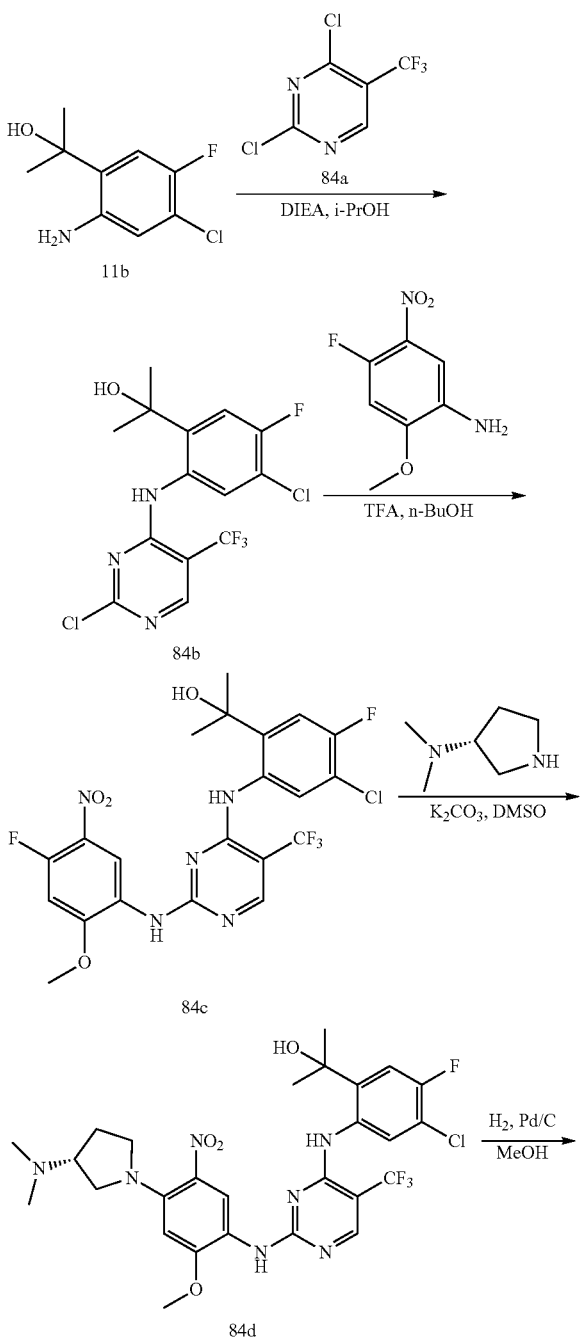

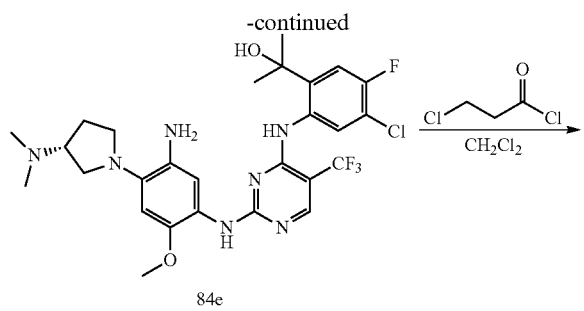

84e

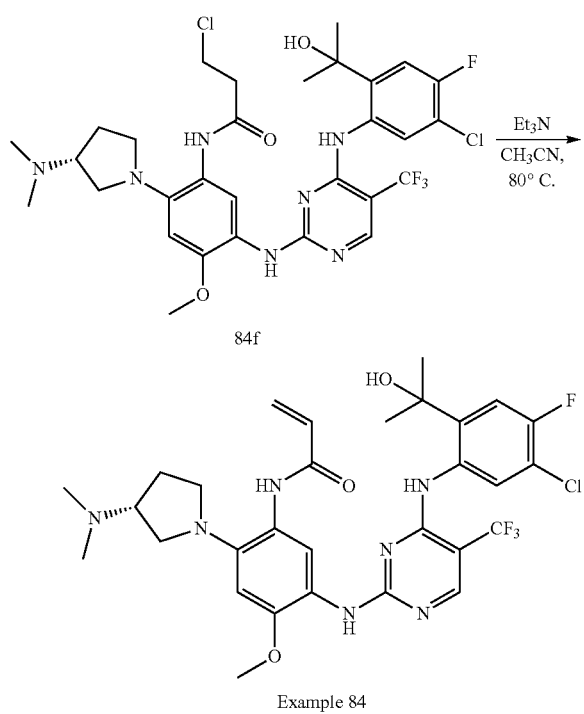

84f

Example 84

Procedure for the Preparation of Compound 84b.

To a solution of compound 11b (1000 mg, 4.91 mmol) and DIEA (1269 mg, 9.82 mmol) in i-PrOH (20 mL) was added compound 84a (1065 mg, 4.91 mmol). The resulting mixture was stirred at 50° C. for 2 h. The reaction was purified by flash reversed-phase C-18 column chromatography eluting with MeOH/H$_2$O (MeOH in water from 10% to 100%) to give compound 84b (300 mg, 16% yield) as a brown solid.

LCMS: R$_t$=0.944 min in 5-95AB_1.5min_220&254 chromatography (MERCK RP18e 25-2 mm), MS (ESI) m/z=366.1[M-OH]$^+$.

Procedure for the Preparation of Compound 84c:

To a solution of compound 84b (300 mg, 0.78 mmol) in n-BuOH (5 mL) with TFA (0.05 mL) was added 4-fluoro-2-methoxy-5-nitroaniline (160 mg, 0.86 mmol). The resulting mixture was stirred at 50° C. for 18 h. The reaction was pour into ice water (50 mL) and yellow solid was precipitated out. The solid was filtered and dissolved with CH$_2$Cl$_2$ (60 mL), then dried over anhydrous Na$_2$SO$_4$ and concentrated under reduced pressure to give compound 84c (320 mg, 77% yield) as a yellow solid.

LCMS: R$_t$=0.931 min in 5-95AB_1.5min_220&254 chromatography (MERCK RP18e 25-2 mm), MS (ESI) m/z=534.1 [M+H]$^+$.

Procedure for the Preparation of Compound 84d:

A solution of compound 84c (300 mg, 0.56 mmol) in DMSO (4 mL) was added (R)—N,N-dimethylpyrrolidin-3-amine (64 mg, 0.56 mmol) and K$_2$CO$_3$ (233 mg, 1.69 mmol).

The mixture was stirred at 80° C. for 18 hours. The reaction was pour into ice water (50 mL) and yellow solid was precipitated out. The yellow solid was filtered and dissolved with CH$_2$Cl$_2$ (60 mL), then dried over anhydrous Na$_2$SO$_4$ and concentrated under reduced pressure to give compound 84d (280 mg, 80% yield) as a yellow solid.

LCMS: R$_t$=0.773 min in 5-95AB_1.5MIN_220&254 chromatography (XBrige Shield RP18 2.1*50 mm), MS (ESI) m/z=628.4 [M+H]$^+$.

Procedure for the Preparation of Compound 84e:

To a solution of compound 84d (280 mg, 0.45 mmol) in MeOH (5 mL) was added Pd/C (28 mg) under N$_2$. The black mixture was stirred at 6-13° C. under H$_2$ balloon (15 Psi) for 1 h. The reaction mixture was filtered and concentrated under reduced pressure to afford compound 84e (250 mg, 95.4% yield) as brown oil.

LCMS: R$_t$=0.720 min in 10-80CD_3MIN_220&254 chromatography (XBrige Shield RP18 2.1*50 mm), MS (ESI) m/z=598.1 [M+H]$^+$.

Procedure for the Preparation of Compound 84f:

To a solution of compound 84e (250 mg, 1.0 eq, 0.42 mmol) in CH$_2$Cl$_2$ (10 mL) was added 3-chloropropanoyl chloride (53 mg, 0.42 mmol) in ice water bath. The resulting mixture was stirred at 0-5° C. for 45 min while color changed from black to brown. The reaction mixture was poured into saturated NaHCO$_3$ (5 mL), extracted with CH$_2$Cl$_2$ (15 mL×2). The combined organic layers were washed with water (10 mL×2) and brine (10 mL) successively, dried and concentrated in vacuum to give compound 84f (200 mg, 69% yield) as brown solid.

LCMS: R$_t$=0.736 min in 5-95AB_1.5MIN_220&254.lcm chromatography (MERCK RP18 2.5-2 mm), MS (ESI) m/z=688.1 [M+H]$^+$.

Procedure for the Preparation of Example 84:

To a solution of compound 84f (200 mg, 0.29 mmol) in CH$_3$CN (10 mL) was added Et$_3$N (118 mg, 1.16 mmol). The resulting mixture was stirred at 80° C. for 12 h. The reaction was purified by prep-HPLC [Column: Waters Xbridge 150*25 5 um; Condition: 42-72% B (A: 0.05% ammonia; B: CH$_3$CN); Flow rate: 25 ml/min]. Fractions containing the desired compound were lyophilized to afford Example 84 (85.7 mg, 45.3% yield) as a white solid.

LCMS: R$_t$=2.312 min in 0-60AB_4min_220&254.lcm; chromatography (Xtimate C18 2.1*30 mm), MS (ESI) m/z=652.0 [M+H]$^+$.

HPLC: R$_t$=3.32 min in 10-80AB_1.2ml.met; chromatography (Ultimate C18 3*50 mm 3 um).

$^1$H NMR: (400 MHz, CDCl$_3$) δ 9.38 (br s, 1H), 8.75 (br s, 1H), 8.36 (br s, 1H), 8.15 (br s, 1H), 7.96 (br s, 1H), 7.43 (s, 1H), 7.04 (d, J=10.6 Hz, 1H), 6.70 (s, 1H), 6.33-6.20 (m, 2H), 5.75-5.68 (m, 1H), 3.87 (s, 3H), 3.21-3.06 (m, 4H), 2.93-2.82 (m, 1H), 2.72 (br s, 1H), 2.30 (s, 6H), 2.23-2.12 (m, 1H), 1.98-1.87 (m, 1H), 1.68 (br d, J=4.0 Hz, 6H)

Example 85

(R)—N-(5-(4-(5-chloro-4-fluoro-2-(2-hydroxypropan-2-yl)phenylamino)-5-cyanopyrimidin-2-ylamino)-2-(3-(dimethylamino)pyrrolidin-1-yl)-4-methoxyphenyl)acrylamide

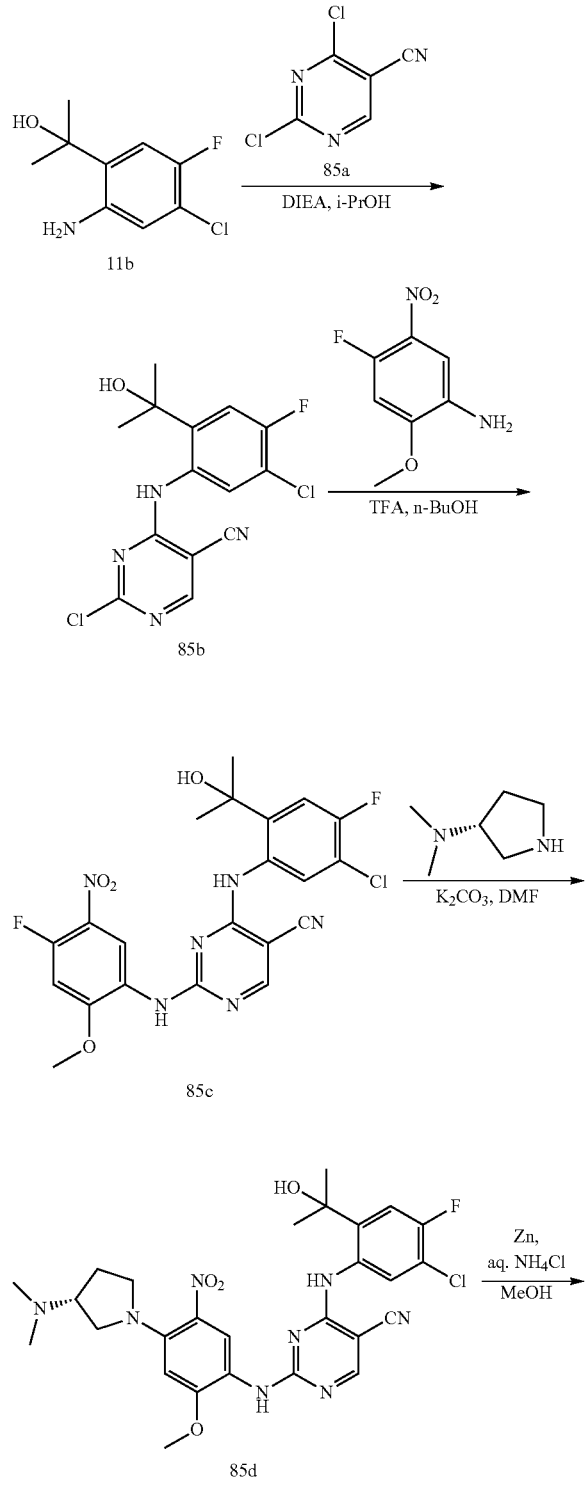

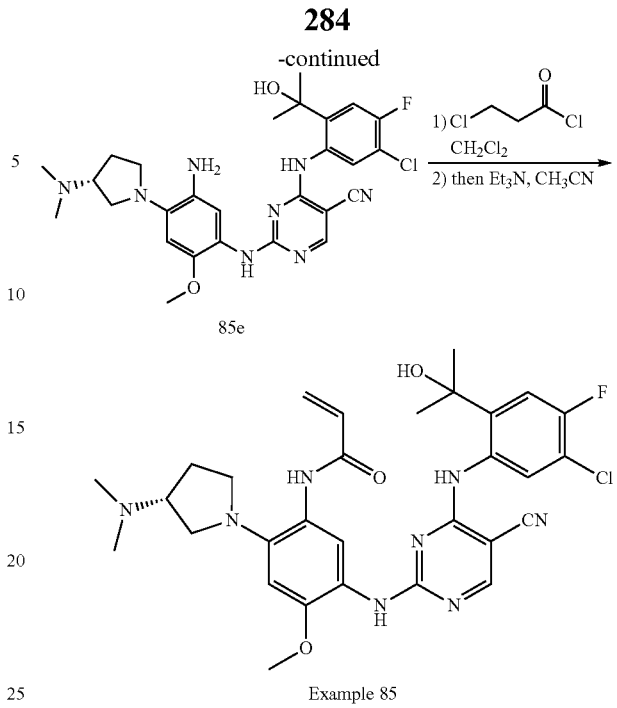

Procedure for the Preparation of Compound 85b:

To a solution of compound 11b (500 mg, 2.46 mmol) in i-PrOH (5 mL) was added DIEA (635 mg, 4.91 mmol) and compound 85a (470 mg, 2.70 mmol). The resulting mixture was stirred at 80° C. for 1 hr. The mixture was poured into water (20 mL) and extracted with EtOAc (100 mL×3). The combined organic layers were dried over $Na_2SO_4$, filtered and concentrated in vacuum to give the crude product, which was purified by prep-HPLC [column Boston Green ODS 150*30 5 um, condition 65% B (A, water/0.1% TFA, B: $CH_3CN$); Flow rate: 25 ml/min]. The pH of the fractions were adjusted to 7-8 with sat. $NaHCO_3$ and extracted with EtOAc (20 mL×3). The combined organic layers were washed with brine (50 mL), dried over $Na_2SO_4$, filtered and concentrated in vacuum to give desired compound 85b (280 mg, 33% yield) and its regioisomer.

LCMS: $R_t$=3.661 in 10-80AB_7.0min_220&254 chromatography (Xtimate C18 2.1*30 mm), MS (ESI) m/z=322.8 [M+H-18]+.

$^1$H NMR (400 MHz, DMSO-$d_6$) δ 11.22 (br s, 1H), 8.82 (s, 1H), 8.23 (d, J=7.2 Hz, 1H), 7.44 (d, J=11.2 Hz, 1H), 6.63 (br s, 1H), 1.53 (s, 6H).

Procedure for the Preparation of Compound 85c:

A mixture of compound 85b (280 mg, 0.82 mmol), 4-fluoro-2-methoxy-5-nitroaniline (168.0 mg, 0.90 mmol) and TFA (300 uL) in n-BuOH (3.0 mL) was stirred at 35° C. for 15 hr. The reaction mixture was filtered and the filtered cake was washed with n-BuOH (3 mL), then dried in vacuum to give the desired product 85c (270 mg, 67.2% yield) as a grey solid. The exact structure was confirmed in this step by 2D-NMR (HMBC, etc.).

LCMS: $R_t$=0.899 min in 5-95AB_220&254.lcm chromatography (MERCK RP-18e 25-2 mm), MS (ESI) m/z=491.1 [M+H]+.

$^1$H NMR: (400 MHz, DMSO-$d_6$) δ 10.81 (s, 1H), 9.47 (br s, 1H), 8.57 (s, 1H), 8.31 (br d, J=6.4 Hz, 1H), 8.02 (br s, 1H), 7.39 (d, J=13.6 Hz, 1H), 7.31 (br d, J=11.2 Hz, 1H), 7.28-7.14 (m, 1H), 6.56 (br s, 1H), 3.89 (s, 3H), 1.52 (s, 6H).

Procedure for the Preparation of Compound 85d:

A mixture of compound 85c (240 mg, 0.489 mmol), (R)—N,N-dimethylpyrrolidin-3-amine (66.3 mg, 0.586 mmol) and K$_2$CO$_3$ (135.0 mg, 0.978 mmol) in DMSO (3 mL) was stirred at 80° C. for 20 h (brown suspension). The reaction was quench with H$_2$O (10 mL) and diluted with EtOAc (10 mL), stirred for 3 hr and then filtered, the filter cake was washed with H$_2$O (5 ml) and then dried in high vacuum to give the title compound 85d (190 mg, 66.4% yield) as a brown solid.

LCMS: R$_t$=0.760 min in 5-95AB_220&254.lcm chromatography (MERCK RP-18e 25-2 mm), MS (ESI) m/z=607.2 [M+Na]$^+$.

Procedure for the Preparation of Compound 85e:

The mixture of compound 85d (140 mg, 0.239 mmol), Zn (77.8 mg, 1.196 mmol) and NH$_4$Cl (64.5 mg, 1.196 mmol) in MeOH/H$_2$O (5.0 mL/2.0 mL) was stirred at 80° C. for 2.0 hr (white suspension). The reaction was filtered and the filtered cake was washed with CH$_2$Cl$_2$ (10 mL) and H$_2$O (10 mL), the filtrate was extracted with CH$_2$Cl$_2$ (20 mL×3), the combined organic layers were washed with brine (20 mL), dried over Na$_2$SO$_4$ and concentrated in vacuum to give compound 85e (120 mg, 90.9% yield) as a grey solid.

LCMS: R$_t$=0.712 min in 5-95AB_220&254.lcm chromatography (MERCK RP-18e 25-2 mm), MS (ESI) m/z=555.1 [M+H]$^+$.

Procedure for the Preparation of Example 85:

A mixture of compound 85e (120 mg, 0.217 mmol) and 3-chloropropanoyl chloride (34.1 mg, 0.238 mmol) in CH$_2$Cl$_2$ (3 mL) was stirred at 0° C. for 1 hr (brown suspension). The reaction was diluted with CH$_3$CN (5 ml), the resulting mixture was concentrated in vacuo to a volume of 4 mL, the residue was added TEA (218 mg, 2.16 mmol) and the resulting mixture was stirred at 100° C. for 4 hr (black suspension). The reaction was purified by prep-HPLC directly [Waters Xbridge 150*25 5 um Condition: 42-72% B (A: 0.05% ammonia hydroxide B: CH$_3$CN); Flow rate: 25 mL/min]. Fractions containing the desired compound were lyophilized to afford Example 85 (59.0 mg, 32.6% yield) as a yellow solid.

LCMS: R$_t$=2.482 min in 0-60AB_4.0min_220&254 chromatography (Xtimate C18 2.1*30 mm), MS (ESI) m/z=609.1 [M+H]$^+$.

HPLC: R$_t$=5.13 min in 0-60_CD_1.2ML chromatography (XBridge Shield RP 18 2.1*50 mm 5 um).

$^1$H NMR: (400 MHz, CDCl$_3$) δ 10.08 (br s, 1H), 9.30-8.03 (m, 2H), 8.01-7.71 (m, 1H), 7.48 (br s, 1H), 6.96 (d, J=10.4 Hz, 1H), 6.64 (s, 1H), 6.21 (br s, 2H), 5.67 (br d, J=6.0 Hz, 1H), 3.82 (s, 3H), 3.70-3.36 (m, 1H), 3.25-2.98 (m, 4H), 2.82 (q, J=7.2 Hz, 1H), 2.24 (s, 6H), 2.17-2.06 (m, 1H), 1.88-1.82 (m, 1H), 1.62 (br s, 6H).

Example 86

(S)—N-(5-(4-(5-chloro-4-fluoro-2-(2-hydroxypropan-2-yl)phenylamino)pyrimidin-2-ylamino)-2-(3-((dimethylamino)methyl)pyrrolidin-1-yl)-4-methoxyphenyl)acrylamide

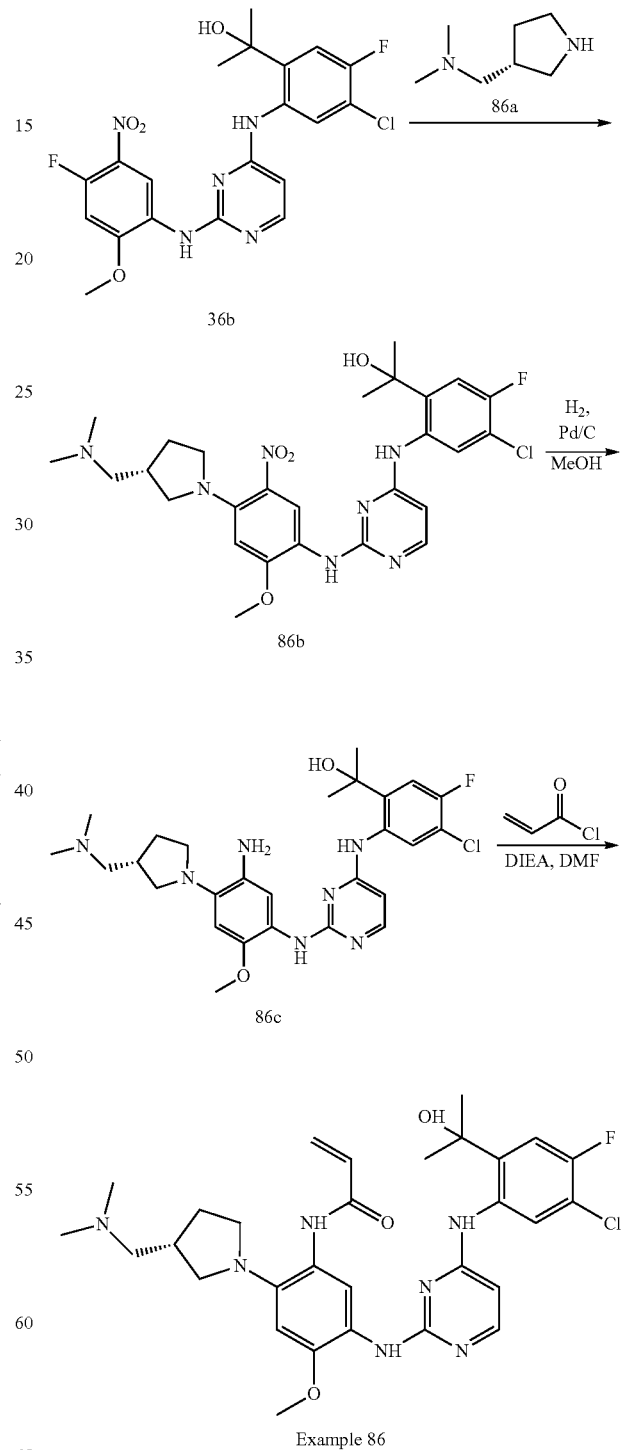

Example 86

Procedure for the Preparation of Compound 86a:

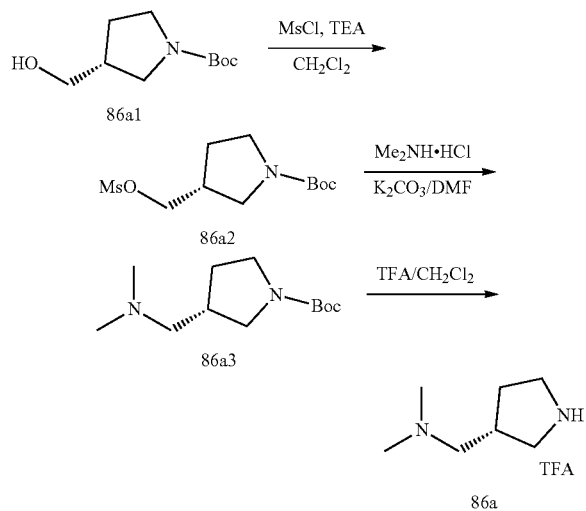

To a solution of compound 86a1 (1 g, 4.98 mmol) and TEA (1.0 g, 9.96 mmol) in CH$_2$Cl$_2$ (10 mL) was added MsCl (800 mg, 6.98 mmol) in ice water bath. The resulting mixture was stirred at 0-5° C. for 30 min. The reaction solution was poured into brine (5 mL), and extracted with CH$_2$Cl$_2$ (10 mL×2). The combined organic layers were washed with water (10 mL×2) and brine (10 mL) successively, then dried over Na$_2$SO$_4$ and concentrated in vacuum to give compound 86a2 (1.2 g, 86% yield) as yellow oil, which was used directly in the next step directly without further purification.

A mixture of compound 86a2 (1.2 g, 4.30 mmol) and Me$_2$NH.HCl (1.75 g, 21.5 mmol) and K$_2$CO$_3$ (4.16 g, 30.1 mmol) in DMF (10 mL) was stirred at 100° C. for 5 h. The reaction mixture was diluted with EtOAc (40 mL) and stirred for additional 30 min, filtered and the filter cake was washed with EtOAc (20 mL). The filtrate was concentrated in vacuum to give crude product, which was purified by column chromatography on silica gel (0-10% MeOH in CH$_2$Cl$_2$) to give compound 86a3 (800 mg, 66.7% yield) as colorless oil.

$^1$H NMR: (400 MHz, CDCl$_3$) δ 3.52-3.42 (m, 1H), 3.41-3.31 (m, 1H), 3.28-3.16 (m, 1H), 2.94-2.85 (m, 1H), 2.34-2.13 (m, 9H), 1.95-1.85 (m, 1H), 1.59-1.44 (m, 1H), 1.38 (s, 9H).

To a solution of 86a3 (800 mg, 3.51 mmol) in CH$_2$Cl$_2$ (10 mL) was added TFA (2.6 g, 35.1 mmol) at 0° C. The mixture was stirred at 6-13° C. for 6 h. The reaction mixture was concentrated in vacuum to give title compound 86a in TFA salt (400 mg, 80.2% yield) as colourless oil.

$^1$H NMR: (400 MHz, CDCl$_3$) δ 3.70 (br s, 1H), 3.51 (br s, 1H), 3.34-3.26 (m, 1H), 3.26-3.22 (m, 1H), 3.00-2.92 (m, 7H), 2.83-2.72 (m, 1H), 2.66-2.54 (m, 1H), 2.16 (br s, 1H), 1.73 (br s, 1H).

Procedure for the Preparation of Compound 86b:

To a solution of compound 36b (200 mg, 0.429 mmol) and K$_2$CO$_3$ (118 mg, 0.858 mmol) in DMSO (3 mL) was added compound 86a (65.9 mg, 0.515 mmol). The resulting mixture was stirred at 85° C. for 2 h while the color was changed from pale yellow to deep yellow. The reaction mixture was poured into ice water (20 mL) with stirring and yellow solid was precipitated. The precipitated solid was collected by filtration and then dissolved into CH$_2$Cl$_2$ (50 mL), dried over anhydrous Na$_2$SO$_4$ and concentrated under reduced pressure to give compound 86b (200 mg, 70.6% yield) as a yellow solid.

LCMS: R$_t$=0.691 min in 5-95AB_220&254.lcm chromatography (Agilent Pursit 5 C18 20*2.0 mm), MS (ESI) m/z=574.5 [M+H]$^+$.

$^1$H NMR: (400 MHz, CDCl$_3$) δ 8.97 (s, 1H), 8.90 (s, 1H), 8.09 (d, J=5.6 Hz, 1H), 7.92 (d, J=7.2 Hz, 1H), 7.18 (s, 1H), 7.10 (d, J=10.4 Hz, 1H), 6.33 (s, 1H), 6.17 (d, J=5.6 Hz, 1H), 3.94 (s, 3H), 3.48-3.41 (m, 1H), 3.32-3.27 (m, 1H), 3.14-3.07 (m, 2H), 2.53-2.43 (m, 1H), 2.38-2.33 (m, 2H), 2.27-2.23 (m, 7H), 2.16-2.10 (m, 1H), 1.67 (s, 6H).

Procedure for the Preparation of Compound 86c:

To a solution of compound 86b (200 mg, 0.348 mmol) in EtOAc (5 mL) was added Pd/C (50 mg, 10% wet). The resulting mixture was purged and degassed with H$_2$ for 3 times, then stirred at 13-20° C. under H$_2$ balloon (15 Psi) for 2 h. The reaction mixture was filtered and concentrated under reduced pressure to give compound 86c (150 mg, 72.8% yield) as light yellow solid.

LCMS: R$_t$=0.667 min in 5-95AB_1.5min_220&254 chromatography (Agilent Pursit 5 C18 20*2.0 mm), MS (ESI) m/z=544.5 [M+H]$^+$.

$^1$H NMR: (400 MHz, CDCl$_3$) δ 8.08 (d, J=6.8 Hz, 1H), 7.95 (d, J=5.6 Hz, 1H), 7.77 (s, 1H), 7.39 (s, 1H), 7.00 (d, J=10.4 Hz, 1H), 6.56 (s, 1H), 5.97 (d, J=5.6 Hz, 1H), 3.74 (s, 3H), 3.52-3.43 (m, 1H), 3.40-3.31 (m, 1H), 3.26-3.16 (m, 1H), 3.08-3.01 (m, 2H), 2.89 (m, 1H), 2.75 (m, 1H), 2.43 (s, 1H), 2.31-2.26 (s, 5H), 2.18-2.13 (s, 3H), 1.95-1.92 (m, 1H), 1.58 (s, 6H).

Procedure for the Preparation of Example 86:

To a solution of compound 86c (150 mg, 0.276 mmol) in CH$_2$Cl$_2$ (150 mL) was added acryloyl chloride (150 mg, 0.276 mmol) in ice water bath. The resulting mixture was stirred at 0-5° C. for 30 min. The reaction mixture was poured into saturated NaHCO$_3$ (5 mL) and stirred at 12-17° C. for 2 h, then extracted with CH$_2$Cl$_2$ (15 mL×2). The combined organic layers were dried over Na$_2$SO$_4$ and concentrated under reduced pressure to give the crude residue, which was purified by column chromatography on silica gel (8% MeOH in CH$_2$Cl$_2$) to give Example 86 (24.5 mg, 15.7% yield) as a yellow solid.

LCMS: R$_t$=1.547 min in 10-80AB_4min_220&254 chromatography (Xtimate C18 2.1*30 mm), MS (ESI) m/z=598.1 [M+H]$^+$.

HPLC: R$_t$=2.26 min in 10-80_ab_1.2ML chromatography (Ultimate C18 3*50 mm 3 um).

$^1$H NMR: (400 MHz, CDCl$_3$) δ 9.52-9.33 (m, 2H), 8.39 (s, 1H), 7.99 (d, J=6.0 Hz, 1H), 7.52-7.41 (m, 2H), 7.07 (d, J=10.8 Hz, 1H), 6.63 (s, 1H), 6.37-6.24 (m, 3H), 5.75-5.67 (m, 1H), 3.79 (s, 3H), 3.18-3.11 (m, 1H), 3.05-2.94 (m, 2H), 2.91-2.85 (m, 1H), 2.81-2.59 (m, 3H), 2.51 (s, 6H), 2.22-2.14 (m, 1H), 1.82-1.74 (m, 1H), 1.64 (s, 6H).

Example 87

(S)—N-(5-(4-(5-chloro-4-fluoro-2-(2-hydroxypropan-2-yl)phenylamino)pyrimidin-2-ylamino)-2-(3-(dimethylamino)pyrrolidin-1-yl)-4-methoxyphenyl) acrylamide

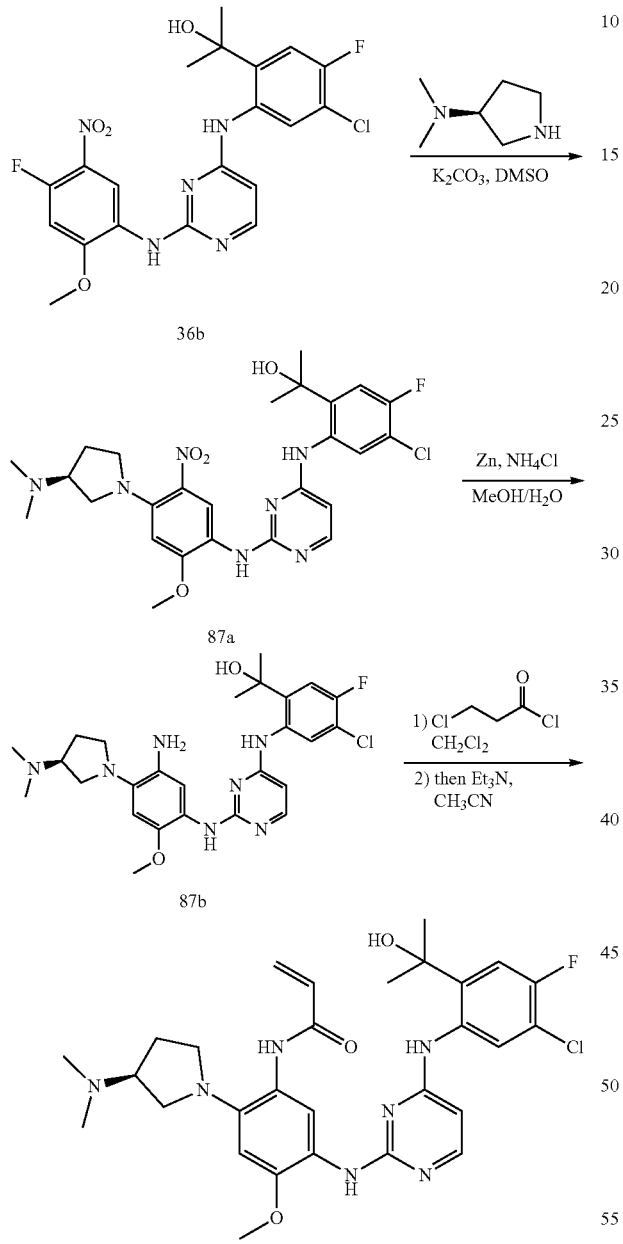

The synthesis followed a similar experimental procedure as Example 76 to afford Example 87 as a white solid.

LCMS: $R_t$=1.446 min in 10-80AB_4min_220&254 chromatography (Xtimate C18 2.1*30 mm), MS (ESI) m/z=584.1 [M+H]$^+$.

HPLC: $R_t$=3.74 min in 10-80_CD_1.2ML chromatography (XBridge Shield RP 18 2.1*50 mm 5 um).

$^1$H NMR: (400 MHz, CDCl$_3$) δ 9.66 (s, 1H), 9.43 (s, 1H), 8.56 (s, 1H), 8.09 (d, J=5.6 Hz, 1H), 7.52 (d, J=7.2 Hz, 1H), 7.47 (s, 1H), 7.15 (d, J=10.4 Hz, 1H), 6.76 (s, 1H), 6.41-6.29 (m, 3H), 5.81-5.75 (m, 1H), 5.64 (br s, 1H), 3.86 (s, 3H), 3.16-3.01 (m, 4H), 2.89 (q, J=6.8 Hz, 1H), 2.30 (s, 6H), 2.23-2.12 (m, 1H), 2.00-1.87 (m, 1H), 1.73 (s, 6H).

Example 88

N-(5-(4-(5-chloro-4-fluoro-2-(2-hydroxypropan-2-yl)phenylamino)pyrimidin-2-ylamino)-2-((2R,4R)-2-((dimethylamino)methyl)-4-fluoropyrrolidin-1-yl)-4-methoxyphenyl) acrylamide formic Acid Salt

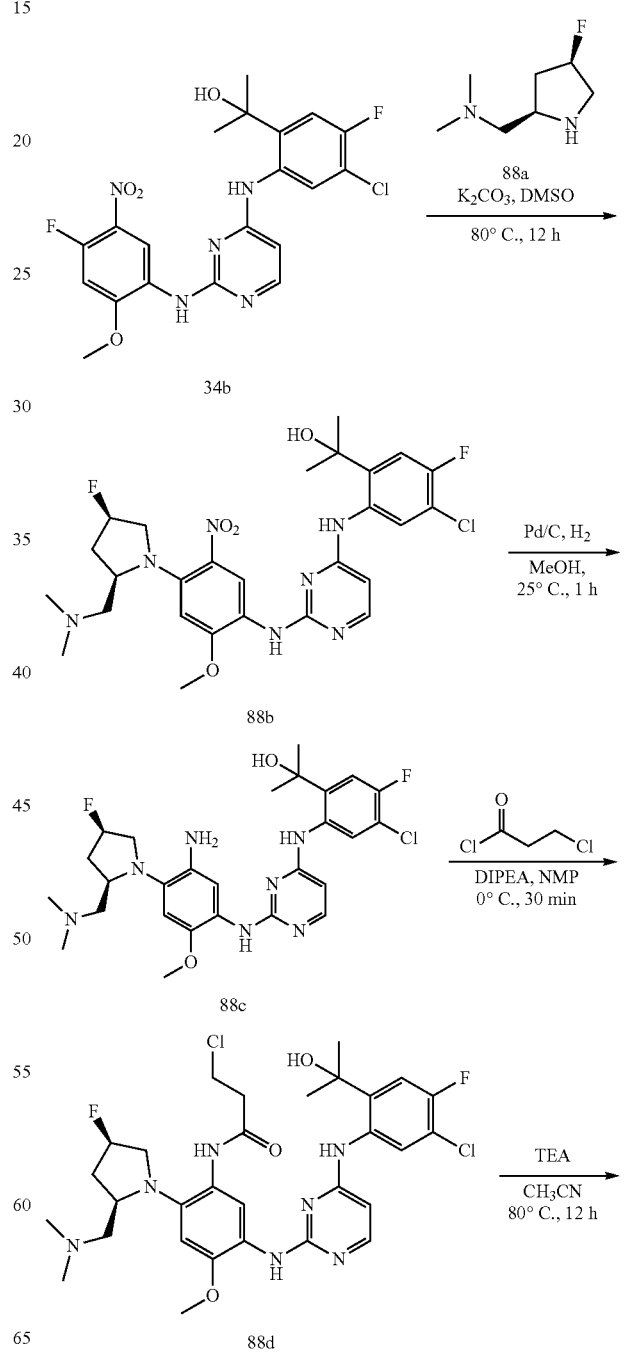

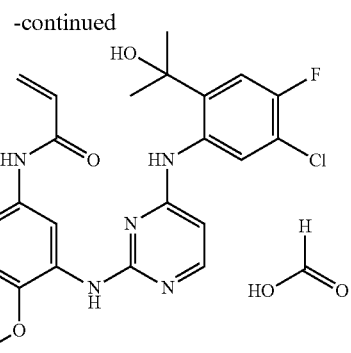

Example 88

Procedure for the Preparation of Compound 88a:

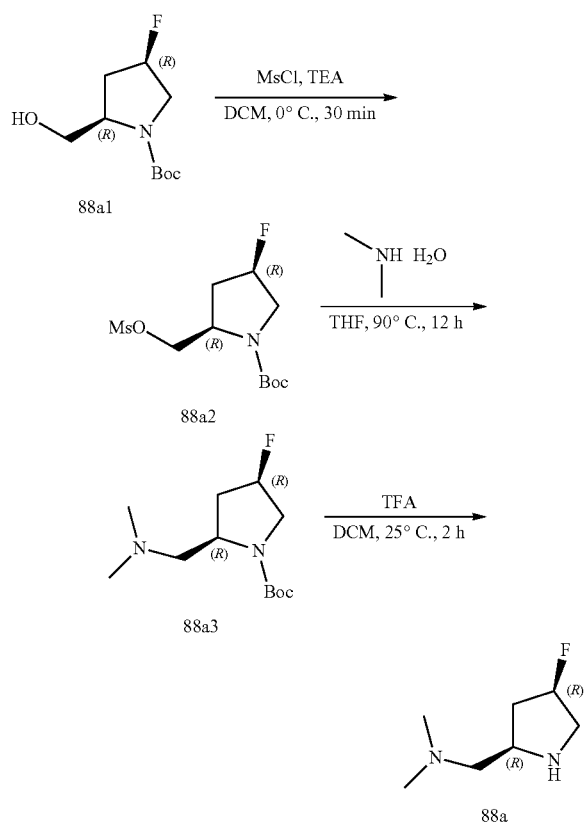

To a stirred solution of compound 88a1 (440 mg, 2.0 mmol) and TEA (404 mg, 4.0229, C3 mmol) in DCM (5 mL) at 0° C. by ice/water bath was added MsCl (276 mg, 2.4 mmol) dropwise. Then the reaction mixture was stirred at 0° C. for 1 h. Then the reaction mixture was diluted with 50 ml of saturated NaHCO$_3$ solution, extracted with DCM (30 mL×3). The combined organic layer was washed with brine (60 mL×2), dried over anhydrous sodium sulfate, filtered and evaporated under reduced pressure to afford compound 88a2 (500 mg, 84% yield) as a brown oil.

LCMS: $R_t$=1.32 min in 3 min chromatography (3 min-5-95% MeCN in water (6 mmol/L NH$_4$HCO$_3$, Waters Acquity UPLC BEH C18 1.7 um, 2.1*50 mm, 40° C.), MS (ESI) m/z 198.1 [M-Boc]$^+$.

To a solution of compound 88a2 (500 mg, 1.7 mmol) in THF was added dimethylamine aqueous solution (3 mL, 40% Wt). The resulting mixture was sealed and heated at 90° C. for 16 h. The reaction was diluted with saturated NaHCO$_3$ solution (50 mL), extracted with EA (20 mL×3), washed with brine (50 mL×1), dried over anhydrous sodium sulfate, filtered and evaporated under reduced pressure to afford compound 88a3 (320 mg, 77% yield) as a colorless oil.

LCMS: $R_t$=1.18 min in 3 min chromatography (3 min-5-95% MeCN in water (6 mmol/L NH$_4$HCO$_3$, Waters Acquity UPLC BEH C18 1.7 um, 2.1*50 mm, 40° C.), MS (ESI) m/z 247.2 [M+H]$^+$.

To a stirred solution of compound 88a3 (320 mg, 1.3 mmol) in DCM (5 mL) was added TFA (2 mL) dropwise at 0° C. The resulting mixture was stirred at 20° C. for 2 h, then the reaction solution was evaporated under reduced pressure to afford compound 88a (180 mg, 95% yield) as a colorless oil.

LCMS: $R_t$=0.25 min in 3 min chromatography (3 min-5-95% MeCN in water (6 mmol/L NH$_4$HCO$_3$, Waters Acquity UPLC BEH C18 1.7 um, 2.1*50 mm, 40° C.), MS (ESI) m/z 147.2 [M+H]$^+$.

Procedure for the Preparation of Compound 88b:

A mixture of compound 36b (225 mg, 0.48 mmol), compound 88a (106 mg, 0.73 mmol), and K$_2$CO$_3$ (200 mg, 1.4 mmol) in DMSO (3.0 mL) was sealed and heated at 85° C. for 24 h. The reaction mixture was diluted with 100 mL of water and extracted with EA (20 mL×5). The combined organic layer was washed with brine (100 mL×1), dried over anhydrous sodium sulfate, filtered and evaporated under reduced pressure. The residue was purified by flash silica chromatography, elution gradient from 0% to 10% MeOH in DCM. Pure fractions were evaporated to dryness to afford compound 88b (240 mg, 85% yield) as a light brown solid.

LCMS: $R_t$=1.48 min in 3 min chromatography (3 min-5-95% MeCN in water (6 mmol/L NH$_4$HCO$_3$, Waters Acquity UPLC BEH C18 1.7 um, 2.1*50 mm, 40° C.), MS (ESI) m/z 592.2 [M+H]$^+$.

Procedure for the Preparation of Compound 88c:

Palladium on carbon (25 mg, 10% Wt %) was added to a solution of compound 88b (70 mg, 0.12 mmol) in MeOH (7 mL) under nitrogen atmosphere. The resulting reaction was stirred at 20° C. for 30 min under hydrogen atmosphere. The mixture was filtered through Celite, and the filtrate was evaporated under reduced pressure to afford compound 88c (62 mg, 94% yield) as a light brown solid.

LCMS: $R_t$=1.34 min in 3 min chromatography (3 min-5-95% MeCN in water (6 mmol/L NH$_4$HCO$_3$, Waters Acquity UPLC BEH C18 1.7 um, 2.1*50 mm, 40° C.), MS (ESI) m/z 562.2 [M+H]$^+$.

Procedure for the Preparation of Compound 88d:

To a solution of compound 88c (62 mg, 0.11 mmol) and DIPEA (14 mg, 0.11 mmol) in NMP (5 mL) was added 3-chloropropionyl chloride (14 mg, 0.11 mmol) at 0° C. The resulting mixture was stirred at 0° C. for 10 min. The reaction mixture was diluted with water (50 mL), extracted with DCM (10 mL×3). The organic layer was washed with brine (30 mL×1), dried over anhydrous sodium sulfate, filtered and evaporated under reduced pressure to afford compound 88d (70 mg, 91% yield) as a white solid.

LCMS: $R_t$=1.37 min in 3 min chromatography (3 min-5-95% MeCN in water (6 mmol/L NH$_4$HCO$_3$, Waters Acquity UPLC BEH C18 1.7 um, 2.1*50 mm, 40° C.), MS (ESI) m/z 652.2 [M+H]$^+$.

Procedure for the Preparation of Example 88:

A solution of compound 88d (70 mg, 0.11 mmol) and TEA (110 mg, 1.1 mmol) in CH$_3$CN (5 mL) was heated at 80° C. for 12 h. Then the solution was purified by C18-flash chromatography, elution gradient from 0% to 80% CH$_3$CN in water (0.02% FA). Pure fractions were evaporated to dryness to afford Example 88 in the form of formic acid (38 mg, 57% yield) as a off-white solid.

LCMS: $R_t$=1.33 min in 3 min chromatography (3 min-5-95% MeCN in water (6 mmol/L NH$_4$HCO$_3$, Waters Acquity UPLC BEH C18 1.7 um, 2.1*50 mm, 40° C.), MS (ESI) m/z 616.2 [M+H]$^+$.

$^1$H NMR (500 MHz, DMSO-d$_6$) δ 1.50 (d, J=2.21 Hz, 6H) 1.89-1.99 (m, 1H) 2.12 (s, 6H) 2.18 (dd, J=12.30, 7.57 Hz, 1H) 2.34 (br dd, J=12.14, 5.83 Hz, 1H) 3.17-3.31 (m, 2H) 3.42-3.51 (m, 1H) 3.55-3.62 (m, 1H) 3.79 (s, 3H) 5.33-5.49 (m, 1H) 5.72 (br d, J=11.66 Hz, 1H) 6.10-6.13 (m, 1H) 6.13-6.20 (m, 2H) 6.38 (dd, J=17.02, 10.40 Hz, 1H) 6.86 (s, 1H) 7.29 (d, J=11.03 Hz, 1H) 7.85 (s, 1H) 7.97-8.01 (m, 1H) 8.11-8.17 (m, 1H) 8.36-8.45 (m, 1H) 9.53-9.56 (m, 1H) 9.57-9.61 (m, 1H).

Example 89

N-(5-(4-(5-chloro-4-fluoro-2-(2-hydroxypropan-2-yl)phenylamino)pyrimidin-2-ylamino)-4-methoxy-2-((1R,5R)-6-methyl-3,6-diazabicyclo[3.2.0]heptan-3-yl)phenyl)acrylamide formic Acid Salt

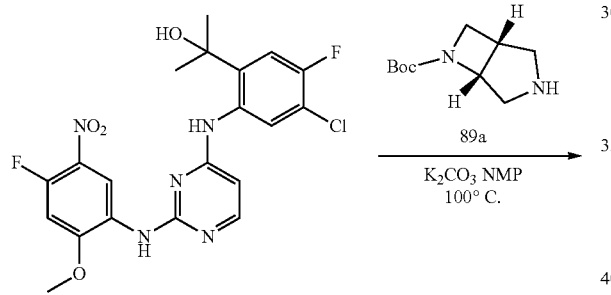

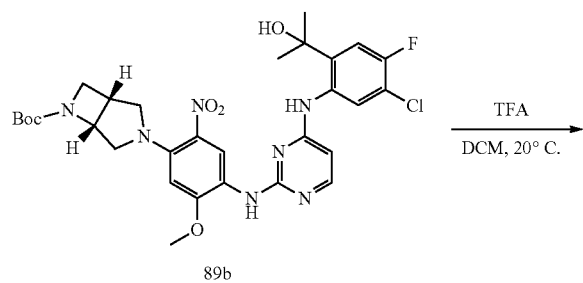

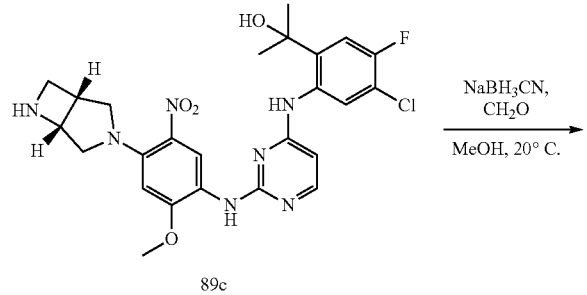

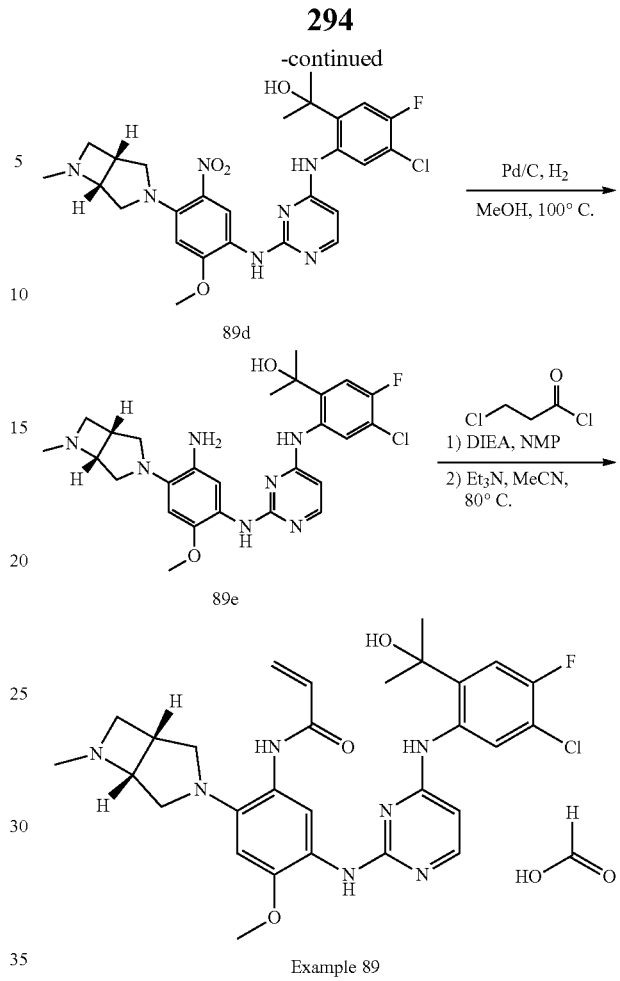

Example 89

Procedure for the Preparation of Compound 89b:

To a mixture of compound 36b (80 mg, 0.17 mmol) in NMP (3 mL) was added compound 89a (34 mg, 0.17 mmol) and potassium carbonate (60 mg, 0.43 mmol). The resulting mixture was heated at 100° C. for 3 hours. The mixture was purified by C18-flash chromatography, elution gradient from 5% to 70% CH$_3$CN in water (0.02% FA). Pure fractions were evaporated to dryness to afford compound 89b (75 mg, 68% yield) as a yellow solid.

LCMS: $R_t$=1.15 min in 3 min chromatography (3 min-5-95% MeCN in water (0.02% FA), Waters Acquity UPLC BEH C18 1.7 um, 2.1*50 mm, 40° C.), MS (ESI) m/z 644.1 [M+H]$^+$.

Procedure for the Preparation of Compound 89c:

To a mixture of compound 5c (75 mg, 0.11 mmol) in DCM (1 mL) was added TFA (1 mL), the resulting mixture was stirred at 20° C. for 30 min. The mixture was diluted with saturated sodium carbonate aqueous solution (50 mL) and EtOAc (50 mL). The organic layer was washed with brine, dried over sodium sulfate, concentrated in vacuum to afford compound 89c (59 mg, 93% yield) as a yellow solid.

LCMS: $R_t$=1.21 min in 3 min chromatography (3 min-5-95% MeCN in water (6 mmol/L NH$_4$HCO$_3$, Waters Acquity UPLC BEH C18 1.7 um, 2.1*50 mm, 40° C.), MS (ESI) m/z 544.1 [M+H]$^+$.

Procedure for the Preparation of Compound 89d:

To a mixture of compound 89c (59 mg, 0.11 mmol) in methanol (3 mL) was added formaldehyde (0.5 mL) and NaBH$_3$CN (34 mg, 0.54 mmol), the resulting mixture was stirred at 20° C. for 1 hour. The mixture was purified by C18-flash chromatography, elution gradient from 5% to 70% CH₃CN in water (0.02% FA). Pure fractions were evaporated to dryness to afford compound 89d (44 mg, 73% yield) as a yellow solid.

LCMS: $R_t$=1.27 min in 3 min chromatography (3 min-5-95% MeCN in water (6 mmol/L NH₄HCO₃), Waters Acquity UPLC BEH C18 1.7 um, 2.1*50 mm, 40° C.), MS (ESI) m/z 558.2 [M+H]⁺.

Procedure for the Preparation of Compound 89e:

To a mixture of compound 89d (59 mg, 0.11 mmol) in methanol (3 mL) was added palladium on carbon (20 mg), the resulting mixture was stirred at 20° C. for 1 hour under hydrogen atmosphere. The mixture was then filter and the filtrate was concentrated in vacuum to afford compound 89e (42 mg, 75% yield) as a yellow solid.

LCMS: $R_t$=1.17 min in 3 min chromatography (3 min-5-95% MeCN in water (6 mmol/L NH₄HCO₃), Waters Acquity UPLC BEH C18 1.7 um, 2.1*50 mm, 40° C.), MS (ESI) m/z 528.1 [M+H]⁺.

Procedure for the Preparation of Example 89:

To a mixture of compound 5f (42 mg, 0.080 mmol) in NMP (2 mL) was added acryloyl chloride (8 mg, 0.089 mmol) and DIEA (12 mg, 0.093 mmol) at 0° C., the resulting solution was stirred at 0° C. for 1 hour. The mixture was purified by C18-flash chromatography, elution gradient from 5% to 50% CH₃CN in water (0.02% FA). Pure fractions were evaporated to dryness to afford Example 89 in the form of formic acid (14 mg, 30% yield) as a white solid.

LCMS: $R_t$=0.78 min in 3 min chromatography (3 min-5-95% MeCN in water (0.02% FA), Waters Acquity UPLC BEH C18 1.7 um, 2.1*50 mm, 40° C.), MS (ESI) m/z 582.0 [M+H]⁺.

¹H NMR (500 MHz, DMSO-d₆) δ 0.99 (t, J=7.09 Hz, 1H) 1.43 (s, 6H) 2.63-2.83 (m, 2H) 3.07 (brs, 1H) 3.15 (br d, J=9.46 Hz, 1H) 3.32-3.54 (m, 5H) 3.66-3.80 (m, 4H) 5.65 (br d, J=11.03 Hz, 1H) 6.04 (d, J=5.67 Hz, 1H) 6.11 (s, 1H) 6.14 (br d, J=17.02 Hz, 1H) 6.34-6.47 (m, 1H) 6.79 (s, 1H) 7.22 (d, J=11.03 Hz, 1H) 7.84 (s, 1H) 7.92 (d, J=5.67 Hz, 1H) 8.04-8.21 (m, 2H) 9.27 (s, 1H) 9.54 (s, 1H).

Example 90

N-(5-(4-(5-chloro-4-fluoro-2-(2-hydroxypropan-2-yl)phenylamino)pyrimidin-2-ylamino)-2-((((2R,4S)-1,4-dimethylpyrrolidin-2-yl)methyl)(methyl)amino)-4-methoxyphenyl) acrylamide formic Acid Salt

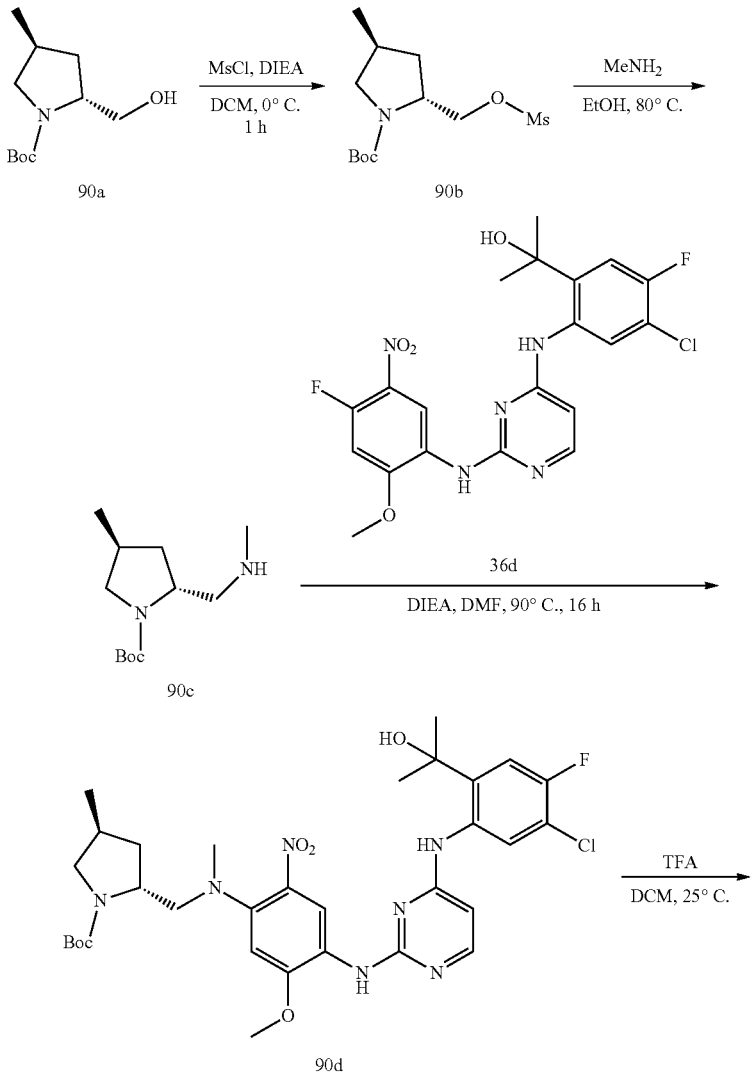

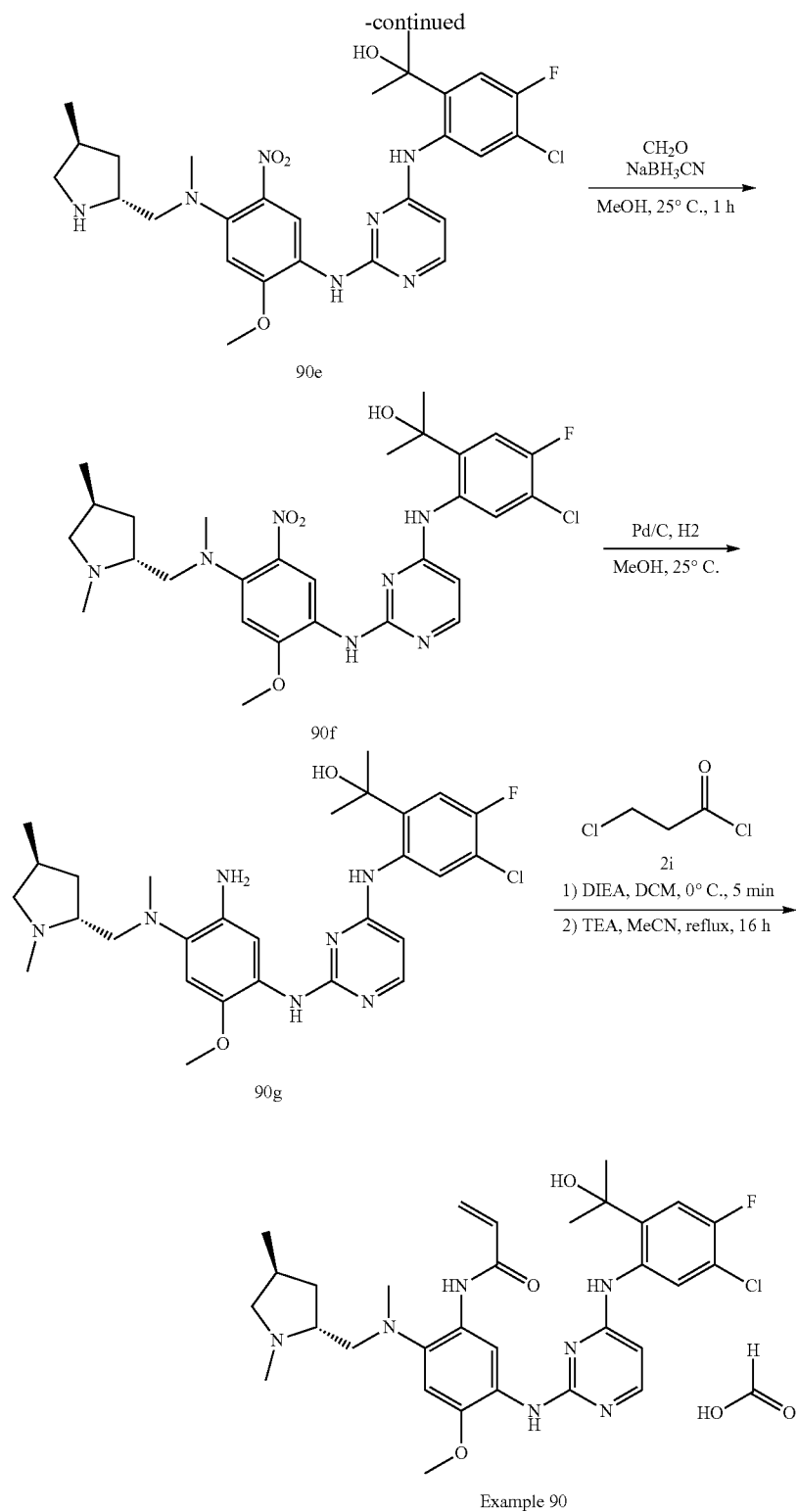

Example 90

Procedure for the Preparation of Compound 90b:

To a stirring solution of compound 90a (215 mg, 1.0 mmol) and DIEA (258 mg, 2.0 mmol) in DCM (2 mL) was added methanesulfonyl chloride (127 mg, 1.1 mmol) at 0° C. The resulting solution was stirred at 0° C. for 1 hour. Then the reaction was quenched with water (10 mL) and extracted with DCM (10 mL) twice. The organic layer was then dried over sodium sulfate and concentrated to give the compound 90b (300 mg, crude) as a colorless oil, which can be used for next step without further purification.

LCMS: $R_t$=1.39 min in 3 min chromatography (3 min-5-95% MeCN in water (6 mmol/L ammonium bicarbonate), Waters Acquity UPLC BEH C18 1.7 um, 2.1*50 mm, 40° C.), MS (ESI) m/z 294.2 [M+H]$^+$.

Procedure for the Preparation of Compound 90c:

To a mixture of compound 90b (150 mg crude, 0.50 mmol) in ethanol (3 mL) was added 25% dimethylamine aqueous solution (1 mL). The resulting mixture was stirred at 80° C. for 16 hours under nitrogen atmosphere. The mixture was then concentrated and the residue was poured to water (10 mL), extracted with ethyl acetate (10 mL) twice. The organic layer was then washed with brine, dried over sodium sulfate, concentrated to give the compound 90c (100 mg, crude) as a colorless oil, which can be used directly without further purification.

LCMS: $R_t$=1.16 min in 3 min chromatography (3 min-5-95% MeCN in water (6 mmol/L ammonium bicarbonate), Waters Acquity UPLC BEH C18 1.7 um, 2.1*50 mm, 40° C.), MS (ESI) m/z 229.3 [M+H]$^+$.

Procedure for the Preparation of Compound 90d:

To a mixture of compound 36d (120 mg, 0.26 mmol) in DMF (3 mL) was added compound 90c (60 mg, 0.26 mmol) and DIEA (74 mg, 0.57 mmol), the resulting mixture was heated at 90° C. for 16 hours. The mixture was purified by C18-flash chromatography, elution gradient from 20% to 100% MeCN in water (6 mmol/L ammonium bicarbonate). Pure fractions were evaporated to dryness to afford compound 90d (100 mg, 58% yield) as an orange solid.

LCMS: $R_t$=1.96 min in 3 min chromatography (3 min-5-95% MeCN in water (6 mmol/L ammonium bicarbonate), Waters Acquity UPLC BEH C18 1.7 um, 2.1*50 mm, 40° C.), MS (ESI) m/z 674.1 [M+H]$^+$.

Procedure for the Preparation of Compound 90e:

To a mixture of compound 90d (100 mg, 0.15 mmol) in DCM (1 mL) was added TFA (1 mL). The resulting mixture was stirred at 20° C. for 90 min. The solution was then concentrated and the residue was diluted with saturated sodium carbonate aqueous solution (20 mL) and ethyl acetate (20 mL). The organic layer was washed with brine, dried over sodium sulfate, concentrated in vacuum to afford compound 90e (80 mg, 93% yield) as a yellow solid.

LCMS: $R_t$=1.28 min in 3 min chromatography (3 min-5-95% MeCN in water (6 mmol/L ammonium bicarbonate), Waters Acquity UPLC BEH C18 1.7 um, 2.1*50 mm, 40° C.), MS (ESI) m/z 574.1 [M+H]$^+$.

Procedure for the Preparation of Compound 90f:

To a mixture of compound 90e (80 mg, 0.14 mmol) in methanol (3 mL) was added 37% formalin (1 mL) and NaBH$_3$CN (54 mg, 0.85 mmol). The resulting mixture was then concentrated and the residue was diluted with saturated sodium carbonate aqueous solution (20 mL) and EA (20 mL). The organic layer was washed with brine, dried over sodium sulfate, concentrated in vacuum to afford compound 90f (80 mg, 98% yield) as a yellow solid.

LCMS: $R_t$=1.53 min in 3 min chromatography (3 min-5-95% MeCN in water (6 mmol/L ammonium bicarbonate), Waters Acquity UPLC BEH C18 1.7 um, 2.1*50 mm, 40° C.), MS (ESI) m/z 588.1 [M+H]$^+$.

Procedure for the Preparation of Compound 90g:

To a mixture of compound 90f (80 mg, 0.14 mmol) in methanol (3 mL) was added palladium on carbon (20 mg), the resulting mixture was stirred at 20° C. for 1 hour under hydrogen atmosphere. The mixture was then filtered and the filtrate was concentrated in vacuo to afford compound 90g (70 mg, 92% yield) as a yellowish solid.

LCMS: $R_t$=0.85 min in 3 min chromatography (3 min-5-95% MeCN in water (6 mmol/L ammonium bicarbonate), Waters Acquity UPLC BEH C18 1.7 um, 2.1*50 mm, 40° C.), MS (ESI) m/z 558.1 [M+H]$^+$.

Procedure for the Preparation of Example 90:

To a cooled stirring solution of compound 90g (70 mg, 0.13 mmol) and DIEA (17 mg, 0.13 mmol) in DCM (2 mL) was added 3-chloropropionyl chloride (17 mg, 0.13 mmol) at 0° C. The resulting solution was stirred at 0° C. for 1 hour. MeCN (2 mL) and TEA (0.5 mL) were added. The mixture was heated at 80° C. for 16 hours. The mixture was concentrated and the residue was purified by C18-flash chromatography, elution gradient from 5% to 50% MeCN in water (0.05% FA). Pure fractions were evaporated to dryness to afford Example 90 in the form of formic acid (36.3 mg, 52% yield) as a white solid.

LCMS: $R_t$=1.68 min in 3 min chromatography (3 min-5-95% MeCN in water (6 mmol ammonium bicarbonate), Waters Acquity UPLC BEH C18 1.7 um, 2.1*50 mm, 40° C.), MS (ESI) m/z 612.0 [M+H]$^+$.

$^1$H NMR (500 MHz, DMSO-d$_6$) δ 9.93 (s, 1H), 9.66 (s, 1H), 8.71 (s, 1H), 8.20 (s, 1H), 8.17 (d, J=7.4 Hz, 1H), 7.97 (d, J=5.7 Hz, 1H), 7.91 (s, 1H), 7.24 (d, J=11.0 Hz, 1H), 6.86 (s, 1H), 6.34 (dd, J=16.9, 10.1 Hz, 1H), 6.16 (dd, J=16.9, 2.1 Hz, 1H), 6.08 (d, J=5.7 Hz, 1H), 5.72 (dd, J=10.1, 2.1 Hz, 1H), 3.78 (s, 3H), 3.13-3.10 (m, 1H), 2.88-2.82 (m, 1H), 2.81-2.75 (m, 1H), 2.72 (s, 3H), 2.63 (dd, J=12.9, 4.4 Hz, 1H), 2.11-1.97 (m, 2H), 1.61-1.47 (m, 8H), 0.96 (d, J=6.2 Hz, 3H).

Example 91

N-(5-(4-(5-chloro-4-fluoro-2-(2-hydroxypropan-2-yl)phenylamino)pyrimidin-2-ylamino)-2-((2R,4S)-2-((dimethylamino)methyl)-4-methylpyrrolidin-1-yl)-4-methoxyphenyl) acrylamide

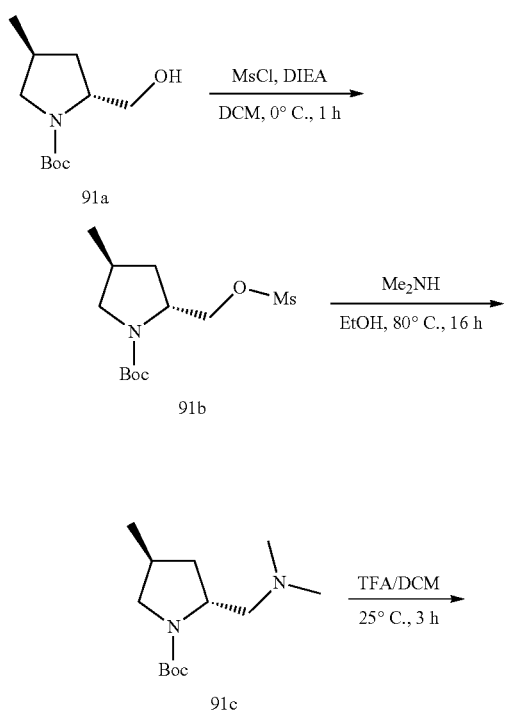

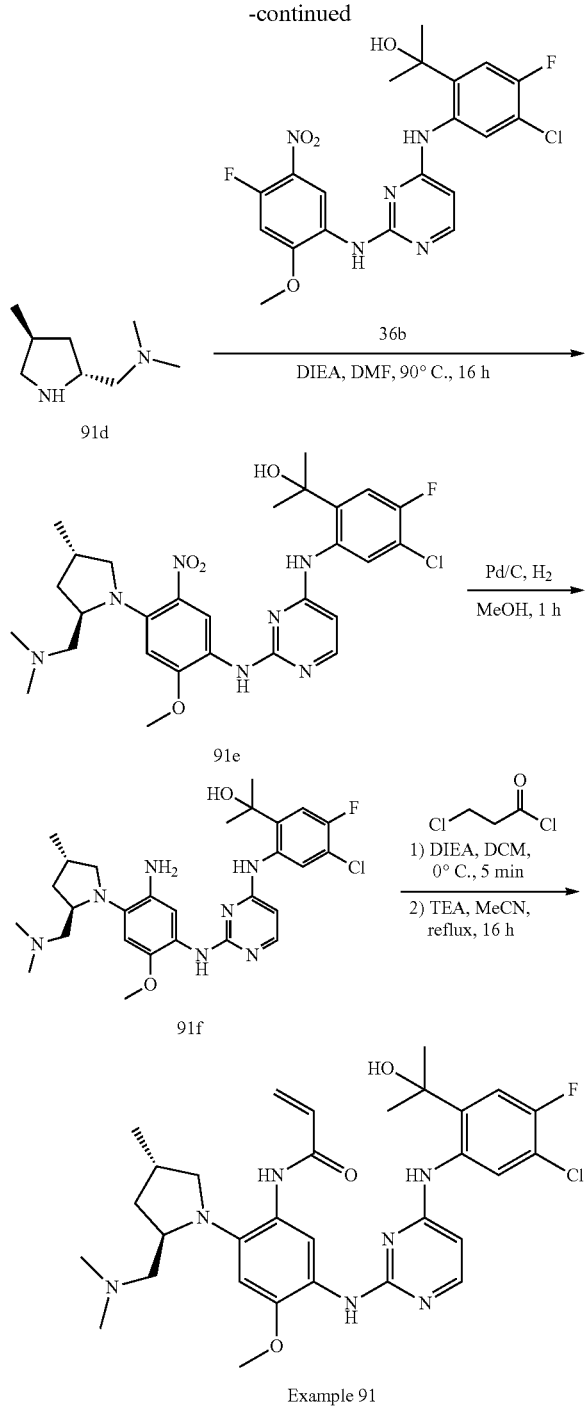

Procedure for the Preparation of Compound 91b:

To a stirring solution of compound 91a (215 mg, 1.0 mmol) and DIEA (258 mg, 2.0 mmol) in DCM (2 mL) was added methanesulfonyl chloride (127 mg, 1.1 mmol) at 0° C.

The resulting solution was stirred at 0° C. for 1 hour. Then the reaction was quenched with water (10 mL) and extracted with DCM (10 mL) twice. The organic layer was then dried over sodium sulfate and concentrated to give the compound 91b (300 mg, crude) as a colorless oil, which can be used for next step without further purification.

LCMS: $R_f$=1.39 min in 3 min chromatography (3 min-5-95% MeCN in water (6 mmol/L ammonium bicarbonate), Waters Acquity UPLC BEH C18 1.7 um, 2.1*50 mm, 40° C.), MS (ESI) m/z 294.2 [M+H]$^+$.

Procedure for the Preparation of Compound 91c:

To a mixture of compound 91b (150 mg crude, 0.50 mmol) in ethanol (3 mL) was added 25% dimethylamine aqueous solution (1 mL). The resulting mixture was stirred at 80° C. for 16 hours under nitrogen atmosphere. The mixture was then concentrated and the residue was poured to water (10 mL), extracted with ethyl acetate (10 mL) twice. The organic layer was washed with brine and dried over sodium sulfate. The solution was concentrated to give the compound 91c (120 mg, crude) as a colorless oil, which can be used directly without further purification.

LCMS: $R_f$=1.29 min in 3 min chromatography (3 min-5-95% MeCN in water (6 mmol/L ammonium bicarbonate), Waters Acquity UPLC BEH C18 1.7 um, 2.1*50 mm, 40° C.), MS (ESI) m/z 243.3 [M+H]$^+$.

Procedure for the Preparation of Compound 91d:

To a mixture of compound 1c (120 mg, 0.50 mmol) in DCM (1 mL) was added TFA (1 mL), the resulting mixture was stirred at 25° C. for 3 hours. The mixture was then concentrated in vacuum and diluted with water (2 mL). The mixture was lyophilized to afford compound 91d (180 mg, 97%) as a white solid (TFA salt).

LCMS: $R_f$=0.27 min in 3 min chromatography (3 min-5-95% MeCN in water (0.02% FA), Waters Acquity UPLC BEH C18 1.7 um, 2.1*50 mm, 40° C.), MS (ESI) m/z 143.2 [M+H]$^+$.

Procedure for the Preparation of Compound 91e:

To a mixture of compound 91d (110 mg, 0.30 mmol) in DMF (3 mL) was added compound 36d (100 mg, 0.21 mmol) and DIEA (129 mg, 1.0 mmol), the resulting mixture was stirred at 90° C. for 16 hours. The mixture was then purified by C18-flash chromatography, elution gradient from 20% to 90% MeCN in water (6 mmol/L ammonium bicarbonate). Pure fractions were evaporated to dryness to afford compound 91e (80 mg, 63% yield) as an orange solid.

LCMS: $R_f$=1.63 min in 3 min chromatography (3 min-5-95% MeCN in water (6 mmol/L ammonium bicarbonate), Waters Acquity UPLC BEH C18 1.7 um, 2.1*50 mm, 40° C.), MS (ESI) m/z 588.1 [M+H]$^+$.

Procedure for the Preparation of Compound 91f:

To a mixture of compound 91e (80 mg, 0.14 mmol) in methanol (6 mL) was added palladium on carbon (20 mg), the resulting mixture was stirred at 20° C. for 1 hours under hydrogen atmosphere. The mixture was then filtered and the filtrate was concentrated in vacuum to afford compound 91f (76 mg, crude) as a yellowish solid, which can be used directly without further purification.

LCMS: $R_f$=0.99 min in 3 min chromatography (3 min-5-95% MeCN in water (0.02% FA), Waters Acquity UPLC BEH C18 1.7 um, 2.1*50 mm, 40° C.), MS (ESI) m/z 558.2 [M+H]$^+$.

Procedure for the Preparation of Example 91:

To a cooled stirring solution of compound 91f (76 mg, 0.14 mmol) and DIEA (17.6 mg, 0.14 mmol) in DCM (2 mL) was added 3-chloropropionyl chloride (17 mg, 0.14 mmol) and at 0° C. The resulting solution was stirred at 0° C. for 1 hour. MeCN (2 mL) and TEA (0.5 mL) were added. The mixture was heated at 80° C. for 16 hours. The mixture was concentrated and the residue was purified by C18-flash chromatography, elution gradient from 10% to 70% MeCN in water (6 mmol/L ammonium bicarbonate). Pure fractions were evaporated to dryness to afford Example 91 (17.6 mg, 21% yield) as a white solid.

LCMS: $R_f$=1.68 min in 3 min chromatography (3 min-5-95% MeCN in water (6 mmol/L ammonium bicarbonate), Waters Acquity UPLC BEH C18 1.7 um, 2.1*50 mm, 40° C.), MS (ESI) m/z 612.0 [M+H]+.

$^1$H NMR (500 MHz, DMSO-$d_6$) δ 9.61 (s, 1H), 9.37 (s, 1H), 8.22-8.15 (m, 2H), 8.00 (d, J=5.7 Hz, 1H), 7.86 (s, 1H), 7.31 (d, J=11.0 Hz, 1H), 6.86 (s, 1H), 6.53 (dd, J=17.0, 10.2 Hz, 1H), 6.19 (s, 1H), 6.13 (dd, J=16.5, 3.9 Hz, 1H), 5.70 (dd, J=10.1, 2.0 Hz, 1H), 3.81 (s, 3H), 3.70 (dq, J=13.6, 7.0, 5.6 Hz, 1H), 3.45 (dd, J=8.9, 6.5 Hz, 1H), 2.38 (h, J=6.8 Hz, 1H), 2.25 (dd, J=11.9, 4.8 Hz, 1H), 2.12 (s, 1H), 1.93-1.75 (m, 2H), 1.52 (s, 6H), 1.05 (d, J=6.7 Hz, 3H).

Example 92

N-(5-(4-(5-chloro-4-fluoro-2-(1,1,1-trifluoro-2-hydroxypropan-2-yl)phenylamino) pyrimidin-2-ylamino)-2-((R)-3-(dimethylamino)pyrrolidin-1-yl)-4-methoxyphenyl) acrylamide

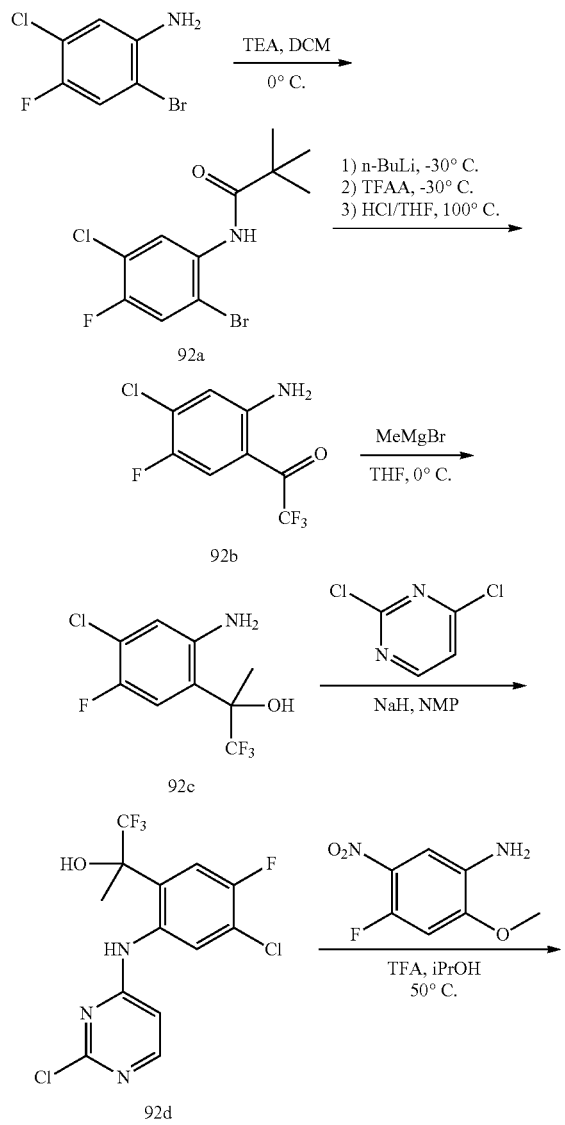

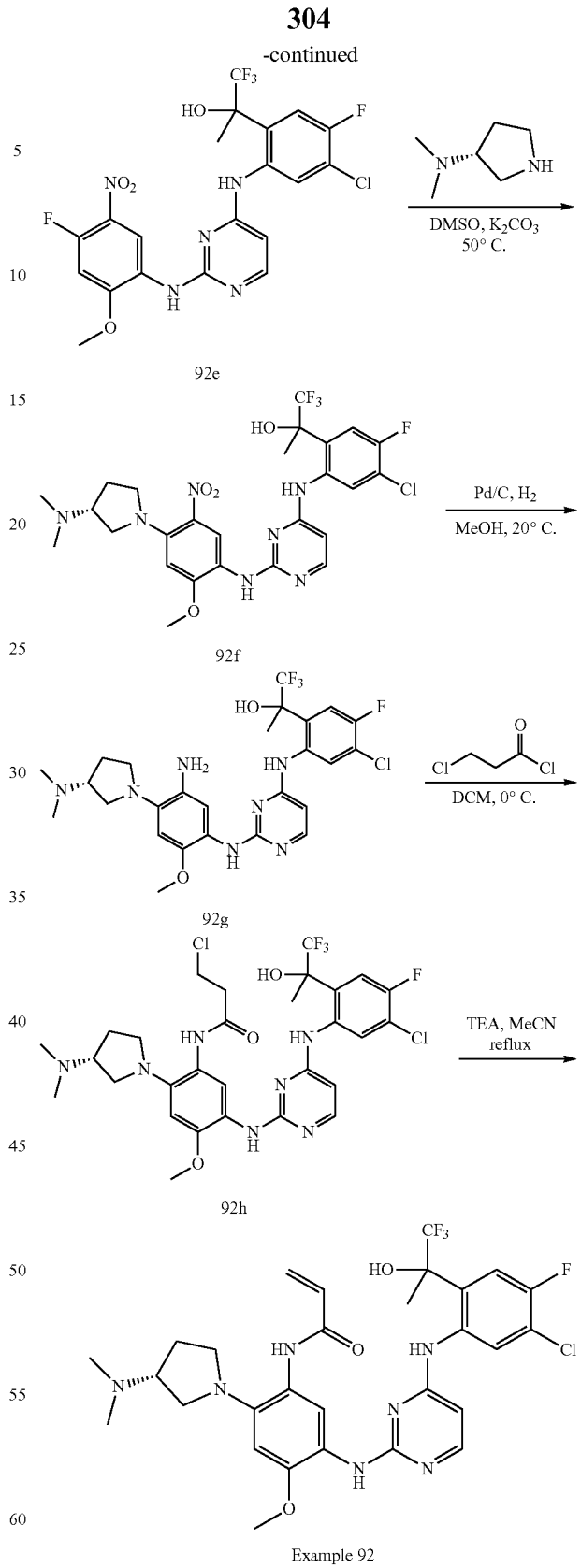

Example 92

Procedure for the Preparation of Compound 92a:

To a solution of 2-bromo-5-chloro-4-fluoroaniline (2.0 g, 8.9 mmol) and triethylamine (1.2 g, 12 mmol) in DCM (40 mL) was added pivaloyl chloride (1.2 g, 9.8 mmol) at 0° C.

The resulting mixture was stirred at 20° C. for 16 h. The mixture was quenched with water (100 mL) and extracted with DCM (50 mL×3). The combined organics was washed with brine, dried over anhydrous $Na_2SO_4$, filtered and the filtrate was evaporated in vacuum. The residue was purified by silica gel flash chromatography, elution gradient from 10% to 20% EtOAc in petroleum ether. Pure fractions were evaporated to dryness to afford compound 92a (2.7 g, 97% yield) as a white solid.

LCMS: $R_f$=1.51 min in 3 min chromatography (3 min-5-95% MeCN in water (6 mmol/L $NH_4HCO_3$), Waters Acquity UPLC BEH C18 1.7 um, 2.1*50 mm, 40° C.), MS (ESI) m/z 309.0 $[M+H]^+$.

Procedure for the Preparation of Compound 92b:

To a solution of compound 92a (2.7 g, 8.6 mmol) in THF (53 mL) was added n-BuLi (13 mL, 1.6 M in hexane) at −30° C., the resulting mixture was stirred at −30° C. for 1 h. TFAA (2.7 g, 13 mmol) was added at −30° C., then the mixture was stirred at 20° C. for further 16 h. The mixture was quenched with 1 M HCl solution (35 mL) and extracted with EA (30 mL×5). The combined organics were dried over anhydrous sodium sulfate, filtered and concentrated in vacuum. The residue was treated with con. HCl (60 mL) and THF (30 mL), then the resulting mixture was heated at 100° C. for 2 h. The reaction mixture was diluted with saturated $NaHCO_3$ solution and extracted with EtOAc (50 mL×5). The combined organics were washed with brine and evaporated in vacuum. The residue was purified by silica gel flash chromatography, elution gradient from 0% to 30% EtOAc in petroleum ether. Pure fractions were evaporated to dryness to afford compound 92b (576 mg, 28% yield) as a brown oil.

$^1$H NMR (500 MHz, DMSO-$d_6$) δ 7.2 (d, J=6.3 Hz, 1H) 7.4 (dd, J=10.6, 1.7 Hz, 1H) 7.8 (br s, 1H).

Procedure for the Preparation of Compound 92c:

To a solution of compound 92b (576 mg, 2.4 mmol) in THF (12 mL) was added methylmagnesium bromide (4.0 mL, 3M in THF) at 0° C. The resulting reaction was stirred at 20° C. for 1 h. The reaction was quenched with saturated $NH_4Cl$ solution (50 mL) and extracted with EA (50 mL×3). The combined organics were washed with brine, dried over anhydrous sodium sulfate, filtered and evaporated in vacuum. The residue was purified by silica gel flash chromatography, elution gradient from 10% to 50% EtOAc in petroleum ether. Pure fractions were evaporated to dryness to afford compound 92c (401 mg, 65% yield) as a brown oil.

LCMS: $R_f$=1.22 min in 3 min chromatography (3 min-5-95% MeCN in water (6 mmol/L $NH_4HCO_3$), Waters Acquity UPLC BEH C18 1.7 um, 2.1*50 mm, 40° C.), MS (ESI) m/z 258.1 $[M+H]^+$.

Procedure for the Preparation of Compound 92d:

To a solution of compound 92c (401 mg, 1.6 mmol) in NMP (7 mL) was added NaH (120 mg, 0.58 mmol, 60% dispersion in mineral oil) at 0° C. The reaction was stirred at 0° C. for 15 min, then 2,4-dichloropyrimidine (232 mg, 1.6 mmol) was added. The resulting mixture was stirred at 20° C. for 1 h. The reaction was quenched with water (100 mL) at 0° C. and extracted with EA (20 mL×5). The combined organics was washed with brine, dried over anhydrous sodium sulfate, filtered and the filtrate was evaporated in vacuum. The residue was purified by silica gel flash chromatography, elution gradient from 30% to 100% EtOAc in petroleum ether. Pure fractions were evaporated to dryness to afford compound 92d (374 mg, 65% yield) as a brown solid.

LCMS: $R_f$=1.36 min in 3 min chromatography (3 min-5-95% MeCN in water (6 mmol/L $NH_4HCO_3$), Waters Acquity UPLC BEH C18 1.7 um, 2.1*50 mm, 40° C.) MS (ESI) m/z 370.0 $[M+H]^+$.

Procedure for the Preparation of Compound 92e:

A solution of compound 92d (374 mg, 1.0 mmol), 4-fluoro-2-methoxy-5-nitroaniline (207 mg, 1.1 mmol), and TFA (576 mg, 5.1 mmol) in propan-2-ol (5.7 mL) was sealed and heated at 50° C. for 16 h. The reaction mixture was evaporated in vacuum. The residue was purified by silica gel flash chromatography, elution gradient from 0% to 10% MeOH in DCM. Pure fractions were evaporated to dryness to afford compound 92e (420 mg, 80% yield) as a brown solid.

LCMS: $R_f$=1.21 min in 3 min chromatography (3 min-5-95% MeCN in water (6 mmol/L $NH_4HCO_3$), Waters Acquity UPLC BEH C18 1.7 um, 2.1*50 mm, 40° C.), MS (ESI) m/z 520.1 $[M+H]^+$.

Procedure for the Preparation of Compound 92f:

To a solution of compound 92e (420 mg, 0.81 mmol) and $K_2CO_3$ (447 mg, 3.2 mmol) in DMSO (8 mL) was added (R)—N,N-dimethylpyrrolidin-3-amine (129 mg, 1.1 mmol). The resulting mixture was stirred at 50° C. for 16 h. The reaction mixture was diluted with ice water (100 mL) and extracted with EA (20 mL×5). The combined organics was washed with brine, dried over anhydrous sodium sulfate filtered and the filtrate was evaporated in vacuum to afford compound 92f (500 mg, crude) as yellow solid.

LCMS: $R_f$=1.51 min in 3 min chromatography (3 min-5-95% MeCN in water (6 mmol/L $NH_4HCO_3$), Waters Acquity UPLC BEH C18 1.7 um, 2.1*50 mm, 40° C.), MS (ESI) m/z 613.9 $[M+H]^+$.

Procedure for the Preparation of Compound 92g: Palladium on carbon (88 mg) was added into a solution of compound 92f (253 mg, 0.41 mmol) in MeOH (8 mL), the resulting mixture was stirred at 20° C. for 30 min under hydrogen atmosphere. The mixture was then filtered and the filtrate was evaporated in vacuum to afford crude compound 92g (241 mg, crude) as a light brown solid.

LCMS: $R_f$=1.10 min in 3 min chromatography (3 min-5-95% MeCN in water (0.02% FA), Waters Acquity UPLC BEH C18 1.7 um, 2.1*50 mm, 40° C.), MS (ESI) m/z 583.9 $[M+H]^+$.

Procedure for the Preparation of Compound 92h:

To a solution of compound 92g (241 mg, 0.41 mmol) in DCM (4 mL) was added 3-chloropropanoyl chloride (55 mg, 0.43 mmol) dropwise at 0° C. The reaction mixture was stirred at 0° C. for 0.5 h. The mixture was then diluted with saturated $NaHCO_3$ aqueous solution (10 mL) and the resulting mixture was stirred at 12-17° C. for 2 h. The mixture was extracted with DCM (20 mL×3). The combined organics were washed with brine, dried over anhydrous sodium sulfate, filtered and the filtrate was concentrated under reduced pressure. The residue was purified by silica gel flash chromatography, elution gradient from 0% to 3% MeOH in DCM. Pure fractions were evaporated to dryness to afford compound 92h (270 mg, 97% yield) as a yellow solid.

LCMS: $R_f$=1.36 min in 3 min chromatography (3 min-5-95% MeCN in water (6 mmol/L $NH_4HCO_3$), Waters Acquity UPLC BEH C18 1.7 um, 2.1*50 mm, 40° C.), MS (ESI) m/z 673.9 $[M+H]^+$.

Procedure for the Preparation of Example 92:

To a solution of compound 92h (270 mg, 0.40 mmol) in MeCN (4 mL) was added TEA (162 mg, 1.60 mmol). The reaction mixture was heated at 80° C. for 16 h. The reaction solution was evaporated in vacuum. The residue was purified by C18-flash chromatography, elution gradient from 0% to 60% MeCN in water (0.02% ammonia). Pure fractions were lyophilized to dryness to afford Example 92 (120 mg, 47% yield) as a light brown solid.

LCMS: $R_f$=1.33 min in 3 min chromatography (3 min-5-95% MeCN in water (6 mmol/L $NH_4HCO_3$), Waters Acquity UPLC BEH C18 1.7 um, 2.1*50 mm, 40° C.), MS (ESI) m/z 638.0 $[M+H]^+$.

$^1$H NMR (500 MHz, DMSO-$d_6$) δ ppm 1.7-1.8 (m, 1H) 1.8 (s, 3H) 2.0-2.1 (m, 1H) 2.2 (s, 6H) 2.7 (quin, J=7.6 Hz, 1H) 3.1-3.2 (m, 3H) 3.3-3.3 (m, 1H) 3.3 (br s, 1H) 3.8 (d, J=6.9 Hz, 3H) 5.7 (br d, J=10.4 Hz, 1H) 6.1 (dd, J=5.5, 3.0 Hz, 1H) 6.2 (dd, J=17.0, 1.6 Hz, 1H) 6.4-6.5 (m, 2H) 7.5 (br dd, J=11.2, 2.0 Hz, 1H) 7.5 (br d, J=7.6 Hz, 1H) 7.9 (br d, J=6.3 Hz, 1H) 7.9 (d, J=5.7 Hz, 2H) 8.3 (dd, J=12.1, 7.4 Hz, 1H) 9.3 (s, 1 H) 9.4 (br s, 1H).

Example 93

N-(5-(4-(5-chloro-4-fluoro-2-(2-hydroxypropan-2-yl)phenylamino)-1,3,5-triazin-2-ylamino)-2-((3S,4R)-3-(dimethylamino)-4-fluoropyrrolidin-1-yl)-4-methoxyphenyl) acrylamide

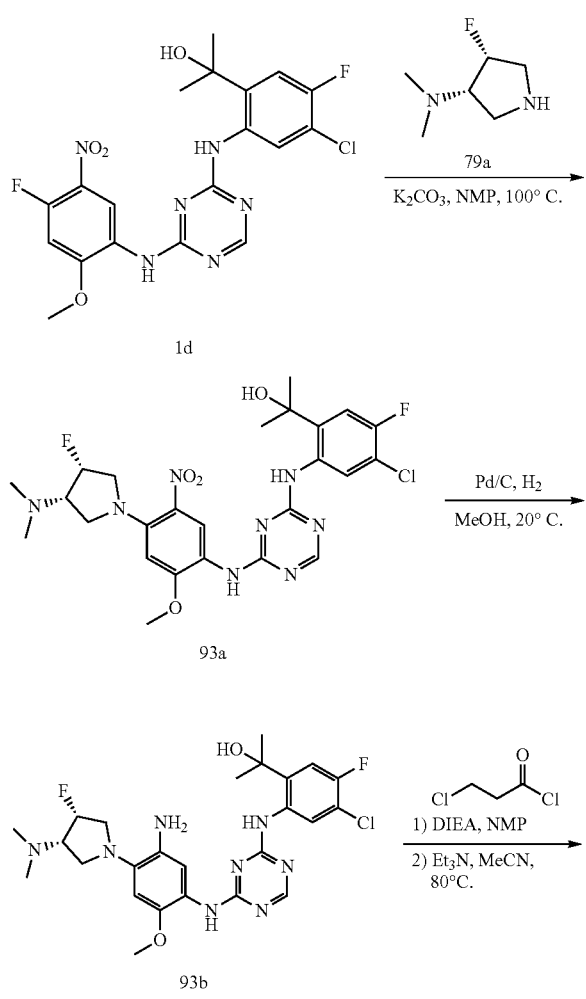

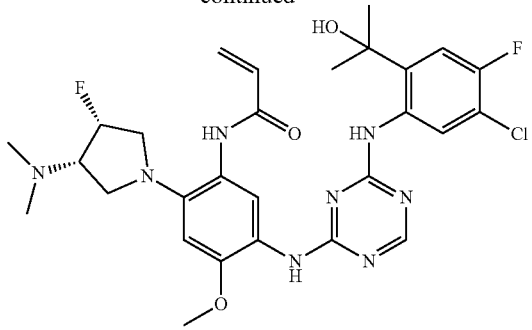

Example 93

Procedure for the Preparation of Compound 93a:

To a mixture of compound 1d (100 mg, 0.21 mmol) in NMP (3 mL) was added compound 79a (28 mg, 0.21 mmol) and potassium carbonate (73 mg, 0.53 mmol), the resulting mixture was heated at 100° C. for 2 hours. The mixture was purified by C18-flash chromatography, elution gradient from 5% to 60% $CH_3CN$ in water (0.02% FA). Pure fractions were evaporated to dryness to afford compound 93a (91 mg, 74% yield) as a yellow solid.

LCMS: $R_f$=0.99 min in 3 min chromatography (3 min-5-95% MeCN in water (0.02% FA), Waters Acquity UPLC BEH C18 1.7 um, 2.1*50 mm, 40° C.), MS (ESI) m/z 579.0 $[M+H]^+$.

Procedure for the Preparation of Compound 93b:

To a mixture of compound 93a (90 mg, 0.16 mmol) in methanol (5 mL) was added palladium on carbon (30 mg), the resulting mixture was stirred at 20° C. for 1 hour under hydrogen atmosphere. The mixture was then filter and the filtrate was concentrated in vacuum to afford compound 93b (78 mg, 91% yield) as a yellow solid.

LCMS: $R_f$=1.24 min in 3 min chromatography (3 min-5-95% MeCN in water (6 mmol/L $NH_4HCO_3$), Waters Acquity UPLC BEH C18 1.7 um, 2.1*50 mm, 40° C.), MS (ESI) m/z 549.1 $[M+H]^+$.

Procedure for the Preparation of Example 93:

To a mixture of compound 93b (78 mg, 0.14 mmol) in NMP (2 mL) was added acryloyl chloride (13 mg, 0.14 mmol) and DIEA (20 mg, 0.16 mmol) at 0° C., the resulting solution was stirred at 0° C. for 1 hour. The mixture was purified by C18-flash chromatography, elution gradient from 5% to 50% $CH_3CN$ in water (0.02% FA). Pure fractions were evaporated to dryness to afford Example 93 (45 mg, 52% yield) as a white solid.

LCMS: $R_f$=0.92 min in 3 min chromatography (3 min-5-95% MeCN in water (0.02% FA), Waters Acquity UPLC BEH C18 1.7 um, 2.1*50 mm, 40° C.), MS (ESI) m/z 603.1 $[M+H]^+$.

$^1$H NMR (500 MHz, DMSO-d6) δ 1.50 (br s, 6H) 2.25 (s, 6H) 2.54-2.66 (m, 1H) 3.38-3.48 (m, 3H) 3.78 (s, 3H) 3.79-3.87 (m, 1H) 5.17-5.34 (m, 1H) 5.21 (brs, 1H) 5.32 (br s, 1H) 5.68 (br d, J=11.03 Hz, 1H) 6.18 (br d, J=16.71 Hz, 1H) 6.27 (br s, 1H) 6.46 (br dd, J=17.02, 10.09 Hz, 2H) 6.95-7.40 (m, 2H) 8.21 (br s, 2H) 8.52-9.11 (m, 1H) 9.37 (br s, 1H) 10.12 (br s, 1H).

Example 94

N-(2-((2-(dimethylamino)ethyl)(methyl)amino)-5-(4-(4-(2-hydroxypropan-2-yl)-1H-indol-5-ylamino)-1,3,5-triazin-2-ylamino)-4-methoxyphenyl)acrylamide

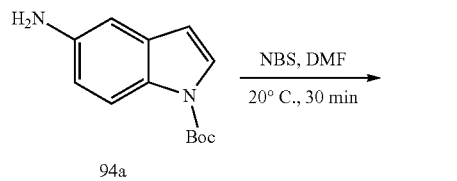
94a

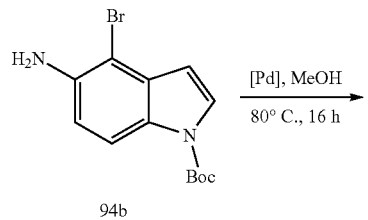
94b

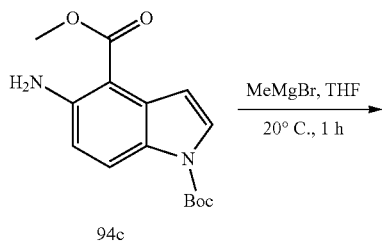
94c

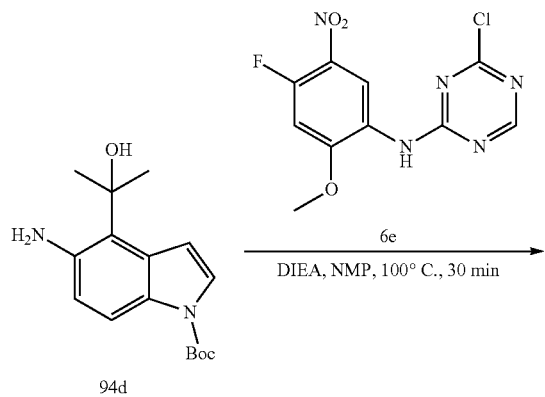
94d

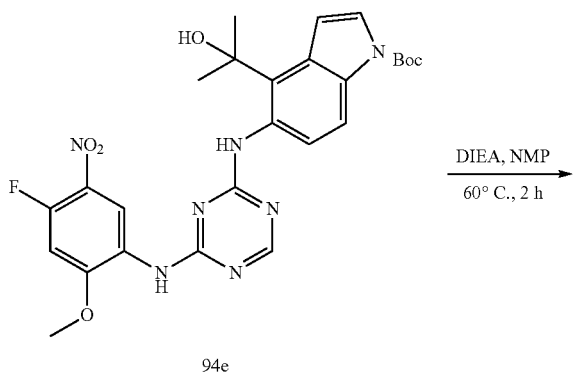
94e

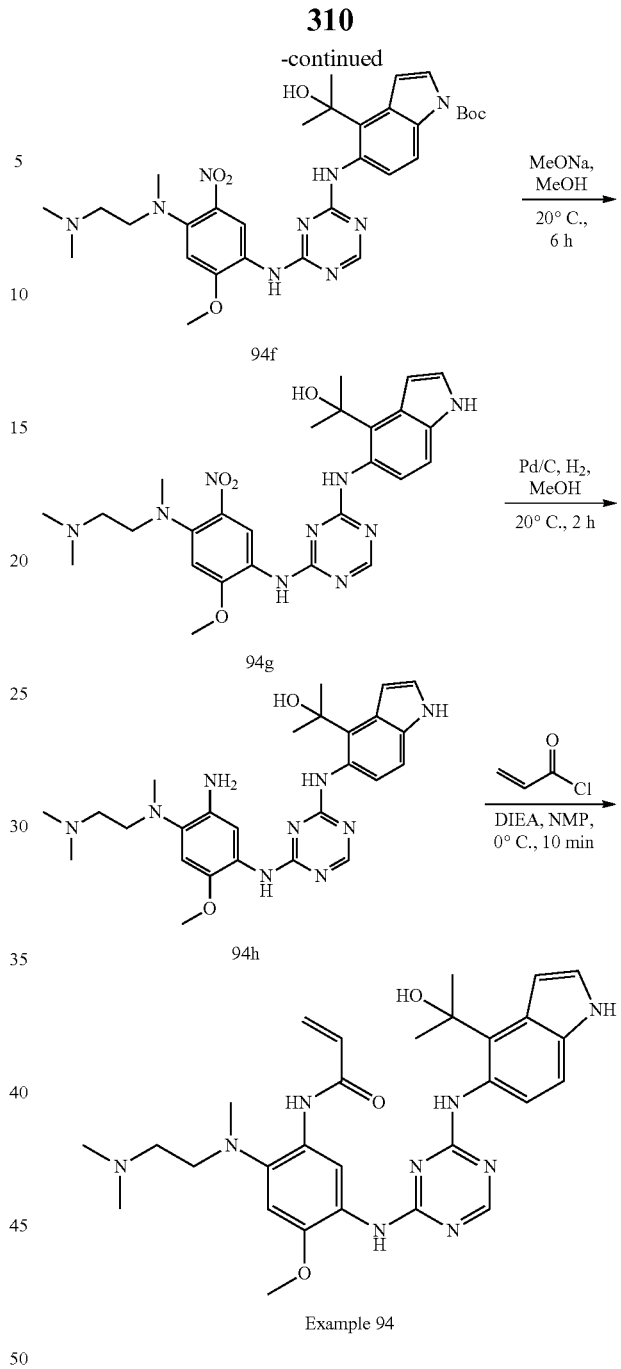

Example 94

Procedure for the Preparation of Compound 94b:

To a mixture of compound 94a (3.0 g, 12.9 mmol) in DMF (10 mL) was added NBS (2.3 g, 12.9 mmol), the resulting mixture was stirred at 20° C. for 30 min. The mixture was diluted with water (50 mL) and extracted with EtOAc (50 mL). The organic layer was concentrated in vacuum, the residue was purified by flash silica chromatography, elution gradient from 5% to 50% EtOAc in petroleum ether. Pure fractions were evaporated to dryness to afford compound 94b (2.0 g, 50% yield) as a yellow solid.

LCMS: $R_f$=1.54 min in 3 min chromatography (3 min-5-95% MeCN in water (0.02% FA), Waters Acquity UPLC BEH C18 1.7 um, 2.1*50 mm, 40° C.), MS (ESI) m/z 313.2 [M+H]$^+$.

Procedure for the Preparation of Compound 94c:

To a mixture of compound 94b (1.6 g, 5.1 mmol) and [1,1'-Bis(diphenyl-phosphino)ferrocene] dichloropalladium (II) dichloromethane complex (200 mg, 0.25 mmol) in methanol (15 mL) was added TEA (1 g, 9.9 mmol). The resulting mixture was heated at 80° C. for 16 hours under carbon monoxide atmosphere. The mixture was concentrated in vacuum, the residue was purified by C18-flash chromatography, elution gradient from 5% to 80% MeCN in water (0.02% FA). Pure fractions were evaporated to dryness to afford compound 94c (350 mg, 24% yield) as a yellow solid.

LCMS: $R_t$=1.49 min in 3 min chromatography (3 min-5-95% MeCN in water (0.02% FA), Waters Acquity UPLC BEH C18 1.7 um, 2.1*50 mm, 40° C.), MS (ESI) m/z 291.3 $[M+H]^+$.

Procedure for the Preparation of Compound 94d:

To a mixture of compound 1c (300 mg, 1.0 mmol) in TH (10 mL) was added MeMgBr (10 mL, 3M in THF), the resulting mixture was stirred at 20° C. for 1 hour under nitrogen atmosphere. The mixture was then diluted with water (50 mL) and extracted with EtOAc (50 mL). The organic layer was concentrated in vacuum, the residue was purified by C18-flash chromatography, elution gradient from 5% to 70% MeCN in water (0.02% FA). Pure fractions were evaporated to dryness to afford compound 1d (120 mg, 40% yield) as a yellow solid.

LCMS: $R_t$=1.39 min in 3 min chromatography (3 min-5-95% MeCN in water (0.02% FA), Waters Acquity UPLC BEH C18 1.7 um, 2.1*50 mm, 40° C.), MS (ESI) m/z 291.3 $[M+H]^+$.

Procedure for the Preparation of Compound 94e:

To a mixture of compound 94d (120 mg, 0.41 mmol) in NMP (5 mL) was added compound 6e (130 mg, 0.43 mmol) and DIEA (150 mg, 1.2 mmol), the resulting mixture was stirred at 100° C. for 30 min. The mixture was then purified by C18-flash chromatography, elution gradient from 5% to 70% MeCN in water (0.02% FA). Pure fractions were evaporated to dryness to afford compound 94e (110 mg, 48% yield) as a yellow solid.

LCMS: $R_t$=1.52 min in 3 min chromatography (3 min-5-95% MeCN in water (0.02% FA), Waters Acquity UPLC BEH C18 1.7 um, 2.1*50 mm, 40° C.), MS (ESI) m/z 554.2 $[M+H]^+$.

Procedure for the Preparation of Compound 94f:

To a mixture of compound 94e (110 mg, 0.20 mmol) in NMP (5 mL) was added N,N,N'-Trimethylethylenediamine (30 mg, 0.29 mmol) and DIEA (40 mg, 0.31 mmol), the resulting mixture was stirred at 60° C. for 2 hours. The mixture was then purified by C18-flash chromatography, elution gradient from 5% to 60% MeCN in water (0.02% FA). Pure fractions were evaporated to dryness to afford compound 94f (120 mg, 95% yield) as a yellow solid.

LCMS: $R_t$=1.04 min in 3 min chromatography (3 min-5-95% MeCN in water (0.02% FA), Waters Acquity UPLC BEH C18 1.7 um, 2.1*50 mm, 40° C.), MS (ESI) m/z 636.2 $[M+H]^+$.

Procedure for the Preparation of Compound 94g:

To a mixture of compound 94f (110 mg, 0.17 mmol) in methanol (5 mL) was added sodium methoxide (500 mg, 4.0 mmol), the resulting mixture was stirred at 20° C. for 6 hours.

The mixture was then diluted with water (50 mL) and extracted with EtOAc (50 mL). The organic layer was concentrated in vacuum to afford compound 94g (75 mg, 81% yield) as a yellow solid.

LCMS: $R_t$=0.78 min in 3 min chromatography (3 min-5-95% MeCN in water (0.02% FA), Waters Acquity UPLC BEH C18 1.7 um, 2.1*50 mm, 40° C.), MS (ESI) m/z 536.2 $[M+H]^+$.

Procedure for the Preparation of Compound 94h:

To a mixture of compound 94g (40 mg, 0.075 mmol) in methanol (5 mL) was added palladium on carbon (20 mg), the resulting mixture was stirred at 20° C. for 2 hours under hydrogen atmosphere. The mixture was then filtered and the filtrate was concentrated in vacuum to afford compound 94h (32 mg, 85% yield) as a brown solid.

LCMS: $R_t$=0.67 min in 3 min chromatography (3 min-5-95% MeCN in water (0.02% FA), Waters Acquity UPLC BEH C18 1.7 um, 2.1*50 mm, 40° C.), MS (ESI) m/z 506.3 $[M+H]^+$.

Procedure for the Preparation of Example 94:

To a mixture of compound 94h (32 mg, 0.063 mmol) in NMP (2 mL) was added acryloyl chloride (7 mg, 0.077 mmol) and DIEA (20 mg, 0.15 mmol) at 0° C., the resulting solution was stirred at 0° C. for 10 min. The mixture was purified by C18-flash chromatography, elution gradient from 5% to 60% MeCN in water (0.02% FA). Pure fractions were evaporated to dryness to afford Example 94 (14 mg, 39% yield) as a white solid.

LCMS: $R_t$=0.70 min in 3 min chromatography (3 min-5-95% MeCN in water (0.02% FA), Waters Acquity UPLC BEH C18 1.7 um, 2.1*50 mm, 40° C.), MS (ESI) m/z 560.3 $[M+H]^+$.

$^1$H NMR (500 MHz, DMSO-$d_6$) δ 1.69 (s, 7H) 2.22 (s, 7H) 2.34 (br t, J=5.83 Hz, 2H) 2.70 (s, 3H) 2.87 (br t, J=5.67 Hz, 2H) 3.77 (br s, 3H) 5.69-5.78 (m, 1H) 5.92 (brs, 1H) 6.23 (dd, J=17.02, 1.89 Hz, 1H) 6.30-6.47 (m, 1H) 6.56-6.71 (m, 1H) 6.96 (s, 1H) 7.06-7.29 (m, 2H) 7.65 (br s, 1H) 8.09-8.27 (m, 1H) 8.12-8.57 (m, 1H) 8.46 (brs, 1H) 10.09 (br s, 2H) 10.86-11.07 (m, 1H).

Example 95

N-(2-((2-(dimethylamino)ethyl)(methyl)amino)-5-(4-(6-(2-hydroxypropan-2-yl)-1H-indol-5-ylamino)-1,3,5-triazin-2-ylamino)-4-methoxyphenyl)acrylamide

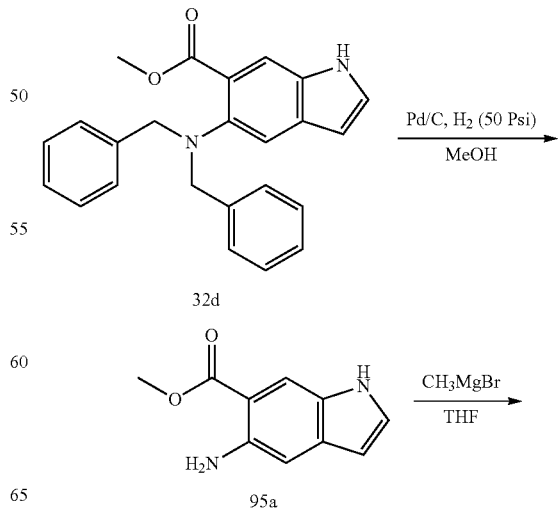

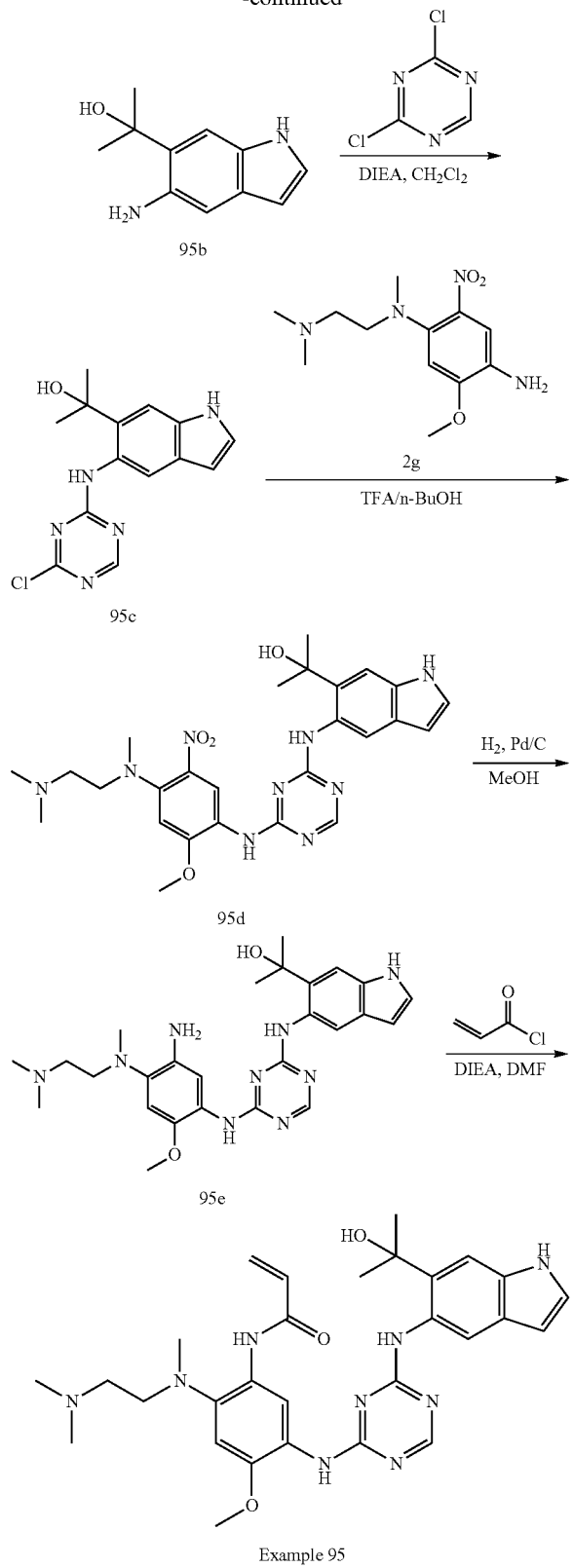

Example 95

Procedure for the Preparation of Compound 95a:

To a solution of compound 32d (3.0 g, 8.10 mmol) in MeOH (50 mL) was added Pd/C (300 mg). The resulting mixture was purged and degassed with $H_2$ for 3 times, then stirred at 29-40° C. under $H_2$ (hydrogen balloon, 15 Psi) for 1 h. The reaction mixture was filtered and concentrated under reduced pressure to afford compound 95a (1.48 g, 95.5% yield) as a brown solid.

LCMS: $R_t$=1.440 min in 10-80CD_3MIN_220&254 chromatography (XBrige Shield RP18 2.1*50 mm), MS (ESI) m/z=191.1 $[M+H]^+$.

$^1$H NMR (400 MHz, DMSO-$d_6$) δ 10.82 (br s, 1H), 7.84 (s, 1H), 7.42 (t, J=2.8 Hz, 1H), 6.80 (s, 1H), 6.16 (br s, 1H), 5.91 (br s, 2H), 3.80 (s, 3H).

Procedure for the Preparation of Compound 95b:

To a solution of compound 95a (1.3 g, 6.84 mmol) in THF (100 mL) was added $CH_3MgBr$ (9.1 mL, 3 M in ether) at 0~5° C. The mixture was stirred at 29-40° C. for 1.5 h. The reaction mixture was quenched by the addition of aqueous $NH_4Cl$ (20 mL), then extracted with EtOAc (3×100 mL). The organic layers were washed with brine (3×100 mL), dried and concentrated in vacuum to give the crude residue, which was purified by column chromatography on silica gel (Petroleum ether/EtOAc=20/1) to afford compound 95b (1.1 g, 84.6% yield) as a brown solid.

LCMS: $R_t$=0.880 min in 10-80CD_7MIN_220&254 chromatography (XBrige Shield RP18 2.1*50 mm), MS (ESI) m/z=191.1 $[M+H]^+$.

$^1$H NMR (400 MHz, DMSO-$d_6$) δ 10.47 (br s, 1H), 7.09 (s, 2H), 6.78-6.62 (m, 1H), 6.07 (s, 1H), 5.18 (br s, 1H), 4.92 (br s, 2H), 1.56 (s, 6H).

Procedure for the Preparation of Compound 95c:

To a solution of compound 95b (200 mg, 1.05 mmol) and DIEA (204 mg, 1.58 mmol) in $CH_2Cl_2$ (5 mL) was added 2,4-dichloro-1,3,5-triazine (174 mg, 1.16 mmol). The resulting mixture was stirred at 25-33° C. (room temperature) for 2 h. The reaction was concentrated under reduced pressure to give the crude residue, which was purified by column chromatography on silica gel (Petroleum ether/EtOAc=5/1) to afford compound 95c (200 mg, 62.7% yield) as a brown solid.

LCMS: $R_t$=0.717 min in 5-95AB_1.5min_220&254 chromatography (Xtimate C18 2.1*30 mm), MS (ESI) m/z=285.9 $[M-18]^+$.

$^1$H NMR (400 MHz, $CDCl_3$) δ 10.13-9.72 (m, 1H), 8.56-8.41 (m, 1H), 8.35-8.09 (m, 2H), 7.40 (s, 1H), 7.26 (t, J=2.6 Hz, 1H), 6.65-6.51 (m, 1H), 1.76 (s, 6H).

Procedure for the Preparation of Compound 95d:

To a solution of compound 95c (190 mg, 0.63 mmol) and compound 2g (168 mg, 0.63 mmol) in n-BuOH (5 mL) was added TFA (0.05 mL). The resulting mixture was stirred at 25-33° C. for 3 h. The reaction was added 10 mL water, and the mixture was extracted with EtOAc (10 mL×3). The combined organic layers were washed with brine (10 mL×3), dried and concentrated in vacuum to give the crude residue, which was purified by prep-TLC ($CH_2Cl_2$/MeOH=15/1 (v/v)) on silica gel to afford compound 95d (250 mg, 73% yield) as red solid.

LCMS: $R_t$=0.728 min in 5-95AB_1.5min_220&254 chromatography (MERCK RP18e 25-2 mm), MS (ESI) m/z=518.3 $[M-18]^+$.

Procedure for the Preparation of Compound 95e:

To a solution of compound 95d (190 mg, 0.35 mmol) in MeOH (3 mL) was added Pd/C (20 mg) under $N_2$ protect. The mixture was stirred at 26-33° C. under $H_2$ (hydrogen balloon, 15 Psi) for 1 h. The reaction mixture was filtered and concentrated under reduced pressure to afford compound 95e (100 mg, 75% yield) as brown oil.

LCMS: $R_t$=0.703 min in 5-95AB_1.5min_220&254 chromatography (MERCK RP18e 25-2 mm), MS (ESI) m/z=506.4 $[M+H]^+$.

Procedure for the Preparation of Example 95:

To a solution of compound 95d (100 mg, 0.20 mmol) and DIEA (38 mg, 0.30 mmol) in DMF (1 mL) was added acryloyl chloride (18 mg, 0.20 mmol) in DMF (1 mL). The resulting mixture was stirred at 0° C. for 30 min. The reaction was purified by prep-HPLC [Column: Waters Xbridge 150*25 5 um; Condition: 25-55% B (A: 0.05% ammonia; B: CH₃CN); Flow rate: 25 ml/min]. Fractions containing the desired compound were lyophilized to afford Example 95 (13.6 mg, 12.2% yield) as a white solid.

LCMS: R$_t$=1.908 min in 10-80CD_3MIN_220&254 chromatography (XBrige Shield RP18 2.1*50 mm), MS (ESI) m/z=560.3 [M+H]$^+$.

HPLC: R$_t$=3.44 mins in 10-80_CD_1.2 mL.MET (XBridge Shield RP 18 2.1*50 mm Sum).

$^1$H NMR (400 MHz, DMSO-d$_6$) δ 10.87 (br s, 1H), 10.04 (br s, 2H), 8.43 (br s, 1H), 8.19 (br s, 2H), 7.28 (br s, 2H), 7.02 (br s, 1H), 6.41 (br d, J=9.4 Hz, 1H), 6.22 (br d, J=16.4 Hz, 2H), 5.91 (br s, 1H), 5.74 (br d, J=10.8 Hz, 1H), 3.80 (s, 3H), 2.90 (br s, 2H), 2.71 (s, 3H), 2.42-2.12 (m, 8H), 1.57 (s, 6H).

Example 96

N-(5-(4-(5-chloro-4-fluoro-2-(2-hydroxypropan-2-yl)phenylamino)pyrimidin-2-ylamino)-4-methoxy-2-((1S,5R)-3-methyl-3,6-diazabicyclo[3.2.0]heptan-6-yl)phenyl)acrylamide

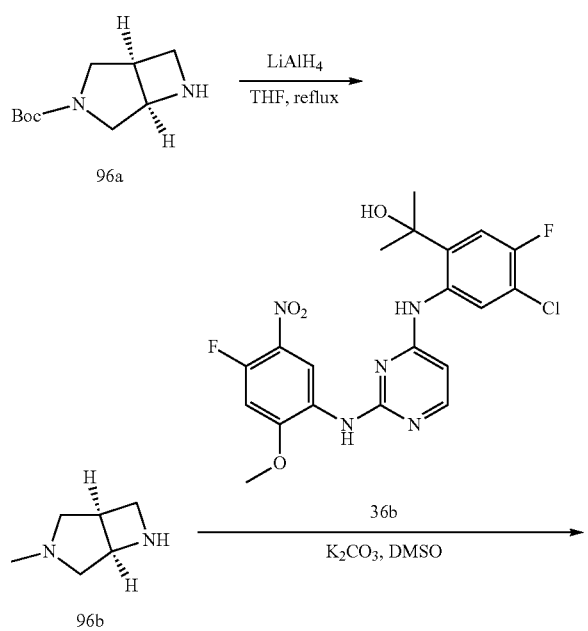

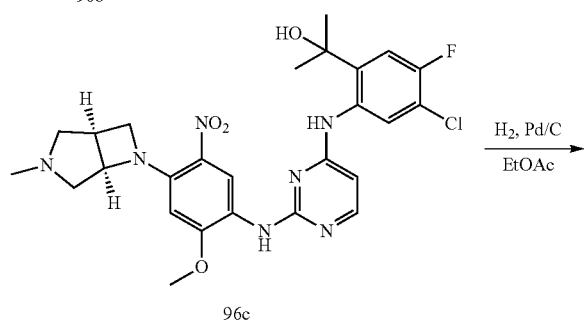

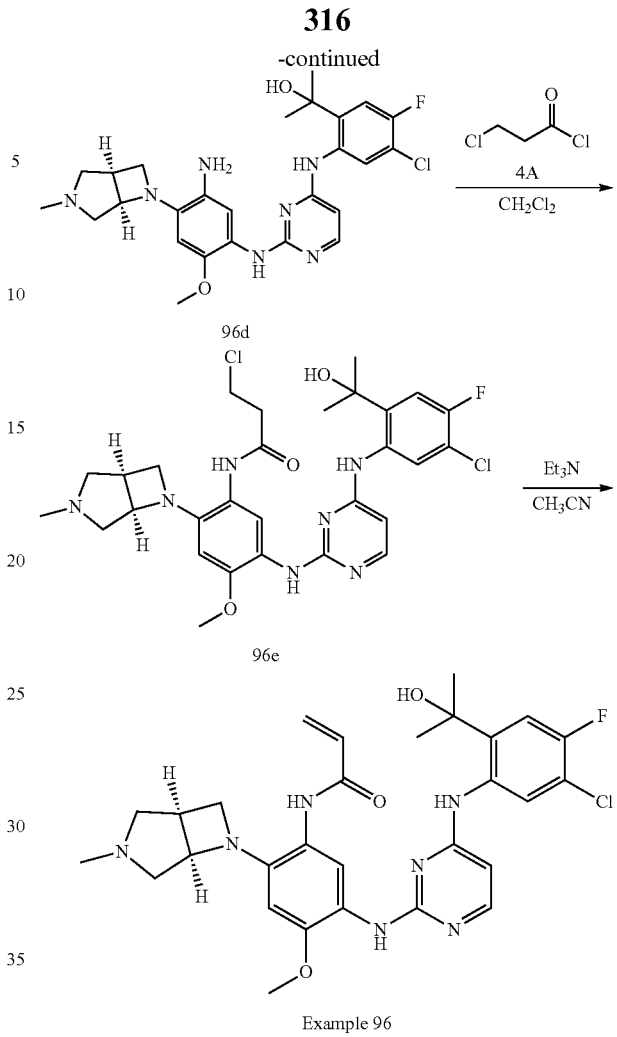

Example 96

Procedure for the Preparation of Compound 96b:

To a solution of compound LiAlH₄ (230 mg, 6.05 mmol) in THF (8 mL) was added compound 96a (300 mg, 1.51 mmol). The resulting grey mixture was heated at 75° C. for 14 h. After cooled to room temperature, the reaction was diluted with THF (15 mL) and treated with H₂O (0.2 mL), 15% aqueous NaOH (0.2 mL), and H₂O (0.6 mL) successively, then stirred for additional 30 min and Na₂SO₄ was added. The mixture was filtered and the filtrate was concentrated in vacuum to give compound 96b (130 mg, 77% yield) as yellow oil.

LCMS: R$_t$=0.079 min in 0-60AB_2MIN_50_E chromatography (Xtimate C18, 2.1*30 mm, 3 um), MS m/z=113.1 [M+H]$^+$.

$^1$H NMR (400 MHz, CDCl₃) δ 4.24 (dd, J=4.4, 6.4 Hz, 1H), 3.68-3.66 (m, 1H), 3.38 (dd, J=4.8, 8.8 Hz, 1H), 3.08-3.03 (m, 1H), 2.98-2.93 (m, 2H), 2.45 (s, 3H), 2.05-2.01 (m, 2H).

Procedure for the Preparation of Compound 96c:

To a solution of compound 36b (200 mg, 0.43 mmol) and K₂CO₃ (119 mg, 0.86 mmol) in DMSO (2 mL) was added compound 96b (58 mg, 0.86 mmol). The reaction mixture was stirred at 50° C. for 14 h while color changed from yellow to orange. The reaction mixture was added drop wise into H₂O (30 mL) with stirring, the precipitated solid was collected by filtration. The solid was dissolved into CH₂Cl₂ (20 mL), dried over Na₂SO₄ and concentrated in vacuum to give compound 96c (220 mg, 92% yield) as an orange solid.

LCMS: R$_f$=0.667 min in 5-95AB_220&254.lcm chromatography (MERCK RP18 2.5-2 mm), MS (ESI) m/z=558.1 [M+H]$^+$.

$^1$H NMR (400 MHz, CDCl$_3$) δ 9.09 (s, 1H), 8.92 (s, 1H), 8.09 (d, J=6.0 Hz, 1H), 7.95 (d, J=6.8 Hz, 1H), 7.19 (s, 1H), 7.09 (d, J=10.4 Hz, 1H), 6.16 (d, J=6.0 Hz, 1H), 5.94 (s, 1H), 5.02 (dd, J=4.4, 6.4 Hz, 1H), 4.07 (t, J=8.0 Hz, 1H), 3.91 (s, 3H), 3.89-3.83 (m, 1H), 3.15-3.06 (m, 1H), 2.96 (d, J=10.0 Hz, 1H), 2.89 (d, J=11.2 Hz, 1H), 2.29 (s, 3H), 2.07 (dd, J=5.2, 10.0 Hz, 1H), 1.85 (dd, J=4.4, 11.2 Hz, 1H), 1.67 (br s, 3H), 1.66 (s, 3H).

Procedure for the Preparation of Compound 96d:

To a solution of compound 96c (220 mg, 0.39 mmol) in EtOAc (10 mL) was added Pd/C (10%, 30 mg). The reaction mixture was stirred under H$_2$ balloon (15 Psi) at 8-13° C. for 15 h, then at 35° C. for another 15 h. The reaction mixture was filtered and the filtrate was concentrated in vacuum to give compound 96d (180 mg, 87% yield) as a black solid.

LCMS: R$_f$=0.640 min in 5-95AB_220&254.lcm chromatography (MERCK RP18 2.5-2 mm), MS (ESI) m/z=528.1 [M+H]$^+$.

$^1$H NMR (400 MHz, CDCl$_3$) δ 8.82 (s, 1H), 8.15 (d, J=7.2 Hz, 1H), 8.01 (d, J=5.6 Hz, 1H), 7.75 (s, 1H), 7.33 (s, 1H), 7.07 (d, J=10.8 Hz, 1H), 6.34 (s, 1H), 6.01 (d, J=5.6 Hz, 1H), 4.65 (dd, J=4.8, 6.4 Hz, 1H), 3.91 (dd, J=4.8, 7.2 Hz, 1H), 3.87-3.79 (m, 4H), 3.13-3.05 (m, 1H), 3.01 (br d, J=10.4 Hz, 2H), 2.35 (s, 3H), 2.10 (br dd, J=6.0, 10.0 Hz, 1H), 1.96 (dd, J=4.4, 10.8 Hz, 1H), 1.65 (s, 3H), 1.65 (s, 3H).

Procedure for the Preparation of Compound 96e:

To a solution of compound 96d (176 mg, 0.33 mmol) in CH$_2$Cl$_2$ (3 mL) was added compound 3-chloropropanoyl chloride (42 mg, 0.33 mmol) drop wise in ice water bath. The resulting black mixture was stirred at 5-10° C. for 1.5 h and solid precipitated out. Saturated aqueous NaHCO$_3$ (10 mL) was added to the reaction mixture and stirred for another 2 h, then stood at room temperature for 12 h. The aqueous phase was separated and extracted with CH$_2$Cl$_2$ (15 mL×3). The combined organic layers was washed with water (10 mL) and brine (10 mL) successively, dried over Na$_2$SO$_4$ and concentrated in vacuum to give the title compound 96e (164 mg, 59% yield) as a dark green solid.

LCMS: R$_f$=0.683 min in 5-95AB_220&254.lcm chromatography (MERCK RP18 2.5-2 mm), MS (ESI) m/z=618.1 [M+H]$^+$.

Procedure for the Preparation of Example 96:

To a solution of compound 96e (164 mg, 0.19 mmol) in CH$_3$CN (5 mL) was added Et$_3$N (79 mg, 0.78 mmol). The resulting black mixture was stirred at 80° C. for 14 h. The solvent was removed under reduced pressure to give the crude residue, which was dissolved with MeOH (2 mL) and purified by prep-TLC (CH$_2$Cl$_2$: MeOH=5:1 (v/v)) first to give the impure product as a deep red solid. It was further purified by prep-HPLC (Column: Xbridge 150*30 mm*10 um; Condition: 37-67% B (A: 0.05% ammonia hydroxide, B: CH$_3$CN); Flow Rate: 25 ml/min) and then lyophilized to give Example 96 (31.3 mg, 28% yield) as a light yellow solid.

LCMS: R$_f$=1.225 min in 10-80AB_4min_220&254. lcm chromatography (Xtimate C18 2.1*30 mm), MS (ESI) m/z=582.1[M+H]$^+$.

HPLC: R$_f$=2.10 min in 10-80AB_1.2ml.met (Ultimate C18 3.0 um 3.0*50 mm).

$^1$H NMR (400 MHz, CDCl$_3$) δ 9.35 (br s, 1H), 9.08 (br s, 1H), 8.16 (br s, 1H), 8.05 (d, J=6.0 Hz, 1H), 7.60 (d, J=6.0 Hz, 1H), 7.35 (s, 1H), 7.12 (d, J=10.8 Hz, 1H), 6.46-6.31 (m, 3H), 6.25 (d, J=5.2 Hz, 1H), 5.75 (dd, J=3.6, 7.6 Hz, 1H), 5.40 (br s, 1H), 4.61 (dd, J=4.0, 6.4 Hz, 1H), 3.92-3.84 (m, 4H), 3.83-3.76 (m, 1H), 3.17-3.01 (m, 3H), 2.43 (s, 3H), 2.18 (dd, J=6.4, 10.0 Hz, 1H), 2.04-1.94 (m, 1H), 1.75-1.63 (m, 6H).

Example 97

N-(5-(4-(5-chloro-4-fluoro-2-(2-hydroxypropan-2-yl)phenylamino)pyrimidin-2-ylamino)-4-methoxy-2-((1S,5S)-6-methyl-3,6-diazabicyclo[3.2.0]heptan-3-yl)phenyl)acrylamide formic Acid Salt

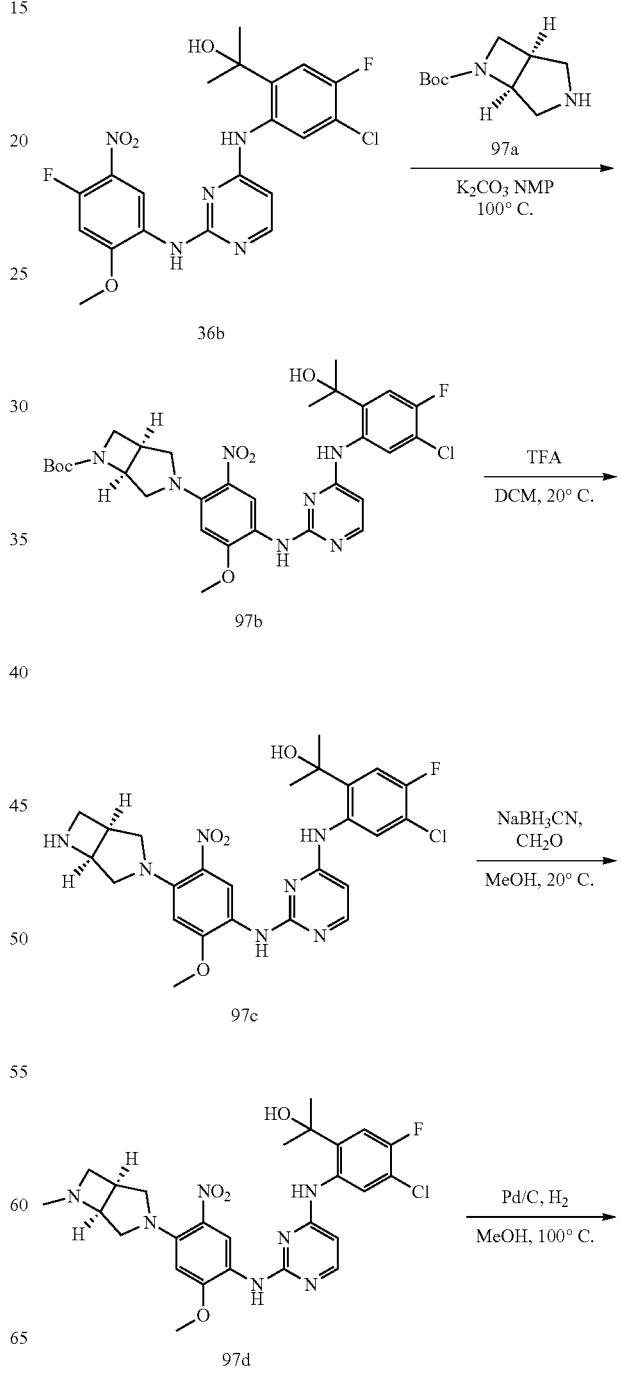

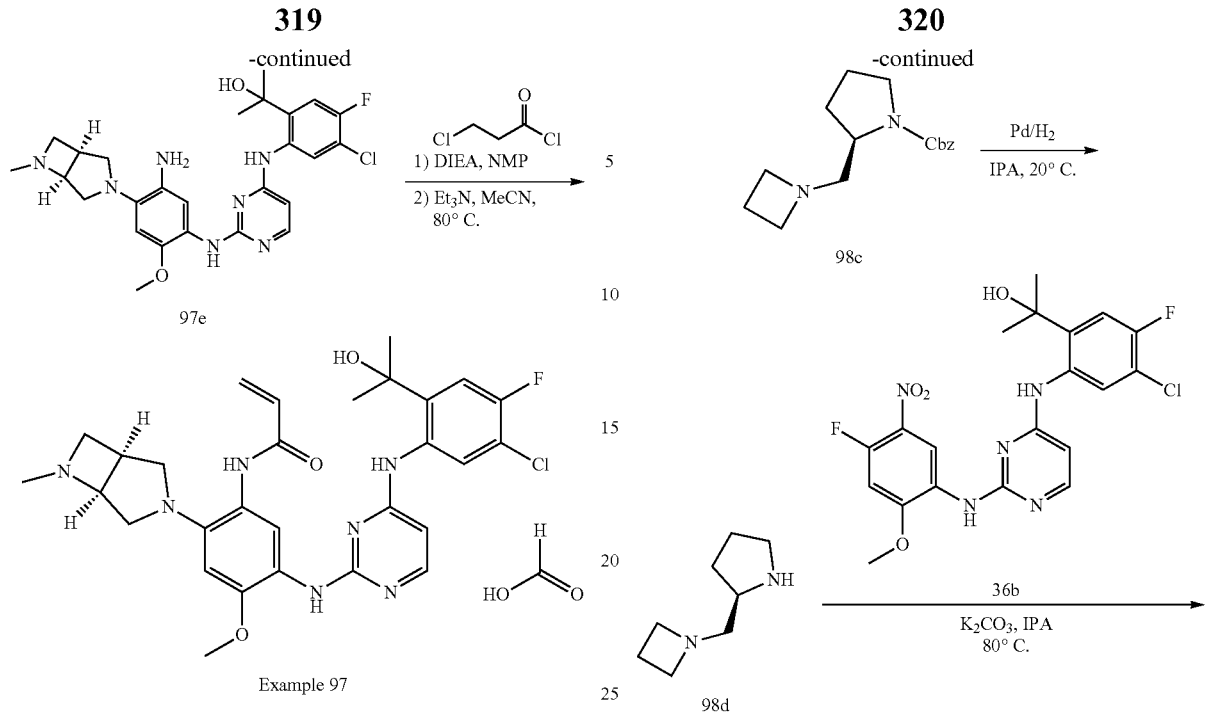

The synthesis followed a similar experimental procedure as Example 89 to afford Example 97 in the form of formic acid as a pale yellow solid.

LCMS: $R_t$=0.75 min in 3 min chromatography (3 min-5-95% MeCN in water (0.02% FA), Waters Acquity UPLC BEH C18 1.7 um, 2.1*50 mm, 40° C.), MS (ESI) m/z 582.0 [M+H]$^+$.

$^1$H NMR (500 MHz, DMSO-d$_6$) δ 9.61 (s, 1H), 9.55 (s, 1H), 8.31 (s, 1H), 8.20 (s, 1H), 8.15 (d, J=7.4 Hz, 1H), 7.99 (d, J=5.7 Hz, 1H), 7.91 (s, 1H), 7.28 (d, J=11.0 Hz, 1H), 6.84 (s, 1H), 6.55 (dd, J=17.1, 10.3 Hz, 1H), 6.20 (dd, J=17.1, 2.0 Hz, 1H), 6.10 (d, J=5.7 Hz, 1H), 5.70 (dd, J=10.2, 2.0 Hz, 1H), 4.25-4.16 (m, 1H), 3.79 (s, 3H), 3.58-3.53 (m, 4H), 3.21 (d, J=9.8 Hz, 2H), 3.17-3.11 (m, 2H), 2.88-2.82 (m, 1H), 2.77-2.72 (m, 1H), 1.50 (s, 6H).

Example 98

(R)—N-(2-(2-(azetidin-1-ylmethyl)pyrrolidin-1-yl)-5-(4-(5-chloro-4-fluoro-2-(2-hydroxypropan-2-yl)phenylamino)pyrimidin-2-ylamino)-4-methoxyphenyl) acrylamide formic Acid Salt

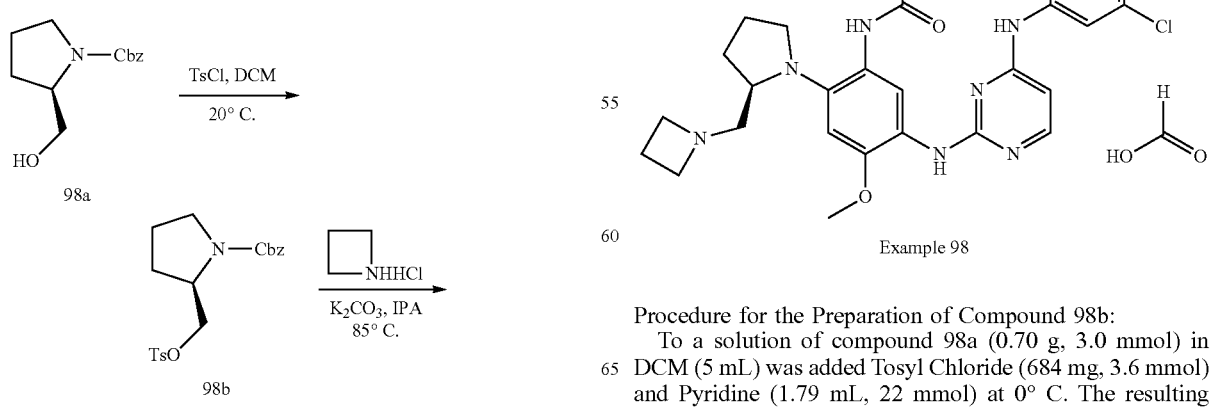

Procedure for the Preparation of Compound 98b:

To a solution of compound 98a (0.70 g, 3.0 mmol) in DCM (5 mL) was added Tosyl Chloride (684 mg, 3.6 mmol) and Pyridine (1.79 mL, 22 mmol) at 0° C. The resulting mixture was stirred at 20° C. for 16 h. The mixture was diluted with 1N HCl (10 mL) and extracted with DCM (20 mL×3). The combined organics were dried over anhydrous sodium sulfate, filtered and the filtrate was evaporated under reduced pressure to afford the crude product, which was purified by flash silica chromatography, elution gradient from 0% to 10% EtOAc in petroleum ether. Pure fractions were evaporated to dryness to afford compound 98b (1.1 g, 75% yield) as colorless oil.

LCMS: $R_f$=1.55 min in 3 min chromatography (3 min-5-95% MeCN in water (6 mmol/L $NH_4HCO_3$), Waters Acquity UPLC BEH C18 1.7 um, 2.1*50 mm, 40° C.), MS (ESI) m/z=390 [M+H]$^+$.

Procedure for the Preparation of Compound 98c:

To a solution of compound 98b (0.47 g, 1.2 mmol) in NMP (10 mL) was added azetidine hydrochloride (673 mg, 7.2 mmol) and potassium carbonate (995 mg, 7.2 mmol).

The mixture was stirred at 85° C. for 16 h. The mixture was diluted with water (20 mL) and extracted with EtOAc (20 mL×3). The combined organics were dried over anhydrous sodium sulfate, filtered and the filtrate was evaporated under reduced pressure to afford the crude product, which was purified by C18-flash chromatography, elution gradient from 0 to 50% $CH_3CN$ in water (0.02% FA). Pure fractions were evaporated to dryness to afford compound 98c (0.20 g, 60% yield) as colorless oil.

LCMS: $R_f$=0.94 min in 3 min chromatography (3 min-5-95% MeCN in water (6 mmol/L $NH_4HCO_3$), Waters Acquity UPLC BEH C18 1.7 um, 2.1*50 mm, 40° C.), MS (ESI) m/z=275 [M+H]$^+$.

Procedure for the Preparation of Compound 98d:

To a solution of compound 98c (90 mg, 0.30 mmol) in IPA (5 mL) was added Palladium on carbon (10 mg). The resulting mixture was stirred at 20° C. under hydrogen atmosphere for 16 h. The mixture was filtered and the filtrate was concentrated in vacuum to afford the crude compound 98d (70 mg, crude) was obtained which was used for next step directly.

LCMS: $R_f$=0.24 min in 3 min chromatography (3 min-5-95% MeCN in water (6 mmol/L $NH_4HCO_3$), Waters Acquity UPLC BEH C18 1.7 um, 2.1*50 mm, 40° C.), MS (ESI) m/z=141 [M+H]$^+$.

Procedure for the Preparation of Compound 98e:

To a solution of compound 98d (70 mg, 0.50 mmol) in IPA (10 mL) was added potassium carbonate (90 mg, 0.65 mmol) and compound 36b (150 mg, 0.32 mmol). The resulting mixture was heated at 80° C. under nitrogen atmosphere for 16 h. Then the mixture was filtered and the filtrate was removed under reduced pressure. The residue was diluted with water (20 mL) and extracted with EtOAc (20 mL×3). The combined organics were dried over anhydrous sodium sulfate, filtered and the filtrate was evaporated under reduced pressure to afford compound 98e (150 mg, 80% yield) as a red solid.

LCMS: $R_f$=1.52 min in 3 min chromatography (3 min-5-95% MeCN in water (6 mmol/L $NH_4HCO_3$), Waters Acquity UPLC BEH C18 1.7 um, 2.1*50 mm, 40° C.) MS (ESI) m/z 586 [M+H]$^+$.

Procedure for the Preparation of Compound 98f:

To a solution of compound 98e (70 mg, 0.12 mmol) in MeOH (15 mL) was added palladium on carbon (20 mg). The resulting mixture was stirred at 20° C. under hydrogen atmosphere for 2 h. The mixture was filtered and the filtrate was concentrated in vacuum to afford compound 98f (50 mg, 60% yield) as a yellow solid.

LCMS: $R_f$=1.16 min in 3 min chromatography (3 min-5-95% MeCN in water (6 mmol/L $NH_4HCO_3$, Waters Acquity UPLC BEH C18 1.7 um, 2.1*50 mm, 40° C.), MS (ESI) m/z 556 [M+H]$^+$.

Procedure for the Preparation of Example 98:

To a solution of compound 98f (40 mg, 0.070 mmol) and DIEA (10 mg, 0.080 mmol) in NMP (3 mL) was added 3-chloropropionyl chloride (10 mg, 0.080 mmol) at 0° C. Then MeCN (3 mL) and TEA (1 mL) were added and the resulting mixture was heated at 80° C. for 16 h. The mixture was concentrated in vacuum and the residue was purified by C18-flash chromatography, elution gradient from 0 to 30% $CH_3CN$ in water (0.02% FA). Pure fractions were evaporated to dryness to afford Example 98 in the form of formic acid (3.9 mg, 8.9% yield) as a white solid.

LCMS: $R_f$=1.16 min in 3 min chromatography (3 min-5-95% MeCN in water (6 mmol/L $NH_4HCO_3$, Waters Acquity UPLC BEH C18 1.7 um, 2.1*50 mm, 40° C.), MS (ESI) m/z 610.1 [M+H]$^+$.

$^1$H NMR (500 MHz, DMSO-$d_6$) δ ppm 9.61 (d, J=8.1 Hz, 1H), 8.28 (s, 1H), 8.16 (d, J=7.4 Hz, 1H), 7.98 (d, J=5.7 Hz, 1H), 7.86 (s, 1H), 7.28 (d, J=11.1 Hz, 1H), 6.78 (s, 1H), 6.57 (dd, J=17.0, 10.2 Hz, 1H), 6.35-6.03 (m, 3H), 5.70 (dd, J=10.4, 1.9 Hz, 1H), 3.97-3.68 (m, 4H), 3.11 (dq, J=22.2, 6.8 Hz, 4H), 2.96-2.85 (m, 1H), 2.48-2.34 (m, 2H), 2.27-2.15 (m, 1H), 2.11-2.00 (m, 1H), 1.98-1.71 (m, 4H), 1.69-1.59 (m, 1H), 1.55-1.40 (m, 6H).

Biological Examples

Described below are assays used to measure the biological activity of provided compounds as selective inhibitors of mutant EGFR as compared to WT EGFR (and other protein kinases).

Example 99: Cell Lines with EGFR or Her2 Mutations

For the purpose of initial in vitro potency analysis, lentiviral system can be used to generate cells lines with different EGFR or Her2 mutations.

Specifically, cell line with human EGFR Exon 20 ASV insertion mutation is generated by subcloning human EGFR exon 20 V769_D770insASV into a lentivirus transfer vector pMT143 (Sunbio Co., Ltd.) and then transfecting said lentivirus transfer vector and lentiviral packaging plasmids into 293T/17 (American Type Culture Collection (ATCC), CRL-11268) cells to generate recombinant lentivirus encoding the human EGFR V769_D770insASV. Due to IL-3-dependent proliferation, parental Ba/F3 (DSMZ, Cat #ACC-300) cells were cultured in RPMI1640 medium (Life Technology, Cat #11835-055) supplemented with 10% FBS, and 10% volume conditioned medium of WEHI-3B cell line (DSMZ, Cat #ACC-26) as a source of mouse IL3. To generate the EGFR exon 20 V769_D770insASV transduced Ba/F3 cell line, the parental Ba/F3 cells were infected with the recombinant EGFR V769_D770insASV lentivirus and then followed by 1 μg/ml of puromycin selection and IL3 depletion. The resulting cell line expresses constitutively phosphorylated EGFR protein and proliferates in the absence of IL3, which could be used for in vitro PD and anti-proliferation assays.

Cell line with human Her2 exon 20 insertion mutation YVMA is generated by subcloning human Her2 exon 20 insertion mutation YVMA into a lentivirus transfer vector pMT143 (Sunbio Co., Ltd.) and then transfecting said lentivirus transfer vector and lentiviral packaging plasmids into 293T/17 (American Type Culture Collection (ATCC), CRL- 11268) cells to generate recombinant lentivirus encoding the human Her2 exon 20 insertion mutation YVMA. Parental NIH-3T3 cells were cultured in DMEM medium (Life Technology, Cat #11835-055) supplemented with 10% NBCS. To generate the Her2 exon 20 insertion YVMA transduced NIH-3T3 cell line, the parental cells were infected with the recombinant Her2 exon 20 insertion YVMA lentivirus and then followed by 1.0 μg/mL of puromycin selection. The resulting cell line expressed phosphorylated Her2 protein and its proliferation depended on the mutation gene, which could be used for in vitro PD and anti-proliferation assays.

Recombinant human EGFR exon 20 H773_V774insNPH Ba/F3 cell line was purchased from Crown Bioscience, Inc., China (Cat #C2058). Similar to recombinant human EGFR exon 20 H769_V770insASV Ba/F3 cell line, the recombinant human EGFR exon 20 H773_V774insNPH Ba/F3 cell line also expresses constitutively phosphorylated EGFR protein and proliferates in the absence of IL3, which could be used for in vitro PD and anti-proliferation assays.

NCI-H1975 cell line (CRL5908™) contains both of the point mutations EGFR L858R&T790M was purchased from American Type Culture Collection (ATCC).

Example 100: Potency Assessment EGFR (Wt) and EGFR Mutants

The inhibition activity and the selectivity of the compounds against mutant EGFR and WT EGFR were assessed by using WT EGFR cell line A-431 (American Type Culture Collection (ATCC), CRL-1555™) and mutant cell lines as described in Example 99.

One day before the test, WT or mutant cells were seeded in 96 well plates at appropriate concentrations with corresponding growth media supplemented with 1% FBS, and incubated overnight. The next day, tested compounds at a series of concentrations were added into each individual well of the plates, and the plates were incubated for 4 h at 37° C. with 5% $CO_2$. For WT EGFR cell line, an additional stimulation with 100 ng/ml recombinant hEGF (RD, Cat #236-EG) for 10 min should be performed after the incubation with the tested compound and before the analysis by MSD kits.

The EGFR (Y1068) phosphorylation level (activity) of cells in each well were then measured with MSD kit named "MULTI-SPOT®96 4-Spot HB Prototype EGFR Triplex ANALYTES: pEGFR(Tyr1068), pEGFR(Tyr1173), Total EGFR" according to the manufacturer's instruction (MESO SCALE DISCOVERY, Cat #N45ZB-1). The assay is an electrochemiluminescent method for determining both phosphorylated and total EGFR of cells with an MSD SECTOR® Imager and the ratio of p-EGFR/total EGFR can be generated by the machine. The Her2 (Y1248) phosphorylation level (activity) of cells in each well were measured with MSD Kit named "Phospho-ErbB2 (Tyr1248) Assay Whole Cell Lysate Kit" according to the manufacturer's instruction (MESO SCALE DISCOVERY, Cat #K151CLD-3). The assay is an electrochemiluminescent method (MESO SCALE DISCOVERY) for determining both phosphorylated and total Her2 of cells with an MSD SECTOR® Imager and then the ratio of p-Her2/total Her2 can be generated by the machine. The percentage of inhibition was calculated based on the formula: % inhibition=100×[1−(ratio of sample well−ratio of Min ctrl well)/(ratio of Max−Ratio of Min ctrl well)]. The $IC_{50}$ values were calculated as the compounds' concentration required for 50% inhibition in best-fit curves using Prism GraphPad 7.0 or Microsoft Xlfit software.

TABLE 2

Parameters of activity inhibition test for each cell line

| Cell | Seeding conc. | Serie conc. of the tested compounds |
|---|---|---|
| Ba/F3 EGFR NPH ins | 50000 cells/well | 3 μM, 0.3 μM, 0.1 μM, 0.03 μM, 0.01 μM, 0.003 μM, 0.001 μM, 0.0001 μM |
| Ba/F3 EGFR ASV ins | 50000 cells/well | 3 μM, 0.3 μM, 0.1 μM, 0.03 μM, 0.01 μM, 0.003 μM, 0.001 μM, 0.0001 μM |
| NCI-H1975 EGFR L858R/T790M | 20000 cells/well | 1 μM, 0.1 μM, 0.03 μM, 0.01 μM, 0.003 μM, 0.001 μM, 0.0003 μM, 0.00003 μM |
| Her2 YVMAins | 20000 cells/well | 3 μM, 0.3 μM, 0.1 μM, 0.03 μM, 0.01 μM, 0.003 μM, 0.001 μM, 0.0001 μM |
| WT EGFR | 20000 cells/well | 3 μM, 0.3 μM, 0.1 μM, 0.03 μM, 0.01 μM, 0.003 μM, 0.001 μM, 0.0001 μM |

Table 3 shows the activity of exemplary compounds of present disclosure and other EGFR inhibitors as positive control in the EGFR inhibition assay described above. The selectivity of the tested compound against mutant EGFR and WT EGFR can be evaluated based on the data for each tested compound. The compound numbers correspond to the compound numbers in Table 1.

TABLE 3

EGFR (Mutant and WT) Cellular Phosphorylation Inhibition Data for exemplary compounds

| Compounds | EGFR Exon20 NPH insertion $IC_{50}$ (nM) | EGFR Exon20 ASV insertion $IC_{50}$ (nM) | EGFR L858R and T790M mutation $IC_{50}$ (nM) | Her2 Exon20 YVMA insertion $IC_{50}$ (nM) | EGFR WT A431 $IC_{50}$ (nM) |
|---|---|---|---|---|---|
| 1 | 422.7 | 385.7 | 5.2 | 318.2 | 599.2 |
| 2 | 19.7 | 13.4 | 0.5 | 4.6 | 21.3 |
| 3 | 296.0 | 92.4 | 3.1 | 51.2 | 103.0 |
| 4 | 8.2 | 6.1 | 0.4 | 5.5 | 11.1 |
| 5 | 271.1 | 170.3 | 6.3 | 36.2 | 90.3 |
| 6 | 381.3 | 191.4 | 8.4 | 97.3 | 102.8 |
| 7 | 46.6 | 40.5 | 1.7 | 19.7 | 88.1 |
| 8 | 91.1 | 116.9 | 2.9 | 25.7 | 43.1 |
| 9 | 51.3 | 62.5 | 2.0 | 13.9 | 131.2 |
| 10 | 119.1 | 73.4 | 2.6 | 230.8 | 62.6 |
| 11 | 9.7 | 6.9 | 0.3 | 3.0 | 7.6 |
| 12 | 10.8 | 6.4 | 0.3 | 3.4 | 7.6 |
| 13 | 40.1 | 22.9 | 1.1 | 36.4 | 20.6 |
| 14 | 38.4 | 26.5 | 1.1 | 15.8 | 31.3 |

TABLE 3-continued

EGFR (Mutant and WT) Cellular Phosphorylation Inhibition Data for exemplary compounds

| Compounds | EGFR Exon20 NPH insertion IC$_{50}$ (nM) | EGFR Exon20 ASV insertion IC$_{50}$ (nM) | EGFR L858R and T790M mutation IC$_{50}$ (nM) | Her2 Exon20 YVMA insertion IC$_{50}$ (nM) | EGFR WT A431 IC$_{50}$ (nM) |
|---|---|---|---|---|---|
| 15 | 15.1 | 7.5 | 0.4 | 3.8 | 8.2 |
| 16 | 36.0 | 35.1 | 0.9 | 16.5 | 47.6 |
| 17 | 13.0 | 7.8 | 0.3 | 6.1 | 13.5 |
| 18 | 61.1 | 42.4 | 1.1 | 22.1 | 58.9 |
| 19 | 46.5 | 29.7 | 0.9 | 21.3 | 29.7 |
| 20 | 25.3 | 9.4 | 0.5 | 11.3 | 27.2 |
| 21 | 6.8 | 2.3 | 0.2 | 1.7 | 5.1 |
| 22 | 11.2 | 8.7 | 0.4 | 5.5 | 12.2 |
| 23 | 320.7 | 87.6 | 1.3 | 52.7 | 100.6 |
| 24 | 65.0 | 30.0 | 1.0 | 49.0 | 104.5 |
| 25 | 376.0 | 388.4 | 7.9 | 534.1 | 838.5 |
| 26 | 43.5 | 40.5 | 1.3 | 9.5 | 103.4 |
| 27 | 28.3 | 19.4 | 0.7 | 15.6 | 34.8 |
| 28 | 50.6 | 21.7 | 1.4 | 15.2 | 42.1 |
| 29 | 22.9 | 17.4 | 1.0 | 7.6 | 45.3 |
| 30 | 11.1 | 5.7 | 0.5 | 5.5 | 13.2 |
| 31 | 13.8 | 5.0 | 0.5 | 4.3 | 5.5 |
| 32 | 14.8 | 3.7 | 0.4 | 7.8 | 11.0 |
| 33 | 14.0 | 6.9 | 0.6 | 7.8 | 12.2 |
| 34 | 6.2 | 4.4 | 0.5 | 4.2 | 6.0 |
| 35 | 9.2 | 5.4 | 0.5 | 4.7 | 13.9 |
| 36 | 14.4 | 12.4 | 0.9 | 5.3 | 45.9 |
| 37 | 8.5 | 8.1 | 0.5 | 3.3 | 9.5 |
| 38 | 19.6 | 8.0 | 0.9 | 9.3 | 18.9 |
| 39 | 45.6 | 29.9 | 1.8 | 13.2 | 30.1 |
| 40 | 10.9 | 13.0 | 0.9 | 5.0 | 19.3 |
| 41 | 12.6 | 6.7 | 0.8 | 9.0 | 13.1 |
| 42 | 35.8 | 63.3 | 1.8 | 33.9 | 133.2 |
| 43 | 3.9 | 5.9 | 0.3 | 2.9 | 8.1 |
| 44 | 6.8 | 12.5 | 0.5 | 8.0 | 30.9 |
| 45 | 2.9 | 6.5 | 0.3 | 3.0 | 7.6 |
| 46 | 2.5 | 6.4 | 0.2 | 1.7 | 8.7 |
| 47 | 5.6 | 10.1 | 0.3 | 4.4 | 23.8 |
| 48 | 11.1 | 16.2 | 0.4 | 2.8 | 28.4 |
| 49 | 19.6 | 9.6 | 0.5 | 6.2 | 22.8 |
| 50 | 2627.9 | 308.5 | 19.0 | 381.9 | 1109.0 |
| 51 | 28.6 | 16.1 | 1.0 | 19.9 | 12.6 |
| 52 | 20.4 | 20.4 | 1.1 | 7.5 | 80.4 |
| 53 | 30.0 | 25.8 | 1.1 | 10.9 | 138.6 |
| 54 | 29.9 | 39.4 | 2.4 | 14.2 | 60.5 |
| 55 | 20.1 | 9.8 | 0.8 | 8.4 | 30.9 |
| 56 | 17.8 | 15.5 | 1.0 | 7.8 | 35.4 |
| 57 | 8.5 | 7.1 | 0.4 | 2.6 | 10.5 |
| 58 | 296.8 | 77.3 | 3.6 | 116.9 | 626.6 |
| 59 | 16.4 | 13.3 | 0.5 | 3.5 | 25.7 |
| 60 | 28.9 | 22.3 | 1.3 | 11.6 | 50.7 |
| 61 | 14.2 | 12.3 | 0.4 | 9.0 | 18.0 |
| 62 | 19.3 | 10.7 | 0.5 | 11.4 | 27.4 |
| 63 | 5.9 | 6.4 | 0.4 | 1.4 | 14.3 |
| 64 | 267.4 | 239.9 | 7.1 | 142.9 | 555.2 |
| 65 | 314.6 | 357.7 | 7.9 | 187.6 | 479.3 |
| 66 | 20.8 | 9.6 | 0.6 | 8.2 | 23.6 |
| 67 | 13.6 | 10.1 | 0.6 | 4.3 | 26.6 |
| 68 | 31.5 | 27.0 | 1.7 | 15.3 | 135.6 |
| 69 | 46.3 | 20.2 | 1.2 | 33.1 | 56.2 |
| 70 | 67.5 | 22.3 | 1.5 | 15.7 | 71.2 |
| 71 | 51.0 | 31.1 | 1.3 | 19.6 | 213.0 |
| 72 | 18.7 | 8.0 | 0.6 | 8.9 | 26.2 |
| 73 | 22.6 | 8.6 | 0.7 | 12.2 | 27.8 |
| 74 | 65.1 | 34.4 | 0.4 | 52.6 | 132.7 |
| 75 | 27.9 | 18.5 | 3.7 | 10.8 | 42.6 |
| 76 | 27.9 | 102.8 | 1.8 | 11.6 | 596.3 |
| 77 | 44.8 | 50.8 | 1.7 | 21.5 | 303.1 |
| 78 | 24.6 | 16.4 | 0.3 | 19.7 | 69.4 |
| 79 | 29.5 | 43.2 | 1.3 | 18.8 | 355.9 |
| 80 | 95.0 | 36.8 | 4.5 | 51.8 | 349.5 |
| 81 | 81.5 | NA | 1.1 | 302.6 | NA |
| 82 | 13.8 | 17.2 | 0.9 | 7.0 | 97.8 |
| 83 | 239.0 | 154.1 | 5.0 | 87.6 | 1005.2 |
| 84 | 259.2 | 115.7 | 0.4 | 1555.7 | 604.5 |
| 85 | 35.5 | 32.1 | 0.5 | 71.6 | 68.5 |
| 86 | 21.5 | 17.9 | 0.6 | 9.3 | 194.9 |

TABLE 3-continued

EGFR (Mutant and WT) Cellular Phosphorylation Inhibition Data for exemplary compounds

| Compounds | EGFR Exon20 NPH insertion $IC_{50}$ (nM) | EGFR Exon20 ASV insertion $IC_{50}$ (nM) | EGFR L858R and T790M mutation $IC_{50}$ (nM) | Her2 Exon20 YVMA insertion $IC_{50}$ (nM) | EGFR WT A431 $IC_{50}$ (nM) |
|---|---|---|---|---|---|
| 87 | 51.2 | 51.9 | 1.0 | 21.2 | 361.7 |
| 88 | 10.1 | 7.5 | 0.5 | 4.5 | 27.8 |
| 89 | 14.8 | 23.0 | 0.7 | 6.8 | 147.6 |
| 90 | 30.8 | 57.2 | 1.4 | 27.6 | 356.6 |
| 91 | 26.2 | 41.2 | 1.5 | 22.5 | 183.1 |
| 92 | 79.9 | 71.2 | 1.7 | 26.0 | 764.7 |
| 93 | 33.1 | 19.4 | 1.6 | 15.1 | 51.6 |
| 94 | 28.5 | 17.7 | 0.7 | 4.4 | 28.9 |
| 95 | 7.1 | 6.2 | 0.3 | 2.2 | 3.5 |
| 96 | 13.5 | 7.1 | 0.4 | 2.1 | 50.4 |
| 97 | 17.4 | 14.4 | 0.7 | 2.8 | 160.1 |
| 98 | 19.1 | 21.4 | 0.9 | 3.1 | 190.2 |
| Afatinib | 20.8 | 14.0 | 4.6 | 2.8 | 5.2 |
| AZD9291 | 165.0 | 127.8 | 1.9 | 73.8 | 229.6 |
| Poziotinib | 2.1 | 2.0 | 1.3 | 0.8 | 1.7 |
| EGF816 | 368.5 | 290.8 | 5.0 | 116.5 | 505.2 |
| Neratinib | 13.2 | 1.9 | 2.3 | 1.2 | 9.7 |

The $IC_{50}$ of the compounds to cells having EGFR L858R and T790M double mutations can be up to 1500 times more potent than the $IC_{50}$ of the compounds to wild-type EGFR. Most compounds of present disclosure show higher inhibitory activity to EGFR exon 20 NPH and ASV insertions, and Her2 exon20 YVMA insertion as compared to AZD9291.

Example 101: Cell Proliferation EGFR (Wt) and EGFR Mutants

WT or mutant cells were seeded in 384 well plates at appropriate concentrations with corresponding growth media supplemented with 10% FBS, for each experiment, identical plates were prepared in duplicates, and the plates were incubated overnight. On the next day, one of each duplicated plates was dosed with tested compounds at a series of concentrations, and another one of the duplicated plate was analysed for G0 value. The dosed plates were incubate for another 72 h at 37° C. with 5% $CO_2$ and the number of viable cells in each well of the G0 plates or the dosed plates were measured by CellTiter-Glo® Luminescent Cell Viability Assay (Promega). This assay is a luminescent method for determining the number viable cells through measurement of cellular ATP concentration by detection of luciferase activity. Detection reagents (15 µl) was dispensed into per well, and the plates were incubate for 30 min at room temperature. Then, the luminescence in each well was measured using the Envision plate reader (PerkinElmer). The percentage of proliferation was calculated based on the formula: % Proliferation=100×(G3 value of sample well–Go value)/(G3 value of DMSO control-Go value). The $GI_{50}$ values were further calculated as the compounds concentration required for 50% Proliferation in best-fit curves using Genedata Screener® software.

TABLE 4

Parameters of proliferation test for each cell line

| Cell | Seeding conc. | Serie conc. of the tested compounds |
|---|---|---|
| Ba/F3 EGFR NPH ins | 1250 cells/well | 3 µM, 1 µM, 0.3 µM, 0.1 µM, 0.03 µM, 0.01 µM, 0.003 µM, 0.001 µM, 0.0001 µM |
| Ba/F3 EGFR ASV ins | 1250 cells/well | 3 µM, 1 µM, 0.3 µM, 0.1 µM, 0.03 µM, 0.01 µM, 0.003 µM, 0.001 µM, 0.0001 µM |
| NCI-H1975 EGFR L858R/T790M | 750 cells/well | 3 µM, 1 µM, 0.3 µM, 0.1 µM, 0.03 µM, 0.01 µM, 0.003 µM, 0.001 µM, 0.0001 µM |
| Her2 YVMAins | 1500 cells/well | 3 µM, 1 µM, 0.3 µM, 0.1 µM, 0.03 µM, 0.01 µM, 0.003 µM, 0.001 µM, 0.0001 µM |
| WT EGFR | 1000 cells/well | 3 µM, 1 µM, 0.3 µM, 0.1 µM, 0.03 µM, 0.01 µM, 0.003 µM, 0.001 µM, 0.0001 µM |

Table 5 shows the proliferation inhibition of exemplary compounds of present disclosure and other EGFR inhibitors as positive control in the proliferation inhibition assay described above.

TABLE 5

EGFR (Mutant and Wild Type) Cell Proliferation

| Example | EGFR Exon20 NPH insertion $GI_{50}$ (nM) | EGFR Exon20 ASV insertion $GI_{50}$ (nM) | EGFR L858R and T790M mutation $GI_{50}$ (nM) | Her2 Exon20 YVMA insertion $GI_{50}$ (nM) | EGFR WT A431 $GI_{50}$ (nM) |
|---|---|---|---|---|---|
| 1 | 998.8 | 926.3 | 281.7 | 904.6 | 334.5 |
| 2 | 56.0 | 42.2 | 13.9 | 45.2 | 26.6 |
| 3 | 306.8 | 252.3 | 55.6 | 182.9 | 69.3 |
| 4 | 32.2 | 20.7 | 6.9 | 31.0 | 15.7 |
| 5 | 460.7 | 234.2 | 113.8 | 68.9 | 116.9 |
| 6 | 624.8 | 249.9 | 93.7 | 534.3 | 64.7 |
| 7 | 211.8 | 144.7 | 25.0 | 161.2 | 37.9 |
| 8 | 258.0 | 250.3 | 32.4 | 352.7 | 99.8 |
| 9 | 180.5 | 190.9 | 44.6 | 155.5 | 83.1 |
| 10 | 189.0 | 197.9 | 76.3 | 273.8 | 79.4 |
| 11 | 21.6 | 25.2 | 7.7 | 20.7 | 13.0 |
| 12 | 21.5 | 25.3 | 8.4 | 24.5 | 14.2 |
| 13 | 76.5 | 53.3 | 15.3 | 155.8 | 22.5 |
| 14 | 55.4 | 84.1 | 18.0 | 58.7 | 29.1 |
| 15 | 32.9 | 21.1 | 7.4 | 32.7 | 7.9 |
| 16 | 81.3 | 114.5 | 33.4 | 73.4 | 52.6 |
| 17 | 25.0 | 19.6 | 3.7 | 37.7 | 13.2 |
| 18 | 93.6 | 91.3 | 10.9 | 136.2 | 42.8 |

TABLE 5-continued

EGFR (Mutant and Wild Type) Cell Proliferation

| Example | EGFR Exon20 NPH insertion GI$_{50}$ (nM) | EGFR Exon20 ASV insertion GI$_{50}$ (nM) | EGFR L858R and T790M mutation GI$_{50}$ (nM) | Her2 Exon20 YVMA insertion GI$_{50}$ (nM) | EGFR WT A431 GI$_{50}$ (nM) |
|---|---|---|---|---|---|
| 19 | 80.0 | 80.9 | 9.5 | 163.2 | 23.1 |
| 20 | 51.5 | 30.8 | 7.7 | 68.1 | 16.5 |
| 21 | 11.2 | 8.2 | 2.5 | 13.2 | 4.1 |
| 22 | 26.5 | 26.5 | 2.7 | 44.4 | 12.0 |
| 23 | 223.9 | 158.8 | 34.7 | 271.0 | 76.8 |
| 24 | 141.6 | 101.4 | 23.0 | 302.7 | 55.5 |
| 25 | 617.5 | 552.2 | 164.6 | 988.8 | 329.4 |
| 26 | 123.0 | 99.5 | 32.4 | 252.7 | 57.8 |
| 27 | 57.9 | 64.7 | 5.2 | 106.4 | 26.2 |
| 28 | 67.7 | 58.2 | 8.9 | 114.3 | 21.2 |
| 29 | 52.7 | 45.2 | 6.9 | 68.3 | 20.1 |
| 30 | 19.3 | 25.9 | 3.7 | 47.5 | 12.4 |
| 31 | 47.9 | 9.2 | 4.2 | 60.1 | 4.2 |
| 32 | 19.1 | 19.3 | 1.8 | 35.2 | 6.0 |
| 33 | 29.6 | 22.1 | 3.1 | 71.1 | 12.7 |
| 34 | 16.4 | 17.6 | 1.6 | 21.1 | 7.5 |
| 35 | 22.2 | 24.3 | 1.5 | 39.4 | 21.9 |
| 36 | 42.7 | 37.8 | 1.6 | 75.2 | 41.6 |
| 37 | 22.9 | 24.0 | 1.5 | 22.3 | 10.3 |
| 38 | 59.4 | 46.2 | 3.9 | 84.8 | 19.7 |
| 39 | 71.8 | 76.6 | 5.5 | 69.9 | 26.5 |
| 40 | 22.0 | 25.7 | 2.1 | 43.4 | 13.6 |
| 41 | 23.2 | 21.8 | 1.6 | 52.1 | 13.8 |
| 42 | 137.0 | 143.8 | 8.5 | 195.4 | 53.2 |
| 43 | 17.4 | 9.3 | 1.2 | 27.6 | 4.3 |
| 44 | 39.0 | 29.8 | 3.6 | 74.6 | 14.8 |
| 45 | 17.8 | 13.6 | 1.1 | 30.8 | 4.3 |
| 46 | 18.8 | 8.2 | 1.4 | 16.8 | 4.5 |
| 47 | 27.1 | 22.1 | 1.9 | 34.1 | 10.9 |
| 48 | 57.9 | 29.1 | 3.2 | 57.9 | 14.1 |
| 49 | 31.6 | 31.9 | 1.5 | 36.1 | 15.3 |
| 50 | 802.1 | 449.0 | 30.0 | 1082.3 | 276.7 |
| 51 | 52.9 | 35.4 | 1.9 | 104.7 | 13.4 |
| 52 | 60.4 | 83.2 | 3.3 | 101.3 | 47.1 |
| 53 | 89.3 | 84.0 | 4.0 | 136.8 | 71.8 |
| 54 | 68.0 | 104.2 | 6.1 | 209.5 | 41.3 |
| 55 | 62.6 | 44.1 | 3.8 | 88.9 | 14.6 |
| 56 | 63.8 | 45.1 | 4.2 | 76.6 | 14.3 |
| 57 | 14.8 | 11.4 | 1.3 | 18.7 | 6.1 |
| 58 | 209.7 | 250.8 | 13.1 | 553.0 | 177.9 |
| 59 | 29.1 | 29.8 | 2.0 | 62.2 | 10.7 |
| 60 | 48.6 | 76.3 | 2.5 | 101.8 | 25.0 |
| 61 | 18.8 | 25.6 | 2.1 | 87.8 | 12.4 |
| 62 | 45.8 | 34.8 | 3.2 | 114.3 | 13.3 |
| 63 | 17.2 | 13.6 | 1.1 | 23.6 | 4.4 |
| 64 | 359.0 | 395.0 | 24.2 | 640.5 | 219.5 |
| 65 | 381.7 | 484.4 | 29.6 | 776.1 | 233.6 |
| 66 | 22.6 | 25.4 | 2.3 | 29.1 | 14.9 |
| 67 | 32.8 | 21.9 | 2.5 | 46.3 | 18.7 |
| 68 | 33.0 | 46.1 | 2.8 | 96.7 | 20.8 |
| 69 | 58.1 | 70.1 | 5.5 | 89.1 | 12.2 |
| 70 | 65.8 | 65.4 | 9.1 | 72.0 | 15.4 |
| 71 | 74.7 | 89.8 | 8.3 | 86.2 | 34.9 |
| 72 | 46.1 | 42.3 | 4.1 | 38.9 | 10.4 |
| 73 | 43.2 | 27.4 | 3.3 | 26.0 | 8.0 |
| 74 | 76.8 | 86.6 | 6.0 | 154.7 | 43.0 |
| 75 | 73.0 | 90.6 | 19.2 | 29.9 | 11.6 |
| 76 | 85.9 | 112.8 | 5.4 | 97.7 | 38.3 |
| 77 | 81.9 | 101.5 | 3.6 | 108.9 | 32.4 |
| 78 | 60.0 | 35.7 | 1.4 | 49.2 | 21.5 |
| 79 | 167.3 | 175.5 | 13.0 | 232.8 | 123.7 |
| 80 | 219.8 | 176.8 | 14.8 | 467.1 | 81.5 |
| 81 | 135.5 | 149.0 | 4.6 | 353.8 | 35.7 |
| 82 | 35.8 | 77.7 | 3.6 | 82.4 | 42.0 |
| 83 | 300.5 | 340.3 | 38.9 | 678.2 | 252.0 |
| 84 | 191.3 | 450.3 | 19.1 | 341.0 | 232.5 |
| 85 | 63.1 | 80.7 | 22.4 | 128.8 | 51.1 |
| 86 | 59.8 | 90.9 | 29.1 | 248.9 | 45.8 |
| 87 | 139.7 | 155.7 | 24.4 | 827.0 | 84.8 |
| 88 | 18.8 | 14.0 | 1.8 | 31.2 | 6.9 |
| 89 | 63.8 | 114.7 | 2.8 | 158.4 | 63.1 |
| 90 | 76.4 | 83.1 | 6.1 | 283.5 | 59.4 |
| 91 | 64.6 | 69.6 | 2.2 | 148.0 | 31.5 |
| 92 | 84.7 | 92.1 | 4.9 | 212.5 | 40.6 |
| 93 | 105.3 | 83.2 | 7.3 | 166.1 | 21.5 |
| 94 | 94.9 | 80.9 | 6.4 | 141.3 | 16.5 |
| 95 | 20.5 | 16.0 | 3.7 | 15.8 | 2.9 |
| 96 | 50.0 | 55.6 | 0.8 | 50.0 | 17.8 |
| 97 | 74.2 | 86.7 | 3.4 | 93.9 | 38.0 |
| 98 | 112.2 | 129.4 | 3.1 | 134.9 | 87.8 |
| Afatinib | 196.7 | 100.5 | 284.9 | 17.8 | 3.9 |
| AZD9291 | 177.4 | 206.7 | 14.5 | 294.5 | 43.7 |
| Poziotinib | 7.2 | 4.1 | 19.4 | 4.7 | 0.5 |
| EGF816 | 491.3 | 501.5 | 42.5 | 241.9 | 264.8 |
| Neratinib | 700.4 | 88.0 | 109.5 | 5.2 | 15.9 |

The GI$_{50}$ of the compounds to cells having EGFR L858R and T790M double mutations can be up to 25 times more potent than the GI$_{50}$ of the compounds to wild-type EGFR. Most compounds of present disclosure show higher inhibitory activity to EGFR exon 20 NPH and ASV insertions, and Her2 exon20 YVMA insertion as compared to AZD9291.

Example 102: Cell Proliferation BTK (WT)

OCI-LY-10 at 3,750 cells/well, TMD-8 and Ri-1 at 2,000 cells/well, and DB at 1,250 cells/well, respectively, were sorted into 384-well plates in RPMI1640 medium with 10% FBS. After overnight incubation, all cells were incubated with compound at a series of concentrations. Meanwhile, a duplicated plate of each cell line was prepared for measuring G0 value. The dosed plates were further incubated for 72 hours and the number of viable cells was measured by CellTiter-Glo® Luminescent Cell Viability Assay (Promega), a luminescent method for determining the number of viable cells through measurement of cellular ATP concentration using Envision plate reader (PerkinElmer). The percentage of proliferation was calculated as: % Proliferation=100×(G3 value of sample well−G0 value)/(G3 value of DMSO control−Ga value). The GI50 values were further calculated as the compound concentration required for 50% proliferation inhibition in best-fit curves using XLFit software.

Table 6 shows the proliferation inhibition of exemplary compounds of present disclosure and other BTK inhibitors as positive control in the proliferation inhibition assay described above.

TABLE 6

BTK Cell Proliferation

| Example | BTK WT OCI-LY-10 GI$_{50}$ (nM) | BTK WT TMD-8 GI$_{50}$ (nM) | BTK WT Ri-1 GI$_{50}$ (nM) | Non-BCR activated DB GI$_{50}$ (nM) |
|---|---|---|---|---|
| 1 | — | — | — | — |
| 2 | 134.1 | 129.9 | 86.6 | >3000 |
| 3 | 2507.7 | 635.4 | >3000 | >3000 |
| 4 | 8.9 | 77.1 | 61.4 | >3000 |
| 5 | — | — | — | — |
| 6 | 210.4 | 334.6 | 288.6 | >3000 |
| 7 | 130.37 | 187.55 | >3000 | >3000 |
| 8 | 88.01 | 1778.2 | >3000 | >3000 |

TABLE 6-continued

BTK Cell Proliferation

| Example | BTK WT OCI-LY-10 GI$_{50}$ (nM) | BTK WT TMD-8 GI$_{50}$ (nM) | BTK WT Ri-1 GI$_{50}$ (nM) | Non-BCR activated DB GI$_{50}$ (nM) |
|---|---|---|---|---|
| 9 | 308.6 | 551.4 | 700.0 | >3000 |
| 10 | >3000 | >3000 | >3000 | >3000 |
| 11 | 2.8 | 10.9 | 26.0 | 2795.0 |
| 12 | 27.8 | 34.5 | 51.2 | >3000 |
| 13 | 54.5 | 56.3 | 120.2 | >3000 |
| 14 | 155.3 | 102.3 | 135.5 | >3000 |
| 15 | 4.95 | 2.44 | 6.68 | 1335.6 |
| 16 | 250.5 | 117.5 | 333.6 | >3000 |
| 17 | 41.5 | 53.7 | 28.0 | >3000 |
| 18 | 276.4 | 81.7 | 446.4 | >3000 |
| 19 | 10.8 | 13.0 | 132.9 | >3000 |
| 20 | 99.8 | 103.1 | 56.2 | >3000 |
| 21 | 9.7 | 19.2 | 11.2 | >3000 |
| 22 | — | — | — | — |
| 23 | 1.49 | 3.93 | 3.71 | >3000 |
| 24 | 324.3 | 107.3 | 414.9 | >3000 |
| 25 | — | — | — | — |
| 26 | 45.3 | 12.6 | 50.5 | >3000 |
| 27 | 17.7 | 11.6 | 120.3 | >3000 |
| 28 | 119.2 | 34.0 | 230.0 | >3000 |
| 29 | 35.5 | 11.3 | 44.8 | >3000 |
| 30 | 13.1 | 17.8 | 28.6 | >3000 |
| 31 | 30.0 | 7.18 | 59.89 | >3000 |
| 32 | 0.29 | 0.26 | 0.71 | >3000 |
| 33 | 0.97 | 2.5 | 2.0 | >3000 |
| 34 | 7.6 | 12.3 | 16.6 | >3000 |
| 35 | 986.3 | 377.1 | 699.0 | >3000 |
| 36 | 6.41 | 8.32 | 8.20 | 880.7 |
| 37 | 14.6 | 10.0 | 34.6 | 2975.8 |
| 38 | 0.70 | 1.62 | 1.49 | >3000 |
| 39 | 1.74 | 1.69 | 1.47 | >3000 |
| 40 | 15.1 | 15.1 | 11.9 | >3000 |
| 41 | 1.57 | 4.57 | 4.92 | >3000 |
| 42 | — | — | — | — |
| 43 | 7.6 | 13.6 | 28.5 | >3000 |
| 44 | 6.75 | 4.32 | 10.4 | >3000 |
| 45 | 5.25 | 2.33 | 11.6 | >3000 |
| 46 | 2.97 | 0.90 | 6.49 | 2583.0 |
| 47 | 775.0 | 55.3 | 207.6 | >3000 |
| 48 | 14.1 | 70.2 | 371.2 | >3000 |
| 49 | 1248.6 | 107.4 | 565.7 | >3000 |
| 50 | — | — | — | — |
| 51 | 6.73 | 3.62 | 10.3 | >3000 |
| 52 | 3.2 | 5.8 | 51.3 | 1983.5 |
| 53 | 9.16 | 6.39 | 17.1 | >3000 |
| 54 | 4.42 | 3.62 | 9.97 | >3000 |
| 55 | 6.68 | 11.5 | 12.0 | >3000 |
| 56 | 14.6 | 7.07 | 13.4 | >3000 |
| 57 | 72.0 | 22.9 | 34.6 | >3000 |
| 58 | 320.4 | 262.0 | 371.7 | >3000 |
| 59 | 17.1 | 4.78 | 26.9 | >3000 |
| 60 | 13.5 | 11.5 | 38.9 | >3000 |
| 61 | 2.72 | 1.03 | 5.62 | 1513.0 |
| 62 | 5.30 | 3.79 | 84.0 | >3000 |
| 63 | 63.3 | 11.6 | 14.9 | >3000 |
| 64 | — | — | — | — |
| 65 | — | — | — | — |
| 66 | >3000 | 581.94 | >3000 | >3000 |
| 67 | 20.4 | 16.0 | 47.9 | >3000 |
| 68 | 11.4 | 3.6 | 13.6 | 2511.0 |
| 69 | 74.5 | 10.1 | 13.9 | >3000 |
| 70 | 22.2 | 10.2 | 88.9 | >3000 |
| 71 | 12.4 | 4.8 | 23.5 | 2954.4 |
| 72 | 2.9 | 7.3 | 33.3 | >3000 |
| 73 | 16.3 | 3.75 | 150.6 | >3000 |
| 74 | 3.9 | 9.1 | 82.0 | >3000 |
| 75 | 45.5 | 133.0 | 250.2 | >3000 |
| 76 | 2.93 | 8.44 | 5.93 | 1071.9 |
| 77 | 1.23 | 1.19 | 1.55 | 1753.0 |
| 78 | 6.2 | 10.3 | 77.8 | >3000 |
| 79 | 8.1 | 14.4 | 80.9 | >3000 |
| 80 | 23.7 | 40.2 | >3000 | >3000 |
| 81 | — | — | — | — |
| 82 | 76.1 | 202.7 | 310.4 | >3000 |
| 83 | — | — | — | — |
| 84 | 31.2 | 39.8 | 136.6 | >3000 |
| 85 | 1.1 | 2.6 | 11.0 | >3000 |
| 86 | 7.8 | 11.4 | 18.6 | >3000 |
| 87 | 22.3 | 13.7 | 48.0 | 1205.3 |
| 88 | 1.57 | 6.49 | 11.97 | >3000 |
| 89 | 11.4 | 9.86 | 17.5 | >3000 |
| 90 | 82.7 | 45.0 | 83.8 | >3000 |
| 91 | 86.8 | 58.0 | 79.4 | >3000 |
| 92 | 227.9 | 63.8 | 145.8 | 1198.8 |
| 93 | 0.92 | 3.1 | 3.2 | >3000 |
| 94 | 21.6 | 94.8 | 209.2 | >3000 |
| 95 | 0.29 | 1.16 | 971.41 | >3000 |
| 96 | 7.04 | 2.80 | 25.1 | 2993.1 |
| 97 | 24.0 | 18.6 | 54.7 | >3000 |
| 98 | 114.6 | 71.5 | 108.3 | >3000 |
| Afatinib | 1035.7 | 1159.2 | 1032.1 | 656.9 |
| AZD9291 | 1043.9 | 1092.7 | 2047.3 | 1017.2 |
| Poziotinib | 1001.4 | 2405.3 | 1227.9 | >3000 |
| EGF816 | 234.8 | 165.9 | 896.7 | >3000 |

As shown in Table 7 below, exemplary compounds disclosed in this invention showed better potency and higher receptor occupancy at lower drugs concentration compared to ACP-196 and Ibrutinib.

p-BTK Assay

Suspensions of Ramos cells in RPMJ16400 (Gibco) with 1.5% FBS (Invitrogen) were equally distributed into a 384-well small volume white plate. Compounds were diluted by Platemate plus (Thermo) and added to assay plates using an ECHO 555 liquid handler (Labcyte) to give a 0.1% DMSO final concentration. The assay plates were then incubated for 30 minutes at 37° C., 5% CO$_2$. 300 uM Per vanadate (3×) was added to each well and the assay plates were again incubated for 60 minutes at 37° C., 5% CO$_2$. Phospho-BTK (Tyr223) is detected using the HTRF® reagents (Cisbio) according to the manufacturer's one-plate assay protocol.

Btk Target Site Occupancy Enzyme-Linked Immunosorbent Assay.

An enzyme-linked immunosorbent assay (ELISA) method for the detection of free uninhibited Btk in mouse and human lysates. Human or mouse whole blood were incubated with compound for 2 hour at 37° C. Whole blood were lysed in ice-cold lysis buffer containing 50 mM Tris-HCl, pH 7.5, 150 mM NaCl, 1 mM EDTA, 1% Triton X-100. Cell lysates were then incubated with Ibrutinib-biotin at final concentration 1 µM. Samples were transferred to a streptavidin-coated 96-well ELISA plate and mixed while shaking for 1 hour at room temperature. The α-Btk antibody (1:500; clone number D3H5, Cell signaling Technology, Danvers, Mass., USA) was then added to the well and incubated for 1 hour at room temperature. After wash, goat α-rabbit-HRP (1:5000 dilution in PBS+0.05% Tween-20+1% BSA) was added to each well and incubated for 1 h at room temperature. The ELISA was developed with addition of tetramethyl benzidine (TMB) followed by Stop Solution and read at OD 450 nm.

TABLE 7

BTK PD marker assay and receptor occupancy assay results

| Compound No. | p-BTK (Romas) IC$_{50}$ (nM) | Occupancy (Romas) IC$_{50}$ (nM) | Occupancy (PBMC) IC$_{50}$ (nM) |
|---|---|---|---|
| 23 | 1.6 | 1.1 | 1.1 |
| 38 | 1.3 | 0.8 | 1.7 |
| 39 | 0.9 | 1.0 | 1.3 |
| 52 | 2.9 | 0.6 | 2.9 |
| 53 | 3.8 | 3.1 | 3.8 |
| 77 | 1.6 | 0.49 | 1.7 |
| 80 | 5.8 | 3.4 | 5.7 |
| ACP-196 | 12.7 | 7.4 | 3.4 |
| Ibrutinib | 1.6 | 0.17 | 0.23 |

Example 103: In Vitro Rat/Human Hepatocytes Clearance Assay

The protocol for rat/human hepatocytes metabolic stability assay is employed to determine the clearance of the compounds of the present disclosure in vitro.

Rat hepatocytes in male gender and human hepatocytes in mixed gender were obtained from commercial vendors (e.g., BioreclamationIVT) and stored at −150° C. prior to use. 10 mM stock solutions of tested compounds were prepared in DMSO. Thawing medium and supplement incubation medium (serum-free) were placed in a 37° C. water bath for at least 15 minutes prior to use. Stock solutions were diluted to 100 μM by combining 198 μL acetonitrile and 2 μL of 10 mM stock solution.

Vials of cryopreserved hepatocytes were removed from storage, ensured that vials remain at cryogenic temperatures. The vials were thawed in a 37° C. water bath with gently shaking. Vials were kept in water bath until all ice crystals had dissolved and were no longer visible. Vials were sprayed with 70% ethanol before being transferred to a biosafety cabinet. And then the contents were poured into the 50 mL thawing medium conical tube. Vials were centrifuged at 100 g for 10 minutes at room temperature. Thawing medium was aspirated and hepatocytes were resuspended with serum-free incubation medium to yield ~1.5×10$^6$ cells/mL.

Cell viability and density were counted using a Trypan Blue exclusion, and then cells were diluted with serum-free incubation medium to a working cell density of 1×10$^6$ viable cells/ml. A portion of the hepatocytes at 1×10$^6$ viable cells/mL was boiled for 10 min prior to adding to the plate as negative control to eliminate the enzymatic activity so that little or no substrate turnover should be observed. The inactivated hepatocytes were used to prepare negative samples, which were used to exclude the misleading factor that resulted from instability of chemical itself.

Aliquots of 247.5 μL hepatocytes were dispensed into each well of a 96-well non-coated plate. The plate was placed in the incubator on an orbital shaker for approximately 10 minutes. Aliquots of 2.5 μL of the 100 μM test compounds were added into respective wells of the non-coated 96-well plate to start the reaction. This assay was performed in duplicate. The plate was incubated in the incubator on an orbital shaker for the designed time points. 20 μL of contents were transferred and mixed with 6 volumes (120 μL) of cold acetonitrile with internal standard to terminate the reaction at time points of 5, 15, 30, 45, 60, 80 and 100 minutes. Samples were centrifuges for 20 minutes at 4000 g and aliquots of 100 μL of the supernatants were used for LC-MS/MS analysis for measurement of test compounds In vitro hepatocyte clearance was estimated based on determination of elimination half-life (T$_{1/2}$) of compounds disappearance from their initial concentrations. Peak area ratios of each compound (test or control) to IS was calculated. Ln (% Control) versus Incubation Time (min) curve was plotted, and the slope of a linear fitting line was calculated. Drug elimination rate constant k (min-1), T$_{1/2}$ (min), and in vitro intrinsic clearance CL$_{int}$ (μL/min/E6) was calculated according to the following equations:

$$k = -\text{slope}$$

$$T_{1/2} = 0.693/k$$

$$CL_{int} = k/C_{hep}$$

where $C_{hep}$ (cells×μL$^{-1}$) is the cell concentration in the incubation system.

Exemplary data are shown in below Table 8.

TABLE 8

Human & rat hepatocyte intrinsinc clearance

| Examples | rat hepatocytes Cl$_{int}$ (μL/min/10$^6$ cells) | human hepatocytes Cl$_{int}$ (μL/min/10$^6$ cells) |
|---|---|---|
| Example 11 | 161 | 7.12 |
| Example 22 | 78.4 | 9.78 |
| Example 33 | 6.99 | 2.77 |
| Example 36 | >300 | 10.33 |
| Example 37 | 67.7 | 11.77 |
| Example 51 | 5.97 | 4.02 |
| Example 52 | 13.3 | 3.29 |
| Example 53 | 12.3 | 4.04 |
| Example 59 | 14.1 | 3.75 |
| Example 61 | 7.9 | 2.71 |
| Example 68 | 17.5 | 3.89 |
| Example 69 | 10.7 | 4.12 |
| Example 70 | 12.9 | 3.69 |
| Example 73 | 6.15 | 1.1 |
| Example 76 | 13.9 | 4.01 |
| Example 77 | 15.8 | 7.87 |
| Example 79 | 24.1 | 7.36 |
| Example 80 | 15.5 | 2.81 |
| Example 86 | 16.2 | 4.32 |
| Example 89 | NA | 3.84 |
| Example 91 | NA | 8.57 |
| Example 93 | 11.5 | 5.01 |
| Example 96 | 13.2 | 1.42 |
| Example 97 | NA | 4.25 |
| Example 98 | NA | 7.6 |

Since hepatocytes contain both phase I and II metabolism enzymes, the clearance assay in rat/human hepatocytes may reflect intrinsic clearance in the liver. As a primary screening assay, it was used to select compounds for next round in vivo rat pharmacokinetic studies, and predict human liver clearance if in vitro-in vivo extrapolation is established in rat.

Example 104: In Vivo Pharmacokinetic Studies

For rat pharmacokinetic studies, six male Han Wistar rats were purchased from Beijing Vital River and orally dosed with the test compound at 10 mg/kg in 0.5% Tween-80 and 0.5% hydroxypropyl methylcellulose (v/w). At, 0.5, 1, 2, 4, 7 and 16 hours post-dose, blood samples (>100 μL/time point) were collected from portal vein and via cardiac puncture into separate K$_2$EDTA coagulated tubes, and then immediately centrifuged at 1500 g, 5 min at 4° C. to separate plasma. The plasma samples were deproteinized with 4 fold acetonitrile (including internal standard), vortex for 10 min and centrifuges for 10 minutes at 4000 g at 4° C. The supernatants were submitted to LC/MS/MS (API 5500, Applied Biosystems, Foster City) analysis. Two sets of standard curves were run at the beginning and end of each batch from plasma sample analysis.

Compound absorption was measured by portal vein AUC ($AUC_{HPV}$) and systemic AUC ($AUC_{SYS}$) observed maximum concentration ($C_{max}$) in rats after oral administration. Dose is the actual dose used in SOA study. Find below in Table 9 data for exemplary tested compounds.

TABLE 9

Rat pharmacokinetic parameters of exemplary tested compounds

| EXAMPLES | Actual oral dose (mg/kg) | SOA $C_{max}$ (ng/mL) | SOA DN $AUC_{SYS}$ (ng · h/mL)/(mg/kg) |
| --- | --- | --- | --- |
| Example 33 | 9.77 | 370 | 432 |
| Example 52 | 7.17 | 99 | 103 |
| Example 53 | 12.6 | 195 | 116 |
| Example 79 | 3.91 | 52.5 | 50.1 |
| Example 86 | 5 | 76.5 | 77.8 |
| Example 93 | 10 | 498 | 249 |

The study aims to evaluate the systemic exposure of test compounds in term of $C_{max}$ and AUC, which is contributed by oral absorption, gut metabolism and liver extraction. It will be used to select compounds for in vivo pharmacokinetic study.

While the present disclosure has been particularly shown and described with reference to specific embodiments (some of which are preferred embodiments), it should be understood by those skilled in the art that various changes in form and detail may be made therein without departing from the spirit and scope of the present disclosure as disclosed herein.

What is claimed is:

1. A compound of Formula (I):

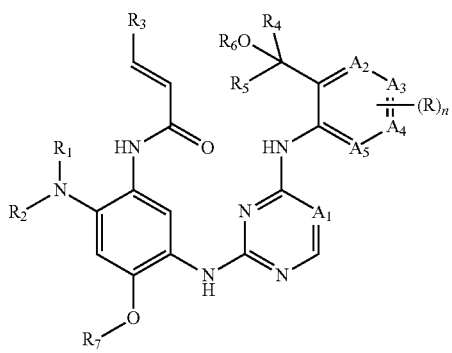

Formula (I)

or a pharmaceutically acceptable salt, hydrate, solvate or stereoisomer thereof, wherein, $A_1$ is N or $CR_8$;

$A_2$, $A_3$, $A_4$ and $A_5$ are each independently N or $CR_9$, wherein no more than one of $A_2$, $A_3$, $A_4$ and $A_5$ is N;

$R_1$ and $R_2$ are each independently hydrogen or $C_{1-12}$ alkyl optionally mono- or independently multi-substituted by one or more of halogen, hydroxyl, —$NR^aR^b$, $C_{1-12}$ alkyl, $C_{1-12}$ alkoxy, 3-10 membered saturated or unsaturated carbocyclyl, 3-10 membered saturated or unsaturated heterocyclyl, wherein each of $C_{1-12}$ alkyl, $C_{1-12}$ alkoxy, 3-10 membered saturated or unsaturated carbocyclyl, 3-10 membered saturated or unsaturated heterocyclyl can be unsubstituted or mono- or multi-substituted by $C_{1-12}$ alkyl, wherein, $R^a$ and $R^b$ are each independently selected from hydrogen or $C_{1-12}$ alkyl, which can be optionally mono- or independently multi-substituted by deuterium, tritium, halogen, hydroxyl, or $C_{1-12}$ alkoxy, or $R^a$ and $R^b$ taken together with the nitrogen atom to which they are bound to form a 3-10 membered saturated or unsaturated heterocyclyl optionally mono- or multi-substituted by halogen, hydroxyl, or $C_{1-12}$ alkyl;

or, $R_1$ and $R_2$ taken together with the nitrogen atom to which they are bound to form a 3-12 membered monocyclic or polycyclic ring optionally comprising one or more additional heteroatoms selected from N, O, and S, which can be optionally mono- or independently multi-substituted by halogen, hydroxyl, $C_{1-12}$ alkyl, $C_{1-12}$ alkoxy, —$NR^aR^b$, or —$C_{1-12}$ alkyl-$NR^aR^b$;

$R_3$ is H, $C_{1-12}$ alkyl, or —$C_{1-12}$ alkyl-$NR^aR^b$;

$R_4$ and $R_5$ are each independently $C_{1-6}$ alkyl optionally mono- or independently multi-substituted by one or more of deuterium, tritium, halogen, hydroxyl, $C_{1-12}$ alkyl, or $C_{1-12}$ alkoxy, or, $R_4$ and $R_5$ taken together with the carbon atom to which they are bound to form a 3-10 membered monocyclic or polycyclic ring optionally comprising one or more heteroatoms selected from N, O, and S, which can be optionally mono- or independently multi-substituted by one or more of deuterium, tritium, halogen, hydroxyl, $C_{1-12}$ alkyl, or $C_{1-12}$ alkoxy, $R_6$ is hydrogen, or $C_{1-12}$ alkyl, which can be optionally mono- or independently multi-substituted by deuterium, tritium, halogen, hydroxyl, $C_{1-12}$ alkyl or $C_{1-12}$ alkoxy, $R_7$ is hydrogen, or $C_{1-12}$ alkyl, which can be optionally mono- or multi-substituted by deuterium, tritium, halogen, or hydroxyl, $R_8$ is hydrogen, deuterium, tritium, halogen, cyano, hydroxyl, $C_{1-12}$ alkyl $C_{1-12}$ alkoxyl, which can be optionally mono- or independently multi-substituted by one or more of deuterium, tritium, halogen, or $C_{1-12}$ alkyl;

$R_9$ is null, hydrogen, deuterium, tritium, halogen, cyano, hydroxyl, $C_{1-12}$ alkyl, or $C_{1-12}$ alkoxyl which can be optionally mono- or independently multi-substituted by one or more of deuterium, tritium, halogen, or $C_{1-12}$ alkyl;

n is 0, 1, 2, 3, or 4;

each R is independently hydrogen, deuterium, tritium; halogen, cyano, hydroxyl, $C_{1-12}$ alkyl, $C_{1-12}$ alkoxy, 3-10 membered saturated or unsaturated carbocyclyl, or 3-10 membered saturated or unsaturated heterocyclyl which is fused with the ring to which it is bound, which can be optionally mono- or independently multi-substituted by one or more of deuterium, tritium, halogen, or $C_{1-12}$ alkyl.

2. The compound of claim 1, wherein $A_1$ is N.

3. The compound of claim 1, wherein $A_1$ is CH.

4. The compound of claim 1, wherein $A_2$, $A_3$, $A_4$ and $A_5$ are each independently $CR_9$.

5. The compound of claim 1, wherein $R_1$ and $R_2$ are each independently selected from:

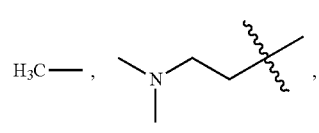

-continued

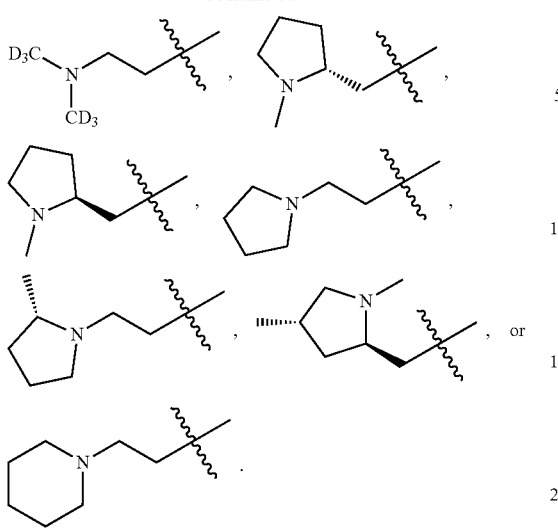

6. The compound of claim 1, wherein $R_1$ and $R_2$ are taken together with the nitrogen atom to which they are bound to form a 3-12 membered monocyclic or polycyclic ring selected from:

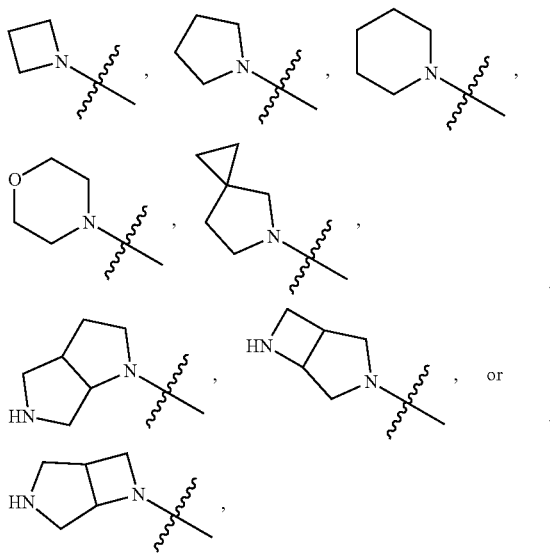

which is optionally mono- or independently multi-substituted by halogen, hydroxy $C_{1-12}$ alkyl, $C_{1-12}$ alkoxy, —$NR^aR^b$, or —$C_{1-12}$ alkyl-$NR^aR^b$.

7. The compound of claim 1, wherein RI and $R_2$ are taken together with the nitrogen atom to which they are bound to form:

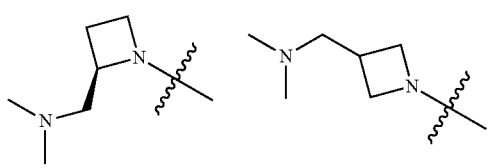

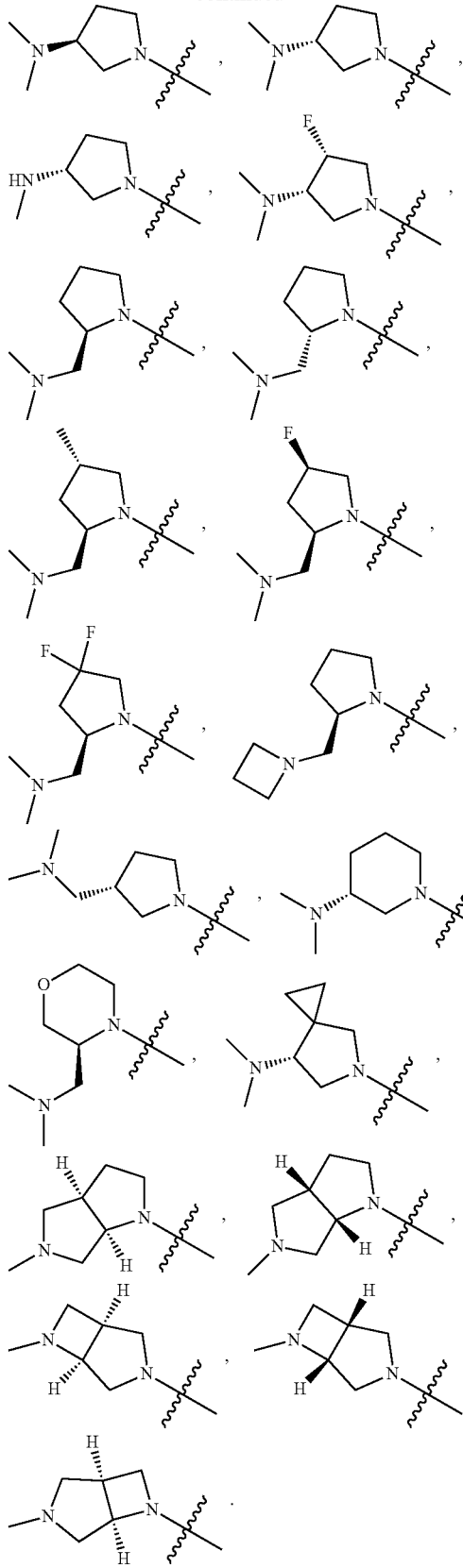

8. The compound of claim 1, wherein n is 2, $A_2$ and $A_5$ are CH, $A_3$ and $A_4$ are each independently CH substituted by R, R is each independently halogen, and $R_4$ and $R_5$ are each independently unsubstituted $C_{1-6}$ alkyl.
9. The compound of claim 1, selected from the group consisting of
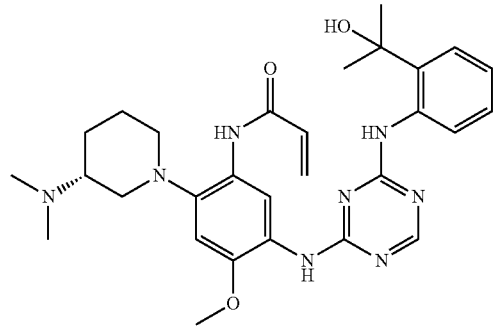
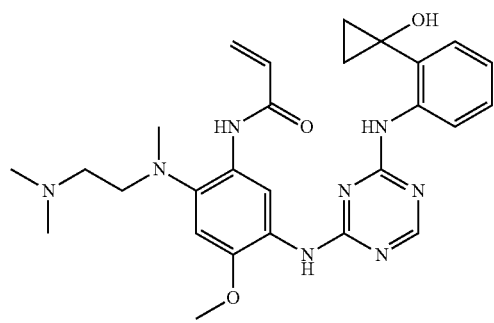
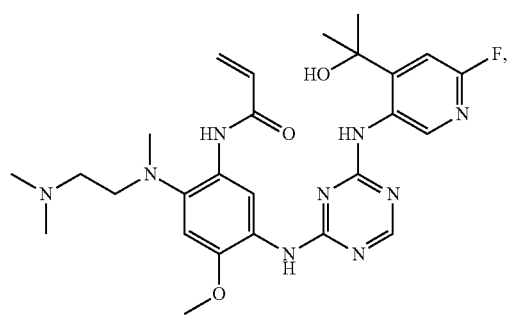
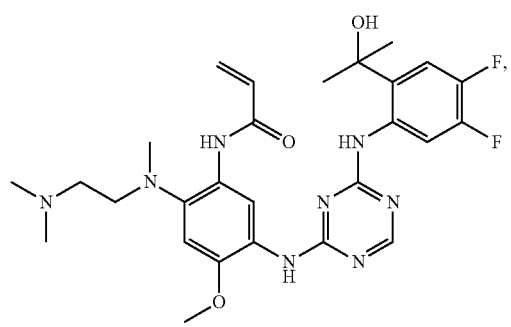
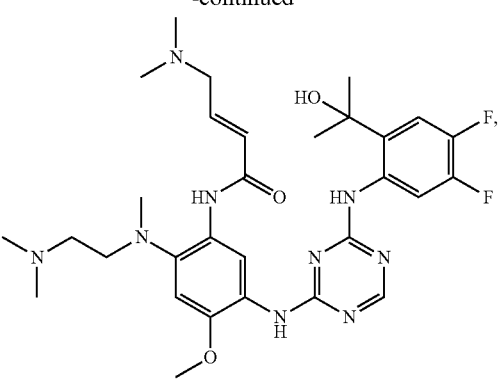
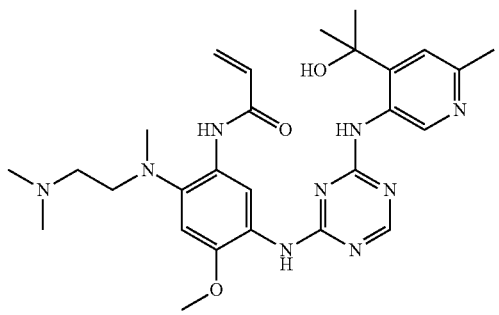
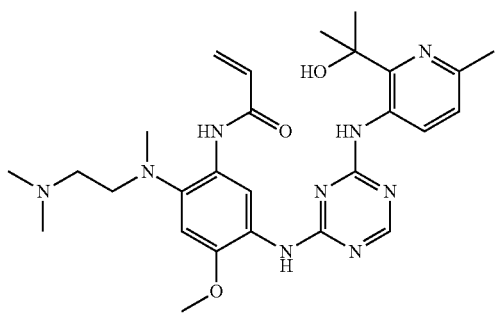
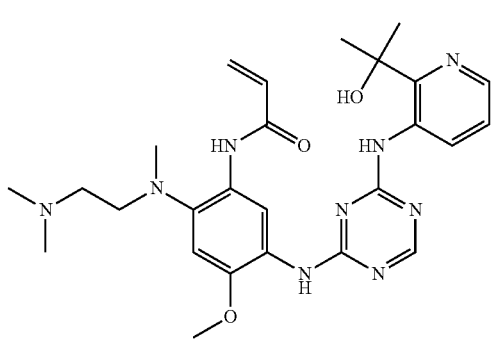
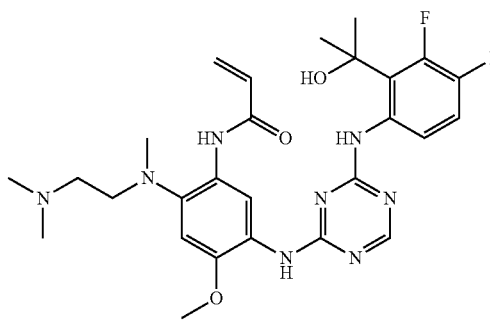

341
-continued
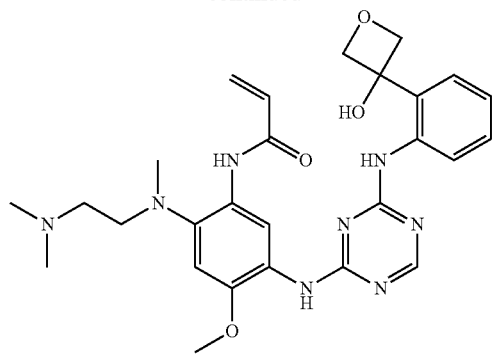
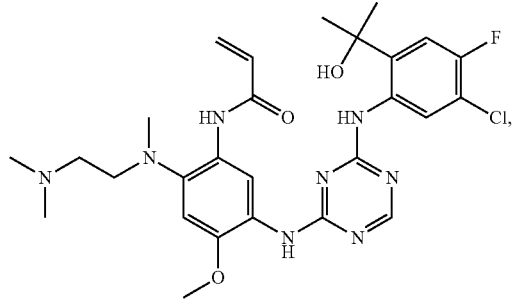
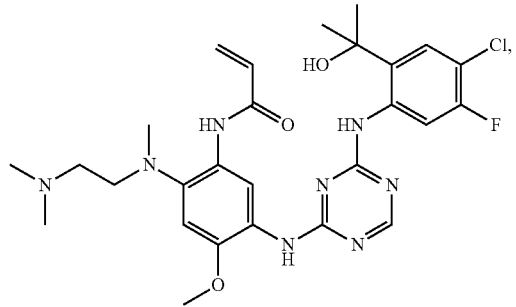
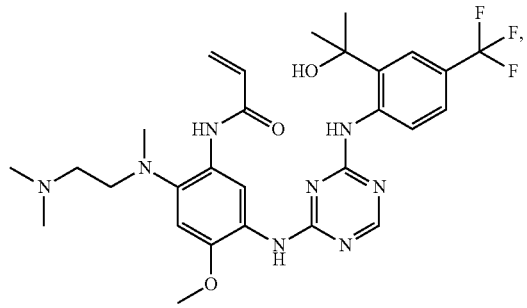
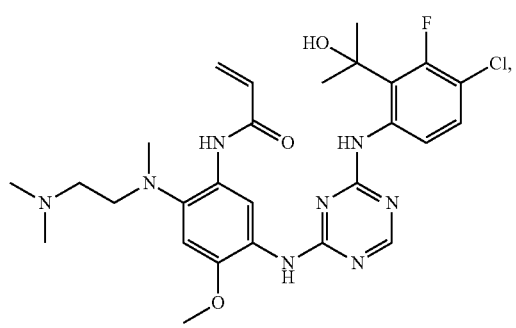
342
-continued
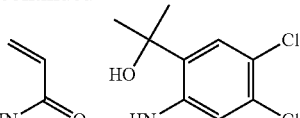
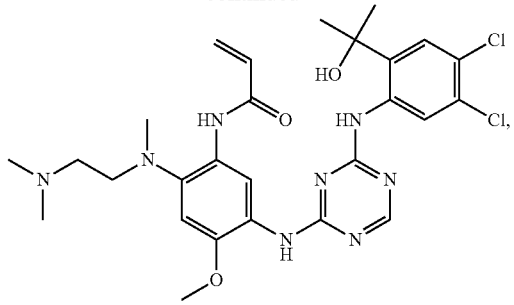
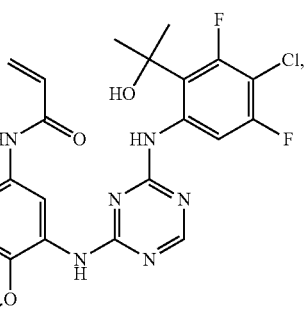
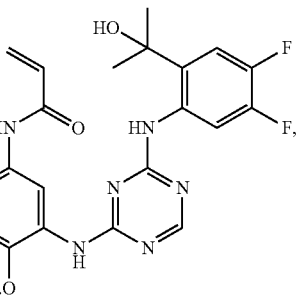
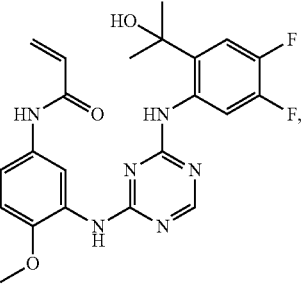
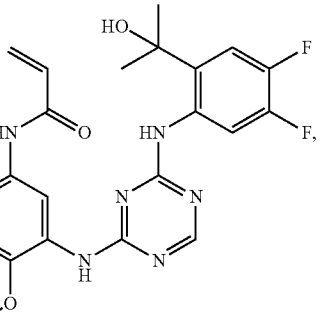

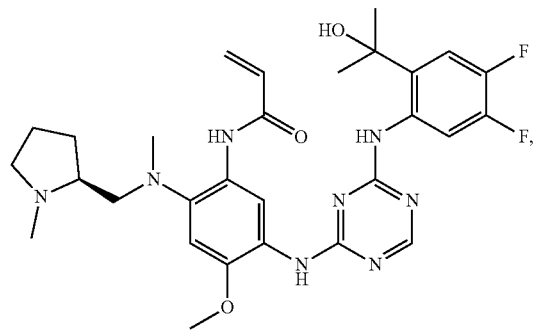
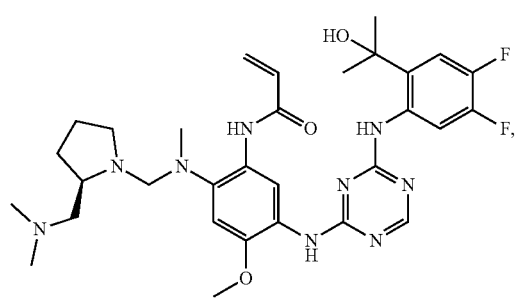
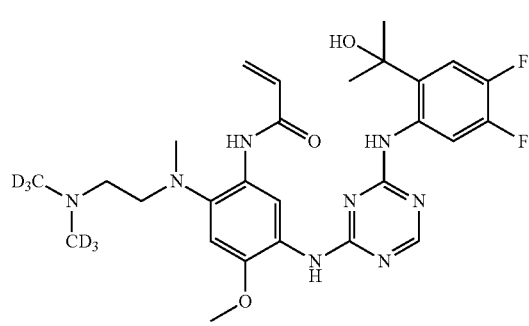
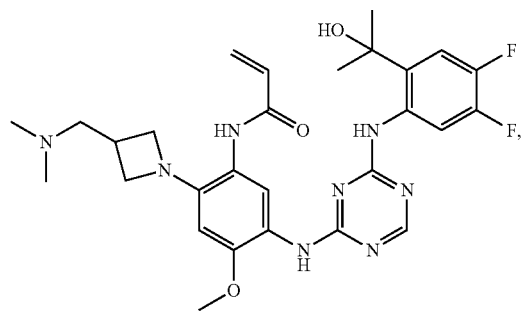
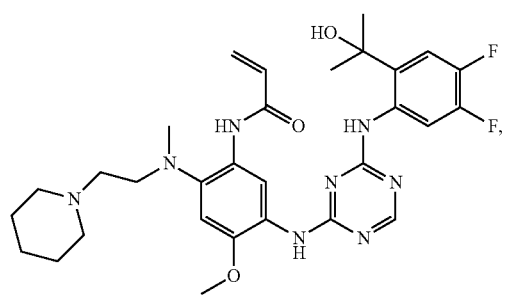
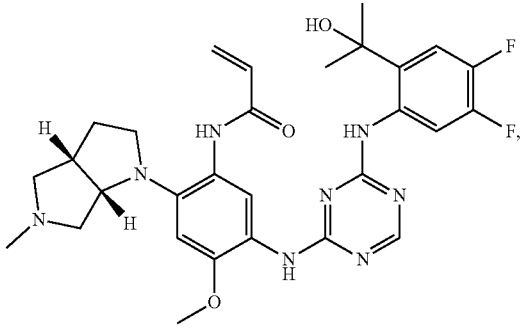
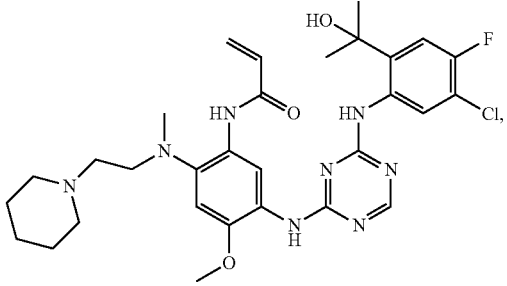
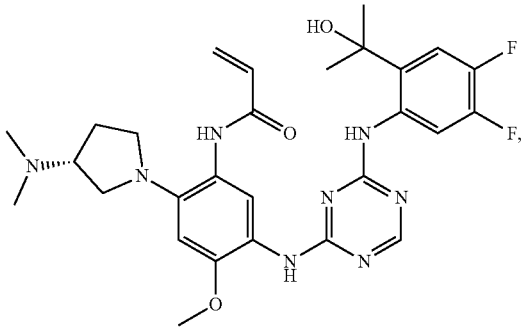
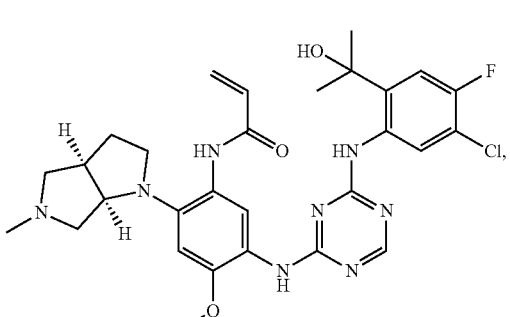
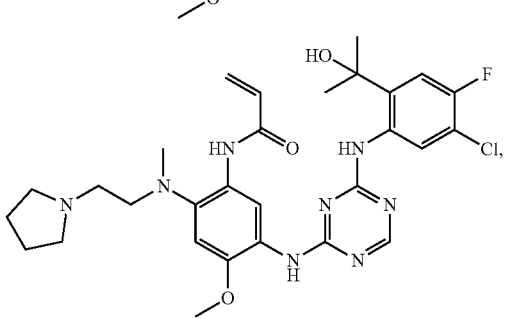

345
-continued
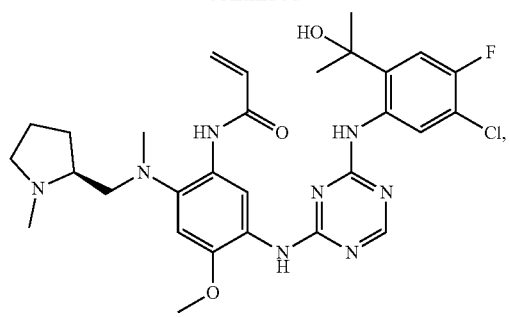
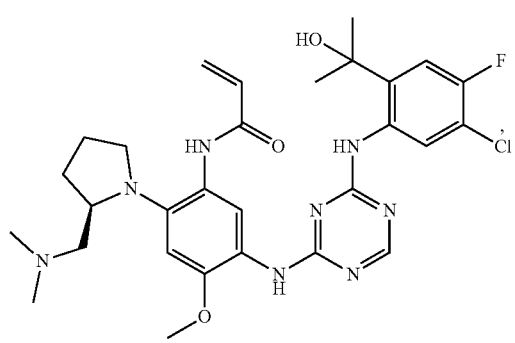
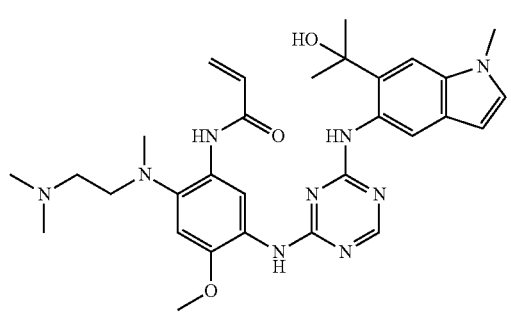
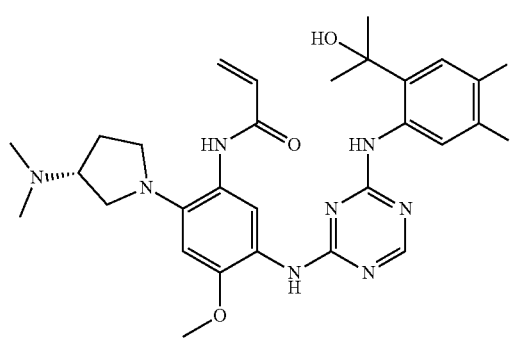
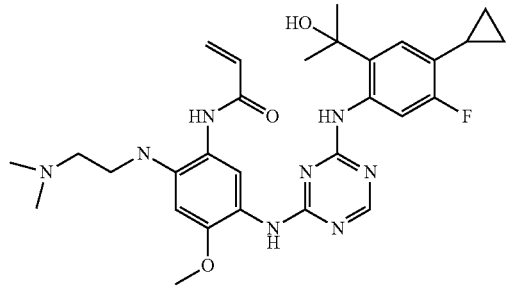
346
-continued
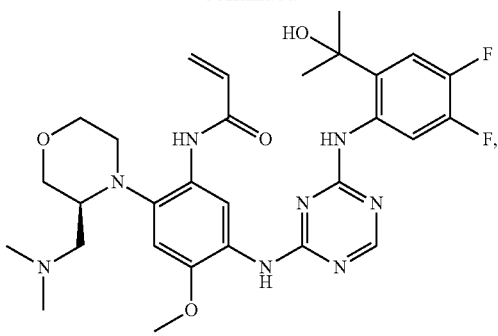
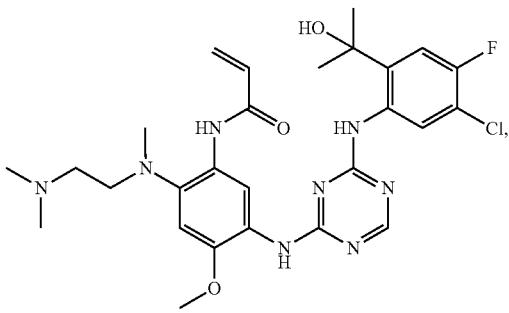
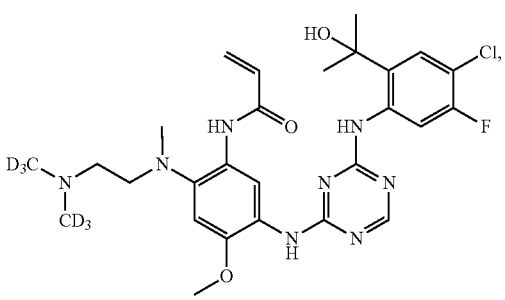
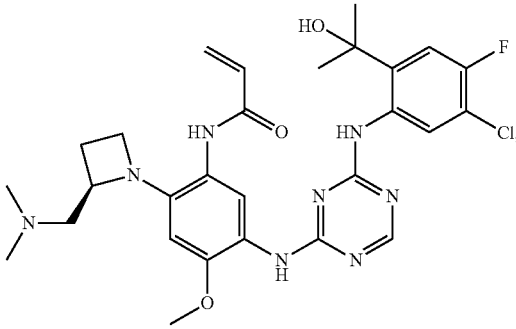
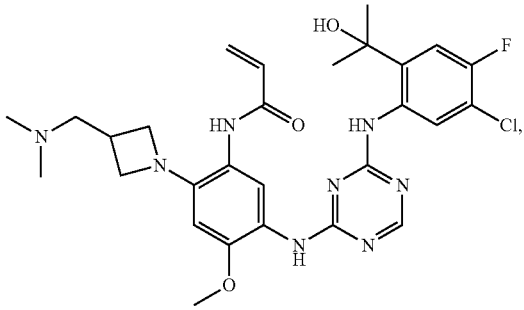

347
-continued
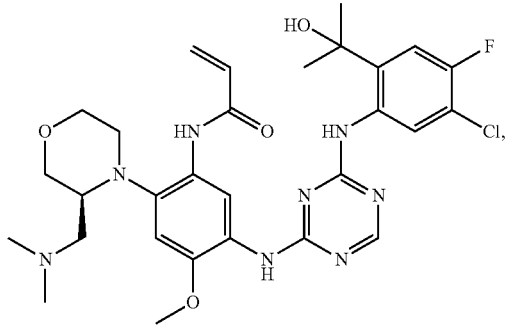
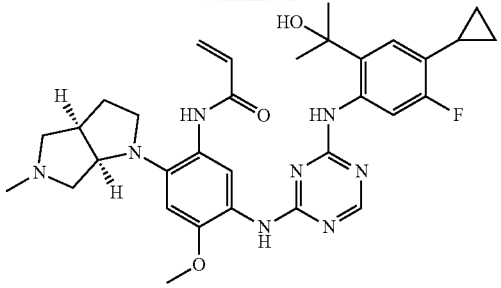
348
-continued
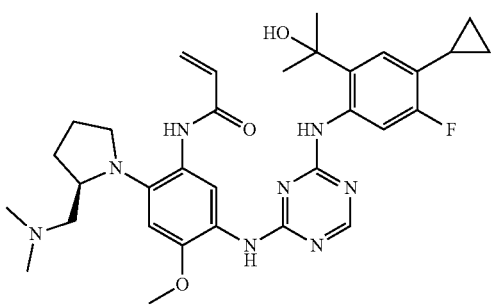
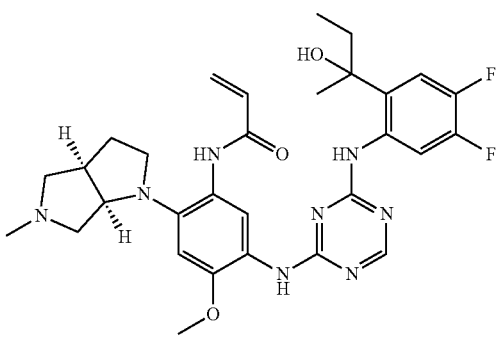
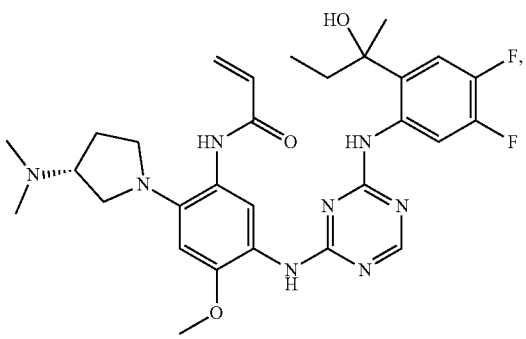
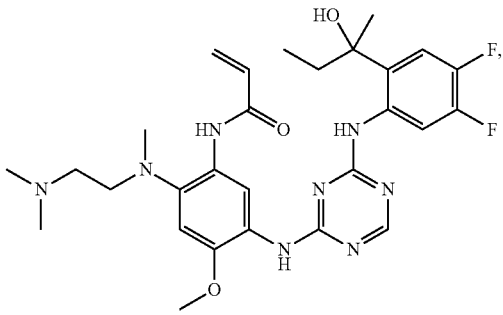

349
-continued
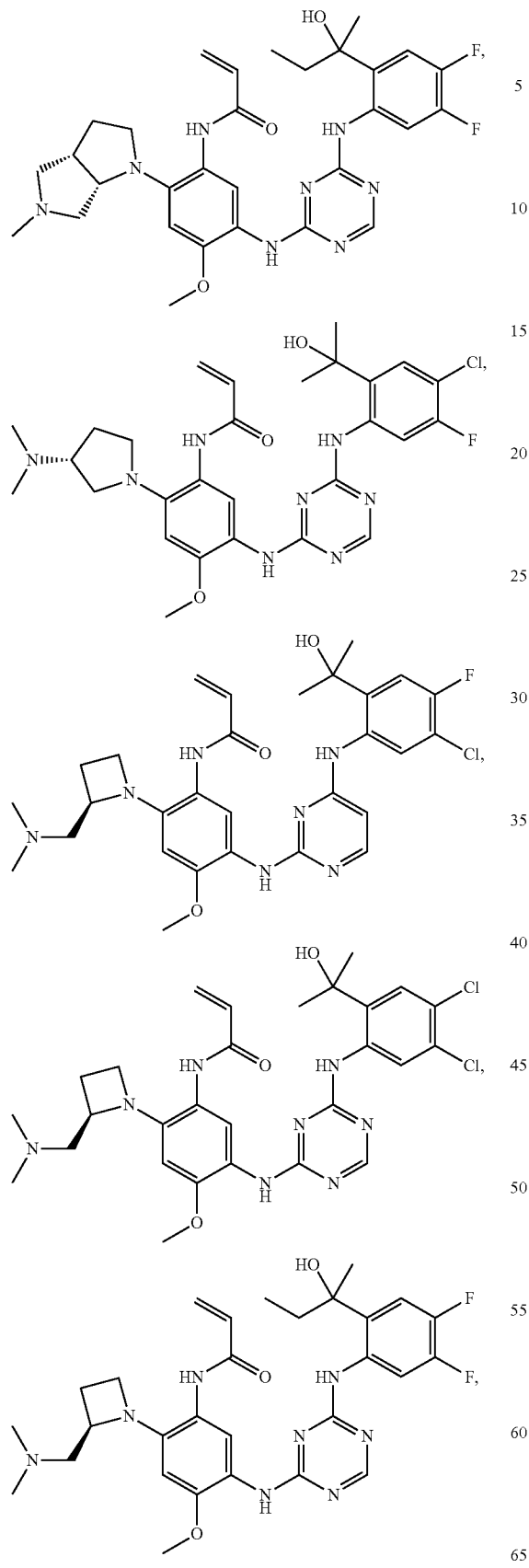
350
-continued
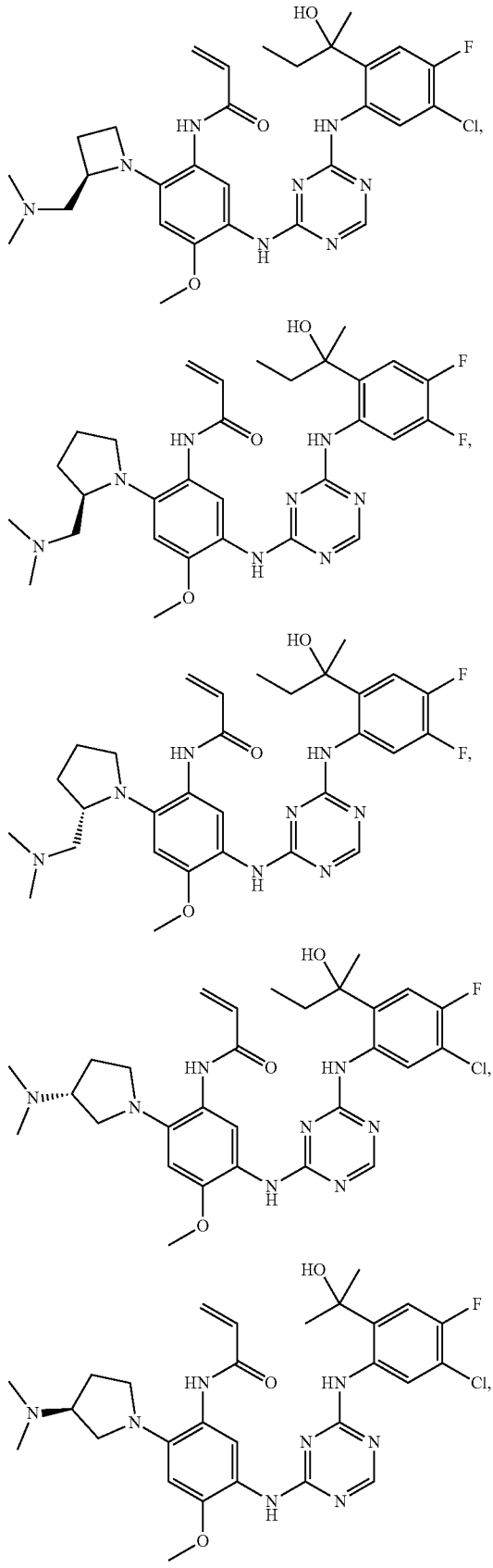

351
-continued
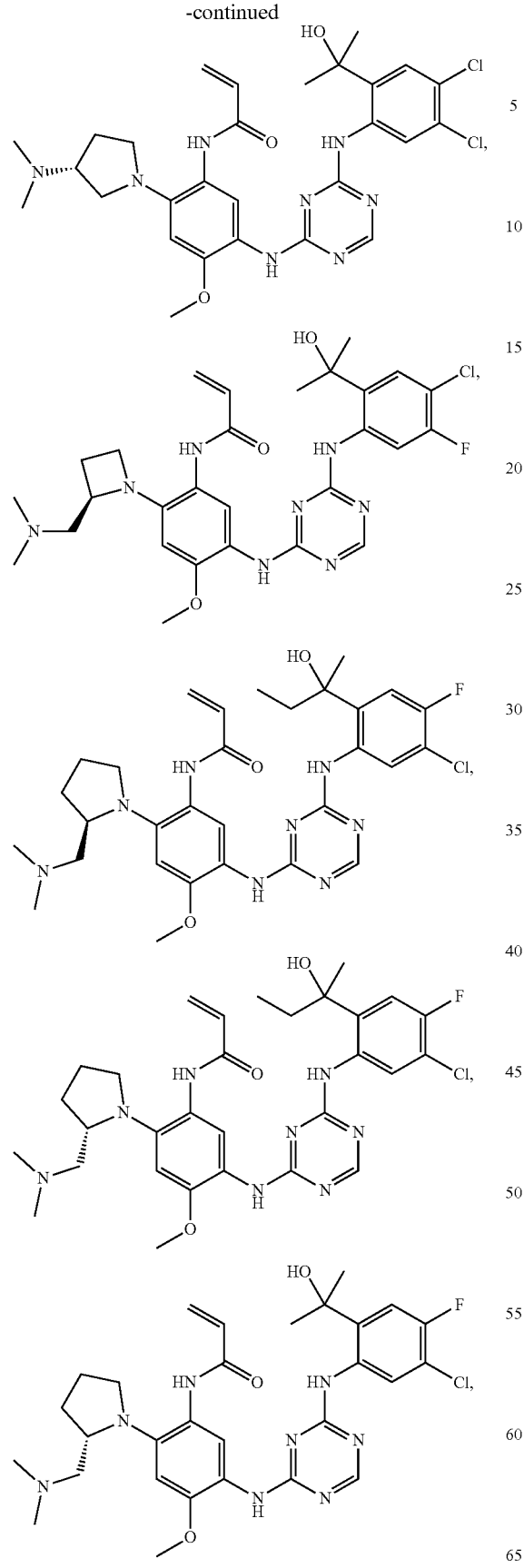
352
-continued
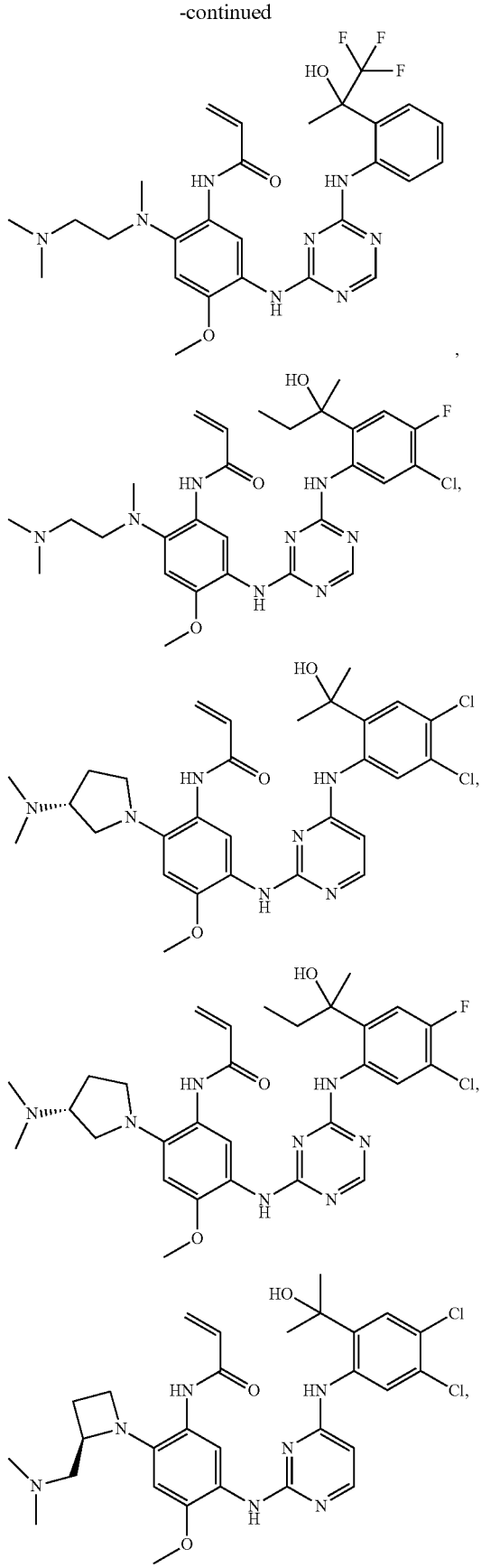

353
-continued
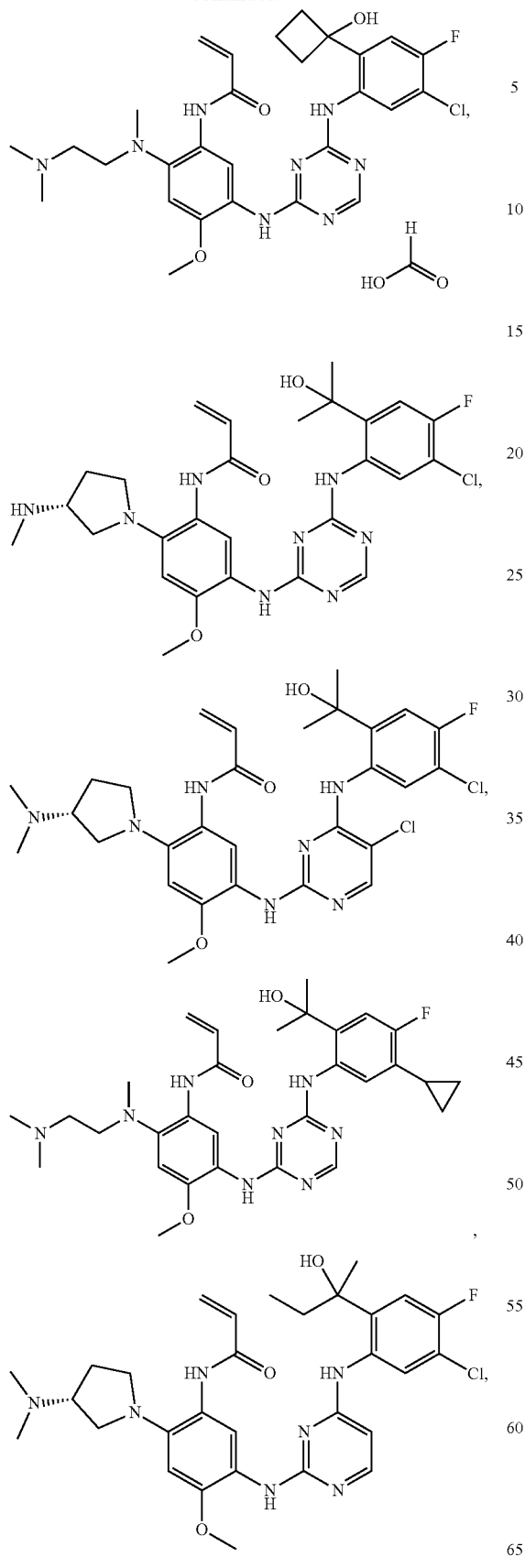
354
-continued
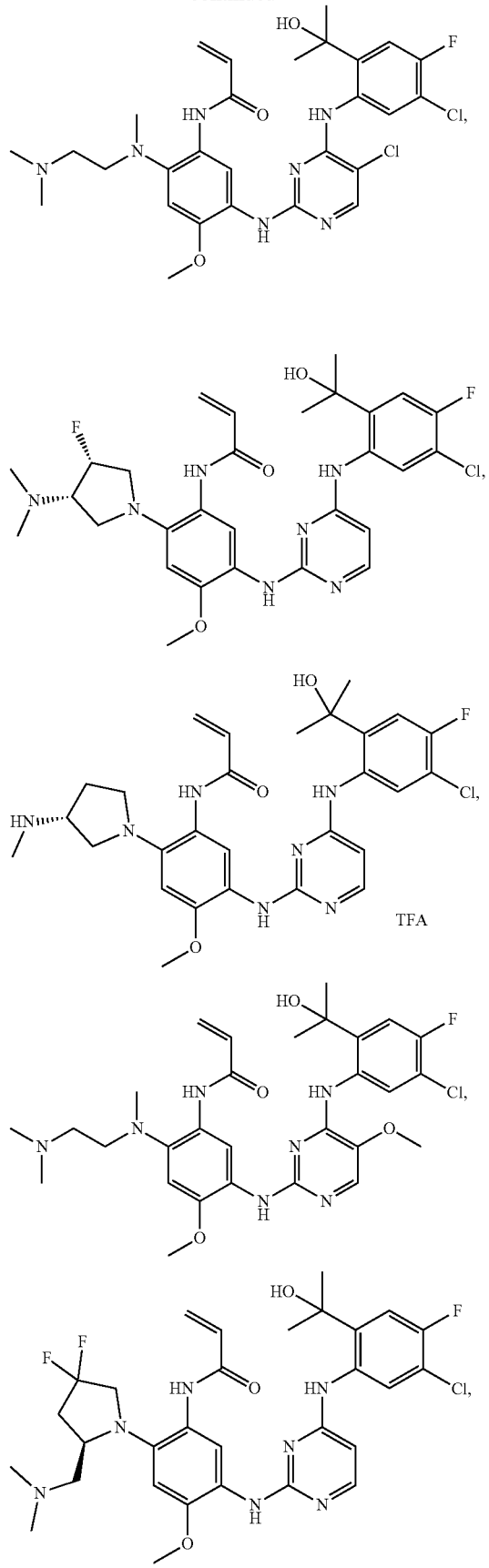

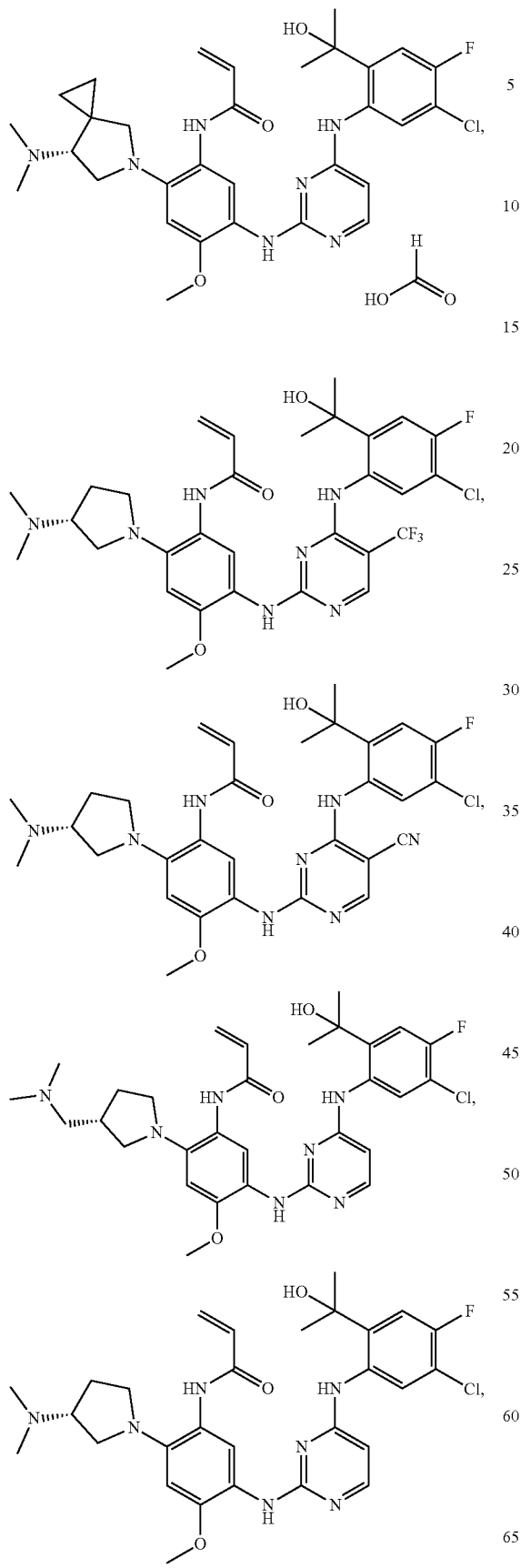
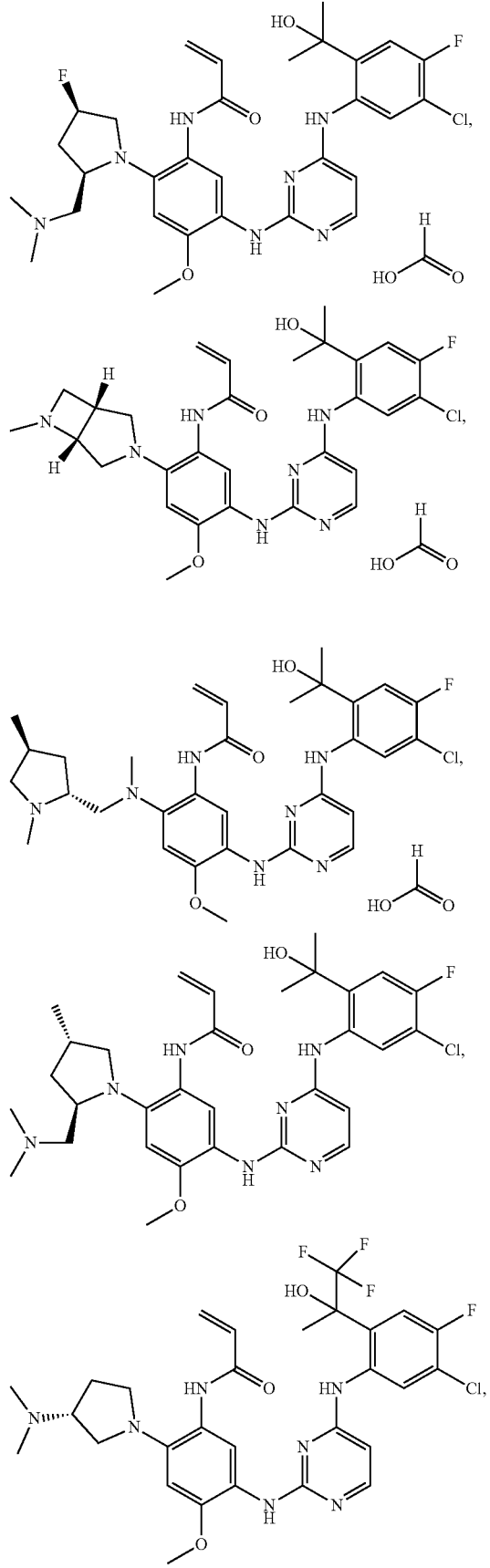

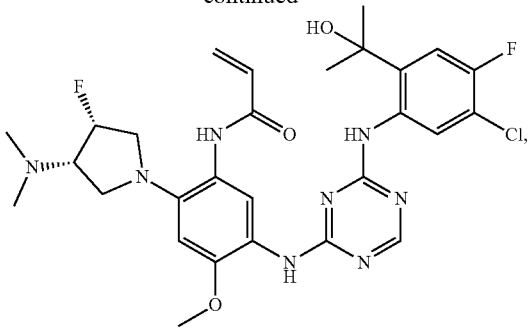

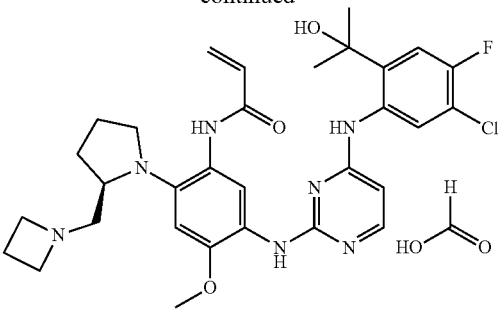

10. A pharmaceutical composition comprising one or more compounds of Formula (I), pharmaceutically acceptable salts, hydrates, solvates or stereoisomers thereof according to claim 1 as a first active ingredient, and a pharmaceutically acceptable diluent, excipient or carrier.

11. A method of inhibiting EGFR, Her2 or BTK by using one or more compounds, pharmaceutically acceptable salts, hydrates, solvates or stereoisomers thereof of claim 1.

12. A method of treating an ErbB associated disease or BTK associated diseases in a subject, comprising administering to the subject an effective amount of one or more compounds, pharmaceutically acceptable salts, hydrates, solvates or stereoisomers thereof of claim 1,
wherein the ErbB associated disease is selected from the group consisting of: lung cancer, colorectal cancer, head and neck cancer, pancreatic cancer, breast cancer, cervix cancer, colon cancer and esophageal cancer;
wherein the BTK associated disease is selected from the group consisting of: lymphoma, leukemia and autoimmune disease.

13. The method according to claim 12, wherein the subject is a warm blooded-animal.

14. The method according to claim 12, wherein the lung cancer is non-small cell lung cancer.

15. The method according to claim 12, wherein the lymphoma is non-Hodgkin's lymphoma (NHL), mantle cell lymphoma (MCL) or diffuse large B-cell lymphoma (DLBCL).

16. The method according to claim 12, wherein the leukemia is chronic lymphocytic leukemia (CLL).

17. The method according to claim 12, wherein the autoimmune disease is rheumatoid arthritis, systemic lupus erythematosus or Sjogren's syndrome.

18. The method according to claim 11, wherein the EGFR or Her2 is mutant EGFR or mutant Her2.

19. The method according to claim 18, wherein the mutant EGFR selected from the group consisting of EGFR D761_E762insEAFQ, EGER A763_Y764insHH, EGFR M766_A767instAI, EGFR A767_V769dupASV, EGFR A767_S768insTLA, EGFR S768_D770 dupSVD, EGFR S768_V769insVAS, EGER S768_V769insAWT, EGFR V769_D770insASV, EGFR V769_D770insGV, EGFR V769_D770insCV, EGER V769_D770insDNV, EGFR V769_D770insGSV, EGFR V769_D770insGVV, EGER V769_D770insMASVD, EGER D770_N771insSVD, EGFR D770_N771insNPG, EGFR D770_N771insAPW, EGFR D770_N771insD, EGFR D770_N771insDG, EGFR D770_N771insG, EGFR D770_N771_insGL, EGFR D770_N771insN, EGER D770_N771insNPH, EGFR D770_N771insSVP, EGFR D770_N771insSVQ, EGER D770_N771insMATP, EGFR delD770insGY, EGER N771_P772insH, EGFR N771_P772insN, EGFR N771_H773dupNPH, EGFR delN771insGY, EGFR delN771insGF, EGFR P772_H773insPR, EGFR P772_H773insYNP, EGFR P772_H773insX, EGFR P772_H773insDPH, EGFR P772_H773insDNP, EGFR P772_H773insQV, EGFR P772_H773insTPH, EGFR P772_H773insN, EGFR P772_H773insV, EGFR H773_V774insNPH, EGFR H773_V774insH, EGFR H773_V774insPH, EGFR H773_V774insGNPH, EGFR H773_V774dupHV, EGFR H773_V774insG, EGFR H773_V774insGH, EGFR V774_C775insHV, EGFR exon19 deletion, EGFR L858R, EGFR T790M, EGFR L858R/T790M, EGFR exon 19 deletion/T790M, EGFR S768I, EGER, G719S, EGFR G719A, EGFR G719C, EGFR E709A/G719S, EGFR E709A/G719A, EGFR E709A/G719C, and EGFR L861Q.

20. The method according to claim 18, wherein the mutant Her2 is selected from the group consisting of Her2 A775 G776insYVMA, Her2 delG776insVC, Her2 V777_G778insCG and Her2 P780_Y781insGSP.

21. A composition comprising compound of Formula (I), or pharmaceutically acceptable salt, hydrates, solvates or stereoisomers thereof, as claimed in claim 1 and a second therapeutic agent.

22. The method according to claim 13, wherein the warm blooded-animal is man.

23. The composition according to claim 21, wherein the second therapeutic agent is an anti-tumour agent.

\* \* \* \* \*